US012759960B2

(12) United States Patent
Novek

(10) Patent No.: US 12,759,960 B2
(45) Date of Patent: Oct. 13, 2026

(54) SODIUM HYDROXIDE PRODUCTION WITH CARBOXYLIC ACID AND SULFUR DIOXIDE INTERMEDIATES

(71) Applicant: INNOVATOR ENERGY, LLC, Houston, TX (US)

(72) Inventor: Ethan Novek, Houston, TX (US)

(73) Assignee: INNOVATOR ENERGY, LLC, Houston, TX (US)

( * ) Notice: Subject to any disclaimer, the term of this patent is extended or adjusted under 35 U.S.C. 154(b) by 239 days.

(21) Appl. No.: 18/611,398

(22) Filed: Mar. 20, 2024

(65) Prior Publication Data

US 2025/0091977 A1 Mar. 20, 2025

Related U.S. Application Data

(63) Continuation of application No. 18/198,664, filed on May 17, 2023, now Pat. No. 12,030,846, which is a (Continued)

(51) Int. Cl.
*C07C 51/02* (2006.01)
*C01F 11/02* (2006.01)
(Continued)

(52) U.S. Cl.
CPC .............. *C07C 51/02* (2013.01); *C01F 11/02* (2013.01); *C01F 11/04* (2013.01); *C01F 11/06* (2013.01); *C07C 51/47* (2013.01)

(58) Field of Classification Search
None
See application file for complete search history.

(56) References Cited

U.S. PATENT DOCUMENTS 2,740,691 A 4/1956 Burnwell
4,331,640 A 5/1982 Tomijiro et al.
(Continued)

FOREIGN PATENT DOCUMENTS

CN 111995264 B 12/2021
DE 3525051 C2 * 5/1990 .............. C01F 11/48

OTHER PUBLICATIONS

European Extended Search Report issued in EP Application No. 23808246.5, mailed May 7, 2026, 6 pages.

*Primary Examiner* — Daniel Berns
(74) *Attorney, Agent, or Firm* — HUNTON ANDREWS KURTH LLP

(57) ABSTRACT

The present application pertains to processes producing oxides using a weak acid intermediate. In one embodiment a material comprising calcium carbonate is reacted with a solution comprising aqueous carboxylic acid to form a gas comprising carbon dioxide and a solution comprising aqueous calcium carboxylate. The solution comprising aqueous calcium carboxylate is reacted with sodium sulfate to form a solution comprising aqueous sodium carboxylate and a solid comprising calcium sulfate. The solution comprising aqueous sodium carboxylate is reacted with sulfur dioxide to form sodium sulfite and an aqueous carboxylic acid. The sodium sulfite is separated from said aqueous carboxylic acid and reacted to form a solid comprising calcium sulfite which is decomposed to form calcium oxide and sulfur dioxide.

19 Claims, 93 Drawing Sheets

Figure 1:
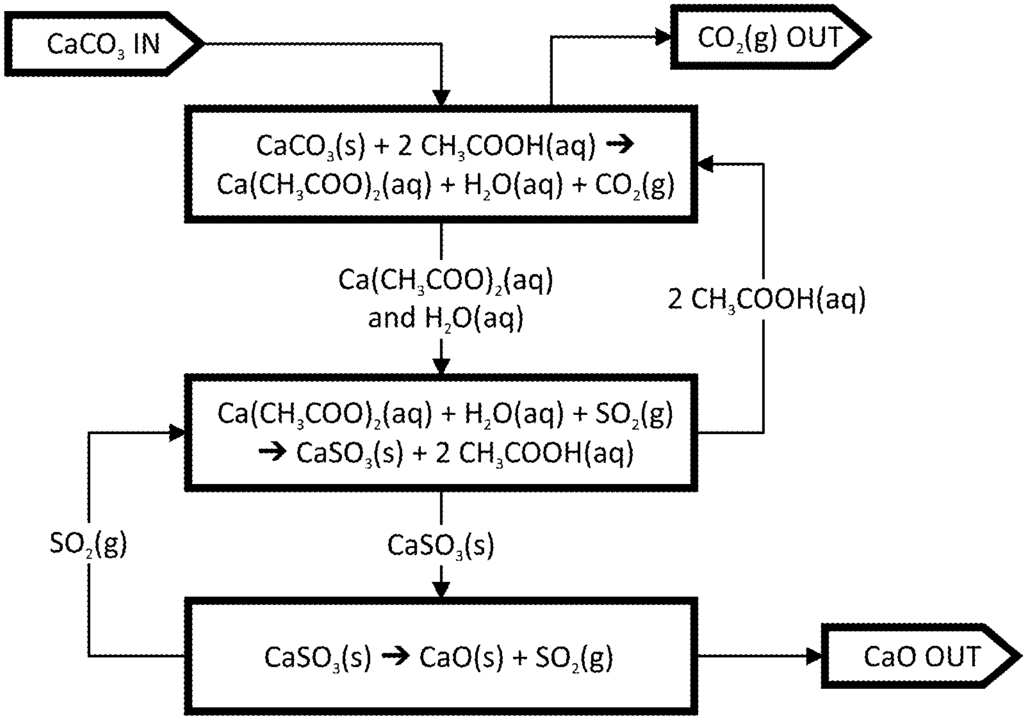

Related U.S. Application Data continuation of application No. 18/087,432, filed on Dec. 22, 2022, which is a continuation of application No. 17/744,161, filed on May 13, 2022, now Pat. No. 11,542,219, which is a continuation-in-part of application No. 17/732,808, filed on Apr. 29, 2022, now Pat. No. 11,512,036, application No. 18/611,398 is a continuation of application No. 17/590,483, filed on Feb. 1, 2022, now Pat. No. 11,897,840, said application No. 18/198,664 is a continuation of application No. 17/590,483, filed on Feb. 1, 2022, now Pat. No. 11,897,840, said application No. 17/732,808 is a continuation-in-part of application No. 17/590,483, filed on Feb. 1, 2022, now Pat. No. 11,897,840, which is a continuation of application No. 17/243,714, filed on Apr. 29, 2021, now Pat. No. 11,236,033, which is a continuation-in-part of application No. 16/944,850, filed on Jul. 31, 2020, now Pat. No. 11,034,619.

(60) Provisional application No. 63/462,797, filed on Apr. 28, 2023, provisional application No. 63/400,883, filed on Aug. 25, 2022, provisional application No. 63/342,870, filed on May 17, 2022, provisional application No. 63/188,275, filed on May 13, 2021, provisional application No. 63/179,822, filed on Apr. 26, 2021, provisional application No. 63/163,993, filed on Mar. 22, 2021, provisional application No. 63/157,847, filed on Mar. 8, 2021, provisional application No. 63/153,461, filed on Feb. 25, 2021, provisional application No. 63/147,286, filed on Feb. 9, 2021, provisional application No. 63/042,397, filed on Jun. 22, 2020, provisional application No. 62/895,557, filed on Sep. 4, 2019, provisional application No. 62/890,254, filed on Aug. 22, 2019.

(51) Int. Cl.

| | |
|---|---|
| ***C01F 11/04*** | (2006.01) |
| ***C01F 11/06*** | (2006.01) |
| ***C07C 51/47*** | (2006.01) |

(56) References Cited

U.S. PATENT DOCUMENTS

| | | | |
|---|---|---|---|
| 11,034,619 | B2 | 6/2021 | Novek |
| 2021/0261427 | A1 | 8/2021 | Novek |

* cited by examiner

SODIUM HYDROXIDE PRODUCTION WITH CARBOXYLIC ACID AND SULFUR DIOXIDE INTERMEDIATES

CROSS-REFERENCE TO RELATED APPLICATIONS

For PCT purposes this application claims priority to U.S. Provisional Application 63/342,870 filed May 17, 2022 which application is incorporated herein by reference.

For U.S. purposes this application claims priority to U.S. Provisional Application 63/342,870 filed May 17, 2022 which application is incorporated herein by reference.

For U.S. purposes the present application also claims priority to U.S. Ser. No. 18/198,664 filed on May 17, 2023 which is a continuation of U.S. Ser. No. 18/087,432 filed on Dec. 22, 2022 which is a continuation of U.S. Ser. No. 17/744,161 filed on May 13, 2022 issuing as U.S. Pat. No. 11,542,219 on Jan. 3, 2023. U.S. Ser. No. 17/744,161 was a continuation-in-part of U.S. application Ser. No. 17/732,808 filed Apr. 29, 2022 which application is a continuation-in-part of U.S. application Ser. No. 17/590,483 filed Feb. 1, 2022 which application is a continuation of U.S. application Ser. No. 17/243,714 filed Apr. 29, 2021 issued as U.S. Pat. No. 11,236,033 which application is a continuation-in-part of U.S. application Ser. No. 16/944,850 filed Jul. 31, 2020 issued as U.S. Pat. No. 11,034,619 which application claims priority from U.S. Provisional Application No. 62/895,557 filed Sep. 4, 2019 and U.S. Provisional Application No. 63/042,397 filed Jun. 22, 2020 and U.S. Provisional Application No. 62/890,254 filed Aug. 22, 2019. The present application also claims priority to U.S. Provisional Application No. 63/188,275 filed May 13, 2021.

The above described continuation which is U.S. application Ser. No. 17/590,483 filed Feb. 1, 2022 also claims priority to U.S. Provisional Application No. 63/147,286 filed Feb. 9, 2021; U.S. Provisional Application No. 63/153,461 filed Feb. 25, 2021; U.S. Provisional Application No. 63/157,847 filed Mar. 8, 2021; U.S. Provisional Application No. 63/163,993 filed Mar. 22, 2021; and U.S. Provisional Application No. 63/179,822 filed Apr. 26, 2021. All of the above applications are incorporated herein by reference.

BACKGROUND AND SUMMARY

Sodium hydroxide is generally produced using the chlor-alkali process, which is energy intensive, requires rare metal anodes and cathodes, and produces hydrochloric acid, which has a limited market and cannot be discharged into the environment. Production of sodium hydroxide in prior art is energy intensive, $CO_2$ emissions intensive, and expensive. Additionally, prior art production of sodium hydroxide may not be employed in $CO_2$ removal, or may not be added to a sea for deacidification or $CO_2$ removal, because they are energy intensive, $CO_2$ emissions intensive, expensive, and environmentally damaging. Commercial applications of hydrochloric acid often involve employing hydrochloric acid in a reaction with a carbonate salt, which may result in the release of $CO_2$ and may counter any $CO_2$ emissions reduction benefit. Additionally, if hydrochloric acid is released into the environment, it will react with carbonate or bicarbonate salts present in the environment, emitting carbon dioxide and acidifying water bodies, such as the ocean. Sodium hydroxide is an essential chemical employed in a wide range of applications, which include, for example, pulp & paper production, lithium processing, soap production, rayon production, aluminum refining, to name a few. Production of sodium hydroxide in prior art is energy intensive, $CO_2$ emissions intensive, and expensive. Reducing the energy, cost, and emissions associated with the production of sodium hydroxide would greatly benefit the economy and environment. There is a significant need for a low energy consumption, low $CO_2$ emissions, environmentally friendly process for producing sodium hydroxide.

Production of calcium oxide, or calcium hydroxide, or cement klinker in prior art produces $CO_2$ emissions, which may be difficult or expensive to capture. It may be highly desirable to develop a calcium oxide, or calcium hydroxide, or cement klinker production process which does not produce $CO_2$ emissions and/or inherently produces high purity, captured $CO_2$.

Some embodiments of the present invention may pertain to low carbon emissions, or low energy consumption, or carbon negative production of sodium hydroxide, or sodium carbonate, or sodium bicarbonate, or sodium sulfite, or sodium bisulfite, or gypsum, or alkaline-earth sulfate, or alkali hydroxide, or alkali carbonate, or alkali bicarbonate, or alkali sulfite. Some embodiments of the present invention may enable ultra-low $CO_2$ emissions production of sodium hydroxide with calcium sulfate as the side product. Calcium sulfate comprises a solid, is minimally soluble in water, is non-toxic, is not dangerous for the environment, and has a multi-billion metric ton per year market in gypsum wallboard, concrete aggregates, fireproofing, plaster, building materials, and other applications. Some embodiments of the present invention may be capable of scaling to greater than 1 billion ton per year $CO_2$ emissions reduction, or carbon removal, or a combination thereof. Some embodiments of the present invention may enable highly scalable, environmentally beneficial systems and methods for ocean deacidification, which are capable of scaling to meaningfully increase ocean pH, rejuvenate marine ecosystems, and permanently sequester carbon dioxide. Additionally some embodiments may lower the required cost and energy consumption of alkali hydroxides, alkali carbonates, and alkali bicarbonates. Some embodiments may be employ equipment comprising abundant and recyclable materials.

Some embodiments of the present invention may pertain to low carbon emissions, or low energy consumption, or carbon negative production of calcium oxide, or calcium hydroxide, or calcium carbonate, or magnesium oxide, or magnesium hydroxide, or cement, or cement klinker, or Portland cement, or magnesium carbonate, or alkaline earth oxide, or alkaline earth hydroxide, or alkaline earth carbonate or any combination thereof. Some embodiments of the present invention may enable ultra-low $CO_2$ emissions production of calcium oxide, or magnesium oxide, or cement. Some embodiments may comprise a $CO_2$ capture process, or a $CO_2$ air capture process, or $CO_2$ removal process, or a $CO_2$ conversion process, or a $CO_2$ separation process, or a process for recovering or separating $CO_2$ from solutions comprising carbonate, or bicarbonate, or any combination thereof. Some embodiments of the present invention may enable calcium oxide or cement production with inherent production of high purity, high pressure carbon dioxide in the nature of the process, which may reduce the cost and energy required to produce low emissions or zero emissions calcium oxide or cement. Some embodiments may be employ equipment comprising abundant and recyclable materials.

Advantages of some embodiments include lower energy consumption, lower cost, or lower $CO_2$ emissions, $CO_2$ emissions negative outputs, or application in carbon dioxide removal, or no strong acid products, or abundant materials, or global scalability.

BRIEF FIGURE DESCRIPTIONS

FIG. 1: Process for producing calcium oxide and captured carbon dioxide with carboxylic acid and sulfur dioxide intermediates.

Figure 2A:
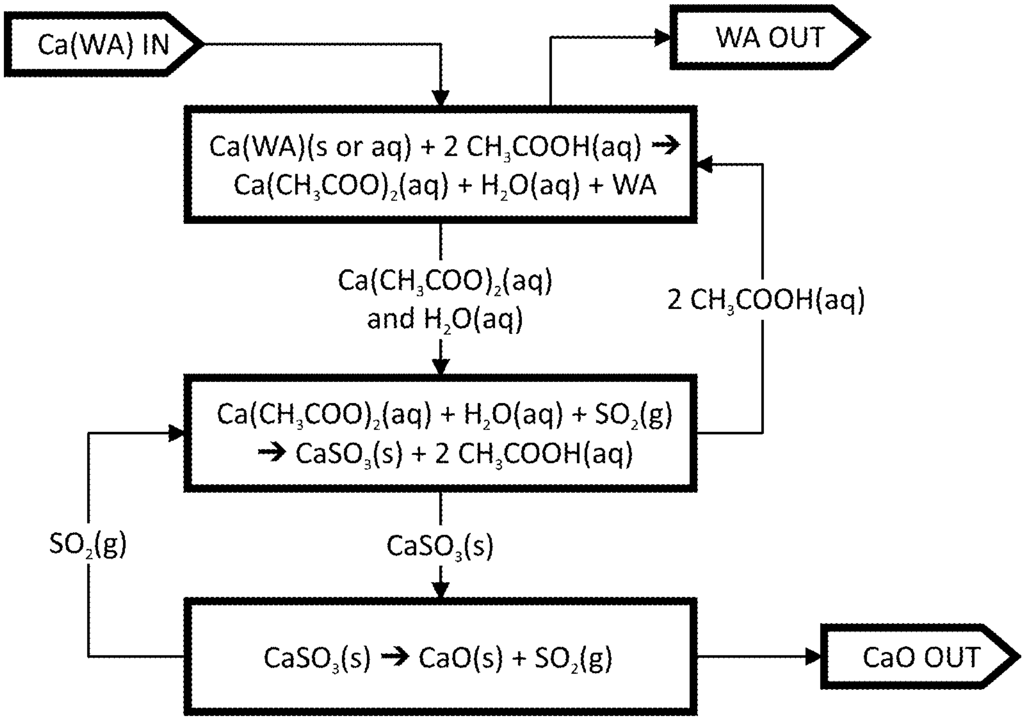

FIG. 2A: Process for producing calcium oxide and weak acid derivative employing carboxylic acid and sulfur dioxide intermediates.

Figure 2B:
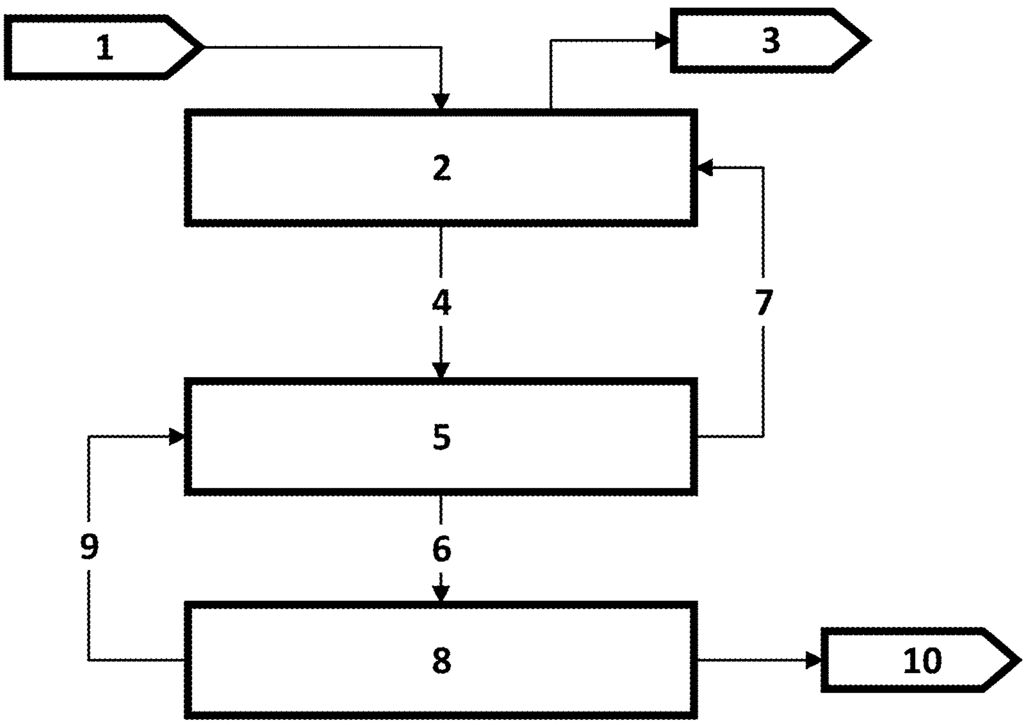

FIG. 2B: Process for producing calcium oxide and weak acid derivative employing carboxylic acid and sulfur dioxide intermediates.

Figure 3A:
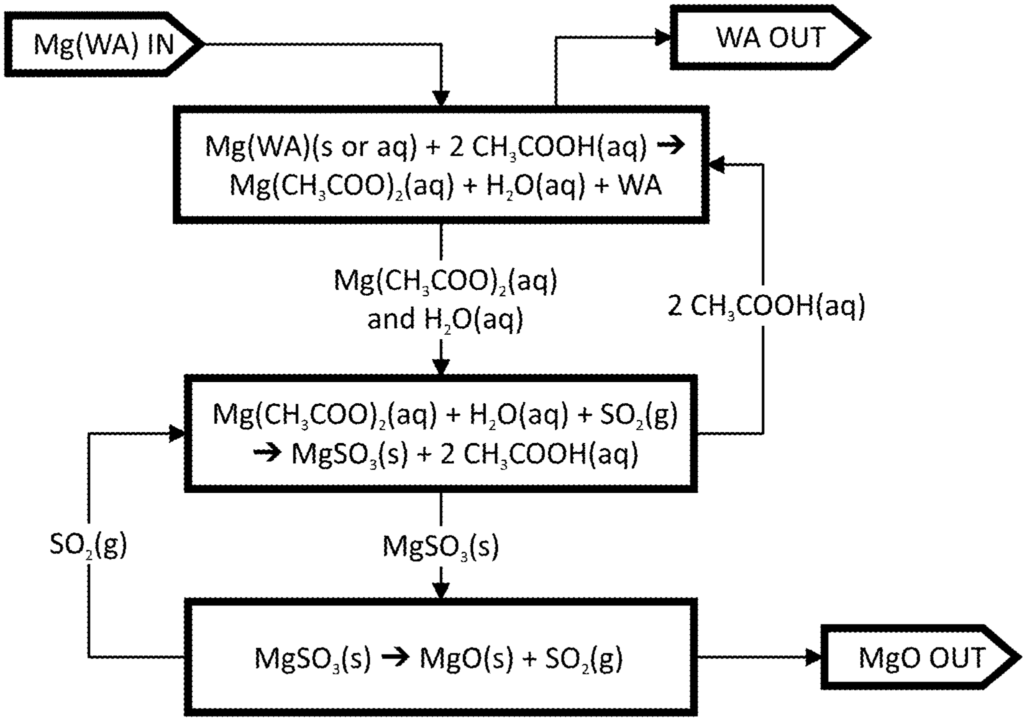

FIG. 3A: Process for producing magnesium oxide and weak acid derivative employing carboxylic acid and sulfur dioxide intermediates.

Figure 3B:
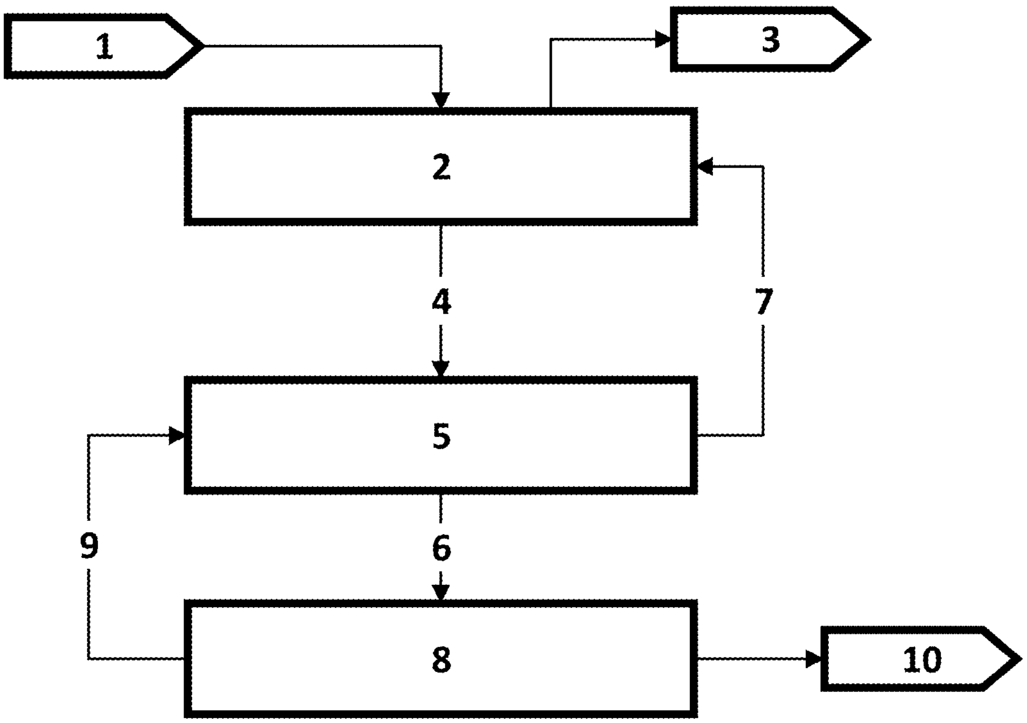

FIG. 3B: Process for producing magnesium oxide and weak acid derivative employing carboxylic acid and sulfur dioxide intermediates.

Figure 4A:
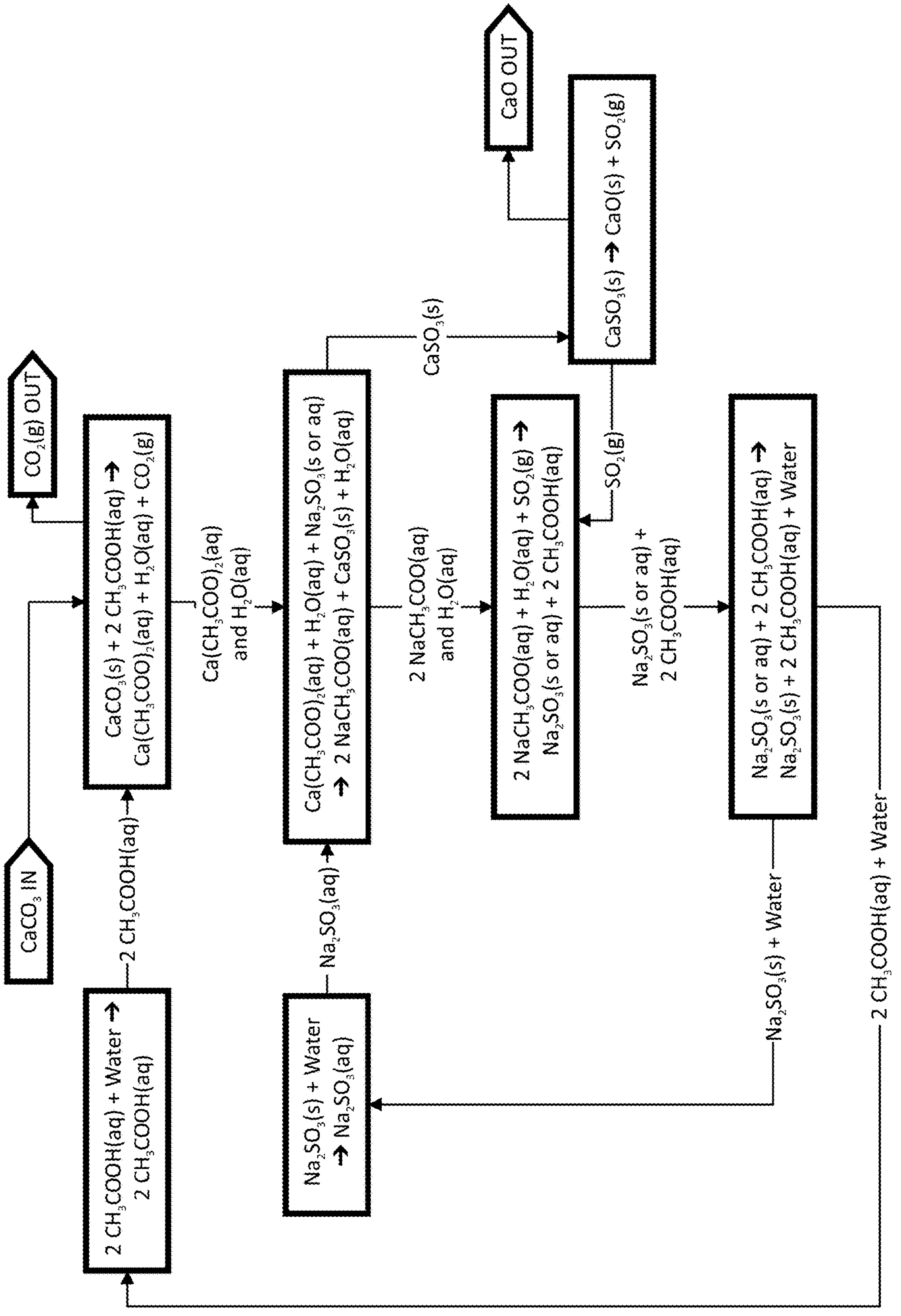

FIG. 4A: Process for producing alkaline earth oxide and captured carbon dioxide employing carboxylic acid, alkali, and sulfur dioxide intermediates.

Figure 4B:
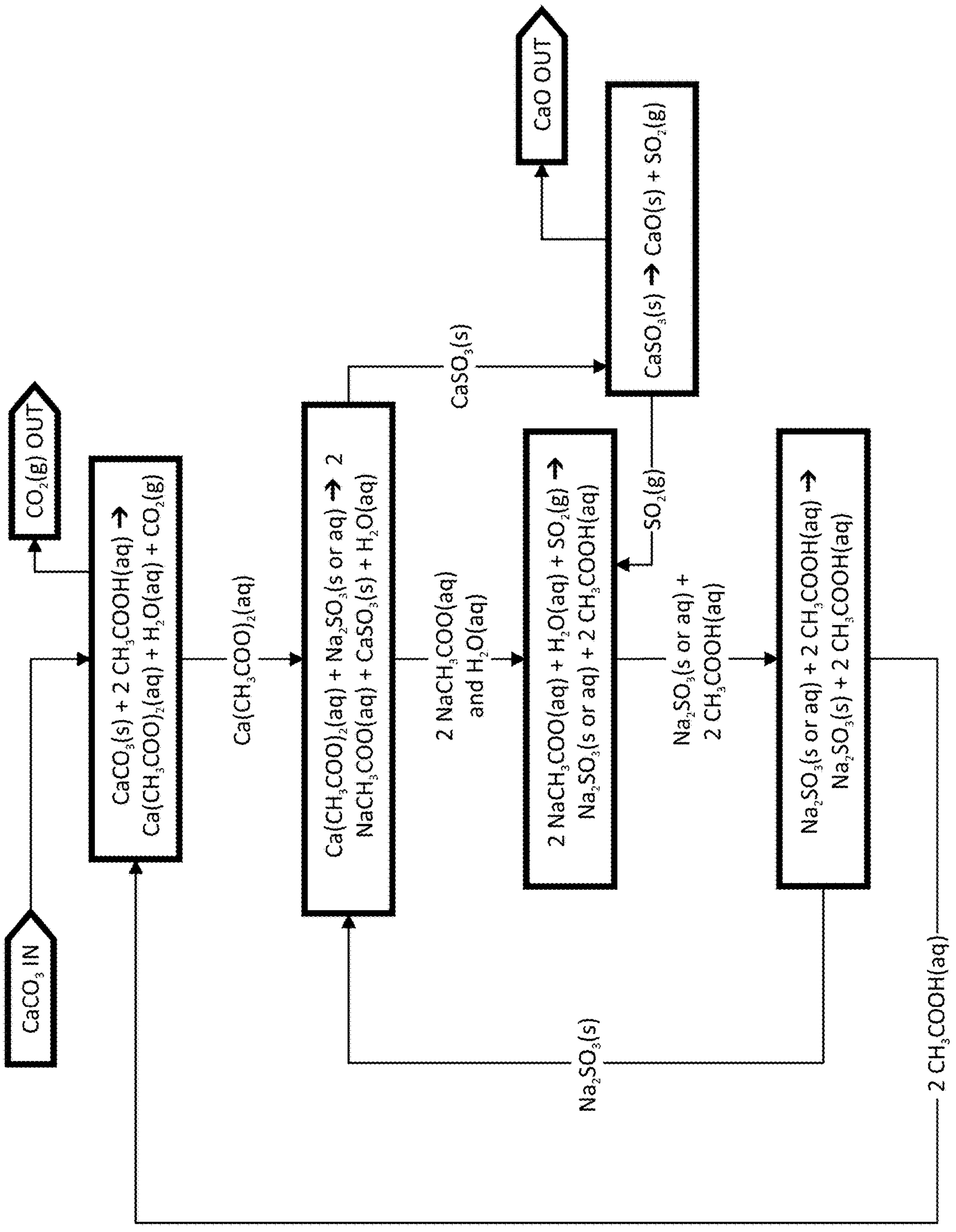

FIG. 4B: Process for producing alkaline earth oxide and captured carbon dioxide employing carboxylic acid, alkali, and sulfur dioxide intermediates.

Figure 4C:
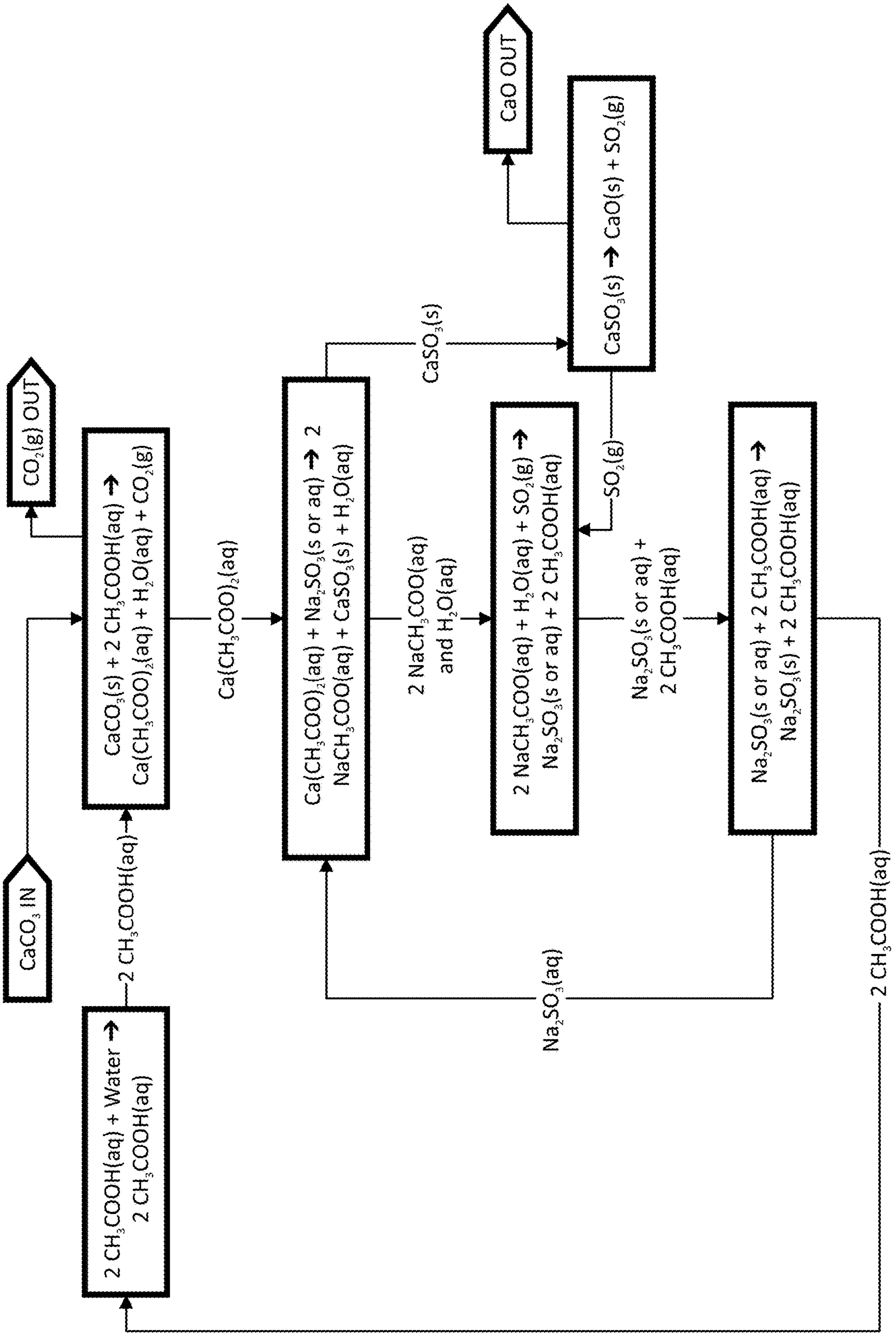

FIG. 4C: Process for producing alkaline earth oxide and captured carbon dioxide employing carboxylic acid, alkali, and sulfur dioxide intermediates.

Figure 5A:
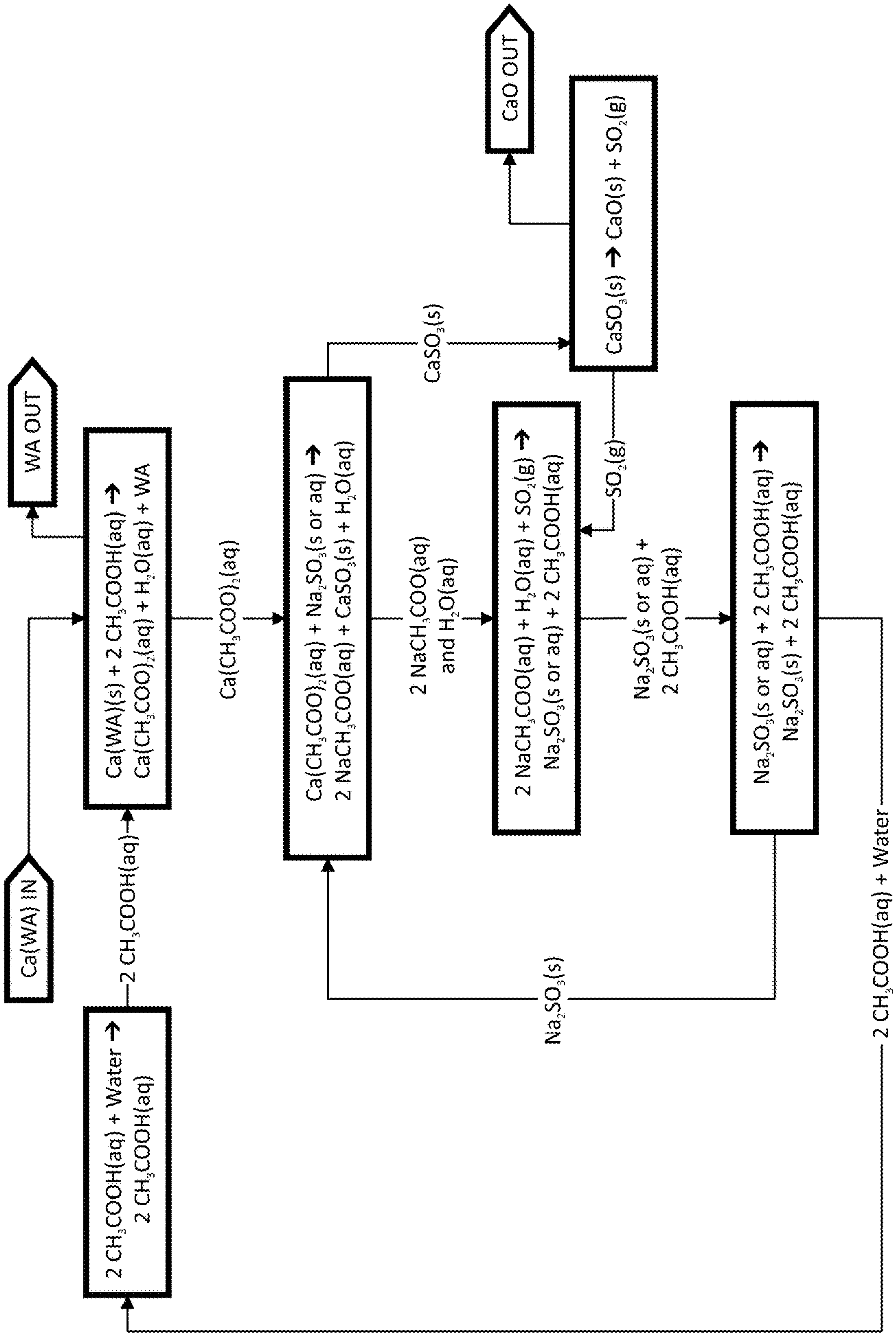

FIG. 5A: Process for producing alkaline earth oxide and weak acid derivative employing carboxylic acid, alkali, and sulfur dioxide intermediates.

Figure 5B:
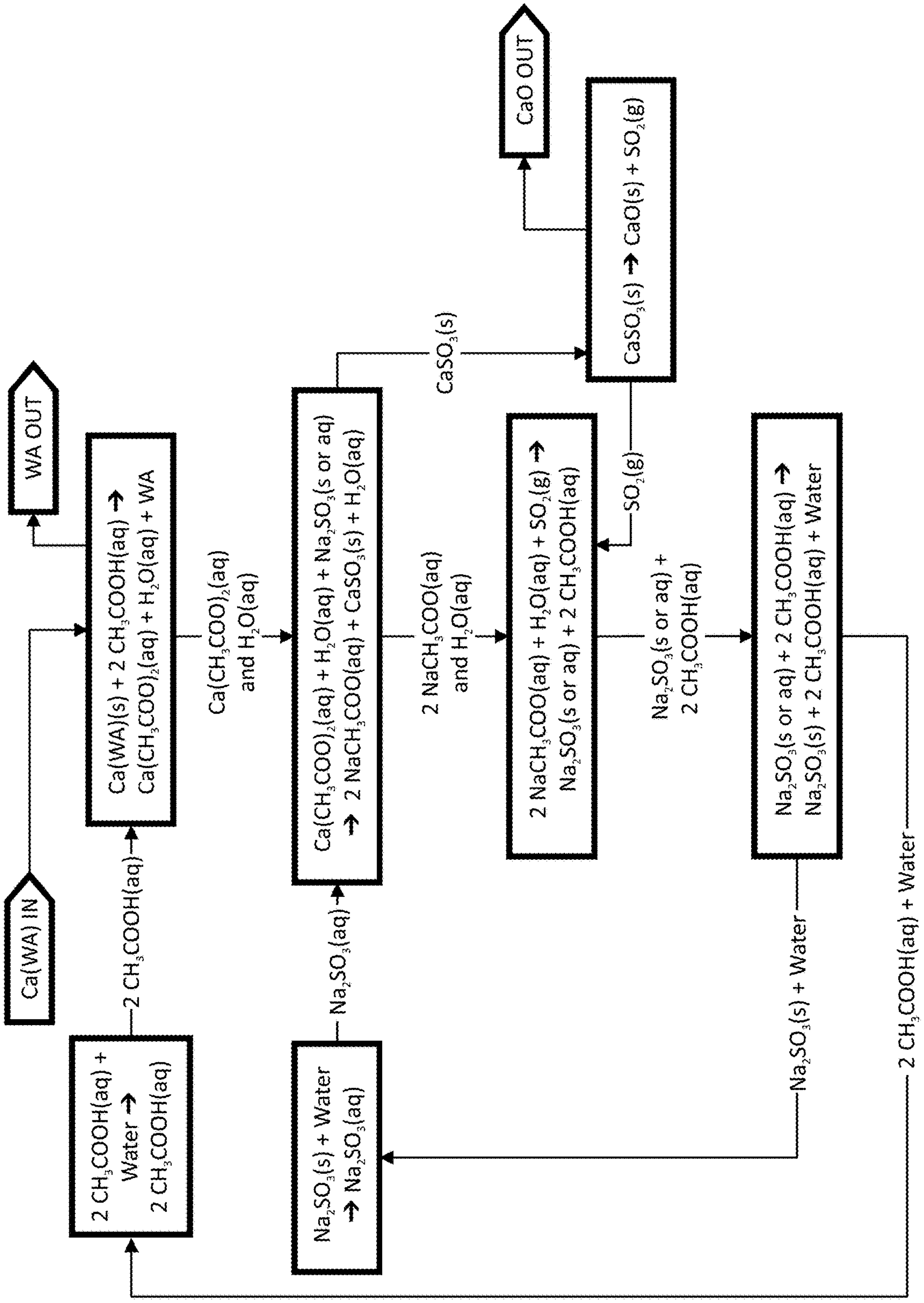

FIG. 5B: Process for producing alkaline earth oxide and weak acid derivative employing carboxylic acid, alkali, and sulfur dioxide intermediates.

Figure 5C:
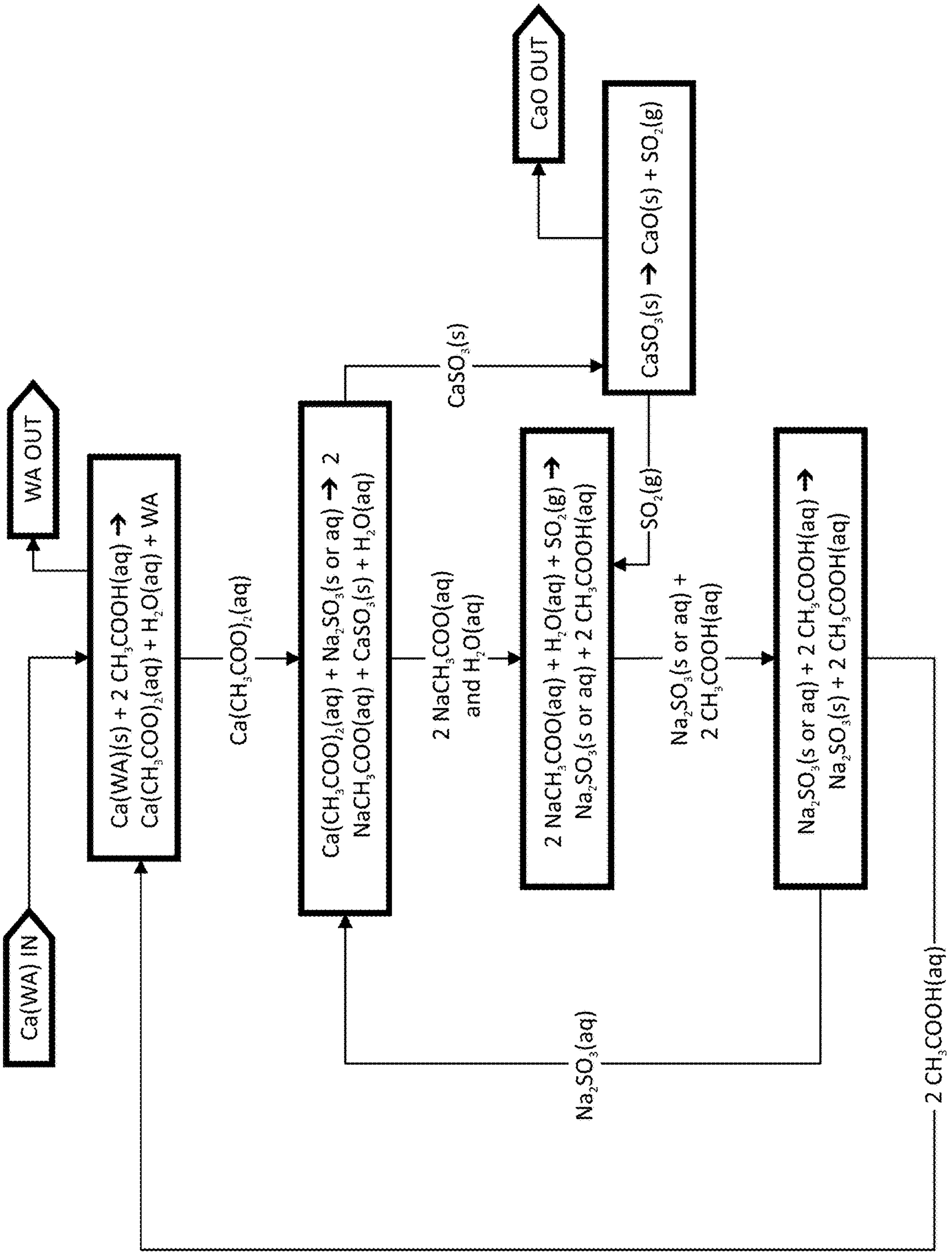

FIG. 5C: Process for producing alkaline earth oxide and weak acid derivative employing carboxylic acid, alkali, and sulfur dioxide intermediates.

Figure 5D:
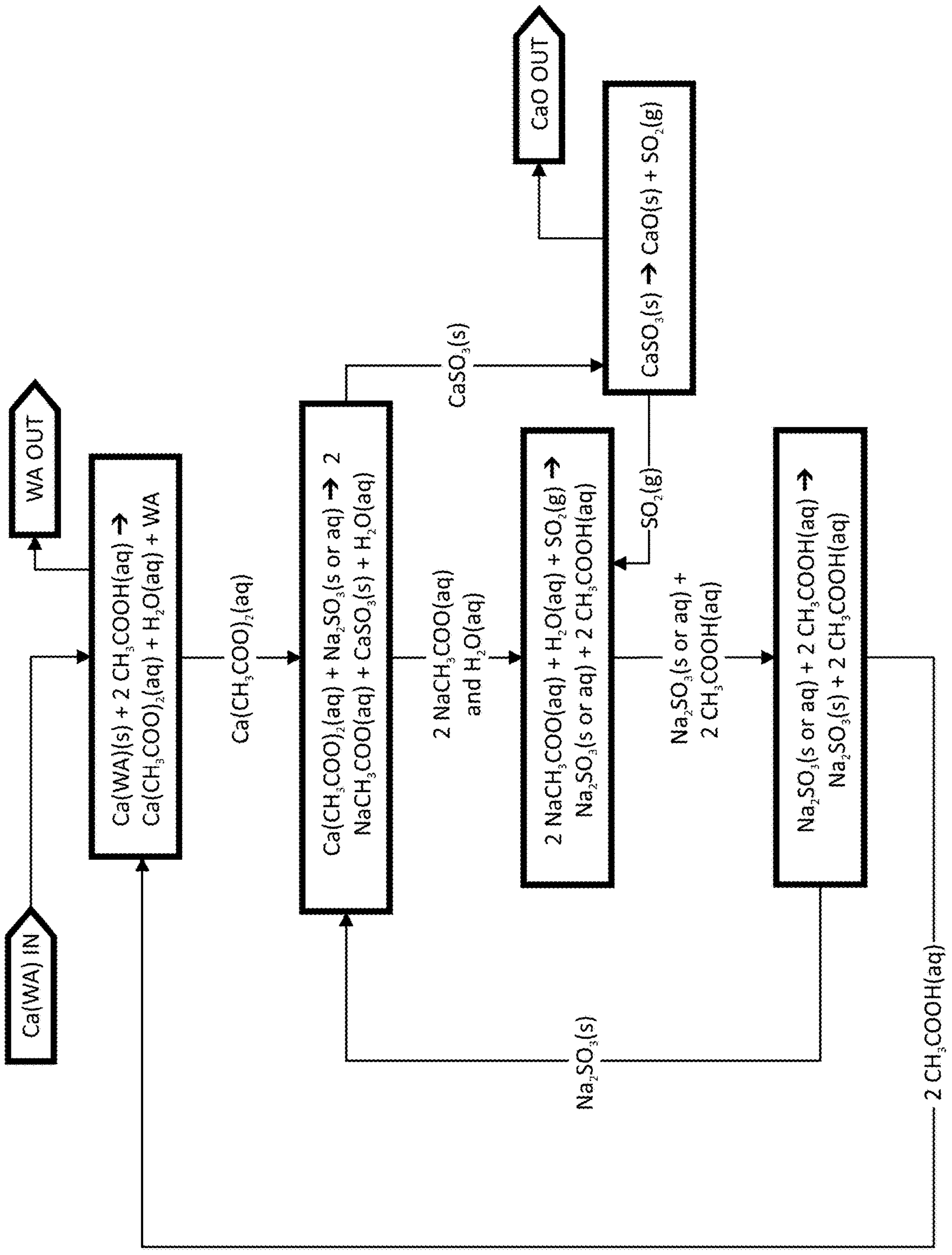

FIG. 5D: Process for producing alkaline earth oxide and weak acid derivative employing carboxylic acid, alkali, and sulfur dioxide intermediates.

Figure 5E:
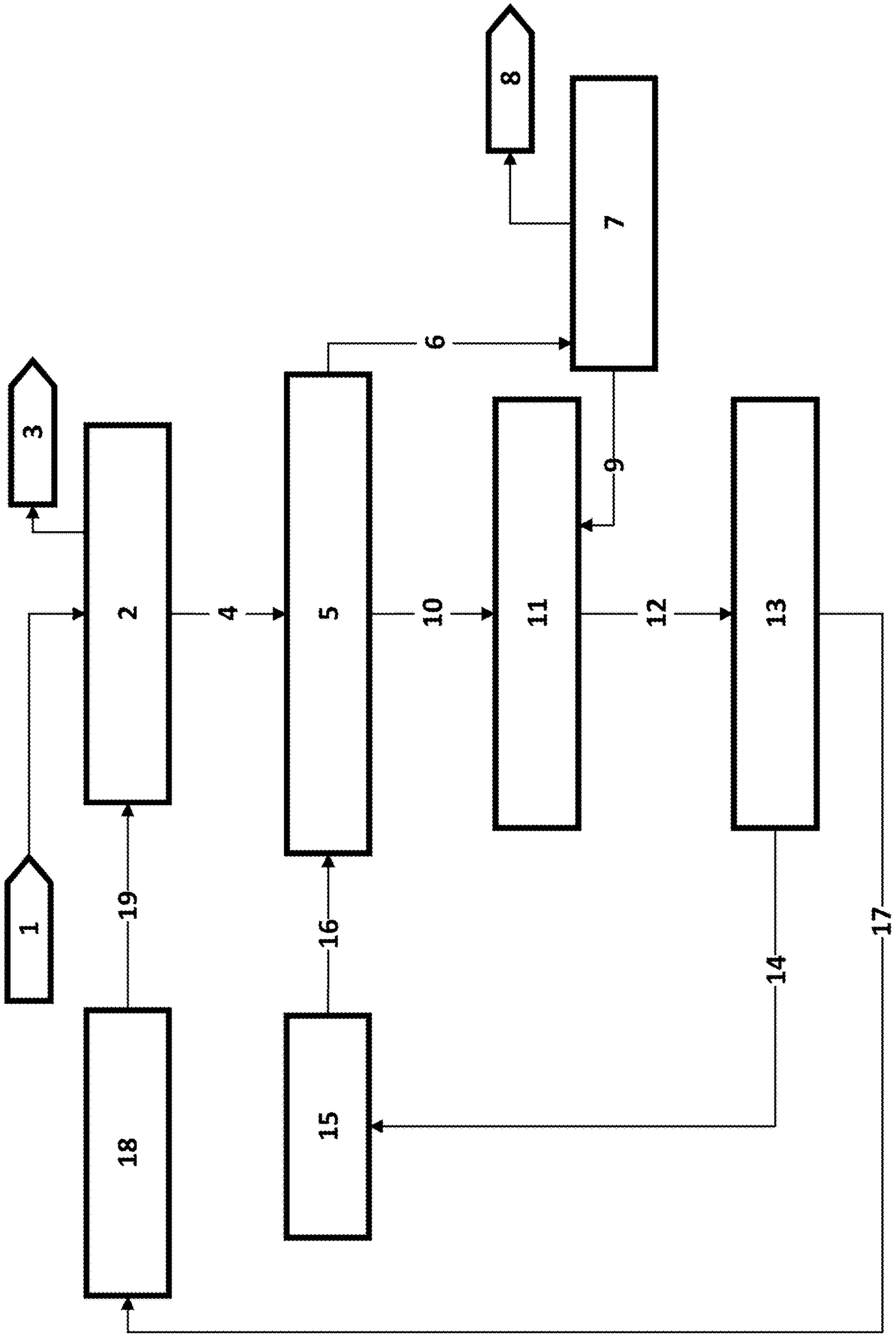

FIG. 5E: Process for producing alkaline earth oxide and weak acid derivative employing carboxylic acid, alkali, and sulfur dioxide intermediates.

Figure 5F:
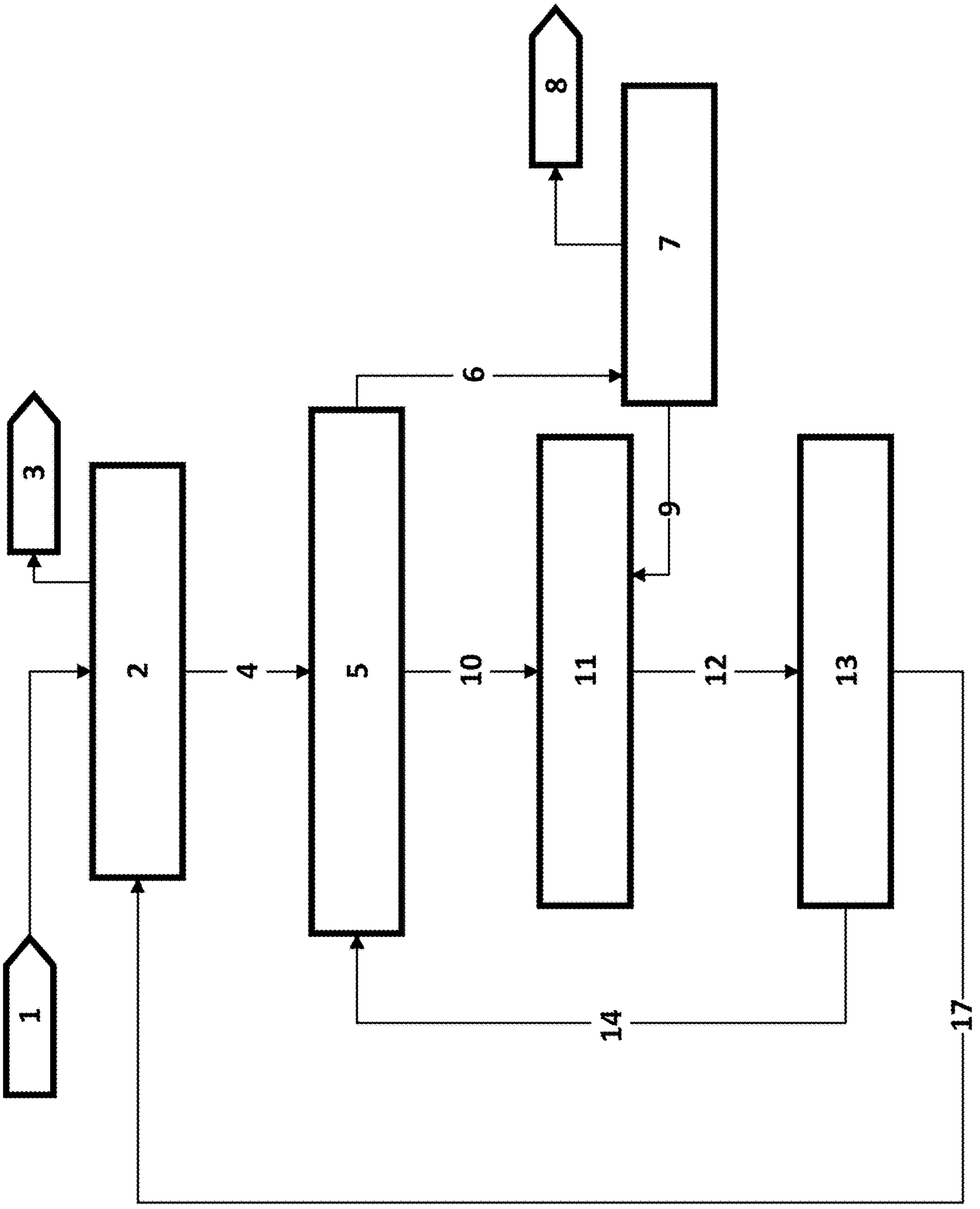

FIG. 5F: Process for producing alkaline earth oxide and weak acid derivative employing carboxylic acid, alkali, and sulfur dioxide intermediates.

Figure 6A:
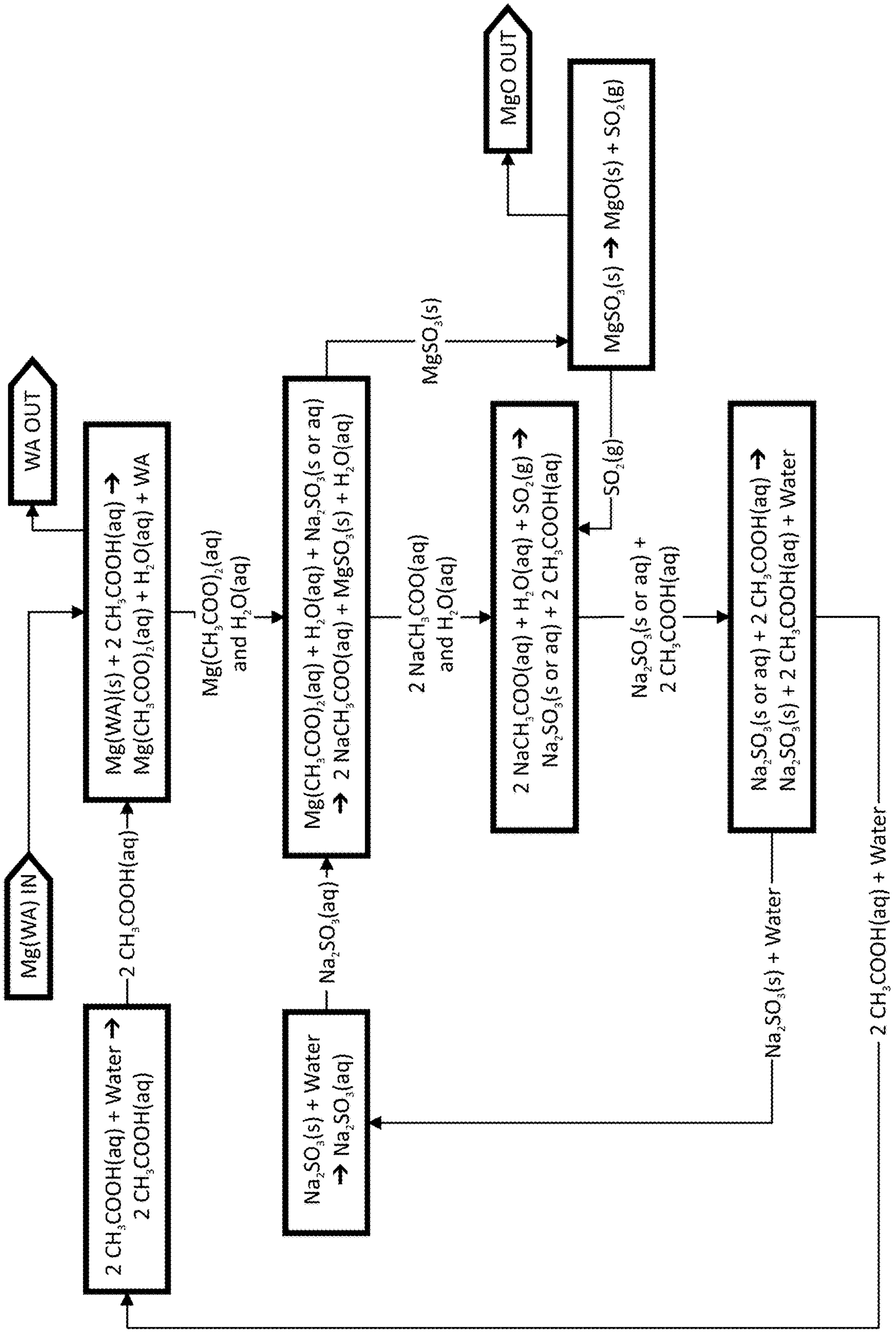

FIG. 6A: Process for producing alkaline earth oxide and weak acid derivative employing carboxylic acid, alkali, and sulfur dioxide intermediates.

Figure 6B:
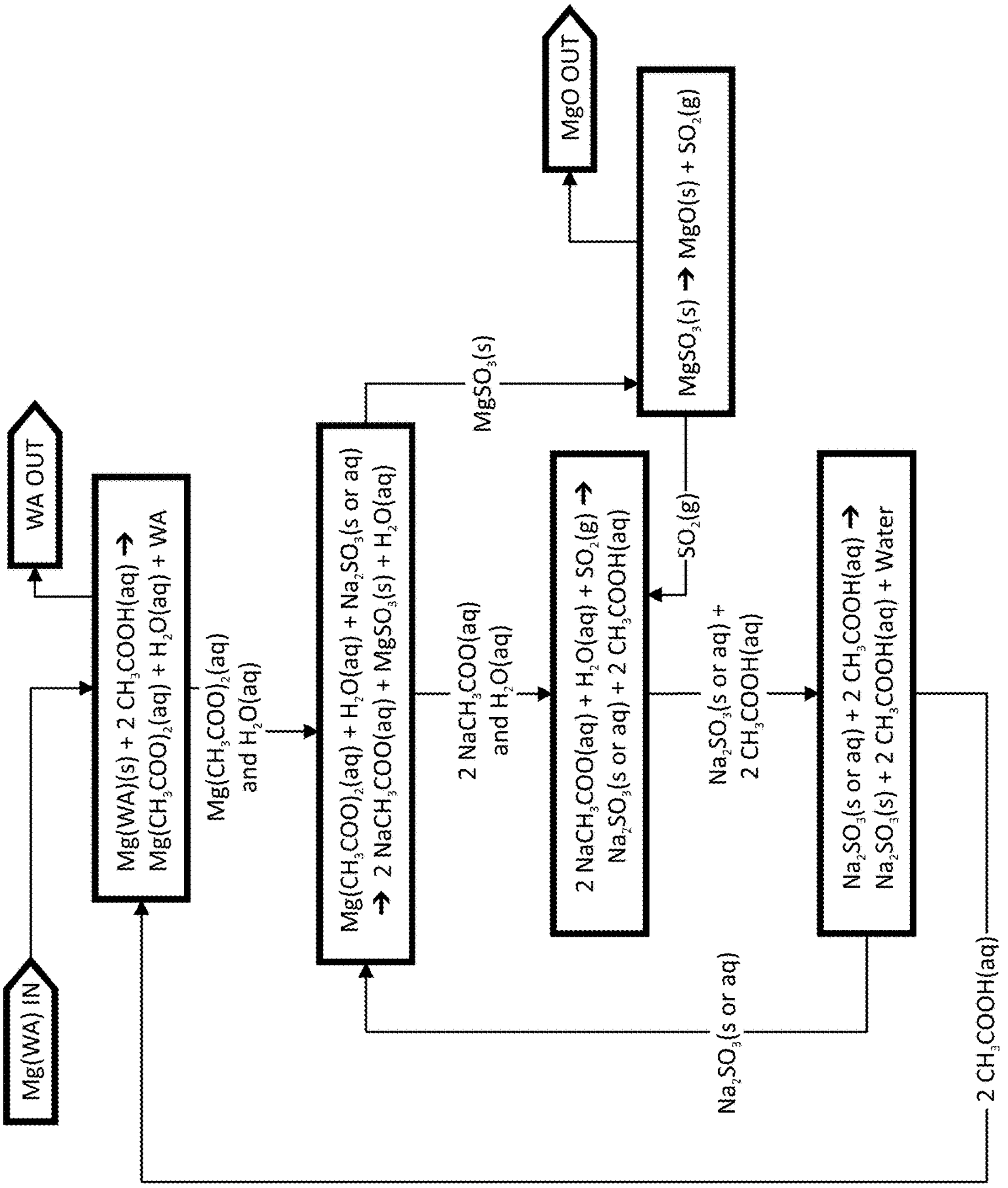

FIG. 6B: Process for producing alkaline earth oxide and weak acid derivative employing carboxylic acid, alkali, and sulfur dioxide intermediates.

Figure 7A:
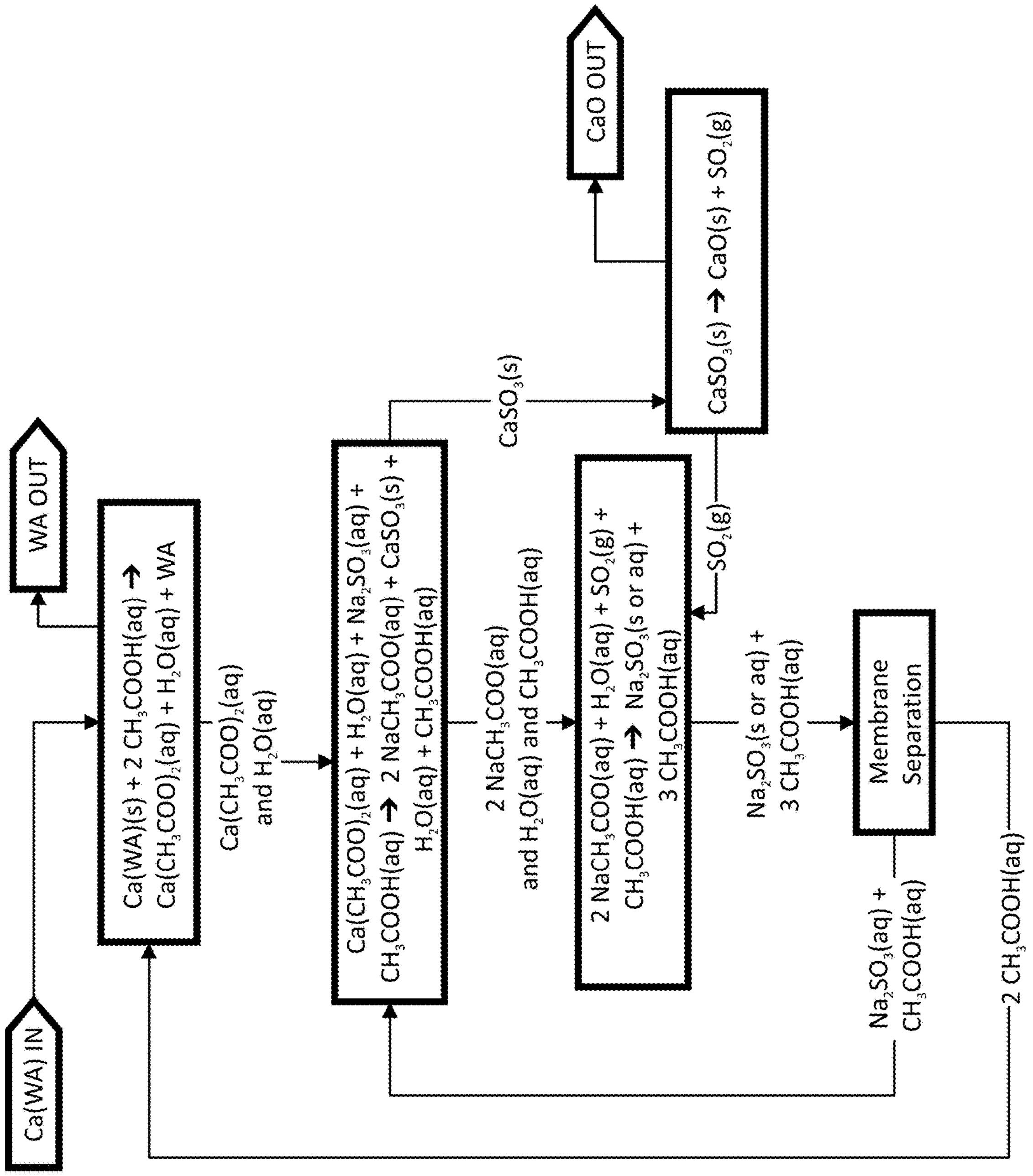

FIG. 7A: Process for producing alkaline earth oxide and weak acid derivative employing carboxylic acid, alkali, and sulfur dioxide intermediates with membrane separation of at least a portion of alkali sulfite.

Figure 7B:
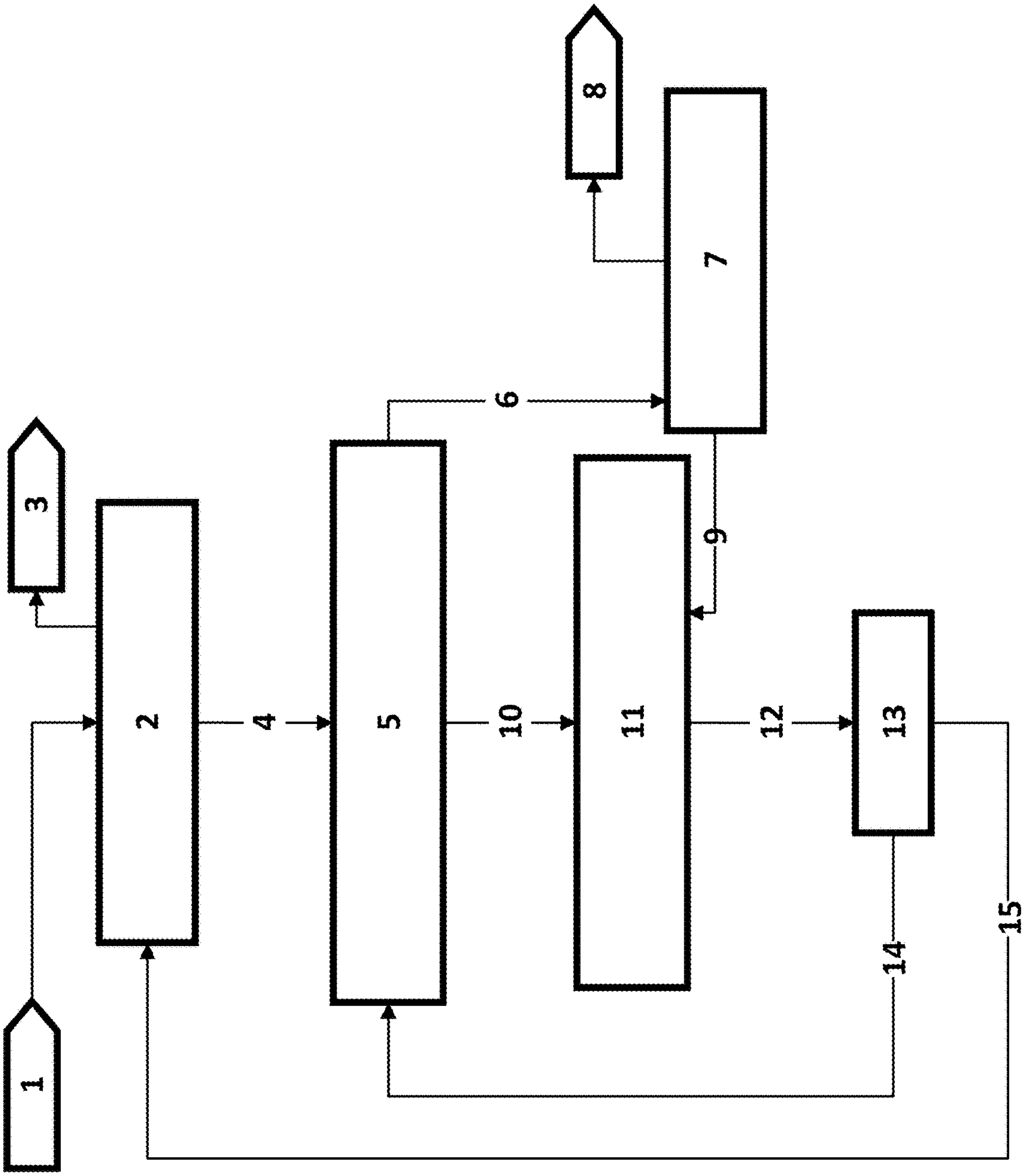

FIG. 7B: Process for producing alkaline earth oxide and weak acid derivative employing carboxylic acid, alkali, and sulfur dioxide intermediates with membrane separation of at least a portion of alkali sulfite.

Figure 8A:
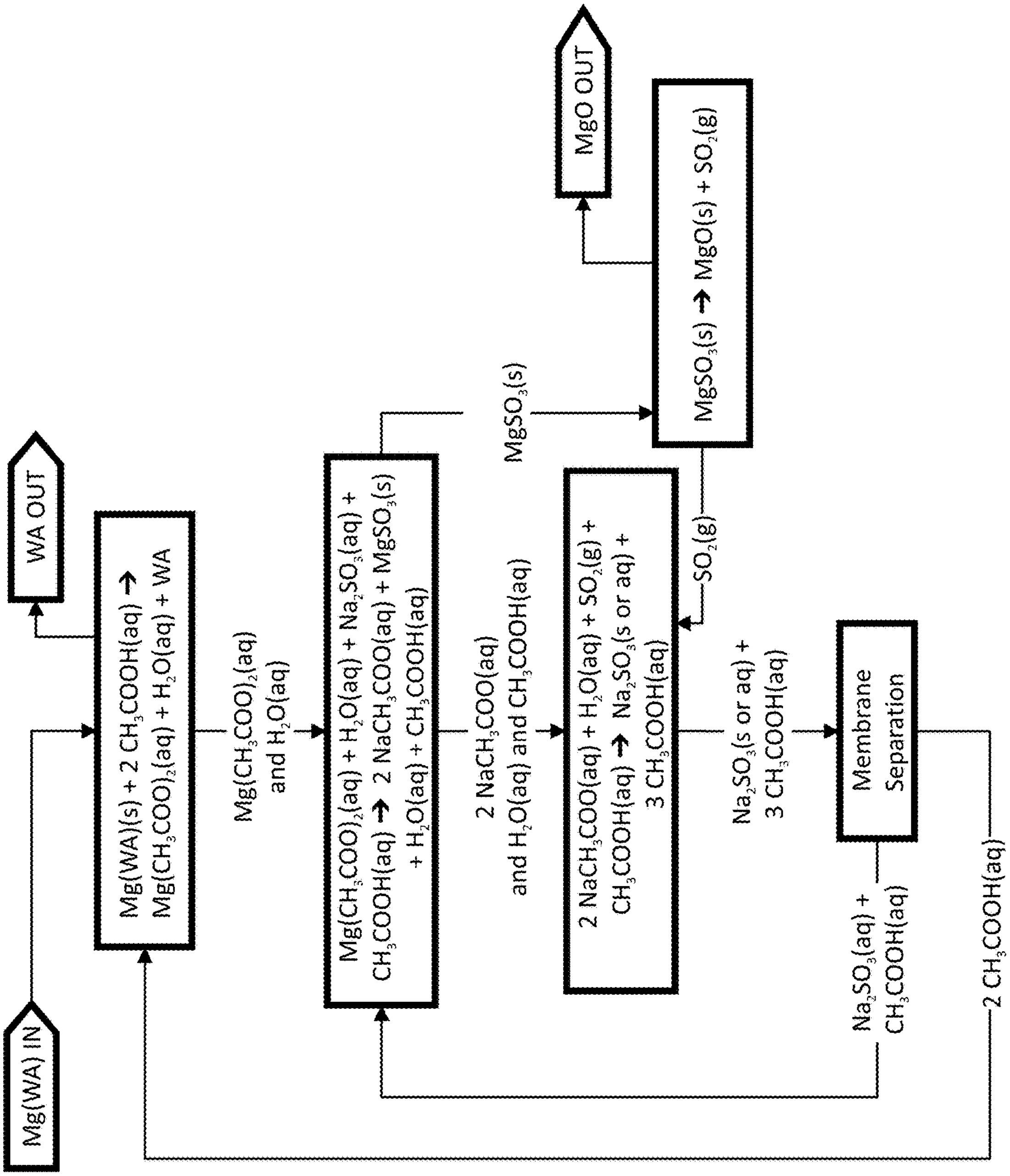

FIG. 8: Process for producing alkaline earth oxide and weak acid derivative employing carboxylic acid, alkali, and sulfur dioxide intermediates with membrane separation of at least a portion of alkali sulfite.

Figure 9A:
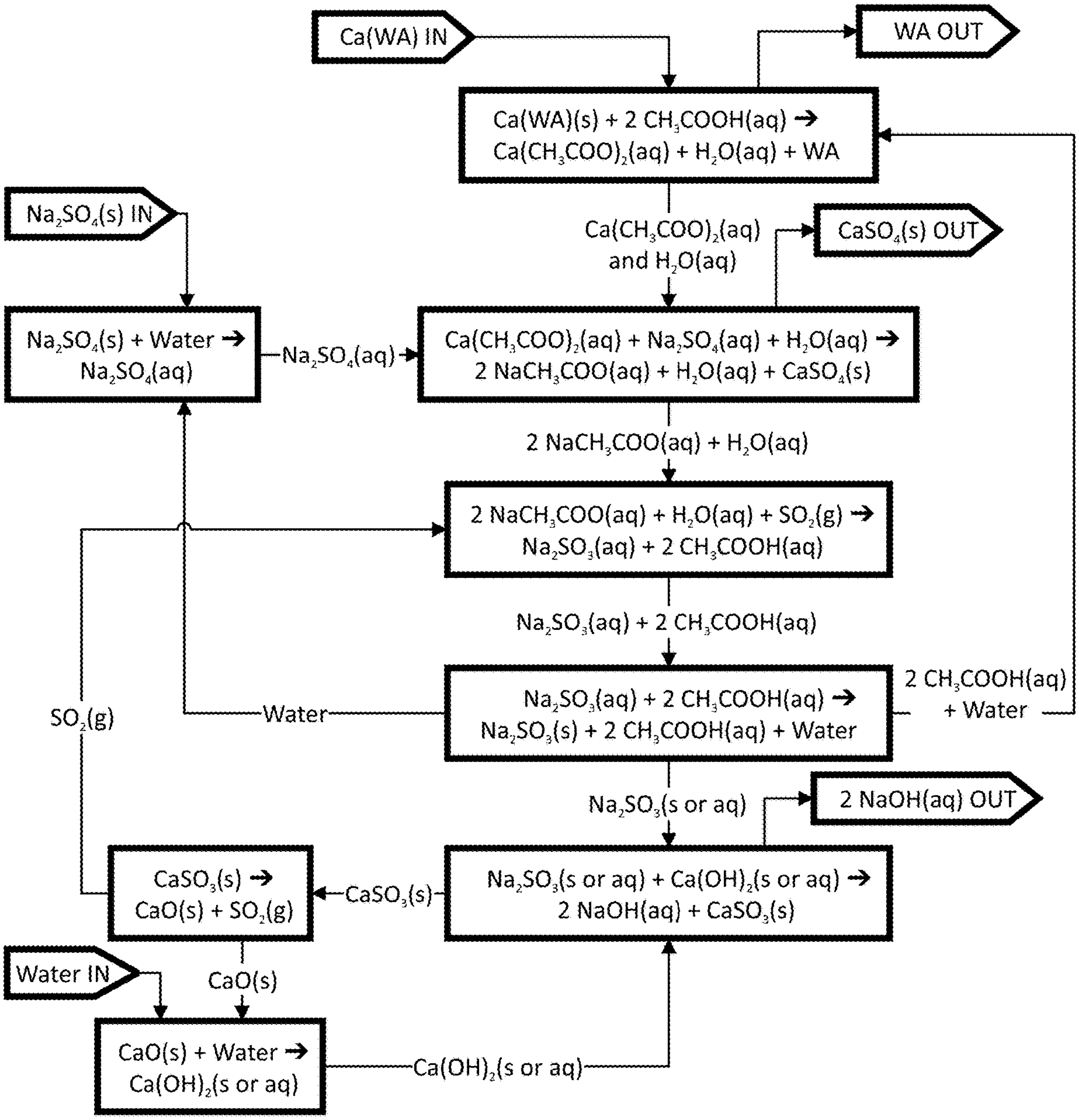

FIG. 9A: Process for producing alkali hydroxide from alkali sulfate using carboxylic acid and sulfur dioxide intermediates.

Figure 9B:
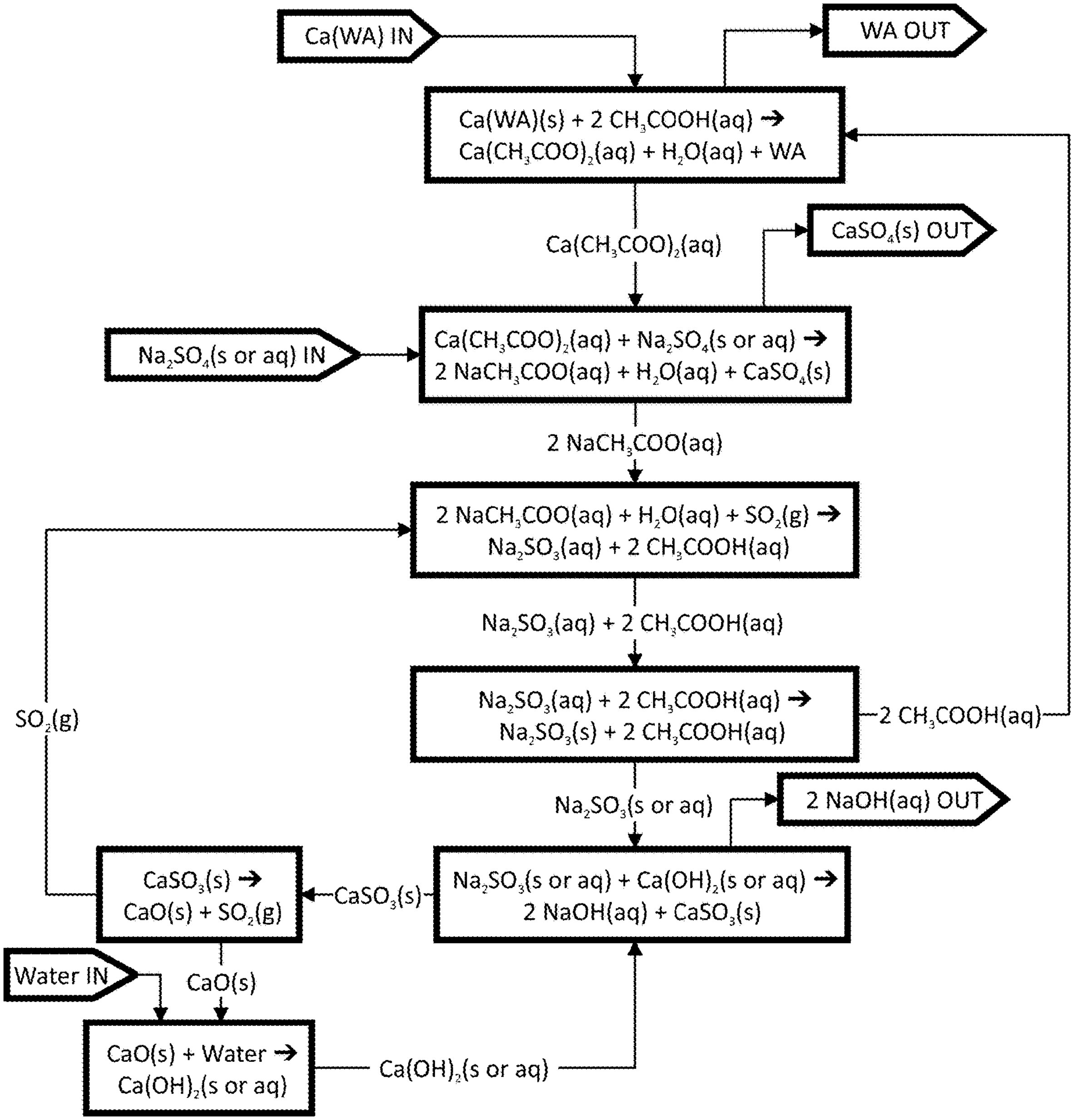

FIG. 9B: Process for producing alkali hydroxide from alkali sulfate using carboxylic acid and sulfur dioxide intermediates.

Figure 9C:
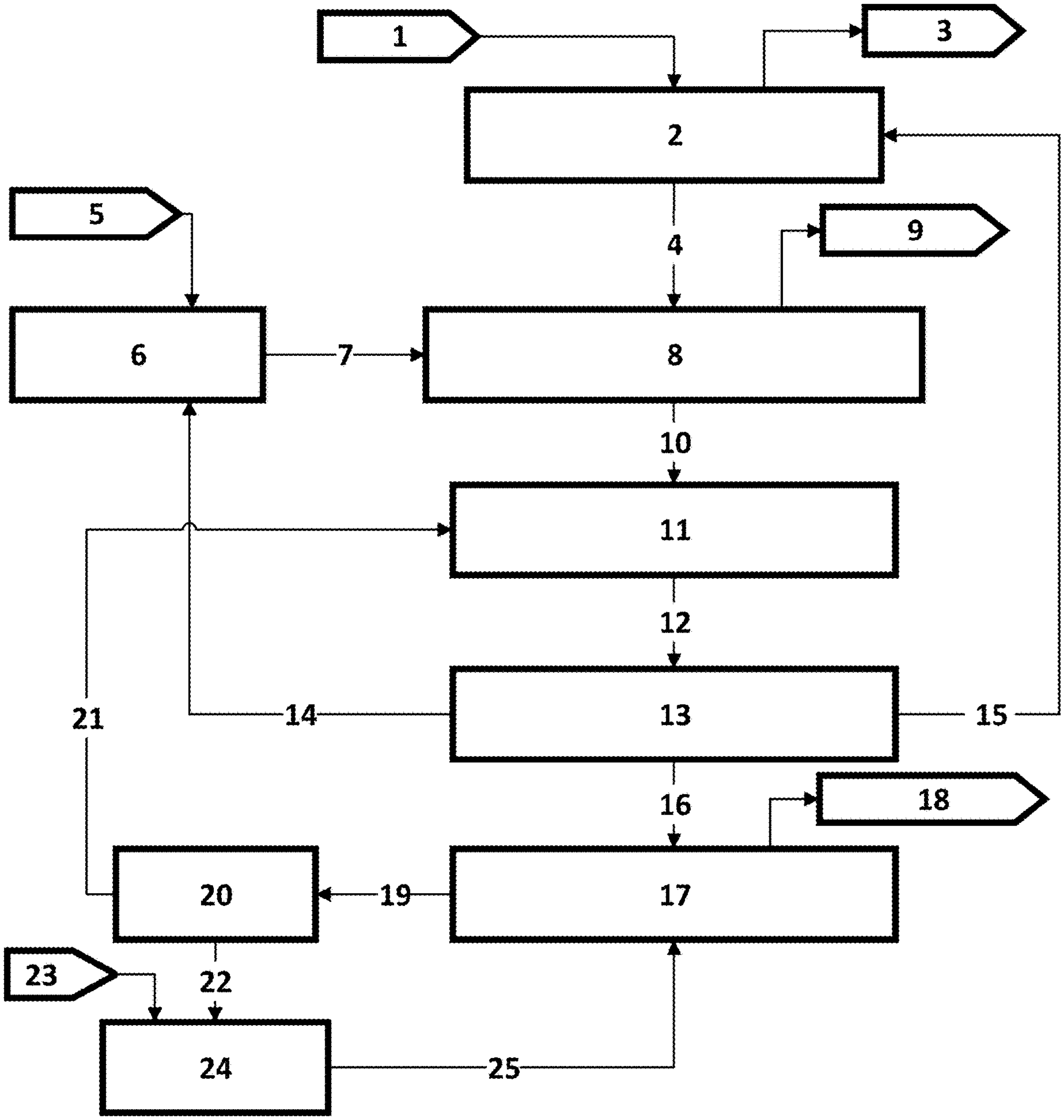

FIG. 9C: Process for producing alkali hydroxide from alkali sulfate using carboxylic acid and sulfur dioxide intermediates.

Figure 9D:
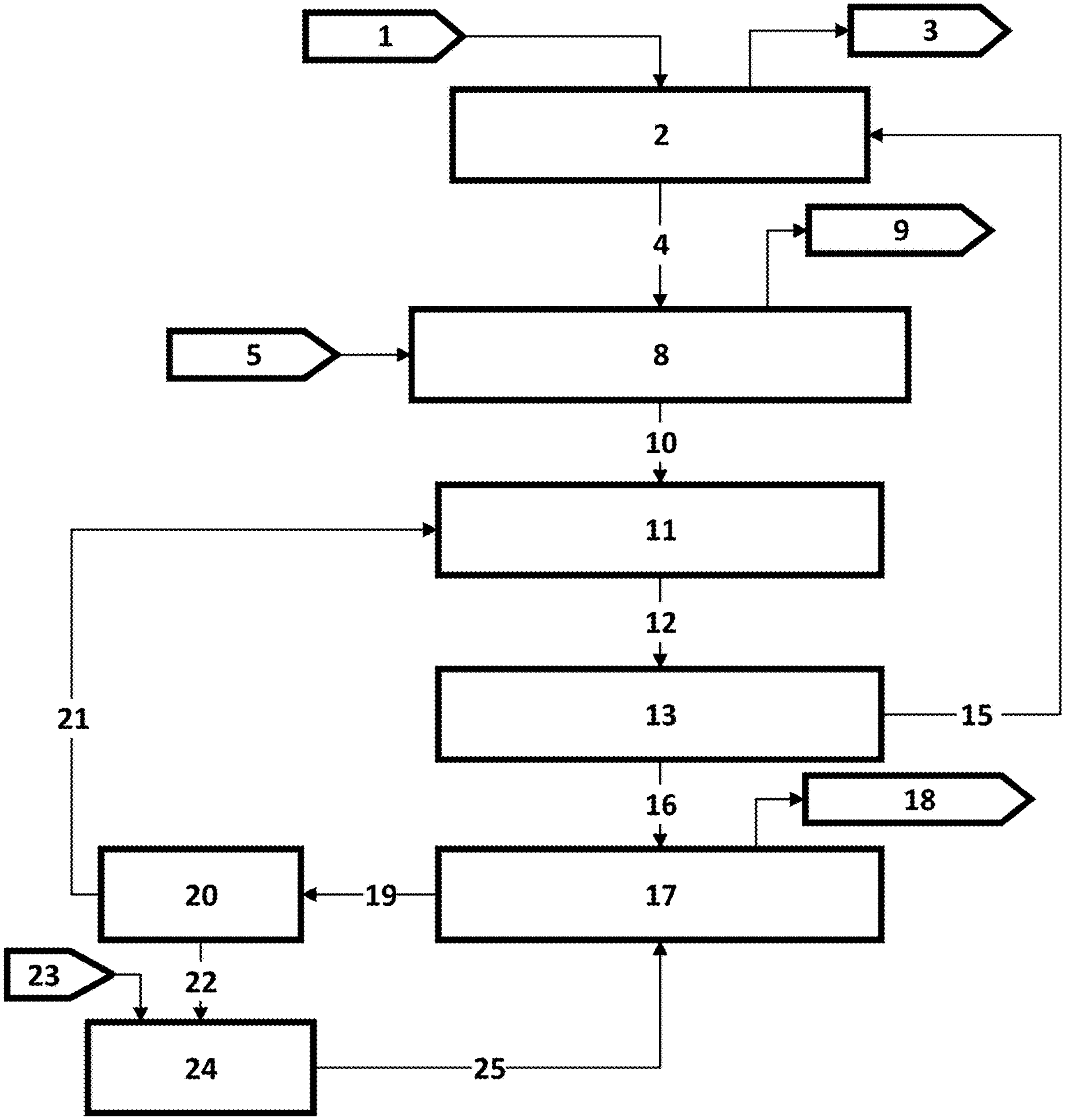

FIG. 9D: Process for producing alkali hydroxide from alkali sulfate using carboxylic acid and sulfur dioxide intermediates.

Figure 10A:
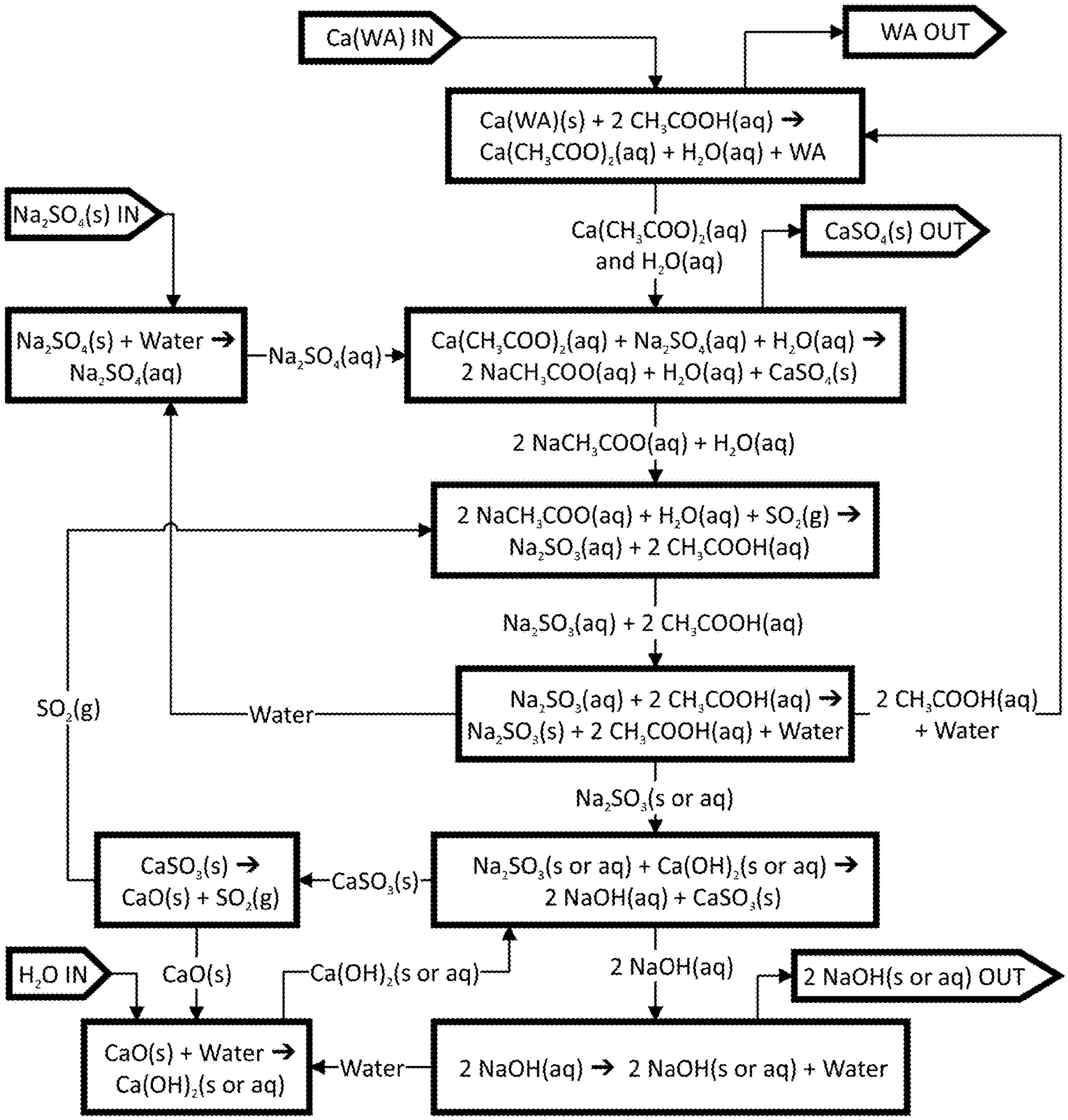

FIG. 10A: Process for producing alkali hydroxide from alkali sulfate using carboxylic acid and sulfur dioxide intermediates.

Figure 10B:
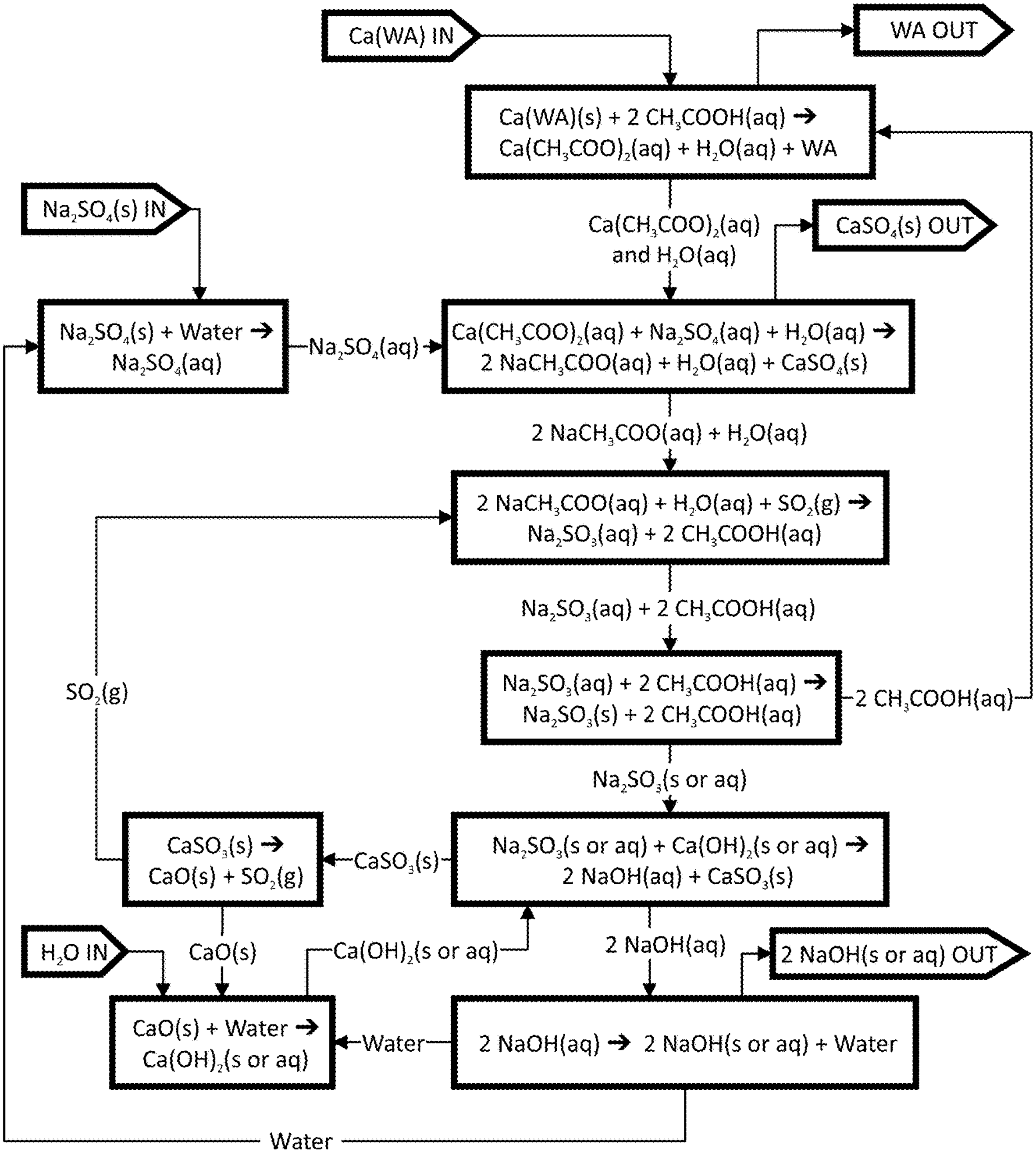

FIG. 10B: Process for producing alkali hydroxide from alkali sulfate using carboxylic acid and sulfur dioxide intermediates.

Figure 10C:
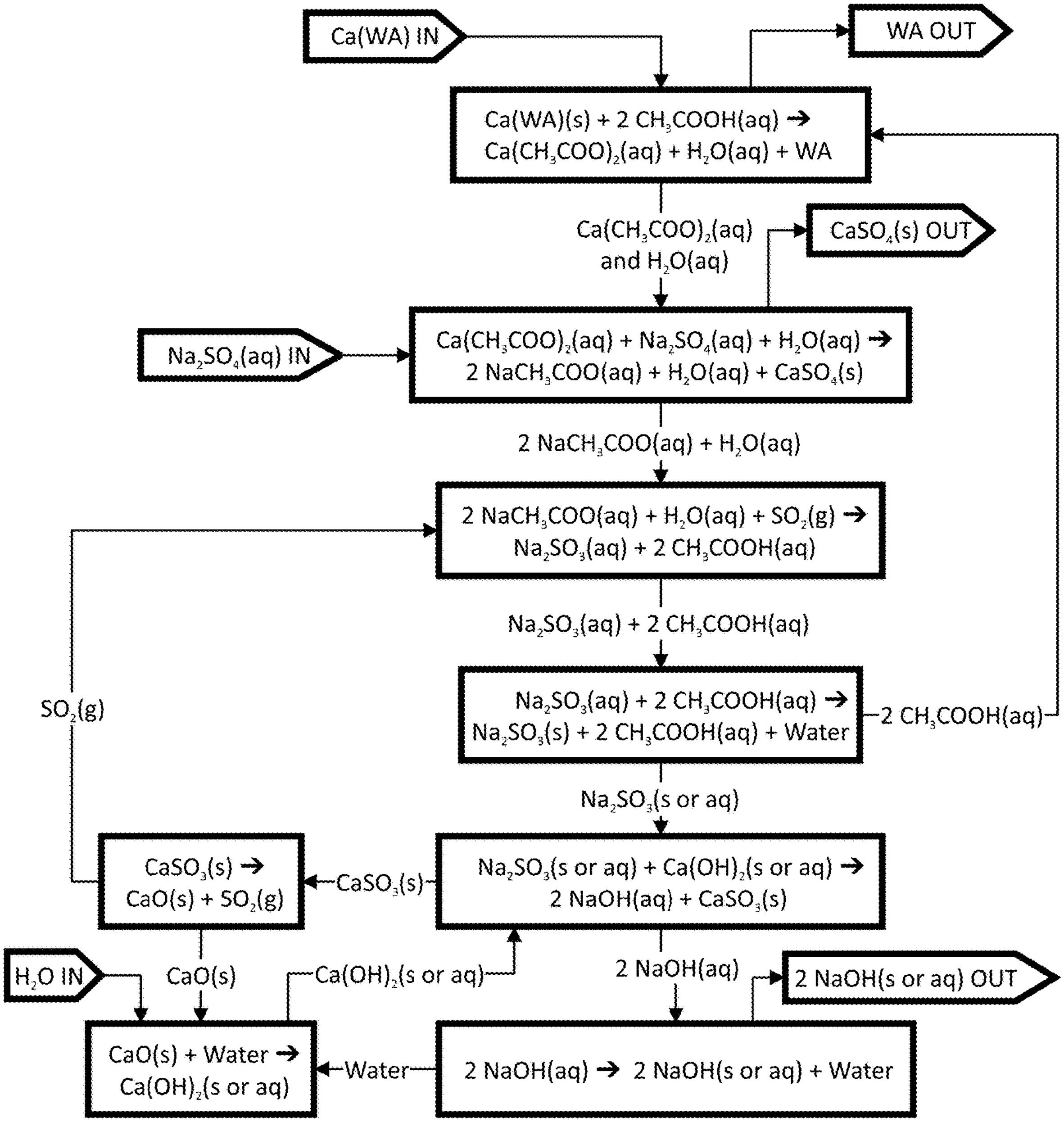

FIG. 10C: Process for producing alkali hydroxide from alkali sulfate using carboxylic acid and sulfur dioxide intermediates.

Figure 10D:
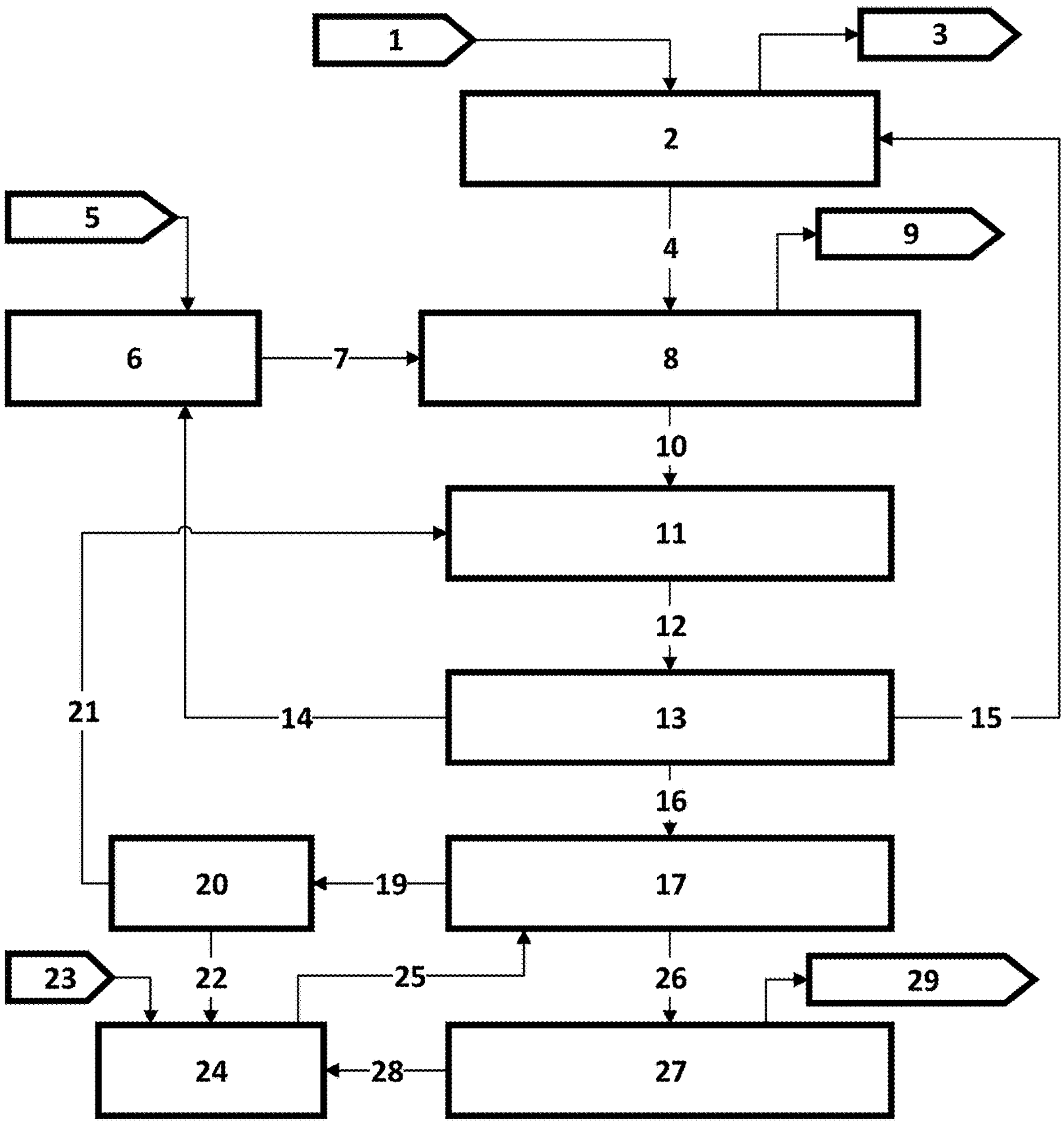

FIG. 10D: Process for producing alkali hydroxide from alkali sulfate using carboxylic acid and sulfur dioxide intermediates.

Figure 10E:
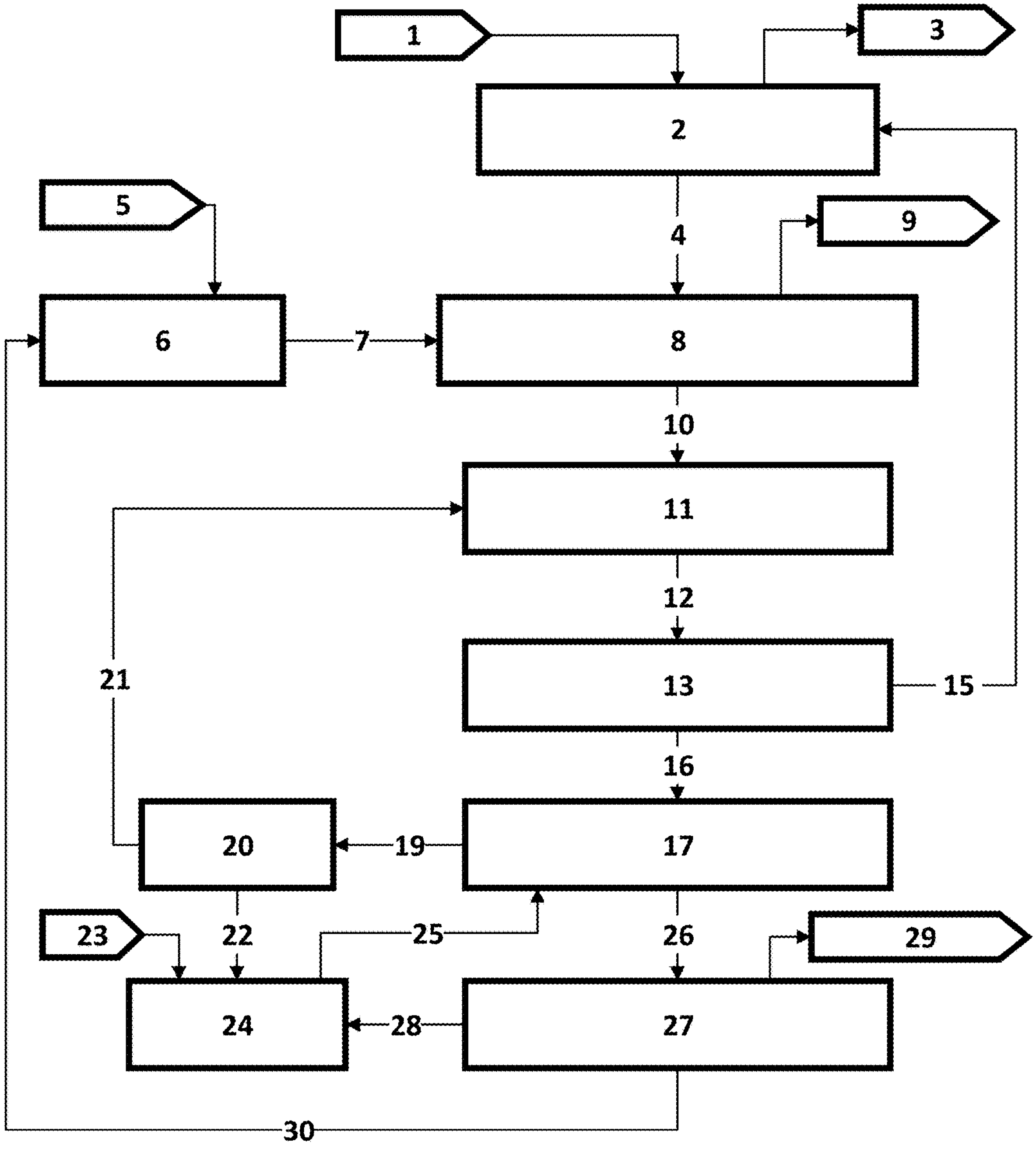
Figure 10E:
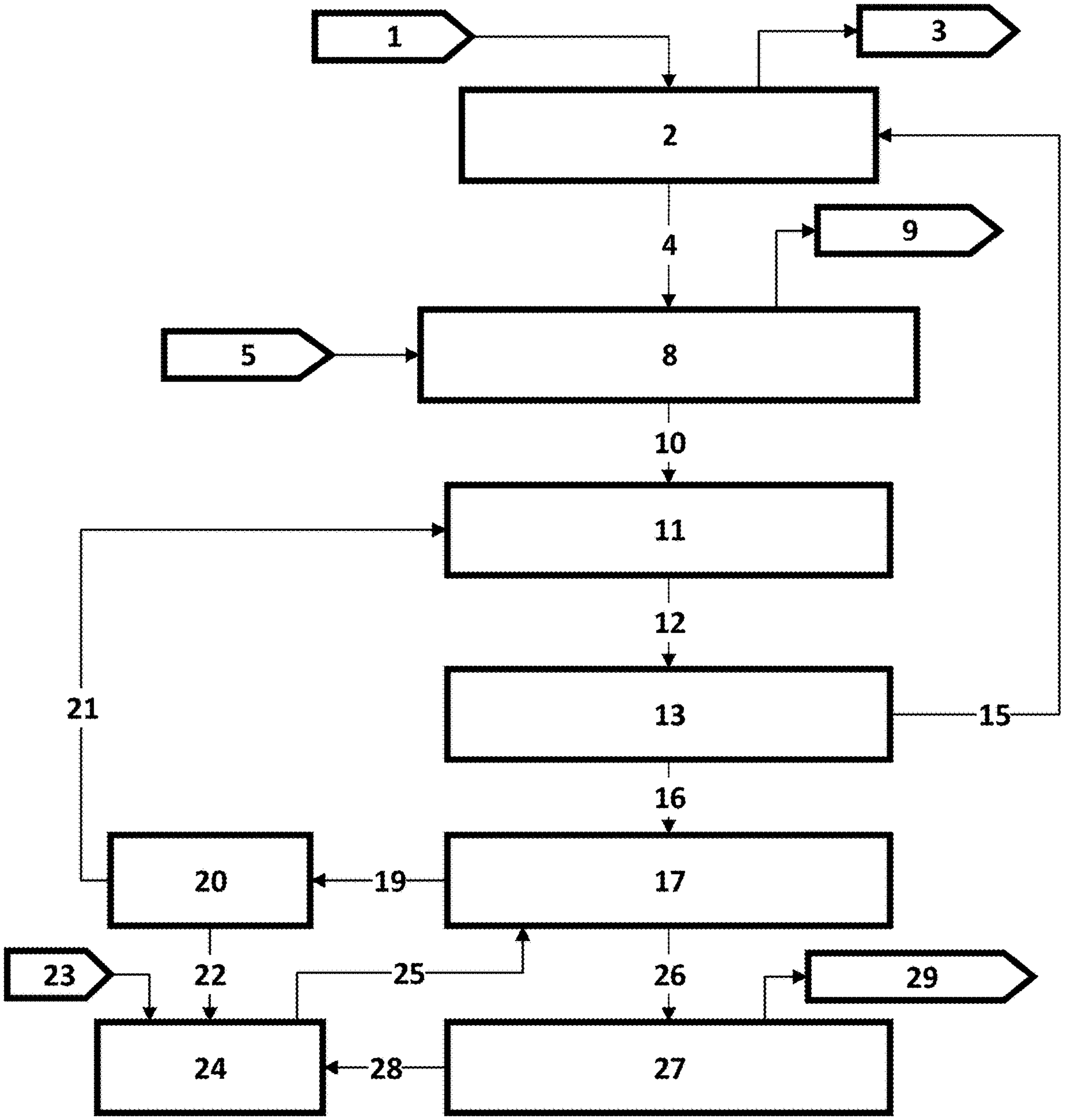

FIG. 10E: Process for producing alkali hydroxide from alkali sulfate using carboxylic acid and sulfur dioxide intermediates.

FIG. 10F: Process for producing alkali hydroxide from alkali sulfate using carboxylic acid and sulfur dioxide intermediates.

Figure 11A:
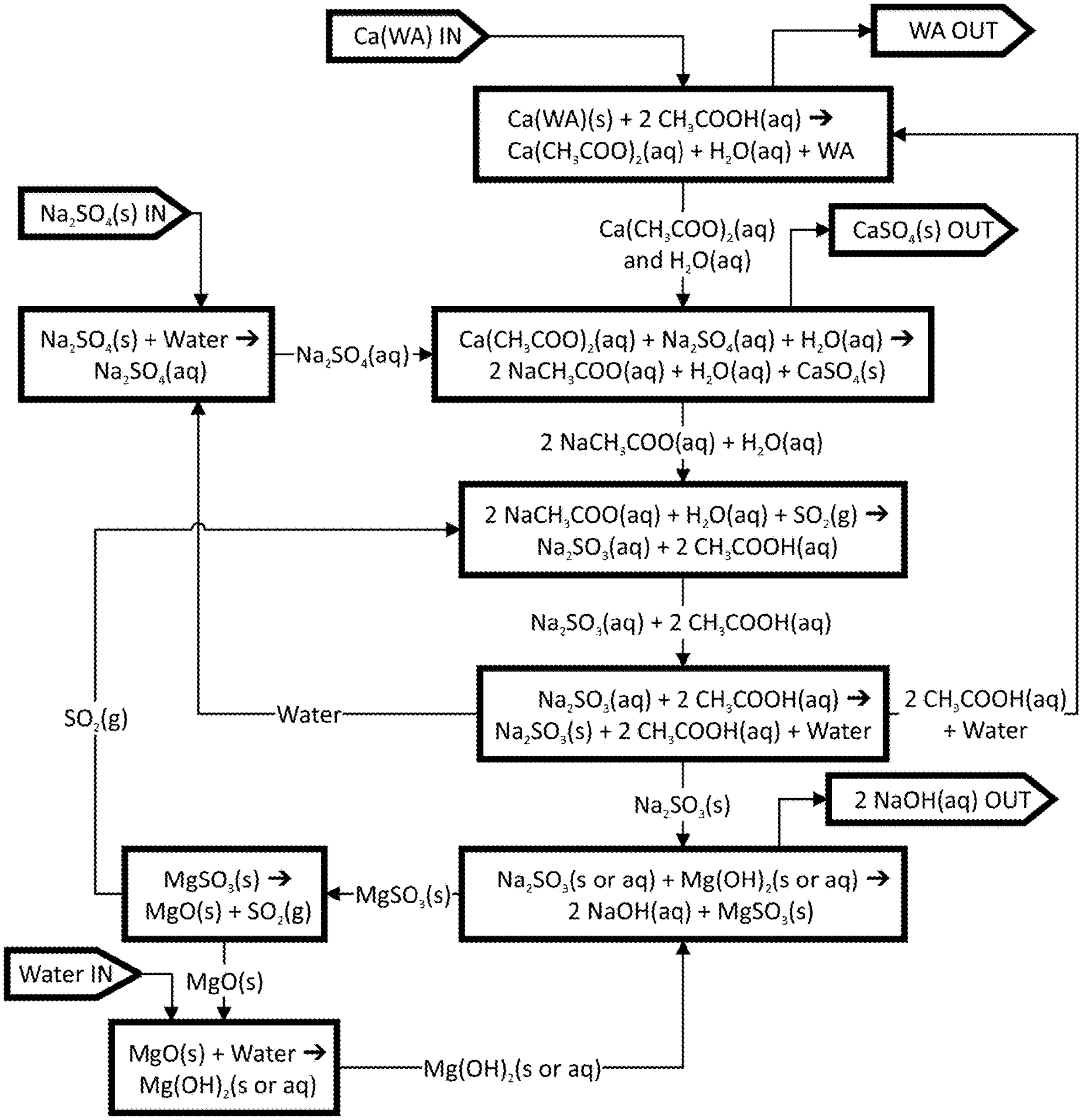

FIG. 11A: Process for producing alkali hydroxide from alkali sulfate using carboxylic acid and sulfur dioxide intermediates.

Figure 11B:
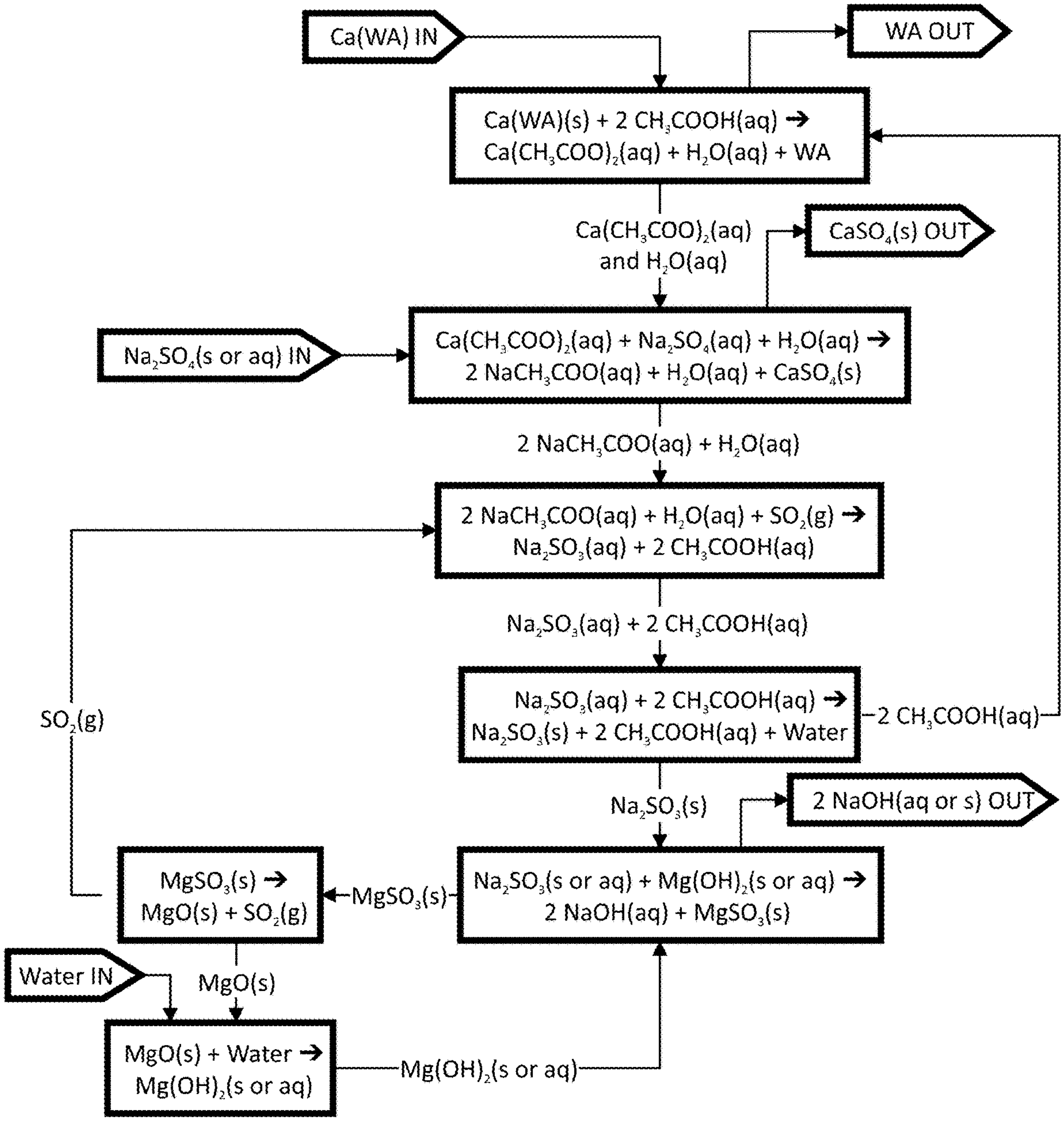

FIG. 11B: Process for producing alkali hydroxide from alkali sulfate using carboxylic acid and sulfur dioxide intermediates.

Figure 11C:
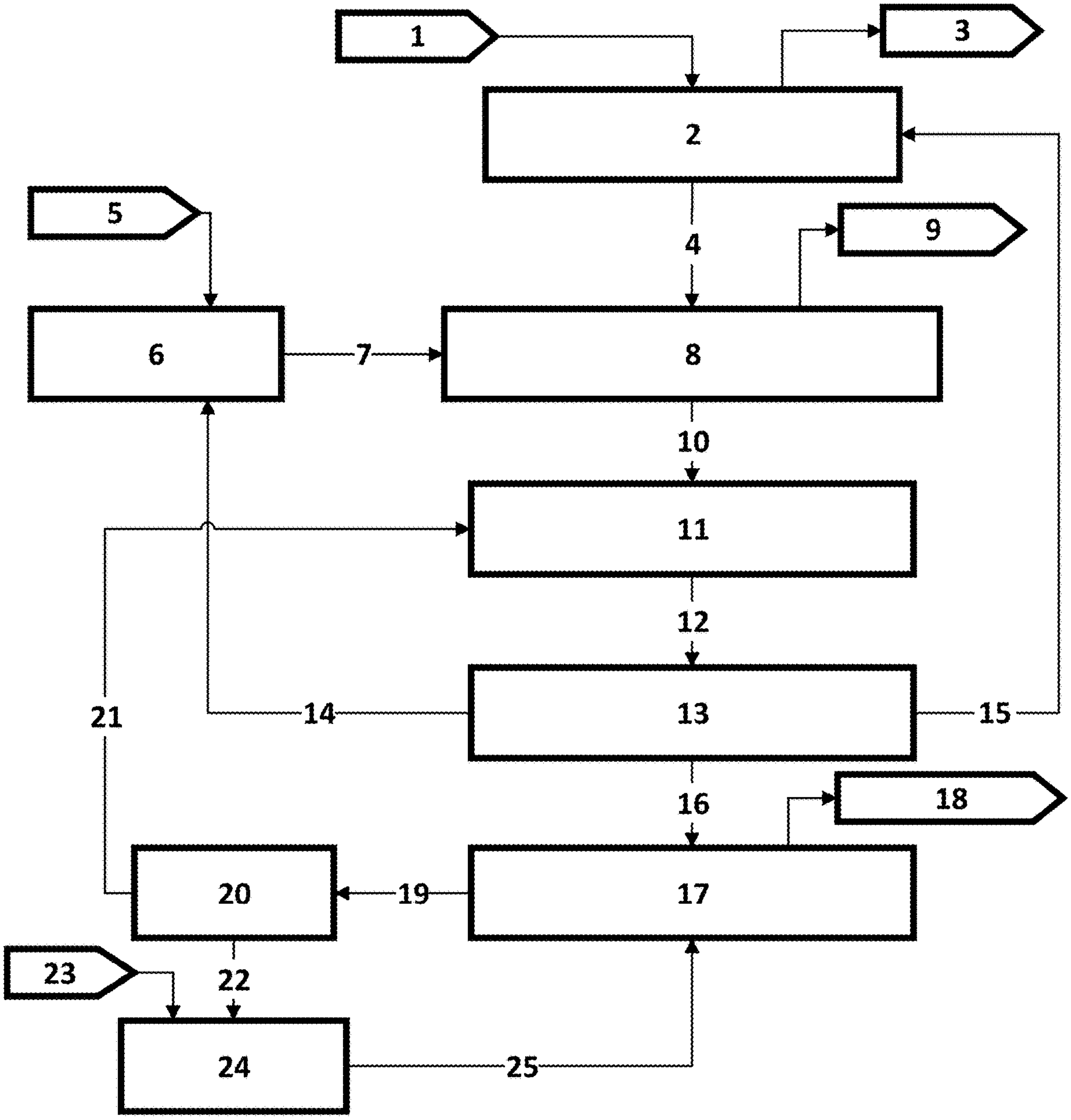

FIG. 11C: Process for producing alkali hydroxide from alkali sulfate using carboxylic acid and sulfur dioxide intermediates.

Figure 12A:
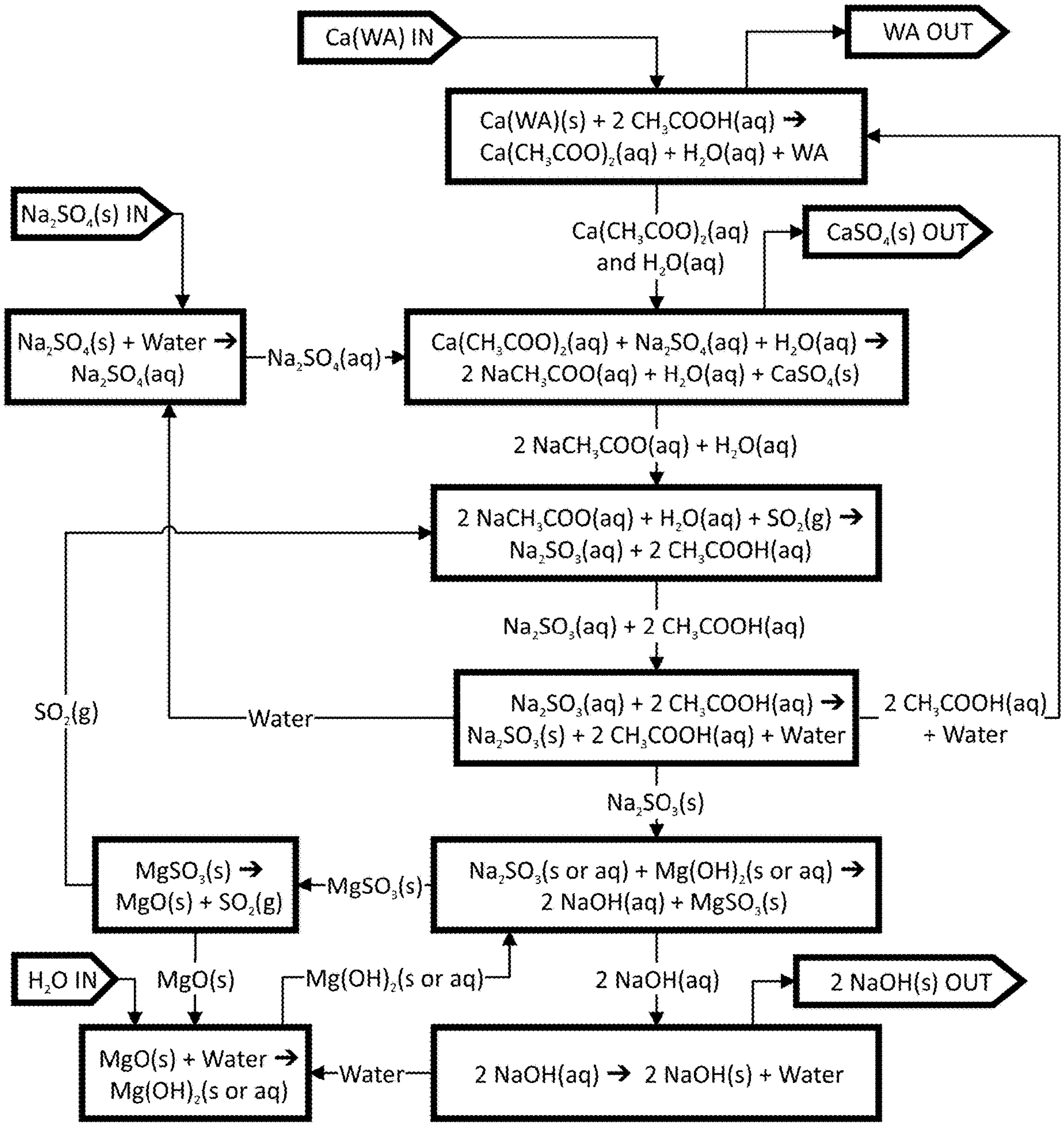

FIG. 12A: Process for producing alkali hydroxide from alkali sulfate using carboxylic acid and sulfur dioxide intermediates.

Figure 12B:
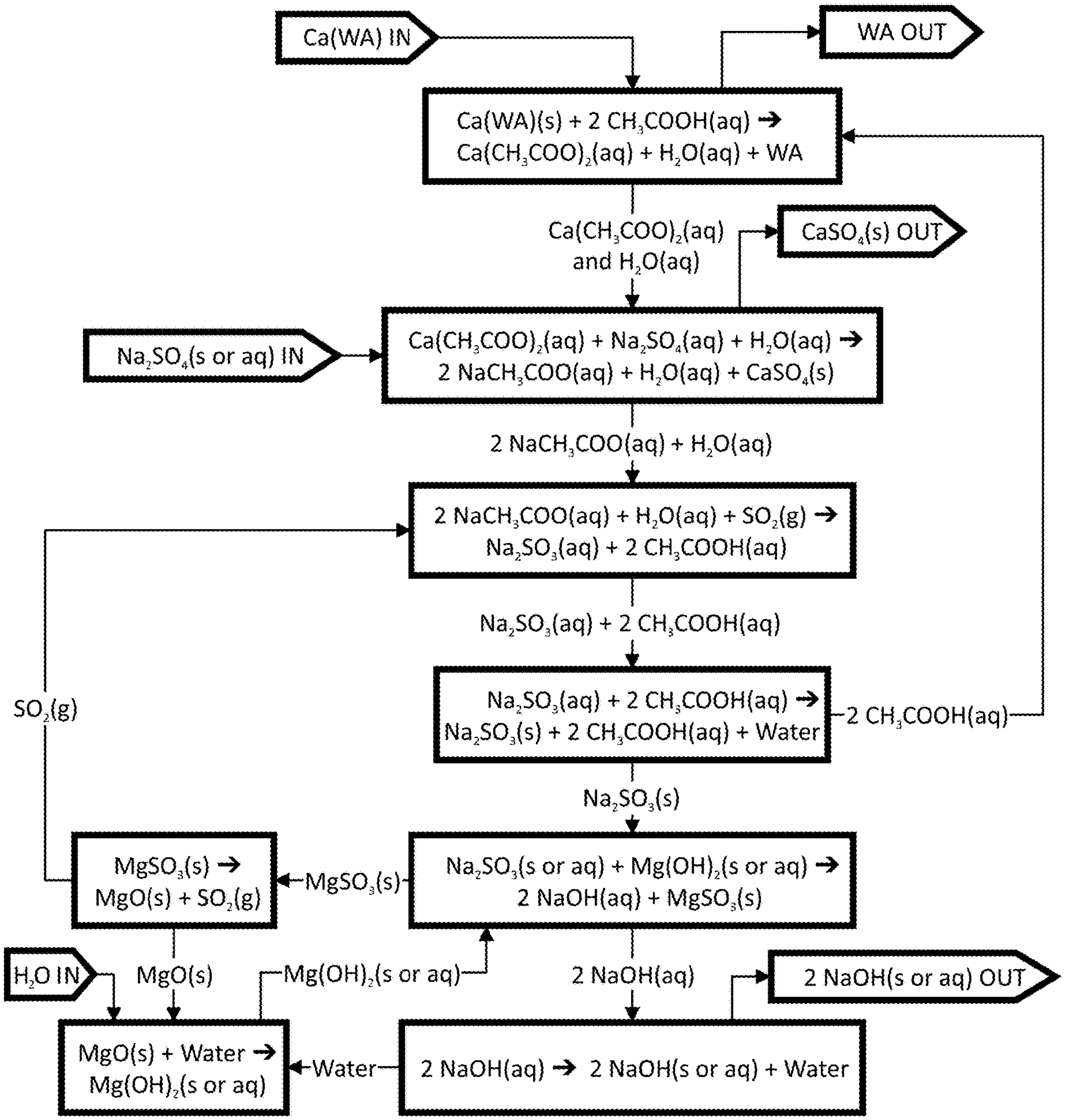

FIG. 12B: Process for producing alkali hydroxide from alkali sulfate using carboxylic acid and sulfur dioxide intermediates.

Figure 12C:
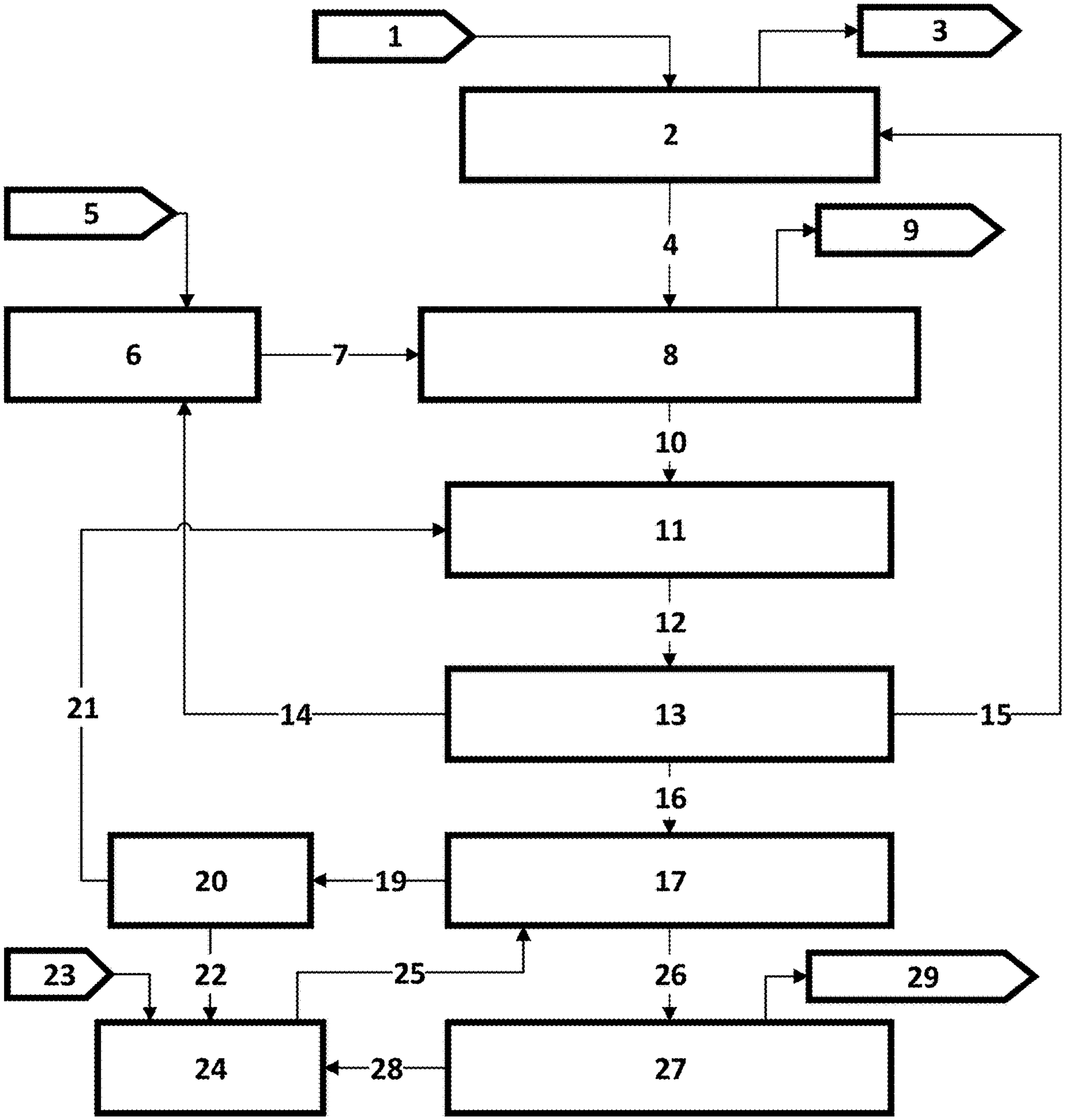

FIG. 12C: Process for producing alkali hydroxide from alkali sulfate using carboxylic acid and sulfur dioxide intermediates.

Figure 13A:
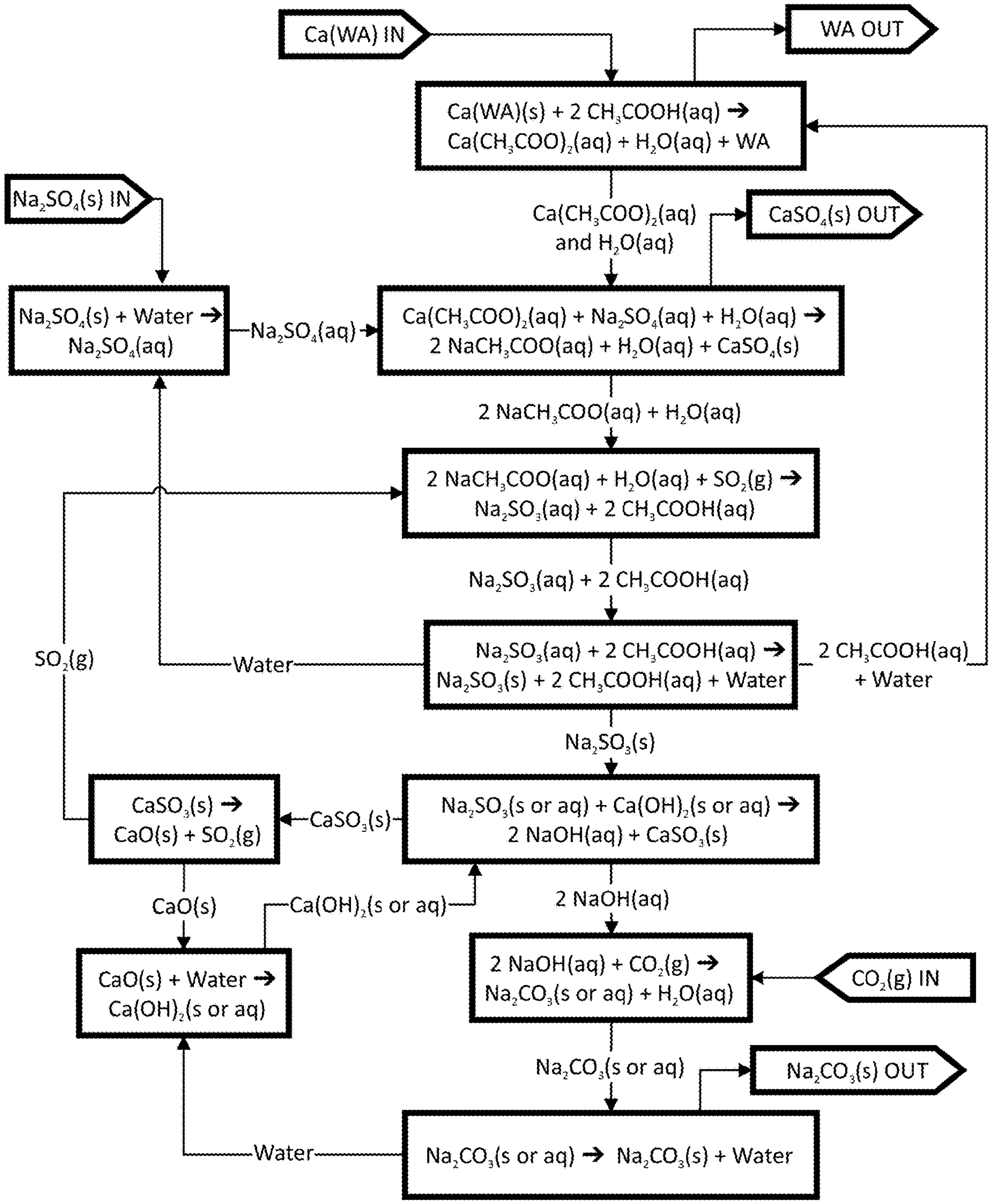

FIG. 13A: Process for producing alkali carbonate and removing or capturing or converting $CO_2$ from alkali sulfate employing acid, such as carboxylic acid, and sulfur dioxide intermediates.

Figure 13B:
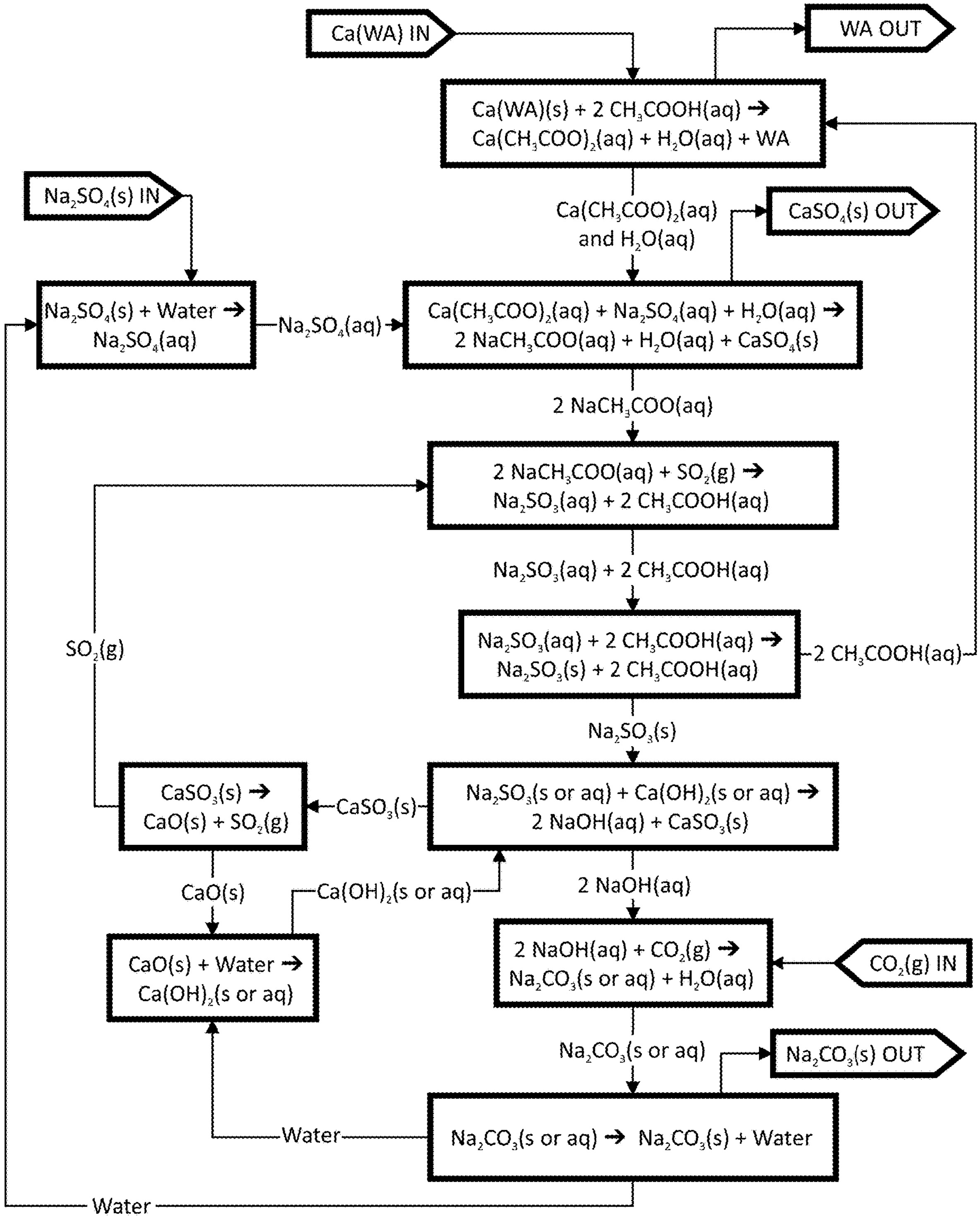

FIG. 13B: Process for producing alkali carbonate and removing or capturing or converting $CO_2$ from alkali sulfate employing acid, such as carboxylic acid, and sulfur dioxide intermediates.

Figure 13C:
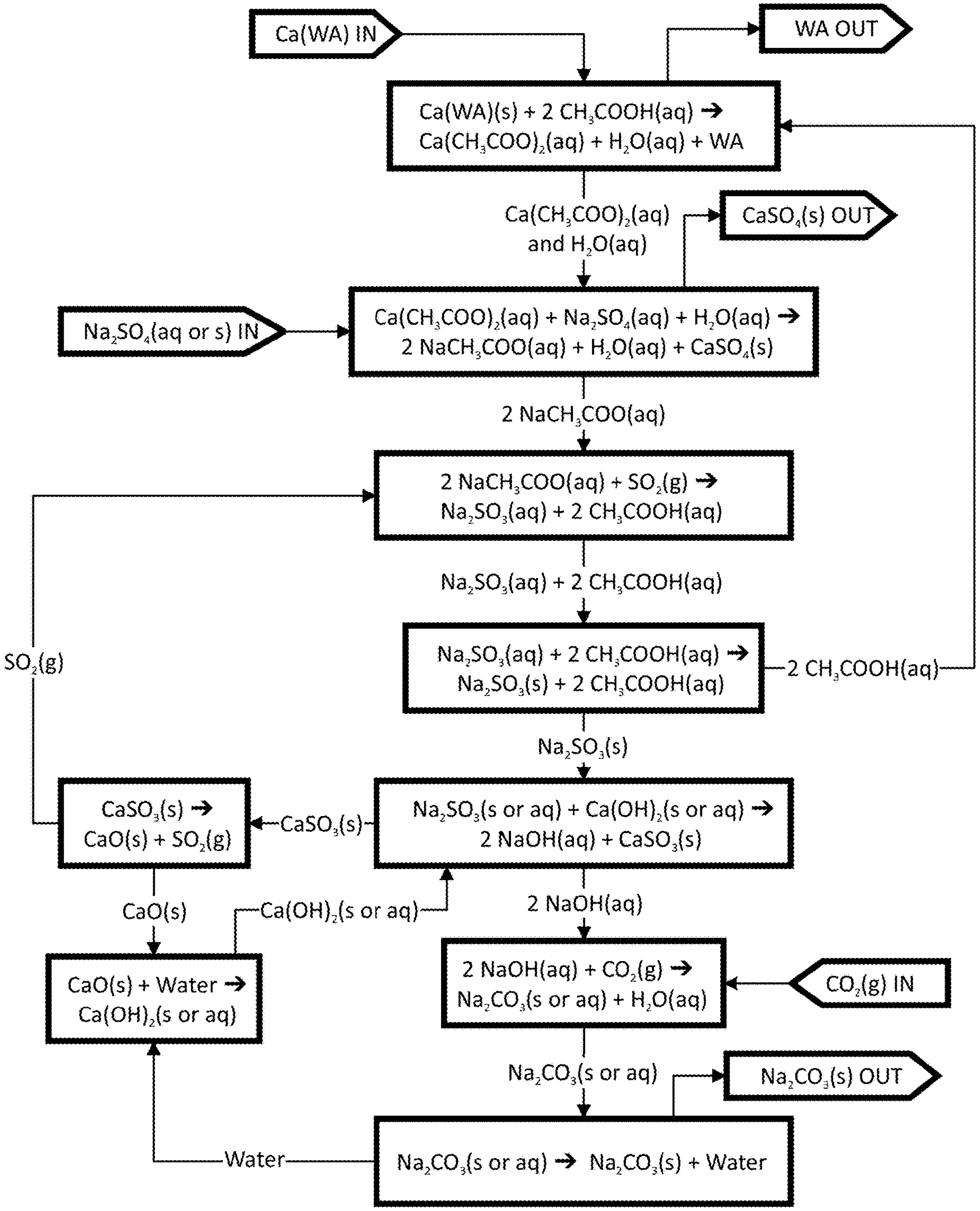

FIG. 13C: Process for producing alkali carbonate and removing or capturing or converting $CO_2$ from alkali sulfate employing acid, such as carboxylic acid, and sulfur dioxide intermediates.

Figure 13D:
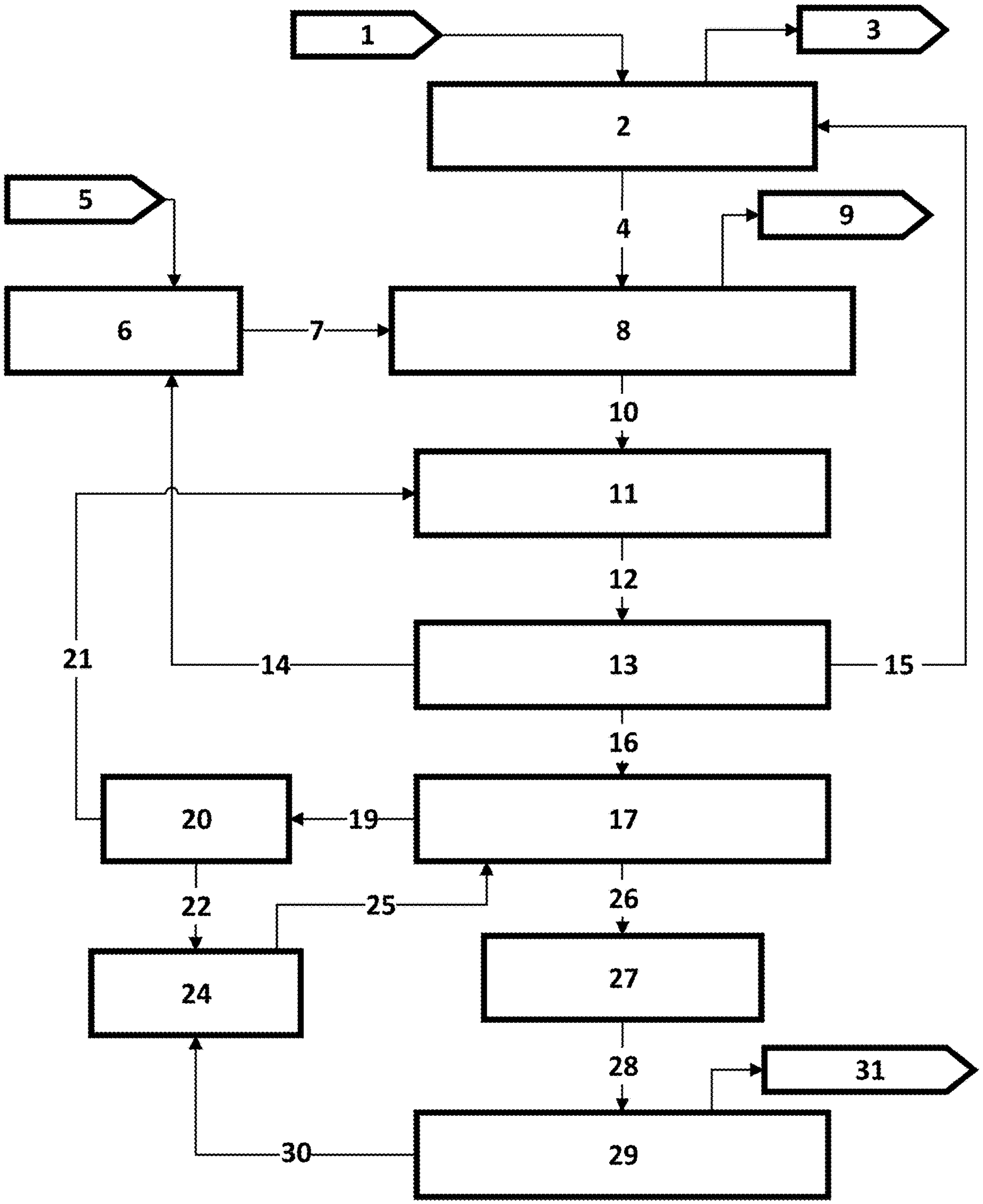

FIG. 13D: Process for producing alkali carbonate and removing or capturing or converting $CO_2$ from alkali sulfate employing acid, such as carboxylic acid, and sulfur dioxide intermediates.

Figure 13E:
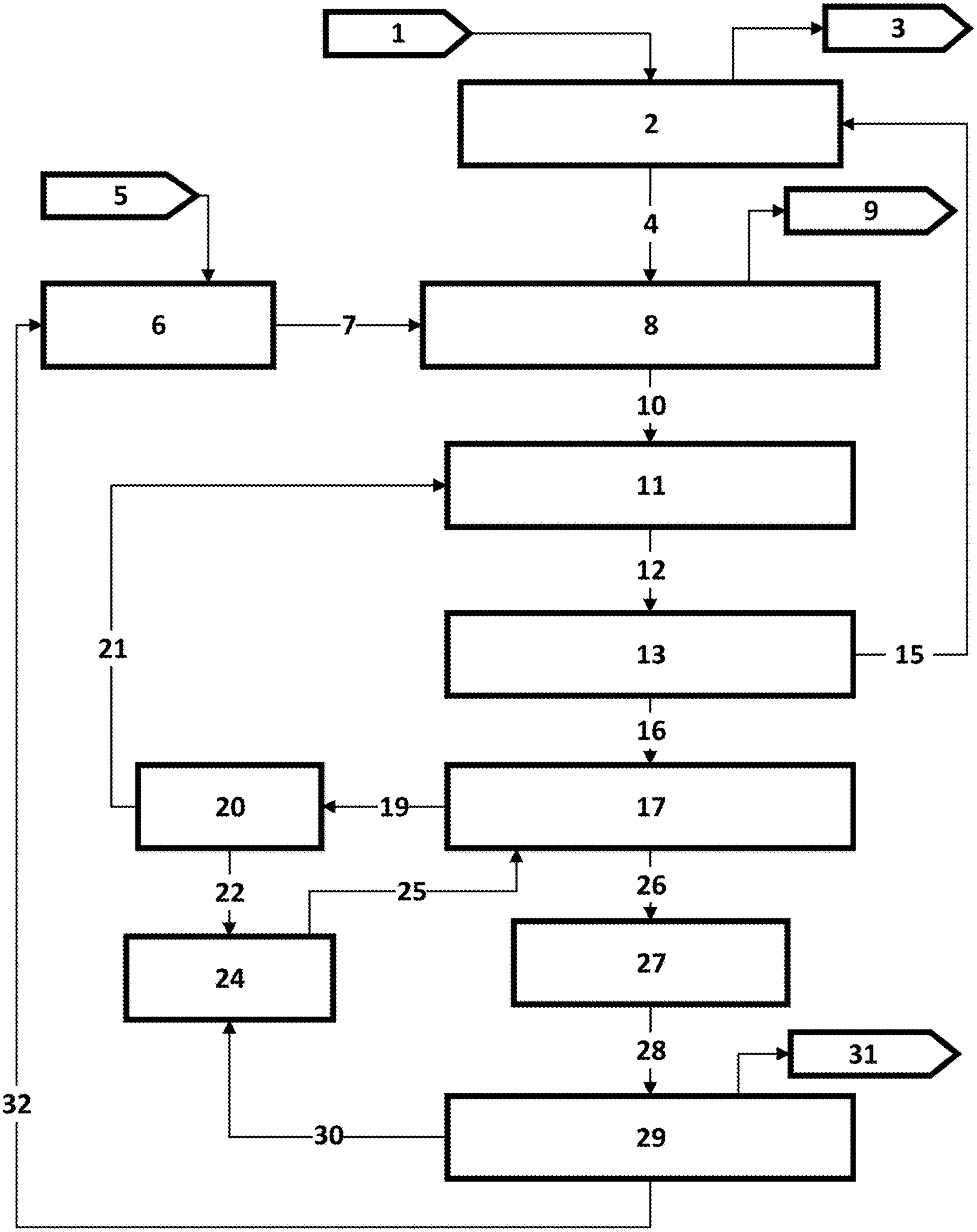

FIG. 13E: Process for producing alkali carbonate and removing or capturing or converting $CO_2$ from alkali sulfate employing acid, such as carboxylic acid, and sulfur dioxide intermediates.

Figure 13F:
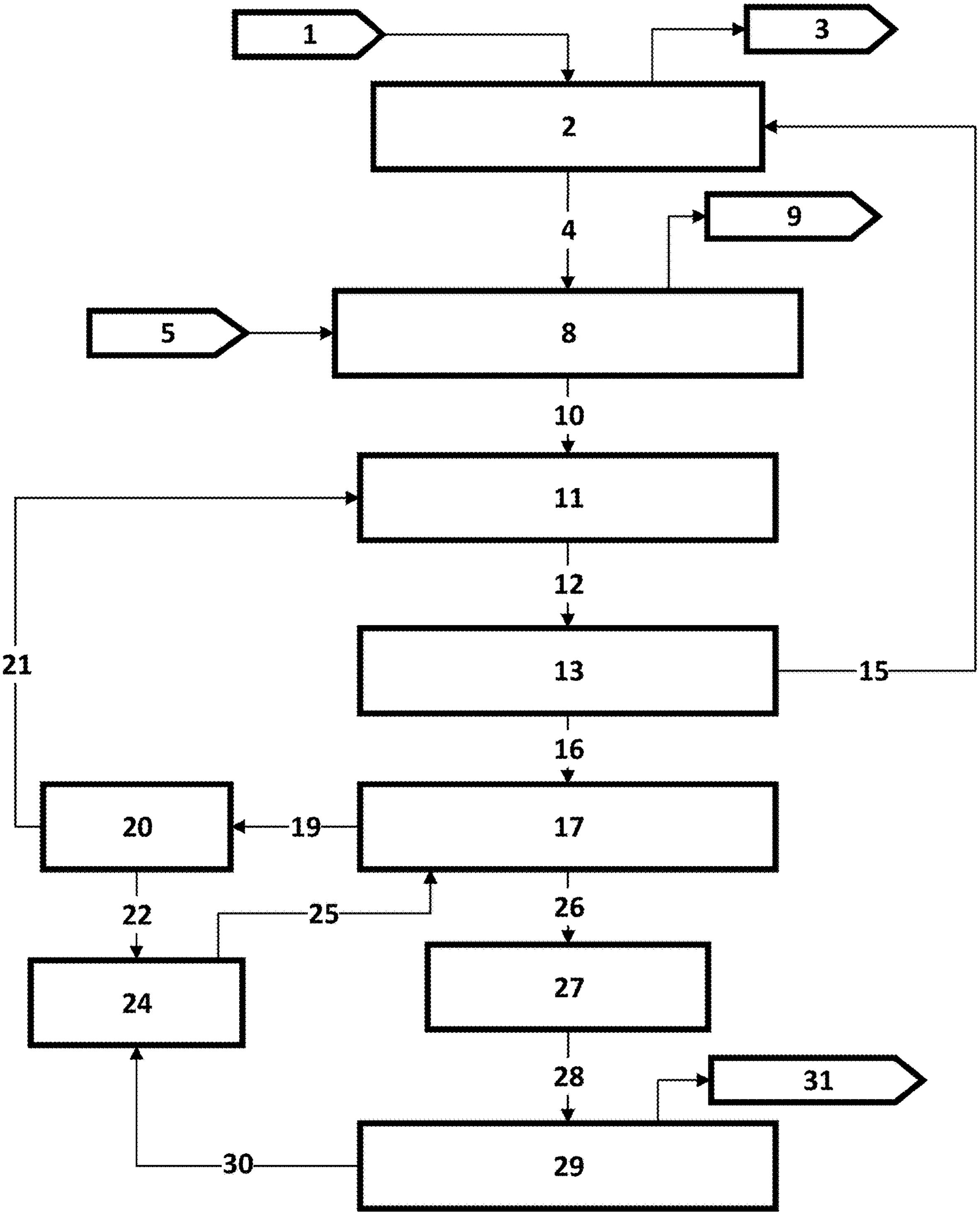

FIG. 13F: Process for producing alkali carbonate and removing or capturing or converting $CO_2$ from alkali sulfate employing acid, such as carboxylic acid, and sulfur dioxide intermediates.

Figure 14A:
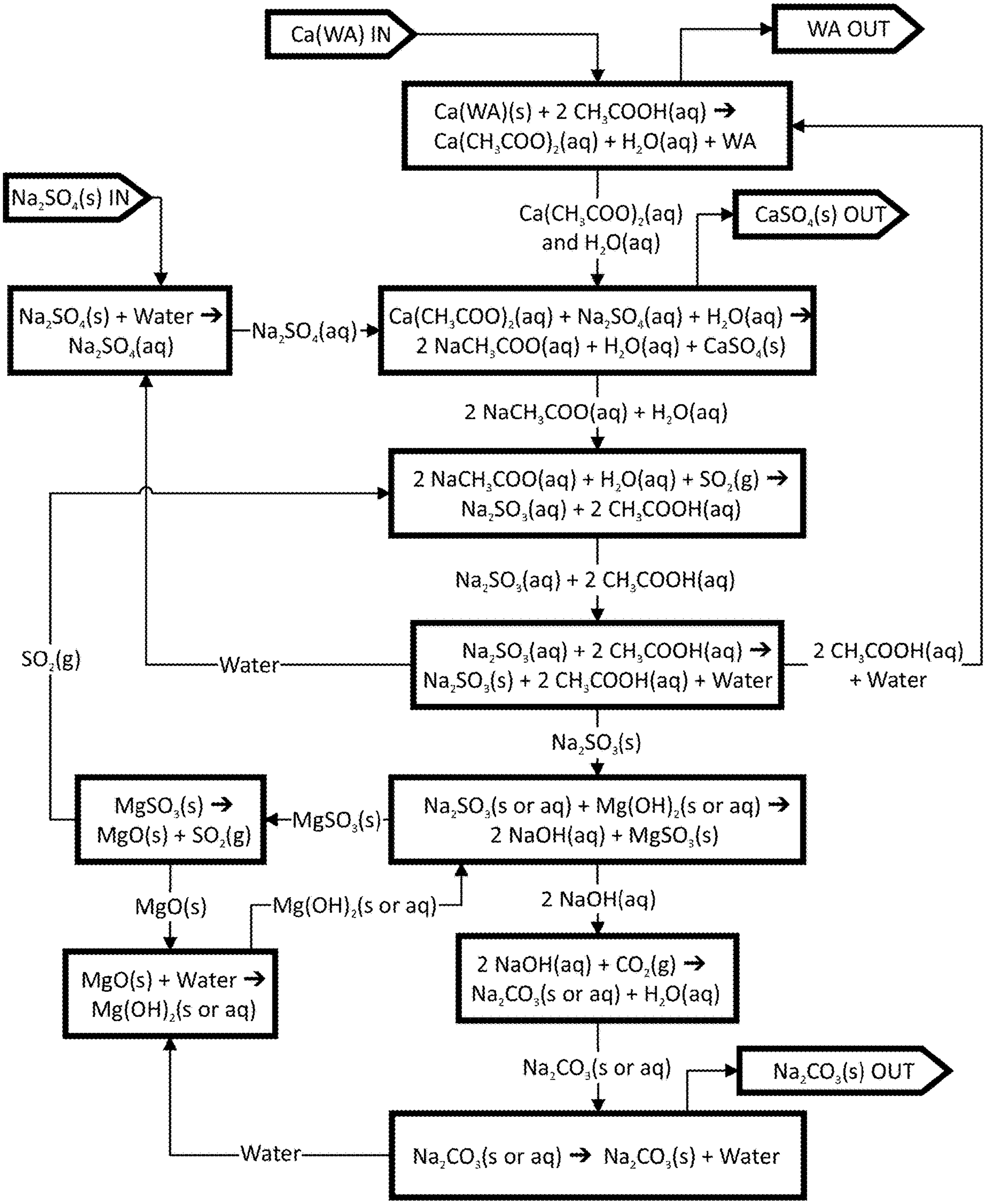

FIG. 14A: Process for producing alkali carbonate and removing or capturing or converting $CO_2$ from alkali sulfate employing carboxylic acid and sulfur dioxide intermediates.

Figure 14B:
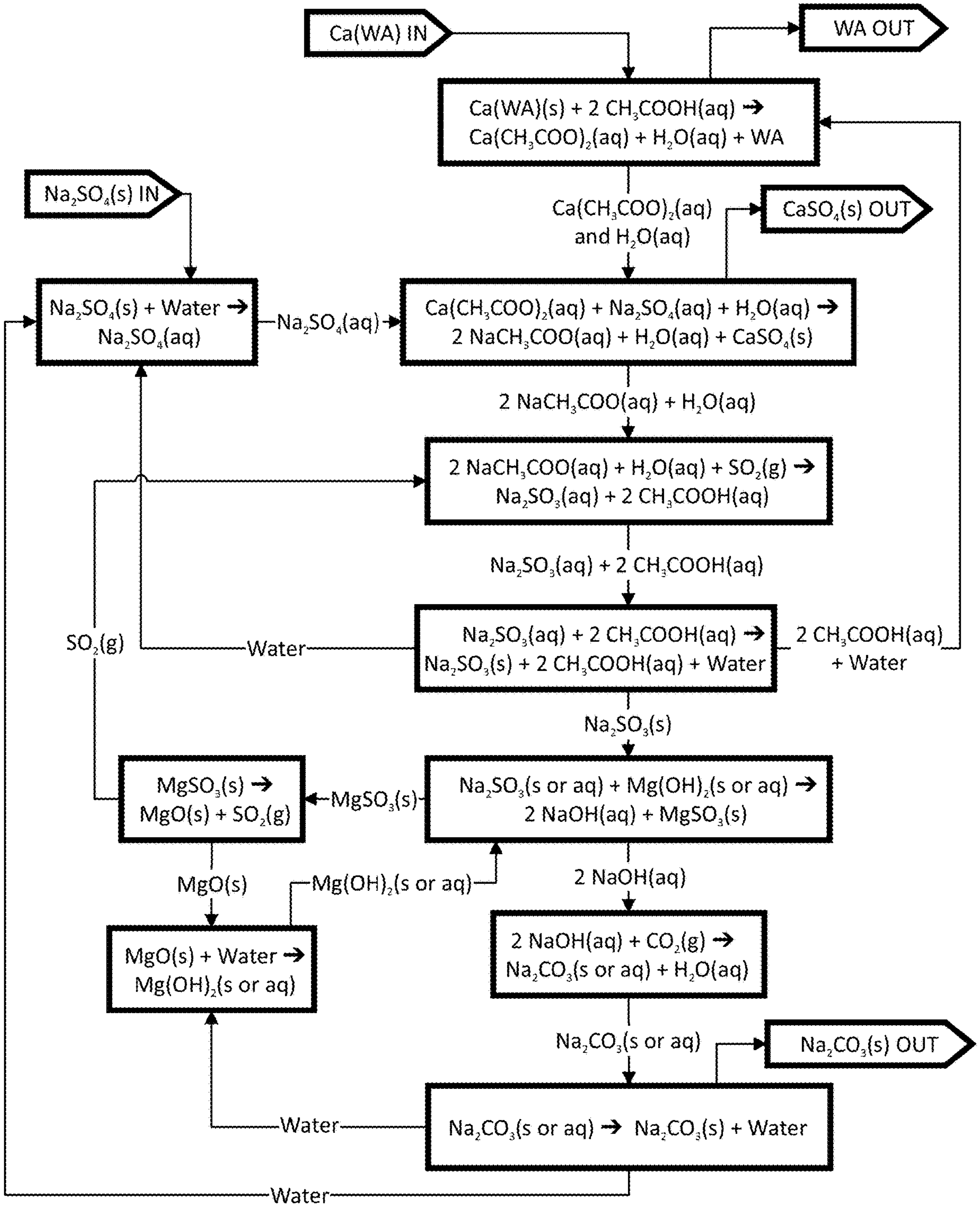

FIG. 14B: Process for producing alkali carbonate and removing or capturing or converting $CO_2$ from alkali sulfate employing carboxylic acid and sulfur dioxide intermediates.

Figure 14C:
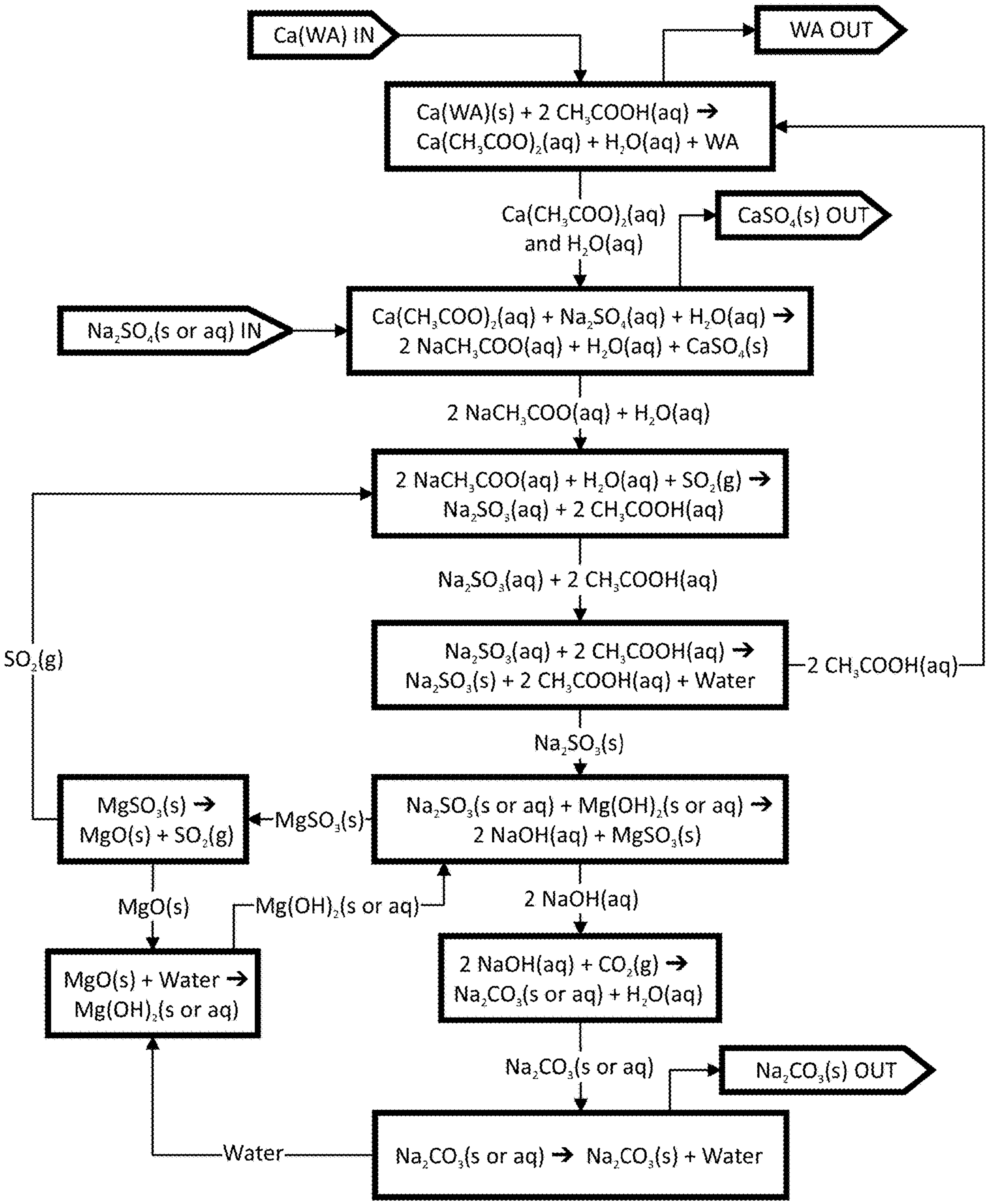

FIG. 14C: Process for producing alkali carbonate and removing or capturing or converting $CO_2$ from alkali sulfate employing carboxylic acid and sulfur dioxide intermediates.

Figure 15A:
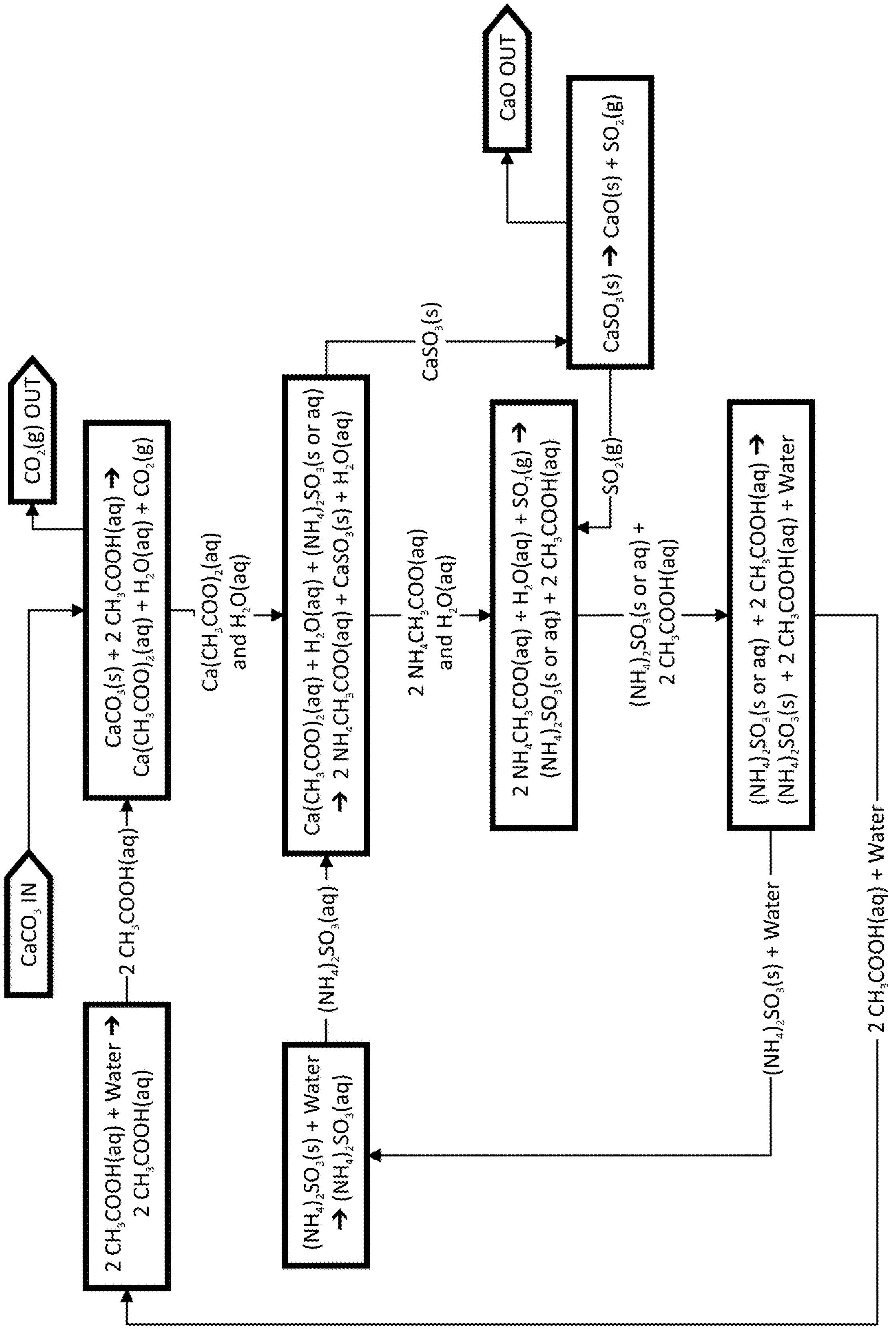

FIG. 15A: Process for producing alkaline earth oxide and weak acid derivative employing carboxylic acid, alkali (such as ammonia or ammonium), and sulfur dioxide intermediates.

Figure 15B:
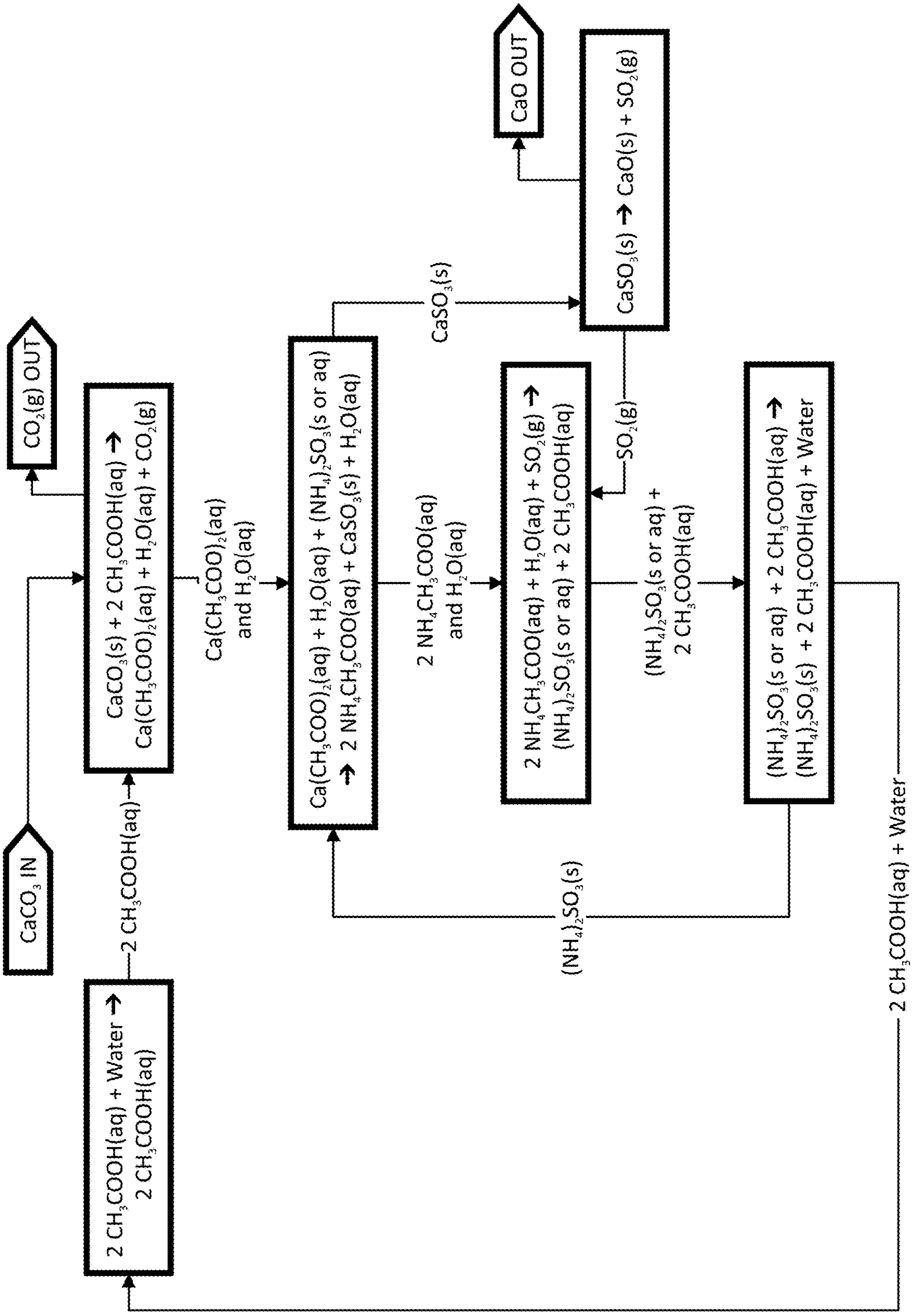

FIG. 15B: Process for producing alkaline earth oxide and weak acid derivative employing carboxylic acid, alkali (such as ammonia or ammonium), and sulfur dioxide intermediates.

Figure 15C:
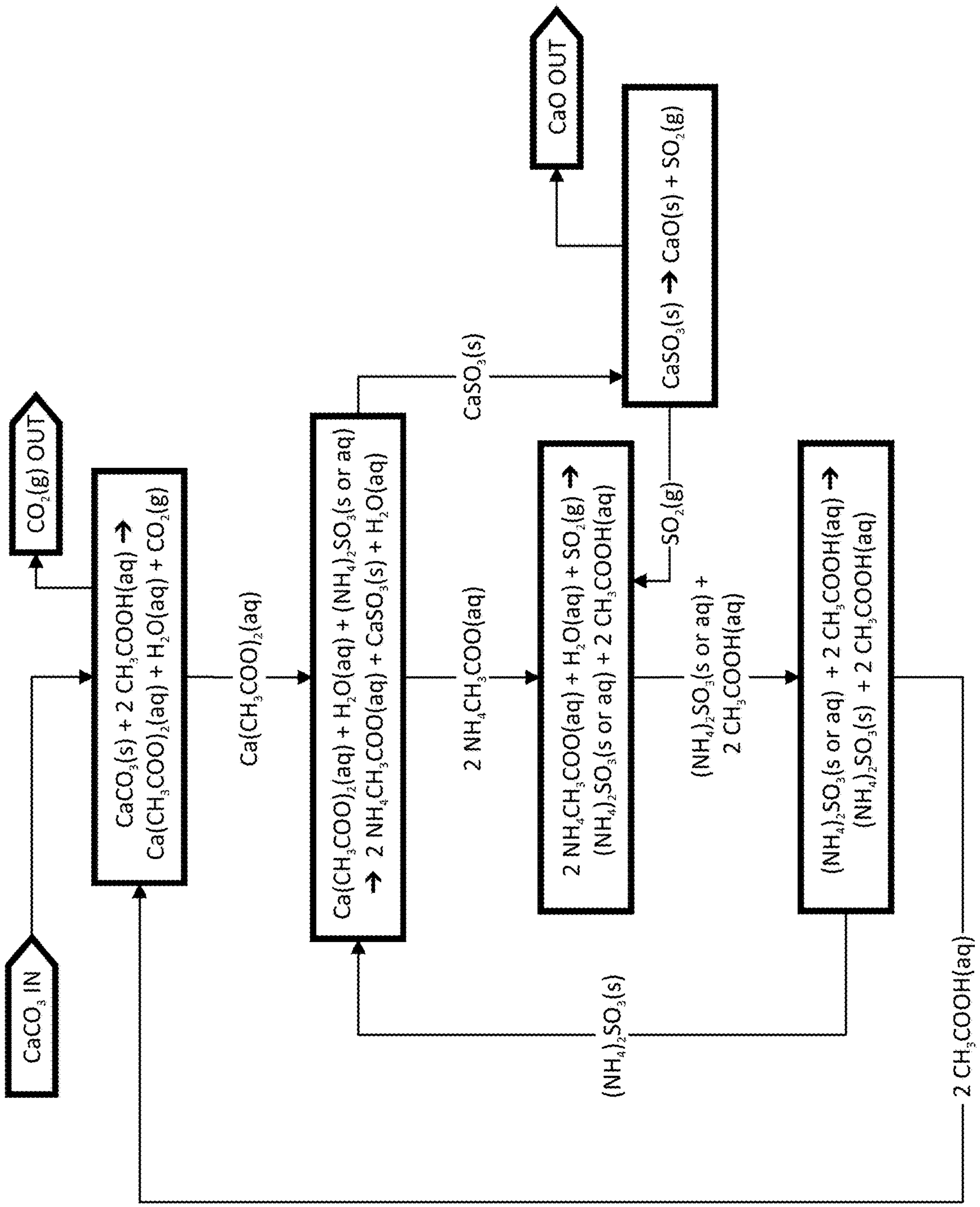

FIG. 15C: Process for producing alkaline earth oxide and weak acid derivative employing carboxylic acid, alkali (such as ammonia or ammonium), and sulfur dioxide intermediates.

Figure 16A:
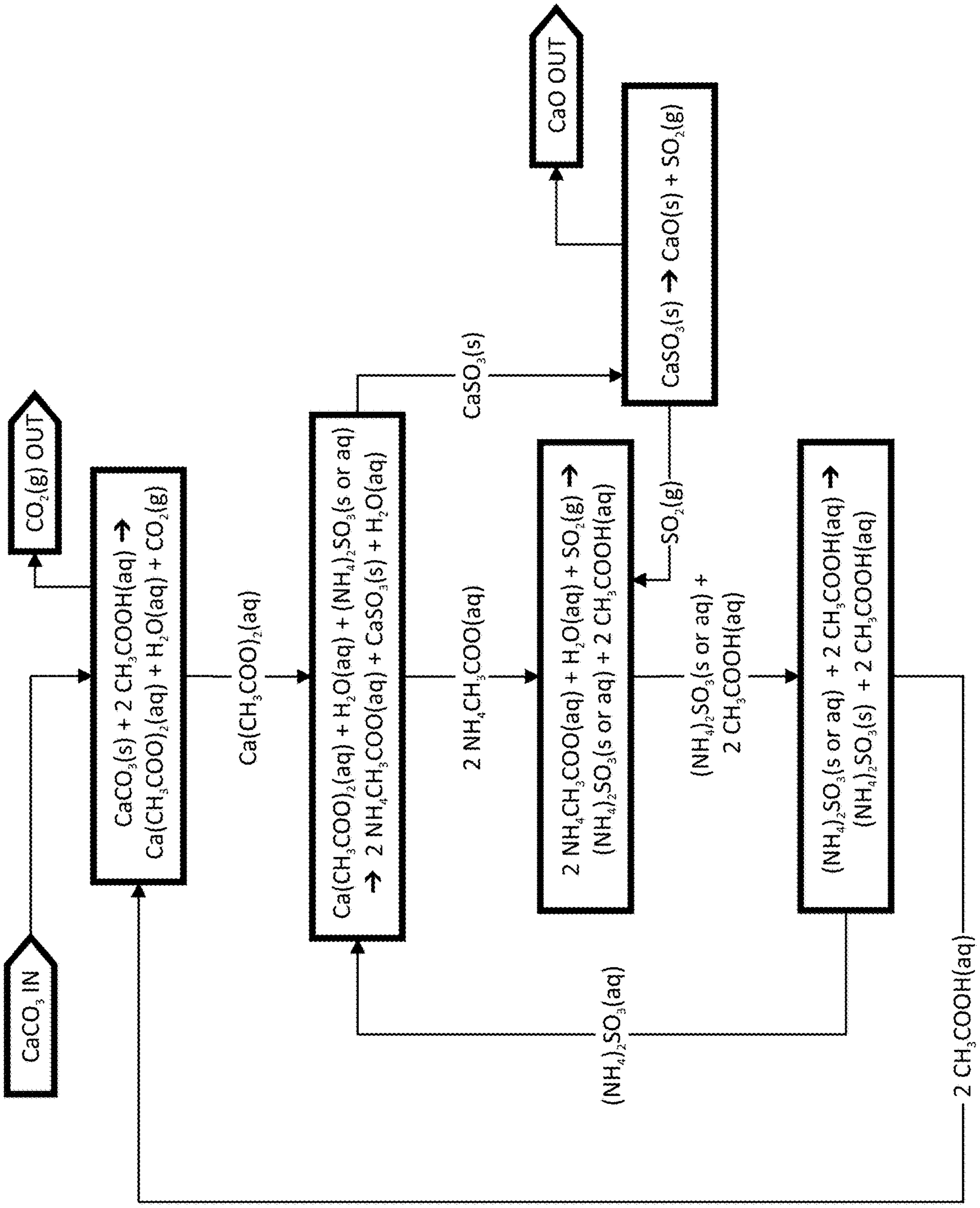

FIG. 16A: Process for producing alkaline earth oxide and weak acid derivative employing carboxylic acid, alkali (such as ammonia or ammonium), and sulfur dioxide intermediates.

Figure 16B:
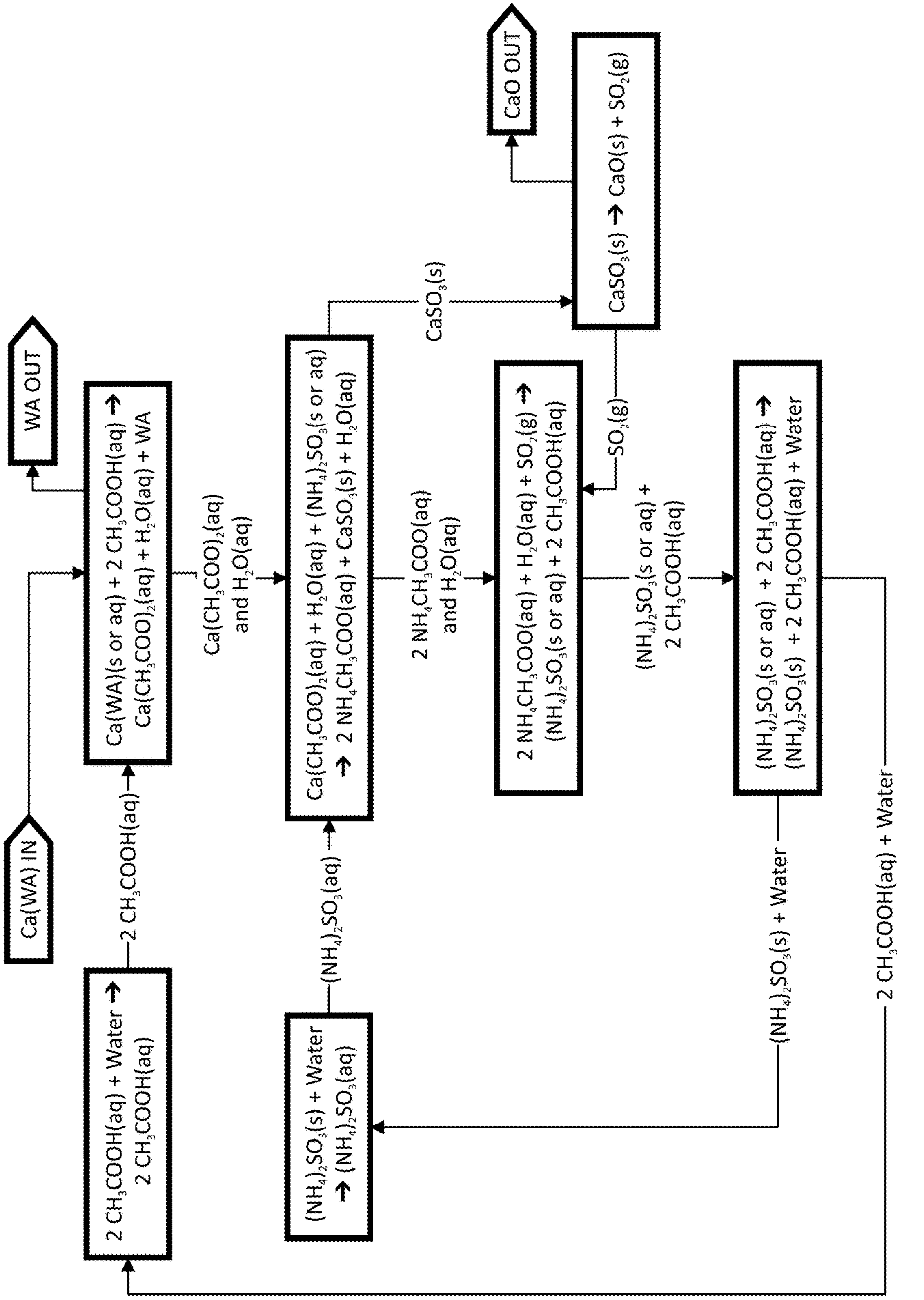

FIG. 16B: Process for producing alkaline earth oxide and weak acid derivative employing carboxylic acid, alkali (such as ammonia or ammonium), and sulfur dioxide intermediates.

Figure 16C:
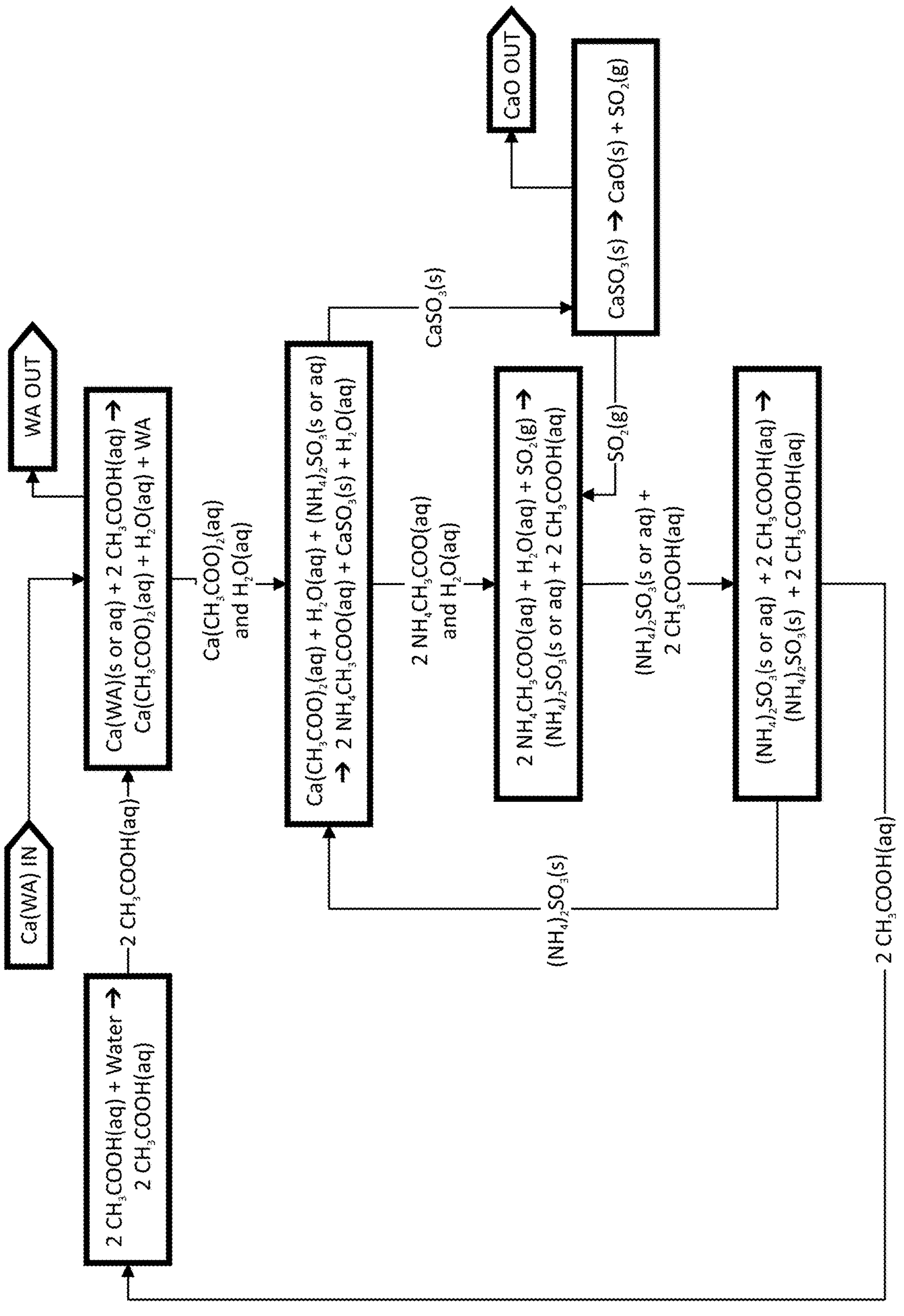

FIG. 16C: Process for producing alkaline earth oxide and weak acid derivative employing carboxylic acid, alkali (such as ammonia or ammonium), and sulfur dioxide intermediates.

Figure 17A:
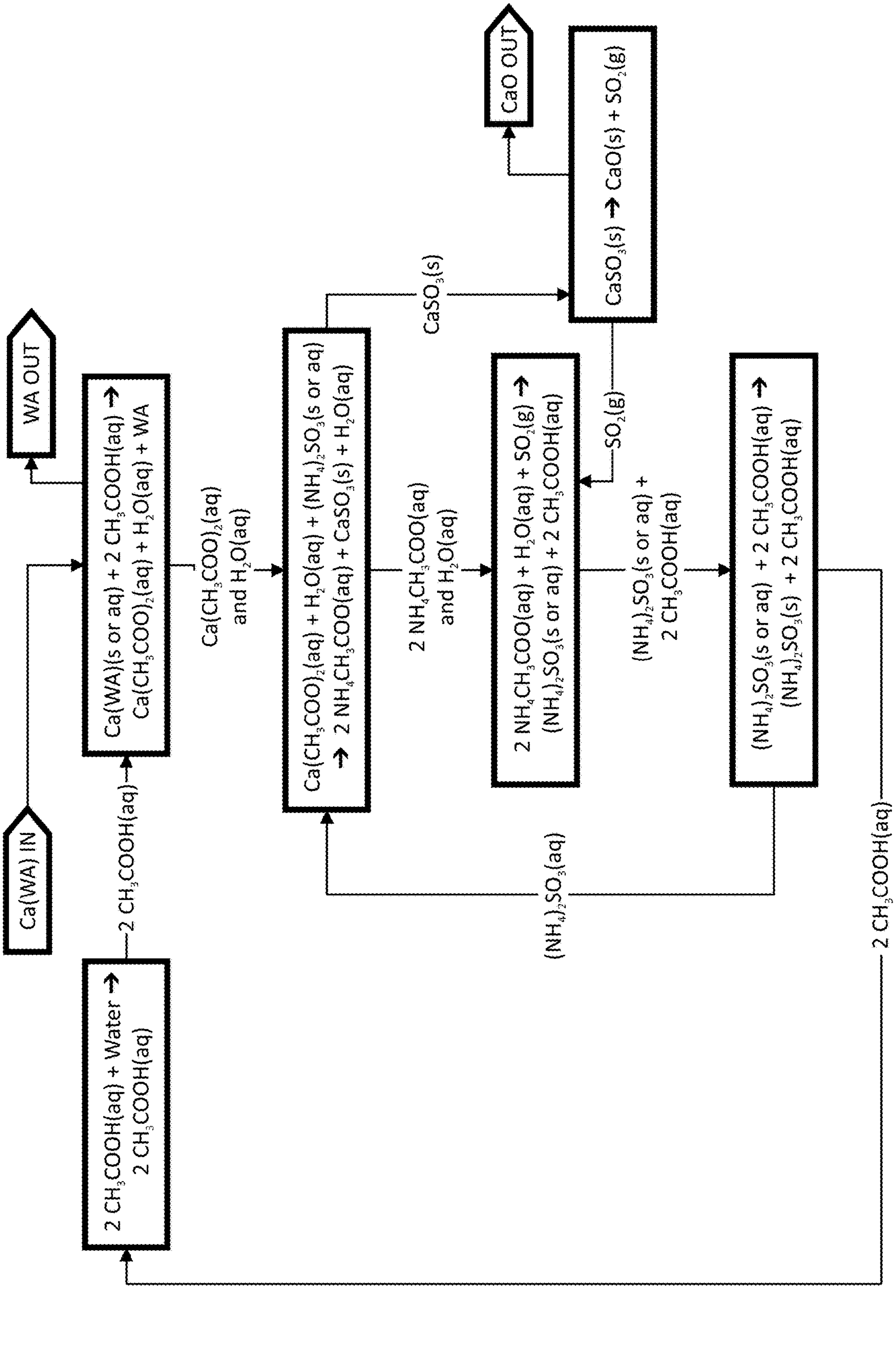

FIG. 17A: Process for producing alkaline earth oxide and weak acid derivative employing carboxylic acid, alkali (such as ammonia or ammonium), and sulfur dioxide intermediates.

Figure 17B:
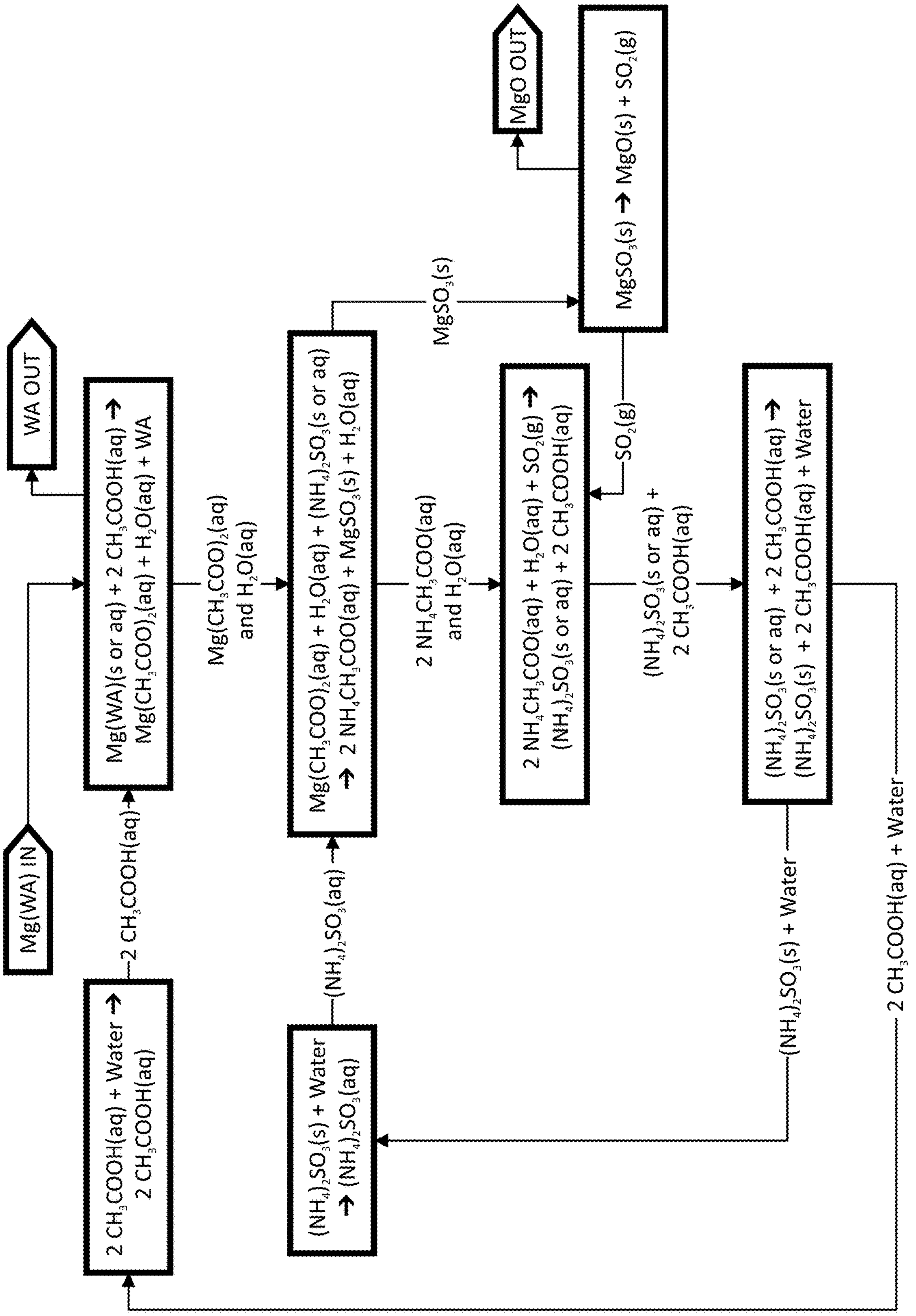

FIG. 17B: Process for producing alkaline earth oxide and weak acid derivative employing carboxylic acid, alkali (such as ammonia or ammonium), and sulfur dioxide intermediates.

Figure 17C:
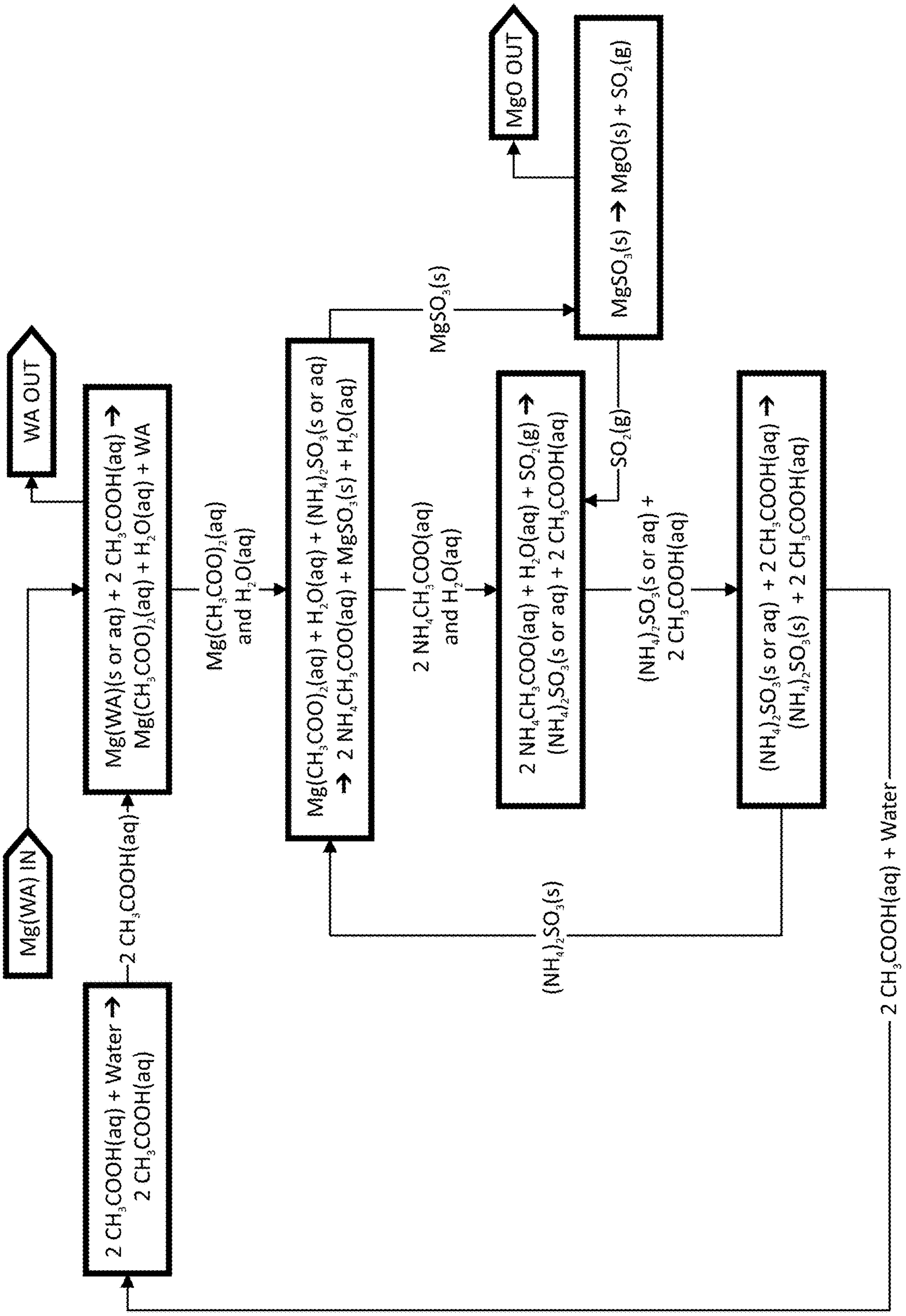

FIG. 17C: Process for producing alkaline earth oxide and weak acid derivative employing carboxylic acid, alkali (such as ammonia or ammonium), and sulfur dioxide intermediates.

Figure 18:
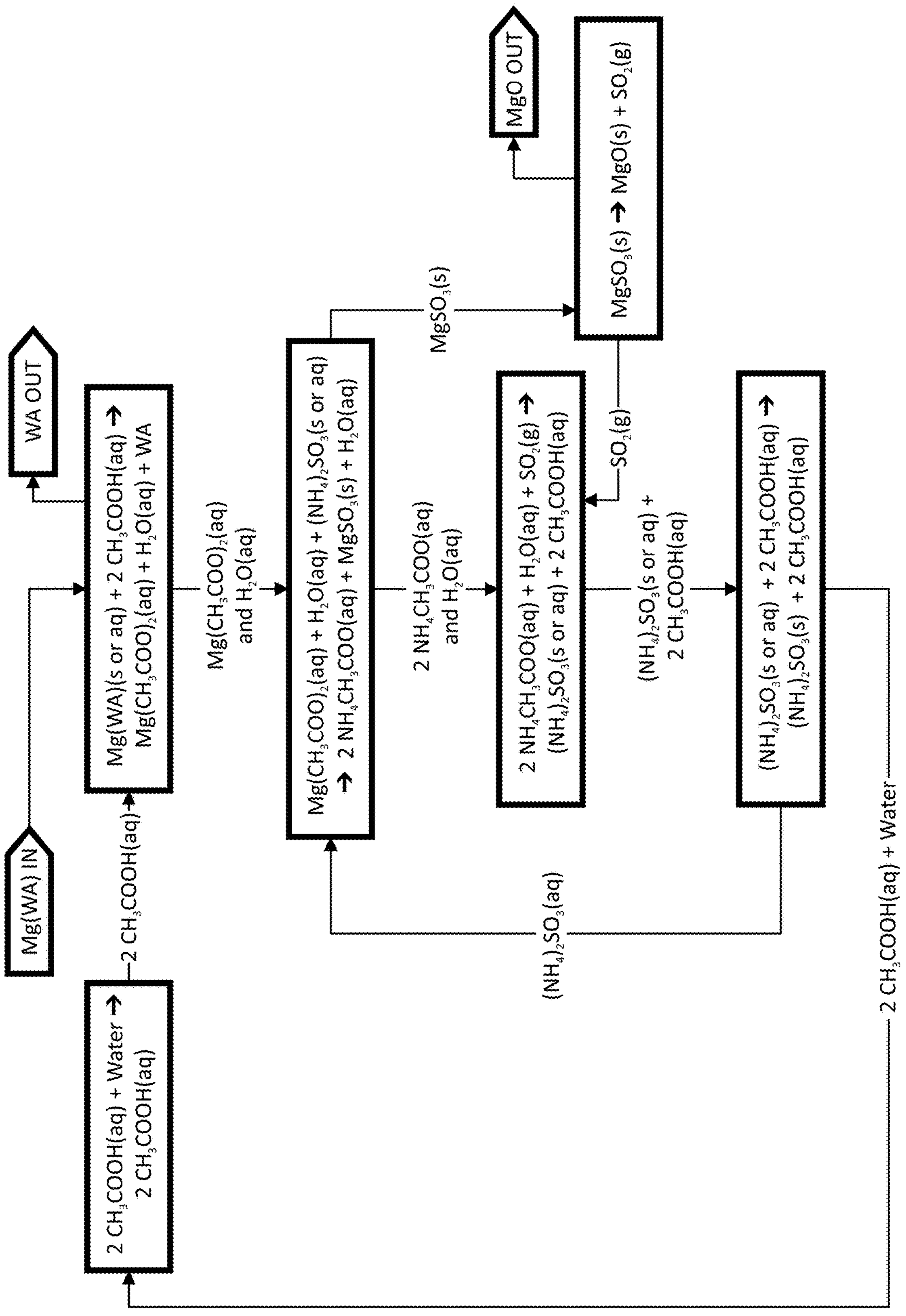

FIG. 18: Process for producing alkaline earth oxide and weak acid derivative employing carboxylic acid, alkali (such as ammonia or ammonium), and sulfur dioxide intermediates.

Figure 19:
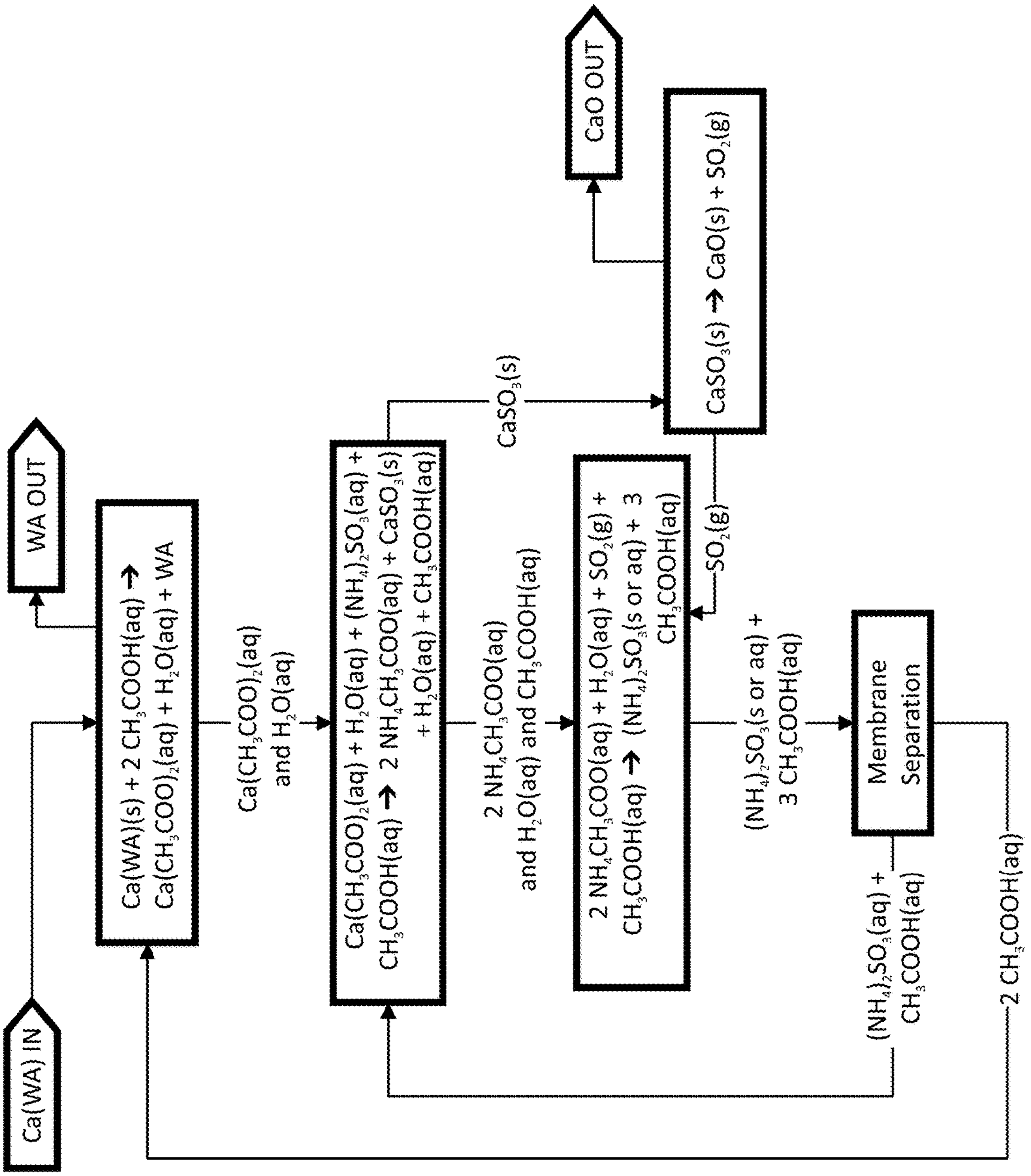

FIG. 19: Process for producing alkaline earth oxide and weak acid derivative employing carboxylic acid, alkali (such as ammonia or ammonium), and sulfur dioxide intermediates.

Figure 20A:
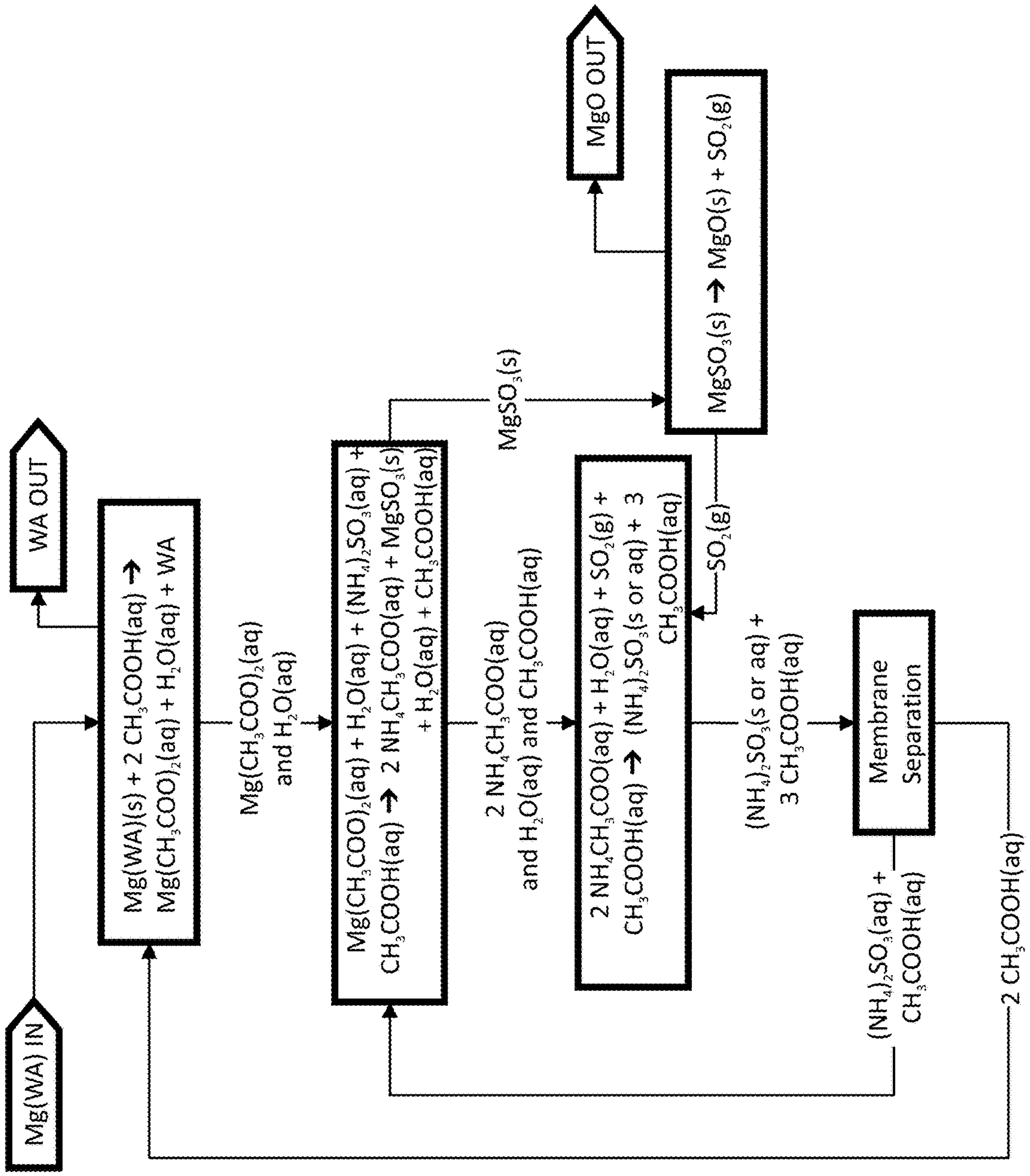

FIG. 20A: Process for producing or recovering ammonia from ammonium sulfate

Figure 20B:
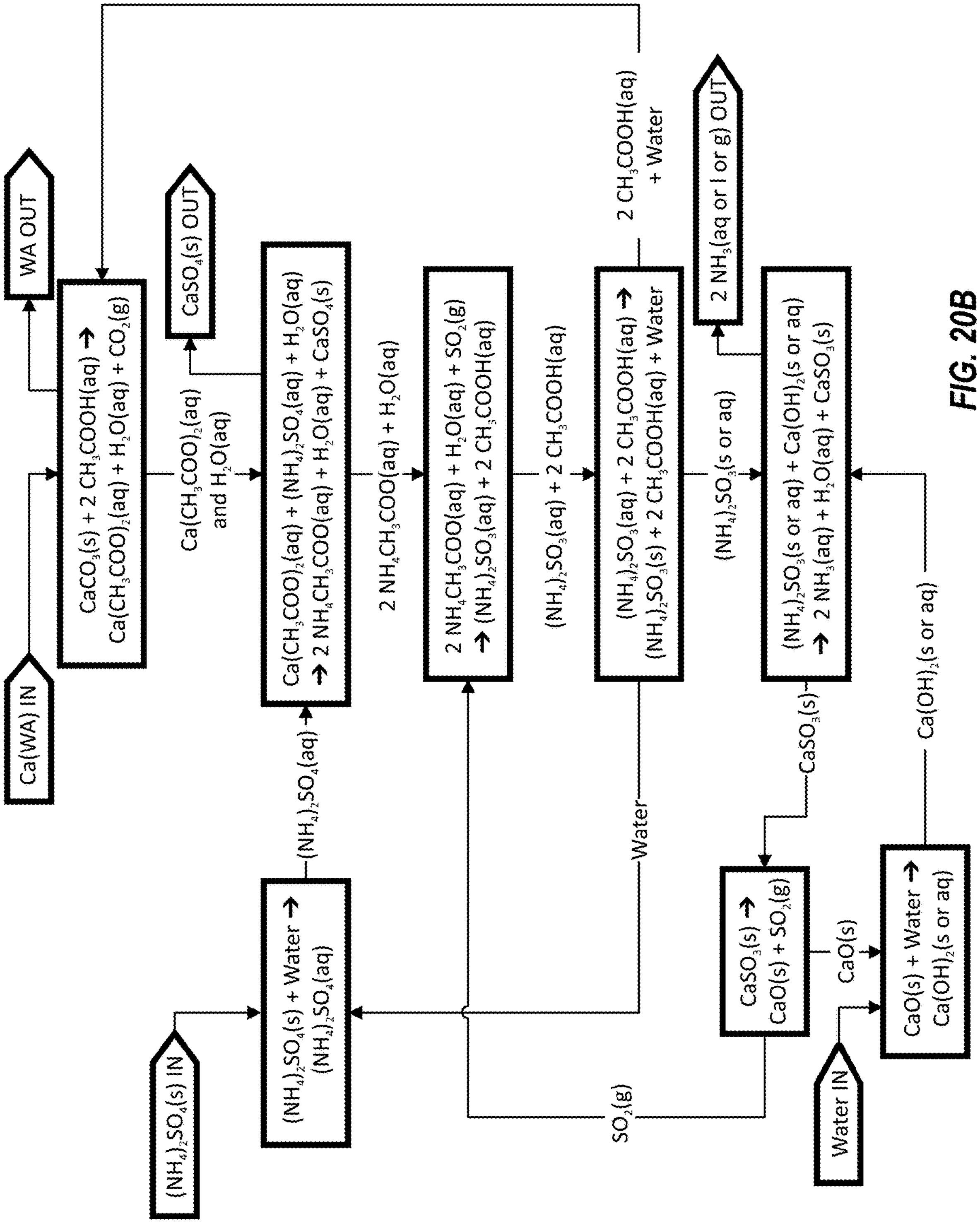

FIG. 20B: Process for producing or recovering ammonia from ammonium sulfate

Figure 20C:
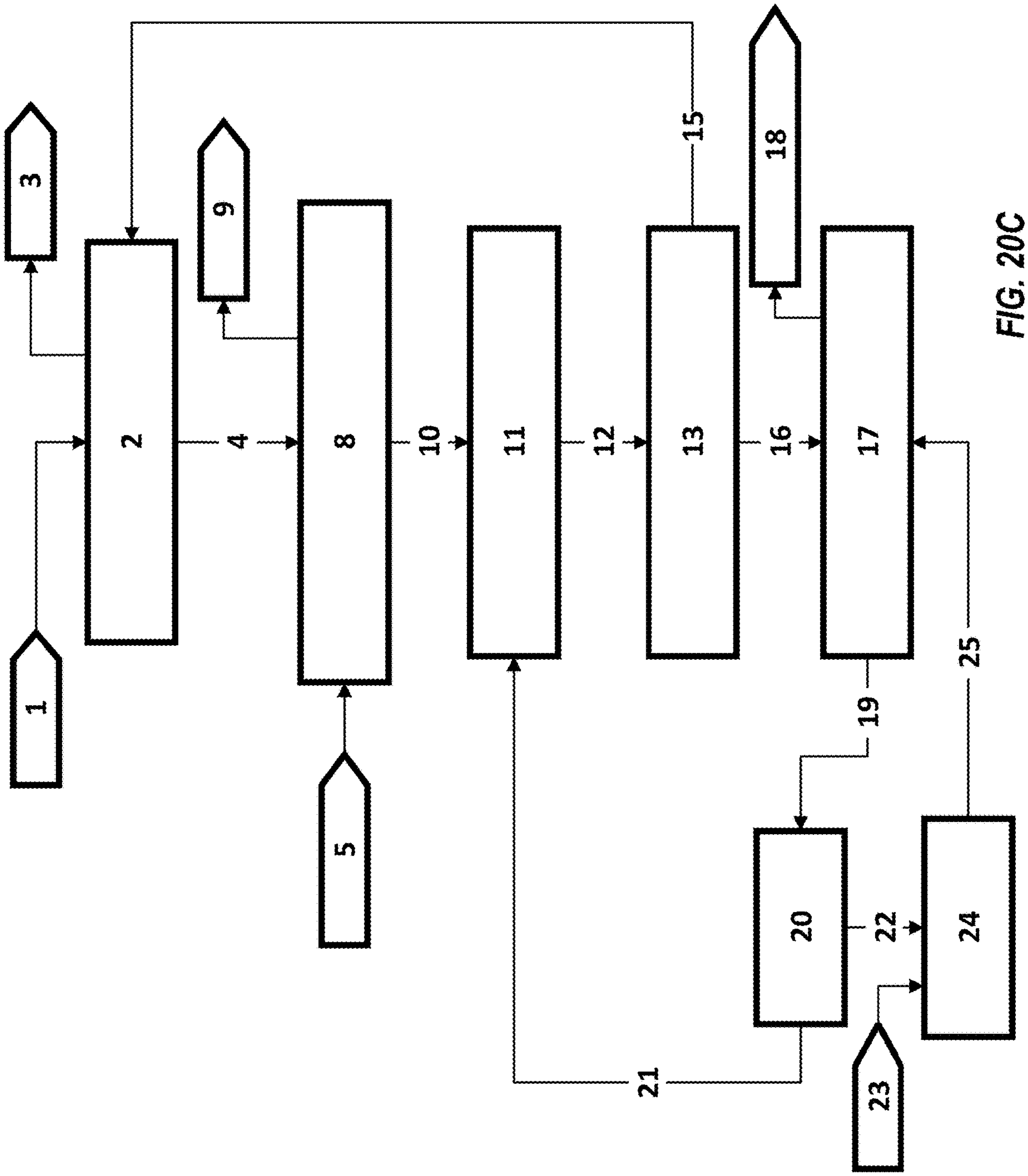

FIG. 20C: Process for producing or recovering ammonia from ammonium sulfate

Figure 21A:
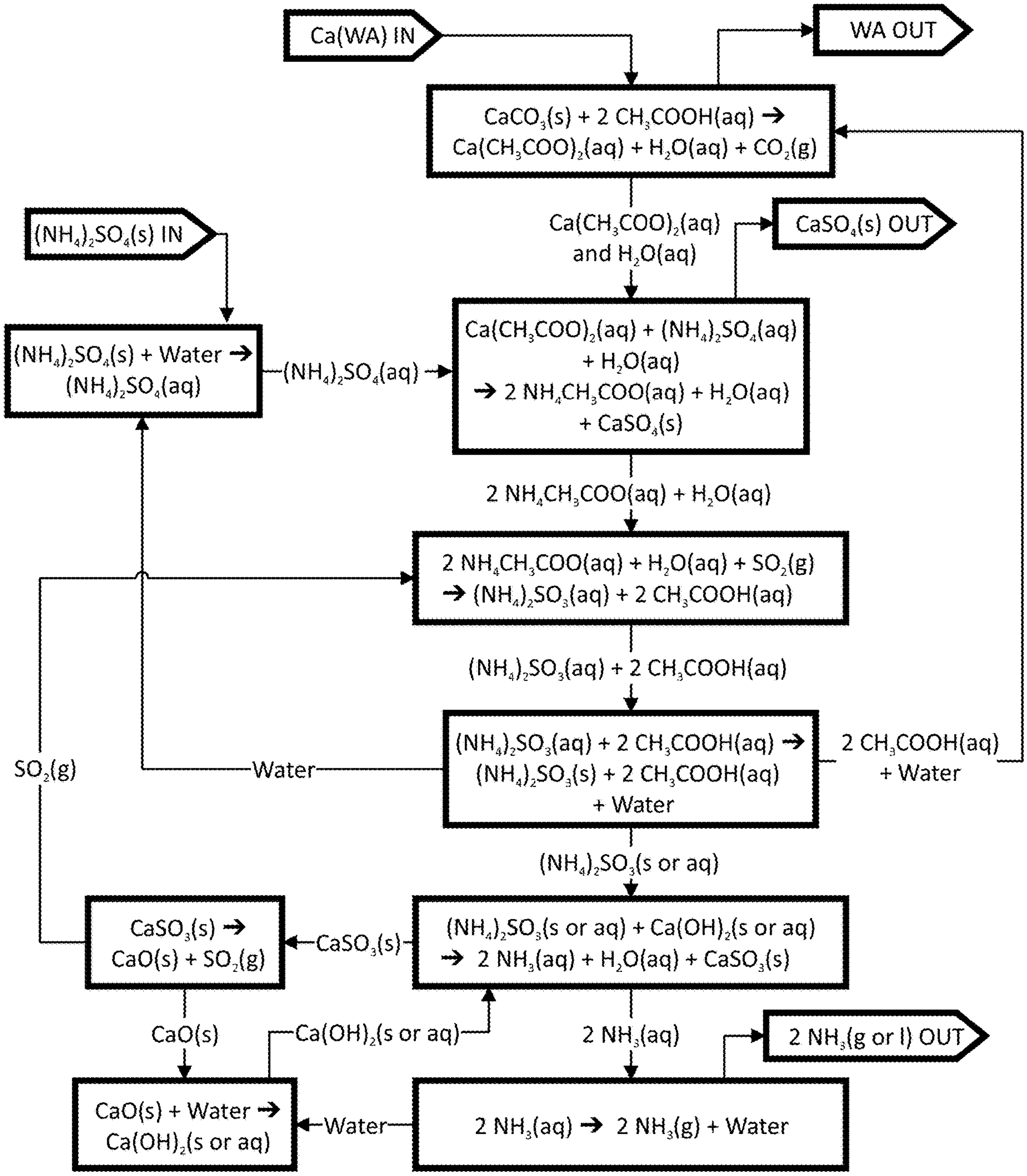

FIG. 21A: Process for producing or recovering ammonia from ammonium sulfate

Figure 21B:
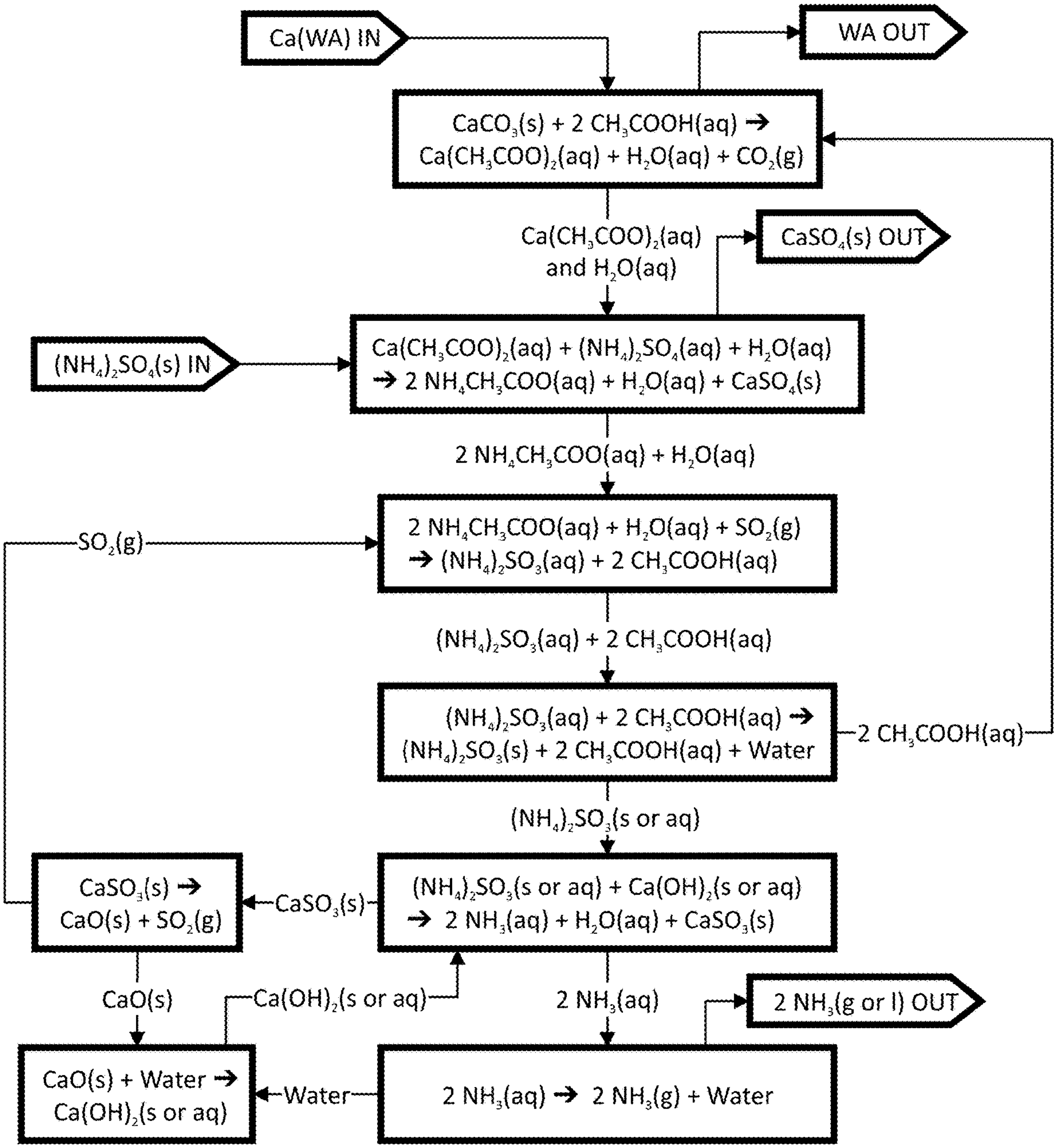

FIG. 21B: Process for producing or recovering ammonia from ammonium sulfate

Figure 21C:
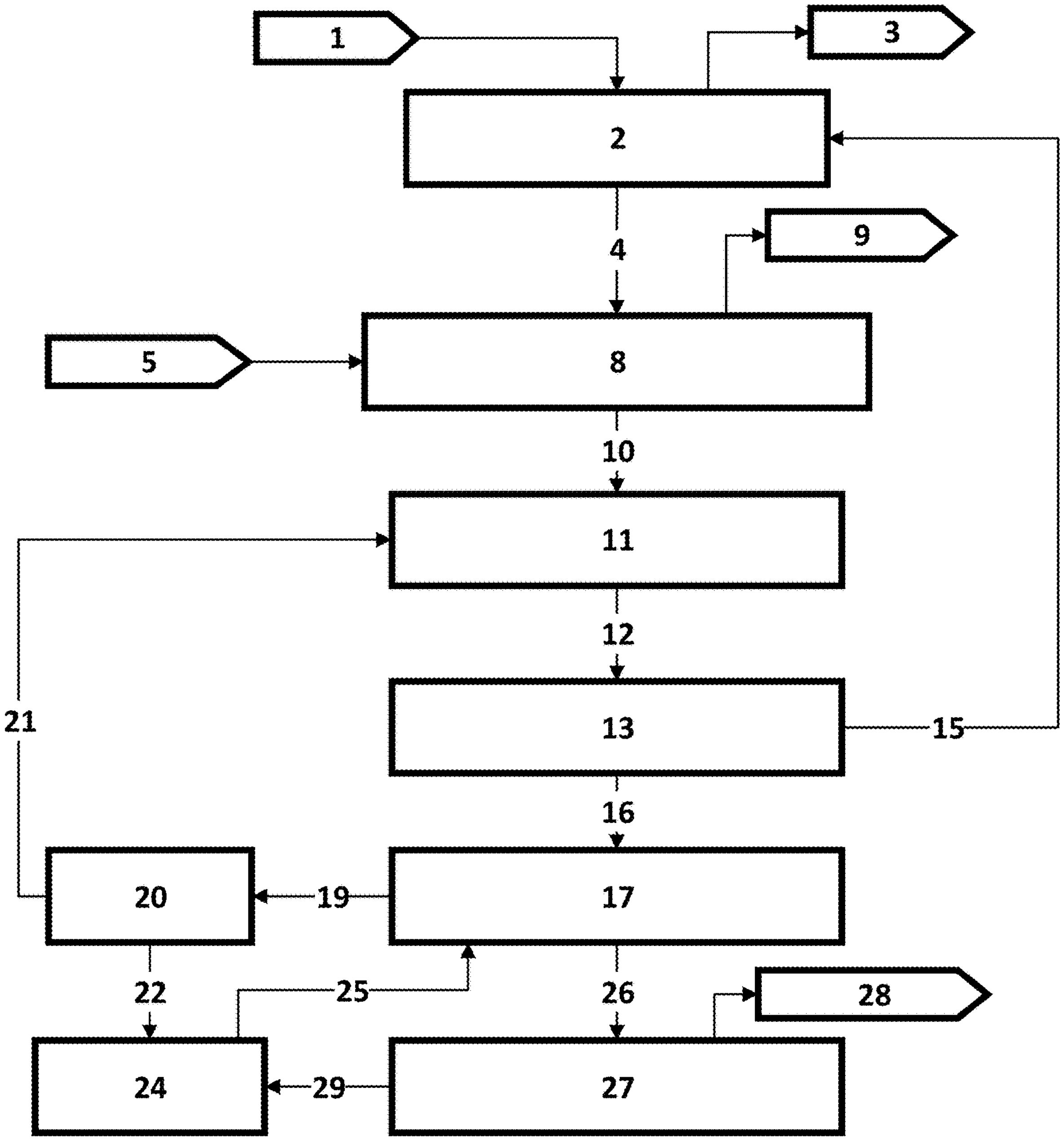

FIG. 21C: Process for producing or recovering ammonia from ammonium sulfate

Figure 22A:
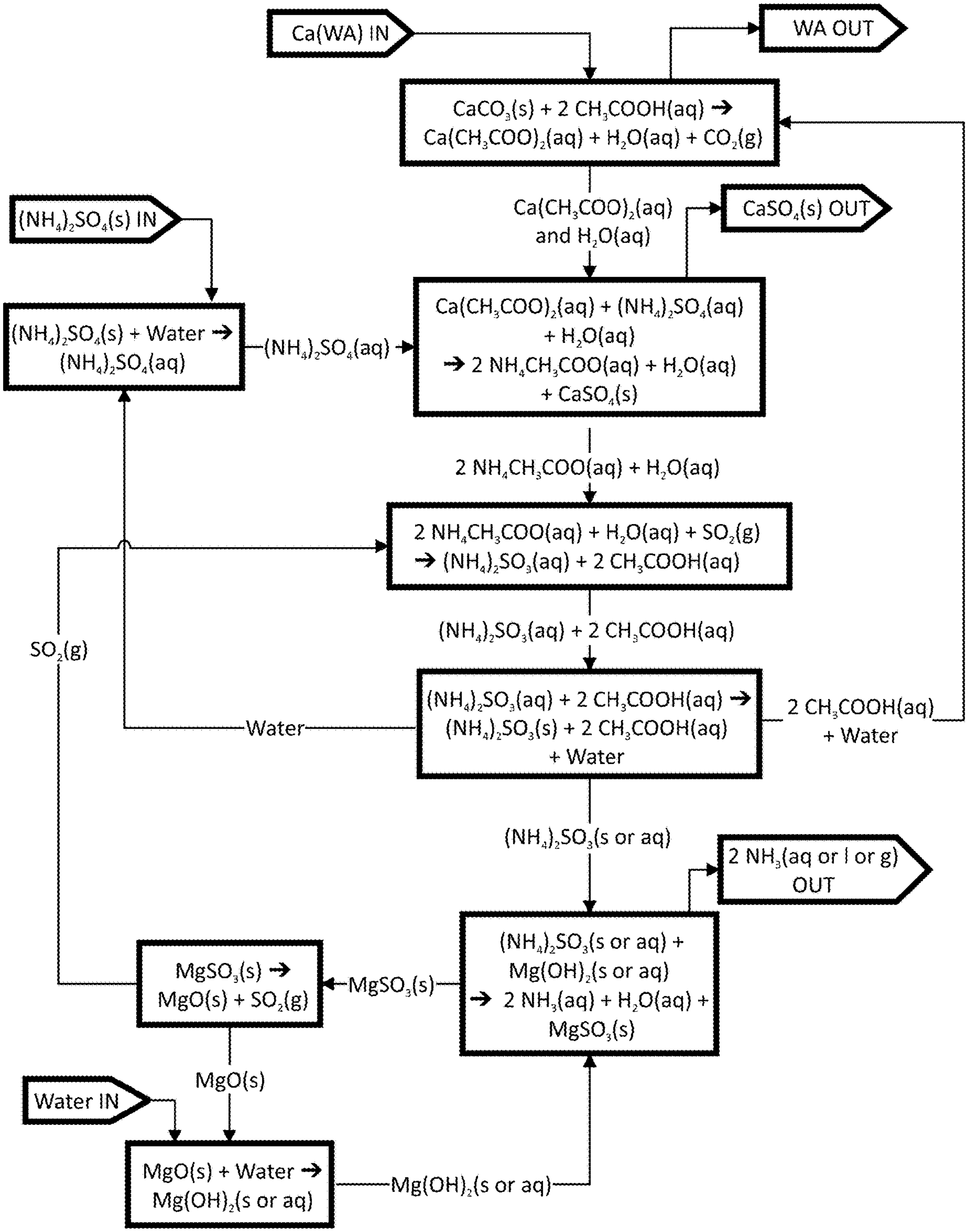

FIG. 22A: Process for producing or recovering ammonia from ammonium sulfate

Figure 22B:
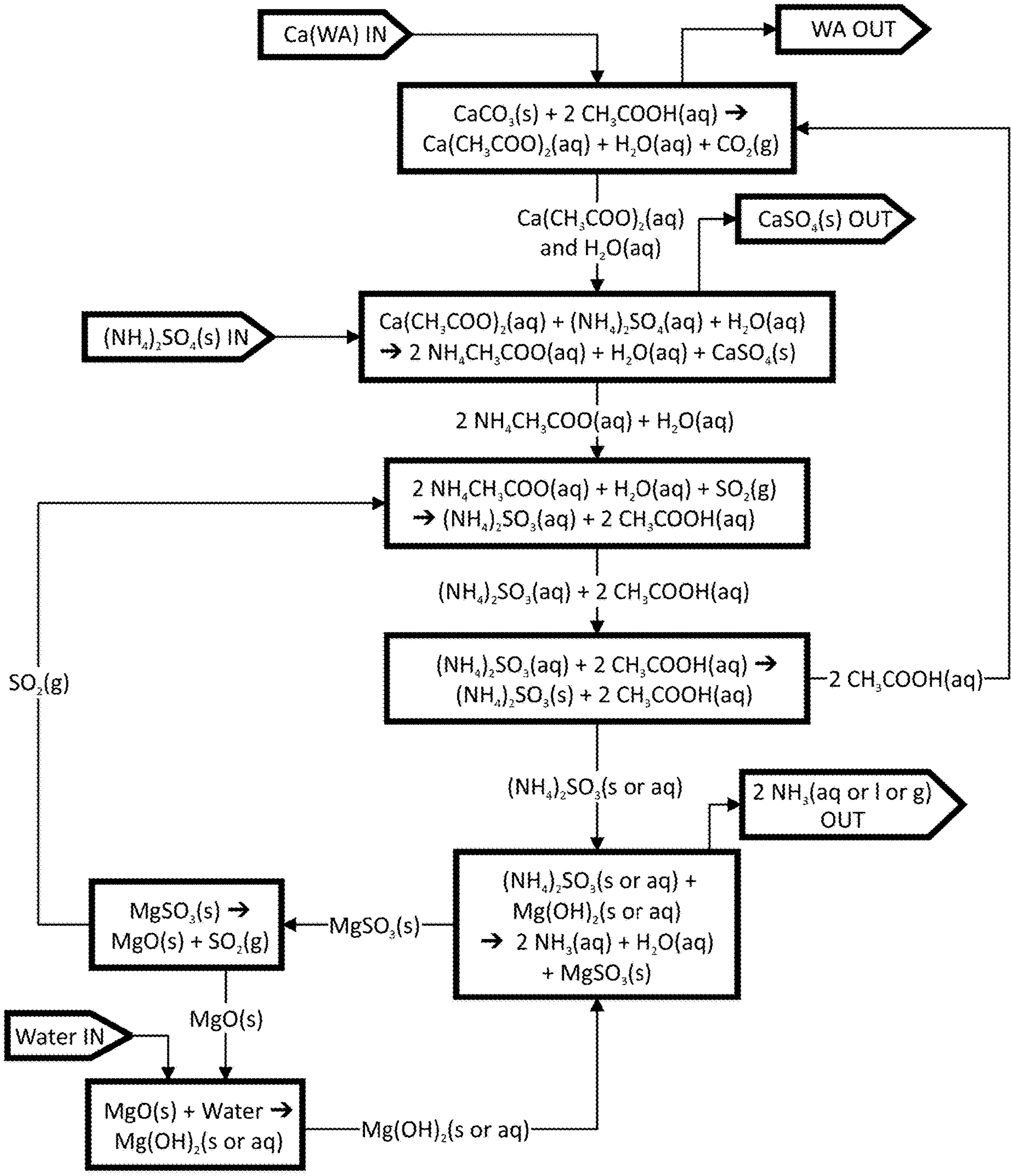

FIG. 22B: Process for producing or recovering ammonia from ammonium sulfate

Figure 22C:
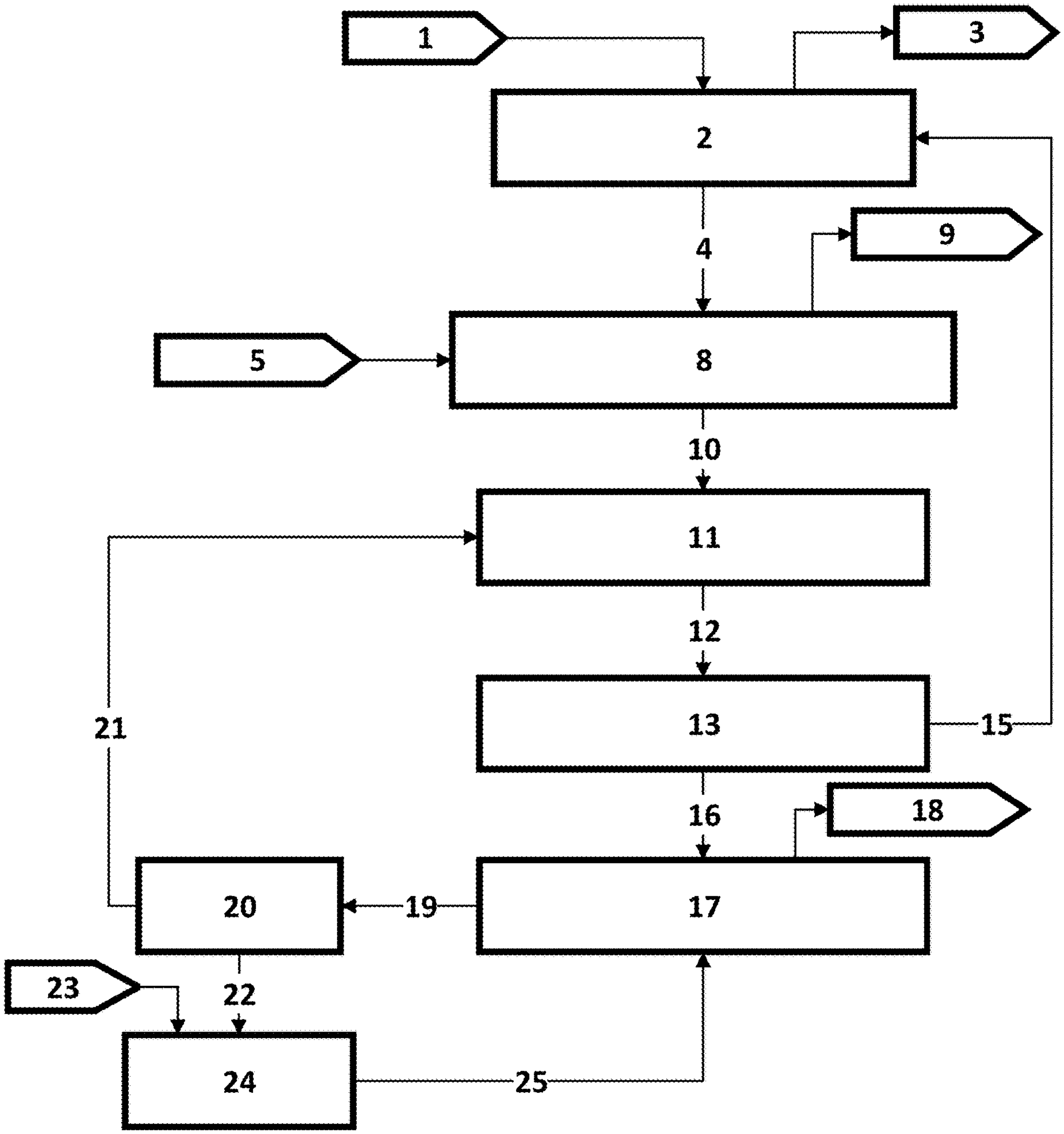

FIG. 22C: Process for producing or recovering ammonia from ammonium sulfate

Figure 23A:
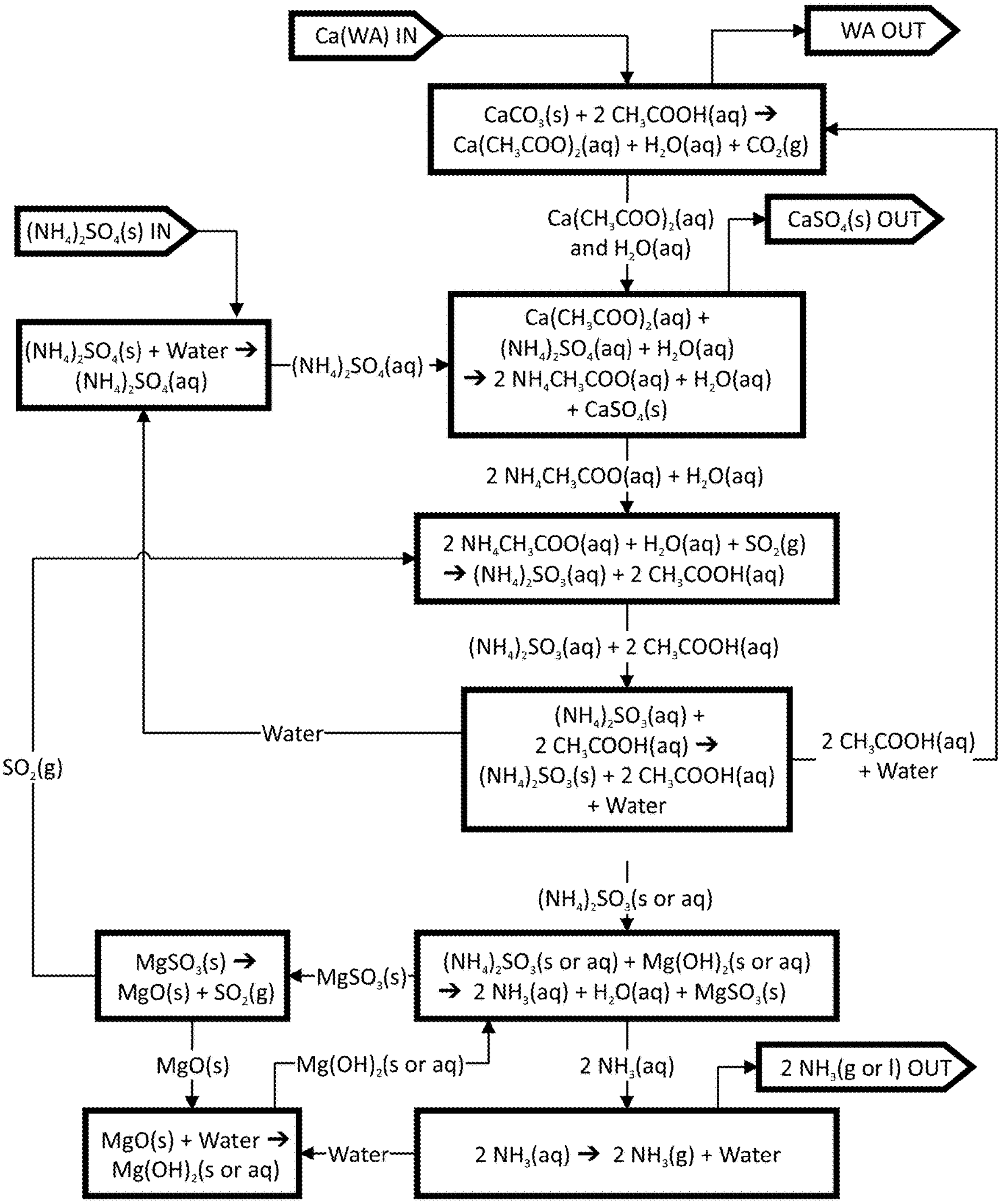

FIG. 23A: Process for producing or recovering ammonia from ammonium sulfate

Figure 23B:
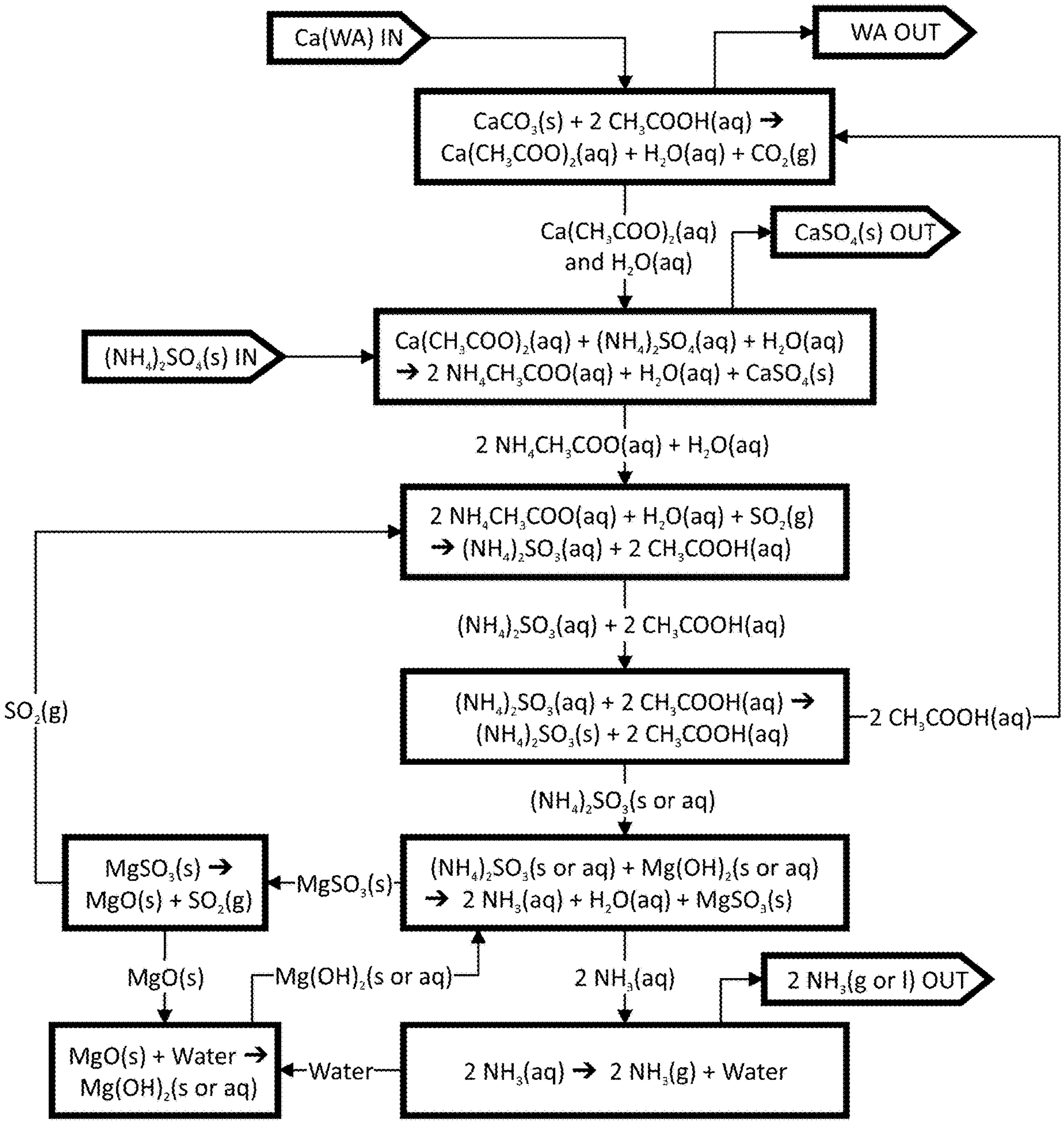

FIG. 23B: Process for producing or recovering ammonia from ammonium sulfate

Figure 23C:
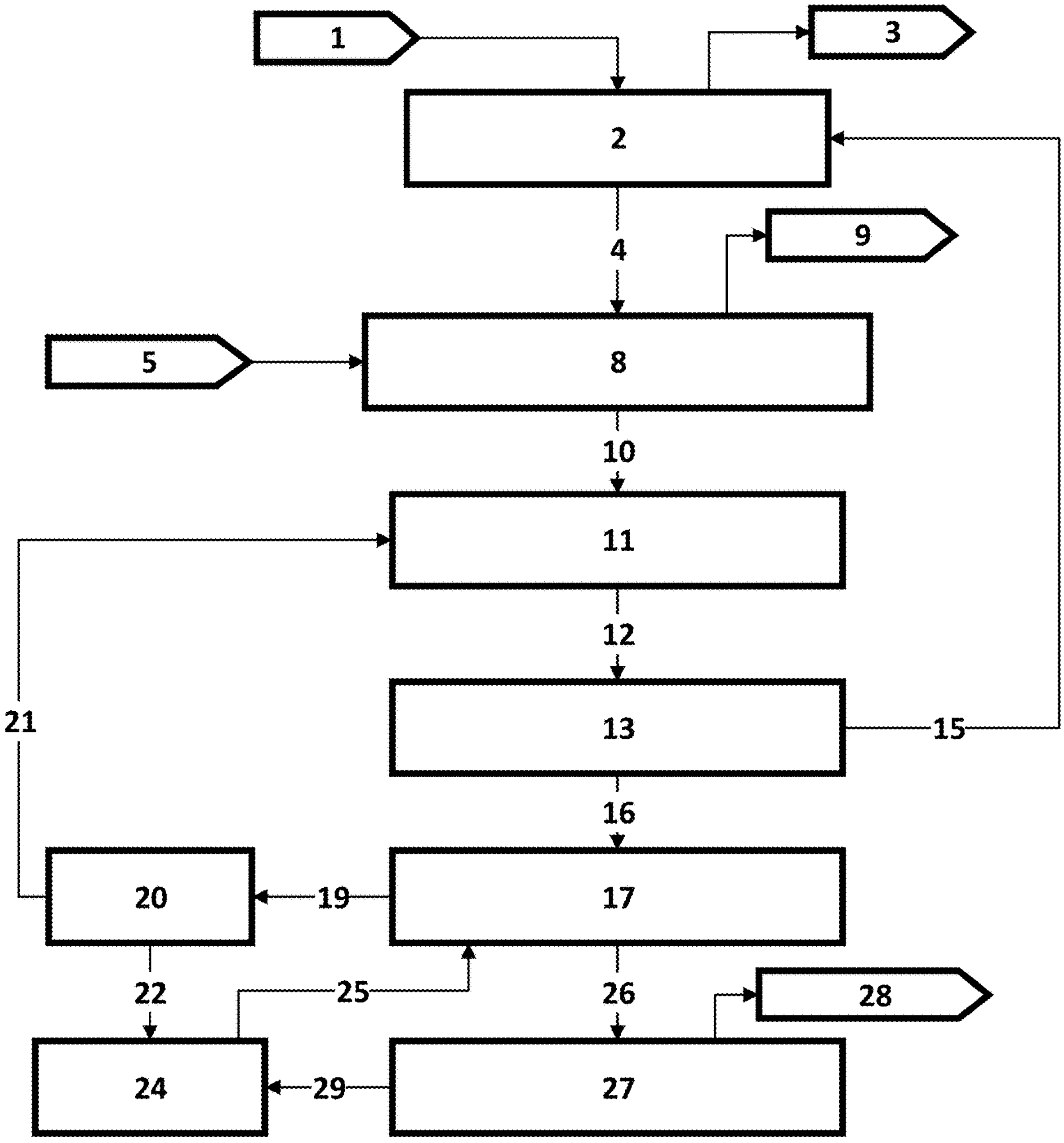

FIG. 23C: Process for producing or recovering ammonia from ammonium sulfate

Figure 24:
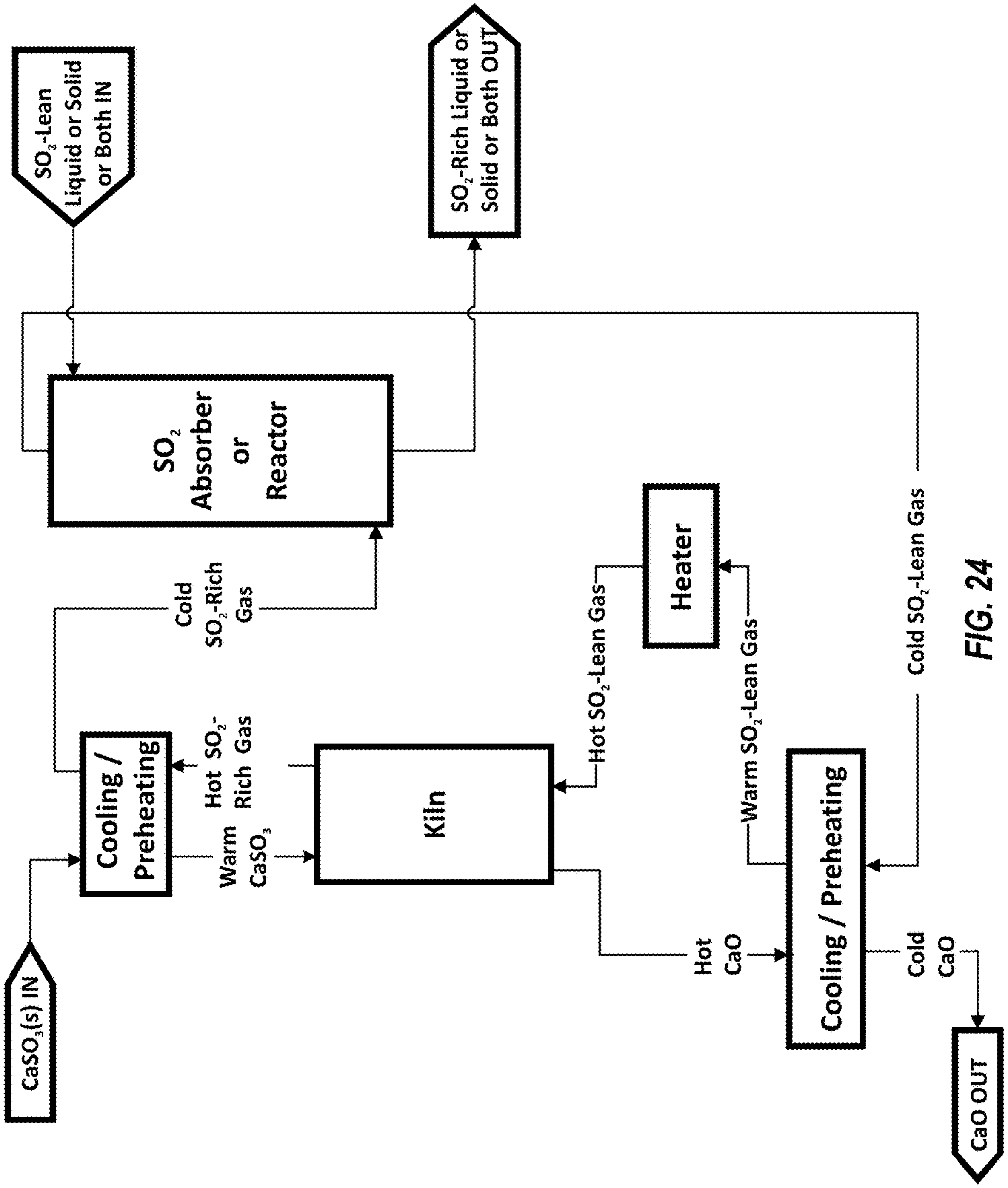
Figure 25:
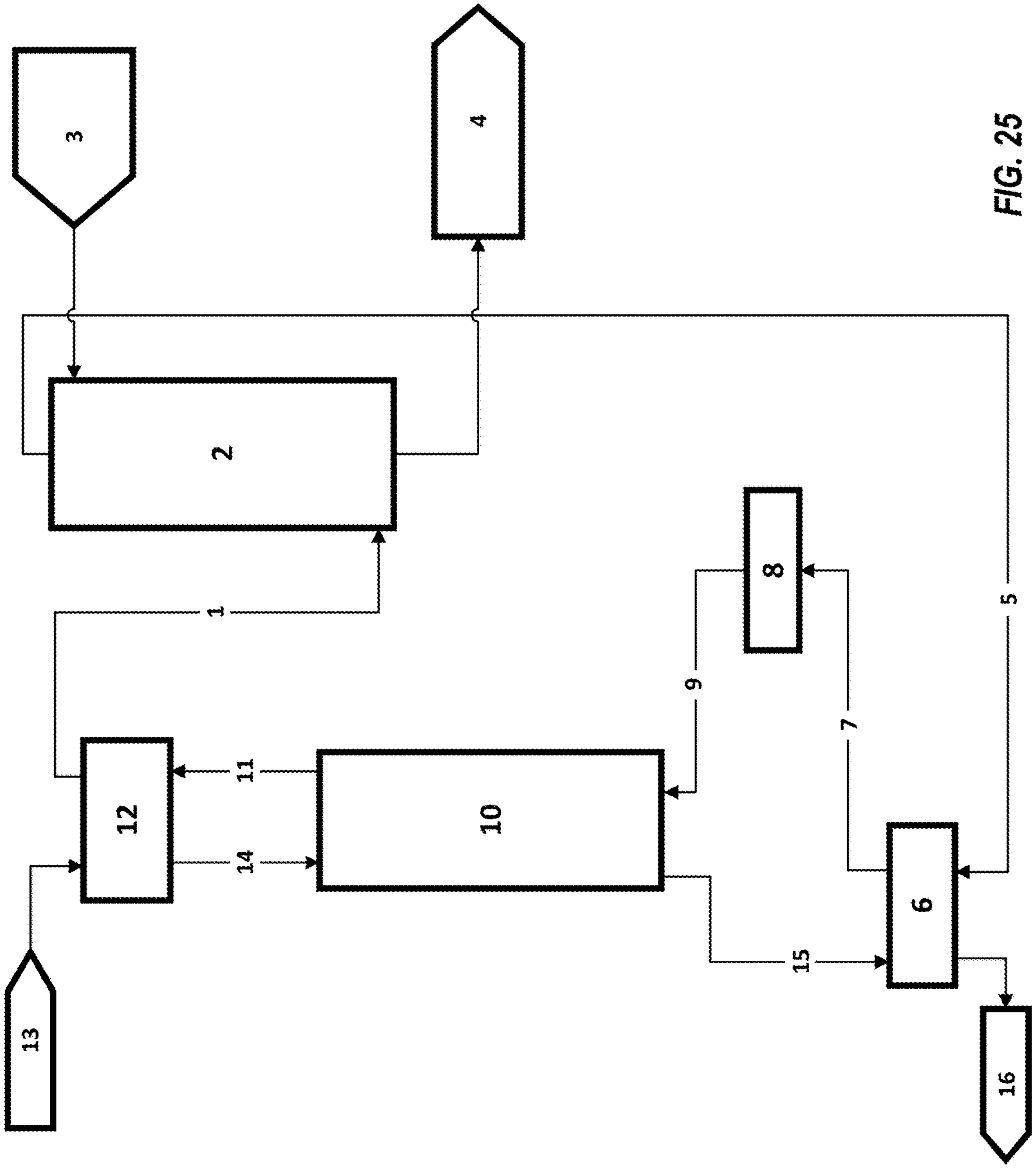
Figure 26A:
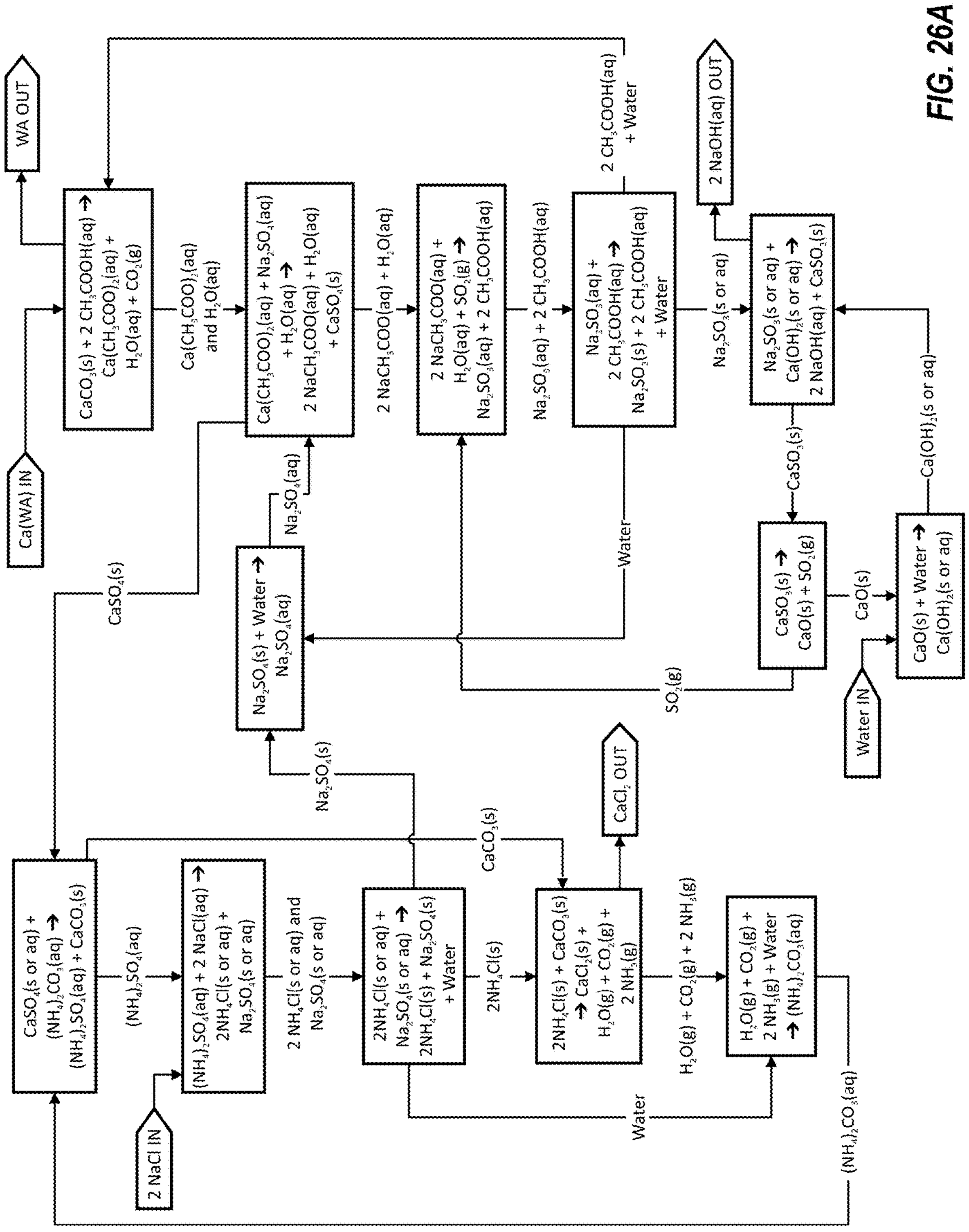

FIG. 24: Process for thermally decomposing or calcining alkaline earth sulfite to form alkaline earth oxide and sulfur dioxide and/or absorbing sulfur dioxide employing a recirculating carrier gas to, for example, enable use of zero emissions heat and/or enable low diatomic oxygen concentrations FIG. 25: Process for thermally decomposing or calcining alkaline earth sulfite to form alkaline earth oxide and sulfur dioxide and/or absorbing sulfur dioxide employing a recirculating carrier gas FIG. 26A: Process for producing alkali hydroxide using carboxylic acid and sulfur dioxide intermediates from alkali chloride.

Figure 26B:
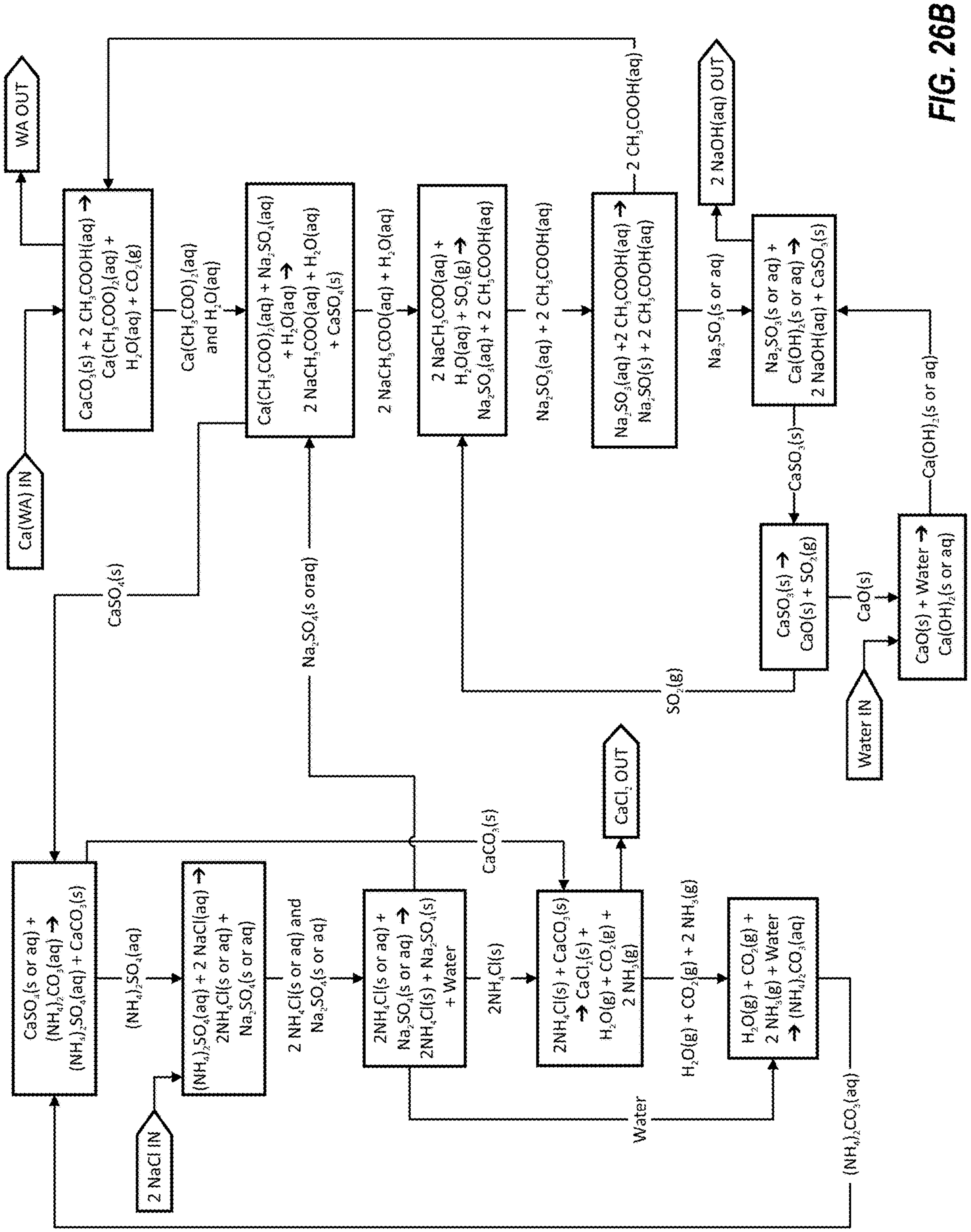

FIG. 26B: Process for producing alkali hydroxide using carboxylic acid and sulfur dioxide intermediates from alkali chloride.

Figure 26C:
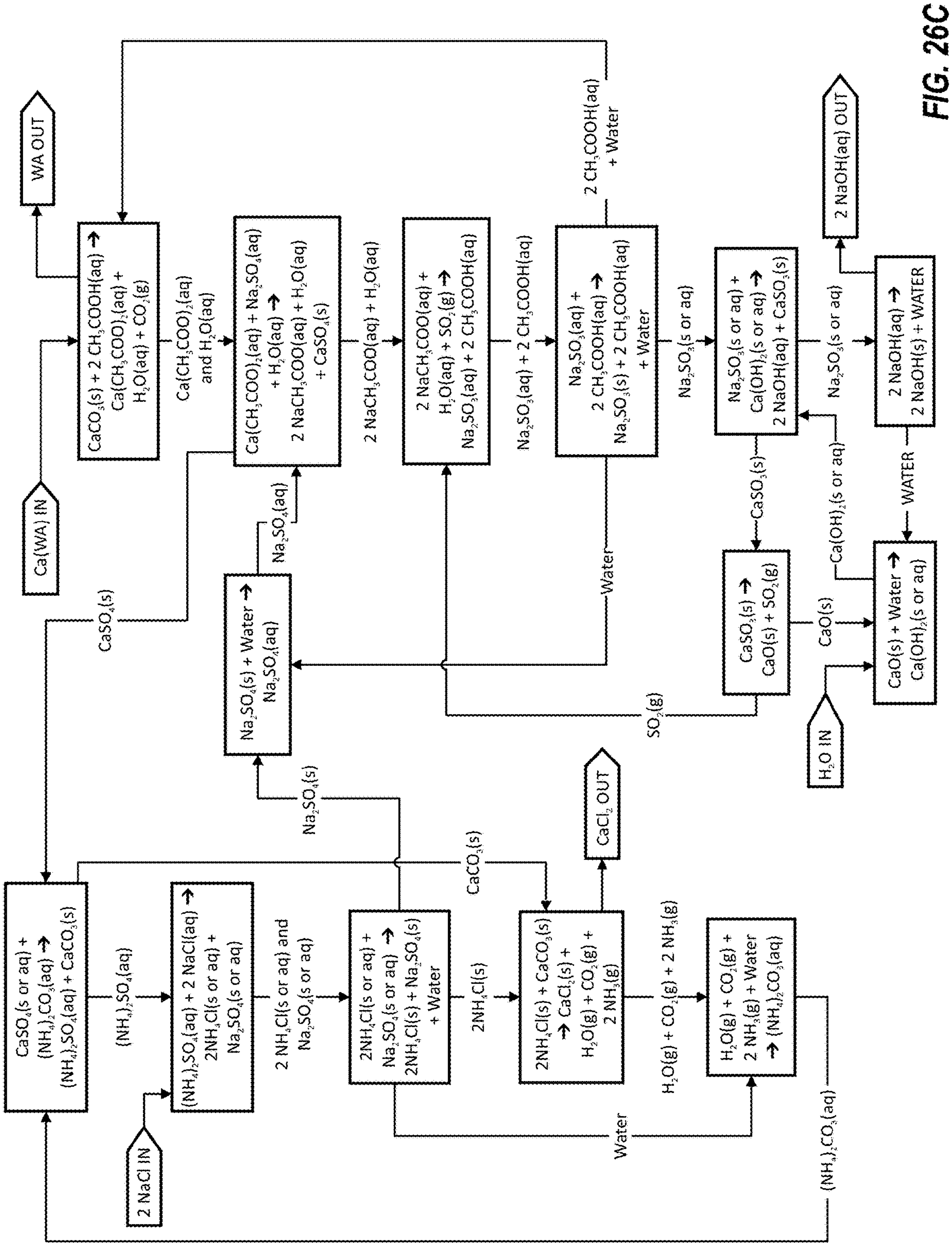

FIG. 26C: Process for producing alkali hydroxide using carboxylic acid and sulfur dioxide intermediates from alkali chloride.

Figure 26D:
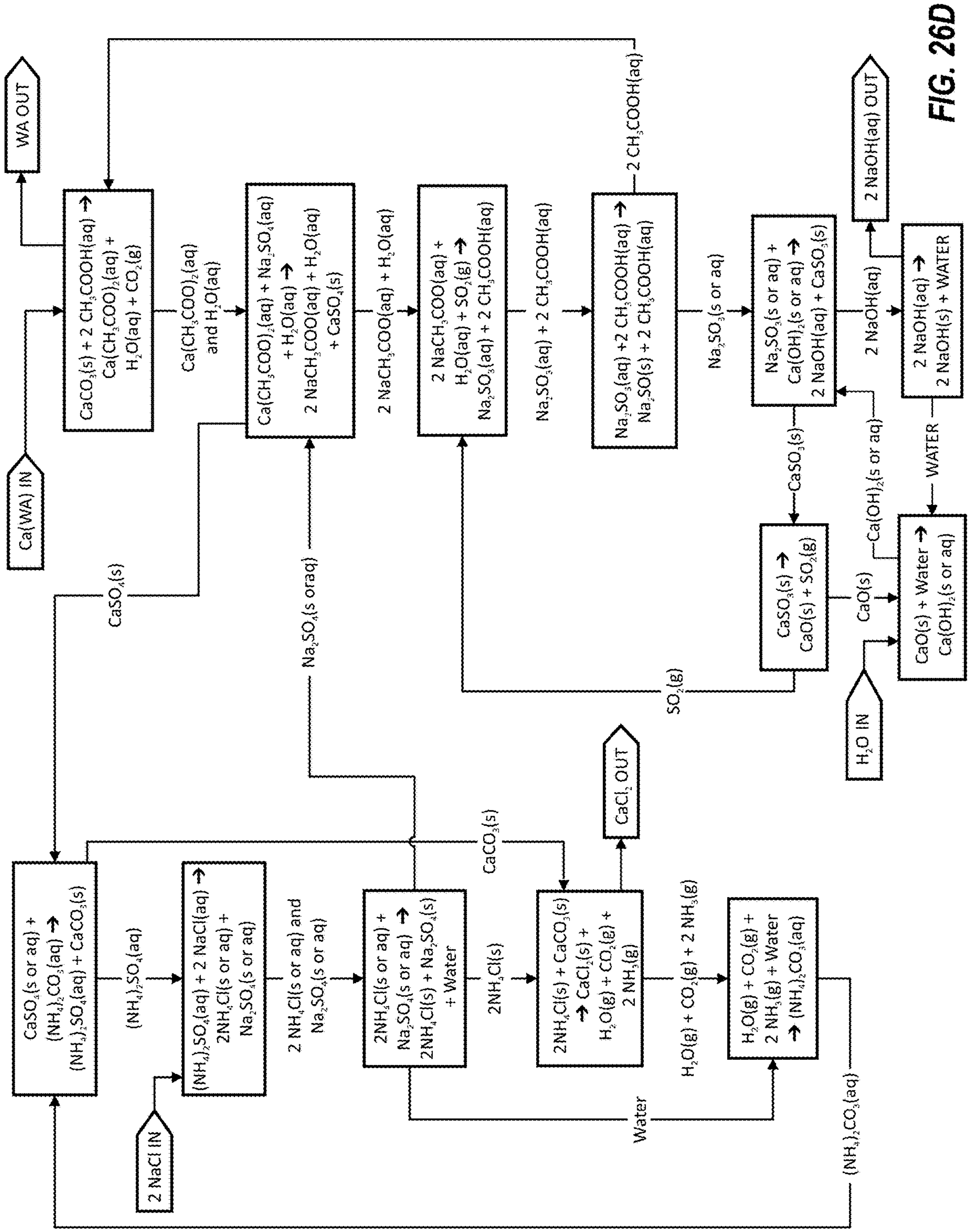

FIG. 26D: Process for producing alkali hydroxide using carboxylic acid and sulfur dioxide intermediates from alkali chloride.

Figure 27:
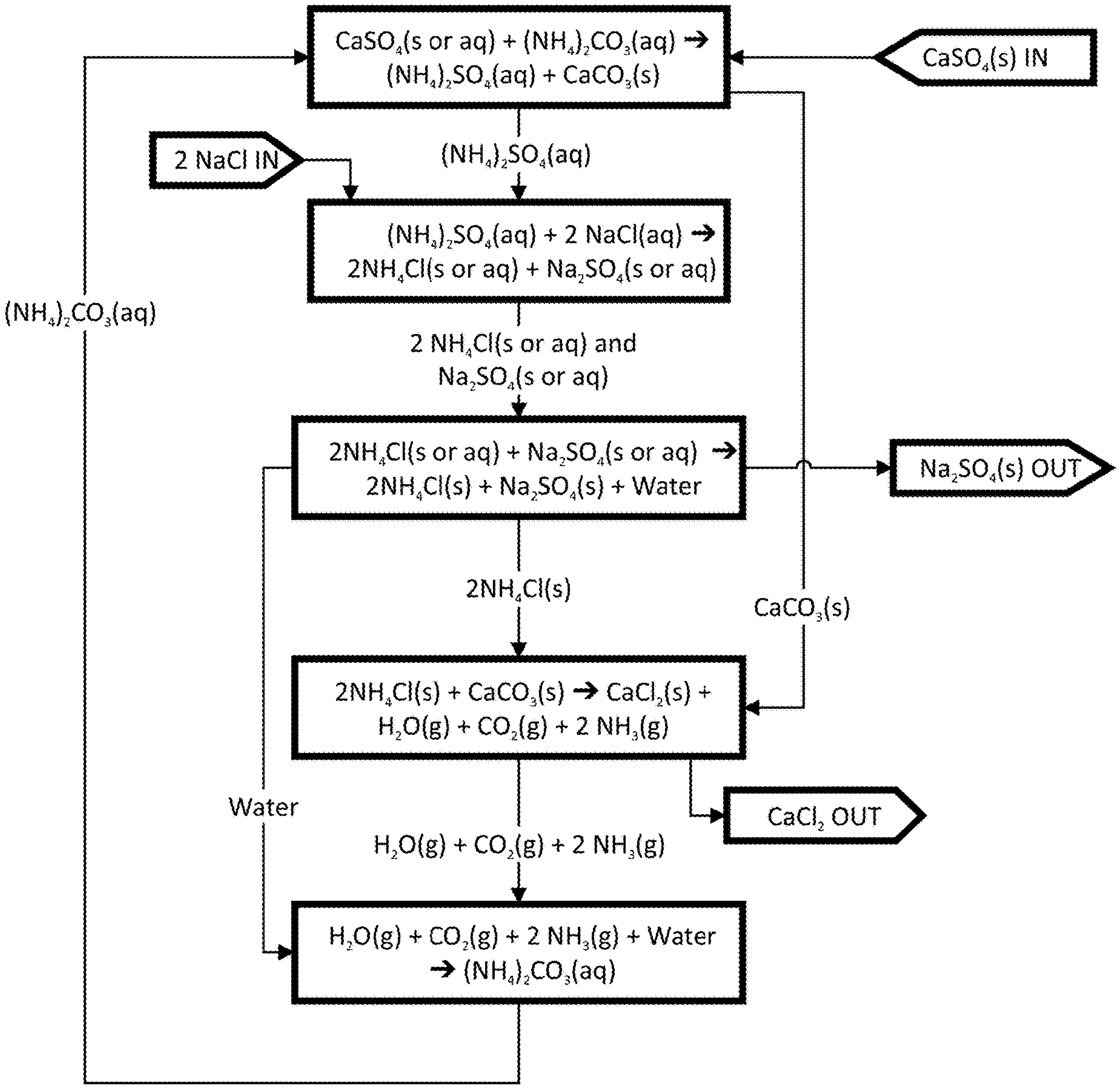
Figure 28A:
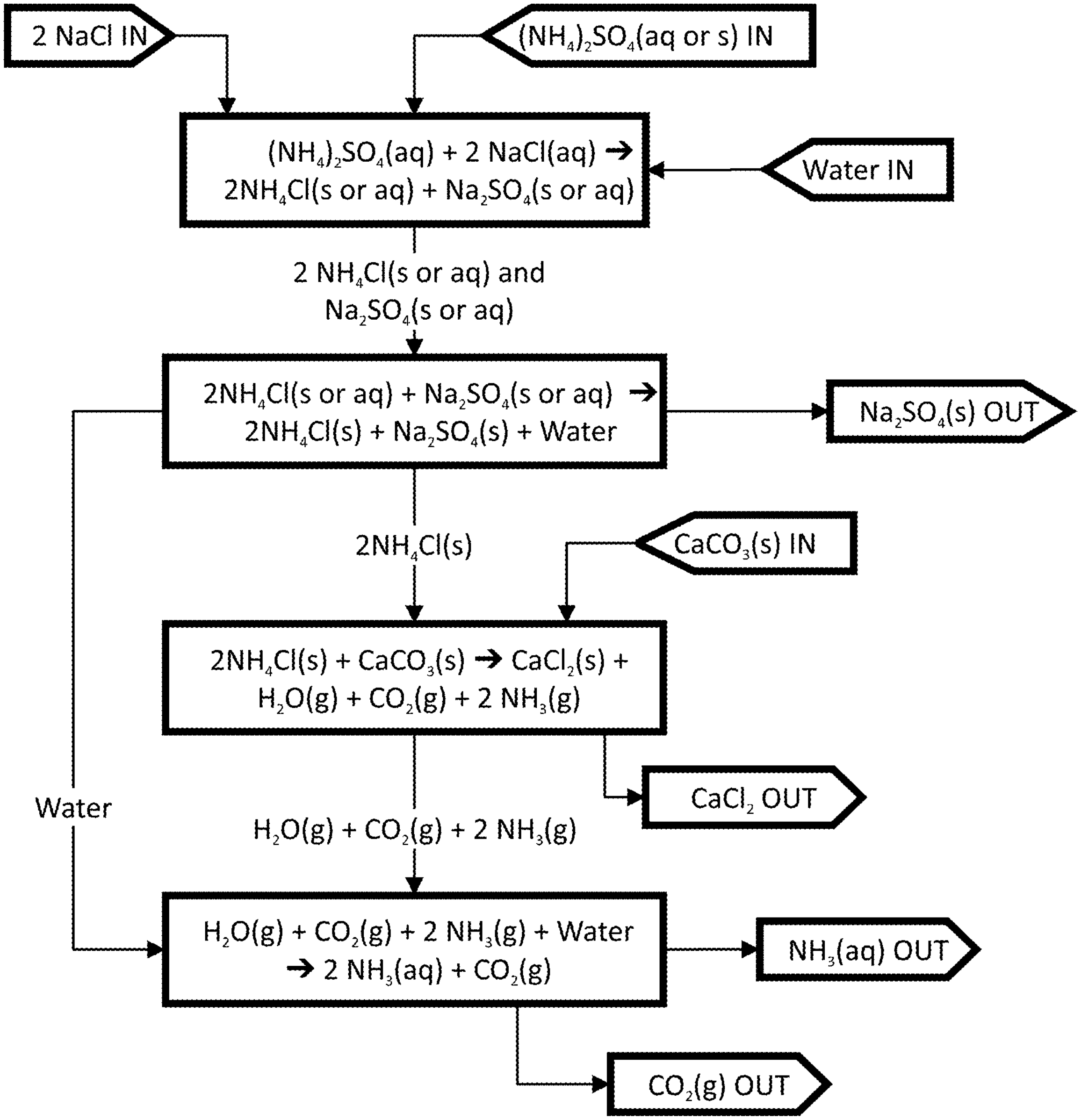
Figure 28B:
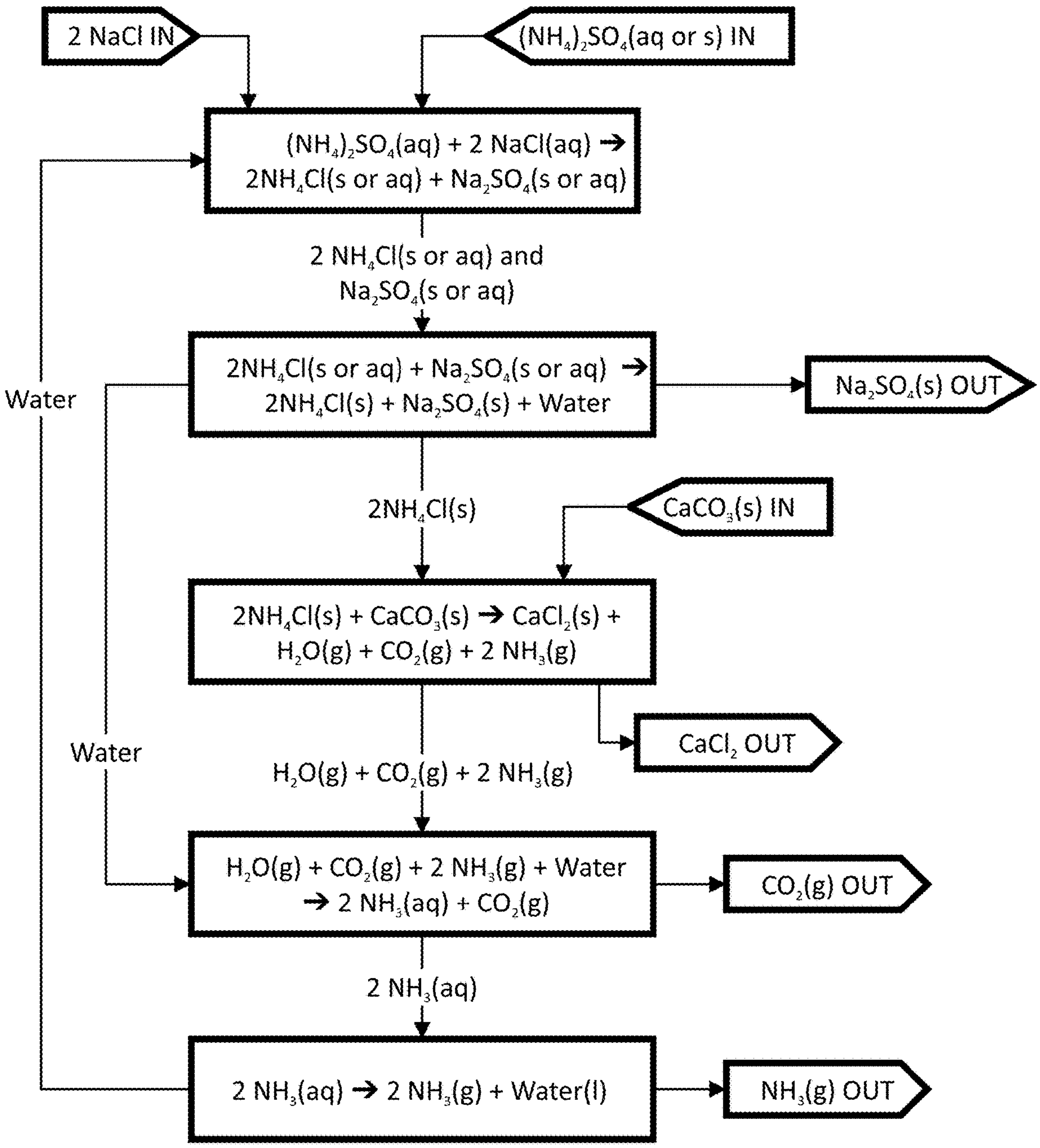
Figure 28C:
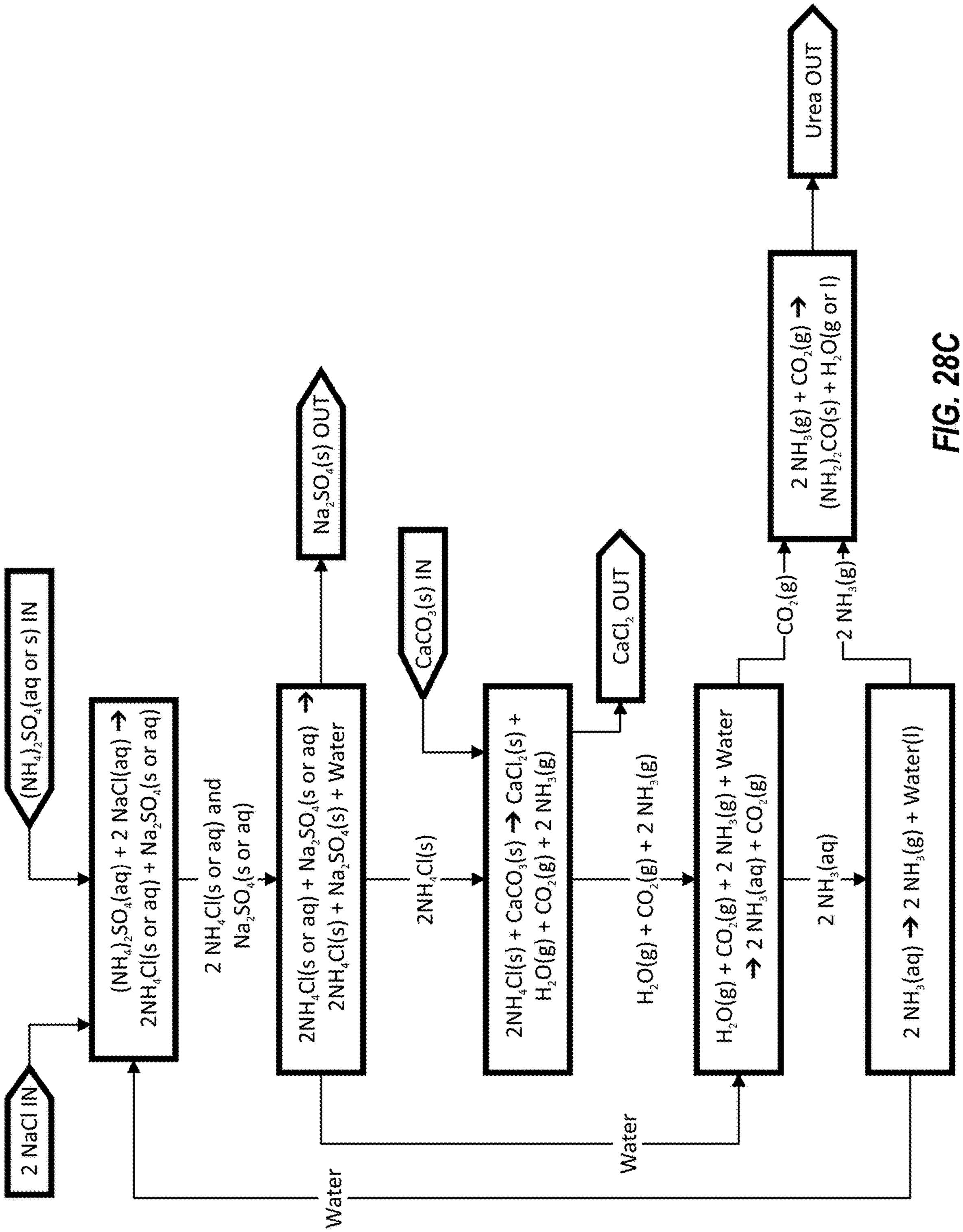
Figure 29:
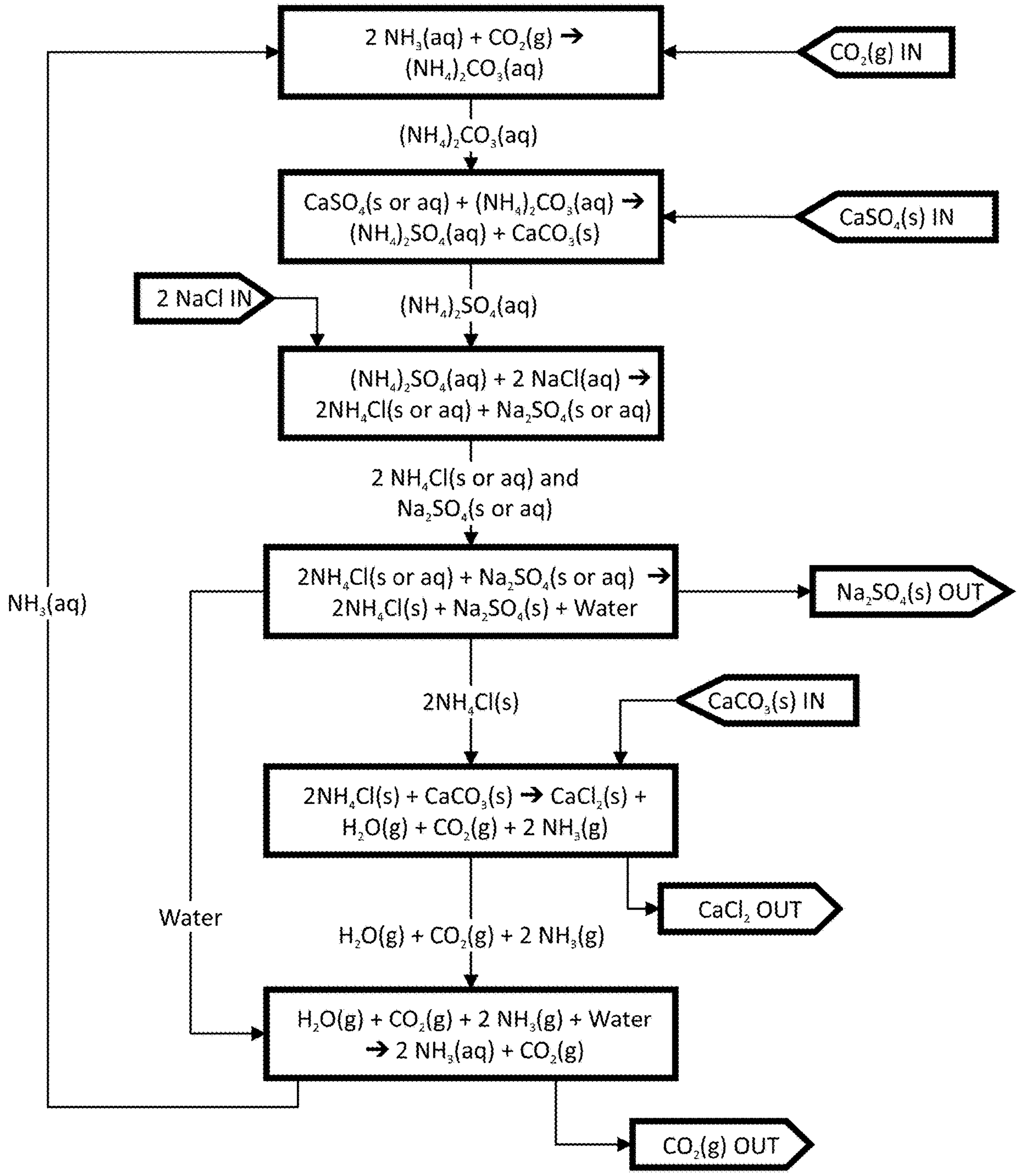
Figure 30:
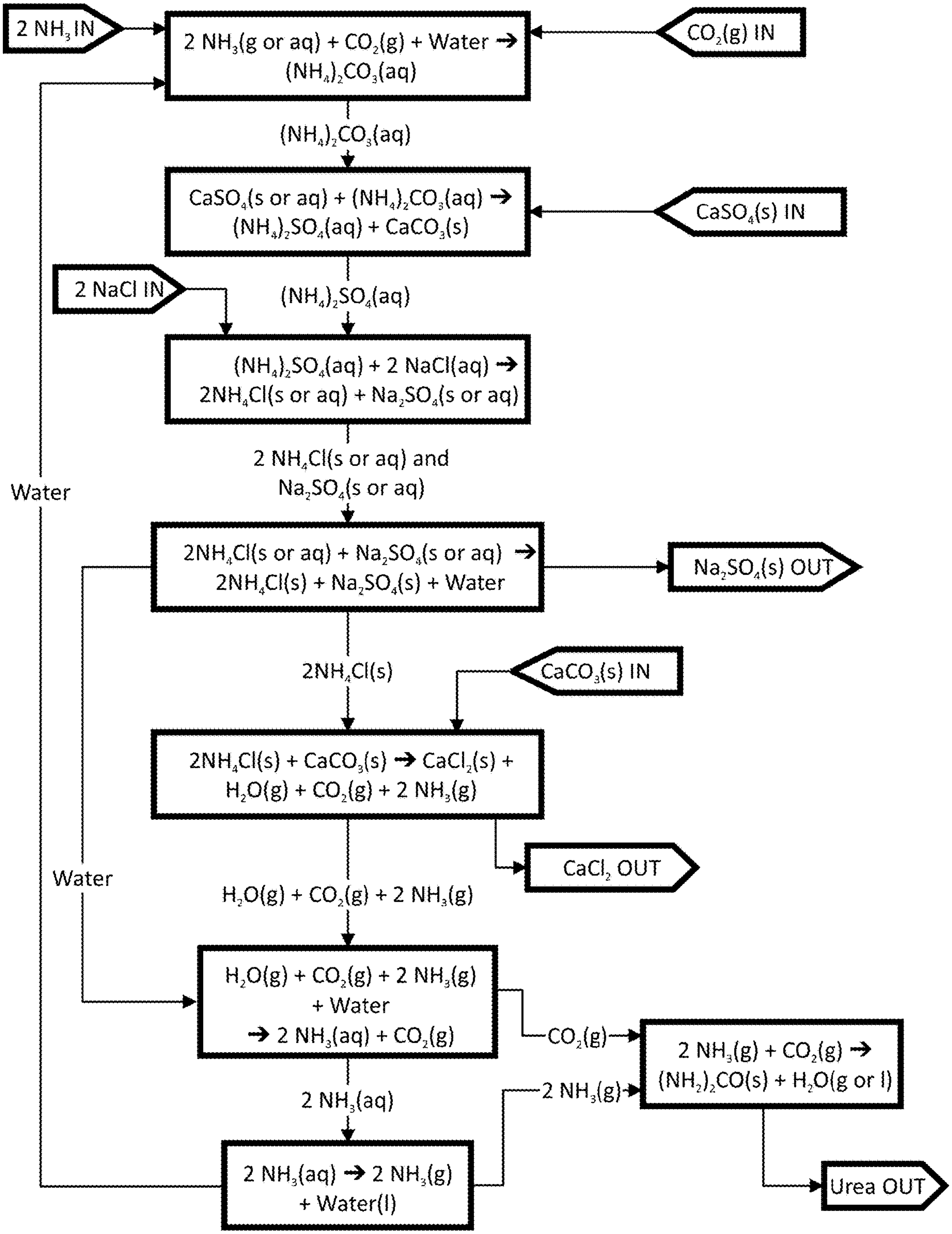
Figure 31A:
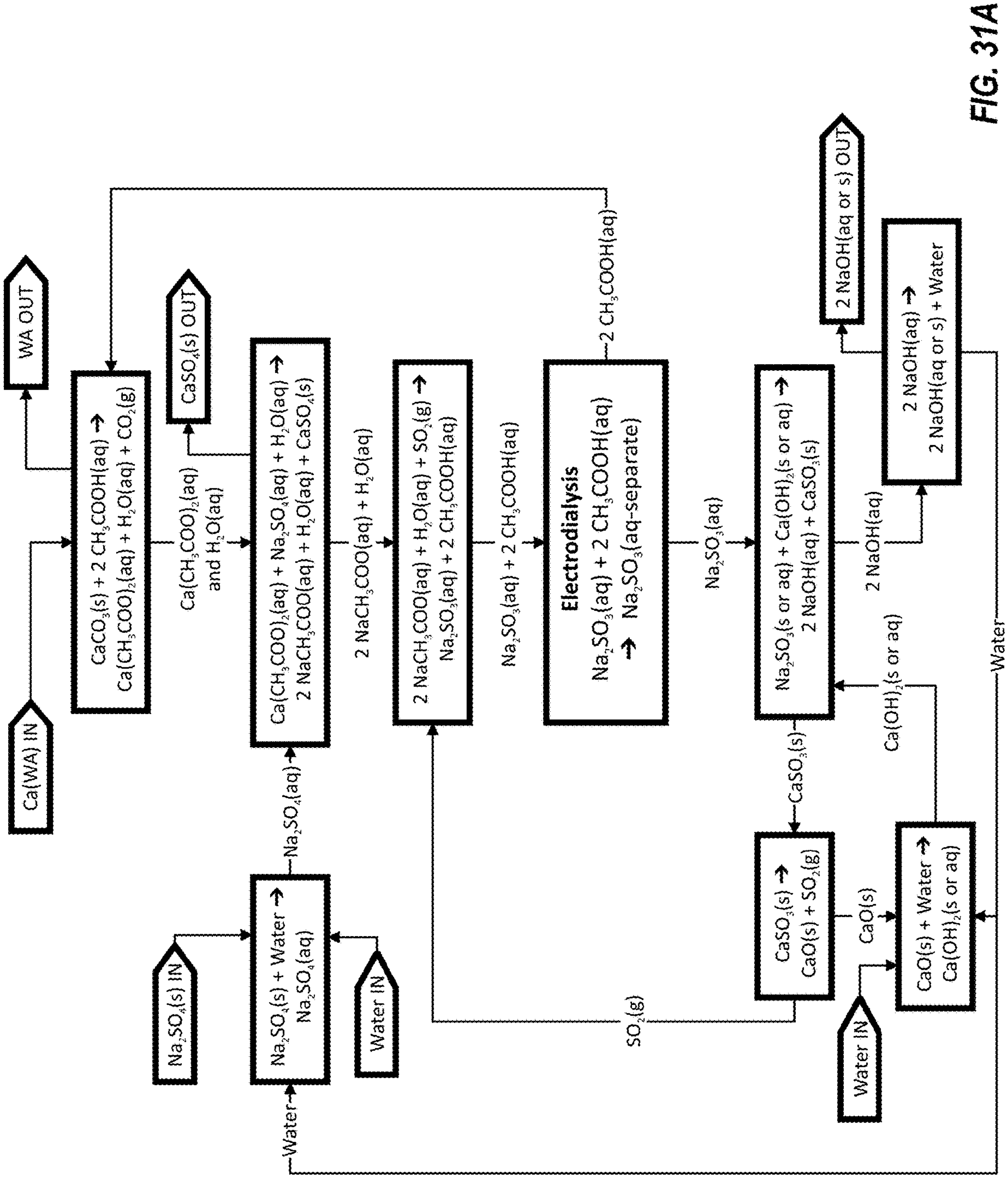
Figure 31B:
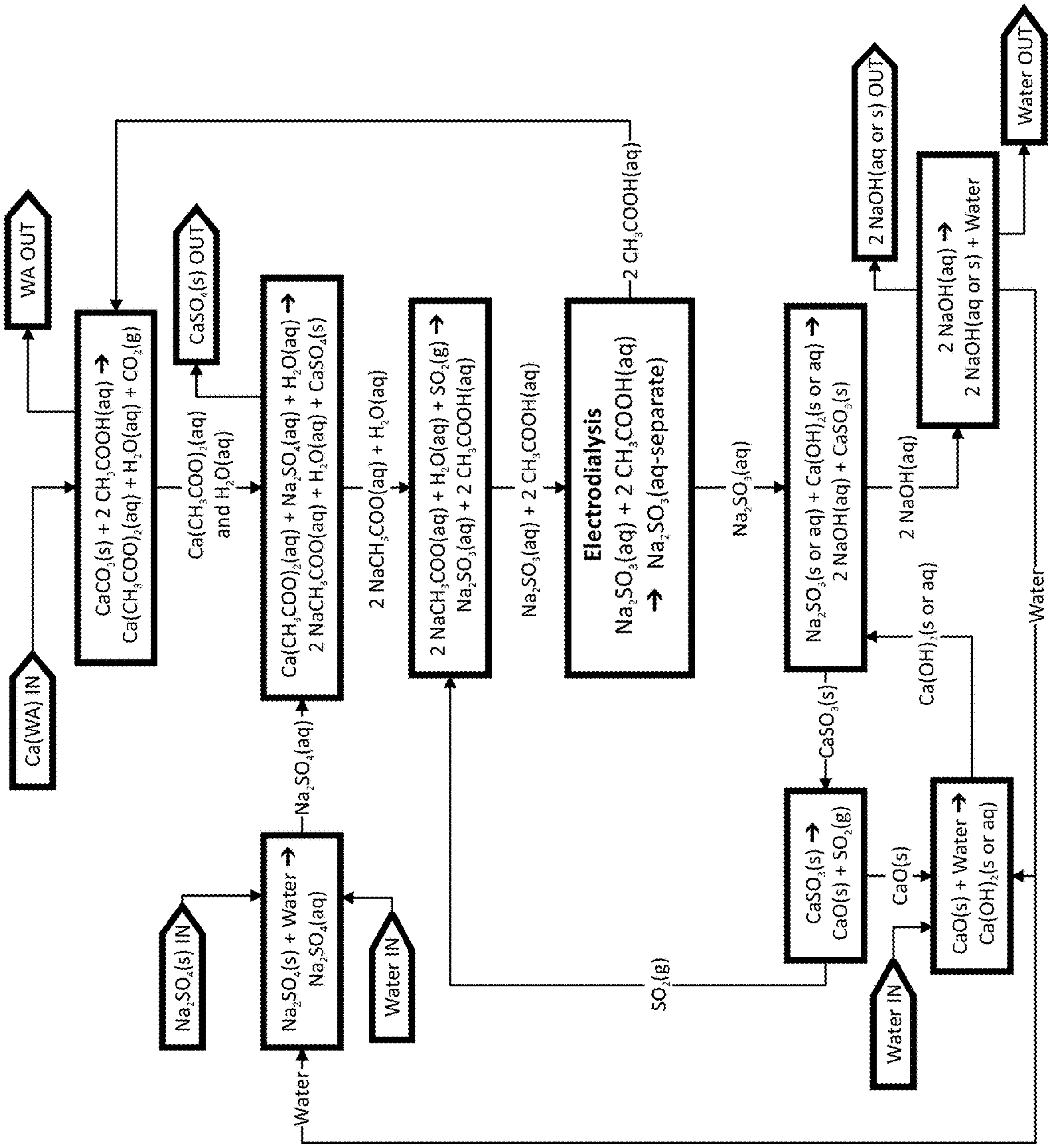
Figure 31C:
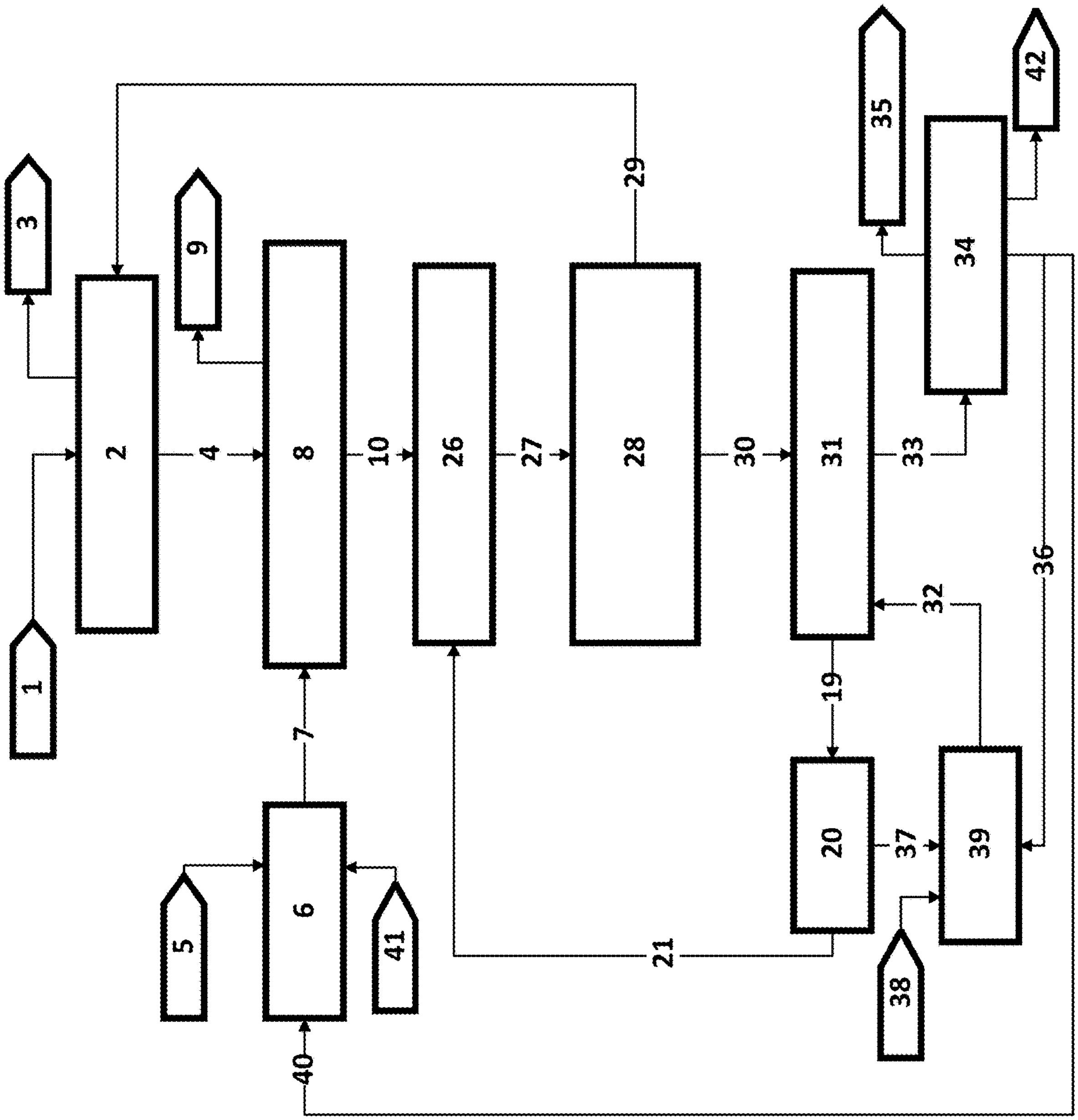
Figure 32A:
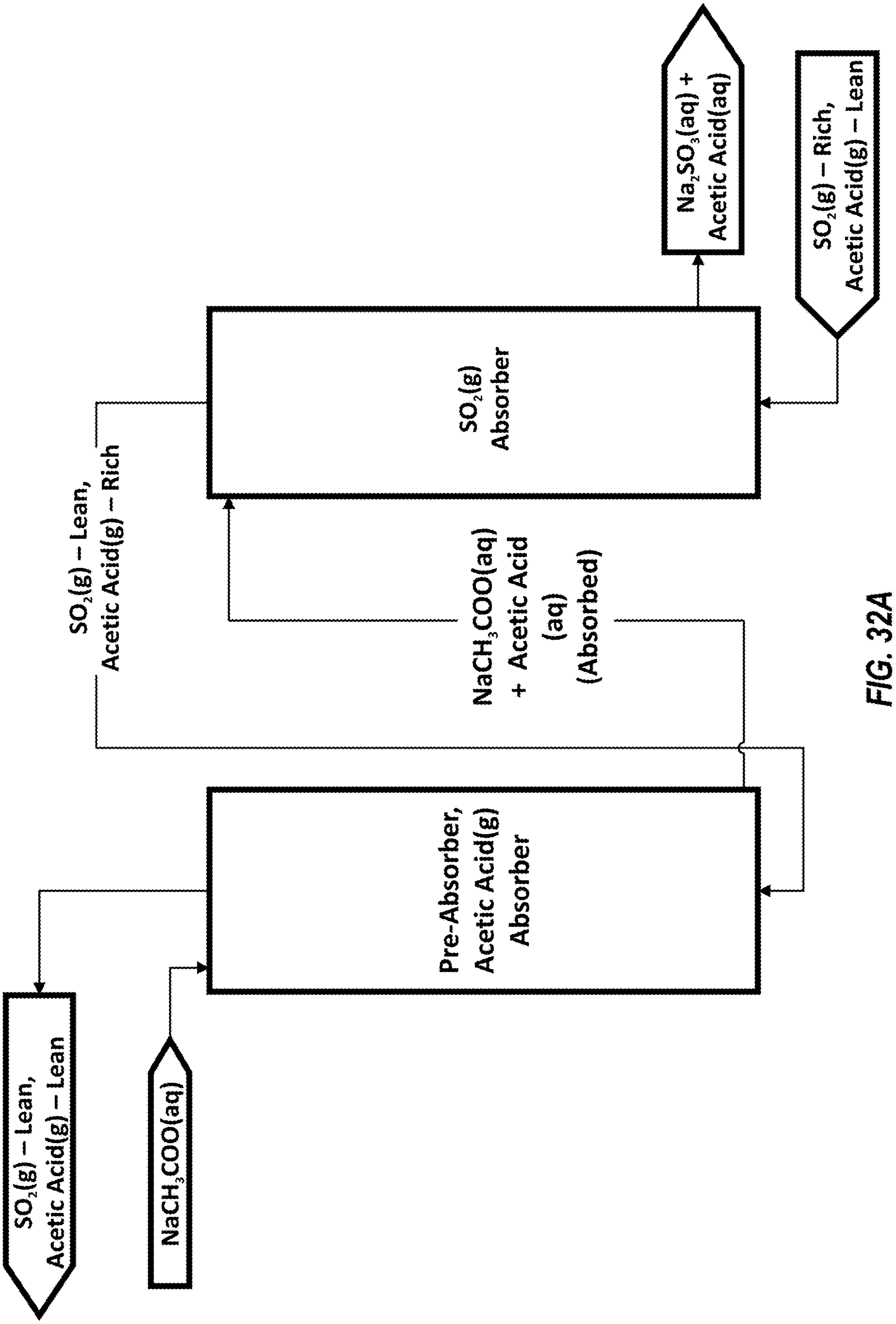

FIG. 27: Process for producing alkali sulfate from alkali chloride and alkaline earth sulfate using ammonia and carbon dioxide intermediates FIG. 28A: Process for producing alkali sulfate from alkali chloride and alkaline earth sulfate using ammonia and carbon dioxide intermediates FIG. 28B: Process for producing alkali sulfate from alkali chloride and alkaline earth sulfate using ammonia and carbon dioxide intermediates FIG. 28C: Process for producing alkali sulfate from alkali chloride and alkaline earth sulfate using ammonia and carbon dioxide intermediates FIG. 29: Process for producing alkali sulfate and capturing $CO_2$ employing alkali chloride and alkaline earth sulfate using ammonia and carbon dioxide intermediates FIG. 30: Process for producing alkali sulfate, capturing $CO_2$, and/or producing urea employing alkali chloride and alkaline earth sulfate using ammonia and carbon dioxide FIG. 31A: Process for producing alkali hydroxide from alkali sulfite employing acid and sulfur dioxide intermediates FIG. 31B: Process for producing alkali hydroxide from alkali sulfite employing acid and sulfur dioxide intermediates FIG. 31C: Process for producing alkali hydroxide from alkali sulfite employing acid and sulfur dioxide intermediates FIG. 32A: Process for absorbing or reacting sulfur dioxide within alkali acid-anion, such as alkali carboxylate, in a manner which may minimize or reduce potential residual vapor in remaining gases.

Figure 32B:
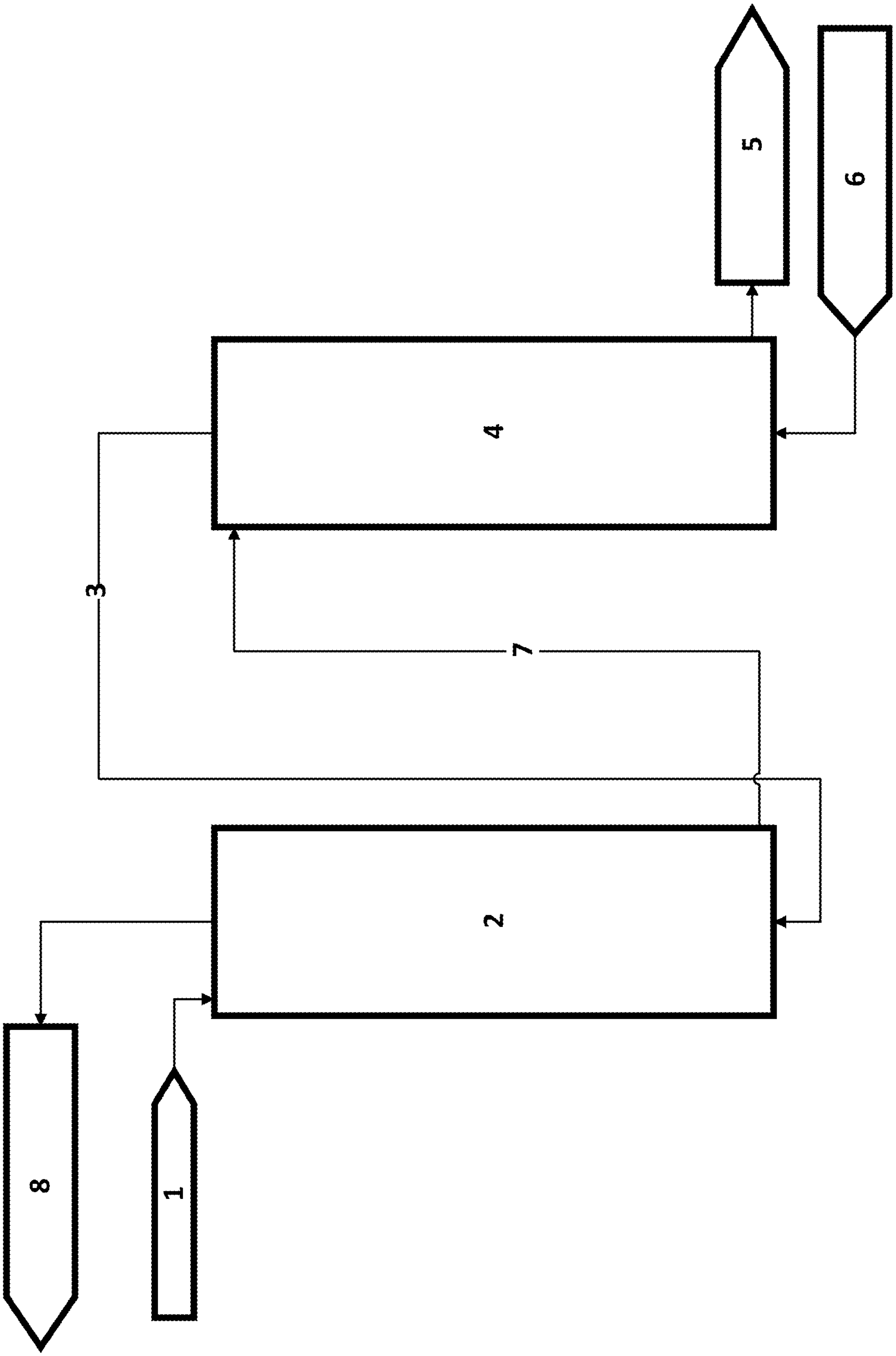

FIG. 32B: Process for absorbing or reacting sulfur dioxide within alkali acid-anion, such as alkali carboxylate, in a manner which may minimize or reduce potential residual vapor in remaining gases.

Figure 33:
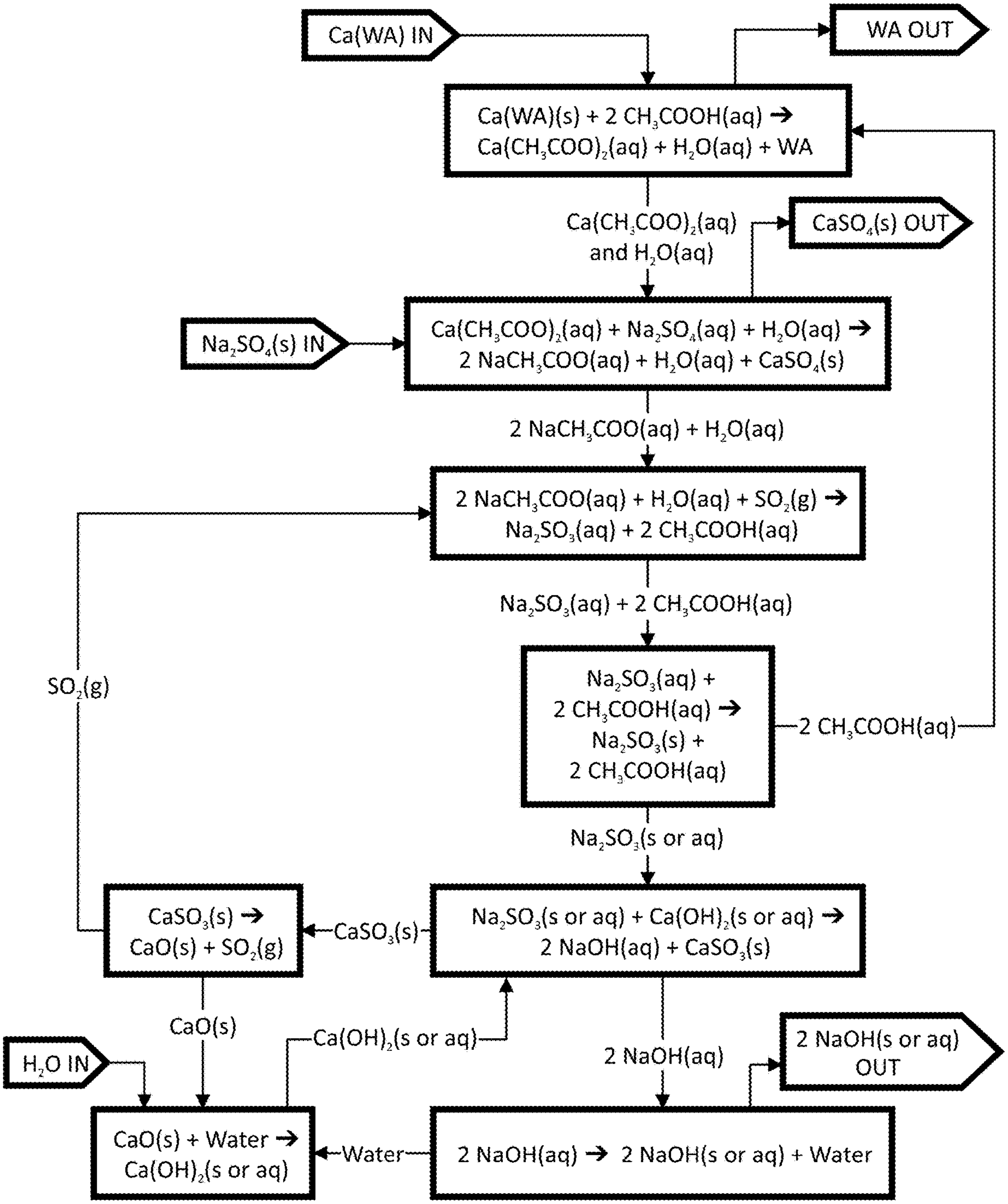

FIG. 33: Process for producing alkali hydroxide from alkali sulfate using carboxylic acid and sulfur dioxide intermediates.

Figure 34:
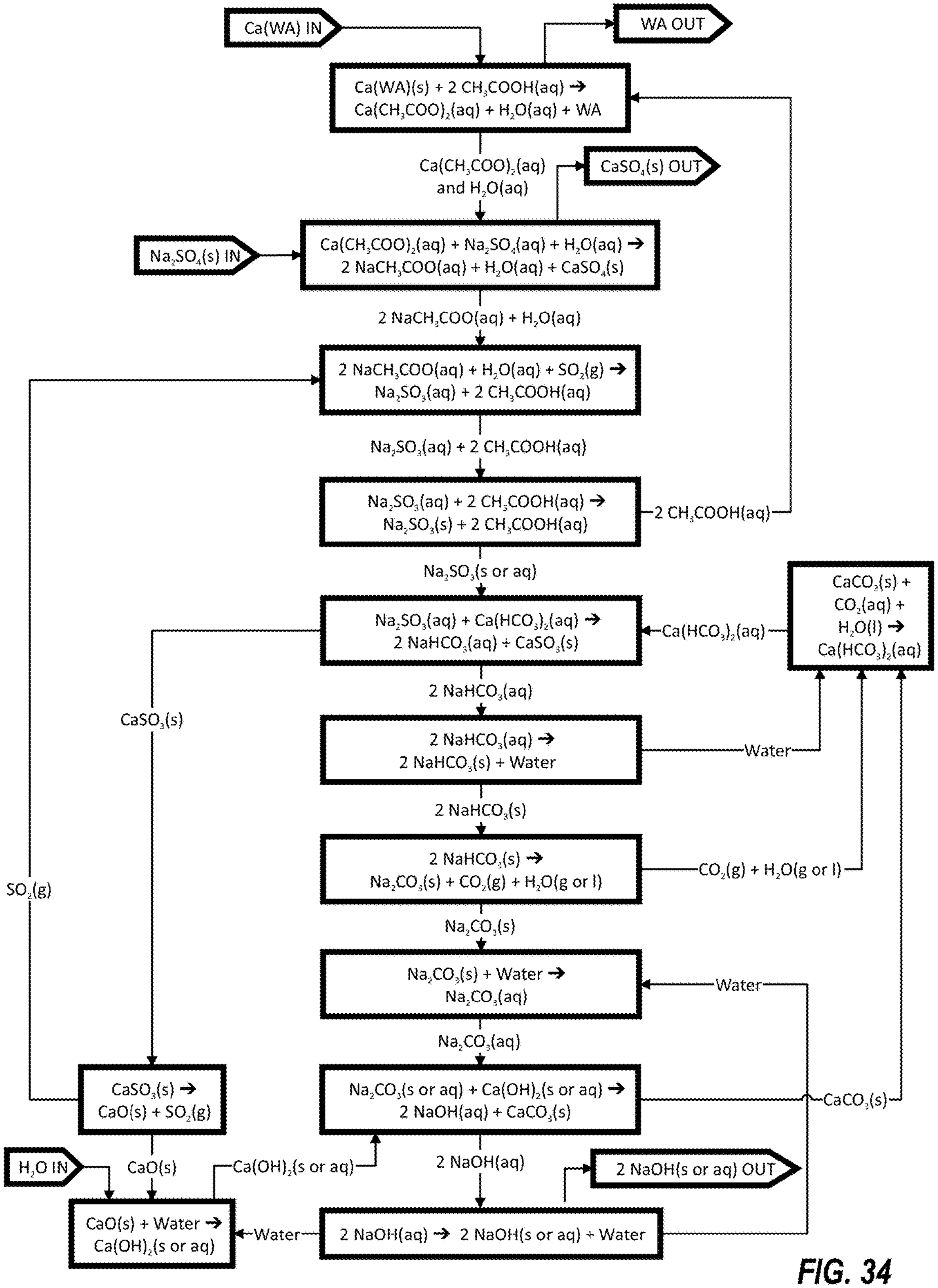

FIG. 34: Process for producing alkali hydroxide from alkali sulfate using carboxylic acid, sulfur dioxide, and carbon dioxide intermediates.

Figure 35:
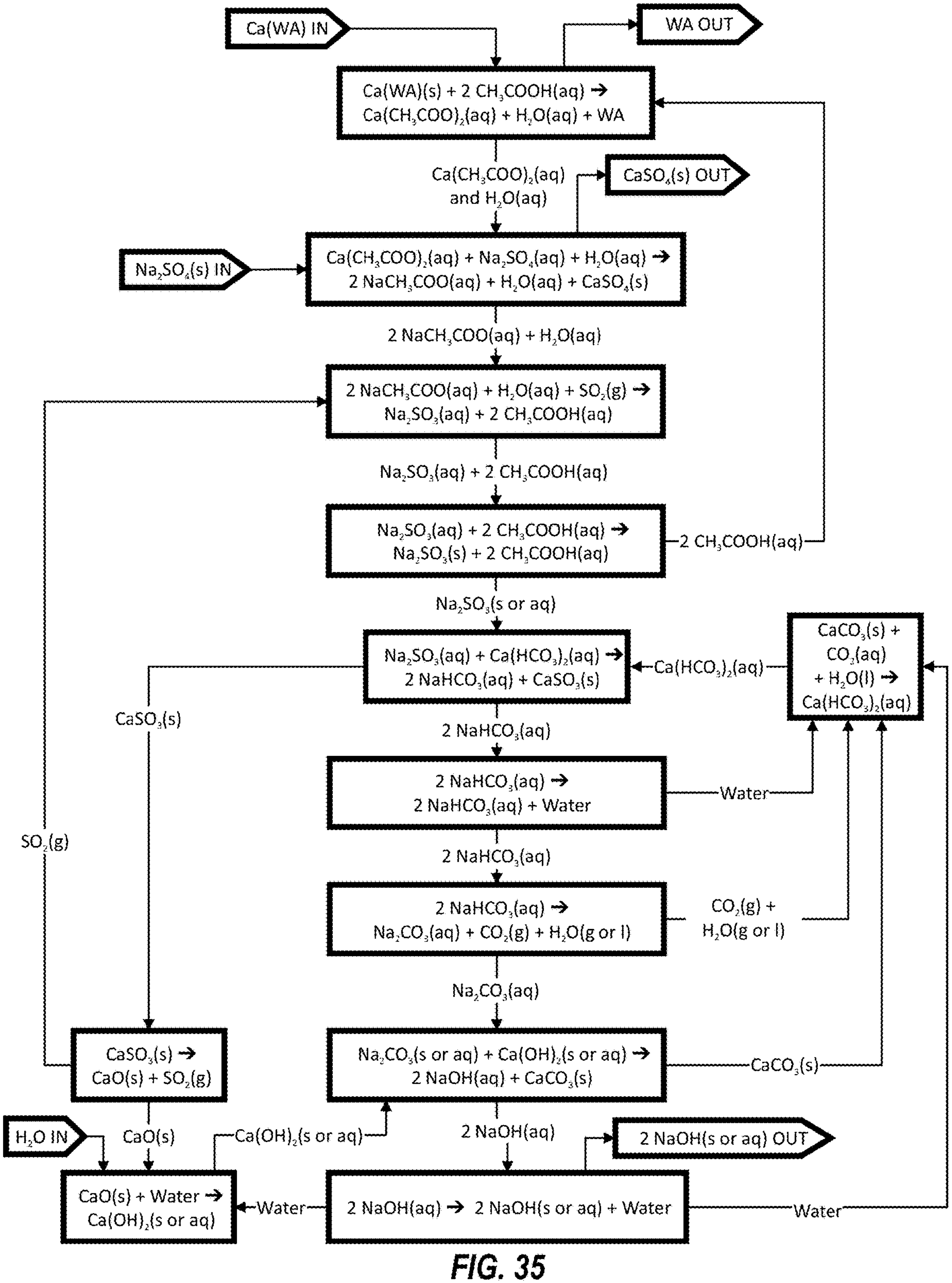

FIG. 35: Process for producing alkali hydroxide from alkali sulfate using carboxylic acid, sulfur dioxide, and carbon dioxide intermediates.

Figure 36A:
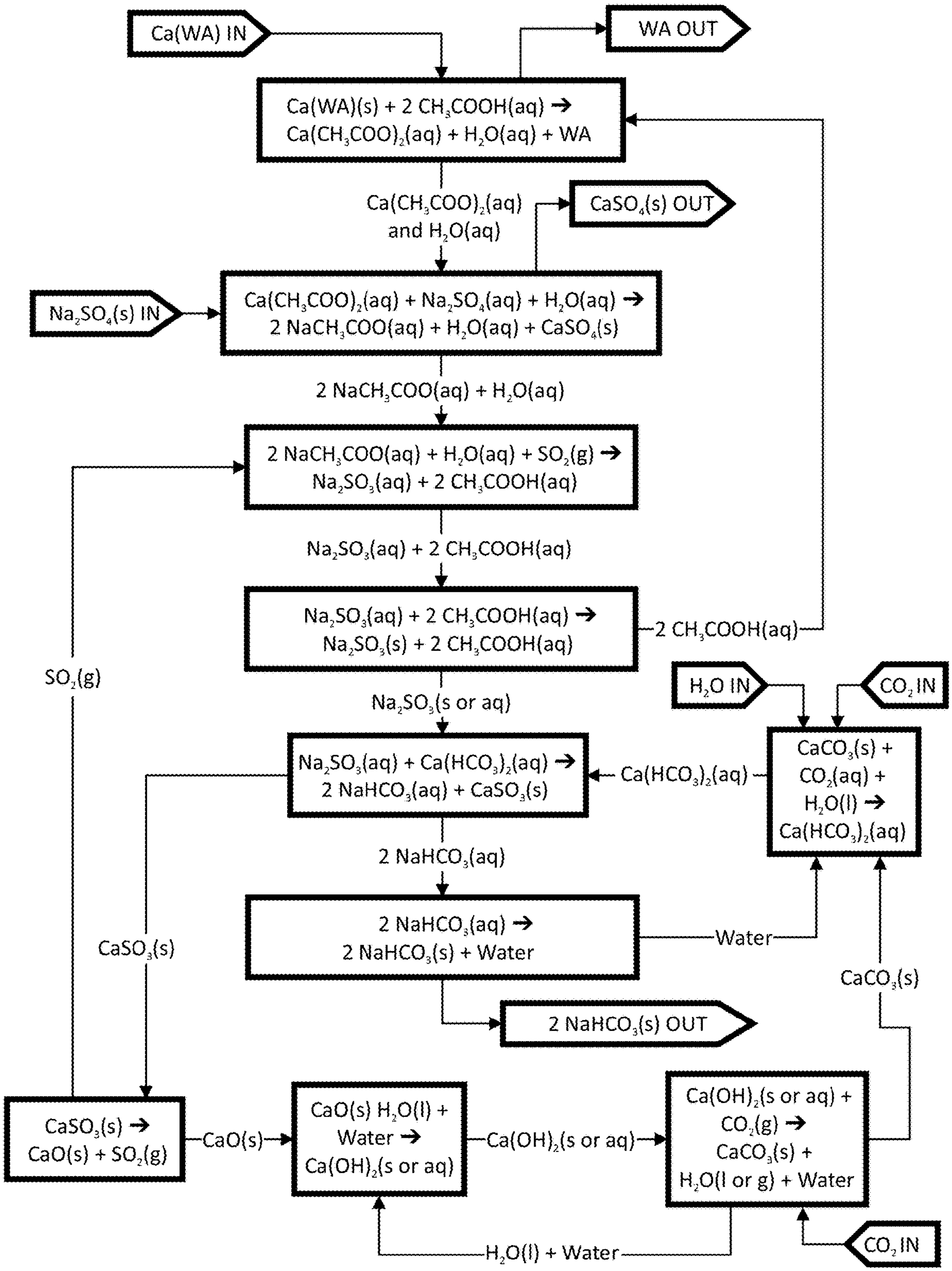

FIG. 36A: Process for producing alkali bicarbonate or carbonate from alkali sulfate using carboxylic acid and sulfur dioxide intermediates and carbon dioxide input and intermediate.

Figure 36B:
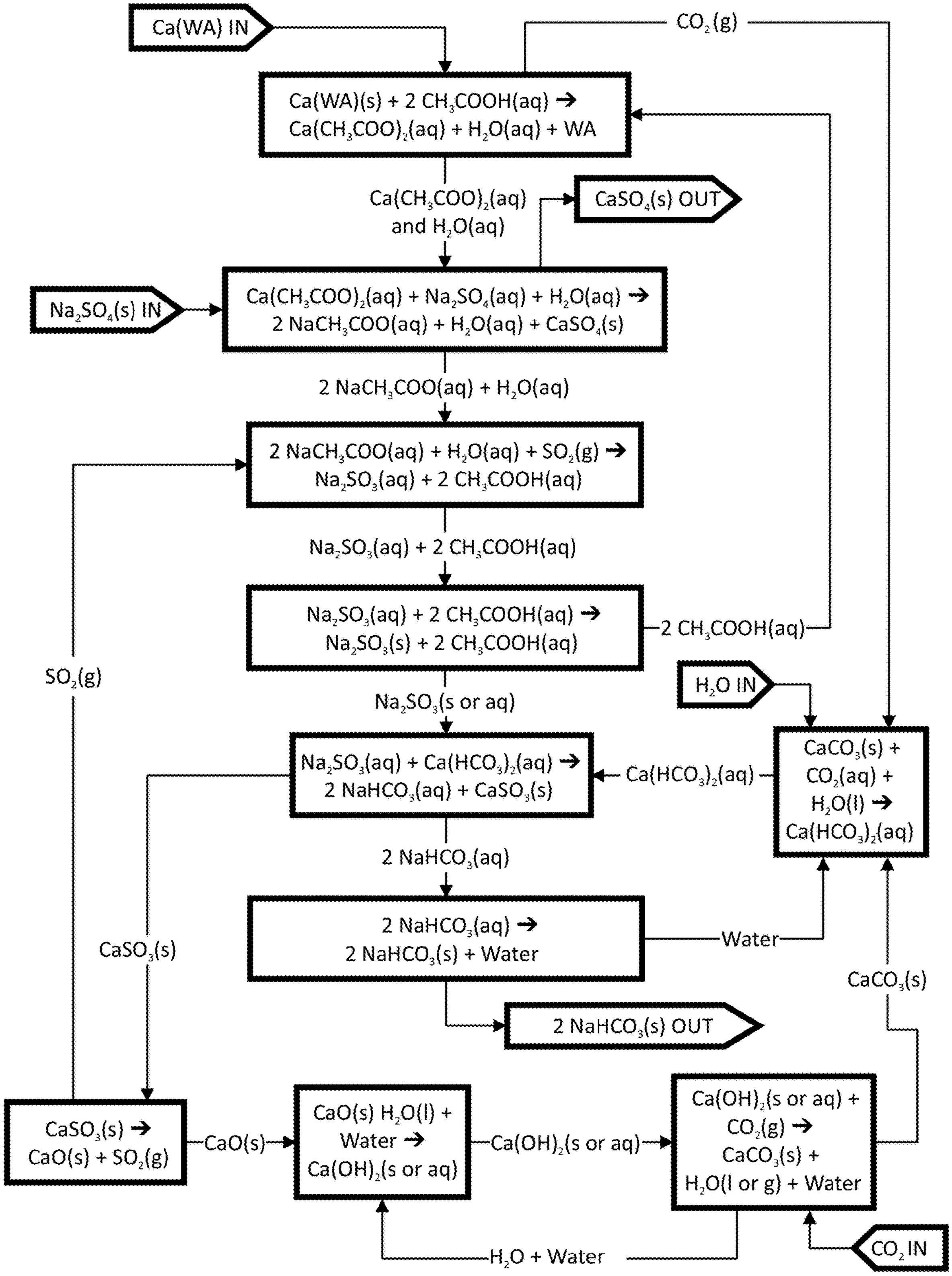

FIG. 36B: Process for producing alkali bicarbonate or carbonate from alkali sulfate using carboxylic acid and sulfur dioxide intermediates and carbon dioxide input and intermediate.

Figure 37:
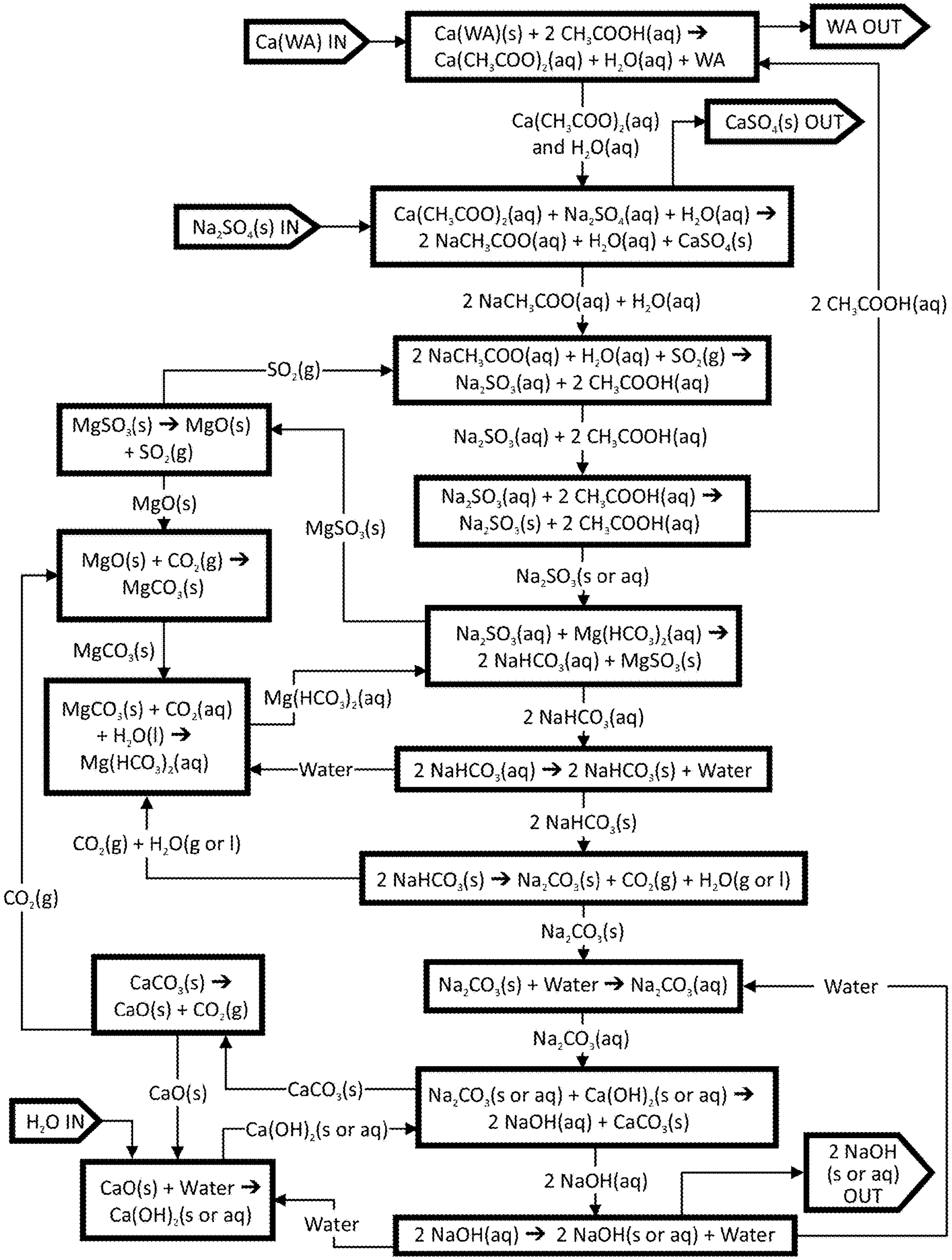

FIG. 37: Process for producing alkali hydroxide from alkali sulfate using carboxylic acid, magnesium, sulfur dioxide, and carbon dioxide intermediates.

Figure 38:
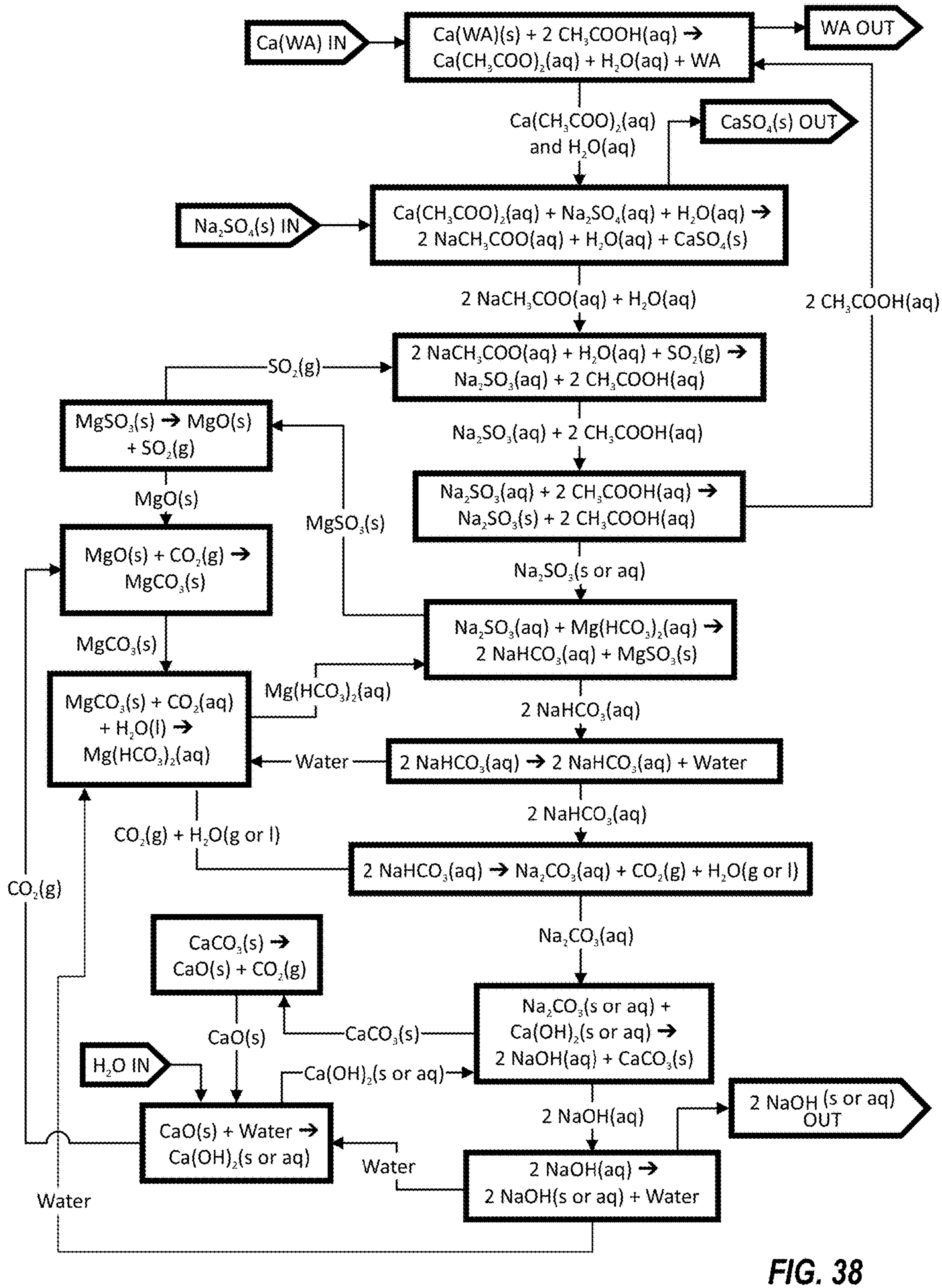

FIG. 38: Process for producing alkali hydroxide from alkali sulfate using carboxylic acid, magnesium, sulfur dioxide, and carbon dioxide intermediates.

Figure 39A:
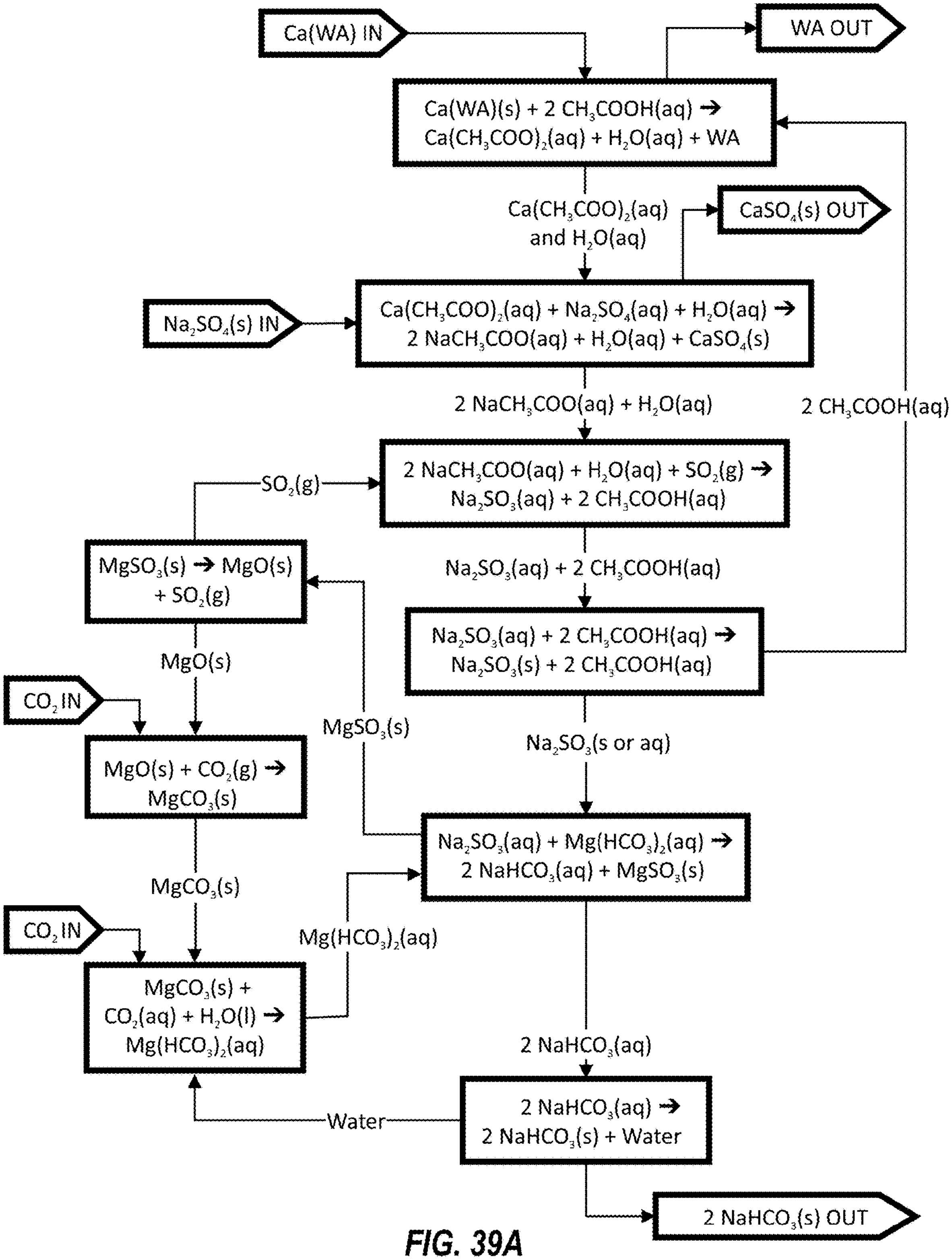

FIG. 39A: Process for producing alkali bicarbonate or carbonate from alkali sulfate using carboxylic acid and sulfur dioxide intermediates and carbon dioxide input and intermediate.

Figure 39B:
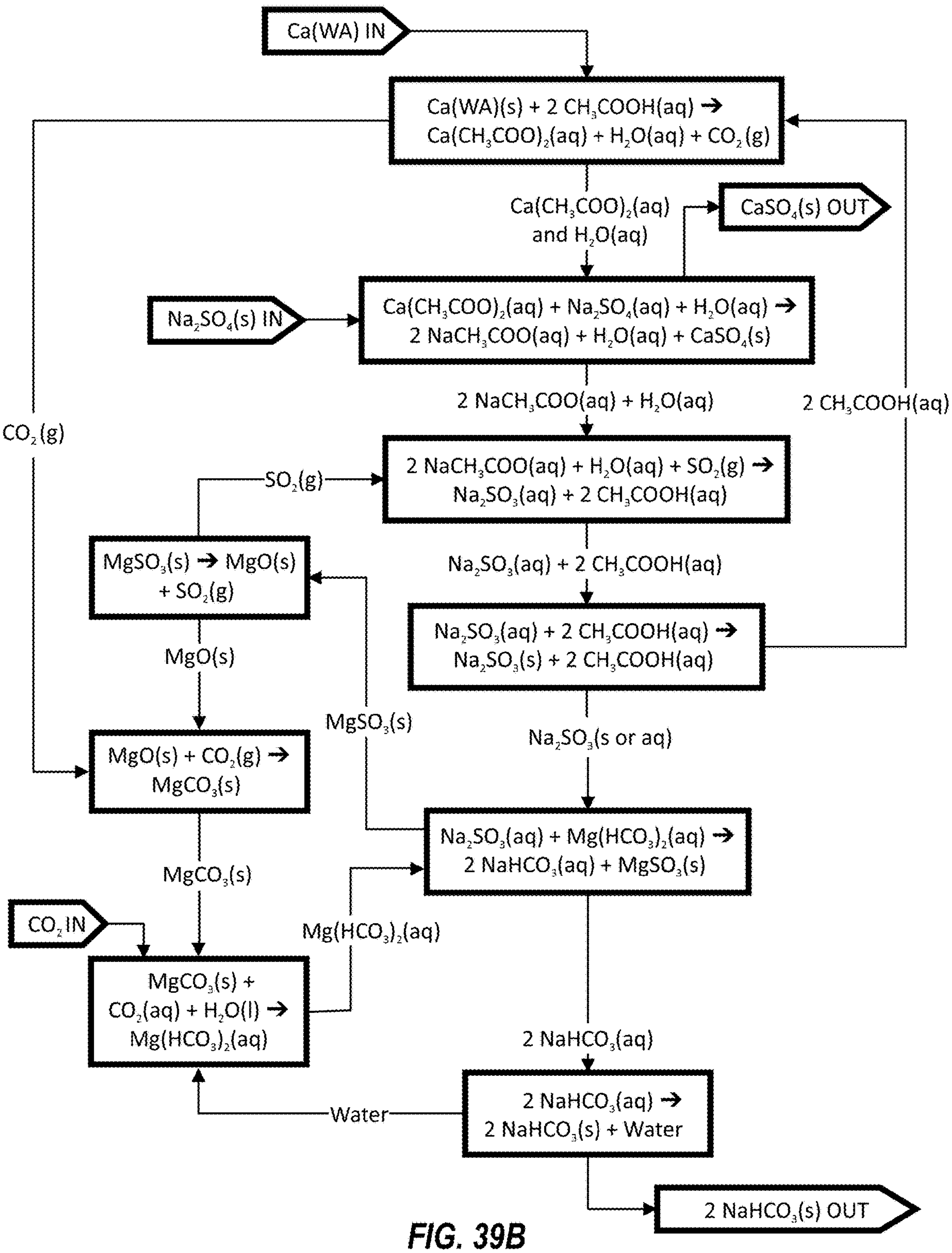

FIG. 39B: Process for producing alkali bicarbonate or carbonate from alkali sulfate using carboxylic acid and sulfur dioxide intermediates and carbon dioxide input and intermediate.

DETAILED DESCRIPTION

Example Chemistry

Example 1: Process for Producing Calcium Oxide or Cement or Clinker (1) React Material comprising Calcium, or Magnesium, or Other Alkaline Earth-Weak Acid Anion with Acetic Acid, which may comprise, including, but not limited to, one or more or any combination of the following:

$CaCO_3$(s or aq)+2 $CH_3COOH$(aq)→$Ca(CH_3COO)_2$(aq)+ $CO_2$(g)

Calcium Silicate(s)+2$CH_3COOH$(aq)→$Ca(CH_3COO)_2$(aq)+Silicon Dioxide(s)

CaS(s)+2$CH_3COOH$(aq)→$Ca(CH_3COO)_2$(aq)+$H_2S$(g)

Calcium(Weak Acid Anion)+2 $CH_3COOH$(aq)→$Ca(CH_3COO)_2$(aq)+Weak Acid(s, or g, or l, or aq)

Note: Residual solids or undissolved solids, such as silicon dioxide or other undissolved solids, may be separated from the liquid solution using a solid-liquid separation.

Note: $CO_2$(g) may comprise captured $CO_2$.

Note: In some embodiments, some chemicals comprising calcium may comprise a portion of magnesium. In some embodiments, for example, input chemicals or input material may comprise a mixture of calcium and magnesium.

Note: In some embodiments, acetic acid vapor and/or water vapor may be separated or recovered from $CO_2$(g).

(2) $Ca(CH_3COO)_2$(aq)+$SO_2$(g or aq)+$H_2O$(l or aq)→$CaSO_3$(s)+2 $CH_3COOH$(aq)

Note: $CaSO_3$(s) may be separated using a solid-liquid separation.

Note: In some embodiments, $SO_2$(g) may comprise other gases in addition to $SO_2$(g). In some embodiments, the remaining gases after the absorption or reaction of at least a portion of $SO_2$(g) may comprise a portion of acetic acid vapor. In some embodiments, the remaining gases after the absorption or reaction of at least a portion of $SO_2$(g) may comprise at least a portion of acetic acid vapor, which may comprise acetic acid evaporated from the products of reaction step '(2)'. In some embodiments, remaining gases comprising at least a portion of acetic acid vapor may be contacted with $Ca(CH_3COO)_2$(aq) before the reaction with $SO_2$(g), which may enable at least a portion of acetic acid vapor to be absorbed in the $Ca(CH_3COO)_2$(aq) and/or removed from the remaining gases. In some embodiments, acetic acid vapor may be removed from remaining gases using, for example, including, but not limited to, one or more or any combination of the following: alkaline earth carbonate, or alkaline earth-weak acid, or alkaline earth carbonate-water slurry, or alkaline earth oxide, or alkaline earth hydroxide, or alkaline earth hydroxide-water slurry, or alkaline earth hydroxide-water suspension, or alkaline earth hydroxide-water solution, or water, or alkali carbonate, or alkali bicarbonate, or alkali hydroxide.

Note: In some embodiments, residual aqueous magnesium sulfite may be present in the '2 $CH_3COOH$(aq)'. In some embodiments, the residual aqueous magnesium sulfite may remain in the '2 $CH_3COOH$(aq)' transferred to reaction '(1)' from, for example, reaction '(2)'. In some embodiments, at least a portion of the aqueous magnesium sulfite may remain in the '2 $CH_3COOH$(aq)' solution transferred to reaction '(1)' from reaction '(2)'/. Additional magnesium sulfite above the solubility limits of magnesium sulfite in the solution may precipitate or co-precipitate during the reaction of $Ca(CH_3COO)_2$(aq) or $Mg(CH_3COO)_2$(aq) with $SO_2$(g or aq), or sulfite, or bisulfite, or any combination thereof.

Note: In some embodiments, residual aqueous magnesium sulfite may be present in the '2 $CH_3COOH$(aq)'. In some embodiments, a portion of the residual aqueous magnesium sulfite may be concentrated and/or separated using, including, but not limited to, one or more, or any combination of the following: heating, or cooling, or reverse osmosis, or membrane based process, or precipitation, or electrodialysis, or forward osmosis, or any combination thereof. For example, the residual aqueous magnesium sulfite may be separated by concentrating the magnesium sulfite using reverse osmosis or nanofiltration, wherein the pore size or properties of the membrane may enable the permeation of at least a portion of the acetic acid and the rejection of at least a portion of magnesium sulfite, and/or cooling the resulting concentrated magnesium sulfite solution to produce at least a portion of a magnesium sulfite precipitate.

(3) $CaSO_3$(s)→CaO(s)+$SO_2$(g)

Note: '(3)' may comprise calcining $CaSO_3$(s), which may employ a kiln.

Note: $CaSO_3$(s) may be dried, or dehydrated, or both before or during '(3)'.

Example 2: Process for Producing Magnesium Oxide or Cement or Clinker (1) React Material Comprising Calcium, or Magnesium, or Other Alkaline Earth—Weak Acid Anion with Acetic Acid $MgCO_3$(s or aq)+2 $CH_3COOH$(aq)→$Mg(CH_3COO)_2$(aq)+$CO_2$(g)

Magnesium Silicate(s)+2 $CH_3COOH$(aq)→$Mg(CH_3COO)_2$(aq)+Silicon Dioxide(s)

MgS(s)+2 $CH_3COOH$(aq)→$Mg(CH_3COO)_2$(aq)+$H_2S$(g)

Magnesium(Weak Acid Anion)+2 $CH_3COOH(aq)\rightarrow Mg(CH_3COO)_2(aq)$+Weak Acid(s, or g, or l, or aq)

Note: Residual solids or undissolved solids, such as silicon dioxide or other undissolved solids, may be separated from the liquid solution using a solid-liquid separation.

Note: In some embodiments, 2 $CH_3COOH(aq)$ may comprise at least a portion of $MgSO_3(aq)$, which may be referred to as residual $MgSO_3(aq)$.

(2) $Mg(CH_3COO)_2(aq)+SO_2$(g or aq)+$H_2O$(l or aq)$\rightarrow MgSO_3(s)$+2 $CH_3COOH(aq)$ Note: $MgSO_3(s)$ may be separated using a solid-liquid separation.

Note: Residual $MgSO_3(aq)$ may be present in the 2 $CH_3COOH(aq)$ solution.

(3) $MgSO_3(s)\rightarrow MgO(s)+SO_2(g)$

Note: '(3)' may comprise calcining $MgSO_3(s)$, which may employ a kiln.

Note: $MgSO_3(s)$ may be dried, or dehydrated, or both before or during '(3)'.

Example 3: Process for Producing Calcium Oxide or Cement or Clinker with Alkali Intermediate (1) React Material comprising Calcium, or Magnesium, or Other Alkaline Earth-Weak Acid Anion with Acetic Acid $CaCO_3$(s or aq)+2 $CH_3COOH(aq)\rightarrow Ca(CH_3COO)_2(aq)+CO_2(g)$ Calcium Silicate(s)+2 $CH_3COOH(aq)\rightarrow Ca(CH_3COO)_2(aq)$+Silicon Dioxide(s)

$CaS(s)$+2 $CH_3COOH(aq)\rightarrow Ca(CH_3COO)_2(aq)+H_2S(g)$

Calcium(Weak Acid Anion)+2 $CH_3COOH(aq)\rightarrow Ca(CH_3COO)_2(aq)$+Weak Acid(s, or g, or l, or aq)

Note: Residual solids or undissolved solids, such as silicon dioxide or other undissolved solids, may be separated from the liquid solution using a solid-liquid separation.

Note: If $CO_2(g)$ is produced, it may be desirable for said $CO_2(g)$ to be produced at a high partial pressure $CO_2(g)$, or purity $CO_2(g)$, or to comprise captured $CO_2(g)$.

(2) $Ca(CH_3COO)_2(aq)+Na_2SO_3$(s or aq)$\rightarrow 2NaCH_3COO(aq)+CaSO_3(s)$

Note: $CaSO_3(s)$ may be separated using a solid-liquid separation.

Note: In some embodiments, $Na_2SO_3$(s or aq) may comprise a solid comprising sodium sulfite, which may be added to or dissolved in a solution comprising calcium acetate.

Note: In some embodiments, $Na_2SO_3$(s or aq) may comprising an aqueous solution comprising sodium sulfite and acetic acid.

(3) 2 $NaCH_3COO(aq)+SO_2$(g or aq)+$H_2O$(l or aq)$\rightarrow Na_2SO_3(aq)$+2 $CH_3COOH(aq)$ Note: In some embodiments, $SO_2(g)$ may comprise other gases in addition to $SO_2(g)$. In some embodiments, the reaction of 2 $NaCH_3COO(aq)+SO_2(g)$ may result in at least a portion of acetic acid vapor in the remaining gases during or after the reaction. In some embodiments, $NaCH_3COO(aq)$ entering the present step may be pre-contacted with or may absorb at least a portion of acetic acid vapor from the remaining gases. In some embodiments, the reactor or absorption column may be configured to absorb acetic acid vapor in $NaCH_3COO(aq)$ before or while reacting $NaCH_3COO(aq)$ with $SO_2(g)$. In some embodiments, acetic acid vapor may be removed from remaining gases using, for example, including, but not limited to, one or more or any combination of the following: alkaline earth carbonate, or alkaline earth-weak acid, or alkaline earth carbonate-water slurry, or alkaline earth oxide, or alkaline earth (4) $Na_2SO_3(aq)$+2 $CH_3COOH(aq)\rightarrow$2 $CH_3COOH$(aq or l)+$Na_2SO_3(s)$ Note: $CH_3COOH$ may be more soluble in water than $Na_2SO_3$. In some embodiments, $Na_2SO_3$ may be separated or precipitated from solution by, for example, including, but not limited to, evaporation, or distillation, or crystallization, or separation systems or methods described herein, or separation systems or methods described in the art, or any combination thereof.

Note: In some embodiments, $CH_3COOH$ and/or water may be separated from $Na_2SO_3$ by, for example, evaporation, or distillation, or crystallization, or any combination thereof. In some embodiments, $CH_3COOH$ may evaporate with water vapor and/or condense with water vapor, which may result in a distillate or condensate comprising $CH_3COOH(aq)$.

Note: In some embodiments, magnesium sulfite(aq) may be present in the $Na_2SO_3(aq)$+2 $CH_3COOH(aq)$. In some embodiments, if present, magnesium sulfite may begin to precipitate or crystalize before $Na_2SO_3$. In some embodiments magnesium sulfite solid may be separated during step '(4)'. In some embodiments, separated magnesium sulfite may be decomposed to magnesium oxide, or decomposed separately from calcium sulfite, or decomposed together with calcium sulfite, or any combination thereof.s Note: $Na_2SO_3(s)$ may be separated from $CH_3COOH(aq)$ by a solid-liquid separation, which may include, but is not limited to, filter, or centrifuge, or decanter, or separation systems or methods described herein, or separation systems or methods described in the art, or any combination thereof.

Note: In some embodiments, a feed solution comprising sodium sulfite and acetic acid may be evaporated, wherein a portion of acetic acid and water vapor evaporate and/or are condensed to form an a separated acetic acid solution, and/or the remaining solution comprises aqueous acetic acid and a higher concentration of sodium sulfite than in the concentration of sodium sulfite in the feed solution.

(5) $CaSO_3(s)\rightarrow CaO(s)+SO_2(g)$

Note: '(5)' may comprise calcining $CaSO_3(s)$, which may employ a kiln.

Note: $CaSO_3(s)$ may be dried, or dehydrated, or both before, or during '(5)'.

Note: In some embodiments, it may be preferred or desired to react $SO_2(g)$ with $NaCH_3COO(aq)$ to form $Na_2SO_3(aq)$, and then react $Na_2SO_3$ with $Ca(CH_3COO)_2(aq)$ to form $CaSO_3(s)$ because, for example, including, but not limited to, one or more or any combination of the following potential benefits:

- In some embodiments, it may be desirable to absorb $SO_2(g)$ in an absorption column. Precipitate formation can be problematic in an absorption column due to, for example, including, but not limited to, precipitate clogging packing material, or plates, or interfering with gas flows, or interfering with liquid flows, or forming scaling, or any combination thereof. The reaction of $Ca(CH_3COO)_2(aq)$ with $SO_2(g)$ may form a precipitate comprising $CaSO_3(s)$, which may be challenging in some absorption columns or a gas absorption processes. The reaction of $NaCH_3COO(aq)$ with $SO_2(g)$ may, if desired, the salt may mostly remain at an aqueous or liquid phase throughout the reaction, because, for example, $Na_2SO_3$ may be soluble in water, which may be desirable in an absorption column.
- In some embodiments, if the $SO_2(g)$ comprises gases in addition to $SO_2(g)$, acetic acid vapor may be present in the remaining gases during or after the reaction of $SO_2(g)$ with an acetate salt. If $SO_2(g)$ is contacted with $NaCH_3COO(aq)$, which may form aqueous phase $Na_2SO_3(aq)$ and/or acetic acid, the reactor or absorption column may be configured such that $NaCH_3COO(aq)$ entering the reactor or absorption column absorbs or recovers at least a portion of acetic acid vapor from the remaining gases. If $SO_2(g)$ is contacted with $NaCH_3COO(aq)$, which may form aqueous phase $Na_2SO_3(aq)$ and/or acetic acid, the reactor or absorption column may be configured such that $NaCH_3COO(aq)$ entering the reactor or absorption column absorbs or recovers at least a portion of acetic acid vapor from the remaining gases before or while $NaCH_3COO(aq)$ is substantially reacted with $SO_2(g)$. The employing $NaCH_3COO(aq)$ may react with residual $SO_2(g)$ potentially present in the remaining gases, which may avoid solid formation or solid handing issues which may occur if $Ca(CH_3COO)_2(aq)$ is reacted with residual $SO_2(g)$.

For example, in some embodiments in some embodiments, the ability for the reaction products to comprise aqueous or pumpable phases may enable absorption column, or absorber, or reactor, or any combination thereof designs or configurations which may facilitate the recovery of acetic acid vapor and/or may reduce the potential amount or concentration of acetic acid vapor in the remaining gases.

For example, it may be desirable to absorb $SO_2(g)$ in an absorption column because the $SO_2(g)$ may be at a dilute concentration, or a low partial pressure, or may comprise a gas mixture, or to improve absorption efficiency, or to facilitate the recovery or removal of any acid vapor from remaining gases, or to facilitate the recovery or removal of acetic acid vapor from remaining gases, or prevent or minimize or reduce the concentration or partial pressure of acetic acid vapor in the remaining gases, or any combination thereof. For example, in some embodiments, the process employed to decompose calcium sulfite to calcium oxide and sulfur dioxide may form a gas mixture comprising sulfur dioxide. For example, in some embodiments, the partial pressure of sulfur dioxide in said gas mixture may be lower than 1 atm, or 0.9 atm, or 0.8 atm, or 0.7 atm, or 0.6 atm, or 0.5 atm, or 0.4 atm, or 0.3 atm, or 0.2 atm, or 0.1 atm, or 0.05 atm, or any combination thereof and/or wherein the volume percent concentration of sulfur dioxide in said gas mixture may be lower than 100%, or 90%, or 80%, or 70%, or 60%, or 50%, or 40%, or 30%, or 20%, or 10%, or 5%, or any combination thereof.

Greater absorption rate or absorption efficiency.

Solid-liquid separations may be easier or simpler or higher yielding. For example, in some embodiments, if the rate of precipitation is dependent on the mixing of two liquids, rather a precipitation reaction from a gas and a liquid, the formation of and/or separation of precipitates may be more controllable.

Example 4: Process for Producing Magnesium Oxide or Cement or Clinker with Alkali Intermediate (1) React Material Comprising Calcium, or Magnesium, or Other Alkaline Earth-Weak Acid Anion with Acetic Acid $MgCO_3$(s or aq)+2 $CH_3COOH(aq) \rightarrow Mg(CH_3COO)_2(aq)+CO_2(g)$ Magnesium Silicate(s)+2 $CH_3COOH(aq) \rightarrow Mg(CH_3COO)_2(aq)$+Silicon Dioxide(s)

$MgS(s)+2\ CH_3COOH(aq) \rightarrow Mg(CH_3COO)_2(aq)+H_2S(g)$

Magnesium(Weak Acid Anion)+2 $CH_3COOH(aq) \rightarrow Mg(CH_3COO)_2(aq)$+Weak Acid(s, or g, or l, or aq)

Note: Residual solids or undissolved solids, such as silicon dioxide or other undissolved solids, may be separated from the liquid solution using a solid-liquid separation.

Note: If $CO_2(g)$ is produced, it may be desirable for said $CO_2(g)$ to be produced at a high partial pressure $CO_2(g)$, or purity $CO_2(g)$, or to comprise captured $CO_2(g)$.

(2) $Mg(CH_3COO)_2(aq)+Na_2SO_3$(s or aq)+2 $NaCH_3COO(aq) \rightarrow MgSO_3(s)$ Note: $MgSO_3(s)$ may be separated using a solid-liquid separation.

(3) 2 $NaCH_3COO(aq)+SO_2$(g or aq)+$H_2O$(l or aq)$\rightarrow Na_2SO_3(aq)+2\ CH_3COOH(aq)$ (4) $Na_2SO_3(aq)+2\ CH_3COOH(aq) \rightarrow 2\ CH_3COOH$(aq or l)+$Na_2SO_3(s)$ Note: $CH_3COOH$ may be more soluble in water than $Na_2SO_3$. In some embodiments, water may be removed and/or $Na_2SO_3$ may be separated or precipitated by, for example, including, but not limited to, evaporation, or distillation, or crystallization, or separation systems or methods described herein, or separation systems or methods described in the art, or any combination thereof.

Note: In some embodiments, magnesium sulfite(aq) may be present in the $Na_2SO_3(aq)+2\ CH_3COOH(aq)$. In some embodiments, if present, magnesium sulfite may precipitate or crystalize before $Na_2SO_3$. In some embodiments, if present, magnesium sulfite may precipitate or crystalize before $Na_2SO_3$, which may enable the separation of at least a portion of magnesium sulfite from $Na_2SO_3$.

Note: $Na_2SO_3(s)$ may be separated from $CH_3COOH$(aq or l) by a solid-liquid separation, which may include, but is not limited to, filter, or centrifuge, or decanter, or separation systems or methods described herein, or separation systems or methods described in the art, or any combination thereof.

Note: In some embodiments, $CH_3COOH$ may evaporate with water vapor and/or condense with water vapor to form a distillate or condensate comprising $CH_3COOH(aq)$.

(5) $MgSO_3(s) \rightarrow MgO(s)+SO_2(g)$

Note: '(5)' may comprise calcining $CaSO_3(s)$, which may employ a kiln.

Note: $CaSO_3(s)$ may be dried, or dehydrated, or both before, or during '(5)'.

Note: In some embodiments, it may be preferred to react $SO_2(g)$ with $NaCH_3COO(aq)$ to form $Na_2SO_3(aq)$, and then react $Na_2SO_3$ with $Mg(CH_3COO)_2(aq)$ to form $MgSO_3(s)$ because, for example, including, but not limited to, one or more or any combination of the following potential benefits:

In some embodiments, it may be desirable to absorb $SO_2(g)$ in an absorption column. Precipitate formation can be problematic in an absorption columns due to, for example, including, but not limited to, precipitate clogging packing material, or plates, or interfering with gas flows, or interfering with liquid flows, or forming scaling, or any combination thereof. The reaction of $Mg(CH_3COO)_2(aq)$ with $SO_2(g)$ may form a precipitate comprising $MgSO_3(s)$, which may be problematic in some absorption columns or a gas absorption processes. The reaction of $NaCH_3COO(aq)$ with $SO_2(g)$ may, if desired, remain an aqueous solution or liquid solution throughout the reaction, because, for example, $Na_2SO_3$ is soluble in water, which may be desirable in an absorption column.

For example, it may be desirable to absorb $SO_2(g)$ in an absorption column because the $SO_2(g)$ may be at a dilute concentration, or a low partial pressure, or may comprise a gas mixture, or to improve absorption efficiency, or to facilitate the recovery or removal of any acid vapor from remaining gases, or any combination thereof. For example, in some embodiments, the process employed to decompose calcium sulfite to calcium oxide and sulfur dioxide may form a gas mixture comprising sulfur dioxide. For example, in some embodiments, the partial pressure of sulfur dioxide in said gas mixture may be lower than 1 atm, or 0.9 atm, or 0.8 atm, or 0.7 atm, or 0.6 atm, or 0.5 atm, or 0.4 atm, or 0.3 atm, or 0.2 atm, or 0.1 atm, or 0.05 atm, or any combination thereof and/or wherein the volume percent concentration of sulfur dioxide in said gas mixture may be lower than 100%, or 90%, or 80%, or 70%, or 60%, or 50%, or 40%, or 30%, or 20%, or 10%, or 5%, or any combination thereof.

In some embodiments, if the $SO_2(g)$ comprises gases in addition to $SO_2(g)$, acetic acid vapor may be present in the remaining gases during or after the reaction of $SO_2(g)$ with an acetate salt. If $SO_2(g)$ is contacted with $NaCH_3COO(aq)$, which may form aqueous phase $Na_2SO_3(aq)$ and/or acetic acid, the reactor or absorption column may be configured such that $NaCH_3COO(aq)$ entering the reactor or absorption column absorbs or recovers at least a portion of acetic acid vapor from the remaining gases. If $SO_2(g)$ is contacted with $NaCH_3COO(aq)$, which may form aqueous phase $Na_2SO_3(aq)$ and/or acetic acid, the reactor or absorption column may be configured such that $NaCH_3COO(aq)$ entering the reactor or absorption column absorbs or recovers at least a portion of acetic acid vapor from the remaining gases before or while $NaCH_3COO(aq)$ is substantially reacted with $SO_2(g)$. The employing $NaCH_3COO(aq)$ may react with residual $SO_2(g)$ potentially present in the remaining gases, which may avoid solid formation or solid handing issues which may occur if $Ca(CH_3COO)_2(aq)$ is reacted with residual $SO_2(g)$.

Greater absorption rate or absorption efficiency.

Solid-liquid separations may be easier or simpler or higher yielding. For example, if the rate of precipitation is dependent on the mixing of two liquids, rather than a gas and a liquid, the formation of and/or separation of precipitates may be more controlled.

Example 5: Process for Producing Calcium Oxide or Cement or Clinker with Alkali Intermediate with Recirculating Separation Process (1) React Material comprising Calcium, or Magnesium, or Other Alkaline Earth-Weak Acid Anion with Acetic Acid $CaCO_3(s \text{ or } aq)+2\ CH_3COOH(aq) \rightarrow Ca(CH_3COO)_2(aq)+CO_2(g)$ Calcium Silicate(s)+2 $CH_3COOH(aq) \rightarrow Ca(CH_3COO)_2(aq)$+Silicon Dioxide(s)

$CaS(s)+2\ CH_3COOH(aq) \rightarrow Ca(CH_3COO)_2(aq)+H_2S(g)$

Calcium(Weak Acid Anion)+2 $CH_3COOH(aq) \rightarrow Ca(CH_3COO)_2(aq)$+Weak Acid(s, or g, or l, or aq)

Note: Residual solids or undissolved solids, such as silicon dioxide or other undissolved solids, may be separated from the liquid solution using a solid-liquid separation.

(2) $Ca(CH_3COO)_2(aq)+Na_2SO_3(s \text{ or } aq)+CH_3COOH(aq) \rightarrow 2\ NaCH_3COO(aq)+CH_3COOH(aq)+CaSO_3(s)$ Note: $CaSO_3(s)$ may be separated using a solid-liquid separation.

Note: $CH_3COOH(aq)$ may be present due to $CH_3COOH(aq)$ being present in the retanate solution comprising $Na_2SO_3(aq)$ from a membrane based separation of $CH_3COOH(aq)$ and $Na_2SO_3(aq)$.

(3) 2 $NaCH_3COO(aq)+SO_2(g \text{ or } aq)+H_2O(l \text{ or } aq) \rightarrow Na_2SO_3(aq)+2\ CH_3COOH(aq)$ (4) $Na_2SO_3(aq)+2\ CH_3COOH(aq) \rightarrow 2\ CH_3COOH(aq)$ separately from $Na_2SO_3(aq)+2\ CH_3COOH(aq)$ Note: A portion of $CH_3COOH(aq)$ may be separated from $Na_2SO_3(aq)$ using a separation process, such as a membrane based process, such as reverse osmosis. In some embodiments, $CH_3COOH(aq)$ may have a hydration radius or molar mass sufficiently small to permeate through a membrane, while said membrane may reject $Na_2SO_3(aq)$. In some embodiments, $Na_2SO_3(aq)+2\ CH_3COOH(aq)$ may be separated into a permeate solution comprising 2 $CH_3COOH(aq)$ and a retentate solution comprising $Na_2SO_3(aq)+2\ CH_3COOH(aq)$.

(5) $CaSO_3(s) \rightarrow CaO(s)+SO_2(g)$

Note: '(5)' may comprise calcining $CaSO_3(s)$, which may employ a kiln.

Note: $CaSO_3(s)$ may be dried, or dehydrated, or both before or during '(5)'.

Example 6: Process for Producing Magnesium Oxide or Cement or Clinker with Alkali Intermediate with Recirculating Separation Process (1) React Material Comprising Calcium, or Magnesium, or Other Alkaline Earth-Weak Acid Anion with Acetic Acid $MgCO_3(s \text{ or } aq)+2\ CH_3COOH(aq) \rightarrow Mg(CH_3COO)_2(aq)+CO_2(g)$ Magnesium Silicate(s)+2 $CH_3COOH(aq) \rightarrow Mg(CH_3COO)_2(aq)$+Silicon Dioxide(s)

$MgS(s)+2\ CH_3COOH(aq) \rightarrow Mg(CH_3COO)_2(aq)+H_2S(g)$

Magnesium(Weak Acid Anion)+2 $CH_3COOH(aq) \rightarrow Mg(CH_3COO)_2(aq)$+Weak Acid(s, or g, or l, or aq)

Note: Residual solids or undissolved solids, such as silicon dioxide or other undissolved solids, may be separated from the liquid solution using a solid-liquid separation.

(2) $Mg(CH_3COO)_2(aq)+Na_2SO_3(s \text{ or } aq)+CH_3COOH(aq) \rightarrow 2\ NaCH_3COO(aq)+CH_3COOH(aq) \rightarrow MgSO_3(s)$ Note: $MgSO_3(s)$ may be separated using a solid-liquid separation.

Note: $CH_3COOH(aq)$ may be present due to $CH_3COOH(aq)$ being present in the retanate solution comprising $Na_2SO_3(aq)$ from a membrane based separation of $CH_3COOH(aq)$ and $Na_2SO_3(aq)$.

(3) 2 $NaCH_3COO(aq)+SO_2(g \text{ or } aq)+H_2O(l \text{ or } aq) \rightarrow Na_2SO_3(aq)+2\ CH_3COOH(aq)$ (4) $Na_2SO_3(aq)+2\ CH_3COOH(aq) \rightarrow 2\ CH_3COOH(aq)$ separately from $Na_2SO_3(aq)+2\ CH_3COOH(aq)$ Note: A portion of $CH_3COOH(aq)$ may be separated from $Na_2SO_3(aq)$ using a separation process, such as a membrane based process, such as reverse osmosis. In some embodiments, $CH_3COOH(aq)$ may have a hydration radius or molar mass sufficiently small to permeate through a membrane, while said membrane may reject $Na_2SO_3(aq)$. In some embodiments, $Na_2SO_3(aq)+2\ CH_3COOH(aq)$ may be separated into a permeate solution comprising 2 $CH_3COOH(aq)$ and a retentate solution comprising $Na_2SO_3(aq)+2\ CH_3COOH(aq)$.

(5) $MgSO_3(s)+MgO(s)+SO_2(g)$

Note: '(5)' may comprise calcining $MgSO_3(s)$, which may employ a kiln.

Note: $MgSO_3(s)$ may be dried, or dehydrated, or both before or during '(5)'.

Example 7: Sodium Hydroxide Production from Sodium Sulfate Using Calcium Precipitation and Acid Intermediate (1) React Material comprising Calcium, or Magnesium, or Other Alkaline Earth-Weak Acid Anion with Acetic Acid $CaCO_3$(s or aq)+2 $CH_3COOH$(aq)→$Ca(CH_3COO)_2$(aq)+ $CO_2$(g)+$H_2O$(l or aq)

Calcium Silicate(s)+2 $CH_3COOH$(aq)→$Ca(CH_3COO)_2$ (aq)+Silicon Dioxide(s)+$H_2O$(l or aq)

CaS(s)+2 $CH_3COOH$(aq)→$Ca(CH_3COO)_2$(aq)+$H_2S$(g)+ $H_2O$(l or aq)

Calcium(Weak Acid Anion)+2 $CH_3COOH$(aq)→Ca $(CH_3COO)_2$(aq)+Weak Acid(s, or g, or l, or aq)+$H_2O$(l or aq)

Note: Residual solids or undissolved solids, such as silicon dioxide or other undissolved solids, may be separated from the liquid solution using a solid-liquid separation.

Note: $CO_2$(g) may comprise captured $CO_2$.

Note: In some embodiments, some chemicals comprising calcium may comprise a portion of magnesium. In some embodiments, for example, input chemicals or input material may comprise a mixture of calcium and magnesium.

Note: In some embodiments, acetic acid vapor and/or water vapor may be separated or recovered from $CO_2$(g).

(2) $Ca(CH_3COO)_2$(aq)+$Na_2SO_4$(s or aq)→2 $NaCH_3COO$ (aq)→$CaSO_4$(s)

Note: In some embodiments, $Na_2SO_4$(s) may be added directly to or dissolved in $Ca(CH_3COO)_2$(aq).

Note: In some embodiments, $Na_2SO_4$(s) may be dissolved in water or an aqueous solution to form $Na_2SO_4$(aq) before mixing with $Ca(CH_3COO)_2$(aq).

Note: In some embodiments, water may be added to the process to make up for water which may leave the process, for example, if NaOH(aq) is an output, or another aqueous solution is an output, or any combination thereof. In some embodiments, water may be added to the process by $Na_2SO_4$ being in the form of $Na_2SO_4$(aq) or an aqueous solution comprising sodium sulfate, wherein at least a portion of the water in $Na_2SO_4$(aq) may comprise water added to the process. In some embodiments, $Na_2SO_4$(aq) may be provided or sourced as an aqueous solution. For example, in some embodiments, $Na_2SO_4$(aq) may be provided to the process in the form of $Na_2SO_4$(aq). In some embodiments, $Na_2SO_4$(aq) may be provided or sourced as a solid or $Na_2SO_4$(s), then dissolved in water to form $Na_2SO_4$(aq).

(3) 2 $NaCH_3COO$(aq)+$SO_2$(g or aq)+$H_2O$(l or aq)→$Na_2SO_3$(aq)+2 $CH_3COOH$(aq)

Note: In some embodiments, $SO_2$(g) may comprise other gases in addition to $SO_2$(g). In some embodiments, the reaction of 2 $NaCH_3COO$(aq)+$SO_2$(g) may result in at least a portion of acetic acid vapor in the remaining gases during or after the reaction. In some embodiments, $NaCH_3COO$(aq) entering the present step may be pre-contacted with or may absorb at least a portion of acetic acid vapor from the remaining gases. In some embodiments, the reactor or absorption column may be configured to absorb acetic acid vapor in $NaCH_3COO$(aq) before or while reacting $NaCH_3COO$(aq) with $SO_2$(g). In some embodiments, acetic acid vapor may be removed from remaining gases using, for example, including, but not limited to, one or more or any combination of the following: alkaline earth carbonate, or alkaline earth-weak acid, or alkaline earth carbonate-water slurry, or alkaline earth oxide, or alkaline earth (4) $Na_2SO_3$(aq)+2 $CH_3COOH$(aq)→2 $CH_3COOH$(aq)+ $Na_2SO_3$(s)

Note: $CH_3COOH$ may be more soluble in water than $Na_2SO_3$. In some embodiments, $Na_2SO_3$ may be separated or precipitated from solution by, for example, including, but not limited to, evaporation, or distillation, or crystallization, or separation systems or methods described herein, or separation systems or methods described in the art, or any combination thereof.

Note: In some embodiments, $CH_3COOH$ and/or water may be separated from $Na_2SO_3$ by, for example, evaporation, or distillation, or crystallization, or any combination thereof. In some embodiments, $CH_3COOH$ may evaporate with water vapor and/or condense with water vapor, which may result in a distillate or condensate comprising $CH_3COOH$(aq).

Note: In some embodiments, magnesium sulfite(aq) may be present in the $Na_2SO_3$(aq)+2 $CH_3COOH$(aq). In some embodiments, if present, magnesium sulfite may begin to precipitate or crystalize before $Na_2SO_3$. In some embodiments magnesium sulfite solid may be separated during step '(4)'. In some embodiments, separated magnesium sulfite may be decomposed to magnesium oxide, or decomposed separately from calcium sulfite, or decomposed together with calcium sulfite, or any combination thereof.s Note: $Na_2SO_3$(s) may be separated from $CH_3COOH$(aq) by a solid-liquid separation, which may include, but is not limited to, filter, or centrifuge, or decanter, or separation systems or methods described herein, or separation systems or methods described in the art, or any combination thereof.

(5) $Na_2SO_3$(s or aq)+$Ca(OH)_2$(s or aq)→2 NaOH(aq or s)+$CaSO_3$(s)

Note: $Ca(OH)_2$(s or aq) may comprise a solid-liquid suspension, such as milk of lime.

Note: $CaSO_3$(s) may be separated using a solid-liquid separation.

(6) $CaSO_3$(s)→CaO(s)+$SO_2$(g)

Note: '(6)' may comprise calcining $CaSO_3$(s), which may employ a kiln.

Note: $CaSO_3$(s) may be dried, or dehydrated, or both before or during '(6)'.

(7) CaO(s)+Water(g or l or aq)→$Ca(OH)_2$(s or aq)

Note: In some embodiments, CaO(s) may be employed to remove water vapor or facilitated drying of $CaSO_3$(s) before or during decomposition of $CaSO_3$(s) to CaO(s).

Note: In some embodiments, calcium oxide may be reacted directly with an aqueous solution comprising sodium sulfite to produce calcium sulfite and sodium hydroxide. In some embodiments, calcium oxide may be reacted directly with an aqueous solution comprising sodium sulfite to produce calcium sulfite and sodium hydroxide, which may comprise combining step '(5)' and step'(7)'.

Note: In some embodiments, calcium oxide may be reacted with water to produce an aqueous solution, or solid-liquid suspension, or milk of lime, or solid, or any combination thereof comprising calcium hydroxide.

(8) 2 NaOH(aq or s)→2 NaOH(aq or s)+Water

Note: In some embodiments, NaOH(aq) may be concentrated into an aqueous solution comprising a greater mass percent concentration of NaOH.

Note: In some embodiments, water may be removed and/or NaOH may be separated or precipitated by, for example, including, but not limited to, evaporation, or distillation, or crystallization, or separation systems or methods described herein, or separation systems or methods described in the art, or any combination thereof.

Note: In some embodiments, it may be desirable for NaOH to comprise a concentrated aqueous solution.

Example 8: Sodium Hydroxide Production from Sodium Sulfate Using Alkaline-Earth Precipitation and Acid Intermediate (1) React Material comprising Calcium, or Magnesium, or Other Alkaline Earth-Weak Acid Anion with Acetic Acid $MgCO_3$(s or aq)+2 $CH_3COOH$(aq)→$Mg(CH_3COO)_2$(aq)+$CO_2$(g)

Magnesium Silicate(s)+2 $CH_3COOH$(aq)→$Mg(CH_3COO)_2$(aq)+Silicon Dioxide(s)

MgS(s)+2 $CH_3COOH$(aq)→$Mg(CH_3COO)_2$(aq)+$H_2S$(g)

Magnesium(Weak Acid Anion)+2 $CH_3COOH$(aq)→$Mg(CH_3COO)_2$(aq)+Weak Acid(s, or g, or l, or aq)

Note: Residual solids or undissolved solids, such as silicon dioxide or other undissolved solids, may be separated from the liquid solution using a solid-liquid separation.

(2) $Mg(CH_3COO)_2$(aq)+$Na_2SO_4$(aq)→2 $NaCH_3COO$(aq)+$MgSO_4$(s or aq)

(3) 2 $NaCH_3COO$(aq)+$SO_2$(g or aq)+$H_2O$(l or aq)→$Na_2SO_3$(aq)+2 $CH_3COOH$(aq)

(4) $Na_2SO_3$(aq)+2 $CH_3COOH$(aq)→2 $CH_3COOH$(aq)+$Na_2SO_3$(s)

Note: $CH_3COOH$ may be more soluble in water than $Na_2SO_3$. In some embodiments, water may be removed and/or $Na_2SO_3$ may be separated or precipitated by, for example, including, but not limited to, evaporation, or distillation, or crystallization, or separation systems or methods described herein, or separation systems or methods described in the art, or any combination thereof.

Note: $Na_2SO_3$(s) may be separated from $CH_3COOH$(aq or l) by a solid-liquid separation, which may include, but is not limited to, filter, or centrifuge, or decanter, or separation systems or methods described herein, or separation systems or methods described in the art, or any combination thereof.

(5) $Na_2SO_3$(s or aq)+$Mg(OH)_2$(s or aq)→2 NaOH(aq or s)+$MgSO_3$(s)

Note: $Mg(OH)_2$(s or aq) may comprise a solid-liquid suspension, such as milk of lime.

Note: $MgSO_3$(s) may be separated using a solid-liquid separation.

(6) $MgSO_3$(s)→MgO(s)+$SO_2$(g)

Note: '(6)' may comprise calcining $MgSO_3$(s), which may employ a kiln.

Note: $MgSO_3$(s) may be dried, or dehydrated, or both before or during '(6)'.

(7) MgO(s)+Water(g or l or aq)→$Mg(OH)_2$(s or aq)

Note: MgO(s) may be employed to remove water vapor or facilitated drying of $MgSO_3$(s) before or during decomposition of $MgSO_3$(s) to MgO(s).

(8) 2 NaOH(aq or s)→2 NaOH(s)+Water

Note: In some embodiments, water may be removed and/or NaOH may be separated or precipitated by, for example, including, but not limited to, evaporation, or distillation, or crystallization, or separation systems or methods described herein, or separation systems or methods described in the art, or any combination thereof.

Note: In some embodiments, it may be desirable for NaOH to comprise a concentrated aqueous solution.

Example 9: Sodium Hydroxide Production from Sodium Sulfate Using Calcium Precipitation and Acid Intermediate (1) React Material Comprising Calcium, or Magnesium, or Other Alkaline Earth-Weak Acid Anion with Acetic Acid $CaCO_3$(s or aq)+2 $CH_3COOH$(aq)→$Ca(CH_3COO)_2$(aq)+$CO_2$(g)

Calcium Silicate(s)+2 $CH_3COOH$(aq)→$Ca(CH_3COO)_2$(aq)+Silicon Dioxide(s)

CaS(s)+2 $CH_3COOH$(aq)→$Ca(CH_3COO)_2$(aq)+$H_2S$(g)

Calcium(Weak Acid Anion)+2 $CH_3COOH$(aq)→$Ca(CH_3COO)_2$(aq)+Weak Acid(s, or g, or l, or aq)

Note: Residual solids or undissolved solids, such as silicon dioxide or other undissolved solids, may be separated from the liquid solution using a solid-liquid separation.

(2) $Ca(CH_3COO)_2$(aq)+$Na_2SO_4$(aq)→2 $NaCH_3COO$(aq)+$CaSO_4$(s)

(3) 2 $NaCH_3COO$(aq)+$SO_2$(g or aq)+$H_2O$(l or aq)→$Na_2SO_3$(aq)+2 $CH_3COOH$(aq)

(4) $Na_2SO_3$(aq)+2 $CH_3COOH$(aq)→2 $CH_3COOH$(aq)+$Na_2SO_3$(s)

Note: $CH_3COOH$ may be more soluble in water than $Na_2SO_3$. In some embodiments, water may be removed and/or $Na_2SO_3$ may be separated or precipitated by, for example, including, but not limited to, evaporation, or distillation, or crystallization, or separation systems or methods described herein, or separation systems or methods described in the art, or any combination thereof.

Note: $Na_2SO_3$(s) may be separated from $CH_3COOH$(aq) by a solid-liquid separation, which may include, but is not limited to, filter, or centrifuge, or decanter, or separation systems or methods described herein, or separation systems or methods described in the art, or any combination thereof.

(5) $Na_2SO_3$(s or aq)+$Mg(OH)_2$(s or aq)→2 NaOH(aq or s)+$MgSO_3$(s or aq)

Note: $Mg(OH)_2$(s or aq) may comprise a solid-liquid suspension, such as milk of lime.

Note: $MgSO_3$(s) may be separated using a solid-liquid separation.

(6) $MgSO_3$(s)→MgO(s)+$SO_2$(g)

Note: '(6)' may comprise calcining $MgSO_3$(s), which may employ a kiln.

Note: $MgSO_3$(s) may be dried, or dehydrated, or both before or during '(6)'.

(7) MgO(s)+Water(g or l or aq)→$Mg(OH)_2$(s or aq)

Note: MgO(s) may be employed to remove water vapor or facilitated drying of $MgSO_3$(s) before or during decomposition of $MgSO_3$(s) to MgO(s).

(8) 2 NaOH(aq or s)→2 NaOH(s)+Water

Or

2 NaOH(aq)→2 NaOH(aq-more concentrated)+Water

Note: In some embodiments, water may be removed and/or NaOH may be separated or precipitated by, for example, including, but not limited to, evaporation, or distillation, or crystallization, or separation systems or methods described herein, or separation systems or methods described in the art, or any combination thereof.

Note: In some embodiments, it may be desirable for NaOH to comprise a concentrated aqueous solution.

Note: Residual $MgSO_3$(aq) may be present or dissolved in the solution comprising NaOH(aq). In some embodiments, during the concentrating of NaOH(aq) or removal of at least a portion of water from the NaOH(aq), at least a portion of the residual $MgSO_3$ may precipitate or may be separated or recovered. For example, in some embodiments, $MgSO_3$(aq) may be less soluble in water than NaOH(aq). Separated or recovered $MgSO_3$ may be transferred, for example, to step '(6)'.

Example 10: Sodium Carbonate Production from Sodium Sulfate Using Alkaline-Earth Precipitation and Acid Intermediate (1) React Material comprising Calcium, or Magnesium, or Other Alkaline Earth-Weak Acid Anion with Acetic Acid $CaCO_3$(s or aq)+2 $CH_3COOH$(aq)→$Ca(CH_3COO)_2$(aq)+$CO_2$(g)

Calcium Silicate(s)+2 $CH_3COOH$(aq)→$Ca(CH_3COO)_2$(aq)+Silicon Dioxide(s)

CaS(s)+2 $CH_3COOH$(aq)→$Ca(CH_3COO)_2$(aq)+$H_2S$(g)

Calcium(Weak Acid Anion)+2 $CH_3COOH$(aq)→Ca$(CH_3COO)_2$(aq)+Weak Acid(s, or g, or l, or aq)

Note: Residual solids or undissolved solids, such as silicon dioxide or other undissolved solids, may be separated from the liquid solution using a solid-liquid separation.

(2) $Ca(CH_3COO)_2$(aq)+$Na_2SO_4$(aq)→2 $NaCH_3COO$(aq)+$CaSO_4$(s)

(3) 2 $NaCH_3COO$(aq)+$SO_2$(g or aq)+$H_2O$(l or aq)→$Na_2SO_3$(aq)+2 $CH_3COOH$(aq)

(4) $Na_2SO_3$(aq)+2 $CH_3COOH$(aq)→2 $CH_3COOH$(aq)+$Na_2SO_3$(s)

Note: $CH_3COOH$ may be more soluble in water than $Na_2SO_3$. In some embodiments, water may be removed and/or $Na_2SO_3$ may be separated or precipitated by, for example, including, but not limited to, evaporation, or distillation, or crystallization, or separation systems or methods described herein, or separation systems or methods described in the art, or any combination thereof.

Note: $Na_2SO_3$(s) may be separated from $CH_3COOH$(aq or l) by a solid-liquid separation, which may include, but is not limited to, filter, or centrifuge, or decanter, or separation systems or methods described herein, or separation systems or methods described in the art, or any combination thereof.

(5) $Na_2SO_3$(s or aq)+$Ca(OH)_2$(s or aq)→2 NaOH(aq or s)+$CaSO_3$(s)

Note: $Ca(OH)_2$(s or aq) may comprise a solid-liquid suspension, such as milk of lime.

Note: $CaSO_3$(s) may be separated using a solid-liquid separation.

Note: In some embodiments, $Na_2SO_3$(s) may be dissolved in water to form $Na_2SO_3$(aq) before step '(5)'. In some embodiments, water may provided from internally within the process, or water may be provided from an external source, or any combination thereof. For example, if net water is consumed, or water is in the sodium hydroxide or sodium carbonate product, or water is in the product, or any combination thereof, it may be desirable for a portion of the water to come from an external source.

(6) $CaSO_3$(s)→CaO(s)+$SO_2$(g)

Note: '(6)' may comprise calcining $CaSO_3$(s), which may employ a kiln.

Note: $CaSO_3$(s) may be dried, or dehydrated, or both before or during '(6)'.

(7) CaO(s)+Water(g or l or aq)→$Ca(OH)_2$(s or aq)

Note: CaO(s) may be employed to remove water vapor or facilitated drying of $CaSO_3$(s) before or during decomposition of $CaSO_3$(s) to CaO(s).

Note: In some embodiments, CaO may be reacted directly with $Na_2SO_3$(s or aq) or an aqueous solution comprising sodium sulfite. For example, in some embodiments, step '(5)' may be combined with step '(7)'

Note: In some embodiments, water may provided from internally within the process, or water may be provided from an external source, or any combination thereof. For example, if net water is consumed, or water is in the sodium hydroxide or sodium carbonate product, or water is in the product, or any combination thereof, it may be desirable for a portion of the water to come from an external source.

(8) 2 NaOH(aq or s)+$CO_2$(g)→$Na_2CO_3$(s or aq)+$H_2O$(l or aq or g)

Note: In some embodiments, $CO_2$ may comprise a gas with a dilute concentration of carbon dioxide, which may include, but is not limited to, $CO_2$ sources described herein or $CO_2$ sources. In some embodiments, NaOH(aq) may be capable of reacting with a wide range of $CO_2$(g) concentrations, including, potentially, for example, very low $CO_2$(g) concentrations, such as $CO_2$(g) in air.

Note: In some embodiments, NaOH(aq or s) may be added to the ocean or sea, where it may react with $CO_2$ or $CO_2$ derivative ions or chemical species in the ocean or air and/or increase ocean pH.

Note: $Na_2CO_3$(s or aq) may be further reacted with carbon dioxide and/or water to form sodium bicarbonate.

Note: $Na_2CO_3$(s) may precipitate and/or be separated from the remaining solution. After precipitation, NaOH(s) may be added and/or dissolved in the remaining solution to, for example, make up for sodium lost during the precipitation and separation of $Na_2CO_3$(s).

Note: In some embodiments, $Na_2CO_3$(aq), which may comprise a 'feed' solution into a concentrating process, may be concentrated using an energy efficient concentrating method, such as reverse osmosis or electrodialysis or heat recovery distillation, at an elevated temperature and/or the resulting concentrate or retentate may be cooled to precipitate a portion of $Na_2CO_3$(s). In some embodiments, the remaining solution after precipitation and separation of $Na_2CO_3$(s) may be mixed with $Na_2CO_3$(aq) feed solution before heating the combined solution and/or concentrating the combined solution using an energy efficient concentrating method. In some embodiments, water recovered during the concentrating, such as water permeate, or diluate, or condensate, may be, including, but not limited to, one or more or any combination of the following: employed dissolve sodium sulfite and form aqueous sodium sulfite, or transferred to a reaction of calcium oxide with water to produce calcium hydroxide, or transferred to dissolve sodium sulfate.

Note: $SO_2$(g) from calcining $CaSO_3$ may be further concentrated, or pressurized, or purified.

Note: $SO_2$(g) from calcining $CaSO_3$ may be absorbed into water or an aqueous solution to form sulfurous acid or aqueous sulfur dioxide.

Note: Weak acid or weak acid anion may comprise an acid or acid anion with an acid strength lower than the acid strength of formic acid, or acetic acid, or propionic acid, or butyric acid, or citric acid, or lactic acid, or valeric acid, or caproic acid, or enanthic acid, or caprylic acid, or pelargonic acid, or capric acid, or carboxylic acid, or sulfurous acid.

Note: Weak acid or weak acid anion may comprise an acid or acid anion with a higher pKa than acetic acid, or carboxylic acid, or sulfurous acid.

Note: Acetic acid may be provided as an example acid with an acid strength greater than 'Weak Acid', and an acid strength lower than sulfurous acid or aqueous sulfur dioxide.

Note: Acetic acid may be provided as an example acid with an pKa lower than 'Weak Acid', and an pKa greater than sulfurous acid or aqueous sulfur dioxide.

Note: Calcium may be provided as an example alkaline earth. Other alkaline earths, which may include beryllium (Be), or magnesium (Mg), or calcium (Ca), or strontium (Sr), or barium (Ba), or radium (Ra), or any combination thereof, may be employed instead or in addition to calcium.

Example 11: Process for Producing Calcium Oxide or Cement or Clinker with Ammonia Intermediate (1) React Material comprising Calcium, or Magnesium, or Other Alkaline Earth-Weak Acid Anion with Acetic Acid $CaCO_3$(s or aq)+2 $CH_3COOH$(aq)→$Ca(CH_3COO)_2$(aq)+$CO_2$(g)

Calcium Silicate(s)+2 $CH_3COOH$(aq)→$Ca(CH_3COO)_2$(aq)+Silicon Dioxide(s)

CaS(s)+2 $CH_3COOH$(aq)→$Ca(CH_3COO)_2$(aq)+$H_2S$(g)

Calcium(Weak Acid Anion)+2 $CH_3COOH$(aq)→$Ca(CH_3COO)_2$(aq)+Weak Acid(s, or g, or l, or aq)

Note: Residual solids or undissolved solids, such as silicon dioxide or other undissolved solids, may be separated from the liquid solution using a solid-liquid separation.

Note: If $CO_2$(g) is produced, it may be desirable for said $CO_2$(g) to be produced at a high partial pressure $CO_2$(g), or purity $CO_2$(g), or to comprise captured $CO_2$(g).

(2) $Ca(CH_3COO)_2$(aq)+$(NH_4)_2SO_3$(s or aq)→2 $NH_4CH_3COO$(aq)+$CaSO_3$(s)

Note: $CaSO_3$(s) may be separated using a solid-liquid separation.

(3) 2 $NH_4CH_3COO$(aq)+$SO_2$(g or aq)+$H_2O$(l or aq)→$(NH_4)_2SO_3$(aq)+2 $CH_3COOH$(aq)

(4) $(NH_4)_2SO_3$(aq)+2 $CH_3COOH$(aq)→2 $CH_3COOH$(aq)+$(NH_4)_2SO_3$(s)

Note: $CH_3COOH$ may be more soluble in water than $(NH_4)_2SO_3$. In some embodiments, water may be removed and/or $(NH_4)_2SO_3$ may be separated or precipitated by, for example, including, but not limited to, evaporation, or distillation, or crystallization, or separation systems or methods described herein, or zero-liquid discharge methods described in the art, or separation systems or methods described in the art, or any combination thereof.

Note: In some embodiments, magnesium sulfite(aq) may be present in the $(NH_4)_2SO_3$(aq)+2 $CH_3COOH$(aq). In some embodiments, if present, at least a portion of magnesium sulfite may begin to precipitate or crystalize before $(NH_4)_2SO_3$. In some embodiments, it may be desirable to separate at least a portion of the magnesium sulfite from $(NH_4)_2SO_3$.

Note: $(NH_4)_2SO_3$(s) may be separated from $CH_3COOH$(aq or l) by a solid-liquid separation, which may include, but is not limited to, filter, or centrifuge, or decanter, or separation systems or methods described herein, or separation systems or methods described in the art, or any combination thereof.

(5) $CaSO_3$(s)→CaO(s)+$SO_2$(g)

Note: '(5)' may comprise calcining $CaSO_3$(s), which may employ a kiln.

Note: $CaSO_3$(s) may be dried, or dehydrated, or both before, or during '(5)'.

Note: In some embodiments, it may be preferred to react $SO_2$(g) with $NH_4CH_3COO$(aq) to form $(NH_4)_2SO_3$(aq), then react $(NH_4)_2SO_3$ with $Ca(CH_3COO)_2$(aq) to form $CaSO_3$(s) because, for example, including, but not limited to, one or more or any combination of the following potential benefits:

In some embodiments, it may be desirable to absorb $SO_2$(g) in an absorption column. Precipitate formation can be problematic in an absorption columns due to, for example, including, but not limited to, precipitate clogging packing material, or plates, or interfering with gas flows, or interfering with liquid flows, or forming scaling, or any combination thereof. The reaction of $Ca(CH_3COO)_2$(aq) with $SO_2$(g) may form a precipitate comprising $CaSO_3$(s), which may be problematic in some absorption columns or a gas absorption processes. The reaction of $NH_4CH_3COO$(aq) with $SO_2$(g) may, if desired, remain an aqueous solution or liquid solution throughout the reaction, because, for example, $(NH_4)_2SO_3$ is soluble in water, which may be desirable in an absorption column.

For example, it may be desirable to absorb $SO_2$(g) in an absorption column because the $SO_2$(g) may be at a dilute concentration, or a low partial pressure, or may comprise a gas mixture, or to improve absorption efficiency, or any combination thereof. For example, in some embodiments, the process employed to decompose calcium sulfite to calcium oxide and sulfur dioxide may form a gas mixture comprising sulfur dioxide. For example, in some embodiments, the partial pressure of sulfur dioxide in said gas mixture may be lower than 1 atm, or 0.9 atm, or 0.8 atm, or 0.7 atm, or 0.6 atm, or 0.5 atm, or 0.4 atm, or 0.3 atm, or 0.2 atm, or 0.1 atm, or 0.05 atm, or any combination thereof and/or wherein the volume percent concentration of sulfur dioxide in said gas mixture may be lower than 100%, or 90%, or 80%, or 70%, or 60%, or 50%, or 40%, or 30%, or 20%, or 10%, or 5%, or any combination thereof.

Greater absorption rate or absorption efficiency.

Solid-liquid separations may be easier or simpler or higher yielding. For example, if the rate of precipitation is dependent on the mixing of two liquids, rather than a gas and a liquid, the formation of and/or separation of precipitates may be more controlled.

Example 12: Process for Producing Alkaline-Earth Oxide or Cement or Clinker with Ammonia Intermediate (1) React Material comprising Calcium, or Magnesium, or Other Alkaline Earth-Weak Acid Anion with Acetic Acid $MgCO_3$(s or aq)+2 $CH_3COOH$(aq)→$Mg(CH_3COO)_2$(aq)+$CO_2$(g)

Magnesium Silicate(s)+2 $CH_3COOH$(aq)→$Mg(CH_3COO)_2$(aq)+Silicon Dioxide(s)

MgS(s)+2 $CH_3COOH$(aq)→$Mg(CH_3COO)_2$(aq)+$H_2S$(g)

Magnesium(Weak Acid Anion)+2 $CH_3COOH$(aq)→$Mg(CH_3COO)_2$(aq)+Weak Acid(s, or g, or l, or aq)

Note: Residual solids or undissolved solids, such as silicon dioxide or other undissolved solids, may be separated from the liquid solution using a solid-liquid separation.

Note: If $CO_2$(g) is produced, it may be desirable for said $CO_2$(g) to be produced at a high partial pressure $CO_2$(g), or purity $CO_2$(g), or to comprise captured $CO_2$(g).

(2) $Mg(CH_3COO)_2$(aq)+$(NH_4)_2SO_3$(s or aq)→2 $NH_4CH_3COO$(aq)→$MgSO_3$(s)

Note: $MgSO_3$(s) may be separated using a solid-liquid separation.

(3) 2 $NH_4CH_3COO$(aq)+$SO_2$(g or aq)+$H_2O$(l or aq)→$(NH_4)_2SO_3$(aq)+2 $CH_3COOH$(aq)

(4) $(NH_4)_2SO_3$(aq)+2 $CH_3COOH$(aq)→2 $CH_3COOH$(aq)+$(NH_4)_2SO_3$(s)

Note: $CH_3COOH$ may be more soluble in water than $(NH_4)_2SO_3$. In some embodiments, water may be removed and/or $(NH_4)_2SO_3$ may be separated or precipitated by, for example, including, but not limited to, evaporation, or distillation, or crystallization, or separation systems or methods described herein, or separation systems or methods described in the art, or any combination thereof.

Note: In some embodiments, magnesium sulfite(aq) may be present in the $(NH_4)_2SO_3$(aq)+2 $CH_3COOH$(aq). In some embodiments, if present, magnesium sulfite may begin to precipitate or crystalize before $(NH_4)_2SO_3$.

Note: $(NH_4)_2SO_3$(s) may be separated from $CH_3COOH$(aq) by a solid-liquid separation, which may include, but is not limited to, filter, or centrifuge, or decanter, or separation systems or methods described herein, or separation systems or methods described in the art, or any combination thereof.

(5) $MgSO_3(s) \rightarrow MgO(s)+SO_2(g)$

Note: '(5)' may comprise calcining $CaSO_3(s)$, which may employ a kiln.

Note: $CaSO_3(s)$ may be dried, or dehydrated, or both before, or during '(5)'.

Note: In some embodiments, it may be preferred to react $SO_2(g)$ with $NH_4CH_3COO(aq)$ to form $(NH_4)_2SO_3(aq)$, then react $(NH_4)_2SO_3$ with $Mg(CH_3COO)_2(aq)$ to form $MgSO_3(s)$ because, for example, including, but not limited to, one or more or any combination of the following potential benefits:

- In some embodiments, it may be desirable to absorb $SO_2(g)$ in an absorption column. Precipitate formation can be problematic in an absorption columns due to, for example, including, but not limited to, precipitate clogging packing material, or plates, or interfering with gas flows, or interfering with liquid flows, or forming scaling, or any combination thereof. The reaction of $Mg(CH_3COO)_2(aq)$ with $SO_2(g)$ may form a precipitate comprising $MgSO_3(s)$, which may be problematic in some absorption columns or a gas absorption processes. The reaction of $NH_4CH_3COO(aq)$ with $SO_2(g)$ may, if desired, remain an aqueous solution or liquid solution throughout the reaction, because, for example, $Na_2SO_3$ is soluble in water, which may be desirable in an absorption column.
- For example, it may be desirable to absorb $SO_2(g)$ in an absorption column because the $SO_2(g)$ may be at a dilute concentration, or a low partial pressure, or may comprise a gas mixture, or to improve absorption efficiency, or any combination thereof. For example, in some embodiments, the process employed to decompose calcium sulfite to calcium oxide and sulfur dioxide may form a gas mixture comprising sulfur dioxide. For example, in some embodiments, the partial pressure of sulfur dioxide in said gas mixture may be lower than 1 atm, or 0.9 atm, or 0.8 atm, or 0.7 atm, or 0.6 atm, or 0.5 atm, or 0.4 atm, or 0.3 atm, or 0.2 atm, or 0.1 atm, or 0.05 atm, or any combination thereof and/or wherein the volume percent concentration of sulfur dioxide in said gas mixture may be lower than 100%, or 90%, or 80%, or 70%, or 60%, or 50%, or 40%, or 30%, or 20%, or 10%, or 5%, or any combination thereof.
- Greater absorption rate or absorption efficiency.
- Solid-liquid separations may be easier or simpler or higher yielding. For example, if the rate of precipitation is dependent on the mixing of two liquids, rather than a gas and a liquid, the formation of and/or separation of precipitates may be more controlled.

Example 13: Process for Producing Calcium Oxide or Cement or Clinker with Ammonia Intermediate with Recirculating Separation (1) React Material comprising Calcium, or Magnesium, or Other Alkaline Earth-Weak Acid Anion with Acetic Acid $CaCO_3(s \text{ or } aq)+2\ CH_3COOH(aq) \rightarrow Ca(CH_3COO)_2(aq)+CO_2(g)$ Calcium Silicate(s)+2 $CH_3COOH(aq) \rightarrow Ca(CH_3COO)_2(aq)$+Silicon Dioxide(s)

$CaS(s)+2\ CH_3COOH(aq) \rightarrow Ca(CH_3COO)_2(aq)+H_2S(g)$

Calcium(Weak Acid Anion)+2 $CH_3COOH(aq) \rightarrow Ca(CH_3COO)_2(aq)$+Weak Acid(s, or g, or l, or aq)

Note: Residual solids or undissolved solids, such as silicon dioxide or other undissolved solids, may be separated from the liquid solution using a solid-liquid separation.

(2) $Ca(CH_3COO)_2(aq)+(NH_4)_2SO_3(s \text{ or } aq)+CH_3COOH(aq) \rightarrow 2\ NH_4CH_3COO(aq)+CH_3COOH(aq)+CaSO_3(s)$ Note: $CaSO_3(s)$ may be separated using a solid-liquid separation.

Note: $CH_3COOH(aq)$ may be present due to $CH_3COOH(aq)$ being present in the retentate solution comprising $(NH_4)_2SO_3(aq)$ from a membrane based separation of $CH_3COOH(aq)$ and $(NH_4)_2SO_3(aq)$.

(3) 2 $(NH_4)CH_3COO(aq)+SO_2(g \text{ or } aq)+H_2O(l \text{ or } aq) \rightarrow (NH_4)_2SO_3(aq)+2\ CH_3COOH(aq)$ (4) $(NH_4)_2SO_3(aq)+2\ CH_3COOH(aq) \rightarrow 2\ CH_3COOH(aq)$ separately from $(NH_4)_2SO_3(aq)+2\ CH_3COOH(aq)$ Note: A portion of $CH_3COOH(aq)$ may be separated from $(NH_4)_2SO_3(aq)$ using a separation process, such as a membrane based process, such as reverse osmosis. In some embodiments, $CH_3COOH(aq)$ may have a hydration radius or molar mass sufficiently small to permeate through a membrane, while said membrane may reject $(NH_4)_2SO_3(aq)$. In some embodiments, $(NH_4)_2SO_3(aq)+2\ CH_3COOH(aq)$ may be separated into a permeate solution comprising 2 $CH_3COOH(aq)$ and a retentate solution comprising $(NH_4)_2\ SO_3(aq)+2\ CH_3COOH(aq)$.

(5) $CaSO_3(s) \rightarrow CaO(s)+SO_2(g)$

Note: '(5)' may comprise calcining $CaSO_3(s)$, which may employ a kiln.

Note: $CaSO_3(s)$ may be dried, or dehydrated, or both before or during '(5)'.

Example 14: Process for Producing Alkaline-Earth Oxide or Cement or Clinker with Ammonia Intermediate with Recirculating Separation (1) React Material comprising Calcium, or Magnesium, or Other Alkaline Earth-Weak Acid Anion with Acetic Acid $MgCO_3(s \text{ or } aq)+2\ CH_3COOH(aq) \rightarrow Mg(CH_3COO)_2(aq)+CO_2(g)$ Magnesium Silicate(s)+2 $CH_3COOH(aq) \rightarrow Mg(CH_3COO)_2(aq)$+Silicon Dioxide(s)

$MgS(s)+2\ CH_3COOH(aq) \rightarrow Mg(CH_3COO)_2(aq)+H_2S(g)$

Magnesium(Weak Acid Anion)+2 $CH_3COOH(aq) \rightarrow Mg(CH_3COO)_2(aq)$+Weak Acid(s, or g, or l, or aq)

Note: Residual solids or undissolved solids, such as silicon dioxide or other undissolved solids, may be separated from the liquid solution using a solid-liquid separation.

(2) $Mg(CH_3COO)_2(aq)+(NH_4)_2SO_3(s \text{ or } aq)+CH_3COOH(aq) \rightarrow 2\ NH_4CH_3COO(aq)+CH_3COOH(aq)+MgSO_3(s)$ Note: $MgSO_3(s)$ may be separated using a solid-liquid separation.

Note: $CH_3COOH(aq)$ may be present due to $CH_3COOH(aq)$ being present in the retanate solution comprising $(NH_4)_2\ SO_3(aq)$ from a membrane based separation of $CH_3COOH(aq)$ and $(NH_4)_2SO_3(aq)$.

(3) 2 $NH_4CH_3COO(aq)+SO_2(g \text{ or } aq)+H_2O(l \text{ or } aq) \rightarrow (NH_4)_2SO_3(aq)+2\ CH_3COOH(aq)$ (4) $(NH_4)_2SO_3(aq)+2\ CH_3COOH(aq) \rightarrow 2\ CH_3COOH(aq)$ separately from $(NH_4)_2SO_3(aq)+2\ CH_3COOH(aq)$ Note: A portion of $CH_3COOH(aq)$ may be separated from $(NH_4)_2SO_3(aq)$ using a separation process, such as a membrane based process, such as reverse osmosis. In some embodiments, $CH_3COOH(aq)$ may have a hydration radius or molar mass sufficiently small to permeate through a membrane, while said membrane may reject $(NH_4)_2SO_3(aq)$. In some embodiments, $(NH_4)_2SO_3(aq)+2\ CH_3COOH(aq)$ may be separated into a permeate solution comprising 2 $CH_3COOH(aq)$ and a retentate solution comprising $(NH_4)_2\ SO_3(aq)+2\ CH_3COOH(aq)$.

(5) $MgSO_3(s) \rightarrow MgO(s)+SO_2(g)$

Note: '(6)' may comprise calcining $MgSO_3(s)$, which may employ a kiln.

Note: $MgSO_3(s)$ may be dried, or dehydrated, or both before or during '(6)'.

Example 15: Ammonia Production from Ammonium Sulfate Using Calcium Precipitation and Acid Intermediate (1) React Material comprising Calcium, or Magnesium, or Other Alkaline Earth-Weak Acid Anion with Acetic Acid $CaCO_3$(s or aq)+2 $CH_3COOH(aq) \rightarrow Ca(CH_3COO)_2(aq)+CO_2(g)$ Calcium Silicate(s)+2 $CH_3COOH(aq) \rightarrow Ca(CH_3COO)_2$(aq)+Silicon Dioxide(s)

$CaS(s)$+2 $CH_3COOH(aq) \rightarrow Ca(CH_3COO)_2(aq)+H_2S(g)$

Calcium(Weak Acid Anion)+2 $CH_3COOH(aq) \rightarrow Ca(CH_3COO)_2$(aq)+Weak Acid(s, or g, or l, or aq)

Note: Residual solids or undissolved solids, such as silicon dioxide or other undissolved solids, may be separated from the liquid solution using a solid-liquid separation.

(2) $Ca(CH_3COO)_2(aq)+(NH_4)_2SO_4(aq) \rightarrow 2\ NH_4CH_3COO\ (aq)+CaSO_4(s)$ (3) 2 $NH_4CH_3COO(aq)+SO_2$(g or aq)+$H_2O$(l or aq)$\rightarrow (NH_4)_2SO_3(aq)$+2 $CH_3COOH(aq)$ (4) $(NH_4)_2SO_3(aq)$+2 $CH_3COOH(aq) \rightarrow$ 2 $CH_3COOH$(aq or l)+$(NH_4)_2SO_3(s)$+Water Note: $CH_3COOH$ may be more soluble in water than $(NH_4)_2SO_3$. In some embodiments, water may be removed and/or $(NH_4)_2SO_3$ may be separated or precipitated by, for example, including, but not limited to, evaporation, or distillation, or crystallization, or separation systems or methods described herein, or separation systems or methods described in the art, or any combination thereof.

Note: $(NH_4)_2SO_3(s)$ may be separated from $CH_3COOH$ (aq or l) by a solid-liquid separation, which may include, but is not limited to, filter, or centrifuge, or decanter, or separation systems or methods described herein, or separation systems or methods described in the art, or any combination thereof.

(5) $(NH_4)_2SO_3$(s or aq)+$Ca(OH)_2$(s or aq)$\rightarrow$[2 $NH_4OH$(aq) or 2 $NH_3$(aq)]+$CaSO_3(s)$ Note: $Ca(OH)_2$(s or aq) may comprise a solid-liquid suspension, such as milk of lime.

Note: $CaSO_3(s)$ may be separated using a solid-liquid separation.

Note: 2 $NH_3(aq)$ may be separated into ammonia gas and water if desired.

(6) $CaSO_3(s) \rightarrow CaO(s)+SO_2(g)$

Note: '(6)' may comprise calcining $CaSO_3(s)$, which may employ a kiln.

Note: $CaSO_3(s)$ may be dried, or dehydrated, or both before or during '(6)'.

(7) $CaO(s)$+Water(g or l or aq)$\rightarrow Ca(OH)_2$(s or aq)

Note: $CaO(s)$ may be employed to remove water vapor or facilitated drying of $CaSO_3(s)$ before or during decomposition of $CaSO_3(s)$ to $CaO(s)$.

(8) 2 $NH_4OH(aq)$ or 2 $NH_3(aq)$+2 $NH_3$(g or l or aq)+Water

Note: In some embodiments, it may be desirable to produce ammonia gas or liquid ammonia. In some embodiments, it may be desirable to produce a high concentration or greater concentration aqueous ammonia or ammonium hydroxide solution.

Note: In some embodiments, it may be desirable for 2 $NH_4OH(aq)$ or 2 $NH_3(aq)$ to comprise an aqueous solution.

If example, in some embodiments, it may be desirable for to keep aqueous ammonia or ammonium hydroxide at an aqueous phase.

Example 16: Ammonia Production from Ammonium Sulfate using Alkaline-Earth Precipitation and Acid Intermediate (1) React Material comprising Calcium, or Magnesium, or Other Alkaline Earth-Weak Acid Anion with Acetic Acid $MgCO_3$(s or aq)+2 $CH_3COOH(aq) \rightarrow Mg(CH_3COO)_2(aq)+CO_2(g)$ Magnesium Silicate(s)+2 $CH_3COOH(aq) \rightarrow Mg(CH_3COO)_2$(aq)+Silicon Dioxide(s)

$MgS(s)$+2 $CH_3COOH(aq) \rightarrow Mg(CH_3COO)_2(aq)+H_2S(g)$

Magnesium(Weak Acid Anion)+2 $CH_3COOH(aq) \rightarrow Mg(CH_3COO)_2$(aq)+Weak Acid(s, or g, or l, or aq)

Note: Residual solids or undissolved solids, such as silicon dioxide or other undissolved solids, may be separated from the liquid solution using a solid-liquid separation.

(2) $Mg(CH_3COO)_2(aq)+(NH_4)_2SO_4(aq) \rightarrow 2\ NH_4CH_3COO(aq)+MgSO_4$(s or aq)

(3) 2 $NH_4CH_3COO(aq)+SO_2$(g or aq)+$H_2O$(l or aq)$\rightarrow (NH_4)_2SO_3(aq)$+2 $CH_3COOH(aq)$ (4) $(NH_4)_2SO_3(aq)$+2 $CH_3COOH(aq) \rightarrow$ 2 $CH_3COOH(aq)+(NH_4)_2SO_3(s)$ Note: $CH_3COOH$ may be more soluble in water than $(NH_4)_2SO_3$. In some embodiments, water may be removed and/or $(NH_4)_2SO_3$ may be separated or precipitated by, for example, including, but not limited to, evaporation, or distillation, or crystallization, or separation systems or methods described herein, or separation systems or methods described in the art, or any combination thereof.

Note: $(NH_4)_2SO_3(s)$ may be separated from $CH_3COOH$ (aq or l) by a solid-liquid separation, which may include, but is not limited to, filter, or centrifuge, or decanter, or separation systems or methods described herein, or separation systems or methods described in the art, or any combination thereof.

(5) $(NH_4)_2SO_3$(s or aq)+$Mg(OH)_2$(s or aq)$\rightarrow$[2 $NH_4OH$(aq) or 2 $NH_3$(aq)]+$MgSO_3(s)$ Note: $Mg(OH)_2$(s or aq) may comprise a solid-liquid suspension, such as milk of lime.

Note: $MgSO_3(s)$ may be separated using a solid-liquid separation.

Note: 2 $NH_3(aq)$ may be separated into ammonia gas and water if desired.

(6) $MgSO_3(s) \rightarrow MgO(s)+SO_2(g)$

Note: '(6)' may comprise calcining $MgSO_3(s)$, which may employ a kiln.

Note: $MgSO_3(s)$ may be dried, or dehydrated, or both before or during '(6)'.

(7) $MgO(s)$+Water(g or l or aq)$\rightarrow Mg(OH)_2$(s or aq)

Note: $MgO(s)$ may be employed to remove water vapor or facilitated drying of $MgSO_3(s)$ before or during decomposition of $MgSO_3(s)$ to $MgO(s)$.

(8) 2 $NH_4OH(aq)$ or 2 $NH_3(aq) \rightarrow$ 2 $NH_3$(g or l or aq)+Water

Note: In some embodiments, it may be desirable to produce ammonia gas or liquid ammonia. In some embodiments, it may be desirable to produce a high concentration or greater concentration aqueous ammonia or ammonium hydroxide solution.

Note: In some embodiments, it may be desirable for 2 $NH_4OH(aq)$ or 2 $NH_3(aq)$ to comprise an aqueous solution.

If example, in some embodiments, it may be desirable for to keep aqueous ammonia or ammonium hydroxide at an aqueous phase.

Example 17: Ammonia Production from Ammonium Sulfate Using Alkaline-Earth Precipitation and Acid Intermediate (1) React Material comprising Calcium, or Magnesium, or Other Alkaline Earth-Weak Acid Anion with Acetic Acid $CaCO_3$(s or aq)+2 $CH_3COOH$(aq)→$Ca(CH_3COO)_2$(aq)+$CO_2$(g)

Calcium Silicate(s)+2 $CH_3COOH$(aq)→$Ca(CH_3COO)_2$(aq)+Silicon Dioxide(s)

CaS(s)+2 $CH_3COOH$(aq)→$Ca(CH_3COO)_2$(aq)+$H_2S$(g)

Calcium(Weak Acid Anion)+2 $CH_3COOH$(aq)→$Ca(CH_3COO)_2$(aq)+Weak Acid(s, or g, or l, or aq)

Note: Residual solids or undissolved solids, such as silicon dioxide or other undissolved solids, may be separated from the liquid solution using a solid-liquid separation.

(2) $Ca(CH_3COO)_2$(aq)+$(NH_4)_2SO_4$(aq)→2 $NH_4CH_3COO$(aq)→$CaSO_4$(s)

(3) 2 $NH_4CH_3COO$(aq)+$SO_2$(g or aq)+$H_2O$(l or aq)→$(NH_4)_2SO_3$(aq)+2 $CH_3COOH$(aq)

(4) $(NH_4)_2SO_3$(aq)+2 $CH_3COOH$(aq)→2 $CH_3COOH$(aq)+$(NH_4)_2SO_3$(s)

Note: $CH_3COOH$ may be more soluble in water than $(NH_4)_2SO_3$. In some embodiments, water may be removed and/or $(NH_4)_2SO_3$ may be separated or precipitated by, for example, including, but not limited to, evaporation, or distillation, or crystallization, or separation systems or methods described herein, or separation systems or methods described in the art, or any combination thereof.

Note: $(NH_4)_2SO_3$(s) may be separated from $CH_3COOH$ (aq or l) by a solid-liquid separation, which may include, but is not limited to, filter, or centrifuge, or decanter, or separation systems or methods described herein, or separation systems or methods described in the art, or any combination thereof.

(5) $(NH_4)_2SO_3$(s or aq)+$Mg(OH)_2$(s or aq)→[2 $NH_4OH$(aq) or 2 $NH_3$(aq)]+$MgSO_3$(s or aq)

Note: $Mg(OH)_2$(s or aq) may comprise a solid-liquid suspension, such as milk of lime.

Note: $MgSO_3$(s) may be separated using a solid-liquid separation.

Note: 2 $NH_3$(aq) may be separated into ammonia gas and water if desired.

(6) $MgSO_3$(s)→MgO(s)+$SO_2$(g)

Note: '(6)' may comprise calcining $MgSO_3$(s), which may employ a kiln.

Note: $MgSO_3$(s) may be dried, or dehydrated, or both before or during '(6)'.

(7) MgO(s)+Water(g or l or aq)→$Mg(OH)_2$(s or aq)

Note: MgO(s) may be employed to remove water vapor or facilitated drying of $MgSO_3$(s) before or during decomposition of $MgSO_3$(s) to MgO(s).

(8) 2 $NH_4OH$(aq) or 2 $NH_3$(aq)→2 $NH_3$(g or l or aq)+Water

Note: In some embodiments, it may be desirable to produce ammonia gas or liquid ammonia. In some embodiments, it may be desirable to produce a high concentration or greater concentration aqueous ammonia or ammonium hydroxide solution.

Note: In some embodiments, it may be desirable for 2 $NH_4OH$(aq) or 2 $NH_3$(aq) to comprise an aqueous solution.

If example, in some embodiments, it may be desirable for to keep aqueous ammonia or ammonium hydroxide at an aqueous phase.

Example 18: Ammonium Carbonate or Ammonium Bicarbonate or Ammonium Carbamate or Urea Production Using Acid Intermediate (1) React Material comprising Calcium, or Magnesium, or Other Alkaline Earth-Weak Acid Anion with Acetic Acid $CaCO_3$(s or aq)+2 $CH_3COOH$(aq)→$Ca(CH_3COO)_2$(aq)+$CO_2$(g)

Calcium Silicate(s)+2 $CH_3COOH$(aq)→$Ca(CH_3COO)_2$(aq)+Silicon Dioxide(s)

CaS(s)+2 $CH_3COOH$(aq)→$Ca(CH_3COO)_2$(aq)+$H_2S$(g)

Calcium(Weak Acid Anion)+2 $CH_3COOH$(aq)→$Ca(CH_3COO)_2$(aq)+Weak Acid(s, or g, or l, or aq)

Note: Residual solids or undissolved solids, such as silicon dioxide or other undissolved solids, may be separated from the liquid solution using a solid-liquid separation.

(2) $Ca(CH_3COO)_2$(aq)+$(NH_4)_2SO_4$(aq)→2 $NH_4CH_3COO$(aq)+$CaSO_4$(s)

(3) 2 $NH_4CH_3COO$(aq)+$SO_2$(g or aq)+$H_2O$(l or aq)→$(NH_4)_2SO_3$(aq)+2 $CH_3COOH$(aq)

(4) $(NH_4)_2SO_3$(aq)+2 $CH_3COOH$(aq)→2 $CH_3COOH$(aq)+$(NH_4)_2SO_3$(s)

Note: $CH_3COOH$ may be more soluble in water than $Na_2SO_3$. In some embodiments, water may be removed and/or $Na_2SO_3$ may be separated or precipitated by, for example, including, but not limited to, evaporation, or distillation, or crystallization, or separation systems or methods described herein, or separation systems or methods described in the art, or any combination thereof.

Note: $(NH_4)_2SO_3$(s) may be separated from $CH_3COOH$ (aq or l) by a solid-liquid separation, which may include, but is not limited to, filter, or centrifuge, or decanter, or separation systems or methods described herein, or separation systems or methods described in the art, or any combination thereof.

(5) $(NH_4)_2SO_3$(s or aq)+$Ca(OH)_2$(s or aq)→[2 $NH_4OH$(aq) or 2 $NH_3$(aq)]+$CaSO_3$(s)

Note: $Ca(OH)_2$(s or aq) may comprise a solid-liquid suspension, such as milk of lime.

Note: $CaSO_3$(s) may be separated using a solid-liquid separation.

(6) $CaSO_3$(s)→CaO(s)+$SO_2$(g)

Note: '(6)' may comprise calcining $CaSO_3$(s), which may employ a kiln.

Note: $CaSO_3$(s) may be dried, or dehydrated, or both before or during '(6)'.

(7) CaO(s)+Water(g or l or aq)→$Ca(OH)_2$(s or aq)

Note: CaO(s) may be employed to remove water vapor or facilitated drying of $CaSO_3$(s) before or during decomposition of $CaSO_3$(s) to CaO(s).

(8) 2 $NH_4OH$(aq)+$CO_2$(g)→$(NH_4)_2CO_3$(s or aq)+$H_2O$(l or aq or g)

Note: In some embodiments, $(NH_4)_2CO_3$(s or aq) may be further reacted with carbon dioxide and/or water to form sodium bicarbonate.

Note: In some embodiments, the aqueous solution may comprise a mixture of ammonium carbonate, or ammonium bicarbonate, or ammonium carbamate, or ammonium sesquicarbonate, or free ammonia, or aqueous ammonia, or ammonium hydroxide, or any combination thereof.

Example 19: Direct Air Capture, or Capture of $CO_2$ from Air, or $CO_2$ Capture Using Alkaline-Earth, Sulfur Dioxide, and Acid (1) Reaction of alkaline-earth oxide, or alkaline-earth hydroxide, or any combination thereof with carbon dioxide.

$CaO(s)+CO_2(g)\rightarrow CaCO_3(s)$ and/or $Ca(OH)_2$(s or aq)+$CO_2(g)\rightarrow CaCO_3(s)+H_2O$(g or l)

(2) $CaCO_3$(s or aq)+2 $CH_3COOH(aq)\rightarrow Ca(CH_3COO)_2(aq)+CO_2(g)$

Note: $CO_2(g)$ in '(2)' may comprise captured $CO_2(g)$.

(3) $Ca(CH_3COO)_2(aq)+SO_2(g)\rightarrow CaSO_3(s)+2\ CH_3COOH(aq)$

Note: In some embodiments, $SO_2(g)$ may comprise a gas comprising a dilute concentration of $SO_2(g)$.

(4) $CaSO_3(s)\rightarrow CaO(s)+SO_2(g)$ (5) $CaO(s)+H_2O$(l or g)$\rightarrow Ca(OH)_2$(s or aq)

Example 20: Direct Air Capture, or Capture of $CO_2$ from Air, or $CO_2$ Capture Using Alkaline-Earth, Sulfur Dioxide, and Acid (1) Reaction of Alkaline-Earth Oxide, or Alkaline-Earth Hydroxide, or any Combination Thereof with Carbon Dioxide.

$MgO(s)+CO_2(g)\rightarrow MgCO_3(s)$ and/or $Mg(OH)_2$(s or aq)+$CO_2(g)\rightarrow MgCO_3(s)+H_2O$(g or l)

(2) $MgCO_3$(s or aq)+2 $CH_3COOH(aq)\rightarrow Mg(CH_3COO)_2(aq)+CO_2(g)$

Note: $CO_2(g)$ in '(2)' may comprise captured $CO_2(g)$.

(3) $Mg(CH_3COO)_2(aq)+SO_2(g)\rightarrow MgSO_3(s)+2\ CH_3COOH(aq)$

Note: In some embodiments, $SO_2(g)$ may comprise a gas comprising a dilute concentration of $SO_2(g)$.

(4) $MgSO_3(s)\rightarrow MgO(s)+SO_2(g)$ (5) $MgO(s)+H_2O$(l or g)$\rightarrow Mg(OH)_2$(s or aq)

Example 21: Direct Air Capture, or Capture of $CO_2$ from Air, or $CO_2$ Capture Using Alkali, Alkaline-Earth, and Sulfur Dioxide (1) 2 $NaOH(aq)+CO_2(g)\rightarrow Na_2CO_3$(aq or s)+$H_2O$(g or l)

(2) $Na_2CO_3$(aq or s)+$SO_2$(l or aq)$\rightarrow Na_2SO_3$(aq or s)+$CO_2(g)$ Note: $CO_2(g)$ in '(2)' may comprise captured $CO_2(g)$.

(3) $Na_2SO_3$(aq or s)+$Ca(OH)_2$(s or aq)$\rightarrow$2 $NaOH(aq)+CaSO_3(s)$ (4) $CaSO_3(s)\rightarrow CaO(s)+SO_2(g)$ (5) $CaO(s)+H_2O$(l or g)$\rightarrow Ca(OH)_2$(s or aq)

Example 22: Direct Air Capture, or Capture of $CO_2$ from Air, or $CO_2$ Capture Using Alkali, Alkaline-Earth, and Sulfur Dioxide (1) 2 $NaOH(aq)+CO_2(g)\rightarrow Na_2CO_3$(aq or s)+$H_2O$(g or l)

(2) $Na_2CO_3$(aq or s)+$SO_2$(l or aq)$\rightarrow Na_2SO_3$(aq or s)+$CO_2(g)$ Note: $CO_2(g)$ in '(2)' may comprise captured $CO_2(g)$.

(3) $Na_2SO_3$(aq or s)+$Mg(OH)_2$(s or aq)$\rightarrow$2 $NaOH(aq)+MgSO_3(s)$ (4) $MgSO_3(s)\rightarrow MgO(s)+SO_2(g)$ (5) $MgO(s)+H_2O$(l or g)$\rightarrow Mg(OH)_2$(s or aq)

Example 23: Direct Air Capture, or Capture of $CO_2$ from Air, or $CO_2$ Capture Using Alkali, Alkaline-Earth, and Sulfur Dioxide (1) 2 $NaOH(aq)+CO_2(g)\rightarrow Na_2CO_3$(aq or s)+$H_2O$(g or l)

(2) $Na_2CO_3$(aq or s)+2 $CH_3COOH$ (l or aq)$\rightarrow$2 $NaCH_3COO(aq)+CO_2(g)$ Note: $CO_2(g)$ in '(2)' may comprise captured $CO_2(g)$.

(3) 2 $NaCH_3COO(aq)+SO_2(g)\rightarrow Na_2SO_3$(aq or s)+2 $CH_3COOH$ (aq)

Note: In some embodiments, $SO_2(g)$ may comprise a gas comprising a dilute concentration of $SO_2(g)$.

(4) Separate $Na_2SO_3$ from 2 $CH_3COOH$ (5) $Na_2SO_3$(aq or s)+$Ca(OH)_2$(s or aq)$\rightarrow$2 $NaOH(aq)\rightarrow CaSO_3(s)$ (6) $CaSO_3(s)\rightarrow CaO(s)+SO_2(g)$ (7) $CaO(s)+H_2O$(l or g)$\rightarrow Ca(OH)_2$(s or aq)

Example 24: Direct Air Capture, or Capture of $CO_2$ from Air, or $CO_2$ Capture Using Alkali, Alkaline-Earth, and Sulfur Dioxide (1) 2 $NaOH(aq)+CO_2(g)\rightarrow Na_2CO_3$(aq or s)+$H_2O$(g or l)

(2) $Na_2CO_3$(aq or s)+2 $CH_3COOH$ (l or aq)$\rightarrow$2 $NaCH_3COO(aq)+CO_2(g)$ Note: $CO_2(g)$ in '(2)' may comprise captured $CO_2(g)$.

(3) 2 $NaCH_3COO(aq)+SO_2(g)\rightarrow Na_2SO_3$(aq or s)+2 $CH_3COOH$ (aq)

Note: In some embodiments, $SO_2(g)$ may comprise a gas comprising a dilute concentration of $SO_2(g)$.

(4) Separate $Na_2SO_3$ from 2 $CH_3COOH$ (5) $Na_2SO_3$(aq or s)+$Mg(OH)_2$(s or aq)$\rightarrow$2 $NaOH(aq)+MgSO_3(s)$ (6) $MgSO_3(s)\rightarrow MgO(s)+SO_2(g)$ (7) $MgO(s)+H_2O$(l or g)$\rightarrow Mg(OH)_2$(s or aq)

Example 25: $CO_2$ Capture with Decoupled $CO_2$ Absorption or Adsorption, $CO_2$ Desorption or Displacement, and Reagent Regeneration (1) $CO_2$ Absorption: $CO_2$ may be absorbed or adsorbed in calcium oxide, or calcium hydroxide, or calcium hydroxide suspension, such as milk of lime, or any combination thereof to produce calcium carbonate solid or suspension.

$Ca(OH)_2$(s or aq)+$CO_2(g)\rightarrow CaCO_3(s)+H_2O$(l or g)

Note: Calcium hydroxide suspension may be transported to the absorption location and/or stored at or near the absorption location.

Note: Calcium carbonate solid may be separated by settling, or solid-liquid separation, or any combination thereof.

Note: Calcium carbonate may be stored at or near the absorption or adsorption location. Calcium carbonate may be transported to an application using calcium carbonate. Calcium carbonate may be transferred to the $CO_2$ desorption or displacement location. In some embodiments, the $CO_2$ desorption or displacement location may be the same as the $CO_2$ absorption or adsorption location. In some embodiments, the $CO_2$ desorption or displacement location may be different than the $CO_2$ absorption or adsorption location. For example, in some embodiments, it may be desirable for the $CO_2$ absorption or adsorption to be located at multiple distributed sites, while the Regeneration may be conducted at a larger and/or more centralized facility or site.

(2) $CO_2$ Desorption or Displacement: Calcium carbonate may be reacted with acetic acid to produce calcium acetate and carbon dioxide.

$CaCO_3(s)+2\ CH_3COOH \rightarrow Ca(CH_3COO)_2(aq)+CO_2(g)$

Note: Calcium carbonate may be stored at or near the $CO_2$ Desorption or Displacement location.

Note: Acetic acid may be stored at or near the $CO_2$ Desorption or Displacement location.

Note: $CO_2$ Desorption or Displacement may be located at an application requiring carbon dioxide, or high purity carbon dioxide, or high pressure carbon dioxide, or captured carbon dioxide, or any combination thereof. For example, $CO_2$ Desorption or Displacement may be located at a site requiring $CO_2$ enhanced oil recovery (EOR).

Note: Calcium acetate may comprise an aqueous calcium acetate solution, or calcium acetate solid, or any combination thereof.

Note: Calcium acetate may be stored at or near the $CO_2$ Desorption or Displacement. Calcium acetate may be transported to an application using calcium acetate. Calcium acetate may be transferred to at or near the Regeneration location. In some embodiments, the $CO_2$ desorption or displacement location may be the same as Regeneration location. In some embodiments, the $CO_2$ desorption or displacement location may be different than the Regeneration location. For example, in some embodiments, it may be desirable for the $CO_2$ Desorption or Displacement to be located at multiple distributed sites, while the Regeneration may be conducted at a larger and/or more centralized facility or site.

Note: Acetic acid vapor may be present in the $CO_2(g)$. In some embodiments, acetic acid vapor may be at least partially removed from $CO_2(g)$ by, for example, including, but not limited to, one or more or any combination of the following: contacting $CO_2(g)$ comprising a portion of acetic acid vapor with $CaCO_3$, or contacting $CO_2(g)$ comprising a portion of acetic acid vapor with sodium carbonate, or contacting $CO_2(g)$ comprising a portion of acetic acid vapor with an alkali carbonate, or compression, or cooling, or condensing, or cryo-separation, or freeze separation.

(3) Regeneration: Calcium acetate may be reacted with sulfur dioxide to produce calcium sulfite. Calcium sulfite may be converted into calcium oxide and sulfur dioxide. Calcium oxide may be reacted with water to form a calcium hydroxide suspension, such as milk of lime.

$Ca(CH_3COO)_2(aq)+SO_2(g\ \text{or}\ aq) \rightarrow CaSO_3(s)+2\ CH_3COOH(aq)$ $CaSO_3(s) \rightarrow CaO(s)+SO_2(g)$ $CaO(s)+H_2O(g\ \text{or}\ l) \rightarrow Ca(OH)_2(s\ \text{or}\ aq)$ Note: Calcium oxide or calcium hydroxide may be transported to the $CO_2$ Absorption or Adsorption location.

Note: Acetic acid may be transported to the $CO_2$ Desorption or Displacement location.

Note: It may be desirable for the regeneration to comprise a centralized facility, or a facility which may benefit from economies of scale, or any combination thereof.

Example 26: $CO_2$ Capture with Decoupled $CO_2$ Absorption or Adsorption, $CO_2$ Desorption or Displacement, and Reagent Regeneration (1) $CO_2$ Absorption: $CO_2$ may be absorbed or adsorbed in calcium oxide, or calcium hydroxide, or calcium hydroxide suspension, such as milk of lime, or any combination thereof to produce calcium carbonate solid or suspension.

$Ca(OH)_2(s\ \text{or}\ aq)+CO_2(g) \rightarrow CaCO_3(s)+H_2O(l\ \text{or}\ g)$ (2) $CO_2$ Desorption or Displacement: Calcium carbonate may be reacted with aqueous sulfurous acid to produce calcium sulfite and carbon dioxide.

$CaCO_3(s)+SO_2(aq) \rightarrow CaSO_3(s)+CO_2(g)$

Note: $SO_2(g)$ vapor may be present in the $CO_2(g)$. In some embodiments, $SO_2(g)$ may be at least partially removed from $CO_2(g)$ by, for example, including, but not limited to, one or more or any combination of the following: contacting $CO_2(g)$ comprising a portion of $SO_2(g)$ with $CaCO_3$, or contacting $CO_2(g)$ comprising a portion of $SO_2(g)$ with sodium carbonate, or contacting $CO_2(g)$ comprising a portion of $SO_2(g)$ with an alkali carbonate, or compression, or cooling, or condensing, or cryo-separation, or freeze separation.

(3) Regeneration: Calcium sulfite is converted into calcium oxide and sulfur dioxide. Calcium oxide is reacted with water to form a calcium hydroxide suspension, such as milk of lime.

$CaSO_3(s) \rightarrow CaO(s)+SO_2(g)$ $CaO(s)+H_2O(g\ \text{or}\ l) \rightarrow Ca(OH)_2(s\ \text{or}\ aq)$ Example 27: $CO_2$ Capture with Decoupled $CO_2$ Absorption or Adsorption, $CO_2$ Desorption or Displacement, and Reagent Regeneration (1) $CO_2$ Adsorption: $CO_2$ adsorption or absorption in calcium oxide or calcium hydroxide to produce calcium carbonate solid $CaO(s)+CO_2(g) \rightarrow CaCO_3(s)$ $Ca(OH)_2(s\ \text{or}\ aq)+CO_2(g) \rightarrow CaCO_3(s)+H_2O(l\ \text{or}\ g)$ (2) $CO_2$ Desorption or Displacement: Calcium carbonate may be reacted with acetic acid to produce calcium acetate and carbon dioxide.

$CaCO_3(s)+2\ CH_3COOH \rightarrow Ca(CH_3COO)_2(aq)+CO_2(g)$ (3) Regeneration: Calcium acetate may be reacted with sulfur dioxide to produce calcium sulfite. Calcium sulfite is converted into calcium oxide and sulfur dioxide. Calcium oxide may be reacted with water to form a calcium hydroxide. In some embodiments, calcium hydroxide may form due to reaction of calcium oxide with water vapor.

$Ca(CH_3COO)_2(aq)+SO_2(g\ \text{or}\ aq) \rightarrow CaSO_3(s)+2\ CH_3COOH(aq)$ $CaSO_3(s) \rightarrow CaO(s)+SO_2(g)$ $CaO(s)+H_2O(g\ \text{or}\ l) \rightarrow Ca(OH)_2(s\ \text{or}\ aq)$ Example 28: $CO_2$ Capture with Decoupled $CO_2$ Absorption or Adsorption, $CO_2$ Desorption or Displacement, and Reagent Regeneration (1) $CO_2$ Adsorption: $CO_2$ adsorption or absorption in calcium oxide or calcium hydroxide to produce calcium carbonate solid.

$CaO(s)+CO_2(g) \rightarrow CaCO_3(s)$ $Ca(OH)_2(s\ \text{or}\ aq)+CO_2(g) \rightarrow CaCO_3(s)+H_2O(l\ \text{or}\ g)$ (2) $CO_2$ Desorption or Displacement: Calcium carbonate may be reacted with sulfurous acid to produce calcium sulfite and carbon dioxide.

$CaCO_3(s)+2\ CH_3COOH \rightarrow Ca(CH_3COO)_2(aq)+CO_2(g)$ (3) Regeneration: Calcium sulfite may be converted into calcium oxide and sulfur dioxide. Calcium oxide may be reacted with water to form a calcium hydroxide. In some embodiments, calcium hydroxide may form due to reaction of calcium oxide with water vapor.

$Ca(CH_3COO)_2(aq)+SO_2(g\ or\ aq) \rightarrow CaSO_3(s)+2\ CH_3COOH(aq)$ $CaSO_3(s) \rightarrow CaO(s)+SO_2(g)$ $CaO(s)+H_2O(g\ or\ l) \rightarrow Ca(OH)_2(s\ or\ aq)$

Example 29: $CO_2$ Capture with Decoupled $CO_2$ Absorption or Adsorption, $CO_2$ Desorption or Displacement, and Reagent Regeneration (1) $CO_2$ Absorption: $CO_2$ absorption in sodium hydroxide solution to produce sodium carbonate solution or sodium carbonate precipitate. If sodium carbonate precipitate forms, sodium carbonate precipitate may be separated using, for example, a solid-liquid separation method.

$2\ NaOH(aq\ or\ s)+CO_2(g) \rightarrow Na_2CO_3(aq\ or\ s)+H_2O(l\ or\ aq\ or\ g)$ Note: Sodium hydroxide solid or solution may be transported to the absorption location and/or stored at or near the absorption location.

Note: Sodium carbonate may be stored at or near the absorption or adsorption location. Sodium carbonate may be transported to an application using calcium carbonate. Sodium carbonate may be transferred to the $CO_2$ desorption or displacement location. In some embodiments, the $CO_2$ desorption or displacement location may be the same as the $CO_2$ absorption or adsorption location. In some embodiments, the $CO_2$ desorption or displacement location may be different than the $CO_2$ absorption or adsorption location. For example, in some embodiments, it may be desirable for the $CO_2$ absorption or adsorption to be located at multiple distributed sites, while the Regeneration may be conducted at a larger and/or more centralized facility or site.

(2) $CO_2$ Desorption or Displacement: Sodium carbonate may be reacted with acetic acid to produce sodium acetate and carbon dioxide.

$Na_2CO_3(aq\ or\ s)+2\ CH_3COOH \rightarrow 2\ NaCH_3COO+CO_2(g)$

Note: Sodium carbonate may be stored at or near the $CO_2$ Desorption or Displacement location.

Note: Acetic acid may be stored at or near the $CO_2$ Desorption or Displacement location.

Note: $CO_2$ Desorption or Displacement may be located at an application requiring carbon dioxide, or high purity carbon dioxide, or high pressure carbon dioxide, or captured carbon dioxide, or any combination thereof. For example, $CO_2$ Desorption or Displacement may be located at a site requiring $CO_2$ enhanced oil recovery (EOR).

Note: Sodium acetate may comprise an aqueous calcium acetate solution, or sodium acetate solid, or any combination thereof.

Note: Sodium acetate may be stored at or near the $CO_2$ Desorption or Displacement. Sodium acetate may be transported to an application using sodium acetate. Sodium acetate may be transferred to at or near the Regeneration location. In some embodiments, the $CO_2$ desorption or displacement location may be the same as Regeneration location. In some embodiments, the $CO_2$ desorption or displacement location may be different than the Regeneration location. For example, in some embodiments, it may be desirable for the $CO_2$ Desorption or Displacement to be located at multiple distributed sites, while the Regeneration may be conducted at a larger and/or more centralized facility or site.

Note: Acetic acid vapor may be present in the $CO_2(g)$. In some embodiments, acetic acid vapor may be at least partially removed from $CO_2(g)$ by, for example, including, but not limited to, one or more or any combination of the following: contacting $CO_2(g)$ comprising a portion of acetic acid vapor with $CaCO_3$, or contacting $CO_2(g)$ comprising a portion of acetic acid vapor with sodium carbonate, or contacting $CO_2(g)$ comprising a portion of acetic acid vapor with an alkali carbonate, or compression, or cooling, or condensing, or cryo-separation, or freeze separation.

(3) Regeneration: Sodium acetate may be reacted with sulfur dioxide to produce sodium sulfite and acetic acid. Sodium sulfite may be separated from acetic acid. Sodium sulfite may be reacted with calcium hydroxide, or calcium oxide, or calcium hydroxide suspension, or any combination thereof to produce sodium hydroxide and calcium sulfite. Calcium sulfite solid may be separated from sodium hydroxide solution. Calcium sulfite solid may be converted into calcium oxide and sulfur dioxide. Calcium oxide may be reacted with water to produce calcium hydroxide or calcium hydroxide suspension.

$2\ NaCH_3COO+SO_2(g\ or\ aq) \rightarrow Na_2SO_3(aq\ or\ s)+2\ CH_3COOH(aq)$

Separate $Na_2SO_3$ and $2\ CH_3COOH$ $Na_2SO_3(aq\ or\ s)+Ca(OH)_2(s\ or\ aq) \rightarrow CaSO_3(s)+2\ NaOH$ $CaSO_3(s) \rightarrow CaO(s)+SO_2(g)$ $CaO(s)+H_2O(g\ or\ l) \rightarrow Ca(OH)_2(s\ or\ aq)$ Note: Sodium hydroxide may be transported to the $CO_2$ Absorption or Adsorption location.

Note: Acetic acid may be transported to the $CO_2$ Desorption or Displacement location.

Note: It may be desirable for the regeneration to comprise a centralized facility, or a facility which may benefit from economies of scale, or any combination thereof.

Example 30: $CO_2$ Capture with Decoupled $CO_2$ Absorption or Adsorption, $CO_2$ Desorption or Displacement, and Reagent Regeneration (1) $CO_2$ Absorption: $CO_2$ absorption in sodium hydroxide solution to produce sodium carbonate solution, or solid precipitate, or any combination thereof.

$2\ NaOH(aq\ or\ s)+CO_2(g) \rightarrow Na_2CO_3(aq\ or\ s)+H_2O(l\ or\ aq\ or\ g)$ (2) $CO_2$ Desorption or Displacement: Sodium carbonate may be reacted with aqueous sulfurous acid or aqueous sulfur dioxide to produce sodium sulfite and carbon dioxide.

$Na_2CO_3(aq\ or\ s)+SO_2(aq) \rightarrow Na_2SO_3(aq\ or\ s)+CO_2(g)$

Note: $SO_2(g)$ vapor may be present in the $CO_2(g)$. In some embodiments, $SO_2(g)$ may be at least partially removed from $CO_2(g)$ by, for example, including, but not limited to, one or more or any combination of the following: contacting $CO_2(g)$ comprising a portion of $SO_2(g)$ with $CaCO_3$, or contacting $CO_2(g)$ comprising a portion of $SO_2(g)$ with sodium carbonate, or contacting $CO_2(g)$ comprising a portion of $SO_2(g)$ with an alkali carbonate, or compression, or cooling, or condensing, or cryo-separation, or freeze separation.

(3) Regeneration: Sodium sulfite may be reacted with calcium hydroxide, or calcium oxide, or calcium hydroxide suspension, or any combination thereof to produce sodium hydroxide and calcium sulfite. Calcium sulfite solid is separated from sodium hydroxide solution. Calcium sulfite solid is converted into calcium oxide and sulfur dioxide. Calcium oxide may be reacted with water to produce calcium hydroxide or calcium hydroxide suspension.

$Na_2SO_3$(aq or s)+$Ca(OH)_2$(s or aq)→$CaSO_3$(s)+2 NaOH (aq or s)

$CaSO_3$(s)→CaO(s)+$SO_2$(g)

CaO(s)+$H_2O$(g or l)→$Ca(OH)_2$(s or aq)

Example 31: $CO_2$ Production and Production of Sodium Hydroxide (1) $CO_2$ Desorption or Displacement: Sodium bicarbonate, which may comprise Nahcolite, may be reacted with aqueous sulfurous acid or aqueous sulfur dioxide to produce sodium sulfite and carbon dioxide.

2 $NaHCO_3$(aq or s)+$SO_2$(aq)→$Na_2SO_3$(aq or s)+$H_2O$+2 $CO_2$(g)

Or

2 $NaHCO_3$(aq or s)+2 $SO_2$(aq)→$NaHSO_3$(aq or s)+2 $CO_2$(g)

(2) Production of Sodium Hydroxide: Sodium sulfite may be reacted with calcium hydroxide, or calcium oxide, or calcium hydroxide suspension, or any combination thereof to produce sodium hydroxide and calcium sulfite. Calcium sulfite solid is separated from sodium hydroxide solution. Calcium sulfite solid is converted into calcium oxide and sulfur dioxide. Calcium oxide may be reacted with water to produce calcium hydroxide or calcium hydroxide suspension.

$Na_2SO_3$(aq or s)+$Ca(OH)_2$(s or aq)→$CaSO_3$(s)+2 NaOH (aq or s)

$CaSO_3$(s)→CaO(s)+$SO_2$(g)

CaO(s)+$H_2O$(g or l)→$Ca(OH)_2$(s or aq)

Example 31: $CO_2$ Production and Production of Sodium Hydroxide (2) $CO_2$ Desorption or Displacement: Sodium bicarbonate, which may comprise Nahcolite, may be reacted with acetic acid to produce sodium acetate and carbon dioxide.

2 $NaHCO_3$(aq or s)+2 $CH_3COOH$→2 $NaCH_3COO$+2 $CO_2$(g)

(3) Regeneration: Sodium acetate may be reacted with sulfur dioxide to produce sodium sulfite and acetic acid. Sodium sulfite is separated from acetic acid. Sodium sulfite may be reacted with calcium hydroxide, or calcium oxide, or calcium hydroxide suspension, or any combination thereof to produce sodium hydroxide and calcium sulfite. Calcium sulfite solid is separated from sodium hydroxide solution. Calcium sulfite solid is converted into calcium oxide and sulfur dioxide. Calcium oxide may be reacted with water to produce calcium hydroxide or calcium hydroxide suspension.

2 $NaCH_3COO$+$SO_2$(g or aq)→$Na_2SO_3$(aq or s)+2 $CH_3COOH$(aq)

Separate $Na_2SO_3$ and 2 $CH_3COOH$ $Na_2SO_3$(aq or s)+$Ca(OH)_2$(s or aq)→$CaSO_3$(s)+2 NaOH $CaSO_3$(s)→CaO(s)+$SO_2$(g)

CaO(s)+$H_2O$(g or l)→$Ca(OH)_2$(s or aq)

Example 32: Lithium Hydroxide Production from Lithium Sulfate Using Calcium Precipitation and Acid Intermediate (1) React Material comprising Calcium, or Magnesium, or Other Alkaline Earth-Weak Acid Anion with Acetic Acid $CaCO_3$(s or aq)+2 $CH_3COOH$(aq)→$Ca(CH_3COO)_2$(aq)+ $CO_2$(g)

Calcium Silicate(s)+2 $CH_3COOH$(aq)→$Ca(CH_3COO)_2$ (aq)+Silicon Dioxide(s)

CaS(s)+2 $CH_3COOH$(aq)→$Ca(CH_3COO)_2$(aq)+$H_2S$(g)

Calcium(Weak Acid Anion)+2 $CH_3COOH$(aq)→Ca $(CH_3COO)_2$(aq)+Weak Acid(s, or g, or l, or aq)

Note: Residual solids or undissolved solids, such as silicon dioxide or other undissolved solids, may be separated from the liquid solution using a solid-liquid separation.

(2) $Ca(CH_3COO)_2$(aq)+$Li_2SO_4$(aq)→2 $LiCH_3COO$ (aq)→ $CaSO_4$(s)

(3) 2 $LiCH_3COO$(aq)+$SO_2$(g or aq)+$H_2O$(l or aq)→$Li_2SO_3$(aq)+2 $CH_3COOH$(aq)

(4) $Li_2SO_3$(aq)+2 $CH_3COOH$(aq)→2 $CH_3COOH$(aq or l)+$Li_2SO_3$(s)+Water

Note: $CH_3COOH$ may be more soluble in water than $Li_2SO_3$. In some embodiments, water may be removed and/or $Li_2SO_3$ may be separated or precipitated by, for example, including, but not limited to, evaporation, or distillation, or crystallization, or separation systems or methods described herein, or separation systems or methods described in the art, or any combination thereof.

Note: $Li_2SO_3$(s) may be separated from $CH_3COOH$(aq or l) by a solid-liquid separation, which may include, but is not limited to, filter, or centrifuge, or decanter, or separation systems or methods described herein, or separation systems or methods described in the art, or any combination thereof.

(5) $Li_2SO_3$(s or aq)+$Ca(OH)_2$(s or aq)→2 LiOH(aq or s)+$CaSO_3$(s)

Note: $Ca(OH)_2$(s or aq) may comprise a solid-liquid suspension, such as milk of lime.

Note: $CaSO_3$(s) may be separated using a solid-liquid separation.

(6) $CaSO_3$(s)→CaO(s)+$SO_2$(g)

Note: '(6)' may comprise calcining $CaSO_3$(s), which may employ a kiln.

Note: $CaSO_3$(s) may be dried, or dehydrated, or both before or during '(6)'.

(7) CaO(s)+Water(g or l or aq)→$Ca(OH)_2$(s or aq)

Note: CaO(s) may be employed to remove water vapor or facilitated drying of $CaSO_3$(s) before or during decomposition of $CaSO_3$(s) to CaO(s).

(8) 2 LiOH(aq or s)→2 LiOH(s)+Water

Note: In some embodiments, water may be removed and/or LiOH may be separated or precipitated by, for example, including, but not limited to, evaporation, or distillation, or crystallization, or separation systems or methods described herein, or separation systems or methods described in the art, or any combination thereof.

Note: In some embodiments, it may be desirable for LiOH to comprise a concentrated aqueous solution.

Example 33: Sodium Hydroxide Production from Sodium Chloride Using Calcium Precipitation, Acid Intermediate, and Process for Producing Sodium Sulfate and Calcium Chloride from Calcium Sulfate and Sodium Chloride (1) React Material comprising Calcium, or Magnesium, or Other Alkaline Earth-Weak Acid Anion with Acetic Acid $CaCO_3$(s or aq)+2 $CH_3COOH$(aq)→$Ca(CH_3COO)_2$(aq)+ $CO_2$(g)

Calcium Silicate(s)+2 $CH_3COOH$(aq)→$Ca(CH_3COO)_2$ (aq)+Silicon Dioxide(s)

CaS(s)+2 $CH_3COOH$(aq)→$Ca(CH_3COO)_2$(aq)+$H_2S$(g)

Calcium(Weak Acid Anion)+2 $CH_3COOH$(aq)→Ca $(CH_3COO)_2$(aq)+Weak Acid(s, or g, or l, or aq)

Note: Residual solids or undissolved solids, such as silicon dioxide or other undissolved solids, may be separated from the liquid solution using a solid-liquid separation.

(2) $Ca(CH_3COO)_2$(aq)+$Na_2SO_4$(s or aq)→2 $NaCH_3COO$(aq)+$CaSO_4$(s)

Note: In some embodiments, $Na_2SO_4$(s or aq) may be transferred from step '(10)'.

(3) 2 $NaCH_3COO$(aq)+$SO_2$(g or aq)+$H_2O$(l or aq)→$Na_2SO_3$(aq)+2 $CH_3COOH$(aq)

(4) $Na_2SO_3$(aq)+2 $CH_3COOH$(aq)→2 $CH_3COOH$(aq or l)+$Na_2SO_3$(s)+Water

Note: $CH_3COOH$ may be more soluble in water than $Na_2SO_3$. In some embodiments, water may be removed and/or $Na_2SO_3$ may be separated or precipitated by, for example, including, but not limited to, evaporation, or distillation, or crystallization, or separation systems or methods described herein, or separation systems or methods described in the art, or any combination thereof.

Note: $Na_2SO_3$(s) may be separated from $CH_3COOH$(aq or l) by a solid-liquid separation, which may include, but is not limited to, filter, or centrifuge, or decanter, or separation systems or methods described herein, or separation systems or methods described in the art, or any combination thereof.

(5) $Na_2SO_3$(s or aq)+$Ca(OH)_2$(s or aq)→2 NaOH(aq or s)+$CaSO_3$(s)

Note: $Ca(OH)_2$(s or aq) may comprise a solid-liquid suspension, such as milk of lime.

Note: $CaSO_3$(s) may be separated using a solid-liquid separation.

(6) $CaSO_3$(s)→CaO(s)+$SO_2$(g)

Note: '(6)' may comprise calcining $CaSO_3$(s), which may employ a kiln.

Note: $CaSO_3$(s) may be dried, or dehydrated, or both before or during '(6)'.

(7) CaO(s)+Water(g or l or aq)→$Ca(OH)_2$(s or aq)

Note: CaO(s) may be employed to remove water vapor or facilitated drying of $CaSO_3$(s) before or during decomposition of $CaSO_3$(s) to CaO(s).

(8) 2 NaOH(aq or s)→2 NaOH(s)+Water

Note: In some embodiments, water may be removed and/or NaOH may be separated or precipitated by, for example, including, but not limited to, evaporation, or distillation, or crystallization, or separation systems or methods described herein, or separation systems or methods described in the art, or any combination thereof.

Note: In some embodiments, it may be desirable for NaOH to comprise a concentrated aqueous solution.

(9) $CaSO_4$(s or aq)+$(NH_4)_2CO_3$(aq)→$CaCO_3$(s or aq)+$(NH_4)_2SO_4$(aq)

Note: $CaSO_4$(s or aq) may be transferred from step '(2)'.

Note: $CaCO_3$(s) may be separated from a solution comprising $(NH_4)_2SO_4$(aq) by a solid-liquid separation.

(10) $(NH_4)_2SO_4$(aq)+2 NaCl(aq)→2 $NH_4Cl$(aq)+$Na_2SO_4$(s or aq)

Note: In some embodiments, a portion of $Na_2SO_4$(s) may be precipitated by cooling precipitation due to, for example, the increasingly lower solubility of $Na_2SO_4$ in water compared to $NH_4Cl$ the lower the temperature below about 32 degrees Celsius or the closer the temperature of the solution is to 0° C.

Note: In some embodiments, $Na_2SO_4$ may be separated from $2NH_4Cl$ by evaporation, or crystallization, or cooling precipitation, or any combination thereof. In some embodiments, $Na_2SO_4$(s), or water, or $2NH_4Cl$(aq), or $2NH_4Cl$(s), or any combination thereof may be produced or may form.

(11) One, or more, or any combination of the following:

$2NH_4Cl$(s)→2 $NH_3$(g)+2 HCl(g)

2 $NH_3$(g)+2 HCl(g)+$CaCO_3$(s)→$CaCl_2$(s)+$H_2O$(g)+$CO_2$(g)+2 $NH_3$(g)

$CaCO_3$(s)+2 $NH_4Cl$(s)→$CaCl_2$(s)+$H_2O$(g)+$CO_2$(g)+2 $NH_3$(g)

Note: $CaCO_3$(s) may be transferred from step '(9)'.

Note: One or more or any combination of the above reactions may require heat input.

Note: In some embodiments, heat may be recovered from one or more or any combination of reactions. For example, the calcium carbonate and hydrogen chloride may be exothermic.

Note: In some embodiments, 2 $NH_4Cl$(s) may be precipitated or crystallized from an aqueous solution in the presence of calcium carbonate to, for example, create a distributed mixture of calcium carbonate and ammonium chloride.

Note: Calcium chloride may comprise an output. In some embodiments, calcium chloride may be sold or utilized. In some embodiments, calcium chloride may comprise a waste product.

(12) 2 $NH_3$(g)+$H_2O$(g)+$CO_2$(g)→$(NH_4)_2CO_3$(s or aq)

Note: $(NH_4)_2CO_3$(s or aq) may be transferred to step '(9)'.

Note: 2 $NH_3$(g), or $H_2O$(g), or $CO_2$(g), or any combination thereof may be recycled or recirculated within the process. In some embodiments, losses may occur and/or make up 2 $NH_3$, or $H_2O$, or $CO_2$, or any combination thereof may be added.

Example 34: Process for Producing Sodium Sulfate, Ammonia, and Calcium Chloride from Ammonium Sulfate, Sodium Chloride, and Calcium-Weak Acid (1) $(NH_4)_2SO_4$(aq)+2 NaCl(aq)→2 $NH_4Cl$(aq)+$Na_2SO_4$(s or aq)

Note: In some embodiments, a portion of $Na_2SO_4$(s) may be precipitated by cooling precipitation due to, for example, the increasingly lower solubility of $Na_2SO_4$ in water compared to $NH_4Cl$ the lower the temperature below about 32 degrees Celsius or the closer the temperature of the solution is to 0° C.

Note: In some embodiments, $Na_2SO_4$ may be separated from $2NH_4Cl$ by evaporation, or crystallization, or cooling precipitation, or any combination thereof. In some embodiments, $Na_2SO_4$(s), or water, or $2NH_4Cl$(aq), or $2NH_4Cl$(s), or any combination thereof may be produced or may form.

(2) One, or more, or any combination of the following:

$2NH_4Cl$(s)→2 $NH_3$(g)+2 HCl(g)

2 $NH_3$(g)+2 HCl(g)+$CaCO_3$(s)→$CaCl_2$(s)+$H_2O$(g)+$CO_2$(g)+2 $NH_3$(g)

$CaCO_3$(s)+2 $NH_4Cl$(s)→$CaCl_2$(s)+$H_2O$(g)+$CO_2$(g)+2 $NH_3$(g)

2 $NH_3$(g)+2 HCl(g)+Ca(WA)(s)→$CaCl_2$(s)+$H_2O$(g)+WA(s or g or l)+2 $NH_3$(g)

Ca(WA)(s)+2 $NH_4Cl$(s)→$CaCl_2$(s)+$H_2O$(g)+WA(s or g or l)+2 $NH_3$(g)

Note: One or more or any combination of the above reactions may require heat input.

Note: In some embodiments, heat may be recovered from one or more or any combination of reactions. For example, the calcium carbonate and hydrogen chloride may be exothermic.

Note: In some embodiments, 2 $NH_4Cl$(s) may be precipitated or crystallized from an aqueous solution in the presence of calcium-weak acid to, for example, create a distributed mixture of calcium-weak acid and ammonium chloride.

Note: Calcium chloride may comprise an output. In some embodiments, calcium chloride may be sold or utilized. In some embodiments, calcium chloride may comprise a waste product.

Note: In some embodiments, carbon dioxide produced may comprise captured carbon dioxide. For example, ammonia and/or water may be separated from carbon dioxide using an aqueous solution and/or high pressures and/or elevated temperatures.

Example 35: Process for Producing Sodium Sulfate and Calcium Chloride from Sodium Chloride and Calcium Sulfate Using an Ammonia and Carbon Dioxide Intermediate (1) $CaSO_4$(s or aq)+$(NH_4)_2CO_3$(aq)→$CaCO_3$(s or aq)+$(NH_4)_2SO_4$(aq)

Note: $CaSO_4$(s or aq) may comprise an input. For example, $CaSO_4$(s) may be a product or byproduct from a process. For example, $CaSO_4$(s) may be mined. For example, $CaSO_4$(s) may comprise phosphogypsum.

Note: $CaCO_3$(s) may be separated from a solution comprising $(NH_4)_2SO_4$(aq) by a solid-liquid separation.

(2) $(NH_4)_2SO_4$(aq)+2 NaCl(aq)→2 $NH_4Cl$(aq)+$Na_2SO_4$(s or aq)

Note: In some embodiments, a portion of $Na_2SO_4$(s) may be precipitated by cooling precipitation due to, for example, the increasingly lower solubility of $Na_2SO_4$ in water compared to $NH_4Cl$ the lower the temperature below about 32 degrees Celsius or the closer the temperature of the solution is to 0° C.

Note: In some embodiments, $Na_2SO_4$ may be separated from 2$NH_4Cl$ by evaporation, or crystallization, or cooling precipitation, or separation method described herein, or any combination thereof. In some embodiments, $Na_2SO_4$(s), or water, or 2$NH_4Cl$(aq), or 2$NH_4Cl$(s), or any combination thereof may be produced or may form.

(3) One, or more, or any combination of the following:

2$NH_4Cl$(s)→2 $NH_3$(g)+2 HCl(g)

2 $NH_3$(g)+2 HCl(g)+$CaCO_3$(s)→$CaCl_2$(s)+$H_2O$(g)+$CO_2$(g)+2 $NH_3$(g)

$CaCO_3$(s)+2 $NH_4Cl$(s)→$CaCl_2$(s)+$H_2O$(g)+$CO_2$(g)+2 $NH_3$(g)

Note: $CaCO_3$(s) may be transferred from step '(1)'.

Note: One or more or any combination of the above reactions may require heat input.

Note: In some embodiments, heat may be recovered from one or more or any combination of reactions. For example, the calcium carbonate and hydrogen chloride may be exothermic.

Note: In some embodiments, 2 $NH_4Cl$(s) may be precipitated or crystallized from an aqueous solution in the presence of calcium carbonate to, for example, create a distributed mixture of calcium carbonate and ammonium chloride.

Note: Calcium chloride may comprise an output. In some embodiments, calcium chloride may be sold or utilized. In some embodiments, calcium chloride may comprise a waste product.

(4) 2 $NH_3$(g)+$H_2O$(g)+$CO_2$(g)→$(NH_4)_2CO_3$(s or aq)

Note: $(NH_4)_2CO_3$(s or aq) may be transferred to step '(1)'.

Note: 2 $NH_3$(g), or $H_2O$(g), or $CO_2$(g), or any combination thereof may be recycled or recirculated within the process. In some embodiments, losses may occur and/or make up 2 $NH_3$, or $H_2O$, or $CO_2$, or any combination thereof may be added.

Example 36: Process for Producing Sodium Sulfate and Calcium Chloride from Sodium Chloride and Calcium Sulfate while Capturing Carbon Dioxide (1) 2 $NH_3$(aq)+$H_2O$(g)+$CO_2$(g)→$(NH_4)_2CO_3$(s or aq)

Note: $CO_2$(g) may comprise a gas comprising $CO_2$(g). In some embodiments, the $CO_2$(g) may comprise a gas comprising a dilute concentration of carbon dioxide, which may include, but is not limited to, flue gas, or emissions gas, or sour gas, or air, or other $CO_2$ sources described herein, or other $CO_2$ sources in the art, or any combination thereof.

(2) $CaSO_4$(s or aq)+$(NH_4)_2CO_3$(aq)→$CaCO_3$(s or aq)+$(NH_4)_2SO_4$(aq)

Note: $CaSO_4$(s or aq) may comprise an input. For example, $CaSO_4$(s) may be a product or byproduct from a process. For example, $CaSO_4$(s) may be mined. For example, $CaSO_4$(s) may comprise phosphogypsum.

Note: $CaCO_3$(s) may be separated from a solution comprising $(NH_4)_2SO_4$(aq) by a solid-liquid separation.

(3) $(NH_4)_2SO_4$(aq)+2 NaCl(aq)→2 $NH_4Cl$(aq)+$Na_2SO_4$(s or aq)

Note: In some embodiments, a portion of $Na_2SO_4$(s) may be precipitated by cooling precipitation due to, for example, the increasingly lower solubility of $Na_2SO_4$ in water compared to $NH_4Cl$ the lower the temperature below about 32 degrees Celsius or the closer the temperature of the solution is to 0° C.

Note: In some embodiments, $Na_2SO_4$ may be separated from 2$NH_4Cl$ by evaporation, or crystallization, or cooling precipitation, or separation method described herein, or any combination thereof. In some embodiments, $Na_2SO_4$(s), or water, or 2$NH_4Cl$(aq), or 2$NH_4Cl$(s), or any combination thereof may be produced or may form.

(4) One, or more, or any combination of the following:

2$NH_4Cl$(s)→2 $NH_3$(g)+2 HCl(g)

2 $NH_3$(g)+2 HCl(g)+$CaCO_3$(s)→$CaCl_2$(s)+$H_2O$(g)+$CO_2$(g)+2 $NH_3$(g)

$CaCO_3$(s)+2 $NH_4Cl$(s)→$CaCl_2$(s)+$H_2O$(g)+$CO_2$(g)+2 $NH_3$(g)

Note: $CaCO_3$(s) may be transferred from step '(1)'.

Note: One or more or any combination of the above reactions may require heat input.

Note: In some embodiments, heat may be recovered from one or more or any combination of reactions. For example, the calcium carbonate and hydrogen chloride may be exothermic.

Note: In some embodiments, 2 $NH_4Cl$(s) may be precipitated or crystallized from an aqueous solution in the presence of calcium carbonate to, for example, create a distributed mixture of calcium carbonate and ammonium chloride.

Note: Calcium chloride may comprise an output. In some embodiments, calcium chloride may be sold or utilized. In some embodiments, calcium chloride may comprise a waste product.

(5) 2 $NH_3$(g)+$H_2O$(g)+$CO_2$(g)→2 $NH_3$(aq)+$CO_2$(g)

Note: 2 $NH_3$(aq) may be transferred to step '(1)'.

Note: If conducted at a pressure greater than 0.9 atm, or 1 atm, or 1.2 atm, or 1.4 atm, or 1.6 atm, or 1.8 atm, or 2 atm, or 2.5 atm, or 3 atm, or 4 atm, or 5 atm, or any combination thereof and/or temperature greater than 50° C., 60° C., or 70° C., or 80° C., or 90° C., or 100° C., or 110° C., or 120° C., or 130° C. or any combination thereof in the presence of liquid water, ammonia may mostly transfer to the aqueous phase, while carbon dioxide may mostly remain at a gas phase.

Note: In some embodiments, $CO_2$ may be further purified to remove residual ammonia. For example, $CO_2$(g) comprising residual ammonia may be cooled, which may result in the removal of at least a portion of the residual ammonia by the formation of ammonia-carbon dioxide derivative salts, such as ammonium carbamate, or ammonium carbonate, or ammonium bicarbonate, or any combination thereof. For example, $CO_2(g)$ comprising residual ammonia may be cooled and/or contacted with water, which may result in the removal of at least a portion of the residual ammonia by the formation of aqueous ammonia, or ammonia-carbon dioxide derivative salts, such as ammonium carbamate, or ammonium carbonate, or ammonium bicarbonate, or any combination thereof.

Example 37: Process for Producing Sodium Sulfate, Calcium Chloride, and Urea from Sodium Chloride, Calcium Sulfate, Ammonia, and Carbon Dioxide (1) 2 $NH_3$(g or aq)+Water→$CO_2$(g)→$(NH_4)_2CO_3$(s or aq)

Note: $CO_2(g)$ may comprise a gas comprising $CO_2(g)$. In some embodiments, the $CO_2(g)$ may comprise a gas comprising a dilute concentration of carbon dioxide, which may include, but is not limited to, flue gas, or emissions gas, or sour gas, or air, or other $CO_2$ sources described herein, or other $CO_2$ sources in the art, or any combination thereof.

(2) $CaSO_4$(s or aq)+$(NH_4)_2CO_3$(aq)→$CaCO_3$(s or aq)+$(NH_4)_2SO_4$(aq)

Note: $CaSO_4$(s or aq) may comprise an input. For example, $CaSO_4(s)$ may be a product or byproduct from a process. For example, $CaSO_4(s)$ may be mined. For example, $CaSO_4(s)$ may comprise phosphogypsum.

Note: $CaCO_3(s)$ may be separated from a solution comprising $(NH_4)_2SO_4(aq)$ by a solid-liquid separation.

(3) $(NH_4)_2SO_4$(aq)+2 NaCl(aq)→2 $NH_4Cl$(aq)+$Na_2SO_4$(s or aq)

Note: In some embodiments, a portion of $Na_2SO_4(s)$ may be precipitated by cooling precipitation due to, for example, the increasingly lower solubility of $Na_2SO_4$ in water compared to $NH_4Cl$ the lower the temperature below about 32 degrees Celsius or the closer the temperature of the solution is to 0° C.

Note: In some embodiments, $Na_2SO_4$ may be separated from $2NH_4Cl$ by evaporation, or crystallization, or cooling precipitation, or separation method described herein, or any combination thereof. In some embodiments, $Na_2SO_4(s)$, or water, or $2NH_4Cl(aq)$, or $2NH_4Cl(s)$, or any combination thereof may be produced or may form.

(4) One, or more, or any combination of the following:

$2NH_4Cl$(s)→2 $NH_3$(g)+2 HCl(g)

2 $NH_3$(g)+2 HCl(g)+$CaCO_3$(s)→$CaCl_2$(s)+$H_2O$(g)+$CO_2$(g)+2 $NH_3$(g)

$CaCO_3$(s)+2 $NH_4Cl$(s)→$CaCl_2$(s)+$H_2O$(g)+$CO_2$(g)+2 $NH_3$(g)

Note: $CaCO_3(s)$ may be transferred from step '(1)'.

Note: One or more or any combination of the above reactions may require heat input.

Note: In some embodiments, heat may be recovered from one or more or any combination of reactions. For example, the calcium carbonate and hydrogen chloride may be exothermic.

Note: In some embodiments, 2 $NH_4Cl(s)$ may be precipitated or crystallized from an aqueous solution in the presence of calcium carbonate to, for example, create a distributed mixture of calcium carbonate and ammonium chloride.

Note: Calcium chloride may comprise an output. In some embodiments, calcium chloride may be sold or utilized. In some embodiments, calcium chloride may comprise a waste product.

(5) 2 $NH_3$(g)+$H_2O$(g)+$CO_2$(g)→2 $NH_3$(aq)+$CO_2$(g)

Note: If conducted at a pressure greater than 0.9 atm, or 1 atm, or 1.2 atm, or 1.4 atm, or 1.6 atm, or 1.8 atm, or 2 atm, or 2.5 atm, or 3 atm, or 4 atm, or 5 atm, or any combination thereof and/or temperature greater than 50° C., 60° C., or 70° C., or 80° C., or 90° C., or 100° C., or 110° C., or 120° C., or 130° C. or any combination thereof in the presence of liquid water, ammonia may mostly transfer to the aqueous phase, while carbon dioxide may mostly remain at a gas phase.

(6) 2 $NH_3$(aq)→2 $NH_3$(g)+Water (7) 2 $NH_3$(g)+$CO_2$(g)→2 $(NH_2)_2CO$(s)+$H_2O$(g or l)

Note: The process may produce urea and/or water.

Note: It may be desirable to further dry the ammonia, or carbon dioxide, or both before use in the production of urea.

Example 38: Sodium Hydroxide Production from Sodium Sulfate Using Calcium Precipitation and Acid Intermediate (1) React Material comprising Calcium, or Magnesium, or Other Alkaline Earth-Weak Acid Anion with Acetic Acid $CaCO_3$(s or aq)+2 $CH_3COOH$(aq)→$Ca(CH_3COO)_2$(aq)+$CO_2$(g)

Calcium Silicate(s)+2 $CH_3COOH$(aq)→$Ca(CH_3COO)_2$(aq)+Silicon Dioxide(s)

CaS(s)+2 $CH_3COOH$(aq)→$Ca(CH_3COO)_2$(aq)+$H_2S$(g)

Calcium(Weak Acid Anion)+2 $CH_3COOH$(aq)→$Ca(CH_3COO)_2$(aq)+Weak Acid(s, or g, or l, or aq)

Note: Residual solids or undissolved solids, such as silicon dioxide or other undissolved solids, may be separated from the liquid solution using a solid-liquid separation.

(2) $Ca(CH_3COO)_2$(aq)+$Na_2SO_4$(aq)→2 $NaCH_3COO$(aq)+$CaSO_4$(s)

(3) 2 $NaCH_3COO$(aq)+$SO_2$(g or aq)+$H_2O$(l or aq)→$Na_2SO_3$(aq)+2 $CH_3COOH$(aq)

(4) $Na_2SO_3$(aq)+2 $CH_3COOH$(aq)→2 $CH_3COOH$(aq-separate)+$Na_2SO_3$(aq-separate)

Note: An aqueous solution comprising sodium sulfite and acetic acid may be separated into a separate aqueous solution comprising acetic acid and a separate aqueous solution comprising sodium sulfite using, for example, electrodialysis, or electrodialysis reversal, or selective electrodialysis.

Note: For example, some embodiments may employ electrodialysis selective for monovalent or divalent or trivalent or tetravalent cations, or monovalent or divalent or trivalent or tetravalent anions, or any combination thereof.

Note: The aqueous solution comprising acetic acid may be employed as the aqueous acetic acid in step '(1)'.

(5) $Na_2SO_3$(aq)+$Ca(OH)_2$(s or aq)→2 NaOH(aq)+$CaSO_3$(s)

Note: $Ca(OH)_2$(s or aq) may comprise a solid-liquid suspension, such as milk of lime.

Note: $CaSO_3(s)$ may be separated using a solid-liquid separation.

(6) $CaSO_3$(s)→CaO(s)+$SO_2$(g)

Note: '(6)' may comprise calcining $CaSO_3(s)$, which may employ a kiln.

Note: $CaSO_3(s)$ may be dried, or dehydrated, or both before or during '(6)'.

(7) $CaO(s)+Water(g\ or\ l\ or\ aq) \rightarrow Ca(OH)_2(s\ or\ aq)$

Note: CaO(s) may be employed to remove water vapor or facilitated drying of $CaSO_3(s)$ before or during decomposition of $CaSO_3(s)$ to CaO(s).

(8) $2\ NaOH(aq) \rightarrow 2\ NaOH(aq\ or\ s)+Water$

Note: In some embodiments, it may be desirable for NaOH to comprise an aqueous solution or concentrated aqueous solution. In some embodiments, NaOH(aq) may be concentrated or further concentration using one or more or any combination of separation methods or water removal methods.

Note: In some embodiments, water may be removed and/or NaOH may be separated or precipitated by, for example, including, but not limited to, evaporation, or distillation, or crystallization, or separation systems or methods described herein, or separation systems or methods described in the art, or any combination thereof.

Note: Water or distillate from concentrating or further concentrating may be employed within the process. For example, water or distillate from concentrating or further concentrating may be employed to, for example, including but not limited to, one or more or any combination of the following: to dissolve sodium sulfate, or to absorb acetic acid vapor, or dilute or mix with the aqueous solution comprising sodium acetate, or dilute or mix with the aqueous solution comprising sodium sulfite and acetic acid, or any combination thereof.

Example 39: Sodium Hydroxide and Calcium Oxide Production from Sodium Sulfate and Calcium Carbonate using Calcium Precipitation and Acid Intermediate (1) React Material comprising Calcium, or Magnesium, or Other Alkaline Earth-Weak Acid Anion with Acetic Acid $CaCO_3(s\ or\ aq)+2\ CH_3COOH(aq) \rightarrow Ca(CH_3COO)_2(aq)+CO_2(g)$ $Calcium\ Silicate(s)+2\ CH_3COOH(aq) \rightarrow Ca(CH_3COO)_2(aq)+Silicon\ Dioxide(s)$ $CaS(s)+2\ CH_3COOH(aq) \rightarrow Ca(CH_3COO)_2(aq)+H_2S(g)$ $Calcium(Weak\ Acid\ Anion)+2\ CH_3COOH(aq) \rightarrow Ca(CH_3COO)_2(aq)+Weak\ Acid(s,\ or\ g,\ or\ l,\ or\ aq)$ Note: Residual solids or undissolved solids, such as silicon dioxide or other undissolved solids, may be separated from the liquid solution using a solid-liquid separation.

(2) $Ca(CH_3COO)_2(aq)+Na_2SO_4(aq) \rightarrow 2\ NaCH_3COO(aq)+CaSO_4(s)$ (3) $2\ NaCH_3COO(aq)+SO_2(g\ or\ aq)+H_2O(l\ or\ aq) \rightarrow Na_2SO_3(aq)+2\ CH_3COOH(aq)$ (4) $Na_2SO_3(aq)+2\ CH_3COOH(aq) \rightarrow 2\ CH_3COOH(aq)+Na_2SO_3(s)$ (5) $CaCO_3(s\ or\ aq)+CO_2(g\ or\ aq)+H_2O(aq) \rightarrow Ca(HCO_3)_2(aq)$ Note: In some embodiments, may be conducted under high $CO_2$ partial pressures and/or elevated temperatures. For example, some embodiments may employ $CO_2$ partial pressures greater than 1 Bar, or 2 Bar, or 3 Bar, or 4 Bar, or 5 Bar, or any combination thereof and/or temperatures greater than 0° C., or 20° C., or 40° C., or 50° C., or 60° C., or 70° C., or 80° C., or 90° C., or 95° C., or 100° C.

Note: $CO_2$ may be sourced from, including, but not limited to, one or more or any combination of the following: the decomposition of sodium bicarbonate, or captured carbon dioxide, or any combination thereof.

(6) $Na_2SO_3(s)+Water \rightarrow Na_2SO_3(aq)$ (7) $Na_2SO_3(aq)+Ca(HCO_3)_2(aq) \rightarrow 2\ NaHCO_3(aq)+CaSO_3(s)$ (8) $CaSO_3(s) \rightarrow CaO(s)+SO_2(g)$ (9) $2\ NaHCO_3(aq) \rightarrow Na_2CO_3(aq)+CO_2(g)+H_2O(g\ or\ l)$

(10) $Na_2CO_3(aq)+Ca(OH)_2(s\ or\ aq) \rightarrow 2\ NaOH(aq)+CaCO_3(s)$

(11) $2\ NaOH(aq) \rightarrow 2\ NaOH(aq\ or\ s)+Water$

(12) $CaCO_3(s) \rightarrow CaO(s)+CO_2(g)$

Note: In some embodiments, calcium carbonate may be decomposed into calcium oxide in a manner which produces high purity or captured carbon dioxide. For example, in some embodiments, calcium carbonate may be calcined or decomposed by indirect calcination or indirect heating, which may result in the production of high purity or captured carbon dioxide.

Note: Captured carbon dioxide may be sequestered or employed in one or more or any combination of applications.

(13) $CaO(s)+Water \rightarrow Ca(OH)_2(s\ or\ aq)$

Note: In some embodiments, calcium oxide may be reacted with water to produce an aqueous solution, or solid-liquid suspension, or milk of lime, or solid, or any combination thereof comprising calcium hydroxide.

Note: In some embodiments, calcium oxide may be reacted directly with an aqueous solution comprising sodium carbonate to produce calcium carbonate and sodium hydroxide. For example, in some embodiments, step '(10)' may be combined with step '(13)'.

Example 40: Sodium Carbonate, or Sodium Bicarbonate Production from Sodium Sulfate Using Calcium Precipitation and Acid Intermediate (1) React Material comprising Calcium, or Magnesium, or Other Alkaline Earth-Weak Acid Anion with Acetic Acid $CaCO_3(s\ or\ aq)+2\ CH_3COOH(aq) \rightarrow Ca(CH_3COO)_2(aq)+CO_2(g)$ $Calcium\ Silicate(s)+2\ CH_3COOH(aq) \rightarrow Ca(CH_3COO)_2(aq)+Silicon\ Dioxide(s)$ $CaS(s)+2\ CH_3COOH(aq) \rightarrow Ca(CH_3COO)_2(aq)+H_2S(g)$ $Calcium(Weak\ Acid\ Anion)+2\ CH_3COOH(aq) \rightarrow Ca(CH_3COO)_2(aq)+Weak\ Acid(s,\ or\ g,\ or\ l,\ or\ aq)$ Note: Residual solids or undissolved solids, such as silicon dioxide or other undissolved solids, may be separated from the liquid solution using a solid-liquid separation.

(2) $Ca(CH_3COO)_2(aq)+Na_2SO_4(aq) \rightarrow 2\ NaCH_3COO(aq)+CaSO_4(s)$ (3) $2\ NaCH_3COO(aq)+SO_2(g\ or\ aq)+H_2O(l\ or\ aq) \rightarrow Na_2SO_3(aq)+2\ CH_3COOH(aq)$ (4) $Na_2SO_3(aq)+2\ CH_3COOH(aq) \rightarrow 2\ CH_3COOH(aq)+Na_2SO_3(s)$ (5) $CaCO_3(s\ or\ aq)+CO_2(g\ or\ aq)+H_2O(aq) \rightarrow Ca(HCO_3)_2(aq)$ Note: In some embodiments, may be conducted under high $CO_2$ partial pressures and/or elevated temperatures. For example, some embodiments may employ $CO_2$ partial pressures greater than 1 Bar, or 2 Bar, or 3 Bar, or 4 Bar, or 5 Bar, or any combination thereof and/or temperatures greater than 0° C., or 20° C., or 40° C., or 50° C., or 60° C., or 70° C., or 80° C., or 90° C., or 95° C., or 100° C.

Note: $CO_2$ may be sourced from, including, but not limited to, one or more or any combination of the following: the decomposition of sodium bicarbonate, or captured carbon dioxide, or any combination thereof.

(6) $Na_2SO_3(s)+Water \rightarrow Na_2SO_3(aq)$ (7) $Na_2SO_3(aq)+Ca(HCO_3)_2(aq) \rightarrow 2\ NaHCO_3(aq)+CaSO_3(s)$ (8) $CaSO_3(s) \rightarrow CaO(s)+SO_2(g)$ (9) $2\ NaHCO_3(aq) \rightarrow Na_2CO_3(aq)+CO_2(g)+H_2O(g\ or\ l)$

(10) $Na_2CO_3(aq) \rightarrow Na_2CO_3(s)+Water$

Example 41: Sodium Hydroxide Production from Sodium Sulfate Using Calcium Precipitation, Acid Intermediate, and Calcium Carbonate Intermediate (1) React Material comprising Calcium, or Magnesium, or Other Alkaline Earth-Weak Acid Anion with Acetic Acid $CaCO_3$(s or aq)+2 $CH_3COOH$(aq)→$Ca(CH_3COO)_2$(aq)+$CO_2$(g)

Calcium Silicate(s)+2 $CH_3COOH$(aq)→$Ca(CH_3COO)_2$(aq)+Silicon Dioxide(s)

CaS(s)+2 $CH_3COOH$(aq)→$Ca(CH_3COO)_2$(aq)+$H_2S$(g)

Calcium(Weak Acid Anion)+2 $CH_3COOH$(aq)→$Ca(CH_3COO)_2$(aq)+Weak Acid(s, or g, or l, or aq)

Note: Residual solids or undissolved solids, such as silicon dioxide or other undissolved solids, may be separated from the liquid solution using a solid-liquid separation.

(2) $Ca(CH_3COO)_2$(aq)+$Na_2SO_4$(aq)→2 $NaCH_3COO$(aq)+$CaSO_4$(s)

(3) 2 $NaCH_3COO$(aq)+$SO_2$(g or aq)+$H_2O$(l or aq)→$Na_2SO_3$(aq)+2 $CH_3COOH$(aq)

(4) $Na_2SO_3$(aq)+2 $CH_3COOH$(aq)→2 $CH_3COOH$(aq)+$Na_2SO_3$(s)

(5) $CaCO_3$(s or aq)+$CO_2$(g or aq)+$H_2O$(aq)→$Ca(HCO_3)_2$(aq)

Note: In some embodiments, may be conducted under high $CO_2$ partial pressures and/or elevated temperatures. For example, some embodiments may employ $CO_2$ partial pressures greater than 1 Bar, or 2 Bar, or 3 Bar, or 4 Bar, or 5 Bar, or 6 Bar, or 7 Bar, or 8 Bar, or 9 Bar, or 10 Bar, or 11 Bar, or 12 Bar, or 13 Bar, or 14 Bar, or 15 Bar, or any combination thereof and/or temperatures greater than 0° C., or 20° C., or 40° C., or 50° C., or 60° C., or 70° C., or 80° C., or 90° C., or 95° C., or 100° C.

Note: $CO_2$ may be sourced from, including, but not limited to, one or more or any combination of the following: the decomposition of sodium bicarbonate, or captured carbon dioxide, or any combination thereof.

(6) $Na_2SO_3$(s)+Water→$Na_2SO_3$(aq)

(7) $Na_2SO_3$(aq)+$Ca(HCO_3)_2$(aq)→2 $NaHCO_3$(aq)+$CaSO_3$(s)

(8) $CaSO_3$(s)→CaO(s)+$SO_2$(g)

Note: CaO(s) may be transferred to step '(9)' or step'(11).'

Note: $SO_2$(g) may be transferred to step '(3).'

(9) CaO(s)+Water→$Ca(OH)_2$(s or aq)

Note: In some embodiments, calcium oxide may be reacted with water to produce an aqueous solution, or solid-liquid suspension, or milk of lime, or solid, or any combination thereof comprising calcium hydroxide.

Note: In some embodiments, calcium oxide may be reacted directly with an aqueous solution comprising sodium carbonate to produce calcium carbonate and sodium hydroxide. In some embodiments, calcium oxide may be reacted directly with an aqueous solution comprising sodium carbonate to produce calcium carbonate and sodium hydroxide, which may comprise combining step '(9)' and step '(11).'

(10) 2 $NaHCO_3$(aq)→$Na_2CO_3$(aq)+$CO_2$(g)+$H_2O$(g or l)

Note: $CO_2$ may be transferred to step '(5)'.

(11) $Na_2CO_3$(aq)+$Ca(OH)_2$(s or aq)→2 NaOH(aq)→$CaCO_3$(s)

Note: An aqueous solution comprising sodium hydroxide may be separated from calcium carbonate by a solid-liquid separation.

Note: Calcium carbonate may be transferred to '(5)'.

(12) 2 NaOH(aq)→2 NaOH(aq or s)+Water

Note: The solution comprising sodium hydroxide may be further concentrated, or at least a portion of water may be removed from the solution comprising sodium hydroxide, or any combination thereof.

Note: In some embodiments, at least a portion of the water removed or recovered from the solution comprising aqueous sodium hydroxide may be transferred to step '(6)'.

Example 42: Sodium Hydroxide Production from Sodium Sulfate and Calcium Carbonate Using Calcium Precipitation and Carbon Dioxide Intermediate (1) $CaCO_3$(s or aq)+$CO_2$(g or aq)+$H_2O$(aq)→$Ca(HCO_3)_2$(aq)

Note: In some embodiments, may be conducted under high $CO_2$ partial pressures and/or elevated temperatures. For example, some embodiments may employ $CO_2$ partial pressures greater than 1 Bar, or 2 Bar, or 3 Bar, or 4 Bar, or 5 Bar, or 6 Bar, or 7 Bar, or 8 Bar, or 9 Bar, or 10 Bar, or 11 Bar, or 12 Bar, or 13 Bar, or 14 Bar, or 15 Bar, or any combination thereof and/or temperatures greater than 0° C., or 20° C., or 40° C., or 50° C., or 60° C., or 70° C., or 80° C., or 90° C., or 95° C., or 100° C.

Note: $CO_2$ may be sourced from, including, but not limited to, one or more or any combination of the following: the decomposition of sodium bicarbonate, or captured carbon dioxide, or any combination thereof.

(2) $Na_2SO_4$(s or aq)+$Ca(HCO_3)_2$(aq)→2 $NaHCO_3$(aq)+$CaSO_4$(s)

(3) 2 $NaHCO_3$(aq)→$Na_2CO_3$(aq)+$CO_2$(g)+$H_2O$(g or l)

Note: $CO_2$ may be transferred to step '(1)'.

(4) $Na_2CO_3$(aq)+$Ca(OH)_2$(s or aq)→2 NaOH(aq)+$CaCO_3$(s)

Note: An aqueous solution comprising sodium hydroxide may be separated from calcium carbonate by a solid-liquid separation.

Note: Calcium carbonate may be transferred to '(5)'.

(5) 2 NaOH(aq)→2 NaOH(aq or s)+Water

Note: The solution comprising sodium hydroxide may be further concentrated, or at least a portion of water may be removed from the solution comprising sodium hydroxide, or any combination thereof.

Note: In some embodiments, at least a portion of the water removed or recovered from the solution comprising aqueous sodium hydroxide may be transferred to step '(1)' or step '(2)'.

(6) $CaCO_3$(s)→CaO(s)+$CO_2$(g)

Note: In some embodiments, calcium carbonate may be decomposed into calcium oxide in a manner which produces high purity or captured carbon dioxide. For example, in some embodiments, calcium carbonate may be calcined or decomposed by indirect calcination or indirect heating, which may result in the production of high purity or captured carbon dioxide.

Note: Captured carbon dioxide may be sequestered or employed in one or more or any combination of applications.

(7) CaO(s)+Water→$Ca(OH)_2$(s or aq)

Note: In some embodiments, calcium oxide may be reacted with water to produce an aqueous solution, or solid-liquid suspension, or milk of lime, or solid, or any combination thereof comprising calcium hydroxide.

Note: In some embodiments, calcium oxide may be reacted directly with an aqueous solution comprising sodium carbonate to produce calcium carbonate and sodium hydroxide. For example, in some embodiments, step '(4)' may be combined with step '(7)'.

Example 43: Sodium Carbonate or Sodium Bicarbonate Production from Sodium Sulfate and Calcium Carbonate (1) $CaCO_3$(s or aq)+$CO_2$(g or aq)+$H_2O$(aq)→$Ca(HCO_3)_2$(aq)

Note: In some embodiments, may be conducted under high $CO_2$ partial pressures and/or elevated temperatures. For example, some embodiments may employ $CO_2$ partial pressures greater than 1 Bar, or 2 Bar, or 3 Bar, or 4 Bar, or 5 Bar, or 6 Bar, or 7 Bar, or 8 Bar, or 9 Bar, or 10 Bar, or 11 Bar, or 12 Bar, or 13 Bar, or 14 Bar, or 15 Bar, or any combination thereof and/or temperatures greater than 0° C., or 20° C., or 40° C., or 50° C., or 60° C., or 70° C., or 80° C., or 90° C., or 95° C., or 100° C.

Note: $CO_2$ may be sourced from, including, but not limited to, one or more or any combination of the following: the decomposition of sodium bicarbonate, or captured carbon dioxide, or any combination thereof.

(2) $Na_2SO_4$(s or aq)+$Ca(HCO_3)_2$(aq)→2 $NaHCO_3$(aq)→$CaSO_4$(s)

Note: In some embodiments, $NaHCO_3$(aq) or $NaHCO_3$(s) may comprise a product which may be sold or utilized.

Note: 2 $NaHCO_3$(aq) may be separated from at least a portion of $CaSO_4$(s) by solid-liquid separation.

(3) 2 $NaHCO_3$(aq)→$Na_2CO_3$(aq)+$CO_2$(g)+$H_2O$(g or l)

Note: $CO_2$ may be transferred to step '(1)'.

Example 44: Process for Producing Sodium Hydroxide and Calcium Sulfate from Sodium Sulfate and Calcium Weak Acid (1) React Material comprising Calcium, or Magnesium, or Other Alkaline Earth-Weak Acid Anion with Acetic Acid $CaCO_3$(s or aq)+2 $CH_3COOH$(aq)→$Ca(CH_3COO)_2$(aq)+$CO_2$(g)

Calcium Silicate(s)+2 $CH_3COOH$(aq)→$Ca(CH_3COO)_2$(aq)+Silicon Dioxide(s)

CaS(s)+2 $CH_3COOH$(aq)→$Ca(CH_3COO)_2$(aq)+$H_2S$(g)

Calcium(Weak Acid Anion)+2 $CH_3COOH$(aq)→$Ca(CH_3COO)_2$(aq)+Weak Acid(s, or g, or l, or aq)

Note: Residual solids or undissolved solids, such as silicon dioxide or other undissolved solids, may be separated from the liquid solution using a solid-liquid separation.

Note: $CO_2$(g) may comprise captured $CO_2$.

Note: In some embodiments, some chemicals comprising calcium may comprise a portion of magnesium. In some embodiments, for example, input chemicals or input material may comprise a mixture of calcium and magnesium.

(2) $Ca(CH_3COO)_2$(aq)+$SO_2$(g or aq)+$H_2O$(l or aq)→$CaSO_3$(s)+2 $CH_3COOH$(aq)

Note: $CaSO_3$(s) may be separated using a solid-liquid separation.

Note: In some embodiments, residual aqueous magnesium sulfite may be present in the '2 $CH_3COOH$(aq)'. In some embodiments, the residual aqueous magnesium sulfite may remain in the '2 $CH_3COOH$(aq)' transferred to reaction '(1)' from reaction'. In some embodiments, the aqueous magnesium sulfite may remain in the '2 $CH_3COOH$(aq)' transferred to reaction '(1)' from reaction '(2)' because, for example, magnesium sulfite additional or accumulated magnesium sulfite above the solubility limits of magnesium sulfite in the solution may precipitate or co-precipitate during the reaction of $Ca(CH_3COO)_2$(aq) or $Mg(CH_3COO)_2$(aq) with $SO_2$(g or aq) or sulfite or bisulfite.

Note: In some embodiments, residual aqueous magnesium sulfite may be present in the '2 $CH_3COOH$(aq)'. In some embodiments, a portion of the residual aqueous magnesium sulfite may be concentrated and/or separated using, including, but not limited to, one or more, or any combination of the following: heating, or cooling, or reverse osmosis, or membrane based process, or precipitation, or electrodialysis, or forward osmosis, or any combination thereof. For example, the residual aqueous magnesium sulfite may be separated by concentrating the magnesium sulfite using reverse osmosis or nanofiltration, wherein the pore size or properties of the membrane may enable the permeation of at least a portion of the acetic acid and the rejection of at least a portion of magnesium sulfite, and/or cooling the resulting concentrated magnesium sulfite solution to produce at least a portion of a magnesium sulfite precipitate.

(3) $CaSO_3$(s)+$SO_2$(g or aq)+$H_2O$(aq)+Water→$Ca(HSO_3)_2$ (aq)

(4) $Na_2SO_4$(s or aq)+$Ca(HSO_3)_2$(aq)→2 $NaHSO_3$(aq)+$CaSO_4$(s)

Note: '(4)' may be conducted at an elevated temperature to reduce the solubility or dissolution of $CaSO_4$(s) or reduce potential formation of $CaSO_4$(aq).

(5) One or more or any combination of the following:

2 $NaHSO_3$(aq)→$Na_2SO_3$(s or aq)+$SO_2$(g)+$H_2O$(g or l)

2 $NaHSO_3$(aq)→$Na_2S_2O_5$(s)+$H_2O$+Water $Na_2S_2O_5$(s)→$Na_2SO_3$(s)+$SO_2$(g)

(6) $SO_2$(g or aq)+Water→$SO_2$(aq)

(7) $Na_2SO_3$(s or aq)+$Ca(OH)_2$(s or aq)→2 NaOH(aq)+$CaSO_3$(s)

(8) $CaSO_3$(s)→CaO(s)+$SO_2$(g)

(9) CaO(s)+$H_2O$+Water→$Ca(OH)_2$(s or aq)

Example 45: Sodium Hydroxide Production from Sodium Sulfate Using Calcium Precipitation and Acid Intermediates (1) React Material comprising Calcium, or Magnesium, or Other Alkaline Earth-Weak Acid Anion with Acetic Acid $CaCO_3$(s or aq)+2 $CH_3COOH$(aq)→$Ca(CH_3COO)_2$(aq)+$CO_2$(g)

Calcium Silicate(s)+2 $CH_3COOH$(aq)→$Ca(CH_3COO)_2$(aq)+Silicon Dioxide(s)

CaS(s)+2 $CH_3COOH$(aq)→$Ca(CH_3COO)_2$(aq)+$H_2S$(g)

Calcium(Weak Acid Anion)+2 $CH_3COOH$(aq)→$Ca(CH_3COO)_2$(aq)+Weak Acid(s, or g, or l, or aq)

Note: Residual solids or undissolved solids, such as silicon dioxide or other undissolved solids, may be separated from the liquid solution using a solid-liquid separation.

(2) $Ca(CH_3COO)_2$(aq)+$Na_2SO_4$(aq)→2 $NaCH_3COO$(aq)+$CaSO_4$(s)

(3) 2 $NaCH_3COO$(aq)+Citric Acid(aq)→Sodium Citrate(aq)+2 $CH_3COOH$(aq)

Note: In some embodiments, other carboxylic acids than citric acid may be employed, such as carboxylic acids which form soluble sodium salts and relatively low solubility calcium salts.

(4) Sodium Citrate(aq)+2 $CH_3COOH$(aq)→Sodium Citrate(s)+2 $CH_3COOH$(aq)

Note: '(4)' may comprise separating sodium citrate from acetic acid. For example, sodium citrate may be separated from an aqueous solution comprising acetic acid or from acetic acid by distillation.

(5) Sodium Citrate(aq)+$Ca(OH)_2$(s or aq)→Calcium Citrate(s)+2 NaOH(aq)

Note: Aqueous solution comprising sodium hydroxide may be separated from a solid comprising calcium citrate by a solid-liquid separation.

(6) 2 NaOH(aq)→2 NaOH(aq or s)+Water

Note: In some embodiments, an aqueous solution comprising sodium hydroxide may be further concentrated, or water may be removed from the solution comprising sodium hydroxide, or any combination thereof. In some embodiments, the aqueous solution comprising sodium hydroxide may undergo further treatment. In some embodiments, the aqueous solution comprising sodium hydroxide may comprise a product and/or may be ready to be sold or utilized.

(7) Calcium Citrate(s)+$SO_2$(aq)→Citric Acid(aq)+$CaSO_3$(s)

(8) $CaSO_3$(s)→CaO(s)+$SO_2$(g)

(9) $SO_2$(g)+Water→$SO_2$(aq)

(10) CaO(s)+$H_2O$+Water→$Ca(OH)_2$(s or aq)

Note: In some embodiments, CaO(s) may be reacted with water. In some embodiments, CaO(s) may be reacted with Sodium Citrate to produce Calcium Citrate and Sodium Hydroxide. In some embodiments, for example, step '(5)' and step'(10)' may be combined.

Example 46: Process for Producing Calcium Oxide or Cement or Clinker with Ascorbic Acid Intermediate (1) React Material comprising Calcium, or Magnesium, or Other Alkaline Earth-Weak Acid Anion with Ascorbic Acid, which may comprise, including, but not limited to, one or more or any combination of the following:

$CaCO_3$(s or aq)+Ascorbic Acid(aq)→Calcium Ascorbate (aq)+$CO_2$(g)

Calcium Silicate(s)+Ascorbic Acid(aq)→Calcium Ascorbate(aq)+Silicon Dioxide(s)

CaS(s)+Ascorbic Acid(aq)→Calcium Ascorbate(aq)+$H_2S$ (g)

Calcium(Weak Acid Anion)+Ascorbic Acid(aq)→Calcium Ascorbate(aq)+Weak Acid(s, or g, or l, or aq)

Note: Residual solids or undissolved solids, such as silicon dioxide or other undissolved solids, may be separated from the liquid solution using a solid-liquid separation.

Note: $CO_2$(g) may comprise captured $CO_2$.

Note: In some embodiments, some chemicals comprising calcium may comprise a portion of magnesium. In some embodiments, for example, input chemicals or input material may comprise a mixture of calcium and magnesium.

(2) Calcium Ascorbate(aq)+$SO_2$(g or aq)+$H_2O$(l or aq)→$CaSO_3$(s)+Ascorbic Acid(aq)

Note: $CaSO_3$(s) may be separated using a solid-liquid separation.

Note: In some embodiments, residual aqueous magnesium sulfite may be present in the '2 $CH_3COOH$(aq)'. In some embodiments, the residual aqueous magnesium sulfite may remain in the '2 $CH_3COOH$(aq)' transferred to reaction '(1)' from reaction'. In some embodiments, the aqueous magnesium sulfite may remain in the '2 $CH_3COOH$(aq)' transferred to reaction '(1)' from reaction '(2)' because, for example, magnesium sulfite additional or accumulated magnesium sulfite above the solubility limits of magnesium sulfite in the solution may precipitate or co-precipitate during the reaction of $Ca(CH_3COO)_2$(aq) or $Mg(CH_3COO)_2$ (aq) with $SO_2$(g or aq) or sulfite or bisulfite.

Note: In some embodiments, residual aqueous magnesium sulfite may be present in the '2 $CH_3COOH$(aq)'. In some embodiments, a portion of the residual aqueous magnesium sulfite may be concentrated and/or separated using, including, but not limited to, one or more, or any combination of the following: heating, or cooling, or reverse osmosis, or membrane based process, or precipitation, or electrodialysis, or forward osmosis, or any combination thereof. For example, the residual aqueous magnesium sulfite may be separated by concentrating the magnesium sulfite using reverse osmosis or nanofiltration, wherein the pore size or properties of the membrane may enable the permeation of at least a portion of the acetic acid and the rejection of at least a portion of magnesium sulfite, and/or cooling the resulting concentrated magnesium sulfite solution to produce at least a portion of a magnesium sulfite precipitate.

Note: In some embodiments, the use of ascorbic acid may be desirable because ascorbic acid may be non-volatile, or may comprise minimal or no vapor phase, or any combination thereof, which may mean ascorbic acid may substantially remain at an aqueous phase, or ascorbic acid may substantially not evaporate into remaining gases, or any combination thereof. In some embodiments, other acids with stronger acid strength than a 'WA' or 'Weak Acid' and weaker acidity than sulfurous acid, or which form water soluble calcium or magnesium or alkaline earth salts, or which are non-volatile or have a lower vapor pressure or higher boiling point than water, or any combination thereof may be employed instead of, or in addition to, ascorbic acid.

(3) $CaSO_3$(s)→CaO(s)+$SO_2$(g)

Note: '(3)' may comprise calcining $CaSO_3$(s), which may employ a kiln.

Note: $CaSO_3$(s) may be dried, or dehydrated, or both before or during '(3)'.

Example 47: Sodium Hydroxide Production from Sodium Sulfate with Calcium Precipitation and Acid Intermediate (1) React Material comprising Calcium, or Magnesium, or Other Alkaline Earth-Weak Acid Anion with Acetic Acid $CaCO_3$(s or aq)+2 $CH_3COOH$(aq)→$Ca(CH_3COO)_2$(aq)+ $CO_2$(g)

Calcium Silicate(s)+2 $CH_3COOH$(aq)→$Ca(CH_3COO)_2$ (aq)+Silicon Dioxide(s)

CaS(s)+2 $CH_3COOH$(aq)→$Ca(CH_3COO)_2$(aq)+$H_2S$(g)

Calcium(Weak Acid Anion)+2 $CH_3COOH$(aq)→Ca $(CH_3COO)_2$(aq)+Weak Acid(s, or g, or l, or aq)

Note: Residual solids or undissolved solids, such as silicon dioxide or other undissolved solids, may be separated from the liquid solution using a solid-liquid separation.

(2) $Ca(CH_3COO)_2$(aq)+$Na_2SO_4$(aq)→2 $NaCH_3COO$ (aq)+$CaSO_4$(s)

(3) 2 $NaCH_3COO$(aq)+$SO_2$(g or aq)+$H_2O$(l or aq)→$Na_2SO_3$(aq)+2 $CH_3COOH$(aq)

(4) $Na_2SO_3$(aq)+2 $CH_3COOH$(aq)→$Na_2SO_3$(s)+2 $CH_3COOH$(aq)

(5) $Na_2SO_3$(s)+$H_2O$(g)→2 NaOH(s or 1)+$SO_2$(g)

Note: In some embodiments, the present reaction may be conducted at an elevated temperature or temperature greater than 100° C., or 200° C., or 300° C., or 400° C., or 500° C., or 600° C., or any combination thereof.

Example 48: Sodium Carbonate Production from Sodium Sulfate with Calcium Precipitation and Acid Intermediate (1) React Material comprising Calcium, or Magnesium, or Other Alkaline Earth-Weak Acid Anion with Acetic Acid $CaCO_3$(s or aq)+2 $CH_3COOH$(aq)→$Ca(CH_3COO)_2$(aq)+ $CO_2$(g)

Calcium Silicate(s)+2 $CH_3COOH$(aq)→$Ca(CH_3COO)_2$(aq)+Silicon Dioxide(s)

CaS(s)+2 $CH_3COOH$(aq)→$Ca(CH_3COO)_2$(aq)+$H_2S$(g)

Calcium(Weak Acid Anion)+2 $CH_3COOH$(aq)→$Ca(CH_3COO)_2$(aq)+Weak Acid(s, or g, or l, or aq)

Note: Residual solids or undissolved solids, such as silicon dioxide or other undissolved solids, may be separated from the liquid solution using a solid-liquid separation.

(2) $Ca(CH_3COO)_2$(aq)+$Na_2SO_4$(aq)→2 $NaCH_3COO$(aq)+$CaSO_4$(s)

(3) 2 $NaCH_3COO$(aq)+$SO_2$(g or aq)+$H_2O$(l or aq)→$Na_2SO_3$(aq)+2 $CH_3COOH$(aq)

(4) $Na_2SO_3$(aq)+2 $CH_3COOH$(aq)→$Na_2SO_3$(s)+2 $CH_3COOH$(aq)

(5) $Na_2SO_3$(s)+$CO_2$(g)→$Na_2CO_3$(s or 1)+$SO_2$(g)

Note: In some embodiments, the present reaction may be conducted at an elevated temperature or temperature greater than 100° C., or 200° C., or 300° C., or 400° C., or 500° C., or 600° C., or any combination thereof.

Example 49: Process for Direct Air Capture with Alkali Intermediate (1) One or more or any combination of the following:

CaO (s or aq)+$CO_2$(g or aq)→$CaCO_3$(s or aq)

$Ca(OH)_2$(s or aq)+$CO_2$(g or aq)→$CaCO_3$(s or aq)+$H_2O$(aq)

Note: If $CO_2$(g) is produced, it may be desirable for said $CO_2$(g) to be produced at a high partial pressure $CO_2$(g), or purity $CO_2$(g), or to comprise captured $CO_2$(g).

(2) $CaCO_3$(s or aq)+2 $CH_3COOH$(aq)→$Ca(CH_3COO)_2$(aq)+$CO_2$(g)

Note: It may be desirable for the $CO_2$(g) to be produced at a high partial pressure $CO_2$(g), or purity $CO_2$(g), or to comprise captured $CO_2$(g).

(3) $Ca(CH_3COO)_2$(aq)+$Na_2SO_3$(s or aq)→2 $NaCH_3COO$(aq)+$CaSO_3$(s)

Note: $CaSO_3$(s) may be separated using a solid-liquid separation.

(4) 2 $NaCH_3COO$(aq)+$SO_2$(g or aq)+$H_2O$(l or aq)→$Na_2SO_3$(aq)+2 $CH_3COOH$(aq)

(5) $Na_2SO_3$(aq)+2 $CH_3COOH$(aq)→2 $CH_3COOH$(aq)+$Na_2SO_3$(s)

(6) $CaSO_3$(s)→CaO(s)+$SO_2$(g)

(7) CaO(s)+Water→$Ca(OH)_2$(s or aq)

Example 50: Process for Producing Precipitated Calcium Carbonate (1) React Material comprising Calcium, or Magnesium, or Other Alkaline Earth-Weak Acid Anion with Acetic Acid, which may comprise, including, but not limited to, one or more or any combination of the following:

$CaCO_3$(s or aq)+2 $CH_3COOH$(aq)→$Ca(CH_3COO)_2$(aq)+$CO_2$(g)

Calcium Silicate(s)+2 $CH_3COOH$(aq)→$Ca(CH_3COO)_2$(aq)+Silicon Dioxide(s)

CaS(s)+2 $CH_3COOH$(aq)→$Ca(CH_3COO)_2$(aq)+$H_2S$(g)

Calcium(Weak Acid Anion)+2 $CH_3COOH$(aq)→$Ca(CH_3COO)_2$(aq)+Weak Acid(s, or g, or l, or aq)

(2) $Ca(CH_3COO)_2$(aq)+$SO_2$(g or aq)+$H_2O$(l or aq)→$CaSO_3$(s)+2 $CH_3COOH$(aq)

(3) $CaSO_3$(s)→CaO(s)+$SO_2$(g)

(4) One or more or any combination of the following:

CaO(s)+$CO_2$→$CaCO_3$(s)

CaO(s)+Water→$Ca(OH)_2$(s or aq)

$Ca(OH)_2$(s or aq)+$CO_2$→$CaCO_3$(s or aq)

Example 51: Sodium Hydroxide Production and Precipitated Calcium Carbonate Production from Sodium Bicarbonate Using Calcium Precipitation and Acid Intermediate (1) React Material comprising Calcium, or Magnesium, or Other Alkaline Earth-Weak Acid Anion with Acetic Acid $CaCO_3$(s or aq)+2 $CH_3COOH$(aq)→$Ca(CH_3COO)_2$(aq)+$CO_2$(g)

Calcium Silicate(s)+2 $CH_3COOH$(aq)→$Ca(CH_3COO)_2$(aq)+Silicon Dioxide(s)

CaS(s)+2 $CH_3COOH$(aq)→$Ca(CH_3COO)_2$(aq)+$H_2S$(g)

Calcium(Weak Acid Anion)+2 $CH_3COOH$(aq)→$Ca(CH_3COO)_2$(aq)+Weak Acid(s, or g, or l, or aq)

Note: Residual solids or undissolved solids, such as silicon dioxide or other undissolved solids, may be separated from the liquid solution using a solid-liquid separation.

Note: $CO_2$(g) may comprise captured $CO_2$.

Note: In some embodiments, some chemicals comprising calcium may comprise a portion of magnesium. In some embodiments, for example, input chemicals or input material may comprise a mixture of calcium and magnesium.

Note: In some embodiments, acetic acid vapor and/or water vapor may be separated or recovered from $CO_2$(g).

(2) $Ca(CH_3COO)_2$(aq)+2 $NaHCO_3$(aq or s)→2 $NaCH_3COO$(aq)+$CaCO_3$(s)+$CO_2$(g)

Note: In some embodiments, $NaHCO_3$(s) may be added directly to or dissolved in $Ca(CH_3COO)_2$(aq).

Note: In some embodiments, $NaHCO_3$(aq or s) may comprise a mineral, or may comprise nahcolite, or any combination thereof.

Note: In some embodiments, $NaHCO_3$(s) may be dissolved in water or an aqueous solution to form $NaHCO_3$(aq) before mixing with $Ca(CH_3COO)_2$(aq).

Note: The $CO_2$(g) may comprise captured $CO_2$(g).

Note: Some embodiments may form dissolved calcium bicarbonate. In some embodiments, dissolved calcium bicarbonate may be decomposed into calcium carbonate and carbon dioxide may heating solution, or depressurizing the solution, or any combination thereof.

Note: $CaCO_3$(s) may comprise precipitated calcium carbonate.

Note: $CaCO_3$(s) may be separated by solid-liquid separation.

(3) 2 $NaCH_3COO$(aq)+$SO_2$(g or aq)+$H_2O$(l or aq)→$Na_2SO_3$(aq)+2 $CH_3COOH$(aq)

Note: In some embodiments, $SO_2$(g) may comprise other gases in addition to $SO_2$(g). In some embodiments, the reaction of 2 $NaCH_3COO$(aq)+$SO_2$(g) may result in at least a portion of acetic acid vapor in the remaining gases during or after the reaction. In some embodiments, $NaCH_3COO$(aq) entering the present step may be pre-contacted with or may absorb at least a portion of acetic acid vapor from the remaining gases. In some embodiments, the reactor or absorption column may be configured to absorb acetic acid vapor in $NaCH_3COO$(aq) before or while reacting $NaCH_3COO$(aq) with $SO_2$(g). In some embodiments, acetic acid vapor may be removed from remaining gases using, for example, including, but not limited to, one or more or any combination of the following: alkaline earth carbonate, or alkaline earth-weak acid, or alkaline earth carbonate-water slurry, or alkaline earth oxide, or alkaline earth (4) $Na_2SO_3$(aq)+2 $CH_3COOH$(aq)→2 $CH_3COOH$(aq)+ $Na_2SO_3$(s)

Note: $CH_3COOH$ may be more soluble in water than $Na_2SO_3$. In some embodiments, $Na_2SO_3$ may be separated or precipitated from solution by, for example, including, but not limited to, evaporation, or distillation, or crystallization, or separation systems or methods described herein, or separation systems or methods described in the art, or any combination thereof.

Note: In some embodiments, $CH_3COOH$ and/or water may be separated from $Na_2SO_3$ by, for example, evaporation, or distillation, or crystallization, or any combination thereof. In some embodiments, $CH_3COOH$ may evaporate with water vapor and/or condense with water vapor, which may result in a distillate or condensate comprising $CH_3COOH$(aq).

Note: In some embodiments, magnesium sulfite(aq) may be present in the $Na_2SO_3$(aq)+2 $CH_3COOH$(aq). In some embodiments, if present, magnesium sulfite may begin to precipitate or crystalize before $Na_2SO_3$. In some embodiments magnesium sulfite solid may be separated during step '(4)'. In some embodiments, separated magnesium sulfite may be decomposed to magnesium oxide, or decomposed separately from calcium sulfite, or decomposed together with calcium sulfite, or any combination thereof.s Note: $Na_2SO_3$(s) may be separated from $CH_3COOH$(aq) by a solid-liquid separation, which may include, but is not limited to, filter, or centrifuge, or decanter, or separation systems or methods described herein, or separation systems or methods described in the art, or any combination thereof.

(5) $Na_2SO_3$(s or aq)+$Ca(OH)_2$(s or aq)→2 NaOH(aq or s)+$CaSO_3$(s)

Note: $Ca(OH)_2$(s or aq) may comprise a solid-liquid suspension, such as milk of lime.

Note: $CaSO_3$(s) may be separated using a solid-liquid separation.

(6) $CaSO_3$(s)→CaO(s)+$SO_2$(g)

Note: '(6)' may comprise calcining $CaSO_3$(s), which may employ a kiln.

Note: $CaSO_3$(s) may be dried, or dehydrated, or both before or during '(6)'.

(7) CaO(s)+Water(g or l or aq)→$Ca(OH)_2$(s or aq)

Note: In some embodiments, CaO(s) may be employed to remove water vapor or facilitated drying of $CaSO_3$(s) before or during decomposition of $CaSO_3$(s) to CaO(s).

Note: In some embodiments, calcium oxide may be reacted directly with an aqueous solution comprising sodium sulfite to produce calcium sulfite and sodium hydroxide. In some embodiments, calcium oxide may be reacted directly with an aqueous solution comprising sodium sulfite to produce calcium sulfite and sodium hydroxide, which may comprise combining step '(5)' and step'(7)'.

Note: In some embodiments, calcium oxide may be reacted with water to produce an aqueous solution, or solid-liquid suspension, or milk of lime, or solid, or any combination thereof comprising calcium hydroxide.

(8) 2 NaOH(aq or s)→2 NaOH(aq or s)+Water

Note: In some embodiments, NaOH(aq) may be concentrated into an aqueous solution comprising a greater mass percent concentration of NaOH.

Note: In some embodiments, water may be removed and/or NaOH may be separated or precipitated by, for example, including, but not limited to, evaporation, or distillation, or crystallization, or separation systems or methods described herein, or separation systems or methods described in the art, or any combination thereof.

Note: In some embodiments, it may be desirable for NaOH to comprise a concentrated aqueous solution Example 52: Sodium Hydroxide Production and Precipitated Calcium Carbonate Production from Sodium Carbonate Using Calcium Precipitation and Acid Intermediate (1) React Material comprising Calcium, or Magnesium, or Other Alkaline Earth-Weak Acid Anion with Acetic Acid $CaCO_3$(s or aq)+2 $CH_3COOH$(aq)→$Ca(CH_3COO)_2$(aq)+ $CO_2$(g)

Calcium Silicate(s)+2 $CH_3COOH$(aq)→$Ca(CH_3COO)_2$(aq)+Silicon Dioxide(s)

CaS(s)+2 $CH_3COOH$(aq)→$Ca(CH_3COO)_2$(aq)+$H_2S$(g)

Calcium(Weak Acid Anion)+2 $CH_3COOH$(aq)→Ca $(CH_3COO)_2$(aq)+Weak Acid(s, or g, or l, or aq)

Note: Residual solids or undissolved solids, such as silicon dioxide or other undissolved solids, may be separated from the liquid solution using a solid-liquid separation.

Note: $CO_2$(g) may comprise captured $CO_2$.

Note: In some embodiments, some chemicals comprising calcium may comprise a portion of magnesium. In some embodiments, for example, input chemicals or input material may comprise a mixture of calcium and magnesium.

Note: In some embodiments, acetic acid vapor and/or water vapor may be separated or recovered from $CO_2$(g).

(2) $Ca(CH_3COO)_2$(aq)+$Na_2CO_3$(aq or s)→2 $NaCH_3COO$(aq)+$CaCO_3$(s)

Note: In some embodiments, $Na_2CO_3$(aq or s) may be added directly to or dissolved in $Ca(CH_3COO)_2$(aq).

Note: In some embodiments, $Na_2CO_3$(aq or s) may comprise a mineral, or may comprise decomposed nahcolite, or any combination thereof.

Note: In some embodiments, $Na_2CO_3$(aq or s) may be dissolved in water or an aqueous solution to form $NaHCO_3$(aq) before mixing with $Ca(CH_3COO)_2$(aq).

Note: Some embodiments may form dissolved calcium bicarbonate. In some embodiments, dissolved calcium bicarbonate may be decomposed into calcium carbonate and carbon dioxide may heating solution, or depressurizing the solution, or any combination thereof.

Note: $CaCO_3$(s) may comprise precipitated calcium carbonate.

Note: $CaCO_3$(s) may be separated by solid-liquid separation.

(3) 2 $NaCH_3COO$(aq)+$SO_2$(g or aq)+$H_2O$(l or aq)→$Na_2SO_3$(aq)+2 $CH_3COOH$(aq)

Note: In some embodiments, $SO_2$(g) may comprise other gases in addition to $SO_2$(g). In some embodiments, the reaction of 2 $NaCH_3COO$(aq)+$SO_2$(g) may result in at least a portion of acetic acid vapor in the remaining gases during or after the reaction. In some embodiments, $NaCH_3COO$(aq) entering the present step may be pre-contacted with or may absorb at least a portion of acetic acid vapor from the remaining gases. In some embodiments, the reactor or absorption column may be configured to absorb acetic acid vapor in $NaCH_3COO$(aq) before or while reacting $NaCH_3COO$(aq) with $SO_2$(g). In some embodiments, acetic acid vapor may be removed from remaining gases using, for example, including, but not limited to, one or more or any combination of the following: alkaline earth carbonate, or alkaline earth-weak acid, or alkaline earth carbonate-water slurry, or alkaline earth oxide, or alkaline earth (4) $Na_2SO_3$(aq)+2 $CH_3COOH$(aq)→2 $CH_3COOH$(aq)+$Na_2SO_3$(s)

Note: $CH_3COOH$ may be more soluble in water than $Na_2SO_3$. In some embodiments, $Na_2SO_3$ may be separated or precipitated from solution by, for example, including, but not limited to, evaporation, or distillation, or crystallization, or separation systems or methods described herein, or separation systems or methods described in the art, or any combination thereof.

Note: In some embodiments, $CH_3COOH$ and/or water may be separated from $Na_2SO_3$ by, for example, evaporation, or distillation, or crystallization, or any combination thereof. In some embodiments, $CH_3COOH$ may evaporate with water vapor and/or condense with water vapor, which may result in a distillate or condensate comprising $CH_3COOH$(aq).

Note: In some embodiments, magnesium sulfite(aq) may be present in the $Na_2SO_3$(aq)+2 $CH_3COOH$(aq). In some embodiments, if present, magnesium sulfite may begin to precipitate or crystalize before $Na_2SO_3$. In some embodiments magnesium sulfite solid may be separated during step '(4)'. In some embodiments, separated magnesium sulfite may be decomposed to magnesium oxide, or decomposed separately from calcium sulfite, or decomposed together with calcium sulfite, or any combination thereof.s Note: $Na_2SO_3$(s) may be separated from $CH_3COOH$(aq) by a solid-liquid separation, which may include, but is not limited to, filter, or centrifuge, or decanter, or separation systems or methods described herein, or separation systems or methods described in the art, or any combination thereof.

(5) $Na_2SO_3$(s or aq)+$Ca(OH)_2$(s or aq)→2 NaOH(aq or s)+$CaSO_3$(s)

Note: $Ca(OH)_2$(s or aq) may comprise a solid-liquid suspension, such as milk of lime.

Note: $CaSO_3$(s) may be separated using a solid-liquid separation.

(6) $CaSO_3$(s)→CaO(s)+$SO_2$(g)

Note: '(6)' may comprise calcining $CaSO_3$(s), which may employ a kiln.

Note: $CaSO_3$(s) may be dried, or dehydrated, or both before or during '(6)'.

(7) CaO(s)+Water(g or l or aq)→$Ca(OH)_2$(s or aq)

Note: In some embodiments, CaO(s) may be employed to remove water vapor or facilitated drying of $CaSO_3$(s) before or during decomposition of $CaSO_3$(s) to CaO(s).

Note: In some embodiments, calcium oxide may be reacted directly with an aqueous solution comprising sodium sulfite to produce calcium sulfite and sodium hydroxide. In some embodiments, calcium oxide may be reacted directly with an aqueous solution comprising sodium sulfite to produce calcium sulfite and sodium hydroxide, which may comprise combining step '(5)' and step'(7)'.

Note: In some embodiments, calcium oxide may be reacted with water to produce an aqueous solution, or solid-liquid suspension, or milk of lime, or solid, or any combination thereof comprising calcium hydroxide.

(8) 2 NaOH(aq or s)→2 NaOH(aq or s)+Water

Note: In some embodiments, NaOH(aq) may be concentrated into an aqueous solution comprising a greater mass percent concentration of NaOH.

Note: In some embodiments, water may be removed and/or NaOH may be separated or precipitated by, for example, including, but not limited to, evaporation, or distillation, or crystallization, or separation systems or methods described herein, or separation systems or methods described in the art, or any combination thereof.

Note: In some embodiments, it may be desirable for NaOH to comprise a concentrated aqueous solution

Example 53: Process for Producing Sodium Hydroxide with Sulfur Dioxide and Carbon Dioxide Intermediates (1) React Material comprising Calcium, or Magnesium, or Other Alkaline Earth-Weak Acid Anion with Acetic Acid $CaCO_3$(s or aq)+2 $CH_3COOH$(aq)→$Ca(CH_3COO)_2$(aq)+$CO_2$(g)+$H_2O$(aq or l)

Calcium Silicate(s)+2 $CH_3COOH$(aq)→$Ca(CH_3COO)_2$(aq)+Silicon Dioxide(s)+$H_2O$(aq or l)

CaS(s)+2 $CH_3COOH$(aq)→$Ca(CH_3COO)_2$(aq)+$H_2S$(g)

Calcium(Weak Acid Anion)+2 $CH_3COOH$(aq)→$Ca(CH_3COO)_2$(aq)+Weak Acid(s, or g, or l, or aq)+$H_2O$(aq or l)

Note: Residual solids or undissolved solids, such as silicon dioxide or other undissolved solids, may be separated from the liquid solution using a solid-liquid separation.

Note: $CO_2$(g) may comprise captured $CO_2$.

Note: In some embodiments, some chemicals comprising calcium may comprise a portion of magnesium. In some embodiments, for example, input chemicals or input material may comprise a mixture of calcium and magnesium.

Note: In some embodiments, acetic acid vapor and/or water vapor may be separated or recovered from $CO_2$(g).

Note: In some embodiments, acetic acid for step '(1)' may comprise aqueous acetic acid produced or regenerated in step '(4)'.

(2) $Ca(CH_3COO)_2$(aq)+$Na_2SO_4$(s or aq)→2 $NaCH_3COO$(aq)+$CaSO_4$(s)

Note: In some embodiments, $Na_2SO_4$(s) may be added directly to or dissolved in $Ca(CH_3COO)_2$(aq).

Note: In some embodiments, $Na_2SO_4$(s) may be dissolved in water or an aqueous solution to form $Na_2SO_4$(aq) before mixing with $Ca(CH_3COO)_2$(aq).

Note: In some embodiments, water may be added to the process to make up for water which may leave the process, for example, if NaOH(aq) is an output, or another aqueous solution is an output, or any combination thereof. In some embodiments, water may be added to the process by $Na_2SO_4$ being in the form of $Na_2SO_4$(aq) or an aqueous solution comprising sodium sulfate, wherein at least a portion of the water in $Na_2SO_4$(aq) may comprise water added to the process. In some embodiments, $Na_2SO_4$(aq) may be provided or sourced as an aqueous solution. For example, in some embodiments, $Na_2SO_4$(aq) may be provided to the process in the form of $Na_2SO_4$(aq). In some embodiments, $Na_2SO_4$(aq) may be provided or sourced as a solid or $Na_2SO_4$(s), then dissolved in water to form $Na_2SO_4$(aq).

Note: In some embodiments, $Ca(CH_3COO)_2$(aq) may comprise $Ca(CH_3COO)_2$(aq) from step '(1)'.

(3) 2 $NaCH_3COO$(aq)+$SO_2$(g or aq)+$H_2O$(l or aq)→$Na_2SO_3$(aq)+2 $CH_3COOH$(aq)

Note: In some embodiments, $SO_2$(g) may comprise other gases in addition to $SO_2$(g). In some embodiments, the reaction of 2 $NaCH_3COO$(aq)+$SO_2$(g) may result in at least a portion of acetic acid vapor in the remaining gases during or after the reaction. In some embodiments, $NaCH_3COO$(aq) entering the present step may be pre-contacted with or may absorb at least a portion of acetic acid vapor from the remaining gases. In some embodiments, the reactor or absorption column may be configured to absorb acetic acid vapor in $NaCH_3COO$(aq) before or while reacting $NaCH_3COO$(aq) with $SO_2$(g). In some embodiments, acetic acid vapor may be removed from remaining gases using, for example, including, but not limited to, one or more or any combination of the following: alkaline earth carbonate, or alkaline earth-weak acid, or alkaline earth carbonate-water slurry, or alkaline earth oxide, or alkaline earth.

Note: In some embodiments, $NaCH_3COO(aq)$ may comprise $NaCH_3COO(aq)$ from step '(2)'.

Note: In some embodiments, $SO_2$ may comprise $SO_2(g)$ from the calcination or decomposition of $CaSO_3(s)$ in step '(9)'.

(4) $Na_2SO_3(aq)+2\ CH_3COOH(aq) \rightarrow 2\ CH_3COOH(aq)+Na_2SO_3(s)$

Note: $CH_3COOH$ may be more soluble in water than $Na_2SO_3$. In some embodiments, $Na_2SO_3$ may be separated or precipitated from solution by, for example, including, but not limited to, evaporation, or distillation, or crystallization, or separation systems or methods described herein, or separation systems or methods described in the art, or any combination thereof.

Note: In some embodiments, $CH_3COOH$ and/or water may be separated from $Na_2SO_3$ by, for example, evaporation, or distillation, or crystallization, or any combination thereof. In some embodiments, $CH_3COOH$ may evaporate with water vapor and/or condense with water vapor, which may result in a distillate or condensate comprising $CH_3COOH(aq)$.

Note: In some embodiments, magnesium sulfite(aq) may be present in the $Na_2SO_3(aq)+2\ CH_3COOH(aq)$. In some embodiments, if present, magnesium sulfite may begin to precipitate or crystalize before $Na_2SO_3$. In some embodiments magnesium sulfite solid may be separated during step '(4)'. In some embodiments, separated magnesium sulfite may be decomposed to magnesium oxide, or decomposed separately from calcium sulfite, or decomposed together with calcium sulfite, or any combination thereof.s Note: $Na_2SO_3(s)$ may be separated from $CH_3COOH(aq)$ by a solid-liquid separation, which may include, but is not limited to, filter, or centrifuge, or decanter, or separation systems or methods described herein, or separation systems or methods described in the art, or any combination thereof.

(5) React an Alkaline-Earth-Weak Acid, such as an Alkaline-Earth Carbonate, with Carbon Dioxide and/or Water to Form an Alkaline-Earth Bicarbonate $CaCO_3(s)+CO_2(g\ or\ aq)+H_2O(aq) \rightarrow Ca(HCO_3)_2(aq)$ $MgCO_3(s)+CO_2(g\ or\ aq)+H_2O(aq) \rightarrow Mg(HCO_3)_2(aq)$ Note: May be conducted under a pressurized $CO_2$ atmosphere or with concentrated carbonic acid or $CO_2(aq)$. For example, the $CO_2$ partial pressure during the reaction may be greater than, for example, 1 Bar, or 2 Bar, or 3 Bar, or 4 Bar, or 5 Bar, or 6 Bar, or 7 Bar, or 8 Bar, or 9 Bar, or 10 Bar, or any combination thereof.

Note: In some embodiments, $CaCO_3(s)$ or $MgCO_3(s)$ may comprise $CaCO_3(s)$ or $MgCO_3(s)$ from step '(10)'.

Note: In some embodiments, $CO_2$(g or aq) may comprise $CO_2$ from step '(1)', or step '(8)', or any combination thereof.

(6) React an Alkali Sulfite with an Alkaline-Earth Bicarbonate to form an Alkali Bicarbonate and an Alkaline-Earth Sulfite $Na_2SO_3(s\ or\ aq)+Ca(HCO_3)_2(aq) \rightarrow 2\ NaHCO_3(aq)+CaSO_3(s)$ $Na_2SO_3(s\ or\ aq)+Mg(HCO_3)_2(aq) \rightarrow 2\ NaHCO_3(aq)+MgSO_3(s)$ Note: In some embodiments, $Na_2SO_3(s)$ may be dissolved in water or may comprise an aqueous solution before mixing with an aqueous solution comprising $Ca(HCO_3)_2(aq)$ or $Mg(HCO_3)_2(aq)$.

Note: At least a portion of $CaSO_3(s)$ or $MgSO_3(s)$ may be separated by a solid-liquid separation.

Note: In some embodiments, $NaHCO_3$ may be sold as a product or employed as a carbon sequestration medium.

Note: In some embodiments, $Na_2SO_3$(s or aq) may comprise $Na_2SO_3$ from step '(4)'.

Note: In some embodiments, $Ca(HCO_3)_2(aq)$ or $Mg(HCO_3)_2(aq)$ may comprise $Ca(HCO_3)_2(aq)$ or $Mg(HCO_3)_2(aq)$ from step '(5)'.

(7) 2 $NaHCO_3(aq)$+2 $NaHCO_3(s)$+Water

Note: In some embodiments, $NaHCO_3$ may be sold as a product and/or employed as a carbon sequestration medium.

Note: In some embodiments, step '(7)' may be combined with step '(8)'.

Note: In some embodiments, 2 $NaHCO_3(aq)$ may be decomposed into $Na_2CO_3(aq)$ and $CO_2(g)$ and water within an aqueous and/or under-pressure or pressurized environment, which may avoid or prevent the need for crystallizing or precipitating $NaHCO_3(s)$.

Note: In some embodiments, 2 $NaHCO_3(aq)$ may comprise $NaHCO_3(aq)$ from step '(6)'.

Note: In some embodiments, at least a portion of residual dissolved $MgSO_3$ or magnesium sulfite, if any, may be separated or precipitated during this step.

Note: Water may be separated from sodium bicarbonate or sodium carbonate using systems and methods for water separation described herein.

Note: In some embodiments, step 8 and step 9 may be combined in a single step, wherein, for example, sodium bicarbonate at an aqueous phase may be decomposed into aqueous sodium carbonate and carbon dioxide, which may comprise captured carbon dioxide.

In some embodiments, said aqueous sodium carbonate may be reacted with calcium oxide, or calcium hydroxide, or magnesium oxide, or magnesium hydroxide, or any combination thereof to produce sodium hydroxide and calcium carbonate or magnesium carbonate.

In some embodiments, said aqueous sodium carbonate may be separated from water to produce solid sodium carbonate and/or said solid sodium carbonate may be dissolved in water and/or said sodium carbonate may be reacted with calcium oxide, or calcium hydroxide, or magnesium oxide, or magnesium hydroxide, or any combination thereof to produce sodium hydroxide and calcium carbonate or magnesium carbonate.

(8) $2\ NaHCO_3(s) \rightarrow Na_2CO_3(s)+CO_2(g)+H_2O(g\ or\ l)$

Note: $CO_2(g)$ may comprise captured $CO_2$.

Note: In some embodiments, $Na_2CO_3$ may be sold as a product and/or employed as a carbon sequestration medium.

Note: In some embodiments, step '(7)' may be combined with step '(8)'.

Note: In some embodiments, 2 $NaHCO_3(aq)$ may be decomposed into $Na_2CO_3(aq)$ and $CO_2(g)$ and water within an aqueous and/or under-pressure or pressurized environment, which may avoid or prevent the need for crystallizing or precipitating $NaHCO_3(s)$.

Note: In some embodiments, 2 $NaHCO_3(s)$ may comprise $NaHCO_3$ from step '(6)' or step '(7)'.

(9) Calcine or decompose an alkaline-earth sulfite to an alkaline earth oxide and sulfur dioxide $CaSO_3(s) \rightarrow CaO(s)+SO_2(g)$ $MgSO_3(s) \rightarrow MgO(s)+SO_2(g)$ Note: May comprise calcining $CaSO_3(s)$ or $MgSO_3(s)$, which may employ a kiln.

Note: $CaSO_3(s)$ or $MgSO_3(s)$ may be dried, or dehydrated, or both before or during calcining.

Note: $CaSO_3$(s) or $MgSO_3$(s) may comprise $CaSO_3$(s) or $MgSO_3$(s) from step '(6)'.

(10) React an alkaline-earth oxide or hydroxide with an alkali carbonate to produce an alkaline-earth carbonate and an alkali hydroxide CaO(s or aq)+$Na_2CO_3$(s or aq)+Water→2 NaOH(aq)+$CaCO_3$(s)

MgO(s or aq)+$Na_2CO_3$(s or aq)+Water→2 NaOH(aq)+$MgCO_3$(s)

Note: In some embodiments, CaO+$Na_2CO_3$(s or aq)+Water or MgO+$Na_2CO_3$(s or aq)+Water may be conducted in multiple steps. For example, in some embodiments, CaO or MgO may be reacted with water to form $Ca(OH)_2$(aq), or $Ca(OH)_2$(s or aq), or $Mg(OH)_2$(aq), or $Mg(OH)_2$(s or aq), which may comprise Milk of Lime or Milk of Magnesia, or a solid-liquid suspension comprising calcium hydroxide or magnesium hydroxide. For example, in some embodiments, $Na_2CO_3$ may comprise an aqueous solution or may be dissolved in water to form an aqueous solution. For example, in some embodiments, a solution or solid-liquid mixture or suspension comprising $Ca(OH)_2$(s or aq), or Milk of Lime, or $Mg(OH)_2$, or Milk of Magnesia may be mixed with an aqueous solution comprising $Na_2CO_3$(aq), which may result in the formation of a solution comprising aqueous sodium hydroxide and a solid comprising calcium carbonate or magnesium carbonate.

Note: In some embodiments, at least a portion of calcium carbonate or magnesium carbonate may be separated from at least a portion of sodium hydroxide using, for example, a solid-liquid separation.

Note: CaO(s) or MgO(s) may comprise CaO(s) or MgO(s) from step '(9)'.

Note: $Na_2CO_3$(s or aq) may comprise $Na_2CO_3$(s or aq) from step '(7)' or step '(8)'.

Note: In some embodiments, $CaCO_3$ or $MgCO_3$ may be transferred to step 5.

Example 54: Process for Producing Sodium Hydroxide with Sulfur Dioxide and Carbon Dioxide Intermediates (1) React Material comprising Calcium, or Magnesium, or Other Alkaline Earth-Weak Acid Anion with Acetic Acid $CaCO_3$(s or aq)+2 $CH_3COOH$(aq)→$Ca(CH_3COO)_2$(aq)+$CO_2$(g)+$H_2O$(aq or l)

Calcium Silicate(s)+2 $CH_3COOH$(aq)→$Ca(CH_3COO)_2$(aq)+Silicon Dioxide(s)+$H_2O$(aq or l)

CaS(s)+2 $CH_3COOH$(aq)→$Ca(CH_3COO)_2$(aq)+$H_2S$(g)

Calcium(Weak Acid Anion)+2 $CH_3COOH$(aq)→$Ca(CH_3COO)_2$(aq)+Weak Acid(s, or g, or l, or aq)+$H_2O$(aq or l)

Note: Residual solids or undissolved solids, such as silicon dioxide or other undissolved solids, may be separated from the liquid solution using a solid-liquid separation.

Note: $CO_2$(g) may comprise captured $CO_2$.

Note: In some embodiments, some chemicals comprising calcium may comprise a portion of magnesium. In some embodiments, for example, input chemicals or input material may comprise a mixture of calcium and magnesium.

Note: In some embodiments, acetic acid vapor and/or water vapor may be separated or recovered from $CO_2$(g).

Note: In some embodiments, acetic acid for step '(1)' may comprise aqueous acetic acid produced or regenerated in step '(4)'.

(2) $Ca(CH_3COO)_2$(aq)+$Na_2SO_4$(s or aq)→2 $NaCH_3COO$(aq)+$CaSO_4$(s)

Note: In some embodiments, $Na_2SO_4$(s) may be added directly to or dissolved in $Ca(CH_3COO)_2$(aq).

Note: In some embodiments, $Na_2SO_4$(s) may be dissolved in water or an aqueous solution to form $Na_2SO_4$(aq) before mixing with $Ca(CH_3COO)_2$(aq).

Note: In some embodiments, water may be added to the process to make up for water which may leave the process, for example, if NaOH(aq) is an output, or another aqueous solution is an output, or any combination thereof. In some embodiments, water may be added to the process by $Na_2SO_4$ being in the form of $Na_2SO_4$(aq) or an aqueous solution comprising sodium sulfate, wherein at least a portion of the water in $Na_2SO_4$(aq) may comprise water added to the process. In some embodiments, $Na_2SO_4$(aq) may be provided or sourced as an aqueous solution. For example, in some embodiments, $Na_2SO_4$(aq) may be provided to the process in the form of $Na_2SO_4$(aq). In some embodiments, $Na_2SO_4$(aq) may be provided or sourced as a solid or $Na_2SO_4$(s), then dissolved in water to form $Na_2SO_4$(aq).

Note: In some embodiments, $Ca(CH_3COO)_2$(aq) may comprise $Ca(CH_3COO)_2$(aq) from step '(1)'.

(3) 2 $NaCH_3COO$(aq)+$SO_2$(g or aq)+$H_2O$(l or aq)→$Na_2SO_3$(aq)+2 $CH_3COOH$(aq)

Note: In some embodiments, $SO_2$(g) may comprise other gases in addition to $SO_2$(g). In some embodiments, the reaction of 2 $NaCH_3COO$(aq)+$SO_2$(g) may result in at least a portion of acetic acid vapor in the remaining gases during or after the reaction. In some embodiments, $NaCH_3COO$(aq) entering the present step may be pre-contacted with or may absorb at least a portion of acetic acid vapor from the remaining gases. In some embodiments, the reactor or absorption column may be configured to absorb acetic acid vapor in $NaCH_3COO$(aq) before or while reacting $NaCH_3COO$(aq) with $SO_2$(g). In some embodiments, acetic acid vapor may be removed from remaining gases using, for example, including, but not limited to, one or more or any combination of the following: alkaline earth carbonate, or alkaline earth-weak acid, or alkaline earth carbonate-water slurry, or alkaline earth oxide, or alkaline earth.

Note: In some embodiments, $NaCH_3COO$(aq) may comprise $NaCH_3COO$(aq) from step '(2)'.

Note: In some embodiments, $SO_2$ may comprise $SO_2$(g) from the calcination or decomposition of $CaSO_3$(s) in step '(9)'.

(4) $Na_2SO_3$(aq)+2 $CH_3COOH$(aq)→2 $CH_3COOH$(aq)+$Na_2SO_3$(s)

Note: $CH_3COOH$ may be more soluble in water than $Na_2SO_3$. In some embodiments, $Na_2SO_3$ may be separated or precipitated from solution by, for example, including, but not limited to, evaporation, or distillation, or crystallization, or separation systems or methods described herein, or separation systems or methods described in the art, or any combination thereof.

Note: In some embodiments, $CH_3COOH$ and/or water may be separated from $Na_2SO_3$ by, for example, evaporation, or distillation, or crystallization, or any combination thereof. In some embodiments, $CH_3COOH$ may evaporate with water vapor and/or condense with water vapor, which may result in a distillate or condensate comprising $CH_3COOH$(aq).

Note: In some embodiments, magnesium sulfite(aq) may be present in the $Na_2SO_3$(aq)+2 $CH_3COOH$(aq). In some embodiments, if present, magnesium sulfite may begin to precipitate or crystalize before $Na_2SO_3$. In some embodiments magnesium sulfite solid may be separated during step '(4)'. In some embodiments, separated magnesium sulfite may be decomposed to magnesium oxide, or decomposed separately from calcium sulfite, or decomposed together with calcium sulfite, or any combination thereof.s Note: $Na_2SO_3$(s) may be separated from $CH_3COOH$(aq) by a solid-liquid separation, which may include, but is not limited to, filter, or centrifuge, or decanter, or separation systems or methods described herein, or separation systems or methods described in the art, or any combination thereof.

(5) React an Alkaline-Earth-Weak Acid, such as an Alkaline-Earth Carbonate, with Carbon Dioxide and/or Water to Form an Alkaline-Earth Bicarbonate $CaCO_3(s)+CO_2(g\ or\ aq)+H_2O(aq)\rightarrow Ca(HCO_3)_2(aq)$ $MgCO_3(s)+CO_2(g\ or\ aq)+H_2O(aq)\rightarrow Mg(HCO_3)_2(aq)$ Note: May be conducted under a pressurized $CO_2$ atmosphere or with concentrated carbonic acid or $CO_2$(aq). For example, the $CO_2$ partial pressure during the reaction may be greater than, for example, 1 Bar, or 2 Bar, or 3 Bar, or 4 Bar, or 5 Bar, or 6 Bar, or 7 Bar, or 8 Bar, or 9 Bar, or 10 Bar, or any combination thereof.

Note: In some embodiments, $CaCO_3$(s) or $MgCO_3$(s) may comprise $CaCO_3$(s) or $MgCO_3$(s) from step '(9)'.

Note: In some embodiments, $CO_2$(g or aq) may comprise $CO_2$ from step '(1)', or step '(8)', or any combination thereof.

(6) React an Alkali Sulfite with an Alkaline-Earth Bicarbonate to form an Alkali Bicarbonate and an Alkaline-Earth Sulfite $Na_2SO_3(s\ or\ aq)+Ca(HCO_3)_2(aq)\rightarrow 2\ NaHCO_3(aq)+CaSO_3(s)$ $Na_2SO_3(s\ or\ aq)+Mg(HCO_3)_2(aq)\rightarrow 2\ NaHCO_3(aq)+MgSO_3(s)$ Note: In some embodiments, $Na_2SO_3$(s) may be dissolved in water or may comprise an aqueous solution before mixing with an aqueous solution comprising $Ca(HCO_3)_2$(aq) or $Mg(HCO_3)_2$(aq).

Note: At least a portion of $CaSO_3$(s) or $MgSO_3$(s) may be separated by a solid-liquid separation.

Note: In some embodiments, $NaHCO_3$ may be sold as a product or employed as a carbon sequestration medium.

Note: In some embodiments, $Na_2SO_3$(s or aq) may comprise $Na_2SO_3$ from step '(4)'.

Note: In some embodiments, $Ca(HCO_3)_2$(aq) or $Mg(HCO_3)_2$(aq) may comprise $Ca(HCO_3)_2$(aq) or $Mg(HCO_3)_2$(aq) from step '(5)'.

(7) $2\ NaHCO_3(aq\ or\ s)\rightarrow Na_2CO_3(aq\ or\ s)+CO_2(g)+H_2O(g\ or\ l)$ Note: $CO_2$(g) may comprise captured $CO_2$.

Note: In some embodiments, $Na_2CO_3$ may be sold as a product and/or employed as a carbon sequestration medium.

Note: In some embodiments, $NaHCO_3$ may be precipitated or separated as 2 $NaHCO_3$(s) and/or 2 $NaHCO_3$(s) may be decomposed into $Na_2CO_3$(s), $CO_2$, and $H_2O$(g or l).

Note: In some embodiments, $Na_2CO_3$(s) may be dissolved in water before, for example, the reaction with calcium hydroxide or magnesium hydroxide in, for example, step 8.

Note: In some embodiments, 2 $NaHCO_3$(aq) may be decomposed into $Na_2CO_3$(aq) and $CO_2$(g) and water within an aqueous and/or under-pressure or pressurized environment, which may avoid or prevent the need for crystallizing or precipitating $NaHCO_3$(s) and/or to minimize or reduce water evaporation during, for example, $CO_2$ desorption.

Note: In some embodiments, 2 $NaHCO_3$(aq) may comprise $NaHCO_3$ from step '(6)'.

(8) Calcine or decompose an alkaline-earth sulfite to an alkaline earth oxide and sulfur dioxide $CaSO_3(s)\rightarrow CaO(s)+SO_2(g)$ $MgSO_3(s)\rightarrow MgO(s)+SO_2(g)$ Note: May comprise calcining $CaSO_3$(s) or $MgSO_3$(s), which may employ a kiln.

Note: $CaSO_3$(s) or $MgSO_3$(s) may be dried, or dehydrated, or both before or during calcining.

Note: $CaSO_3$(s) or $MgSO_3$(s) may comprise $CaSO_3$(s) or $MgSO_3$(s) from step '(6)'.

(9) React an alkaline-earth oxide or hydroxide with an alkali carbonate to produce an alkaline-earth carbonate and an alkali hydroxide $CaO(s\ or\ aq)+Na_2CO_3(s\ or\ aq)+Water\rightarrow 2\ NaOH(aq)\rightarrow CaCO_3(s)$ $MgO(s\ or\ aq)+Na_2CO_3(s\ or\ aq)+Water\rightarrow 2\ NaOH(aq)\rightarrow MgCO_3(s)$ Note: In some embodiments, $CaO+Na_2CO_3$(s or aq)+Water or $MgO+Na_2CO_3$(s or aq)+Water may be conducted in multiple steps. For example, in some embodiments, CaO or MgO may be reacted with water to form $Ca(OH)_2$(aq), or $Ca(OH)_2$(s or aq), or $Mg(OH)_2$(aq), or $Mg(OH)_2$(s or aq), which may comprise Milk of Lime or Milk of Magnesia, or a solid-liquid suspension comprising calcium hydroxide or magnesium hydroxide. For example, in some embodiments, $Na_2CO_3$ may comprise an aqueous solution or may be dissolved in water to form an aqueous solution. For example, in some embodiments, a solution or solid-liquid mixture or suspension comprising $Ca(OH)_2$(s or aq), or Milk of Lime, or $Mg(OH)_2$, or Milk of Magnesia may be mixed with an aqueous solution comprising $Na_2CO_3$(aq), which may result in the formation of a solution comprising aqueous sodium hydroxide and a solid comprising calcium carbonate or magnesium carbonate.

Note: In some embodiments, at least a portion of calcium carbonate or magnesium carbonate may be separated from at least a portion of sodium hydroxide using, for example, a solid-liquid separation.

Note: CaO(s) or MgO(s) may comprise CaO(s) or MgO(s) from step '(8)'.

Note: $Na_2CO_3$(aq) may comprise $Na_2CO_3$(aq) from step '(6)' or step '(7)'.

Note: In some embodiments, $CaCO_3$ or $MgCO_3$ may be transferred to step 5.

Note: In some embodiments, NaOH(aq) may be concentrated, or at least a portion of water may be removed. Separated or recovered water may be transferred to or employed as a solvent or input in, for example, step '5'. In some embodiments, NaOH(aq) may be concentrated to a concentrated solution, or 33 wt % solution, or a 50 wt % solution, or solid NaOH, or any combination thereof using one or more or any combination of water separation systems and/or methods.

Example 55: Process for Producing Sodium Bicarbonate and/or Calcium Oxide or Calcium Carbonate (1) React Material comprising Calcium, or Magnesium, or Other Alkaline Earth-Weak Acid Anion with Acetic Acid $CaCO_3(s\ or\ aq)+2\ CH_3COOH(aq)\rightarrow Ca(CH_3COO)_2(aq)+CO_2(g)+H_2O(aq\ or\ l)$ $Calcium\ Silicate(s)+2\ CH_3COOH(aq)\rightarrow Ca(CH_3COO)_2(aq)+Silicon\ Dioxide(s)+H_2O(aq\ or\ l)$ $CaS(s)+2\ CH_3COOH(aq)\rightarrow Ca(CH_3COO)_2(aq)+H_2S(g)$ Calcium(Weak Acid Anion)+2 $CH_3COOH(aq)\rightarrow Ca(CH_3COO)_2(aq)$+Weak Acid(s, or g, or l, or aq)+$H_2O$(aq or l)

Note: Residual solids or undissolved solids, such as silicon dioxide or other undissolved solids, may be separated from the liquid solution using a solid-liquid separation.

Note: $CO_2(g)$ may comprise captured $CO_2$.

Note: In some embodiments, $CO_2(g)$ may be employed internally or employed in other steps. For example, in some embodiments, $CO_2(g)$ may be employed in step '(5)'.

Note: In some embodiments, $CO_2(g)$ may be utilized or sequestered or sold or comprise a product. For example, $CO_2(g)$ may be utilized or sequestered or sold to a $CO_2$ sequestration site or a $CO_2$ EOR application or an external application.

Note: In some embodiments, some chemicals comprising calcium may comprise a portion of magnesium. In some embodiments, for example, input chemicals or input material may comprise a mixture of calcium and magnesium.

Note: In some embodiments, acetic acid vapor and/or water vapor may be separated or recovered from $CO_2(g)$.

Note: In some embodiments, acetic acid for step '(1)' may comprise aqueous acetic acid produced or regenerated in step '(4)'.

(2) $Ca(CH_3COO)_2(aq)+Na_2SO_4$(s or aq)$\rightarrow$2 $NaCH_3COO(aq)+CaSO_4(s)$ Note: In some embodiments, $Na_2SO_4(s)$ may be added directly to or dissolved in $Ca(CH_3COO)_2(aq)$.

Note: In some embodiments, $Na_2SO_4(s)$ may be dissolved in water or an aqueous solution to form $Na_2SO_4(aq)$ before mixing with $Ca(CH_3COO)_2(aq)$.

Note: In some embodiments, water may be added to the process to make up for water which may leave the process, for example, if NaOH(aq) is an output, or another aqueous solution is an output, or any combination thereof. In some embodiments, water may be added to the process by $Na_2SO_4$ being in the form of $Na_2SO_4(aq)$ or an aqueous solution comprising sodium sulfate, wherein at least a portion of the water in $Na_2SO_4(aq)$ may comprise water added to the process. In some embodiments, $Na_2SO_4(aq)$ may be provided or sourced as an aqueous solution. For example, in some embodiments, $Na_2SO_4(aq)$ may be provided to the process in the form of $Na_2SO_4(aq)$. In some embodiments, $Na_2SO_4(aq)$ may be provided or sourced as a solid or $Na_2SO_4(s)$, then dissolved in water to form $Na_2SO_4(aq)$.

Note: In some embodiments, $Ca(CH_3COO)_2(aq)$ may comprise $Ca(CH_3COO)_2(aq)$ from step '(1)'.

(3) 2 $NaCH_3COO(aq)+SO_2$(g or aq)$+H_2O$(l or aq)$\rightarrow Na_2SO_3(aq)$+2 $CH_3COOH(aq)$ Note: In some embodiments, $SO_2(g)$ may comprise other gases in addition to $SO_2(g)$. In some embodiments, the reaction of 2 $NaCH_3COO(aq)+SO_2(g)$ may result in at least a portion of acetic acid vapor in the remaining gases during or after the reaction. In some embodiments, $NaCH_3COO(aq)$ entering the present step may be pre-contacted with or may absorb at least a portion of acetic acid vapor from the remaining gases. In some embodiments, the reactor or absorption column may be configured to absorb acetic acid vapor in $NaCH_3COO(aq)$ before or while reacting $NaCH_3COO(aq)$ with $SO_2(g)$. In some embodiments, acetic acid vapor may be removed from remaining gases using, for example, including, but not limited to, one or more or any combination of the following: alkaline earth carbonate, or alkaline earth-weak acid, or alkaline earth carbonate-water slurry, or alkaline earth oxide, or alkaline earth.

Note: In some embodiments, $NaCH_3COO(aq)$ may comprise $NaCH_3COO(aq)$ from step '(2)'.

Note: In some embodiments, $SO_2$ may comprise $SO_2(g)$ from the calcination or decomposition of $CaSO_3(s)$ in step '(7)'.

(4) $Na_2SO_3(aq)$+2 $CH_3COOH(aq)\rightarrow$2 $CH_3COOH(aq)+Na_2SO_3(s)$

Note: $CH_3COOH$ may be more soluble in water than $Na_2SO_3$. In some embodiments, $Na_2SO_3$ may be separated or precipitated from solution by, for example, including, but not limited to, evaporation, or distillation, or crystallization, or separation systems or methods described herein, or separation systems or methods described in the art, or any combination thereof.

Note: In some embodiments, $CH_3COOH$ and/or water may be separated from $Na_2SO_3$ by, for example, evaporation, or distillation, or crystallization, or any combination thereof. In some embodiments, $CH_3COOH$ may evaporate with water vapor and/or condense with water vapor, which may result in a distillate or condensate comprising $CH_3COOH(aq)$.

Note: In some embodiments, magnesium sulfite(aq) may be present in the $Na_2SO_3(aq)$+2 $CH_3COOH(aq)$. In some embodiments, if present, magnesium sulfite may begin to precipitate or crystalize before $Na_2SO_3$. In some embodiments magnesium sulfite solid may be separated during step '(4)'. In some embodiments, separated magnesium sulfite may be decomposed to magnesium oxide, or decomposed separately from calcium sulfite, or decomposed together with calcium sulfite, or any combination thereof.s Note: $Na_2SO_3(s)$ may be separated from $CH_3COOH(aq)$ by a solid-liquid separation, which may include, but is not limited to, filter, or centrifuge, or decanter, or separation systems or methods described herein, or separation systems or methods described in the art, or any combination thereof.

(5) React an Alkaline-Earth-Weak Acid, such as an Alkaline-Earth Carbonate, with Carbon Dioxide and/or Water to Form an Alkaline-Earth Bicarbonate $CaCO_3(s)+CO_2$(g or aq)$+H_2O(aq)\rightarrow Ca(HCO_3)_2(aq)$ $MgCO_3(s)+CO_2$(g or aq)$+H_2O(aq)\rightarrow Mg(HCO_3)_2(aq)$ Note: May be conducted under a pressurized $CO_2$ atmosphere or with concentrated carbonic acid or $CO_2(aq)$. For example, the $CO_2$ partial pressure during the reaction may be greater than, for example, 1 Bar, or 2 Bar, or 3 Bar, or 4 Bar, or 5 Bar, or 6 Bar, or 7 Bar, or 8 Bar, or 9 Bar, or 10 Bar, or any combination thereof.

Note: In some embodiments, $CaCO_3(s)$ or $MgCO_3(s)$ may comprise $CaCO_3(s)$ or $MgCO_3(s)$ from step '(8)'.

Note: In some embodiments, $CaCO_3(s)$ or $MgCO_3(s)$ may comprise an input, such as limestone, or dolomite.

Note: In some embodiments, $CO_2$(g or aq) may comprise $CO_2$ from step '(1)'.

Note: In some embodiments, $CO_2$(g or aq) may comprise $CO_2$ from an emissions source, or another $CO_2$ source, or captured $CO_2$, or any combination thereof. For example, in some embodiments, $CO_2$(g or aq) may comprise, including, but not limited to, one or more or any combination of the following: $CO_2$ from a blue hydrogen or blue ammonia facility, or an ammonia facility, or an ethanol plant, or a carbon capture plant.

(6) React an Alkali Sulfite with an Alkaline-Earth Bicarbonate to form an Alkali Bicarbonate and an Alkaline-Earth Sulfite $Na_2SO_3$(s or aq)$+Ca(HCO_3)_2(aq)\rightarrow$2 $NaHCO_3(aq)+CaSO_3(s)$ $Na_2SO_3$(s or aq)$+Mg(HCO_3)_2(aq)\rightarrow$2 $NaHCO_3(aq)+MgSO_3(s)$ Note: In some embodiments, $Na_2SO_3(s)$ may be dissolved in water or may comprise an aqueous solution before or during mixing with an aqueous solution comprising $Ca(HCO_3)_2(aq)$ or $Mg(HCO_3)_2(aq)$.

Note: At least a portion of $CaSO_3(s)$ or $MgSO_3(s)$ may be separated by a solid-liquid separation.

Note: In some embodiments, $NaHCO_3$ may be sold as a product or employed as a carbon sequestration medium.

Note: In some embodiments, $NaHCO_3$ may be concentrated and/or crystalized into a solid, such as, for example, solid sodium bicarbonate or solid sodium carbonate.

(7) Decompose an Alkaline-Earth Sulfite into an Alkaline-Earth Oxide and Sulfur Dioxide $CaSO_3(s) \rightarrow CaO(s)+SO_2(g)$ $MgSO_3(s) \rightarrow MgO(s)+SO_2(g)$ Note: May comprise calcining $CaSO_3(s)$ or $MgSO_3(s)$, which may employ a kiln.

Note: $CaSO_3(s)$ or $MgSO_3(s)$ may be dried, or dehydrated, or both before or during calcining.

Note: $CaSO_3(s)$ or $MgSO_3(s)$ may comprise $CaSO_3(s)$ or $MgSO_3(s)$ from step '(6)'.

Note: CaO or MgO may comprise a valuable product if desired. For example, CaO or MgO may comprise an ultra-low carbon emissions CaO or MgO product. In some embodiments, calcium oxide, or calcium hydroxide, or magnesium oxide, or magnesium hydroxide, or any combination thereof may comprise a product or may be sold or may be sold. In some embodiments, calcium oxide, or calcium hydroxide, or magnesium oxide, or magnesium hydroxide, or any combination thereof may comprise a product or may be sold or may be sold from the present example embodiment.

(8) React an Alkaline-Earth Oxide or Hydroxide with Carbon Dioxide to form an Alkaline Earth Carbonate $CaO(s)+CO_2(g) \rightarrow CaCO_3(s)$ $MgO(s)+CO_2(g) \rightarrow MgCO_3(s)$ $CaO(s)+H_2O \rightarrow Ca(OH)_2(s \text{ or } aq)$ $MgO(s)+H_2O \rightarrow Mg(OH)_2(s \text{ or } aq)$ $Ca(OH)_2(s \text{ or } aq)+CO_2(g) \rightarrow CaCO_3(s)+H_2O$ $Mg(OH)_2(s \text{ or } aq)+CO_2(g) \rightarrow MgCO_3(s)+H_2O$ Note: In some embodiments, CaO(s) or MgO(s) may be reacted with water to form $Ca(OH)_2(aq)$, or $Ca(OH)_2$(s or aq), or $Mg(OH)_2(aq)$, or $Mg(OH)_2$(s or aq), or any combination thereof which may comprise Milk of Lime, or Milk of Magnesia, or a solid-liquid suspension comprising calcium hydroxide and/or magnesium hydroxide. In some embodiments, $Ca(OH)_2$ or $Mg(OH)_2$ may be reacted with a carbonate salt, such as sodium carbonate or sodium bicarbonate, to form $CaCO_3$ or $MgCO_3$, or may be reacted with $CO_2$ to form $CaCO_3$ or $MgCO_3$. For example, said sodium carbonate or sodium bicarbonate may comprise sodium carbonate, or sodium bicarbonate, or potassium carbonate, or potassium bicarbonate, or alkali carbonate, or alkali bicarbonate, or any combination thereof employed in or as a $CO_2$ absorption solution.

Note: In some embodiments, $CO_2(g)$ may comprise $CO_2$ in or from a point source $CO_2$ emissions source. For example, $CO_2(g)$ may comprise flue gas, or dilute $CO_2$, or high purity $CO_2$, or captured $CO_2$.

Note: In some embodiments, $CO_2(g)$ may comprise $CO_2$ in or from air. For example, $CO_2(g)$ may comprise air which may comprise at least a portion of $CO_2$ even if at a very dilute concentration. For example, calcium oxide may be capable of reacting with very low concentrations or very dilute concentrations of $CO_2$ if desired. For example, $CO_2(g)$ may comprise a carbonate salt, such as sodium carbonate or potassium carbonate, wherein the carbonate may comprise carbonate originating from the reaction of carbon dioxide in the air with a sodium or potassium or other alkali salt, such as sodium hydroxide or potassium hydroxide, forming the alkali carbonate salt, and/or wherein the reaction of calcium oxide or calcium hydroxide with the alkali carbonate may result in the regeneration or formation of an alkali hydroxide or alkali oxide or other alkali salt which may be employed to absorb carbon dioxide from the air a regenerate or re-form the alkali carbonate salt.

Note: In some embodiments, $CaCO_3$ or $MgCO_3$ may comprise a valuable product. In some embodiments, $CaCO_3$ or $MgCO_3$ may comprise precipitated calcium carbonate. In some embodiments, $CaCO_3$ or $MgCO_3$ may comprise a carbon sequestration medium.

Note: In some embodiments, for example, including, but not limited to, Example 53, or Example 54, or Example 55, or Example 61, or Example 62, or any combination thereof may comprise processes operating separately and/or simultaneously. For example, in some embodiments, $CO_2$ produced in step '(1)' of Example 53 or Example 54 may comprise an input to Example 55.

Example 56: Process for Producing Calcium Carbonate from Ca(WA) Using Ammonium Chloride Intermediate (1) React Material comprising Calcium, or Magnesium, or Other Alkaline Earth-Weak Acid Anion with Ammonium Chloride $Ca(WA)(s)+2\ NH_4Cl(s \text{ or } g \text{ or } aq) \rightarrow CaCl_2(s \text{ or } aq)+2\ NH_3(g \text{ or } aq)+H_2O(g \text{ or } aq)$ Note: In some embodiments, the reaction of Ca(WA) with ammonium chloride may be conducted at a solid phase or at a solid-gas mixture phase. For example, 2 $NH_4Cl(s)$ and Ca(WA)(s) may be heated, which may result in the vaporization of $NH_4Cl$ into $NH_3(g)$ and HCl(g), wherein the HCl(g) may react with the Ca(WA)(s) to form, for example, $CaCl_2(s)$ and/or (WA) and/or water.

Note: In some embodiments, WA may comprise, for example, including, but not limited to, one or more or any combination of the following; a silicon oxide, or iron oxide, or aluminum oxide, or hydroxide, or oxide.

Note: In some embodiments, the reaction of Ca(WA) with ammonium chloride may be conducted at a solid-liquid phase or a solid-aqueous phase. For example, 2 $NH_4Cl(aq)$ and Ca(WA)(s) may be mixed, and/or may react to form, for example, $CaCl_2(aq)$ and 2 $NH_3$(aq or g).

(2) $CaCl_2(s)+\text{Water} \rightarrow CaCl_2(aq)$

Note: In some embodiments, $CaCl_2$ from step 1 may comprise a solid and/or may be dissolved in water to form an aqueous solution.

(3) Ammonia or weak base may be dissolved in water or aqueous solution to form aqueous ammonia, and/or ammonia may be dissolved in water and/or reacted with carbon dioxide to form ammonium carbonate or ammonium bicarbonate.

$CaCl_2(aq)+2\ NH_3(g) \rightarrow CaCl_2(aq)+2\ NH_3(aq)$ $2\ NH_3(g)+\text{Water} \rightarrow NH_3(aq)$ $2\ NH_3(g \text{ or } aq)+CO_2(g)+H_2O(l \text{ or } aq) \rightarrow (NH_4)_2CO_3(aq)$ $2NH_3(g \text{ or } aq)+2\ CO_2(g)+2\ H_2O(l \text{ or } aq) \rightarrow 2\ NH_4HCO_3(aq)$ $(NH_4)_2CO_3(aq)+CO_2(g)+H_2O(l \text{ or } aq) \rightarrow 2\ NH_4HCO_3(aq)$ Note: In some embodiments, $NH_3$ from step 1 may comprise a gas and/or may be dissolved in $CaCl_2(aq)$.

Note: In some embodiments, $NH_3$ may be dissolved in water and/or reacted with $CO_2$ separately from $CaCl_2$.

(4) Calcium chloride may be reacted with ammonia, or carbon dioxide, or ammonium carbonate, or ammonium bicarbonate, or any combination thereof to form ammonium chloride and calcium carbonate.

$CaCl_2)(aq)+2\ NH_3(aq)+CO_2(g)+H_2O \rightarrow 2\ NH_4Cl(aq)+CaCO_3(s)$ $CaCl_2(aq)+2\ NH_3(aq)+2\ CO_2(g)+H_2O \rightarrow 2\ NH_4Cl(aq)+CaCO_3(s)+CO_2(g)$ $CaCl_2)(aq)+(NH_4)_2CO_3(aq) \rightarrow 2\ NH_4Cl(aq)+CaCO_3(s)$ $CaCl_2(aq)+2\ NH_4HCO_3(aq) \rightarrow 2\ NH_4Cl(aq)+CaCO_3(s)+CO_2(g)$ Note: In some embodiments, if excess $CO_2$ is present or $CO_2$ is in the product, in some embodiments, said excess $CO_2$ may be transferred to the inputs or reactants of step 4 and/or the inputs or reactants of step 3.

Note: In some embodiments, a $CaCl_2(aq)+NH_3(aq)$ solution may be produced in step 1 and/or may be transferred to step 4, potentially skipping step 2 and step 3.

Note: In some embodiments, $CO_2(g)$ may comprise captured $CO_2$ from another embodiment described herein. For example, in some embodiments, $CO_2(g)$ may comprise $CO_2$ from the reaction of calcium carbonate with acetic acid.

Note: In some embodiments, $CaCO_3(s)$ may be transferred to or may comprise an input to one or more or any combination of embodiments described herein. For example, $CaCO_3(s)$ may be an input to a process for producing sodium hydroxide, or calcium oxide, or calcium hydroxide, or sodium bicarbonate, or sodium carbonate, or any combination thereof.

Note: In some embodiments, $CO_2(g)$ may comprise $CO_2$ from an emissions source, or a point source, or air, or from an external source, or any combination thereof.

Note: In some embodiments, 2 $NH_4Cl(aq)$ may be transferred to step 1.

Note: In some embodiments, 2 $NH_4Cl(aq)$ may be transferred to step 5.

(5) 2 $NH_4Cl(aq) \rightarrow 2\ NH_4Cl(s)+Water$

Note: In some embodiments, 2 $NH_4Cl(s)$ may be transferred to step 1.

Note: In some embodiments, Water may be transferred to step 3 and/or step 4.

Note: In some embodiments, the present example embodiment may be integrated with other embodiments described herein to further increase the $CO_2$ conversion or $CO_2$ removal potential, or enable the production of chemicals without requiring a $CO_2$ output exiting the process, or to enable the use of other Ca(WA) inputs or less reactive Ca(WA) inputs, or any combination thereof.

For example, in some embodiments, $CaCO_3$ may be transferred from the present embodiment to a second embodiment, then the captured $CO_2$ from the second embodiment may be transferred to the present embodiment. For example, in some embodiments, the $CO_2$ transferred between the present embodiment and the second embodiment may comprise an intermediate in the production of a chemical, such as, for example, including, but not limited to, one or more or any combination of the following: sodium hydroxide, or calcium oxide, or calcium hydroxide, or sodium bicarbonate, or sodium carbonate, or any combination thereof.

For example, in some embodiments, $CO_2$ in the production of $CaCO_3$ may be from an emissions source or air, and/or the produced $CaCO_3$ may be transferred from the present embodiment to a second embodiment, such as an embodiment for producing sodium carbonate or sodium bicarbonate, which may increase the net $CO_2$ conversion or $CO_2$ removal potential of said second embodiment.

Example 57: Process for Producing Alkali Hydroxide with Carbon Dioxide and/or Sulfur Dioxide Intermediates (1) React Material comprising Calcium, or Magnesium, or Other Alkaline Earth-Weak Acid Anion with Ammonium Chloride $Ca(WA)(s)+2\ NH_4Cl(s\ or\ g\ or\ aq) \rightarrow CaCl_2(s\ or\ aq)+2\ NH_3(g\ or\ aq)+H_2O(g\ or\ aq)$ Note: In some embodiments, the reaction of Ca(WA) with ammonium chloride may be conducted at a solid phase or at a solid-gas mixture phase. For example, 2 $NH_4Cl(s)$ and Ca(WA)(s) may be heated, which may result in the vaporization of $NH_4Cl$ into $NH_3(g)$ and HCl(g), wherein the HCl(g) may react with the Ca(WA)(s) to form, for example, $CaCl_2(s)$ and/or (WA) and/or water.

Note: In some embodiments, WA may comprise, for example, including, but not limited to, one or more or any combination of the following; a silicon oxide, or iron oxide, or aluminum oxide, or hydroxide, or oxide.

Note: In some embodiments, the reaction of Ca(WA) with ammonium chloride may be conducted at a solid-liquid phase or a solid-aqueous phase. For example, 2 $NH_4Cl(aq)$ and Ca(WA)(s) may be mixed, and/or may react to form, for example, $CaCl_2(aq)$ and 2 $NH_3(aq\ or\ g)$.

(2) $CaCl_2(s)+Water \rightarrow CaCl_2(aq)$

Note: In some embodiments, $CaCl_2$ from step 1 may comprise a solid and/or may be dissolved in water to form an aqueous solution.

(3) Ammonia or weak base may be dissolved in water or aqueous solution to form aqueous ammonia, and/or ammonia may be dissolved in water and/or reacted with carbon dioxide to form ammonium carbonate or ammonium bicarbonate.

$CaCl_2(aq)+2\ NH_3(g) \rightarrow CaCl_2(aq)+2\ NH_3(aq)$ $2\ NH_3(g)+Water \rightarrow NH_3(aq)$ $2\ NH_3(g\ or\ aq)+CO_2(g)+H_2O(l\ or\ aq) \rightarrow (NH_4)_2CO_3(aq)$ $2NH_3(g\ or\ aq)+2\ CO_2(g)+2\ H_2O(l\ or\ aq) \rightarrow 2\ NH_4HCO_3(aq)$ $(NH_4)_2CO_3(aq)+CO_2(g)+H_2O(l\ or\ aq) \rightarrow 2\ NH_4HCO_3(aq)$ Note: In some embodiments, $NH_3$ from step 1 may comprise a gas and/or may be dissolved in $CaCl_2(aq)$.

Note: In some embodiments, $NH_3$ may be dissolved in water and/or reacted with $CO_2$ separately from $CaCl_2$.

(4) Calcium chloride may be reacted with ammonia, or carbon dioxide, or ammonium carbonate, or ammonium bicarbonate, or any combination thereof to form ammonium chloride and calcium carbonate.

$CaCl_2)(aq)+2\ NH_3(aq)+CO_2(g)+H_2O \rightarrow 2\ NH_4Cl(aq)+CaCO_3(s)$ $CaCl_2(aq)+2\ NH_3(aq)+2\ CO_2(g)+H_2O \rightarrow 2\ NH_4Cl(aq)+CaCO_3(s)+CO_2(g)$ $CaCl_2)(aq)+(NH_4)_2CO_3(aq) \rightarrow 2\ NH_4Cl(aq)+CaCO_3(s)$ $CaCl_2(aq)+2\ NH_4HCO_3(aq) \rightarrow 2\ NH_4Cl(aq)+CaCO_3(s)+CO_2(g)$ Note: In some embodiments, if excess $CO_2$ is present or $CO_2$ is in the product, in some embodiments, said excess $CO_2$ may be transferred to the inputs or reactants of step 4 and/or the inputs or reactants of step 3.

Note: In some embodiments, a $CaCl_2(aq)+NH_3(aq)$ solution may be produced in step 1 and/or may be transferred to step 4, potentially skipping step 2 and step 3.

Note: In some embodiments, $CO_2(g)$ may comprise captured $CO_2$ from another embodiment described herein. For example, in some embodiments, $CO_2(g)$ may comprise $CO_2$ from the reaction of calcium carbonate with acetic acid.

Note: In some embodiments, $CaCO_3$(s) may be transferred to or may comprise an input to one or more or any combination of embodiments described herein. For example, $CaCO_3$(s) may be an input to a process for producing sodium hydroxide, or calcium oxide, or calcium hydroxide, or sodium bicarbonate, or sodium carbonate, or any combination thereof.

Note: In some embodiments, $CO_2$(g) may comprise $CO_2$ from an emissions source, or a point source, or air, or from an external source, or any combination thereof.

Note: In some embodiments, 2 $NH_4Cl$(aq) may be transferred to step 1.

Note: In some embodiments, 2 $NH_4Cl$(aq) may be transferred to step 5.

(5) 2 $NH_4Cl$(aq)→2 $NH_4Cl$(s)+Water

Note: In some embodiments, 2 $NH_4Cl$(s) may be transferred to step 1.

Note: In some embodiments, Water may be transferred to step 3 and/or step 4.

(6) React Material comprising Calcium, or Magnesium, or Other Alkaline Earth-Weak Acid Anion with Acetic Acid $CaCO_3$(s or aq)+2 $CH_3COOH$(aq)→$Ca(CH_3COO)_2$(aq)+$CO_2$(g)+$H_2O$(l or aq)

Calcium Silicate(s)+2 $CH_3COOH$(aq)→$Ca(CH_3COO)_2$(aq)+Silicon Dioxide(s)+$H_2O$(l or aq)

CaS(s)+2 $CH_3COOH$(aq)→$Ca(CH_3COO)_2$(aq)+$H_2S$(g)+$H_2O$(l or aq)

Calcium(Weak Acid Anion)+2 $CH_3COOH$(aq)→$Ca(CH_3COO)_2$(aq)+Weak Acid(s, or g, or l, or aq)+$H_2O$(l or aq)

Note: Residual solids or undissolved solids, such as silicon dioxide or other undissolved solids, may be separated from the liquid solution using a solid-liquid separation.

Note: $CO_2$(g) may comprise captured $CO_2$.

Note: In some embodiments, $CO_2$ may be transferred to step 4.

Note: In some embodiments, some chemicals comprising calcium may comprise a portion of magnesium. In some embodiments, for example, input chemicals or input material may comprise a mixture of calcium and magnesium.

Note: In some embodiments, acetic acid vapor and/or water vapor may be separated or recovered from $CO_2$(g).

(7) $Ca(CH_3COO)_2$(aq)+$Na_2SO_4$(s or aq)→2 $NaCH_3COO$(aq)+$CaSO_4$(s)

Note: In some embodiments, $Na_2SO_4$(s) may be added directly to or dissolved in $Ca(CH_3COO)_2$(aq).

Note: In some embodiments, $Na_2SO_4$(s) may be dissolved in water or an aqueous solution to form $Na_2SO_4$(aq) before mixing with $Ca(CH_3COO)_2$(aq).

Note: In some embodiments, water may be added to the process to make up for water which may leave the process, for example, if NaOH(aq) is an output, or another aqueous solution is an output, or any combination thereof. In some embodiments, water may be added to the process by $Na_2SO_4$ being in the form of $Na_2SO_4$(aq) or an aqueous solution comprising sodium sulfate, wherein at least a portion of the water in $Na_2SO_4$(aq) may comprise water added to the process. In some embodiments, $Na_2SO_4$(aq) may be provided or sourced as an aqueous solution. For example, in some embodiments, $Na_2SO_4$(aq) may be provided to the process in the form of $Na_2SO_4$(aq). In some embodiments, $Na_2SO_4$(aq) may be provided or sourced as a solid or $Na_2SO_4$(s), then dissolved in water to form $Na_2SO_4$(aq).

(8) 2 $NaCH_3COO$(aq)+$SO_2$(g or aq)+$H_2O$(l or aq)→$Na_2SO_3$(aq)+2 $CH_3COOH$(aq)

Note: In some embodiments, $SO_2$(g) may comprise other gases in addition to $SO_2$(g). In some embodiments, the reaction of 2 $NaCH_3COO$(aq)+$SO_2$(g) may result in at least a portion of acetic acid vapor in the remaining gases during or after the reaction. In some embodiments, $NaCH_3COO$(aq) entering the present step may be pre-contacted with or may absorb at least a portion of acetic acid vapor from the remaining gases. In some embodiments, the reactor or absorption column may be configured to absorb acetic acid vapor in $NaCH_3COO$(aq) before or while reacting $NaCH_3COO$(aq) with $SO_2$(g). In some embodiments, acetic acid vapor may be removed from remaining gases using, for example, including, but not limited to, one or more or any combination of the following: alkaline earth carbonate, or alkaline earth-weak acid, or alkaline earth carbonate-water slurry, or alkaline earth oxide, or alkaline earth (9) $Na_2SO_3$(aq)+2 $CH_3COOH$(aq)→2 $CH_3COOH$(aq)+$Na_2SO_3$(s)

Note: $CH_3COOH$ may be more soluble in water than $Na_2SO_3$. In some embodiments, $Na_2SO_3$ may be separated or precipitated from solution by, for example, including, but not limited to, evaporation, or distillation, or crystallization, or separation systems or methods described herein, or separation systems or methods described in the art, or any combination thereof.

Note: In some embodiments, $CH_3COOH$ and/or water may be separated from $Na_2SO_3$ by, for example, evaporation, or distillation, or crystallization, or any combination thereof. In some embodiments, $CH_3COOH$ may evaporate with water vapor and/or condense with water vapor, which may result in a distillate or condensate comprising $CH_3COOH$(aq).

Note: In some embodiments, magnesium sulfite(aq) may be present in the $Na_2SO_3$(aq)+2 $CH_3COOH$(aq). In some embodiments, if present, magnesium sulfite may begin to precipitate or crystalize before $Na_2SO_3$. In some embodiments magnesium sulfite solid may be separated during step '(9)'. In some embodiments, separated magnesium sulfite may be decomposed to magnesium oxide, or decomposed separately from calcium sulfite, or decomposed together with calcium sulfite, or any combination thereof.s Note: $Na_2SO_3$(s) may be separated from $CH_3COOH$(aq) by a solid-liquid separation, which may include, but is not limited to, filter, or centrifuge, or decanter, or separation systems or methods described herein, or separation systems or methods described in the art, or any combination thereof.

(10) $Na_2SO_3$(s or aq)+$Ca(OH)_2$(s or aq)→2 NaOH(aq or s)+$CaSO_3$(s)

Note: $Ca(OH)_2$(s or aq) may comprise a solid-liquid suspension, such as milk of lime.

Note: $CaSO_3$(s) may be separated using a solid-liquid separation.

(11) $CaSO_3$(s)→CaO(s)+$SO_2$(g)

Note: '(11)' may comprise calcining $CaSO_3$(s), which may employ a kiln.

Note: $CaSO_3$(s) may be dried, or dehydrated, or both before or during '(11)'.

(12) CaO(s)+Water(g or l or aq)→$Ca(OH)_2$(s or aq)

Note: In some embodiments, CaO(s) may be employed to remove water vapor or facilitated drying of $CaSO_3$(s) before or during decomposition of $CaSO_3$(s) to CaO(s).

Note: In some embodiments, calcium oxide may be reacted directly with an aqueous solution comprising sodium sulfite to produce calcium sulfite and sodium hydroxide. In some embodiments, calcium oxide may be reacted directly with an aqueous solution comprising sodium sulfite to produce calcium sulfite and sodium hydroxide, which may comprise combining step '(10)' and step'(12)'.

Note: In some embodiments, calcium oxide may be reacted with water to produce an aqueous solution, or solid-liquid suspension, or milk of lime, or solid, or any combination thereof comprising calcium hydroxide.

(13) 2 NaOH(aq or s)→2 NaOH(aq or s)+Water

Note: In some embodiments, NaOH(aq) may be concentrated into an aqueous solution comprising a greater mass percent concentration of NaOH.

Note: In some embodiments, water may be removed and/or NaOH may be separated or precipitated by, for example, including, but not limited to, evaporation, or distillation, or crystallization, or separation systems or methods described herein, or separation systems or methods described in the art, or any combination thereof.

Note: In some embodiments, it may be desirable for NaOH to comprise a concentrated aqueous solution.

Example 58: Process for Producing Alkali Hydroxide with Carbon Dioxide, Alkali Carbonate, and/or Sulfur Dioxide Intermediates (1) React Material comprising Calcium, or Magnesium, or Other Alkaline Earth-Weak Acid Anion with Ammonium Chloride Ca(WA)(s)+2 $NH_4Cl$(s or g or aq)→$CaCl_2$(s or aq)+2 $NH_3$(g or aq)+$H_2O$(g or aq)

Note: In some embodiments, the reaction of Ca(WA) with ammonium chloride may be conducted at a solid phase or at a solid-gas mixture phase. For example, 2 $NH_4Cl$(s) and Ca(WA)(s) may be heated, which may result in the vaporization of $NH_4Cl$ into $NH_3$(g) and HCl(g), wherein the HCl(g) may react with the Ca(WA)(s) to form, for example, $CaCl_2$(s) and/or (WA) and/or water.

Note: In some embodiments, WA may comprise, for example, including, but not limited to, one or more or any combination of the following; a silicon oxide, or iron oxide, or aluminum oxide, or hydroxide, or oxide.

Note: In some embodiments, the reaction of Ca(WA) with ammonium chloride may be conducted at a solid-liquid phase or a solid-aqueous phase. For example, 2 $NH_4Cl$(aq) and Ca(WA)(s) may be mixed, and/or may react to form, for example, $CaCl_2$(aq) and 2 $NH_3$(aq or g).

(2) $CaCl_2$(s)+Water→$CaCl_2$(aq)

Note: In some embodiments, $CaCl_2$ from step 1 may comprise a solid and/or may be dissolved in water to form an aqueous solution.

(3) Ammonia or weak base may be dissolved in water or aqueous solution to form aqueous ammonia, and/or ammonia may be dissolved in water and/or reacted with carbon dioxide to form ammonium carbonate or ammonium bicarbonate.

$CaCl_2$(aq)+2 $NH_3$(g)→$CaCl_2$(aq)+2 $NH_3$(aq)

2 $NH_3$(g)+Water→$NH_3$(aq)

2 $NH_3$(g or aq)+$CO_2$(g)+$H_2O$(l or aq)→$(NH_4)_2CO_3$(aq)

2$NH_3$(g or aq)+2 $CO_2$(g)+2 $H_2O$(l or aq)→2 $NH_4HCO_3$(aq)

$(NH_4)_2CO_3$(aq)+$CO_2$(g)+$H_2O$(l or aq)→2 $NH_4HCO_3$(aq)

Note: In some embodiments, $NH_3$ from step 1 may comprise a gas and/or may be dissolved in $CaCl_2$(aq).

Note: In some embodiments, $NH_3$ may be dissolved in water and/or reacted with $CO_2$ separately from $CaCl_2$.

(4) Calcium chloride may be reacted with ammonia, or carbon dioxide, or ammonium carbonate, or ammonium bicarbonate, or any combination thereof to form ammonium chloride and calcium carbonate.

$CaCl_2$)(aq)+2 $NH_3$(aq)+$CO_2$(g)+$H_2O$→2 $NH_4Cl$(aq)+$CaCO_3$(s)

$CaCl_2$(aq)+2 $NH_3$(aq)+2 $CO_2$(g)+$H_2O$→2 $NH_4Cl$(aq)+$CaCO_3$(s)+$CO_2$(g)

$CaCl_2$)(aq)+$(NH_4)_2CO_3$(aq)+2 $NH_4Cl$(aq)→$CaCO_3$(s)

$CaCl_2$(aq)+2 $NH_4HCO_3$(aq)→2 $NH_4Cl$(aq)+$CaCO_3$(s)+$CO_2$(g)

Note: In some embodiments, if excess $CO_2$ is present or $CO_2$ is in the product, in some embodiments, said excess $CO_2$ may be transferred to the inputs or reactants of step 4 and/or the inputs or reactants of step 3.

Note: In some embodiments, a $CaCl_2$(aq)+$NH_3$(aq) solution may be produced in step 1 and/or may be transferred to step 4, potentially skipping step 2 and step 3.

Note: In some embodiments, $CO_2$(g) may comprise captured $CO_2$ from another embodiment described herein. For example, in some embodiments, $CO_2$(g) may comprise $CO_2$ from the reaction of calcium carbonate with acetic acid.

Note: In some embodiments, $CaCO_3$(s) may be transferred to or may comprise an input to one or more or any combination of embodiments described herein. For example, $CaCO_3$(s) may be an input to a process for producing sodium hydroxide, or calcium oxide, or calcium hydroxide, or sodium bicarbonate, or sodium carbonate, or any combination thereof.

Note: In some embodiments, $CO_2$(g) may comprise $CO_2$ from an emissions source, or a point source, or air, or from an external source, or any combination thereof.

Note: In some embodiments, 2 $NH_4Cl$(aq) may be transferred to step 1.

Note: In some embodiments, 2 $NH_4Cl$(aq) may be transferred to step 5.

(5) 2 $NH_4Cl$(aq)→2 $NH_4Cl$(s)+Water

Note: In some embodiments, 2 $NH_4Cl$(s) may be transferred to step 1.

Note: In some embodiments, Water may be transferred to step 3 and/or step 4.

(6) React Material comprising Calcium, or Magnesium, or Other Alkaline Earth-Weak Acid Anion with Acetic Acid $CaCO_3$(s or aq)+2 $CH_3COOH$(aq)→$Ca(CH_3COO)_2$(aq)+$CO_2$(g)+$H_2O$(aq or l)

Calcium Silicate(s)+2 $CH_3COOH$(aq)→$Ca(CH_3COO)_2$(aq)+Silicon Dioxide(s)+$H_2O$(aq or l)

CaS(s)+2 $CH_3COOH$(aq)→$Ca(CH_3COO)_2$(aq)+$H_2S$(g)

Calcium(Weak Acid Anion)+2 $CH_3COOH$(aq)→$Ca(CH_3COO)_2$(aq)+Weak Acid(s, or g, or l, or aq)+$H_2O$(aq or l)

Note: Residual solids or undissolved solids, such as silicon dioxide or other undissolved solids, may be separated from the liquid solution using a solid-liquid separation.

Note: $CO_2$(g) may comprise captured $CO_2$.

Note: In some embodiments, $CO_2$ may be transferred to step 4.

Note: In some embodiments, some chemicals comprising calcium may comprise a portion of magnesium. In some embodiments, for example, input chemicals or input material may comprise a mixture of calcium and magnesium.

Note: In some embodiments, acetic acid vapor and/or water vapor may be separated or recovered from $CO_2$(g).

Note: In some embodiments, acetic acid for step '(6)' may comprise aqueous acetic acid produced or regenerated in step '(9)'.

(7) $Ca(CH_3COO)_2$(aq)+$Na_2SO_4$(s or aq)→2 $NaCH_3COO$(aq)+$CaSO_4$(s)

Note: In some embodiments, $Na_2SO_4$(s) may be added directly to or dissolved in $Ca(CH_3COO)_2$(aq).

Note: In some embodiments, $Na_2SO_4$(s) may be dissolved in water or an aqueous solution to form $Na_2SO_4$(aq) before mixing with $Ca(CH_3COO)_2$(aq).

Note: In some embodiments, water may be added to the process to make up for water which may leave the process, for example, if NaOH(aq) is an output, or another aqueous solution is an output, or any combination thereof. In some embodiments, water may be added to the process by $Na_2SO_4$ being in the form of $Na_2SO_4$(aq) or an aqueous solution comprising sodium sulfate, wherein at least a portion of the water in $Na_2SO_4$(aq) may comprise water added to the process. In some embodiments, $Na_2SO_4$(aq) may be provided or sourced as an aqueous solution. For example, in some embodiments, $Na_2SO_4$(aq) may be provided to the process in the form of $Na_2SO_4$(aq). In some embodiments, $Na_2SO_4$(aq) may be provided or sourced as a solid or $Na_2SO_4$(s), then dissolved in water to form $Na_2SO_4$(aq).

Note: In some embodiments, $Ca(CH_3COO)_2$(aq) may comprise $Ca(CH_3COO)_2$(aq) from step '(6)'.

(8) 2 $NaCH_3COO$(aq)+$SO_2$(g or aq)+$H_2O$(l or aq)→$Na_2SO_3$(aq)+2 $CH_3COOH$(aq)

Note: In some embodiments, $SO_2$(g) may comprise other gases in addition to $SO_2$(g). In some embodiments, the reaction of 2 $NaCH_3COO$(aq)+$SO_2$(g) may result in at least a portion of acetic acid vapor in the remaining gases during or after the reaction. In some embodiments, $NaCH_3COO$(aq) entering the present step may be pre-contacted with or may absorb at least a portion of acetic acid vapor from the remaining gases. In some embodiments, the reactor or absorption column may be configured to absorb acetic acid vapor in $NaCH_3COO$(aq) before or while reacting $NaCH_3COO$(aq) with $SO_2$(g). In some embodiments, acetic acid vapor may be removed from remaining gases using, for example, including, but not limited to, one or more or any combination of the following: alkaline earth carbonate, or alkaline earth-weak acid, or alkaline earth carbonate-water slurry, or alkaline earth oxide, or alkaline earth.

Note: In some embodiments, $NaCH_3COO$(aq) may comprise $NaCH_3COO$(aq) from step '(7)'.

Note: In some embodiments, $SO_2$ may comprise $SO_2$(g) from the calcination or decomposition of $CaSO_3$(s) in step '(14)'.

(9) $Na_2SO_3$(aq)+2 $CH_3COOH$(aq)→2 $CH_3COOH$(aq)+ $Na_2SO_3$(s)

Note: $CH_3COOH$ may be more soluble in water than $Na_2SO_3$. In some embodiments, $Na_2SO_3$ may be separated or precipitated from solution by, for example, including, but not limited to, evaporation, or distillation, or crystallization, or separation systems or methods described herein, or separation systems or methods described in the art, or any combination thereof.

Note: In some embodiments, $CH_3COOH$ and/or water may be separated from $Na_2SO_3$ by, for example, evaporation, or distillation, or crystallization, or any combination thereof. In some embodiments, $CH_3COOH$ may evaporate with water vapor and/or condense with water vapor, which may result in a distillate or condensate comprising $CH_3COOH$(aq).

Note: In some embodiments, magnesium sulfite(aq) may be present in the $Na_2SO_3$(aq)+2 $CH_3COOH$(aq). In some embodiments, if present, magnesium sulfite may begin to precipitate or crystalize before $Na_2SO_3$. In some embodiments magnesium sulfite solid may be separated during step '(9)'. In some embodiments, separated magnesium sulfite may be decomposed to magnesium oxide, or decomposed separately from calcium sulfite, or decomposed together with calcium sulfite, or any combination thereof.s Note: $Na_2SO_3$(s) may be separated from $CH_3COOH$(aq) by a solid-liquid separation, which may include, but is not limited to, filter, or centrifuge, or decanter, or separation systems or methods described herein, or separation systems or methods described in the art, or any combination thereof.

(10) React an Alkaline-Earth-Weak Acid, such as an Alkaline-Earth Carbonate, with Carbon Dioxide and/or Water to Form an Alkaline-Earth Bicarbonate $CaCO_3$(s)+$CO_2$(g or aq)+$H_2O$(aq)→$Ca(HCO_3)_2$(aq)

$MgCO_3$(s)+$CO_2$(g or aq)+$H_2O$(aq)→$Mg(HCO_3)_2$(aq)

Note: May be conducted under a pressurized $CO_2$ atmosphere or with concentrated carbonic acid or $CO_2$(aq). For example, the $CO_2$ partial pressure during the reaction may be greater than, for example, 1 Bar, or 2 Bar, or 3 Bar, or 4 Bar, or 5 Bar, or 6 Bar, or 7 Bar, or 8 Bar, or 9 Bar, or 10 Bar, or any combination thereof.

Note: In some embodiments, $CaCO_3$(s) or $MgCO_3$(s) may comprise $CaCO_3$(s) or $MgCO_3$(s) from step '(14)'.

Note: In some embodiments, $CO_2$(g or aq) may comprise $CO_2$ from step '(6)', or step '(13)', or any combination thereof.

(11) React an Alkali Sulfite with an Alkaline-Earth Bicarbonate to form an Alkali Bicarbonate and an Alkaline-Earth Sulfite $Na_2SO_3$(s or aq)+$Ca(HCO_3)_2$(aq)→2 $NaHCO_3$(aq)+ $CaSO_3$(s)

$Na_2SO_3$(s or aq)+$Mg(HCO_3)_2$(aq)→2 $NaHCO_3$(aq)+ $MgSO_3$(s)

Note: In some embodiments, $Na_2SO_3$(s) may be dissolved in water or may comprise an aqueous solution before mixing with an aqueous solution comprising $Ca(HCO_3)_2$(aq) or $Mg(HCO_3)_2$(aq).

Note: At least a portion of $CaSO_3$(s) or $MgSO_3$(s) may be separated by a solid-liquid separation.

Note: In some embodiments, $NaHCO_3$ may be sold as a product or employed as a carbon sequestration medium.

Note: In some embodiments, $Na_2SO_3$(s or aq) may comprise $Na_2SO_3$ from step '(4)'.

Note: In some embodiments, $Ca(HCO_3)_2$(aq) or $Mg(HCO_3)_2$(aq) may comprise $Ca(HCO_3)_2$(aq) or $Mg(HCO_3)_2$(aq) from step '(5)'.

(12) 2 $NaHCO_3$(aq)→$Na_2CO_3$(aq)+$CO_2$(g)+$H_2O$(g or l)

Note: $CO_2$(g) may comprise captured $CO_2$.

Note: In some embodiments, $Na_2CO_3$ may be sold as a product and/or employed as a carbon sequestration medium.

Note: In some embodiments, 2 $NaHCO_3$(aq) may be decomposed into $Na_2CO_3$(aq) and $CO_2$(g) and water within an aqueous and/or under-pressure or pressurized environment, which may avoid or prevent the need for crystallizing or precipitating $NaHCO_3$(s) and/or to minimize or reduce water evaporation during, for example, $CO_2$ desorption.

Note: In some embodiments, 2 $NaHCO_3$(aq) may comprise $NaHCO_3$ from step '(11)'.

(13) Calcine or decompose an alkaline-earth sulfite to an alkaline earth oxide and sulfur dioxide $CaSO_3$(s)→CaO(s)+$SO_2$(g)

$MgSO_3$(s)→MgO(s)+$SO_2$(g)

Note: May comprise calcining $CaSO_3$(s) or $MgSO_3$(s), which may employ a kiln.

Note: $CaSO_3$(s) or $MgSO_3$(s) may be dried, or dehydrated, or both before or during calcining.

Note: $CaSO_3$(s) or $MgSO_3$(s) may comprise $CaSO_3$(s) or $MgSO_3$(s) from step '(11)'.

(14) React an alkaline-earth oxide or hydroxide with an alkali carbonate to produce an alkaline-earth carbonate and an alkali hydroxide CaO(s or aq)+$Na_2CO_3$(s or aq)+Water→NaOH (aq)→$CaCO_3$(s)

MgO(s or aq)+$Na_2CO_3$(s or aq)+Water→NaOH (aq)→$MgCO_3$(s)

Note: In some embodiments, $CaO+Na_2CO_3$(s or aq)+Water or $MgO+Na_2CO_3$(s or aq)+Water may be conducted in multiple steps. For example, in some embodiments, CaO or MgO may be reacted with water to form $Ca(OH)_2$(aq), or $Ca(OH)_2$(s or aq), or $Mg(OH)_2$(aq), or $Mg(OH)_2$(s or aq), which may comprise Milk of Lime or Milk of Magnesia, or a solid-liquid suspension comprising calcium hydroxide or magnesium hydroxide. For example, in some embodiments, $Na_2CO_3$ may comprise an aqueous solution or may be dissolved in water to form an aqueous solution. For example, in some embodiments, a solution or solid-liquid mixture or suspension comprising $Ca(OH)_2$(s or aq), or Milk of Lime, or $Mg(OH)_2$, or Milk of Magnesia may be mixed with an aqueous solution comprising $Na_2CO_3$(aq), which may result in the formation of a solution comprising aqueous sodium hydroxide and a solid comprising calcium carbonate or magnesium carbonate.

Note: In some embodiments, at least a portion of calcium carbonate or magnesium carbonate may be separated from at least a portion of sodium hydroxide using, for example, a solid-liquid separation.

Note: CaO(s) or MgO(s) may comprise CaO(s) or MgO(s) from step '(13)'.

Note: $Na_2CO_3$(aq) may comprise $Na_2CO_3$(aq) from step '(11)' or step '(12)'.

Note: In some embodiments, $CaCO_3$ or $MgCO_3$ may be transferred to step 10.

Note: In some embodiments, NaOH(aq) may be concentrated, or at least a portion of water may be removed. Separated or recovered water may be transferred to or employed as a solvent or input in, for example, step '10'. In some embodiments, NaOH(aq) may be concentrated to a concentrated solution, or 33 wt % solution, or a 50 wt % solution, or solid NaOH, or any combination thereof using one or more or any combination of water separation systems and/or methods.

Example 59: Process for Producing Alkaline-Earth Oxide or Alkaline-Earth Hydroxide with Carbon Dioxide, Sulfur Dioxide, and/or Alkali Intermediate (1) React Material comprising Calcium, or Magnesium, or Other Alkaline Earth-Weak Acid Anion with Ammonium Chloride $Ca(WA)(s)+2\ NH_4Cl$(s or g or aq)$\rightarrow CaCl_2$(s or aq)$+2\ NH_3$(g or aq)$+H_2O$(g or aq)

Note: In some embodiments, the reaction of Ca(WA) with ammonium chloride may be conducted at a solid phase or at a solid-gas mixture phase. For example, 2 $NH_4Cl$(s) and Ca(WA)(s) may be heated, which may result in the vaporization of $NH_4Cl$ into $NH_3$(g) and HCl(g), wherein the HCl(g) may react with the Ca(WA)(s) to form, for example, $CaCl_2$(s) and/or (WA) and/or water.

Note: In some embodiments, WA may comprise, for example, including, but not limited to, one or more or any combination of the following; a silicon oxide, or iron oxide, or aluminum oxide, or hydroxide, or oxide.

Note: In some embodiments, the reaction of Ca(WA) with ammonium chloride may be conducted at a solid-liquid phase or a solid-aqueous phase. For example, 2 $NH_4Cl$(aq) and Ca(WA)(s) may be mixed, and/or may react to form, for example, $CaCl_2$(aq) and 2 $NH_3$(aq or g).

(2) $CaCl_2(s)+Water\rightarrow CaCl_2(aq)$

Note: In some embodiments, $CaCl_2$ from step 1 may comprise a solid and/or may be dissolved in water to form an aqueous solution.

(3) Ammonia or weak base may be dissolved in water or aqueous solution to form aqueous ammonia, and/or ammonia may be dissolved in water and/or reacted with carbon dioxide to form ammonium carbonate or ammonium bicarbonate.

$CaCl_2(aq)+2\ NH_3(g)\rightarrow CaCl_2(aq)+2\ NH_3(aq)$ $2\ NH_3(g)+Water\rightarrow NH_3(aq)$ $2\ NH_3$(g or aq)$+CO_2(g)+H_2O$(l or aq)$\rightarrow(NH_4)_2CO_3(aq)$ $2NH_3$(g or aq)$+2\ CO_2(g)+2\ H_2O$(l or aq)$\rightarrow 2\ NH_4HCO_3(aq)$ $(NH_4)_2CO_3(aq)+CO_2(g)+H_2O$(l or aq)$\rightarrow 2\ NH_4HCO_3(aq)$ Note: In some embodiments, $NH_3$ from step 1 may comprise a gas and/or may be dissolved in $CaCl_2$(aq).

Note: In some embodiments, $NH_3$ may be dissolved in water and/or reacted with $CO_2$ separately from $CaCl_2$.

(4) Calcium chloride may be reacted with ammonia, or carbon dioxide, or ammonium carbonate, or ammonium bicarbonate, or any combination thereof to form ammonium chloride and calcium carbonate.

$CaCl_2(aq)+2\ NH_3(aq)+CO_2(g)+H_2O\rightarrow 2\ NH_4Cl(aq)+CaCO_3(s)$ $CaCl_2(aq)+2\ NH_3(aq)+2\ CO_2(g)+H_2O\rightarrow 2\ NH_4Cl(aq)+CaCO_3(s)+CO_2(g)$ $CaCl_2(aq)+(NH_4)_2CO_3(aq)\rightarrow 2\ NH_4Cl(aq)+CaCO_3(s)$ $CaCl_2(aq)+2\ NH_4HCO_3(aq)\rightarrow 2\ NH_4Cl(aq)+CaCO_3(s)+CO_2(g)$ Note: In some embodiments, if excess $CO_2$ is present or $CO_2$ is in the product, in some embodiments, said excess $CO_2$ may be transferred to the inputs or reactants of step 4 and/or the inputs or reactants of step 3.

Note: In some embodiments, a $CaCl_2(aq)+NH_3(aq)$ solution may be produced in step 1 and/or may be transferred to step 4, potentially skipping step 2 and step 3.

Note: In some embodiments, $CO_2$(g) may comprise captured $CO_2$ from another embodiment described herein. For example, in some embodiments, $CO_2$(g) may comprise $CO_2$ from the reaction of calcium carbonate with acetic acid.

Note: In some embodiments, $CaCO_3$(s) may be transferred to or may comprise an input to one or more or any combination of embodiments described herein. For example, $CaCO_3$(s) may be an input to a process for producing sodium hydroxide, or calcium oxide, or calcium hydroxide, or sodium bicarbonate, or sodium carbonate, or any combination thereof.

Note: In some embodiments, $CO_2$(g) may comprise $CO_2$ from an emissions source, or a point source, or air, or from an external source, or any combination thereof.

Note: In some embodiments, 2 $NH_4Cl$(aq) may be transferred to step 1.

Note: In some embodiments, 2 $NH_4Cl$(aq) may be transferred to step 5.

(5) $2\ NH_4Cl(aq)\rightarrow 2\ NH_4Cl(s)+Water$

Note: In some embodiments, 2 $NH_4Cl$(s) may be transferred to step 1.

Note: In some embodiments, Water may be transferred to step 3 and/or step 4.

(6) React Material comprising Calcium, or Magnesium, or Other Alkaline Earth-Weak Acid Anion with Acetic Acid $CaCO_3$(s or aq)$+2\ CH_3COOH(aq)\rightarrow Ca(CH_3COO)_2(aq)+CO_2(g)$ Calcium Silicate(s)$+2\ CH_3COOH(aq)\rightarrow Ca(CH_3COO)_2$(aq)+Silicon Dioxide(s)

$CaS(s)+2\ CH_3COOH(aq)\rightarrow Ca(CH_3COO)_2(aq)+H_2S(g)$

Calcium(Weak Acid Anion)$+2\ CH_3COOH(aq)\rightarrow Ca(CH_3COO)_2$(aq)+Weak Acid(s, or g, or l, or aq)

Note: Residual solids or undissolved solids, such as silicon dioxide or other undissolved solids, may be separated from the liquid solution using a solid-liquid separation.

Note: If $CO_2$(g) is produced, it may be desirable for said $CO_2$(g) to be produced at a high partial pressure $CO_2$(g), or purity $CO_2$(g), or to comprise captured $CO_2$(g).

Note: $CaCO_3$ may be from step '4'.

Note: $CO_2$ may be transferred to step '3' or step '4'.

(7) $Ca(CH_3COO)_2$(aq)+$Na_2SO_3$(s or aq)→2 $NaCH_3COO$(aq)+$CaSO_3$(s)

Note: $CaSO_3$(s) may be separated using a solid-liquid separation.

Note: In some embodiments, $Na_2SO_3$(s or aq) may comprise a solid comprising sodium sulfite, which may be added to or dissolved in a solution comprising calcium acetate.

Note: In some embodiments, $Na_2SO_3$(s or aq) may comprising an aqueous solution comprising sodium sulfite and acetic acid.

(8) 2 $NaCH_3COO$(aq)+$SO_2$(g or aq)+$H_2O$(l or aq)→$Na_2SO_3$(aq)+2 $CH_3COOH$(aq)

Note: In some embodiments, $SO_2$(g) may comprise other gases in addition to $SO_2$(g). In some embodiments, the reaction of 2 $NaCH_3COO$(aq)+$SO_2$(g) may result in at least a portion of acetic acid vapor in the remaining gases during or after the reaction. In some embodiments, $NaCH_3COO$(aq) entering the present step may be pre-contacted with or may absorb at least a portion of acetic acid vapor from the remaining gases. In some embodiments, the reactor or absorption column may be configured to absorb acetic acid vapor in $NaCH_3COO$(aq) before or while reacting $NaCH_3COO$(aq) with $SO_2$(g). In some embodiments, acetic acid vapor may be removed from remaining gases using, for example, including, but not limited to, one or more or any combination of the following: alkaline earth carbonate, or alkaline earth-weak acid, or alkaline earth carbonate-water slurry, or alkaline earth oxide, or alkaline earth (9) $Na_2SO_3$(aq)+2 $CH_3COOH$(aq)→2 $CH_3COOH$(aq or l)+$Na_2SO_3$(s)

Note: $CH_3COOH$ may be more soluble in water than $Na_2SO_3$. In some embodiments, $Na_2SO_3$ may be separated or precipitated from solution by, for example, including, but not limited to, evaporation, or distillation, or crystallization, or separation systems or methods described herein, or separation systems or methods described in the art, or any combination thereof.

Note: In some embodiments, $CH_3COOH$ and/or water may be separated from $Na_2SO_3$ by, for example, evaporation, or distillation, or crystallization, or any combination thereof. In some embodiments, $CH_3COOH$ may evaporate with water vapor and/or condense with water vapor, which may result in a distillate or condensate comprising $CH_3COOH$(aq).

Note: In some embodiments, magnesium sulfite(aq) may be present in the $Na_2SO_3$(aq)+2 $CH_3COOH$(aq). In some embodiments, if present, magnesium sulfite may begin to precipitate or crystalize before $Na_2SO_3$. In some embodiments magnesium sulfite solid may be separated during step '(9)'. In some embodiments, separated magnesium sulfite may be decomposed to magnesium oxide, or decomposed separately from calcium sulfite, or decomposed together with calcium sulfite, or any combination thereof.s Note: $Na_2SO_3$(s) may be separated from $CH_3COOH$(aq) by a solid-liquid separation, which may include, but is not limited to, filter, or centrifuge, or decanter, or separation systems or methods described herein, or separation systems or methods described in the art, or any combination thereof.

Note: In some embodiments, a feed solution comprising sodium sulfite and acetic acid may be evaporated, wherein a portion of acetic acid and water vapor evaporate and/or are condensed to form an a separated acetic acid solution, and/or the remaining solution comprises aqueous acetic acid and a higher concentration of sodium sulfite than in the concentration of sodium sulfite in the feed solution.

(10) $CaSO_3$(s)→$CaO$(s)+$SO_2$(g)

Note: '(10)' may comprise calcining $CaSO_3$(s), which may employ a kiln.

Note: $CaSO_3$(s) may be dried, or dehydrated, or both before, or during '(10)'.

Example 60: Process for Producing Alkali Carbonate or Alkali Bicarbonate with Carbon Dioxide, Alkali Carbonate, and/or Sulfur Dioxide Intermediates (1) React Material comprising Calcium, or Magnesium, or Other Alkaline Earth-Weak Acid Anion with Ammonium Chloride Ca(WA)(s)+2 $NH_4Cl$(s or g or aq)→$CaCl_2$(s or aq)+2 $NH_3$(g or aq)+$H_2O$(g or aq)

Note: In some embodiments, the reaction of Ca(WA) with ammonium chloride may be conducted at a solid phase or at a solid-gas mixture phase. For example, 2 $NH_4Cl$(s) and Ca(WA)(s) may be heated, which may result in the vaporization of $NH_4Cl$ into $NH_3$(g) and HCl(g), wherein the HCl(g) may react with the Ca(WA)(s) to form, for example, $CaCl_2$(s) and/or (WA) and/or water.

Note: In some embodiments, WA may comprise, for example, including, but not limited to, one or more or any combination of the following; a silicon oxide, or iron oxide, or aluminum oxide, or hydroxide, or oxide.

Note: In some embodiments, the reaction of Ca(WA) with ammonium chloride may be conducted at a solid-liquid phase or a solid-aqueous phase. For example, 2 $NH_4Cl$(aq) and Ca(WA)(s) may be mixed, and/or may react to form, for example, $CaCl_2$(aq) and 2 $NH_3$(aq or g).

(2) $CaCl_2$(s)+Water→$CaCl_2$(aq)

Note: In some embodiments, $CaCl_2$ from step 1 may comprise a solid and/or may be dissolved in water to form an aqueous solution.

(3) Ammonia or weak base may be dissolved in water or aqueous solution to form aqueous ammonia, and/or ammonia may be dissolved in water and/or reacted with carbon dioxide to form ammonium carbonate or ammonium bicarbonate.

$CaCl_2$(aq)+2 $NH_3$(g)→$CaCl_2$(aq)+2 $NH_3$(aq)

2 $NH_3$(g)+Water→$NH_3$(aq)

2 $NH_3$(g or aq)+$CO_2$(g)+$H_2O$(l or aq)→$(NH_4)_2CO_3$(aq)

2$NH_3$(g or aq)+2 $CO_2$(g)+2 $H_2O$(l or aq)→2 $NH_4HCO_3$(aq)

$(NH_4)_2CO_3$(aq)+$CO_2$(g)+$H_2O$(l or aq)→2 $NH_4HCO_3$(aq)

Note: In some embodiments, $NH_3$ from step 1 may comprise a gas and/or may be dissolved in $CaCl_2$(aq).

Note: In some embodiments, $NH_3$ may be dissolved in water and/or reacted with $CO_2$ separately from $CaCl_2$.

(4) Calcium chloride may be reacted with ammonia, or carbon dioxide, or ammonium carbonate, or ammonium bicarbonate, or any combination thereof to form ammonium chloride and calcium carbonate.

$CaCl_2$)(aq)+2 $NH_3$(aq)+$CO_2$(g)+$H_2O$→2 $NH_4Cl$(aq)+$CaCO_3$(s)

$CaCl_2$(aq)+2 $NH_3$(aq)+2 $CO_2$(g)+$H_2O$→2 $NH_4Cl$(aq)+$CaCO_3$(s)+$CO_2$(g)

$CaCl_2$(aq)+$(NH_4)_2CO_3$(aq)→2 $NH_4Cl$(aq)+$CaCO_3$(s)

$CaCl_2(aq)+2\ NH_4HCO_3(aq) \rightarrow 2\ NH_4Cl(aq)+CaCO_3(s)+CO_2(g)$

Note: In some embodiments, if excess $CO_2$ is present or $CO_2$ is in the product, in some embodiments, said excess $CO_2$ may be transferred to the inputs or reactants of step 4 and/or the inputs or reactants of step 3.

Note: In some embodiments, a $CaCl_2(aq)+NH_3(aq)$ solution may be produced in step 1 and/or may be transferred to step 4, potentially skipping step 2 and step 3.

Note: In some embodiments, $CO_2(g)$ may comprise captured $CO_2$ from another embodiment described herein. For example, in some embodiments, $CO_2(g)$ may comprise $CO_2$ from the reaction of calcium carbonate with acetic acid.

Note: In some embodiments, $CaCO_3(s)$ may be transferred to or may comprise an input to one or more or any combination of embodiments described herein. For example, $CaCO_3(s)$ may be an input to a process for producing sodium hydroxide, or calcium oxide, or calcium hydroxide, or sodium bicarbonate, or sodium carbonate, or any combination thereof.

Note: In some embodiments, $CO_2(g)$ may comprise $CO_2$ from an emissions source, or a point source, or air, or from an external source, or any combination thereof.

Note: In some embodiments, 2 $NH_4Cl(aq)$ may be transferred to step 1.

Note: In some embodiments, 2 $NH_4Cl(aq)$ may be transferred to step 5.

(5) $2\ NH_4Cl(aq) \rightarrow 2\ NH_4Cl(s)+Water$

Note: In some embodiments, 2 $NH_4Cl(s)$ may be transferred to step 1.

Note: In some embodiments, Water may be transferred to step 3 and/or step 4.

(6) React Material comprising Calcium, or Magnesium, or Other Alkaline Earth-Weak Acid Anion with Acetic Acid $CaCO_3(s\ or\ aq)+2\ CH_3COOH(aq) \rightarrow Ca(CH_3COO)_2(aq)+CO_2(g)+H_2O(aq\ or\ l)$ Calcium Silicate(s)+2 $CH_3COOH(aq) \rightarrow Ca(CH_3COO)_2(aq)$+Silicon Dioxide(s)+$H_2O(aq\ or\ l)$ $CaS(s)+2\ CH_3COOH(aq) \rightarrow Ca(CH_3COO)_2(aq)+H_2S(g)$ Calcium(Weak Acid Anion)+2 $CH_3COOH(aq) \rightarrow Ca(CH_3COO)_2(aq)$+Weak Acid(s, or g, or l, or aq)+$H_2O(aq\ or\ l)$ Note: Residual solids or undissolved solids, such as silicon dioxide or other undissolved solids, may be separated from the liquid solution using a solid-liquid separation.

Note: $CaCO_3$ may be from step '4'.

Note: $CO_2(g)$ may comprise captured $CO_2$.

Note: In some embodiments, $CO_2(g)$ may be employed internally or employed in other steps. For example, in some embodiments, $CO_2(g)$ may be employed in step '(10)'.

Note: In some embodiments, $CO_2(g)$ may be utilized or sequestered or sold or comprise a product. For example, $CO_2(g)$ may be utilized or sequestered or sold to a $CO_2$ sequestration site or a $CO_2$ EOR application or an external application.

Note: In some embodiments, some chemicals comprising calcium may comprise a portion of magnesium. In some embodiments, for example, input chemicals or input material may comprise a mixture of calcium and magnesium.

Note: In some embodiments, acetic acid vapor and/or water vapor may be separated or recovered from $CO_2(g)$.

Note: In some embodiments, acetic acid for step '(6)' may comprise aqueous acetic acid produced or regenerated in step '(9)'.

(2) $Ca(CH_3COO)_2(aq)+Na_2SO_4(s\ or\ aq) \rightarrow 2\ NaCH_3COO(aq)+CaSO_4(s)$ Note: In some embodiments, $Na_2SO_4(s)$ may be added directly to or dissolved in $Ca(CH_3COO)_2(aq)$.

Note: In some embodiments, $Na_2SO_4(s)$ may be dissolved in water or an aqueous solution to form $Na_2SO_4(aq)$ before mixing with $Ca(CH_3COO)_2(aq)$.

Note: In some embodiments, water may be added to the process to make up for water which may leave the process, for example, if NaOH(aq) is an output, or another aqueous solution is an output, or any combination thereof. In some embodiments, water may be added to the process by $Na_2SO_4$ being in the form of $Na_2SO_4(aq)$ or an aqueous solution comprising sodium sulfate, wherein at least a portion of the water in $Na_2SO_4(aq)$ may comprise water added to the process. In some embodiments, $Na_2SO_4(aq)$ may be provided or sourced as an aqueous solution. For example, in some embodiments, $Na_2SO_4(aq)$ may be provided to the process in the form of $Na_2SO_4(aq)$. In some embodiments, $Na_2SO_4(aq)$ may be provided or sourced as a solid or $Na_2SO_4(s)$, then dissolved in water to form $Na_2SO_4(aq)$.

Note: In some embodiments, $Ca(CH_3COO)_2(aq)$ may comprise $Ca(CH_3COO)_2(aq)$ from step '(6)'.

(8) $2\ NaCH_3COO(aq)+SO_2(g\ or\ aq)+H_2O(l\ or\ aq) \rightarrow Na_2SO_3(aq)+2\ CH_3COOH(aq)$ Note: In some embodiments, $SO_2(g)$ may comprise other gases in addition to $SO_2(g)$. In some embodiments, the reaction of 2 $NaCH_3COO(aq)+SO_2(g)$ may result in at least a portion of acetic acid vapor in the remaining gases during or after the reaction. In some embodiments, $NaCH_3COO(aq)$ entering the present step may be pre-contacted with or may absorb at least a portion of acetic acid vapor from the remaining gases. In some embodiments, the reactor or absorption column may be configured to absorb acetic acid vapor in $NaCH_3COO(aq)$ before or while reacting $NaCH_3COO(aq)$ with $SO_2(g)$. In some embodiments, acetic acid vapor may be removed from remaining gases using, for example, including, but not limited to, one or more or any combination of the following: alkaline earth carbonate, or alkaline earth-weak acid, or alkaline earth carbonate-water slurry, or alkaline earth oxide, or alkaline earth.

Note: In some embodiments, $NaCH_3COO(aq)$ may comprise $NaCH_3COO(aq)$ from step '(7)'.

Note: In some embodiments, $SO_2$ may comprise $SO_2(g)$ from the calcination or decomposition of $CaSO_3(s)$ in step '(12)'.

(9) $Na_2SO_3(aq)+2\ CH_3COOH(aq) \rightarrow 2\ CH_3COOH(aq)+Na_2SO_3(s)$

Note: $CH_3COOH$ may be more soluble in water than $Na_2SO_3$. In some embodiments, $Na_2SO_3$ may be separated or precipitated from solution by, for example, including, but not limited to, evaporation, or distillation, or crystallization, or separation systems or methods described herein, or separation systems or methods described in the art, or any combination thereof.

Note: In some embodiments, $CH_3COOH$ and/or water may be separated from $Na_2SO_3$ by, for example, evaporation, or distillation, or crystallization, or any combination thereof. In some embodiments, $CH_3COOH$ may evaporate with water vapor and/or condense with water vapor, which may result in a distillate or condensate comprising $CH_3COOH(aq)$.

Note: In some embodiments, magnesium sulfite(aq) may be present in the $Na_2SO_3(aq)+2\ CH_3COOH(aq)$. In some embodiments, if present, magnesium sulfite may begin to precipitate or crystalize before $Na_2SO_3$. In some embodiments magnesium sulfite solid may be separated during step '(9)'. In some embodiments, separated magnesium sulfite may be decomposed to magnesium oxide, or decomposed separately from calcium sulfite, or decomposed together with calcium sulfite, or any combination thereof.s Note: $Na_2SO_3$(s) may be separated from $CH_3COOH$(aq) by a solid-liquid separation, which may include, but is not limited to, filter, or centrifuge, or decanter, or separation systems or methods described herein, or separation systems or methods described in the art, or any combination thereof.

(10) React an Alkaline-Earth-Weak Acid, such as an Alkaline-Earth Carbonate, with Carbon Dioxide and/or Water to Form an Alkaline-Earth Bicarbonate $CaCO_3(s)+CO_2(g\text{ or }aq)+H_2O(aq)\rightarrow Ca(HCO_3)_2(aq)$ $MgCO_3(s)+CO_2(g\text{ or }aq)+H_2O(aq)\rightarrow Mg(HCO_3)_2(aq)$ Note: May be conducted under a pressurized $CO_2$ atmosphere or with concentrated carbonic acid or $CO_2$(aq). For example, the $CO_2$ partial pressure during the reaction may be greater than, for example, 1 Bar, or 2 Bar, or 3 Bar, or 4 Bar, or 5 Bar, or 6 Bar, or 7 Bar, or 8 Bar, or 9 Bar, or 10 Bar, or any combination thereof.

Note: In some embodiments, $CaCO_3$(s) or $MgCO_3$(s) may comprise $CaCO_3$(s) or $MgCO_3$(s) from step '(13)'.

Note: In some embodiments, $CaCO_3$(s) or $MgCO_3$(s) may comprise an input, such as limestone, or dolomite.

Note: In some embodiments, $CO_2$(g or aq) may comprise $CO_2$ from step '(6)'.

Note: In some embodiments, $CO_2$(g or aq) may comprise $CO_2$ from an emissions source, or another $CO_2$ source, or captured $CO_2$, or any combination thereof. For example, in some embodiments, $CO_2$(g or aq) may comprise, including, but not limited to, one or more or any combination of the following: $CO_2$ from a blue hydrogen or blue ammonia facility, or an ammonia facility, or an ethanol plant, or a carbon capture plant.

(11) React an Alkali Sulfite with an Alkaline-Earth Bicarbonate to form an Alkali Bicarbonate and an Alkaline-Earth Sulfite $Na_2SO_3(s\text{ or }aq)+Ca(HCO_3)_2(aq)\rightarrow 2\ NaHCO_3(aq)+CaSO_3(s)$ $Na_2SO_3(s\text{ or }aq)+Mg(HCO_3)_2(aq)\rightarrow 2\ NaHCO_3(aq)+MgSO_3(s)$ Note: In some embodiments, $Na_2SO_3$(s) may be dissolved in water or may comprise an aqueous solution before or during mixing with an aqueous solution comprising $Ca(HCO_3)_2$(aq) or $Mg(HCO_3)_2$(aq).

Note: At least a portion of $CaSO_3$(s) or $MgSO_3$(s) may be separated by a solid-liquid separation.

Note: In some embodiments, $NaHCO_3$ may be sold as a product or employed as a carbon sequestration medium.

Note: In some embodiments, $NaHCO_3$ may be concentrated and/or crystalized into a solid, such as, for example, solid sodium bicarbonate or solid sodium carbonate.

(12) Decompose an Alkaline-Earth Sulfite into an Alkaline-Earth Oxide and Sulfur Dioxide $CaSO_3(s)\rightarrow CaO(s)+SO_2(g)$ $MgSO_3(s)\rightarrow MgO(s)+SO_2(g)$ Note: May comprise calcining $CaSO_3$(s) or $MgSO_3$(s), which may employ a kiln.

Note: $CaSO_3$(s) or $MgSO_3$(s) may be dried, or dehydrated, or both before or during calcining.

Note: $CaSO_3$(s) or $MgSO_3$(s) may comprise $CaSO_3$(s) or $MgSO_3$(s) from step '(11)'.

Note: CaO or MgO may comprise a valuable product if desired. For example, CaO or MgO may comprise an ultra-low carbon emissions CaO or MgO product.

(13) React an Alkaline-Earth Oxide or Hydroxide with Carbon Dioxide to form an Alkaline Earth Carbonate $CaO(s)+CO_2(g)\rightarrow CaCO_3(s)$ $MgO(s)+CO_2(g)\rightarrow MgCO_3(s)$ Note: In some embodiments, CaO(s) or MgO(s) may be reacted with water to form $Ca(OH)_2$(aq), or $Ca(OH)_2$(s or aq), or $Mg(OH)_2$(aq), or $Mg(OH)_2$(s or aq), or any combination thereof which may comprise Milk of Lime, or Milk of Magnesia, or a solid-liquid suspension comprising calcium hydroxide and/or magnesium hydroxide. In some embodiments, $Ca(OH)_2$ or $Mg(OH)_2$ may be reacted with a carbonate salt, such as sodium carbonate or sodium bicarbonate, to form $CaCO_3$ or $MgCO_3$, or may be reacted with $CO_2$ to form $CaCO_3$ or $MgCO_3$. For example, said sodium carbonate or sodium bicarbonate may comprise sodium carbonate, or sodium bicarbonate, or potassium carbonate, or potassium bicarbonate, or alkali carbonate, or alkali bicarbonate, or any combination thereof employed in or as a $CO_2$ absorption solution.

Note: In some embodiments, $CO_2$(g) may comprise $CO_2$ in or from a point source $CO_2$ emissions source. For example, $CO_2$(g) may comprise flue gas, or dilute $CO_2$, or high purity $CO_2$, or captured $CO_2$.

Note: In some embodiments, $CO_2$(g) may comprise $CO_2$ in or from air. For example, $CO_2$(g) may comprise air which may comprise at least a portion of $CO_2$ even if at a very dilute concentration. For example, calcium oxide may be capable of reacting with very low concentrations or very dilute concentrations of $CO_2$ if desired. For example, $CO_2$(g) may comprise a carbonate salt, such as sodium carbonate or potassium carbonate, wherein the carbonate may comprise carbonate originating from the reaction of carbon dioxide in the air with a sodium or potassium or other alkali salt, such as sodium hydroxide or potassium hydroxide, forming the alkali carbonate salt, and/or wherein the reaction of calcium oxide or calcium hydroxide with the alkali carbonate may result in the regeneration or formation of an alkali hydroxide or alkali oxide or other alkali salt which may be employed to absorb carbon dioxide from the air a regenerate or re-form the alkali carbonate salt.

Note: In some embodiments, $CaCO_3$ or $MgCO_3$ may comprise a valuable product. In some embodiments, $CaCO_3$ or $MgCO_3$ may comprise a carbon sequestration medium.

Example 61: Process for Producing Sodium Hydroxide with Sulfur Dioxide, Carbon Dioxide, Carboxylic Acid, and Magnesium Intermediates (1) React Material comprising Calcium, or Magnesium, or Other Alkaline Earth-Weak Acid Anion with Acetic Acid $CaCO_3(s\text{ or }aq)+2\ CH_3COOH(aq)\rightarrow Ca(CH_3COO)_2(aq)+CO_2(g)+H_2O(aq\text{ or }l)$ $\text{Calcium Silicate}(s)+2\ CH_3COOH(aq)\rightarrow Ca(CH_3COO)_2(aq)+\text{Silicon Dioxide}(s)+H_2O(aq\text{ or }l)$ $CaS(s)+2\ CH_3COOH(aq)\rightarrow Ca(CH_3COO)_2(aq)+H_2S(g)$ $\text{Calcium(Weak Acid Anion)}+2\ CH_3COOH(aq)\rightarrow Ca(CH_3COO)_2(aq)+\text{Weak Acid}(s,\text{ or }g,\text{ or }l,\text{ or }aq)+H_2O(aq\text{ or }l)$ Note: Residual solids or undissolved solids, such as silicon dioxide or other undissolved solids, may be separated from the liquid solution using a solid-liquid separation.

Note: $CO_2$(g) may comprise captured $CO_2$.

Note: In some embodiments, some chemicals comprising calcium may comprise a portion of magnesium. In some embodiments, for example, input chemicals or input material may comprise a mixture of calcium and magnesium.

Note: In some embodiments, acetic acid vapor and/or water vapor may be separated or recovered from $CO_2$(g).

Note: In some embodiments, acetic acid for step '(1)' may comprise aqueous acetic acid produced or regenerated in step '(4)'.

(2) $Ca(CH_3COO)_2$(aq)+$Na_2SO_4$(s or aq)→2 $NaCH_3COO$(aq)+$CaSO_4$(s)

(3) 2 $NaCH_3COO$(aq)+$SO_2$(g or aq)+$H_2O$(l or aq)→$Na_2SO_3$(aq)+2 $CH_3COOH$(aq)

(4) $Na_2SO_3$(aq)+2 $CH_3COOH$(aq)→2 $CH_3COOH$(aq)+$Na_2SO_3$(s)

(5) $MgCO_3$(s)+$CO_2$(g or aq)+$H_2O$(aq)→$Mg(HCO_3)_2$(aq)

Note: May be conducted under a pressurized $CO_2$ atmosphere or with concentrated carbonic acid or $CO_2$(aq). For example, the $CO_2$ partial pressure during the reaction may be greater than, for example, 0.5 Bar, or 1 Bar, or 2 Bar, or 3 Bar, or 4 Bar, or 5 Bar, or 6 Bar, or 7 Bar, or 8 Bar, or 9 Bar, or 10 Bar, or any combination thereof.

Note: In some embodiments, $MgCO_3$(s) may comprise $MgCO_3$(s) from the reaction of MgO or $Mg(OH)_2$ with $CO_2$.

Note: In some embodiments, $CO_2$(g or aq) may comprise $CO_2$ from step '(1)', or step '(9)', or any combination thereof. For example, in some embodiments, the reaction of MgO or $Mg(OH)_2$ with $CO_2$ may comprise capturing $CO_2$ from the calcination or decomposition of calcium carbonate and/or may enable the calcium carbonate calciner to produce dilute carbon dioxide or flue gas carbon dioxide because carbon dioxide in said dilute or flue gas carbon dioxide may be captured by the reaction with magnesium oxide and/or magnesium hydroxide.

(6) $Na_2SO_3$(s or aq)+$Mg(HCO_3)_2$(aq)→2 $NaHCO_3$(aq)+$MgSO_3$(s)

Note: In some embodiments, $Na_2SO_3$(s) may be dissolved in water or may comprise an aqueous solution before mixing with an aqueous solution comprising $Mg(HCO_3)_2$(aq).

Note: At least a portion of $CaSO_3$(s) or $MgSO_3$(s) may be separated by a solid-liquid separation.

Note: In some embodiments, $NaHCO_3$ may be sold as a product or employed as a carbon sequestration medium.

Note: In some embodiments, $Na_2SO_3$(s or aq) may comprise $Na_2SO_3$ from step '(4)'.

Note: In some embodiments, $Mg(HCO_3)_2$(aq) may comprise $Mg(HCO_3)_2$(aq) from step '(5)'.

Note: In some embodiments, residual $MgSO_3$ may be present as, for example, $MgSO_3$(aq) in the solution comprising sodium bicarbonate. In some embodiments, it may be desirable to separate at least a portion of residual $MgSO_3$ from at least a portion of sodium bicarbonate. For example, in some embodiments, said separation may comprise, including, but not limited to, one or more or any combination of the following: electrodialysis, or selective electrodialysis, or monovalent selective electrodialysis (MSED), or divalent selective electrodialysis (DSED), or concentrating, or cooling precipitation, or reverse osmosis, or membrane based process, or nanofiltration.

(7) $MgSO_3$(s)→MgO(s)+$SO_2$(g)

Note: The thermal decomposition of magnesium sulfite may be conducted with less energy and/or at lower temperatures than the thermal decomposition of calcium sulfite.

Note: Sulfur dioxide formed may be employed, for example, in the reaction of alkali acetate or alkali carboxylate with sulfur dioxide.

(8) React Magnesium Oxide or Magnesium Hydroxide with Carbon Dioxide to Form Magnesium Carbonate MgO(s)+$CO_2$(g)→$MgCO_3$(s)

MgO(s)+$H_2O$(l or g or s)→$Mg(OH)_2$(s or aq)

$Mg(OH)_2$(s or aq)+$CO_2$(g)→$MgCO_3$(s)+$H_2O$(l or g or s)

Note: In some embodiments, the $CO_2$(g) may comprise $CO_2$(g) from the decomposition of calcium carbonate.

Note: In some embodiments, the $CO_2$(g) may comprise $CO_2$(g) from an emissions source, or point source, or air.

Note: $MgCO_3$(s) may comprise the $MgCO_3$(s) in the reaction of $MgCO_3$(s)+$CO_2$+$H_2O$.

(9) 2 $NaHCO_3$(aq)→2 $NaHCO_3$(s)+Water

Note: In some embodiments, $NaHCO_3$(s) may be formed by process or cycle comprising concentrating and cooling precipitation, or a precipitation or crystallization process, or any combination thereof.

Note: In some embodiments, $NaHCO_3$ may be sold as a product and/or employed as a carbon sequestration medium.

Note: In some embodiments, 2 $NaHCO_3$(aq) may be decomposed into $Na_2CO_3$(aq) and $CO_2$(g) and water within an aqueous and/or under-pressure or pressurized environment, which may avoid or prevent the need for crystallizing or precipitating $NaHCO_3$(s).

Note: In some embodiments, at least a portion of residual dissolved $MgSO_3$ or magnesium sulfite, if any, may be separated and/or precipitated.

Note: Water may be separated from sodium bicarbonate or sodium carbonate using systems and methods for water separation, or systems and methods for salt precipitation or crystallization, or any combination thereof.

(10) 2 $NaHCO_3$(s)→$Na_2CO_3$(s)+$CO_2$(g)+$H_2O$(g or l)

Note: $CO_2$(g) may comprise captured $CO_2$.

Note: In some embodiments, $Na_2CO_3$ may be sold as a product and/or employed as a carbon sequestration medium.

Note: In some embodiments, $Na_2CO_3$(s) may be dissolved in water or an aqueous solution and/or comprise the $Na_2CO_3$(s) in the reaction of $Ca(OH)_2$ and $Na_2CO_3$(s)

(11) Calcine or decompose an alkaline-earth carbonate to form an alkaline earth oxide and carbon dioxide $CaCO_3$(s)→CaO(s)+$CO_2$(g)

$MgCO_3$(s)→MgO(s)+$CO_2$(g)

Note: In some embodiments, it may be desirable to decompose calcium carbonate or magnesium carbonate in a manner which the carbon dioxide is high purity, or in a manner which the carbon dioxide is captured, or in a manner which the carbon dioxide is dilute but then captured, or any combination thereof.

Note: In some embodiments, carbon dioxide from the decomposition of calcium carbonate or magnesium carbonate may comprise the carbon dioxide in the reaction of magnesium oxide or magnesium hydroxide and carbon dioxide.

(12) React an alkaline-earth oxide or hydroxide with an alkali carbonate to form an alkaline-earth carbonate and an alkali hydroxide CaO(s or aq)+$Na_2CO_3$(s or aq)+Water→2 NaOH(aq)+$CaCO_3$(s)

MgO(s or aq)+$Na_2CO_3$(s or aq)+Water→2 NaOH(aq)+$MgCO_3$(s)

$Ca(OH)_2$(s or aq)+$Na_2CO_3$(s or aq)→2 NaOH(aq)+$CaCO_3$(s)

MgO(s or aq)+$Na_2CO_3$(s or aq)+Water→2 NaOH(aq)+$MgCO_3$(s)

Note: In some embodiments, CaO+$Na_2CO_3$(s or aq)+Water or MgO+$Na_2CO_3$(s or aq)+Water may be conducted in multiple steps. For example, in some embodiments, CaO or MgO may be reacted with water to form $Ca(OH)_2$(s), $Ca(OH)_2$(aq), or $Ca(OH)_2$(s or aq), or $Mg(OH)_2$(aq), or $Mg(OH)_2$(s or aq), which may comprise Milk of Lime or Milk of Magnesia, or a solid-liquid suspension comprising calcium hydroxide or magnesium hydroxide. For example, in some embodiments, $Na_2CO_3$ may comprise an aqueous solution or may be dissolved in water to form an aqueous solution. For example, in some embodiments, a solution or solid-liquid mixture or suspension comprising $Ca(OH)_2$(s or aq), or Milk of Lime, or $Mg(OH)_2$, or Milk of Magnesia may be mixed with an aqueous solution comprising $Na_2CO_3$(aq), which may result in the formation of a solution comprising aqueous sodium hydroxide and a solid comprising calcium carbonate or magnesium carbonate.

Note: In some embodiments, at least a portion of calcium carbonate or magnesium carbonate may be separated from at least a portion of sodium hydroxide using, for example, a solid-liquid separation.

Example 62: Process for Producing Sodium Bicarbonate, or Sodium Carbonate, and/or Calcium Oxide or Calcium Carbonate (1) React Material comprising Calcium, or Magnesium, or Other Alkaline Earth-Weak Acid Anion with Acetic Acid $CaCO_3$(s or aq)+2 $CH_3COOH$(aq)→$Ca(CH_3COO)_2$(aq)+$CO_2$(g)+$H_2O$(aq or l)

Calcium Silicate(s)+2 $CH_3COOH$(aq)→$Ca(CH_3COO)_2$(aq)+Silicon Dioxide(s)+$H_2O$(aq or l)

CaS(s)+2 $CH_3COOH$(aq)→$Ca(CH_3COO)_2$(aq)+$H_2S$(g)

Calcium(Weak Acid Anion)+2 $CH_3COOH$(aq)→$Ca(CH_3COO)_2$(aq)+Weak Acid(s, or g, or l, or aq)+$H_2O$(aq or l)

Note: Residual solids or undissolved solids, such as silicon dioxide or other undissolved solids, may be separated from the liquid solution using a solid-liquid separation.

Note: $CO_2$(g) may comprise captured $CO_2$.

Note: In some embodiments, $CO_2$(g) may be employed internally or employed in other steps.

Note: In some embodiments, $CO_2$(g) may be utilized or sequestered or sold or comprise a product. For example, $CO_2$(g) may be utilized or sequestered or sold to a $CO_2$ sequestration site or a $CO_2$ EOR application or an external application.

Note: In some embodiments, some chemicals comprising calcium may comprise a portion of magnesium. In some embodiments, for example, input chemicals or input material may comprise a mixture of calcium and magnesium.

Note: In some embodiments, acetic acid vapor and/or water vapor may be separated or recovered from $CO_2$(g).

(2) $Ca(CH_3COO)_2$(aq)+$Na_2SO_4$(s or aq)→2 $NaCH_3COO$(aq)+$CaSO_4$(s)

Note: In some embodiments, $Na_2SO_4$(s) may be added directly to or dissolved in $Ca(CH_3COO)_2$(aq).

Note: In some embodiments, $Na_2SO_4$(s) may be dissolved in water or an aqueous solution to form $Na_2SO_4$(aq) before mixing with $Ca(CH_3COO)_2$(aq).

Note: In some embodiments, water may be added to the process to make up for water which may leave the process, for example, if NaOH(aq) is an output, or another aqueous solution is an output, or any combination thereof. In some embodiments, water may be added to the process by $Na_2SO_4$ being in the form of $Na_2SO_4$(aq) or an aqueous solution comprising sodium sulfate, wherein at least a portion of the water in $Na_2SO_4$(aq) may comprise water added to the process. In some embodiments, $Na_2SO_4$(aq) may be provided or sourced as an aqueous solution. For example, in some embodiments, $Na_2SO_4$(aq) may be provided to the process in the form of $Na_2SO_4$(aq). In some embodiments, $Na_2SO_4$(aq) may be provided or sourced as a solid or $Na_2SO_4$(s), then dissolved in water to form $Na_2SO_4$(aq).

Note: In some embodiments, $Ca(CH_3COO)_2$(aq) may comprise $Ca(CH_3COO)_2$(aq) from step '(1)'.

(3) 2 $NaCH_3COO$(aq)+$SO_2$(g or aq)+$H_2O$(l or aq)→$Na_2SO_3$(aq)+2 $CH_3COOH$(aq)

Note: In some embodiments, $SO_2$(g) may comprise other gases in addition to $SO_2$(g). In some embodiments, the reaction of 2 $NaCH_3COO$(aq)+$SO_2$(g) may result in at least a portion of acetic acid vapor in the remaining gases during or after the reaction. In some embodiments, $NaCH_3COO$(aq) entering the present step may be pre-contacted with or may absorb at least a portion of acetic acid vapor from the remaining gases. In some embodiments, the reactor or absorption column may be configured to absorb acetic acid vapor in $NaCH_3COO$(aq) before or while reacting $NaCH_3COO$(aq) with $SO_2$(g). In some embodiments, acetic acid vapor may be removed from remaining gases using, for example, including, but not limited to, one or more or any combination of the following: alkaline earth carbonate, or alkaline earth-weak acid, or alkaline earth carbonate-water slurry, or alkaline earth oxide, or alkaline earth.

Note: In some embodiments, $NaCH_3COO$(aq) may comprise $NaCH_3COO$(aq) from step '(2)'.

Note: In some embodiments, $SO_2$ may comprise $SO_2$(g) from the calcination or decomposition of $CaSO_3$(s) in step '(7)'.

(4) $Na_2SO_3$(aq)+2 $CH_3COOH$(aq)→2 $CH_3COOH$(aq)+$Na_2SO_3$(s)

Note: $CH_3COOH$ may be more soluble in water than $Na_2SO_3$. In some embodiments, $Na_2SO_3$ may be separated or precipitated from solution by, for example, including, but not limited to, evaporation, or distillation, or crystallization, or separation systems or methods described herein, or separation systems or methods described in the art, or any combination thereof.

Note: In some embodiments, $CH_3COOH$ and/or water may be separated from $Na_2SO_3$ by, for example, evaporation, or distillation, or crystallization, or any combination thereof. In some embodiments, $CH_3COOH$ may evaporate with water vapor and/or condense with water vapor, which may result in a distillate or condensate comprising $CH_3COOH$(aq).

Note: In some embodiments, magnesium sulfite(aq) may be present in the $Na_2SO_3$(aq)+2 $CH_3COOH$(aq). In some embodiments, if present, magnesium sulfite may begin to precipitate or crystalize before $Na_2SO_3$. In some embodiments magnesium sulfite solid may be separated during step '(4)'. In some embodiments, separated magnesium sulfite may be decomposed to magnesium oxide, or decomposed separately from calcium sulfite, or decomposed together with calcium sulfite, or any combination thereof.s Note: $Na_2SO_3$(s) may be separated from $CH_3COOH$(aq) by a solid-liquid separation, which may include, but is not limited to, filter, or centrifuge, or decanter, or separation systems or methods described herein, or separation systems or methods described in the art, or any combination thereof.

(5) $MgCO_3$(s)+$CO_2$(g or aq)+$H_2O$(aq)→$Mg(HCO_3)_2$(aq)

Note: May be conducted under a pressurized $CO_2$ atmosphere or with concentrated carbonic acid or $CO_2$(aq). For example, the $CO_2$ partial pressure during the reaction may be greater than, for example, 0.5 Bar, or 1 Bar, or 2 Bar, or 3 Bar, or 4 Bar, or 5 Bar, or 6 Bar, or 7 Bar, or 8 Bar, or 9 Bar, or 10 Bar, or any combination thereof.

Note: In some embodiments, $MgCO_3$(s) may comprise $MgCO_3$(s) from the reaction of MgO or $Mg(OH)_2$ with $CO_2$.

Note: In some embodiments, $CO_2$(g or aq) may comprise $CO_2$ from step '(1)', or step '(9)', or any combination thereof. For example, in some embodiments, the reaction of MgO or $Mg(OH)_2$ with $CO_2$ may comprise capturing $CO_2$ from the calcination or decomposition of calcium carbonate and/or may enable the calcium carbonate calciner to produce dilute carbon dioxide or flue gas carbon dioxide because carbon dioxide in said dilute or flue gas carbon dioxide may be captured by the reaction with magnesium oxide and/or magnesium hydroxide.

(6) $Na_2SO_3$(s or aq)+$Mg(HCO_3)_2$(aq)→2 $NaHCO_3$(aq)+$MgSO_3$(s)

Note: In some embodiments, $Na_2SO_3$(s) may be dissolved in water or may comprise an aqueous solution before mixing with an aqueous solution comprising $Mg(HCO_3)_2$(aq).

Note: At least a portion of $CaSO_3$(s) or $MgSO_3$(s) may be separated by a solid-liquid separation.

Note: In some embodiments, $NaHCO_3$ may be sold as a product or employed as a carbon sequestration medium.

Note: In some embodiments, $Na_2SO_3$(s or aq) may comprise $Na_2SO_3$ from step '(4)'.

Note: In some embodiments, $Mg(HCO_3)_2$(aq) may comprise $Mg(HCO_3)_2$(aq) from step '(5)'.

Note: In some embodiments, residual $MgSO_3$ may be present as, for example, $MgSO_3$(aq) in the solution comprising sodium bicarbonate. In some embodiments, it may be desirable to separate at least a portion of residual $MgSO_3$ from at least a portion of sodium bicarbonate. For example, in some embodiments, said separation may comprise, including, but not limited to, one or more or any combination of the following: electrodialysis, or selective electrodialysis, or monovalent selective electrodialysis (MSED), or divalent selective electrodialysis (DSED), or concentrating, or cooling precipitation, or reverse osmosis, or membrane based process, or nanofiltration.

(7) $MgSO_3$(s)→MgO(s)+$SO_2$(g)

Note: The thermal decomposition of magnesium sulfite may be conducted with less energy and/or at lower temperatures than the thermal decomposition of calcium sulfite.

Note: Sulfur dioxide formed may be employed, for example, in the reaction of alkali acetate or alkali carboxylate with sulfur dioxide.

(8) React Magnesium Oxide or Magnesium Hydroxide with Carbon Dioxide to Form Magnesium Carbonate MgO(s)+$CO_2$(g)→$MgCO_3$(s)

MgO(s)+$H_2O$(l or g or s)→$Mg(OH)_2$(s or aq)

$Mg(OH)_2$(s or aq)+$CO_2$(g)→$MgCO_3$(s)+$H_2O$(l or g or s)

Note: In some embodiments, the $CO_2$(g) may comprise $CO_2$(g) from the decomposition of calcium carbonate.

Note: In some embodiments, the $CO_2$(g) may comprise $CO_2$(g) from an emissions source, or point source, or air, or any combination thereof.

Note: $MgCO_3$(s) may comprise the $MgCO_3$(s) in the reaction of $MgCO_3$(s)+$CO_2$+$H_2O$.

Note: In some embodiments, carbon dioxide from the decomposition of calcium carbonate or magnesium carbonate may comprise the carbon dioxide in the reaction of magnesium oxide or magnesium hydroxide and carbon dioxide.

Note: In some embodiments, CaO(s) or MgO(s) may be reacted with water to form $Ca(OH)_2$(aq), or $Ca(OH)_2$(s or aq), or $Mg(OH)_2$(aq), or $Mg(OH)_2$(s or aq), or any combination thereof which may comprise Milk of Lime, or Milk of Magnesia, or a solid-liquid suspension comprising calcium hydroxide and/or magnesium hydroxide. In some embodiments, $Ca(OH)_2$ or $Mg(OH)_2$ may be reacted with a carbonate salt, such as sodium carbonate or sodium bicarbonate, to form $CaCO_3$ or $MgCO_3$, or may be reacted with $CO_2$ to form $CaCO_3$ or $MgCO_3$. For example, said sodium carbonate or sodium bicarbonate may comprise sodium carbonate, or sodium bicarbonate, or potassium carbonate, or potassium bicarbonate, or alkali carbonate, or alkali bicarbonate, or any combination thereof employed in or as a $CO_2$ absorption solution.

Note: In some embodiments, $CO_2$(g) may comprise $CO_2$ in or from a point source $CO_2$ emissions source. For example, $CO_2$(g) may comprise flue gas, or dilute $CO_2$, or high purity $CO_2$, or captured $CO_2$.

Note: In some embodiments, $CO_2$(g) may comprise $CO_2$ in or from air. For example, $CO_2$(g) may comprise air which may comprise at least a portion of $CO_2$ even if at a very dilute concentration. For example, calcium oxide may be capable of reacting with very low concentrations or very dilute concentrations of $CO_2$ if desired. For example, $CO_2$(g) may comprise a carbonate salt, such as sodium carbonate or potassium carbonate, wherein the carbonate may comprise carbonate originating from the reaction of carbon dioxide in the air with a sodium or potassium or other alkali salt, such as sodium hydroxide or potassium hydroxide, forming the alkali carbonate salt, and/or wherein the reaction of calcium oxide or calcium hydroxide with the alkali carbonate may result in the regeneration or formation of an alkali hydroxide or alkali oxide or other alkali salt which may be employed to absorb carbon dioxide from the air a regenerate or re-form the alkali carbonate salt.

Note: In some embodiments, $CaCO_3$ or $MgCO_3$ may comprise a valuable product. In some embodiments, $CaCO_3$ or $MgCO_3$ may comprise precipitated calcium carbonate. In some embodiments, $CaCO_3$ or $MgCO_3$ may comprise a carbon sequestration medium.

Example Description Alkaline Earth Oxide Production Systems and Methods

Description

Some embodiments of the present invention may pertain to systems and methods for producing alkaline earth oxides, or alkaline earth hydroxides, or cement, or clinker. Some embodiments of the present invention may pertain to producing alkaline earth oxides, or alkaline earth hydroxides, or cement, or clinker, which may comprise a chemical or material comprising calcium, or magnesium, or other alkaline earth.

Some embodiments may involve producing alkaline earth oxides, or alkaline earth hydroxides, or cement, or clinker using an input material comprising an alkaline-earth weak acid material. For example, in some embodiments, the alkaline-earth weak acid material may comprise a carbonate, which may include, but is not limited to, one or more or any combination of the following: calcium carbonate, or magnesium carbonate, or limestone, or calcium-magnesium carbonate, or dolomite, or any combination thereof. For example, in some embodiments, the alkaline-earth weak acid material may comprise a silicate material, which may include, but is not limited to, one or more or any combination of the following: a calcium silicate, or a magnesium silicate, or orthosilicate, or fluorosilicate, or metasilicate, or pyrosilicate, or aluminosilicate, or silicon oxide, or silicon material, or any combination thereof. In some embodiments, the alkaline-earth weak acid material may comprise a sulfide material, which may include, but is not limited to, one or more or any combination of the following: a calcium sulfide, or a magnesium sulfide, or any combination thereof. For example, in some embodiments, the alkaline-earth weak acid material may comprise a metal oxide or metal oxide derivative anion material, which may include, but is not limited to, one or more any combination of the following:

aluminate, or ferrate, ferrite, or zincate, or manganate, or clay, or permanganate. In some embodiments, the alkaline-earth weak acid material may comprise an alkaline earth metal in a compound with an anion or acid derivative or any combination thereof, wherein the anion or acid derivative may comprise a derivative or may originate from an acid with a lower acid strength or weaker acid strength than sulfur dioxide, or aqueous sulfur dioxide, or sulfurous acid, or sulfite, or any combination thereof. In some embodiments, the alkaline-earth weak acid material may comprise metal oxides or metal hydroxides which may possess overlapping or similar chemistry or similar properties to calcium, or magnesium, or other alkaline-earths. In some embodiments, the alkaline-earth weak acid material may comprise impurities. In some embodiments, the alkaline-earth weak acid material may comprise, including, but not limited to, one or more or any combination of any of the aforementioned chemistries or properties.

In some embodiments producing cement, or clinker, or any combination thereof, it may be desirable to mix clay, or silicon material, or other cement raw mix components with the alkaline earth at one or more or a combination of points in the process. For example, in some embodiments, raw mix components may be added to calcium sulfite or magnesium sulfite before or during decomposing the sulfite into sulfur dioxide. For example, in some embodiments, raw mix components may be added to calcium oxide or magnesium oxide before or during sintering or fusing to form cement or clinker.

Some embodiments may involve producing alkaline earth oxides, or alkaline earth hydroxides, or cement, or clinker, or any combination thereof using an input material comprising an alkaline-earth weak acid material. In some embodiments, the alkaline-earth weak acid material may be reacted with or mixed with an acid with an acid strength greater than the 'weak acid' and an acid strength weaker than sulfurous acid. In some embodiments, the alkaline-earth weak acid material may be reacted with or mixed with an acid with an acid strength greater than the 'weak acid' and an acid strength weaker than sulfurous acid, which may result in the formation of an aqueous solution comprising a salt comprising the alkaline earth and an anion of the acid with an acid strength greater than the 'weak acid' and an acid strength weaker than sulfurous acid. In some embodiments, the alkaline-earth weak acid material may be reacted with or mixed with an acid which displaces the weak acid from the alkaline earth or reacts with the alkaline earth. In some embodiments, the alkaline-earth weak acid material may be reacted with or mixed with an acid which displaces the weak acid from the alkaline earth or reacts with the alkaline earth, which may result in the formation of an aqueous solution comprising a salt comprising the alkaline earth and an anion of the acid which can displace the weak acid from the alkaline earth. For example, some carboxylic acids, such as formic acid, or acetic acid, or propanoic acid, may have an acid strength greater than some weak acids and weak acid derivatives, such as carbonates, or bicarbonates, or sulfides, or silicates, and/or may react with the alkaline earth weak acid material to produce an aqueous solution comprising an alkaline earth-carboxylic acid anion and/or a displaced weak acid. For example, in some embodiments, it may be desirable to react the alkaline earth-weak acid material with an acid or aqueous acid to form an aqueous alkaline earth solution. For example, in some embodiments, an alkaline-earth weak acid solid comprising calcium carbonate may be reacted with an acid comprising acetic acid, which may result in the formation of a dissolved alkaline earth-carboxylic acid anion solution comprising dissolved aqueous calcium acetate and a displaced weak acid comprising carbonic acid, or aqueous carbon dioxide, or gaseous carbon dioxide, or any combination thereof. For example, in some embodiments, an alkaline-earth weak acid solid comprising a calcium silicate may be reacted with an acid comprising acetic acid, which may result in the formation of a dissolved alkaline earth-carboxylic acid anion solution comprising dissolved aqueous calcium acetate and a displaced weak acid comprising silicon dioxide solid.

In some embodiments, the reaction of an alkaline earth weak acid with an acid may be gas evolving, or solid evolving, or liquid evolving or aqueous solution evolving, or any combination thereof. In some embodiments, the 'weak acid' may be displaced by the acid which may be stronger than the weak acid and/or weaker than sulfurous acid. In some embodiments, the weak acid may be displaced and may form a gas or aqueous solution, which may include, but it not limited to, one or more or any combination of the following: carbon dioxide, or carbonic acid, or hydrogen sulfide, or hydrosulfuric acid. In some embodiments, it may be desirable for evolved gas or gas comprising the displaced weak acid to be captured or isolated. For example, the reaction of an alkaline earth weak acid with an acid may be conducted in an environment or container such that evolved gas may pressurize, or accumulate, or be produced at a partial pressure greater than the partial pressure of the chemical in ambient air or the Earth's atmosphere. For example, the reaction of an alkaline earth weak acid with an acid may be conducted in an environment or container such that evolved gas may comprise a volumetric concentration greater than the volumetric concentration greater than the volumetric concentration of the gas in the Earth's atmosphere or ambient air. For example, a solid comprising calcium carbonate or magnesium carbonate may be reacted with acetic acid to form calcium acetate and a gas comprising carbon dioxide, wherein the reactor may be configured to enable the pressurization or accumulation of carbon dioxide gas such that the carbon dioxide gas produced is at a partial pressure, for example, greater than 0.01 Bar, or 0.1 Bar, or 0.3 Bar, or 0.5 Bar, or 0.7 Bar, or 1.0 Bar, or 2 Bar, or 3 Bar, or 4 Bar, or 5 Bar, or any combination thereof or, for example, a concentration greater than 1 vol %, or 5 vol %, or 10 vol %, or 20 vol %, or 30 vol %, or 40 vol %, or 50 vol %, or 60 vol %, or 70 vol %, or 80 vol %, or 90 vol %, or 95 vol %, or any combination thereof. In some embodiments, it may be desirable for the gas evolving reaction to be conducted in a batch configuration, due to, for example, the fast reaction kinetics and/or the ability to achieve greater evolved gas partial pressures. In some embodiments, it may be desirable for the gas evolving reaction to be conducted in a semi-continuous, or continuous fashion or configuration. In some embodiments, it may be desirable for the gas produced to be stored, or transferred, or converted, or transported, or utilized, or sequestered, or further compressed, or further treated, or any combination thereof. For example, if carbon dioxide is produced, it may be desirable to, including, but not limited to, one or more or any combination of the following: convert the carbon dioxide into a valuable product, or convert the carbon dioxide into a sequestration product, or compress the carbon dioxide, or liquefy the carbon dioxide, or turn the carbon dioxide in to a supercritical fluid, or transfer the carbon dioxide to a utilization application, or sequester the carbon dioxide, or employ the carbon dioxide in enhanced oil recovery, or any combination thereof. For example, if hydrogen sulfide is produced, it may be desirable to, including, but not limited to, one or more or any combination of the following: convert to sulfur, or employ in the Claus process, or produce heat, or combust, or produce sulfur dioxide, or produce sulfur dioxide makeup, or convert sulfate to sulfite or sulfide, or produce power, or produce steam, or produce sulfurous acid, or produce sulfuric acid, or employ in an application, or transport, or store, or any combination thereof.

In some embodiments, the reaction of an alkaline earth weak acid with an acid may be gas evolving, or solid evolving, or liquid evolving or aqueous solution evolving, or any combination thereof. In some embodiments, the 'weak acid' may be displaced by the acid which may be stronger than the weak acid and/or weaker than sulfurous acid. In some embodiments, the weak acid may be displaced and may form a solid, which may include, but it not limited to, one or more or any combination of the following: silicon dioxide, or silicon oxide, or metal oxide. For example, a calcium silicate may be reacted with acetic acid to form aqueous calcium acetate and a solid comprise silicon dioxide. The solid silicon dioxide may be separated from the aqueous calcium acetate by, for example, a solid-liquid separation. In some embodiments, the solid may be utilized. For example, silicon dioxide may be employed as an aggregate for concrete production. In some embodiments, the solid may be discarded. In some embodiments, a solid forming reaction may be desirable because, for example, a solid forming reaction may avoid, or minimize, or prevent, or reduce the potential production of and/or handling of a greenhouse gas, such as carbon dioxide, or a relatively toxic gas, such as hydrogen sulfide. A solid forming reaction may enable the production of calcium oxide or cement while potentially reducing, or preventing the co-production of carbon dioxide.

The aqueous alkaline earth cation-acid anion salt solution may be reacted with sulfur dioxide gas, or sulfurous acid, or dissolved sulfur dioxide, or any combination thereof to produce, for example, an alkaline earth cation-sulfite anion salt and/or an acid. In some embodiments, the alkaline earth cation-sulfite may be produced mostly as a solid precipitate, while the acid may comprise an aqueous solution. For example, in some embodiments, the produced the alkaline earth cation-sulfite may comprise a solid which may be separated from the aqueous acid by a solid-liquid separation system or method. In some embodiments, residual dissolved alkaline earth cation-sulfite may be present in the aqueous acid. In some embodiments, said residual dissolved alkaline earth cation-sulfite may remain present in the aqueous acid while, for example, the aqueous acid is recirculated or recycled in the process. In some embodiments, a portion of said residual dissolved alkaline earth cation-sulfite may be recovered or precipitated, using, for example, including, but not limited to, one or more or any combination of the following: cooling, or reverse osmosis concentrating, or nanofiltration concentration, or electrodialysis, or electrodialysis reversal, or precipitation, or evaporation. For example, in some embodiments employing calcium sulfite, calcium sulfite may be sufficiently insoluble where it may be less desirable or undesirable to recover residual dissolved calcium sulfite from the aqueous acid solution. For example, in some embodiments employing magnesium sulfite, magnesium sulfite may be sufficiently soluble where it may be desirable to recover residual dissolved magnesium sulfite from the aqueous acid solution.

In some embodiments, aqueous alkaline earth cation-acid anion salt solution may be reacted with a gas comprising sulfur dioxide to produce an alkaline earth cation-sulfite anion salt and an acid. In some embodiments, the alkaline earth cation-sulfite anion salt may comprise a solid. In some embodiments, the acid may comprise an aqueous solution. In some embodiments, sulfur dioxide gas may be at a dilute concentration in the gas comprising sulfur dioxide. In some embodiments, if the sulfur dioxide gas forms from the decomposition of calcium sulfite, it may be desirable for the concentration of sulfur dioxide gas to be dilute because, for example, the decomposition temperature and the decomposition rate may have a relationship with the concentration or partial pressure of sulfur dioxide gas formed, wherein, for example, the lower the concentration or partial pressure of sulfur dioxide gas formed the higher the rate of calcium sulfite decomposition and/or the lower the required temperature to decompose the calcium sulfite. For example, in some embodiments, a dilute concentration of sulfur dioxide gas may comprise a concentration lower than 1 vol %, or 5 vol %, or 10 vol %, or 20 vol %, or 30 vol %, or 40 vol %, or 50 vol %, or 60 vol %, or 70 vol %, or 80 vol %, or 90 vol %, or 100 vol %, or any combination thereof. For example, in some embodiments, a dilute concentration of sulfur dioxide gas may comprise a sulfur dioxide gas partial pressure lower than 0.01 Bar, or 0.05 Bar, or 0.1 Bar, or 0.2 Bar, or 0.3 Bar, or 0.4 Bar, or 0.5 Bar, or 0.6 Bar, or 0.7 Bar, or 0.8 Bar, or 0.9 Bar, or 1.0 Bar, or any combination thereof. In some embodiments, sulfur dioxide gas may be at a high concentration in the gas comprising sulfur dioxide. For example, in some embodiments, a high concentration of sulfur dioxide gas may comprise a concentration greater than 1 vol %, or 5 vol %, or 10 vol %, or 20 vol %, or 30 vol %, or 40 vol %, or 50 vol %, or 60 vol %, or 70 vol %, or 80 vol %, or 90 vol %, or 100 vol %, or any combination thereof. For example, in some embodiments, a high concentration of sulfur dioxide gas may comprise a sulfur dioxide gas partial pressure greater than 0.01 Bar, or 0.05 Bar, or 0.1 Bar, or 0.2 Bar, or 0.3 Bar, or 0.4 Bar, or 0.5 Bar, or 0.6 Bar, or 0.7 Bar, or 0.8 Bar, or 0.9 Bar, or 1.0 Bar, or 2.0 Bar, or 3.0 Bar, or 4.0 Bar, or 5.0 Bar, or any combination thereof.

In some embodiments, the reaction of a gas comprising sulfur dioxide with a solid or aqueous alkaline earth cation-acid anion salt may be conducted in a gas liquid contactor. For example, the reaction of a gas comprising sulfur dioxide with an aqueous alkaline earth cation-acid anion salt may be conducted in a gas-liquid contactor, which may include, but is not limited to, one or more or any combination of the following: an absorption column, or a spray tower, or bubble column, or a static mixer, or a mixer, or a sparger, or a membrane contactor, or packed column, or a plate column, or a disc column, or a column, or a precipitator. In some embodiments, it may be desirable for the reaction of a gas comprising sulfur dioxide with an aqueous alkaline earth cation-acid anion salt to be conducted in a reactor configured to handle precipitate or solid formation. For example, in some embodiments, it may be desirable for the reaction of a gas comprising sulfur dioxide with an aqueous alkaline earth cation-acid anion salt to be conducted in a bubble column or a sparger. In some embodiments, the formed alkaline earth sulfite, which may comprise a solid, may settle or may otherwise be separated by a solid-liquid separation from the aqueous acid solution. In some embodiments, the formed alkaline earth sulfite may settle within the reactor. In some embodiments, the formed alkaline earth sulfite may remain suspended within the reactor and/or may be separated from the aqueous acid solution after the mixture is transferred from the reactor. In some embodiments, the reactor may comprise a batch, or semi-batch, or continuous, or any combination thereof operation or configuration. In some embodiments, the solid phase formation reaction may enable fast reaction kinetics and/or high absorption or reaction efficiency due to, for example, the lack of accumulation of sulfur dioxide or sulfite ion in the aqueous phase. In some embodiments, an aqueous calcium acetate solution may be contacted with a gas comprise sulfur dioxide, which may result in the formation of solid calcium sulfite precipitate and an aqueous solution comprising acetic acid. The aqueous acetic acid may be separated from the solid calcium sulfite precipitate by a solid-liquid separation.

In some embodiments, the reaction of an alkaline earth cation-acid anion salt with sulfur dioxide may form an alkaline earth sulfite and an acid, wherein said formed acid may possess a vapor pressure. For example, the reaction of calcium acetate with sulfur dioxide may form calcium sulfite and acetic acid, wherein acetic acid may possess a vapor pressure. In some embodiments, it may be desirable to minimize or prevent losses of acid due to release of acid vapor, or carryover or slip of acid vapor, or any combination thereof.

For example, in some embodiments, if a gas stream comprising sulfur dioxide comprises other gases or comprises dilute sulfur dioxide, acid vapor may be present in the remaining gases during or after the reaction of sulfur dioxide with an alkaline earth acid and the formation of acid and alkaline earth sulfite. For example, in some embodiments, as a dilute sulfur dioxide gas is contacted with an alkaline earth acid, sulfur dioxide may react or absorb to form alkaline earth sulfite and/or an acid, wherein a portion of the formed acid may evaporate as acid vapor or acid vapor pressure into the remaining gases. In some embodiments, for example, it may be desirable to design a sulfur dioxide absorption column or absorption process to contact a solution comprising alkaline earth acid with the gas lean in sulfur dioxide and rich in acid vapor. For example, in some embodiments, aqueous solution comprising alkaline earth acid entering an absorption process, which may not have substantially reacted with sulfur dioxide, may comprise little free acid or acid unreacted with alkaline earth or may comprise solution with the least, or near lowest, or lowest concentration or vapor pressure. For example, in some embodiments, a sulfur dioxide absorption may be configured such that first, a gas rich in sulfur dioxide and lean in acid vapor is contacted with a solution comprising alkaline earth acid to form alkaline earth sulfite and an aqueous solution comprising an acid and a gas lean in sulfur dioxide and rich in acid vapor, then, second, the gas lean in sulfur dioxide and rich in acid vapor may be contacted with solution comprising alkaline earth acid which is lean in aqueous acid or free acid, absorbing at least a portion of the acid vapor and forming a solution comprising alkaline earth acid relatively rich in aqueous acid or free acid and a gas lean in sulfur dioxide and lean in acid vapor. For example, in some embodiments, an aqueous solution comprising alkaline earth acid may be first contacted with a gas rich in acid vapor and lean in sulfur dioxide, which may result in the absorption of acid vapor and the formation of a solution comprising aqueous alkaline earth acid relatively rich in in dissolved acid or free acid; then, second, the aqueous alkaline earth acid relatively rich in absorbed acid or free acid may be contacted with a gas rich in sulfur dioxide and lean in acid vapor to form alkaline earth sulfite and a solution comprising aqueous acid. For example, some embodiments may utilize the inherently low concentration of acid, or low acid vapor pressure, or any combination thereof of some solutions comprising alkaline earth acid to absorb acid vapor. In some embodiments, it may be desirable to contact gas comprising acid vapor and/or absorb acid vapor into a solution comprising alkaline earth acid, for example, substantially before reacting the alkaline earth acid with sulfur dioxide because, for example, the reaction of alkaline earth acid with sulfur dioxide may produce acid or free acid and/or increase the solution's acid vapor pressure. For example, in some embodiments, an aqueous solution comprising calcium acetate may be first contacted with a gas comprising remaining gases and/or acetic acid vapor, which may result in the formation of an aqueous solution comprising calcium acetate with dissolved or absorbed acetic acid vapor and/or a gas comprising remaining gases comprising a lower concentration of acetic acid vapor. For example, in some embodiments, the aqueous solution comprising calcium acetate with dissolved or absorbed acetic acid vapor may be then, second, contacted with a gas comprising sulfur dioxide, which may result in the formation of calcium sulfite and an aqueous solution comprising acetic acid. For example, in some embodiments, the aqueous solution comprising calcium may enter the process at the first step, then may be transferred into the second step, then may exit the process at or after the second step. For example, in some embodiments, the gas may enter the process at the second step, then may be transferred into the first step, then may exit the process at or after the first step.

For example, in some embodiments, a sulfur dioxide absorption process with acid vapor recovery or removal may comprise an absorption column, wherein a higher elevation portion of the column, or the 'top portion', may comprise absorbing acid vapor into the alkaline acid salt solution to form alkaline acid salt solution with dissolved acid vapor, and then the lower elevation portion of the column, or 'bottom portion', may comprise absorbing or reacting sulfur dioxide into the alkaline acid salt solution with dissolved acid vapor transferred from the higher elevation portion of the column. For example, in some embodiments, a gas comprising sulfur dioxide may enter the absorption process in the bottom portion of the absorption column and/or the remaining gases after sulfur dioxide absorption may exit the top portion of the absorption column.

For example, in some embodiments, a sulfur dioxide absorption process with acid vapor recovery may comprise at least two absorption steps, comprising a first absorption step and a second absorption step. The first absorption step may be configured to absorb acid vapor slip or carryover. The second absorption step may be configured to absorb sulfur dioxide. An aqueous solution comprising an alkaline earth acid may enter the absorption process in the first absorption step, then may be transferred into the second absorption step, and then may exit the second absorption step as a solid comprising an alkaline earth sulfite and an aqueous solution comprising an acid. A gas comprising sulfur dioxide may enter the absorption process in the second absorption step, then may be transferred into the first absorption step, and then may exit the first absorption step as a gas lean in sulfur dioxide. In the second absorption step, a gas comprising sulfur dioxide may be reacted with an aqueous solution comprising an alkaline earth acid and absorbed acid vapor, wherein a solution comprising alkaline earth acid and absorbed acid vapor may enter the second absorption step and then exit as a solid comprising alkaline earth sulfite and an aqueous solution comprising an acid; and/or wherein a gas comprising sulfur dioxide may enter the second absorption step and then exit as a gas comprising remaining gases and acid vapor. In some embodiments, gas may enter the second absorption step near the bottom of the absorption step and/or liquid or solution may enter the second absorption step near the top of the absorption step. In the first absorption step, a gas comprising remaining gases and acid vapor may be contacted with an aqueous solution comprising an alkaline earth acid, wherein a solution comprising alkaline earth acid may enter the first absorption step and exit as a solution comprising an alkaline earth acid and absorbed acid vapor; and/or wherein a gas comprising remaining gases and acid vapor may enter the first absorption step and exit as a gas comprising remaining gases with a lower concentration of acid vapor. In some embodiments, gas may enter the first absorption step near the bottom of the absorption step and/or liquid or solution may enter the first absorption step near the top of the absorption column. In some embodiments, remaining gases may comprise unabsorbed gases, or gases remaining after absorption, or gases exiting an absorption process, or gases exiting an adsorption process, or any combination thereof.

For example, in some embodiments, alkaline earth acid may be reacted with high pressure, or high purity, or liquid, or aqueous, or solid, or any combination thereof sulfur dioxide. For example, in some embodiments, acid vapor release, or slip, or production may be prevented by employing, for example, high pressure, or high purity, or liquid, or aqueous, or solid, or any combination thereof sulfur dioxide in the reaction of alkaline earth acid with sulfur dioxide. For example, in some embodiments, by employing high pressure, or high purity, or liquid, or aqueous, or solid, or any combination thereof sulfur dioxide in the reaction of alkaline earth acid and sulfur dioxide, a lower proportion of acid vapor may evaporate or form. In some embodiments, for example, an aqueous solution comprising calcium acetate may be reacted with liquid sulfur dioxide, which may result in the formation of a solid comprising calcium sulfite and an aqueous solution comprising acetic acid and/or minimal remaining gases, if any, into which a portion acetic acid may evaporate.

For example, in some embodiments, acid vapor may be removed or further removed from a gas comprising acid vapor, or acid vapor slip, or acid vapor carryover, or any combination thereof by, for example, contacting or reacting said gas with an alkali hydroxide, or alkali carbonate, alkali-weak acid or an alkaline earth oxide, or alkaline earth hydroxide, or alkaline earth carbonate, or alkaline earth-weak acid, or ammonium hydroxide, or ammonium carbonate, or a bicarbonate, or an ammonium-weak acid, or any combination thereof to form, for example, an alkali acid, or alkaline earth-acid, or ammonium-acid, or any combination thereof. In some embodiments, alkali acid, or alkaline earth-acid, or ammonium-acid, or any combination thereof may be, for example, added to a process, or a process described herein employing alkali acid, or alkaline earth-acid, or ammonium-acid, or any combination thereof.

For example, in some embodiments, water produced or sourced without or with a low concentration of dissolved acid, or a low vapor pressure of acid, or a vapor pressure of acid lower than the vapor pressure of acid in a gas, or any combination thereof may be employed to absorb at least a portion of acid vapor from a gas. For example, in some embodiments, water added to the process as makeup water, or to makeup for water removed from the process in aqueous solutions exiting the process, or water added in the nature of process operations, or any combination thereof may be contacted with gas comprising acid vapor to remove or absorb at least a portion of acid vapor.

For example, in some embodiments, a portion of acid vapor may be recovered or absorbed by contacting remaining gases comprising acid vapor with a solvent with which the acid vapor is soluble. In some embodiments, it may be desirable for the solvent to enable or allow for the separation or regeneration of absorbed acid and/or solvent and/or may enable or allow for the separation of the acid from the solvent after absorption of the acid vapor into the solvent. In some embodiments, the solvent may comprise a liquid with a significantly lower vapor pressure, or significantly lower vapor pressure of the acid, or higher boiling point, or any combination thereof than the acid, or remaining gases comprising acid vapor, or any combination thereof. For example, in some embodiments, remaining gases comprising acid vapor comprising acetic acid may be contacted with a solvent comprising, including, but not limited to, one or more or any combination thereof: a glycol, or glycol ether, or glycol polymer, or glycol ether polymer, or an ester, or any combination thereof. For example, in some embodiments, it may be desirable for the absorbed acid to be regenerated or desorbed from the solvent by heating, or stripping, or steam stripping, or distillation, or fractional distillation. In some embodiments, it may be desirable to absorb acid vapor into water. In some embodiments, it may be desirable to absorb acid vapor into a solvent from which the acid may be separated by extractive distillation, or azeotropic distillation, or melt separation, or pressure swing, or electrical method, or other separation method described herein, or a separation method in the art. In some embodiments, it may be desirable to absorb acid vapor into a solvent from which the acid may be separated by a separation method described herein, or a separation method in the art, or any combination thereof. In some embodiments, it may be desirable to absorb and concentrate the acid in the solvent, which may result in a partially separated acid, or a concentrated acid solution.

For example, in some embodiments, acid vapor may be adsorbed to a solid or adsorbent with which the acid vapor has affinity. For example, in some embodiments, acid vapor may be adsorbed to a solid or adsorbent with which the acid vapor has affinity and from which the adsorbed acid may be separated. For example, in some embodiments, acid may be regenerated or separated from an adsorbent by heat, or stripping, or steam stripping, or electrical method, or pressure swing, or any combination thereof.

For example, in some embodiments, acid vapor may be separated or recovered by cryogenic separation, or cooling, or condensing, or absorbing in a cooled solution, or liquefaction, or deposition, or any combination thereof.

In some embodiments, a solid or aqueous alkaline earth cation-acid anion salt may be reacted with an aqueous solution comprising aqueous sulfur dioxide, or aqueous sulfurous acid, or any combination thereof. In some embodiments, the aqueous sulfur dioxide, or aqueous sulfurous acid, or any combination thereof may comprise a solution comprising sulfur dioxide and water, with lower than 5 wt % other chemicals. In some embodiment, the aqueous sulfur dioxide, or aqueous sulfurous acid, or any combination thereof may comprise a solution comprising sulfur dioxide and water, with greater than 5 wt % other chemicals. In some embodiments, the aqueous sulfur dioxide, or aqueous sulfurous acid, or any combination thereof may comprise a solution comprising aqueous sulfur dioxide and another acid. For example, in some embodiments, the aqueous sulfur dioxide, or aqueous sulfurous acid, or any combination thereof may further comprise acetic acid. In some embodiments, an aqueous alkaline earth cation-acid anion salt may be reacted with an aqueous solution comprising aqueous sulfur dioxide, or aqueous sulfurous acid, or any combination thereof, which may result in the formation of an alkaline earth sulfite, which may comprise a solid or solid precipitate, and an aqueous acid. The alkaline earth sulfite solid may be separated from the aqueous acid in a solid-liquid separation. For example, a solution comprising calcium acetate may be reacted with an aqueous solution comprising sulfur dioxide, which may result in the formation of solid calcium sulfite and aqueous acetic acid. The aqueous acetic acid may be separated from the solid calcium sulfite by a solid-liquid separation. In some embodiments, the reactor may comprise a batch, or semi-batch, or continuous, or any combination thereof operation or configuration. In some embodiments, the acid may need to be further concentrated or water removed to make up for, for example, any water added or dilution of the acid during the reaction with aqueous sulfur dioxide. In some embodiments, the acid formed from the reaction, or concentrating, or any combination thereof may comprise an aqueous solution, a solid, or a liquid, or any combination thereof.

In some embodiments, a solid or aqueous alkaline earth cation-acid anion salt may be reacted with liquid sulfur dioxide, or solid sulfur dioxide, or supercritical sulfur dioxide, or any combination thereof.

In some embodiments, a solid or aqueous alkaline earth cation-acid anion salt may be reacted with a solid or aqueous alkali sulfite. In some embodiments, a solid or aqueous alkaline earth cation-acid anion salt may be reacted with a solid or aqueous alkali sulfite, which may result in the formation of an alkaline earth sulfite, which may comprise a solid, and an alkali cation-acid anion salt, which may comprise an aqueous salt or dissolved salt. In some embodiments, an aqueous solution comprising alkali cation-acid anion salt may be separated from the alkaline earth sulfite solid using, for example, a solid-liquid separation. In some embodiments, the reaction may comprise mixing an aqueous solution comprising an alkali sulfite with an aqueous solution comprising an alkaline earth cation-acid anion salt, which may result in forming an alkaline earth sulfite precipitate. It may be desirable to conduct the reaction in a mixing reactor, or mixer, or continuous mixer, or continuous stirred reactor, or any combination thereof because, for example, the reaction may possess relatively fast reaction kinetics. The rate of solid formation, or the location of solid formation, or the rate of production of reaction products, or any combination thereof may be controlled due to, for example, the input reagents being at a liquid phase.

In some embodiments, it may be desirable to react the solution comprising an alkaline earth cation-acid anion salt with a salt comprising a sulfite. In some embodiments, it may be desirable to react the solution comprising an alkaline earth cation-acid anion salt with a salt comprising a sulfite because, for example, the absorption of sulfur dioxide gas may be conducted at a gas or liquid phase and/or may be separate from a solid formation step, which may avoid challenges related to solid handling in a gas absorbing environment. In some embodiments it may be desirable to react the solution comprising an alkaline earth cation-acid anion salt with a salt comprising a sulfite to enable fast reaction kinetics and/or easier or more controlled solid-liquid separation and/or faster solid-liquid separation. In some embodiments, a solution comprising an alkaline earth cation-acid anion salt may be reacted with an alkali sulfite, which may result in the formation of an alkaline earth sulfite and an alkali acid. In some embodiments, the alkaline earth sulfite which forms may comprise a solid.

In some embodiments, for example, an aqueous calcium acetate solution may be mixed with an aqueous sodium sulfite solution, or solid sodium sulfite, or any combination thereof, which may result in the formation of aqueous sodium acetate and solid calcium sulfite. Some embodiments may involve employing a cation or base which forms soluble salts with the sulfite and/or the acid. For example, some embodiments may employ ammonia or ammonium. In some embodiments, for example, an aqueous calcium acetate solution may be mixed with an aqueous ammonium sulfite solution, or solid ammonium sulfite, or any combination thereof, which may result in the formation of solution comprising aqueous ammonium acetate and a solid comprising calcium sulfite.

In some embodiments, an alkaline earth sulfite may be thermally decomposed or thermally converted. In some embodiments, an alkaline earth sulfite may be thermally decomposed in an alkaline earth oxide and sulfur dioxide gas. For example, in some embodiments, calcium sulfite may be thermally decomposed into calcium oxide and sulfur dioxide gas. For example, in some embodiments, calcium sulfite may, in the presence of other raw mix materials, be thermally converted into clinker or cement. The thermal conversion or decomposition of an alkaline earth sulfite may be conducted in, for example, a calciner or kiln. It may be desirable for the thermal conversion or decomposition to be conducted in a low oxygen environment, or to be conducted at a desirable temperature range, or any combination thereof.

In some embodiments, alkaline earth sulfite may be wet, or comprise hydrated alkaline earth sulfite, or any combination thereof. In some embodiments, it may be desirable to dry, or de-wet, or dehydrate, or any combination thereof the alkaline earth sulfite. For example, in some embodiments, alkaline earth oxide, which may be produced by the process, may be employed as a desiccant to indirectly dry or remove water from the alkaline earth sulfite and/or produce alkaline earth hydroxide. For example, in some embodiments, a gas, such as an inert gas or nitrogen gas, may be circulated between contacting the alkaline earth sulfite and the alkaline earth oxide, wherein, for example, water vapor and/or heat may be transferred from the alkaline earth sulfite to the alkaline earth oxide. In some embodiments, residual heat from the alkaline earth oxide and/or clinker may be employed to facilitate the drying of the alkaline earth sulfite. In some embodiments, waste heat may be employed facilitate the drying of the alkaline earth sulfite. In some embodiments, heat from the reaction of alkaline earth oxide and water to form alkaline earth hydroxide may be employed to facilitate the drying of the alkaline earth sulfite. In some embodiments, a kiln, or heater, or preheater, or any combination thereof, which may be desired to facilitate the dehydration of alkaline earth sulfite or the liberation of water from alkaline earth sulfite, may be employed to dry or dehydrate the alkaline earth sulfite. In some embodiments, a heat pump may be employed to facilitate the drying of an alkaline earth sulfite. In some embodiments, it may be desirable to dry the alkaline earth sulfite in a low oxygen environment, to, for example, prevent or inhibit the oxidation of alkaline earth sulfite, or the formation of alkaline earth sulfate, or any combination thereof. In some embodiments, the temperature of heat required for dehydrating an alkaline earth sulfite may be substantially lower than the temperature of heat required to thermally decompose an alkaline earth sulfite into an alkaline earth oxide and sulfur dioxide. It may be desirable to employ potentially lower cost sources of heat or energy to dry and/or dehydrate alkaline earth sulfite. For example, it may be desirable to employ a heat pump, or waste heat, or solar heat, or recovered heat, or any combination thereof as a heat source or energy source for the thermal decomposition of an alkaline earth sulfite.

In some embodiments, alkaline earth oxide may be reacted with water or water vapor to produce an alkaline earth hydroxide. For example, in some embodiments, the reaction of alkaline earth oxide with water may produce an alkaline earth hydroxide suspension, or milk of lime, or milk of magnesia, or an alkaline earth hydroxide solid, or an aqueous dissolved alkaline earth hydroxide or any combination thereof. In some embodiments, the reaction of alkaline earth oxide with water may produce heat and/or said heat may be utilized or employed productively, which may include, but is not limited to, employing said heat in drying, or dehydration, or preheating, or heating, or any combination thereof. In some embodiments, alkaline earth oxide or alkaline earth hydroxide may be reacted with carbon dioxide to produce calcium carbonate, or precipitated calcium carbonate, or high purity calcium carbonate, or any combination thereof. In some embodiments, alkaline earth oxide or alkaline earth hydroxide may be reacted with carbon dioxide to capture or remove carbon dioxide from one or more or any combination of gas sources, which may include, but is not limited to, one or more or any combination of the following: air, or combustion flue gases, or other gas described herein, or other gas comprising carbon dioxide.

In some embodiments, alkaline earth, or alkaline earth sulfite, or alkaline earth oxide, or any combination thereof may be in the presence of or may be mixed with other raw mix materials to produce cement, or clinker, or any combination thereof. In some embodiments, the alkaline earth sulfite may be thermally decomposed into a solid comprising alkaline earth oxide and then the alkaline earth oxide may be mixed with other raw mix materials and sintered in a cement kiln to produce clinker or cement. In some embodiments, the alkaline earth sulfite may be thermally decomposed and/or sintered in a mixture with or in the presence of other raw mix materials to produce cement, or clinker, or any combination thereof. Raw mix materials may vary depending on, for example, including, but not limited to, one or more or any combination of the following: the desired properties of the cement or clinker, or the available materials, or the composition of input alkaline earth materials, or the composition of input alkaline earth-weak acid materials.

In some embodiments, alkaline earth sulfite may be thermally decomposed or thermally converted. In some embodiments, alkaline earth sulfite may be thermally decomposed into a material comprising an alkaline earth oxide and a gas comprising sulfur dioxide. In some embodiments, the thermal decomposition or thermal conversion may be conducted in a kiln, or a calciner, or any combination thereof. In some embodiments, the kiln or calciner may comprise a multistage kiln or calciner. For example, in some embodiments, the kiln or calciner may include a preheating/precooling stage, a calcining stage, and a precooling/preheating stage. For example, in some embodiments, the kiln or calciner may include a preheating/precooling stage, a calcining stage, a sintering stage, and a precooling/preheating stage. In some embodiments, the kiln or calciner may be powered or heated by one or more or any combination of energy sources, which include, but are not limited to, one or more or any combination of the following: heat, or electricity, or combustion of fuels. In some embodiments, the thermal reaction of alkaline earth sulfite to alkaline earth oxide may be sensitive to the conditions. It may be desirable to adjust or optimize conditions to, for example, facilitate formation of alkaline earth oxide and sulfur dioxide and/or prevent the formation of alkaline earth sulfate, or alkaline earth sulfide, or sulfur. For example, conditions may include, but are not limited to, one or more or any combination of the following: temperature, or pressure, or residence time, or gas composition, or heat carrying gas composition, or heat carrying gas flow characteristics, or employing indirect heating, or employ direct heating, or heat transfer method, or gas partial pressures, or particle size, or turbulence. In some embodiments, it may be desirable to reduce or minimize exposure to dissolved oxygen, or oxygen gas, or diatomic oxygen, or any combination thereof, to, for example, inhibit the formation of alkaline earth sulfate. In some embodiments, it may be desirable to decompose in a carbon dioxide rich atmosphere or gas phase. In some embodiments, it may be desirable to employ a recirculating carrier gas. In some embodiments, it may be desirable to employ a recirculating carrier gas, which may comprise an inert gas, or carbon dioxide, or nitrogen, or any combination thereof. In some embodiments, it may be desirable to reduce or minimize the concentration of carbon monoxide. In some embodiments, it may be desirable to employ combustion gases or flue gases as a heat transfer or heat carrying medium. In some embodiments, it may be desirable to employ indirect heating. In some embodiments, it may be desirable to heat the walls of a kiln or calciner to facilitate the heating or decomposition of the alkaline earth sulfite. In some embodiments, it may be desirable to employ sulfur dioxide as a recirculating carrier gas. In some embodiments, the kiln or calciner configuration may include, but is not limited to, one or more or any combination of the following: rotating kiln, or vertical shaft kiln, or flare kiln, or draw kiln, or shaft kiln, or Counter-current shaft kiln, or Regenerative kiln, or Annular kilns, or a pyroprocessing device. In some embodiments, kilns or calciners may emplou electrostatic precipitators, or bag filters, or other emissions control device to, for example, separate or remove potential air pollutants and/or gas contaminents. It may be desirable for the kiln, or calciner, or overall process, or any combination thereof to employ one or more or a combination of heat recovery, or heat transfer, or heat exchange, or any combination thereof to optimize energy efficiency and performance.

In some embodiments, sulfur dioxide may be produced from the decomposition of alkaline earth sulfite. In some embodiments, at least a portion of the sulfur dioxide may be absorbed into an aqueous solution. In some embodiments, at least a portion of the sulfur dioxide may be absorbed into water. In some embodiments, at least a portion of the sulfur dioxide may be absorbed into a solution comprising an alkaline earth-acid, which may result in the formation of an alkaline earth sulfite and/or an acid. In some embodiments, at least a portion of the alkaline earth sulfite may precipitate during or after the reaction of the sulfur dioxide with the alkaline earth-acid. In some embodiments, at least a portion of the sulfur dioxide may be absorbed into a solution comprising an alkali-acid, which may result in the formation of an alkali sulfite and/or an acid. In some embodiments, the alkali sulfite may remain at an aqueous phase in the absorption device or absorption column. In some embodiments, at least a portion of the alkali sulfite may precipitate during or after the reaction of the sulfur dioxide with the alkali-acid. In some embodiments, at least a portion of the alkali sulfite may be separated from the acid during or after the reaction of the sulfur dioxide with the alkali-acid. In some embodiments, at least a portion of the solution comprising alkali sulfite may be concentrated or evaporated or cooled or heated or treated, which may resulting in the precipitation or crystallization of at least a portion of alkali sulfite. In some embodiments, the sulfur dioxide may comprise a gas comprising sulfur dioxide. In some embodiments, the sulfur dioxide may comprise a relatively dilute concentration of sulfur dioxide in a gas comprising sulfur dioxide. In some embodiments, it may be desirable for the process to react or absorb the sulfur dioxide to be capable of recovering sulfur dioxide from a relatively low or dilute concentration of sulfur dioxide. In some embodiments, it may be desirable for the gases other than sulfur dioxide to comprise relatively inert gases. For example, sulfur dioxide may react with a salt, or an alkaline earth-acid salt, or alkali-acid salt, or any combination thereof in the presence of an inert gas. For example, in some embodiments, an inert gas may comprise a relatively non-reactive gas, such as diatomic nitrogen or argon. For example, in some embodiments, at certain concentrations or in some instances, diatomic oxygen may be considered a relatively inert gas due to, for example, its relatively low solubility in water compared to sulfur dioxide. In some embodiments, carbon dioxide may be an inert gas because, for example, sulfur dioxide may react with an alkaline earth-acid salt, or an alkali-acid salt, or any combination thereof in the presence of carbon dioxide, or because carbonic acid may be a weaker acid than the 'acid', or any combination thereof. For example, an aqueous solution of calcium acetate contacted with a gas comprising sulfur dioxide and carbon dioxide may react to form calcium sulfite and/or the carbon dioxide gas may remain substantially unreacted due to, for example, carbonic acid comprising a weaker acid than acetic acid and/or due to the relatively low solubility of carbon dioxide compared to sulfur dioxide. For example, an aqueous solution of sodium acetate contacted with a gas comprising sulfur dioxide and carbon dioxide may react to form sodium sulfite and/or the carbon dioxide gas may remain substantially unreacted due to, for example, carbonic acid comprising a weaker acid than acetic acid and/or due to the relatively low solubility of carbon dioxide compared to sulfur dioxide. It is important to note, however, that in some embodiments, sulfur trioxide or sulfuric acid may be present in the gas comprising sulfur dioxide, wherein sulfur trioxide or sulfuric acid may comprise reactive gases and/or may not be inert.

In some embodiments, a solution comprising an alkali acid salt may be contacted with or reacted with a gas or liquid comprising sulfur dioxide. In some embodiments, a gas comprising sulfur dioxide may be absorbed in a solution comprising alkali acid salt. In some embodiments, a solution comprising an alkali acid salt may be contacted with sulfur dioxide in a gas-liquid contactor, which may include, but is not limited to, one or more or any combination of the following: an absorption column, or a bubble column, or a mixer, or a membrane contactor, or any combination thereof. In some embodiments, it may be desirable for the reaction of sulfur dioxide with an alkali acid salt to form an alkali sulfite and an acid to result in products which mostly at an aqueous phase or liquid phase within the reactor. For example, an alkali acid salt solution comprising sodium acetate may be reacted with a gas comprising sulfur dioxide, which may result in the formation of sodium sulfite and acetic acid. Sodium sulfite may be soluble in water and/or form at an aqueous phase. In some embodiments, it may be desirable for the alkali sulfite to remain at least a portion at an aqueous phase in the absorber or reactor. In some embodiments, it may be desirable for a portion of the alkali sulfite to precipitate in the absorber or reactor. In some embodiments, it may be desirable for the alkali sulfite to remain at an aqueous phase in the absorber or reactor, then crystalized or precipitated in a subsequent separation of the alkali sulfite and the acid. In some embodiments, it may be desirable for the alkali sulfite to remain at an aqueous phase. In some embodiments, alkali acid may be reacted with aqueous sulfur dioxide or sulfurous acid. In some embodiments, if the alkali acid may reacted with a solution comprising aqueous sulfur dioxide, excess water or aqueous acid removal or recovery may be required.

In some embodiments, an aqueous solution comprising alkali sulfite and an acid may be separated into alkali sulfite solid, water, and an acid. In some embodiments, an aqueous solution comprising alkali sulfite and an acid may be separated into alkali sulfite solid and an aqueous acid. In some embodiments, an aqueous solution comprising alkali sulfite and an acid may be separated into alkali sulfite solid, water, and an acid, which may comprise a liquid acid, or solid acid, or aqueous acid, or any combination thereof. In some embodiments, an aqueous solution comprising alkali sulfite and an acid may be separated into alkali sulfite solid, and an aqueous acid. For example, an aqueous solution comprising sodium sulfite and acetic acid may be separated into sodium sulfite solid and aqueous acetic acid, or gaseous acetic acid, or water vapor, or any combination thereof. For example, in some embodiments, an aqueous alkali sulfite may be separated from an aqueous acid by evaporation and/or crystallization and/or precipitation. In some embodiments, the acid may be more soluble in water than the alkali sulfite. In some embodiments, the acid may possess a vapor pressure and/or make be evaporated or distilled For example, acetic acid may possess greater solubility in water than sodium sulfite. For example, water and/or acetic acid may be evaporated from a solution comprising sodium sulfite and acetic acid, and/or sodium sulfite may crystallize or precipitate, while acetic acid may remain at an aqueous phase, or at a liquid phase, or may vaporize or evaporate, or may vaporize or evaporate simultaneous to water, or any combination thereof. Sodium sulfite solid may be separated from the liquid by solid-liquid separation, which may include, but is not limited to, one or more or any combination of the following: a filter, or a decanter, or a settler, or a gravity based separation method, or a centrifuge, or a press, or a belt press or a rotary filter. For example, acetic acid may possess a lower melting point temperature than sodium sulfite. For example, water may be evaporated from a solution comprising sodium sulfite and acetic acid, and/or sodium sulfite may crystallize or precipitate, while acetic acid may exist at a liquid phase. In some embodiments, the solution may be preconcentrated by an energy efficient water separation method, then concentrated or crystalized using an evaporator or crystallizer. For example, the solution may be preconcentrated or concentrated using energy efficient methods, which may include, but are not limited to, one or more or any combination of the following: Reverse Osmosis, or Nanofiltration, or Forward Osmosis, or Membrane Based Process, or Multistage Flash Distillation, or Multi-Effect Distillation, or Mechanical Vapor Compression Distillation, or Electrodialysis Reversal, or Electrodialysis, or Membrane Distillation, or Evaporator, or Crystallizer, or Falling-Film Evaporator, or other separation methods described herein, or separation methods in the art. In some embodiments, a concentrated solution comprising sodium sulfite and/or acetic acid may be separated by evaporating water and/or crystallizing or precipitating sodium sulfite solid. In some embodiments, the solution comprising an alkali sulfite and an acid may be sufficiently concentrated for energy efficient use in an evaporator or crystallizer. In some embodiments, it may be desirable to employ energy efficient crystallizers, such as crystallizers with heat recovery. For example, energy efficient evaporators or crystallizers may include, but are not limited to, one or more or any combination of the following: falling film evaporators, or heat recovery evaporators, or mechanical vapor compression distillation, or mechanical vapor compression evaporator, or distillation, or forced-circulation crystallizer.

In some embodiments, a solution comprising alkali sulfite and an acid may be at least partially separated by reverse osmosis (RO), or nanofiltration (NF), or any combination thereof. For example, acetic acid may be at least partially separated from sodium sulfite using RO or NF due to, for example, the hydration radius of sodium sulfite being greater than the hydration radius of acetic acid, which may enable acetic acid to permeate the membrane, while sodium sulfite may remain at an aqueous phase. In some embodiments, the permeate may comprise acetic acid, which may be recirculated. In some embodiments, the concentrate may comprise a solution comprising sodium sulfite and acetic acid. In some embodiments, the concentrate comprising sodium sulfite and acetic acid may be recirculated within the process. For example, in some embodiments, the concentrate comprising sodium sulfite and acetic acid may be mixed with the feed solution comprising a solution comprising sodium sulfite and acetic acid before feeding the solution into the RO, or NF, or any combination thereof. In some embodiments, the concentrate comprising sodium sulfite and acetic acid may be further concentrated and/or the sodium sulfite may be separated, or precipitated, or crystalized by an evaporator or crystallizer. In some embodiments, sodium sulfite may be at least partially separated or concentrated from the concentrate comprising sodium sulfite and acetic acid by electrodialysis or electrodialysis reversal. In some embodiments, the concentrate comprising sodium sulfite and acetic acid may be further concentrated by concentrating or preconcentrating processes, which may include, but are not limited to, one or more or any combination of the following: Forward Osmosis, or Multistage Flash Distillation, or Multi-Effect Distillation, or Mechanical Vapor Compression Distillation, or Electrodialysis Reversal, or Electrodialysis, or Membrane Distillation. In some embodiments, a concentrated solution comprising sodium sulfite and/or acetic acid may be separated by evaporating water and/or crystallizing or precipitating sodium sulfite solid.

In some embodiments, a solution comprising alkali sulfite and an acid may be at least partially separated by electrodialysis (ED), or electrodialysis reversal (EDR), or any combination thereof. For example, sodium sulfite may be at least partially separated using ED or EDR. For example, sodium sulfite may be at least partially separated using ED or EDR due to, for example, the sodium sulfite comprising charged ions of sodium cation and sulfite anion. In some embodiments, the permeate may comprise acetic acid, which may be recirculated. In some embodiments, the concentrate may comprise a solution comprising sodium sulfite and/or acetic acid. In some embodiments, the concentrate comprising sodium sulfite and/or acetic acid may be recirculated within the process. For example, in some embodiments, the concentrate comprising sodium sulfite and/or acetic acid may be mixed with the feed solution comprising a solution comprising sodium sulfite and acetic acid before feeding the solution into the ED, or EDR, or any combination thereof. In some embodiments, the concentrate comprising sodium sulfite and/or acetic acid may be further concentrated and/or the sodium sulfite may be separated, or precipitated, or crystalized by an evaporator or crystallizer. In some embodiments, the concentrate comprising sodium sulfite and/or acetic acid may be further concentrated by concentrating or preconcentrating processes, which may include, but are not limited to, one or more or any combination of the following: Forward Osmosis, or Multistage Flash Distillation, or Multi-Effect Distillation, or Mechanical Vapor Compression Distillation, or Electrodialysis Reversal, or Electrodialysis, or Membrane Distillation. In some embodiments, a concentrated solution comprising sodium sulfite and/or acetic acid may be separated by evaporating water and/or crystallizing or precipitating sodium sulfite solid.

In some embodiments, alkali sulfite, or water, or acid, or any combination thereof may be separated. For example, in some embodiments, alkali sulfite may be separated as a solid, or at least a portion of water may be separated as a liquid, or vapor, or solid, or any combination thereof and/or acid may be separated as a vapor, or liquid, or solid, or aqueous solution, or any combination thereof. For example, in some embodiments, sodium sulfite may be separated as a solid, or water may be separated as a liquid, or vapor, or solid, or any combination thereof and/or acetic acid may be separated as a liquid, or solid, or aqueous solution, or vapor, or any combination thereof. In some embodiments, separated water may be mixed with alkali sulfite to form an aqueous solution comprising an alkali sulfite. In some embodiments, separated water may be mixed with an acid to produce an aqueous acid solution. In some embodiments, separated water may be mixed with an acid to produce an aqueous acid solution with a sufficiently low concentration aqueous acid, which may be desirable to ensure the alkaline earth-acid, which may form in a reaction between acid and alkaline earth-weak acid salt, is at least partially soluble in the aqueous solution or the alkaline earth-acid can dissolve in the solution. For example, a sufficiently low concentration of aqueous acid may comprise, for example, including, but not limited to, lower than one or more or any combination of the following: 80 wt % aqueous acid, or 70 wt % aqueous acid, or 60 wt % aqueous acid, or 50 wt % aqueous acid, or 40 wt % aqueous acid, or 30 wt % aqueous acid, or 20 wt % aqueous acid, or 10 wt % aqueous acid. For example, in some embodiments, if the acid is acetic acid and the alkaline earth-weak acid is calcium acetate, it may be desirable for the concentration of acetic acid, or the residence time of the reaction, or both to enable the dissolution of at least a portion of formed calcium acetate. For example, the solubility of calcium acetate in water may be 30 g per 100 g $H_2O$ or about 1.6 moles per liter solution, which, with a stoichiometric ratio of 1 calcium:2 acetate, may mean a sufficient acetic acid concentration may comprise 3.2 moles per liter solution. In some embodiments, it may be desirable to provide acid to the reaction in stoichiometric excess to the available alkaline earth. For example, it may be desirable to provide acid to the reaction in stoichiometric excess to the available alkaline earth to enable faster reaction kinetics. In some embodiments, it may be desirable to optimize the concentration of aqueous acid to ensure the alkaline-earth acid and/or alkali acid is soluble in the solution, however minimize the excess water or excess dilution beyond the excess water required to ensure solubility or suitable rate of dissolution of the alkaline-earth acid and/or alkali acid to, for example, optimize or minimize energy required to evaporate and/or crystalize alkali sulfite and/or separate at least a portion of alkali sulfite, or water, or acid, or any combination thereof. In some embodiments, excess water may be removed, or solid, or utilized, or any combination thereof. In some embodiments, water losses may occur and/or make up water may be added. In some embodiments, it may be desirable to optimize the acid concentration to ensure the concentration is in a desirable range or is appropriate for electrodialysis separation of alkali sulfite and acid in later process steps.

In some embodiments, some acids, such as some carboxylic acids, may have a boiling point near the boiling point of water and/or may form azeotropes with water. In some embodiments, 'water' may comprise an aqueous acid solution, or aqueous carboxylic acid solution, or any combination thereof. In some embodiments, the 'water' or liquid formed from the condensation of vapor from distillation, or evaporation, or crystallization, or any combination thereof may comprise an aqueous carboxylic acid solution. For example, formic acid may form an azeotrope with water, or propanoic acid may form an azeotrope with water, or butyric acid may form an azeotrope with water, or iso-butyric acid may form an azeotrope with water, or any combination thereof. For example, acetic acid may be zeotropic with water, however acetic acid may have a boiling point close to the boiling point of water, which may mean vapor or distillate from a solution comprising water and acetic acid may comprise substantial proportions of both water vapor and acetic acid vapor.

In some embodiments, an alkali sulfite may be separated from an acid, or water, or any combination thereof. In some embodiments, the alkali sulfite may be separated by evaporation, or crystallization, or any combination thereof. For example, an aqueous solution comprising sodium sulfite and acetic acid may be separated by evaporation and/or crystallization, which may result in the formation of a vapor phase or condensate liquid comprising acetic acid and water or aqueous acetic acid and/or a solid comprising sodium sulfite. Sodium sulfite may be separated by solid-liquid separation.

In some embodiments, higher purity water or acid may be desired, or water or acid of purity greater than can be achieved by evaporation or boiling or fractional distillation may be desired, or any combination thereof. For example, if higher purity water or acid is desired, techniques or methods for separating water and acid may be employed. If higher purity water or acetic acid is desired, techniques or methods for separating water and carboxylic acid may be employed. For example, techniques or methods for separating liquids or solutions with similar boiling points, azeotropes, or any combination thereof may comprise, including, but not limited to, one or more or any combination thereof: extractive distillation, or azeotropic distillation, or liquid-liquid extraction, or fractional crystallization, or fractional melt crystallization, or salting out, or methods for separating acetic acid in the art, or methods for separating carboxylic acids in the art, or methods for separating carboxylic acids from water in the art, or any combination thereof. For example, acetic acid may be separated from water by extractive liquid-liquid extraction, or distillation, or azeotropic distillation, or any combination thereof by employing an entrainer or extractant comprising, for example, ethyl acetate or Methyl tert-butyl ether (MTBE). For example, in some embodiments, water may be separated from ethyl acetate, or MTBE, or both by mixing with or dissolving an alkali sulfite, or alkali sulfate, or alkali carbonate, or sodium sulfite, or sodium sulfate, or sodium carbonate, or potassium sulfite, or potassium sulfate, or potassium carbonate, or alkaline earth salt, or any combination thereof, which may salt out at least a portion of the ethyl acetate, or MTBE. For example, a portion of some carboxylic acids may be 'salted-out' from solution by the dissolution of or addition of an alkali sulfate, or alkali sulfite, or alkali salt, or alkaline-earth salt, or ammonium salt, or alkaline earth salt, or salt, or any combination thereof into an aqueous solution comprising carboxylic acid.

In some embodiments, a solution comprising alkali sulfite and acid may be at least partially separated. In some embodiments, at least a portion of the concentrating or separation of alkali sulfite and/or acid may be conducted using, for example, a membrane-based process, an electrochemical process, or any combination thereof. In some embodiments, a portion of an acid may be separated from an alkali sulfite by electrodialysis. For example, a solution comprising sodium sulfite and acetic acid may be separated into a separate solution comprising sodium sulfite and a separate solution comprising acetic acid using electrodialysis. For example, in some embodiments, a feed solution comprising an alkali sulfite and an acid may be separated into a concentrate solution comprising a greater concentration of alkali sulfite than the feed solution and a permeate or diluate solution comprising the acid. For example, in some embodiments, a feed solution comprising sodium sulfite and acetic acid may be separated into a concentrate solution comprising a greater concentration of sodium sulfite than the feed solution and a permeate or diluate solution comprising acetic acid. In some embodiments, the concentrate solution may comprise a portion of acid. In some embodiments, the permeate or diluate solution may comprise a portion of alkali sulfite.

In some embodiments, an aqueous solution comprising alkali sulfite and acid may be at least partially separated or concentrated using reverse osmosis, or nanofiltration, or forward osmosis, or any combination thereof. For example, in some embodiments, an aqueous solution comprising sodium sulfite and acetic acid may be at least partially separated or concentrated using reverse osmosis, or nanofiltration, or forward osmosis, or any combination thereof. For example, in some embodiments, a feed solution comprising an aqueous solution comprising sodium sulfite and acetic acid may be transformed into a concentrate solution comprising sodium sulfite at a higher concentration than in the feed solution and acetic acid, and/or a permeate solution comprising acetic acid. In some embodiments, some acids may permeate a semi-permeable membrane or may have a lower rejection rate while the alkali sulfite may be rejected by the semi-permeable membrane or may have a higher rejection rate, because, for example, some acids may possess a smaller hydration radius than the dissolved ionic salt comprising alkali sulfite. In some embodiments, the concentrate comprising sodium sulfite and acetic acid may be distilled, or evaporated, or any combination thereof and/or sodium sulfite may be precipitated or crystallized. Precipitated or crystallized sodium sulfite may be separated by, for example, a solid-liquid separation. Concentrating the sodium sulfite using a membrane-based process may reduce the quantity of water or acetic acid removal required using more energy intensive methods, such as methods employing gas-liquid phase transitions. In some embodiments, the concentrate comprising sodium sulfite and acetic acid may be mixed with feed solution before or while feed solution is concentrated or separated using the membrane based process, and/or the combined solution of concentrate comprising sodium sulfite and acetic acid and feed solution comprising sodium sulfite and acetic acid may comprise the feed solution entering the membrane based separation. In some embodiments, the permeate comprising acetic acid may be transferred to the reaction with alkaline earth-weak acid. In some embodiments, the permeate comprising aqueous acetic acid may be mixed with distillate comprising aqueous acetic acid before, or while being transferred to, or during, or any combination thereof the reaction with alkaline earth-weak acid.

In some embodiments, an aqueous solution comprising alkali sulfite and acid may be at least partially separated or concentrated using electrodialysis, electrodialysis reversal, or any combination thereof. For example, in some embodiments, an aqueous solution comprising sodium sulfite and acetic acid may be at least partially separated or concentrated using electrodialysis, electrodialysis reversal, or any combination thereof. For example, in some embodiments, a feed solution comprising aqueous sodium sulfite and acetic acid may be transferred into an electrodialysis or electrodialysis reversal process, wherein the feed solution may be separated into a concentrate solution comprising sodium sulfite and a diluate solution comprising acetic acid. In some embodiments, the acid, which may comprise acetic acid, may comprise mostly uncharged aqueous species, while the alkali sulfite, which may comprise sodium sulfite, may comprise mostly charged ionic aqueous species. For example, in an ED or EDR process, the charged species may be transferred into the concentrate solution, while uncharged species may remain in the diluate solution. In some embodiments, it may be desirable for the feed solution to comprise an alkali sulfite concentration which may be low, or low relative to the alkali sulfite salt's solubility limit, or desirable concentration of electrodialysis, or any combination thereof to, for example, reduce or optimize energy consumption of the electrodialysis system, or to enable proper function of the electrodialysis system, or any combination thereof. In some embodiments, it may be desirable for the concentration of alkali sulfite in the feed solution to be lower than, for example, 100 g per kg of water, or 150 g per kg of water, or 200 g per kg of water, or 250 g per kg of water, or any combination thereof. For example, a concentration desirable for electrodialysis, or a low concentration, or any combination thereof may comprise lower than or equal to a concentration of, including, but not limited to, one or more or any combination of the following: 5 g per kg of water, or 10 g per kg of water, or 25 g per kg of water, or 50 g per kg of water, or 75 g per kg of water, or 100 g per kg of water, or 150 g per kg of water, or 200 g per kg of water, or 250 g per kg of water, or any combination thereof.

In some embodiments, the concentrate solution comprising aqueous alkali sulfite may be reacted with an alkaline earth hydroxide, which may result in the formation of an aqueous solution comprising alkali hydroxide and solid comprising alkaline earth sulfite. For example, in some embodiments, a concentrate solution comprising aqueous sodiu sulfite may be reacted with calcium hydroxide, which may result in the formation of an aqueous solution comprising sodium hydroxide and solid comprising calcium sulfite. In some embodiments, it may be desirable to further concentrate the aqueous solution comprising alkali hydroxide. For example, the aqueous solution comprising alkali hydroxide may be concentrated using, including, but not limited to, one or more or any combination thereof: MVC distillation, or MSF distillation, or MED distillation, or other an evaporator, or a crystallizer, or another separation method described herein, or another concentrating method described herein, or a separation method described in the art, or any combination thereof. In some embodiments, it may be desirable to crystallize the alkali hydroxide or produce alkali hydroxide solid. In some embodiments, it may be desirable to produce an alkali hydroxide solution, or a concentrated alkali hydroxide solution, or any combination thereof. In some embodiments, it may be desirable to further react the alkali hydroxide solution, with, for example, carbon dioxide, to produce alkali carbonate or alkali bicarbonate. In some embodiments, some dissolved alkaline earth sulfite may be present in the alkali hydroxide or aqueous solution comprising alkali hydroxide. In some embodiments, it may be desirable to separate or remove at least a portion of said dissolved alkaline earth sulfite. For example, in some embodiments, a portion of dissolved alkaline earth sulfite may precipitate during further concentrating of the alkali hydroxide and/or may be separated using a solid-liquid separation. For example, if the alkaline earth sulfite comprises magnesium sulfite, the solution comprising aqueous alkali hydroxide may comprise some aqueous magnesium sulfite because magnesium sulfite may exhibit some solubility in water.

In some embodiments, the diluate solution comprising acid may be transferred to or employed in the reaction of the acid with alkaline earth-weak acid. For example, a diluate comprising aqueous acetic acid may be transferred to and/or reacted with alkaline earth-weak acid.

In some embodiments, at least a portion of alkali sulfite, or sodium sulfite or potassium sulfite may be separated from at least a portion of carboxylic acid, such as acetic acid. For example, in some embodiments, a solution comprising sodium sulfite and carboxylic acid may be transferred into a reverse osmosis system as a feed solution, forming a permeate comprising carboxylic acid and a retentate comprising sodium sulfite and carboxylic acid. In some embodiments, the molecular weight or hydration radius of the carboxylic acid may be sufficiently small to enable permeation of at least a portion of the aqueous carboxylic acid through the semi-permeable membrane, while at least a portion of the aqueous sodium sulfite may be rejected by the membrane. In some embodiments, the permeate may comprise carboxylic acid and/or may comprise the carboxylic acid in the reaction of calcium carbonate or magnesium carbonate or alkaline earth carbonate or alkaline earth weak acid and an acid, such as a carboxylic acid. In some embodiments, the concentrate or retentate may comprise a solution comprising aqueous sodium sulfite and carboxylic acid, and/or said sodium sulfite may be at a greater concentration than the concentration of sodium sulfite in the feed solution. In some embodiments, said concentrate or retentate may comprise the sodium sulfite in the reaction of sodium sulfite or potassium sulfite or alkali sulfite and calcium carboxylate, or magnesium carboxylate, or alkaline earth acid, or any combination thereof. In some embodiments, the reaction of alkali sulfite and alkaline earth carboxylate may successfully form reaction products comprising alkaline earth sulfite and alkali carboxylate in the presence of aqueous carboxylic acid, or even if carboxylic acid is present in the reagent comprising alkali sulfite or aqueous alkali sulfite.

Some embodiments may comprise a $CO_2$ capture or $CO_2$ separation process. For example, in some embodiments:

(1) Carbon dioxide, or carbonate, or bicarbonate, or carbamate, or any combination thereof may be reacted with an alkaline earth oxide or alkaline earth hydroxide, such as magnesium or calcium, to form, for example, a solid comprising an alkaline earth carbonate. In some embodiments, said reacted carbon dioxide, or carbonate, or bicarbonate, or carbamate, or any combination thereof may comprise for example, including, but not limited to, one or more or any combination of the following: flue gas, or a gas comprising $CO_2$ from an emissions source, or a gas comprising $CO_2$ from a point source, or $CO_2$ from the air, or air, or ocean, or body of water, or a carbonated absorption solution, or an alkali carbonate from a $CO_2$ removal system or air capture system.

(2) Alkaline earth carbonate from '1' may be reacted with an acid, such as a carboxylic acid, to form, for example, an alkaline earth cation-acid anion solution, such as an alkaline earth carboxylate or aqueous calcium acetate or magnesium acetate, and a gas comprising carbon dioxide. Said gas comprising carbon dioxide may comprise a high pressure and/or high purity $CO_2$ gas stream, which may comprise captured $CO_2$.

(3optionA) A solution comprising aqueous alkaline earth carboxylate may be reacted with sulfur dioxide to form, for example, an alkaline earth sulfite. In some embodiments, at least a portion of said alkaline earth sulfite may comprise a solid or a solid precipitate. In some embodiments, said sulfur dioxide may comprise a gas comprising sulfur dioxide from the decomposition of alkaline earth sulfite into alkaline earth oxide and sulfur dioxide, such as from '7'.

(3optionB) A solution comprising aqueous alkaline earth carboxylate may be reacted with an alkali sulfite to form, for example, an alkaline earth sulfite and an alkali carboxylate. In some embodiments, at least a portion of said alkaline earth sulfite may comprise a solid or a solid precipitate. In some embodiments, at least a portion of said alkali carboxylate may comprise a liquid or an aqueous solution comprising alkali carboxylate.

(4) A liquid, such as a liquid comprising a solution comprising aqueous alkali carboxylate or aqueous carboxylic acid, and a solid, such as a solid comprising an alkaline earth sulfite, may be separated using, for example, a solid-liquid separation method. For example, if from 3optionA, then separated aqueous carboxylic acid may be transferred to '2' and the solid comprising alkaline earth sulfite may be transferred to '7'. For example, if from 3optionB, then the solution comprising aqueous alkali carboxylate may be transferred to '5optionB' and the solid comprising alkaline earth sulfite may be transferred to '7.'

(5optionB) A solution comprising aqueous alkali carboxylate may be reacted with a gas comprising sulfur dioxide to form, for example, at least a portion of a solution comprising aqueous alkali sulfite and carboxylic acid.

(6optionB) At least a portion of an aqueous solution comprising aqueous alkali sulfite and carboxylic acid may be separated into an aqueous solution or solid comprising alkali sulfite and an aqueous solution comprising carboxylic acid. Systems and methods for separating at least a portion of alkali sulfite from at least a portion of carboxylic acid may be described in more detail elsewhere herein. At least a portion of said separated alkali sulfite may be transferred to '3optionB' and at least a portion of said separated solution comprising aqueous carboxylic acid may be transferred to '2'.

(7) An alkaline earth sulfite may be decomposed into an alkaline earth oxide and sulfur dioxide. Said alkaline earth oxide may be further reacted with water to form, for example, alkaline earth hydroxide. In some embodiments, said alkaline earth oxide or alkaline earth hydroxide may be transferred to '2' and/or said sulfur dioxide may be transferred to '3optionA' or '5optionB'.

Note: In some embodiments, it may be desirable to employ magnesium in a $CO_2$ capture embodiment, due to, for example, the lower energy consumption and/or temperature required to decompose magnesium sulfite into magnesium oxide and sulfur dioxide, compared to, for example, calcium.

Systems and Methods for Decoupling or Distributing $CO_2$ Absorption or Adsorption, $CO_2$ Desorption or Displacement and/or Use, and Regeneration of Reagents In some applications, the timing of availability of $CO_2$, or the rate of production of $CO_2$, or the rate of capturing $CO_2$, or any combination thereof may differ from the timing of demand for $CO_2$, or the rate of consumption of $CO_2$, or any combination thereof and/or may differ from the rate or capacity which reagents can be regenerated to capture $CO_2$. In some applications, the timing and/or rate of the production of $CO_2$ or the absorption of $CO_2$, or the demand or need for $CO_2$, or the regeneration of reagents, or any combination thereof may not match. In some applications, the $CO_2$ emissions sources requiring $CO_2$ capture may be dispersed or inconsistent or intermittent. In some applications, the demand for $CO_2$ or applications consuming $CO_2$ may be dispersed, or inconsistent, or intermittent, or mobile, or space constrained, or any combination thereof. In some embodiments, the distributed, or dispersed, or inconsistent, or intermittent, or mobile, or space constrained, or any combination thereof of a $CO_2$ source, or $CO_2$ user, or any combination thereof may make co-locating the process for regenerating of $CO_2$ capture reagents with the $CO_2$ source or $CO_2$ demand cost prohibitive, or inefficient, or arduous.

For example, $CO_2$ emissions sources or $CO_2$ sources may be dispersed, or inconsistent, or intermittent, or mobile, or in space limited environments, or any combination thereof, which may include, but are not limited to, one or more or any combination of the following: flare gas, or upstream oil & gas production, or electric generator, or midstream oil & gas production, or downstream oil & gas production, or residential heating system, or combustion fired heating or hot water system, or commercial heating system, or kitchen, or cooking, or industrial cooking, or commercial kitchen, or residential kitchen, or fireplace, or peaker power plant, or diesel generator, or backup generator, or drilling rig, or combustion engine powered oil well jack, or oil drilling systems, or locomotive, or train, or offshore vessel, or refinery flare, or refinery flare gas, or associated gas, or acid gas rich natural gas, or sour gas, or abandoned oil well, or vehicle emissions, or medical facility, or dry ice, or water treatment, or sewerage treatment, or landfill gas, or waste incineration, or respiration, or indoor air, or air, or gas processing, or LPG gas processing, or LNG, or offshore oil & gas production, or mobile generator, or methods for artificial lift of oil & gas, or mobile heater, or construction equipment, or mining equipment, or roasting, or drying, or melting, or boiling, or cooling, or $CO_2$ emissions source in a remote location, or $CO_2$ emissions source on an island, or an island power plant, or a remote power plant, or a remote refinery, or a remote manufacturing site, or a remote waste incinerator, or a remote commercial building, or a remote industrial site.

For example, $CO_2$ demand or consumption may be dispersed, or inconsistent, or intermittent, or mobile, or in space limited environments, or in regulated environments, or any combination thereof which may include, but are not limited to, one or more or any combination of the following: enhanced oil recovery, or greenhouses, or $CO_2$ enriched photosynthesis, or mosquito magnet, or insect attractant, or $CO_2$ sequestration, or $CO_2$ conversion into salts, or $CO_2$ conversion into chemicals, or $CO_2$ conversion into fuels, or beverage carbonation, or beverage production, or beer production, or carbonate production, or bicarbonate production, or urea production, or nitrogenous compound production, or dry ice, or medical application, or biological application, or research application, or laboratory application, or industrial gas application, or fire retarding application, or fire suppression application, or $CO_2$ sequestration, or acidifying water, or acidifying materials or chemicals.

Some embodiments may pertain to distributed or decoupled $CO_2$ absorption or adsorption, $CO_2$ desorption or displacement and/or use, and regeneration of reagents to, for example, enable cost effective and efficient $CO_2$ capture, or $CO_2$ utilization or storage, or $CO_2$ capture reagent regeneration.

$CO_2$ Absorption or $CO_2$ Adsorption: For example, in some embodiments, $CO_2$ may be absorbed from an emissions source, or air, or any combination thereof into a solid or solution which may react with or absorb $CO_2$ with fast reaction kinetics, which may include, but are not limited to, one or more or any combination of the following: sodium hydroxide aqueous solution, or a calcium hydroxide suspension, or milk of lime, or milk of magnesium, or calcium oxide solid, or calcium hydroxide solid, or sodium hydroxide solid, or alkali solution, or alkali hydroxide solution, or alkaline earth solid, or alkali solid, or alkaline earth suspension, or alkaline earth solution, or alkaline earth hydroxide solution. Fast reaction kinetics may be desired to enable, for example, relatively compact, or mobile or inexpensive absorption or adsorption equipment. In some embodiments, low CAPEX, or small land footprint, or any combination thereof may be desired if the utilization rate of the $CO_2$ absorption or adsorption equipment is relatively low, or if the $CO_2$ absorption or adsorption equipment is frequently transported, or if the $CO_2$ absorption or adsorption uptake or rate is slow, or any combination thereof. In some embodiments, solutions or suspensions may react with $CO_2$ to form a carbon dioxide derivative salt, such as a carbonate, or carbamate, or bicarbonate, or sesquicarbonate, or any combination thereof, which may form a $CO_2$-rich precipitate, which may be separated by a solid-liquid separation method, or by settling, or any combination thereof. The $CO_2$-rich precipitate may be stored, or transported, or any combination thereof. In some embodiments, solutions or suspensions may react with $CO_2$ to form a carbon dioxide derivative salt, such as a carbonate, or carbamate, or bicarbonate, or sesquicarbonate, or any combination thereof, which may comprise a $CO_2$-rich solution. The $CO_2$-rich solution may be stored, or transported, or any combination thereof. In some embodiments, solids may react with $CO_2$ to form a carbon dioxide derivative salt, such as a carbonate, or carbamate, or bicarbonate, or sesquicarbonate, or any combination thereof, which may comprise a $CO_2$-rich solid. The $CO_2$-rich solid may be stored, or transported, or any combination thereof.

For example, some embodiments may comprise a containerized system or method. For example, in some embodiments, a container storing a $CO_2$-lean concentrated solution or suspension comprising, including, but not limited to, hydroxide solution, or hydroxide suspension, or sodium hydroxide solution, or milk of lime, or milk of magnesia, or any combination thereof, may be transported to and/or located at a source of carbon dioxide. A gas comprising carbon dioxide may be transferred into the container and absorbed into a $CO_2$-lean concentrated solution or suspension to form a $CO_2$-rich salt solid, or solution, or any combination thereof. The containerized system or method may be designed to absorb carbon dioxide and/or store the resulting $CO_2$-rich salt within the container. In some embodiments, when the desired amount of $CO_2$ absorbed as a proportion of total potential $CO_2$ absorption capacity is reached, or when the absorbent or adsorbent in the container is fully or desirably '$CO_2$-Rich', or any combination thereof, the $CO_2$-Rich container may be swapped with a container comprising $CO_2$-lean concentrated solution or suspension. The '$CO_2$-Rich' container may be stored or transported to an application requiring $CO_2$ or an application with demand for $CO_2$, or other chemical within the container, or any combination thereof. In some embodiments, the '$CO_2$-Rich' container may be stored or stacked with other containers. In some embodiments, the '$CO_2$-Rich' container may be transported using, for example, a vehicle, to an application requiring $CO_2$.

In some embodiments, $CO_2$-Rich solid may form and/or may settle at the bottom of the container, while, above the $CO_2$-Rich solid may primarily comprise liquid. In some embodiments, liquid may be removed or drained from the container. For example, liquid may be removed or drained from the container to, for example, including, but not limited to, one or more or any combination of the following: reduce transportation weight, or provide space for acid to be added, or provide space for $CO_2$-lean solution or suspension to be added, or provide space for hydroxide solution or suspension to be added, or any combination thereof. In some embodiments, removed liquid may be, for example, employed as agricultural water, or may be employed in industrial use, or may be drained to a sewerage or wastewater system, or any combination thereof.

In some embodiments, the container may comprise a relatively simple and/or transportable design. For example, in some embodiments, the container may comprise a cylindrical or tank with an inlet port for gas, a port for liquid or suspension or fluid, an outlet port for gas, and an internal gas disperser or sparger or distributer. In some embodiments, the container may be transportable by truck, or trailer, or train, or any combination thereof. In some embodiments, the container may comprise a skid mounted or connected gas blower or gas compressor to, for example, feed $CO_2$-rich gas into the container. It may be desirable for the container to be positioned vertically during $CO_2$ absorption. It may be desirable for the container to be designed to handle pressures, which may include, but are not limited to, greater than or equal to 1 Bar, or 2 Bar, or 3 Bar, or 4 Bar, or 5 Bar, or 7 bar, or 10 Bar, or 13 Bar, or 15 Bar, or 17 Bar, or 20 Bar, or any combination thereof to, for example, enable the production of high pressure carbon dioxide when employed in $CO_2$ desorption or production, or to, for example, enable absorption of $CO_2$ from high pressure gas streams, or any combination thereof. It may be desirable for the container to be mobile or transportable. For example, the container may be skid mounted. It may be desirable for the container to be modular or stackable, or any combination thereof.

Storage and/or Transportation of $CO_2$-Rich Solid or Solution: In some embodiments, it may be desirable to store the $CO_2$-Rich solid or solution on or near the site of the $CO_2$ absorption or absorption, or in an intermediate storage location, or at or near the application or use of $CO_2$, or any combination thereof.

It is important to note that in some embodiments, it may be easier, or less expensive, or any combination thereof to store carbon dioxide in the form of a $CO_2$-Rich solid, or solution, or any combination thereof than it is to store carbon dioxide as a compressed gaseous carbon dioxide, or as liquid carbon dioxide, or as supercritical carbon dioxide, or as solid carbon dioxide. For example, if desired, calcium carbonate solid may be stored in piles, or in warehouses, or in open air space, or in non-pressure resistant containers, or any combination thereof. If an application requires a significant amount of carbon dioxide, or requires a large carbon dioxide storage requirement, it may be lower cost or easier to store carbon dioxide in the form of a $CO_2$-Rich solid, or solution, or any combination thereof than to store carbon dioxide as a compressed gaseous carbon dioxide, or as liquid carbon dioxide, or as supercritical carbon dioxide, or as solid carbon dioxide. Some embodiments of the present invention may enable generation of high quality or high partial pressure carbon dioxide from $CO_2$-Rich solid, or solution, or any combination thereof, which may be stored, without requiring direct heat input or an onsite heat source to generate the carbon dioxide.

For example, in some embodiments, a source of $CO_2$ may have a relatively low rate of $CO_2$ production. $CO_2$ may be absorbed or adsorbed from the source of $CO_2$ and the resulting produced $CO_2$-Rich solid or solution may stored. When the accumulated $CO_2$-Rich solid or solution is of a sufficient quantity to be economically or desirably transported, at least a portion of the $CO_2$-Rich solid or solution may be transported to another storage facility, or to an application requiring carbon dioxide, or any combination thereof.

For example, some embodiments may comprise a containerized system. For example, in some embodiments, a $CO_2$-Rich container may be uninstalled and the $CO_2$-Lean container may be installed. A $CO_2$-Rich container may be stored, or stacked, or transported. For example, a $CO_2$-Rich container may be transported to an application requiring $CO_2$ or with demand for $CO_2$. In some embodiments, the container may be stored at the $CO_2$ absorption location, or at an intermediate site, or at the $CO_2$ production or demand location, or any combination thereof.

In some embodiments, a portion of liquid may be drained from the containerized system to provide space or volume for the acid or acid solution to be added.

In some embodiments, the containerized system may be similar to mobile compressed or liquified gas tanks. For example, LPG tanks, or propane tanks, or butane tanks, or compressed gas tanks, or liquid nitrogen tanks, or any combination thereof may be swapped, or refilled, or transported, or stored, or any combination thereof.

Desorption or Displacement or Production or Use or Conversion or Sequestration of $CO_2$:

In some embodiments, $CO_2$-Rich solid, or suspension, or solution, or any combination thereof may be transferred to an application with demand for $CO_2$. In some embodiments, a $CO_2$-Rich solid, or suspension, or solution, or any combination thereof may be mined and/or mined onsite and/or transported and/or may include, but is not limited to, one or more or any combination of the following: calcium carbonate or magnesium carbonate, or calcium-magnesium carbonate, or limestone, or dolomite, or sodium carbonate, or sodium bicarbonate, or Nahcolite. In some embodiments, a $CO_2$-Rich solid, or suspension, or solution, or any combination thereof may be mined and/or mined onsite and/or transported to an application with demand for $CO_2$. In some embodiments, a $CO_2$-Rich solid, or suspension, or solution, or any combination thereof may be from a $CO_2$ absorption process, which may be in a different location or in the same location as the $CO_2$ demand.

In some embodiments, $CO_2$-Rich solid, or suspension, or solution, or any combination thereof may be reacted with an acid to produce carbon dioxide gas. In some embodiments, said acid may possess stronger acid strength than carbonic acid and/or weaker acid strength than sulfurous acid and/or equal acid strength to sulfurous acid. It may be desirable for said acid to be non-volatile, or non-toxic, or inexpensive, or abundant, or environmentally friendly, or have a regeneration pathway, or be regenerable, or any combination thereof. In some embodiments, it may be desirable for the reaction of the $CO_2$-Rich solid, or suspension, or solution, or any combination thereof with the acid to result in the formation of a high pressure gas comprising carbon dioxide which may include, but is not limited to, a partial pressure of carbon dioxide greater than, or equal to, one or more or any combination of the following: 1 Bar, or 2 Bar, or 3 Bar, or 4 Bar, or 5 Bar, or 7 bar, or 10 Bar, or 13 Bar, or 15 Bar, or 17 Bar, or 20 Bar.

In some embodiments, it may be desirable to optimize, or minimize, or prevent, or reduce, or limit, or any combination thereof the concentration or presence of acid vapor in the product carbon dioxide. In some embodiments, the acid may possess a vapor pressure. For example, including, but not limited to, some carboxylic acids, or formic acid, or acetic acid, or propanoic acid, or any combination thereof may possess a vapor pressure and/or some vapor may evaporate into the carbon dioxide.

For example, in some embodiments, the configuration or design of the reactor for the reaction of acid and the $CO_2$-Rich solid, or suspension, or solution, or any combination thereof may prevent or reduce the presence of acid vapor in product carbon dioxide. For example, in some embodiments, the reactor may be configured such that $CO_2$-Rich solid, or suspension, or solution, or any combination thereof may be contacted with produced $CO_2$ comprising acid vapor to remove a portion of acid vapor before, for example, $CO_2$-Rich solid, or suspension, or solution, or any combination thereof is contacted with the bulk of the acid. For example, in some embodiments, an aqueous solution comprising sodium carbonate or sodium bicarbonate may be contacted with produced $CO_2$ comprising acetic acid vapor, which may result in the formation of produced $CO_2$ comprising a significantly lower concentration of acid vapor due to, the reactor or absorption of acetic acid vapor, and then the aqueous solution comprising sodium carbonate or sodium bicarbonate may be contacted with or reacted an aqueous solution comprising acetic acid. In some embodiments, for example, the reactor may comprise at least two stages. The first reactor stage may comprise reacting acid with the $CO_2$-Rich solid, or suspension, or solution, or any combination thereof with some salt of the acid, which may sourced from or transferred from the second reactor stage, to produce a $CO_2$-Lean solid, or suspension, or solution, or any combination thereof, which may comprise a salt of the acid, and carbon dioxide gas comprising acid vapor. The second reactor stage may comprise reacting or contacting the carbon dioxide gas comprising acid vapor from the first reactor stage with $CO_2$-Rich solid, or suspension, or solution, or any combination thereof transferred into the first reactor from, for example, outside the reactor, which may result in the formation of the $CO_2$-Rich solid, or suspension, or solution, or any combination thereof with some salt of the acid and $CO_2$ gas with a significantly lower concentration of acid vapor. In some embodiments, carbon dioxide gas may be produced in the first reactor stage and may be transferred to the second reactor stage to be scrubbed of at least a portion of acid vapor before, for example, being transferred out of the reactor. $CO_2$ transferred out of the reactor may comprise product $CO_2$, or may undergo further treatment or compression before comprising production $CO_2$, or any combination thereof. In some embodiments, $CO_2$-Rich solid, or suspension, or solution, or any combination thereof may enter the reactor in the second reactor stage and may be transferred to the first reactor stage to be reacted with acid to produce carbon dioxide, and/or may exit the second reactor stage as $CO_2$-Lean solid, or suspension, or solution, or any combination thereof, which may comprise a salt of the acid. In some embodiments, for example, the first reactor stage may comprise a pre-absorber, or pre-reactor, or pre-scrubber, while the second reactor stage may comprise a mixer, or reactor, or any combination thereof. In some embodiments, the first reactor stage may comprise a separate vessel comprising an absorption column or bubble column, and the second reactor stage may comprise a separate vessel comprising a mixing reactor. In some embodiments, the first reactor stage and second reactor stage may comprise the same vessel. In some embodiments, the first reactor stage and second reactor stage may comprise an integrated vessel wherein the first reactor stage may be located at the top portion of the vessel or at a higher elevation position in the vessel and/or the second reactor stage may be located at the bottom portion of the vessel or at a lower elevation position in the vessel and/or liquid solution travels from the top of the vessel to the bottom of the vessel and/or formed gases travel from the bottom of the vessel to the top of the vessel.

For example, in some embodiments, it may be desirable to employ an acid without a vapor pressure, or without an acid vapor phase, or with a low vapor pressure, or any combination thereof in the reaction of acid and the $CO_2$-Rich solid, or suspension, or solution, or any combination thereof, to, for example, prevent or reduce the presence of acid vapor in the product carbon dioxide. For example, in some embodiments, the acid may comprise citric acid, or ascorbic acid, or glycolic acid, or maleic acid, or any combination thereof.

For example, in some embodiments, it may be desirable to contact the produced carbon dioxide with a carbonate, or bicarbonate, or carbon dioxide derivative, or any combination thereof salt, or an aqueous solution comprising a carbonate, or bicarbonate, or carbon dioxide derivative, or any combination thereof salt, or any combination thereof to, for example, scrub or remove acid vapor from the produced carbon dioxide. For example, acid vapor may react with the carbonate, or bicarbonate, or carbon dioxide derivative, or any combination thereof salt, which may remove at least a portion of acid vapor, or increase $CO_2$ yield, or improve $CO_2$ purity, or any combination thereof.

In some embodiments, the production of high pressure and/or high quality carbon dioxide by reacting a $CO_2$-Rich solid, or suspension, or solution, or any combination thereof with an acid, which may be a regenerable, may:

Reduce or eliminate the need for extensive pipelines to transport carbon dioxide from a carbon dioxide source to an application requiring carbon dioxide. $CO_2$ pipelines can be generally expensive and difficult to permit. The significant cost and development timeline of a $CO_2$ pipeline may be unjustified for distributed or dispersed sources of $CO_2$, or distributed or dispersed applications for $CO_2$, or temporary sources of $CO_2$, or temporary applications for $CO_2$, or any combination thereof.

Reduce or eliminate the need for expensive and energy intensive thermal desorption, or thermal regeneration, or compression, or any combination thereof equipment to produce high pressure and/or high quality $CO_2$ at or near application requiring $CO_2$. Thermal desorption of $CO_2$ may require complex, expensive equipment which may require large scale to be economically justifiable. The significant cost and development timeline of thermal desorption may be unjustified for distributed or dispersed sources of $CO_2$, or distributed or dispersed applications for $CO_2$, or temporary sources of $CO_2$, or temporary applications for $CO_2$, or any combination thereof. Additionally, thermal desorption generally produces lower pressure, or high temperature, or high water vapor concentration, or any combination thereof carbon dioxide gas, which may require significantly cooling, or treatment, or compression, or any combination thereof before the carbon dioxide may be used in many applications. Additionally, thermal desorption may require a continuous supply of heat or other energy to power thermal desorption which may be expensive or unavailable in some locations. Additionally, the rate of $CO_2$ production from thermal desorption may be limited by available heat supply and/or gas compression and treatment rates and/or heat transfer rates.

Provide high rate of $CO_2$ production, or adjustable rate of $CO_2$ production, or adjustable pressure of $CO_2$ production, or any combination thereof if desired.

Provide a reliable supply of carbon dioxide, as a primary source of carbon dioxide, or as a backup source of carbon dioxide, or any combination thereof. $CO_2$ shortages may be relatively common and/or it may be desirable for processes which consume or use carbon dioxide to have a reliable supply of carbon dioxide.

Provide a source of carbon dioxide to applications with significant fluctuations in pressure or temperature. Some embodiments may enable the storage of carbon dioxide at a solid phase while at, for example, high temperatures, or low pressures, or fluctuating temperatures, or fluctuating pressures, or any combination thereof. For example, storing carbon dioxide as pure gaseous $CO_2$, or liquid $CO_2$, or solid $CO_2$, or supercritical $CO_2$, or other phase of $CO_2$ may be vulnerable to significant changes in pressure and/or temperature, and/or may require expensive vessels and equipment for storage and transport and/or may present a safety hazard.

Enable large scale, low cost storage of carbon dioxide. For example, some embodiments herein may enable the storage of significant quantities of carbon dioxide at a solid state in regular ambient pressure or temperature conditions, if desired. For example, some embodiments may involve storing carbon dioxide as including, but not limited to, calcium carbonate or magnesium carbonate, or calcium-magnesium carbonate, or limestone, or dolomite, or sodium carbonate, or sodium bicarbonate, or Nahcolite, or any combination thereof, which may be stored in significantly lower cost containers or storage methods than compressed or liquified carbon dioxide. Some embodiments may enable the storage of significant quantities of carbon dioxide to prevent or alleviate carbon dioxide shortages.

Enable lower cost transport or logistics for carbon dioxide.

In some embodiments, it may be desirable for the acid to form a salt which is soluble. In some embodiments, it may be desirable the reaction of a $CO_2$-Rich solid, or suspension, or solution, or any combination thereof with an acid may result in the formation of a soluble salt, or a solution comprising a soluble salt, or any combination thereof. For example, $CO_2$-rich salt may comprise calcium carbonate and the acid added may comprise acetic acid, the resulting salt may comprise calcium acetate, which may be significantly more water soluble than calcium carbonate. For example, $CO_2$-rich salt may comprise sodium carbonate and the acid added may comprise acetic acid, and/or the resulting salt may comprise sodium acetate, which may be significantly more water soluble than sodium carbonate. For example, it may be desirable for the formed salt to be soluble or dissolved to enable the resulting $CO_2$-lean salt to be pumpable, or removable, or transferrable before or during, for example, regeneration of reagents.

In some embodiments, the acid may be stored on or near the site of the application with $CO_2$ demand. In some embodiments, the acid may be transferred or transported to the site of the application with $CO_2$ demand. In some embodiments, the acid may be transferred by truck, or tanker truck, or rail, or pipeline, or ship, or any combination thereof. In some embodiments, the acid may comprise a solid, or liquid, or aqueous solution, or solution, or organic solution, or nonaqueous solution, or any combination thereof. In some embodiments, the acid may be stored separately from or non-contiguously separately from the $CO_2$-Rich salt to, for example, prevent untimely or undesired reaction of the $CO_2$-Rich salt with the acid.

Some embodiments may comprise a containerized system. For example, in some embodiments, a container comprising a $CO_2$-Rich solid, or suspension, or solution, or any combination thereof may be transported to, or stored, or located near the application with demand for carbon dioxide. Acid may be mixed with the $CO_2$-Rich container, or mixed with the $CO_2$-rich solid, or suspension, or solution, or any combination thereof from the container, or any combination thereof, which may result in the formation of carbon dioxide and/or a $CO_2$-lean, acid rich salt solution. In some embodiments, it may be desirable for containers comprising $CO_2$-lean, acid rich salt solution to be transported to a regeneration process. In some embodiments, it may be desirable to pump out $CO_2$-lean, acid rich salt from containers comprising $CO_2$-lean, acid rich salt solution, transporting or transferring the $CO_2$-lean, acid rich salt solution to a regeneration step, and transferring the empty container to the $CO_2$ absorption step, or to a $CO_2$-lean hydroxide solution filling station, or any combination thereof.

Storage and/or Transportation of $CO_2$-Lean, Acid-Rich Solid or Solution:

In some embodiments, it may be desirable to store the $CO_2$-Lean, Acid-Rich Solid or Solution on or near the site of the $CO_2$ production, or in an intermediate storage location, or at or near the application or use of $CO_2$, or at or near a $CO_2$-Lean absorbent or adsorbent regeneration system or method, or at or near an acid regeneration system or method, or any combination thereof.

For example, in some embodiments, an application with demand for $CO_2$ may have relatively low rate of $CO_2$ demand, or an inconsistent level of $CO_2$ demand, or any combination thereof. $CO_2$ may be produced and the resulting produced $CO_2$-Lean, Acid-Rich Solid or Solution may stored. When the accumulated $CO_2$-Lean, Acid-Rich Solid or Solution is of a sufficient quantity to be economically or desirably transported, at least a portion of the $CO_2$-Lean, Acid-Rich Solid or Solution may be transported to a storage facility, or to an application requiring $CO_2$-Lean, Acid-Rich Solid or Solution, or a $CO_2$-Lean absorbent or adsorbent regeneration system or method, or an acid regeneration system or method, or to a regeneration system or method, or any combination thereof.

For example, some embodiments may comprise a containerized system. For example, in some embodiments, a $CO_2$-Lean, Acid-Rich container may be uninstalled and the $CO_2$-Rich container may be installed. A $CO_2$-Lean, Acid-Rich container may be stored, or stacked, or transported. For example, a $CO_2$-Lean, Acid-Rich container may be transported to a storage facility, or to an application requiring $CO_2$-Lean, Acid-Rich Solid or Solution, or a $CO_2$-Lean absorbent or adsorbent regeneration system or method, or an acid regeneration system or method, or to a regeneration system or method, or any combination thereof.

In some embodiments, $CO_2$-Lean, Acid-Rich solution may be transferred by pipeline. In some embodiments, the acid may be transferred by pipeline.

Regeneration of Reagents:

In some embodiments, $CO_2$-Lean, Acid-Rich Solid or Solution may be transferred to a system and/or method for converting $CO_2$-Lean, Acid-Rich Solid or Solution into $CO_2$-Lean absorbent or adsorbent, or into a hydroxide salt, or an acid, or regenerated acid, or any combination thereof.

For example, in some embodiments, the $CO_2$-Lean, Acid-Rich Solid or Solution may comprise calcium acetate. In some embodiments, the regeneration process may comprise reacting calcium acetate solution with sulfur dioxide to produce calcium sulfite solid and acetic acid. The acetic acid may be further concentrated, or stored, or any combination thereof. The acetic acid may be transferred or transported to an application with demand for carbon dioxide or a $CO_2$ production step. The calcium sulfite solid may be separated from the solution and/or decomposed into calcium oxide and sulfur dioxide. The calcium oxide may be reacted with water to form calcium hydroxide, or calcium hydroxide suspension, or milk of lime, or magnesium hydroxide, or magnesium hydroxide suspension, or milk of magnesia, or any combination thereof. The calcium oxide or calcium hydroxide may be stored. The calcium oxide or calcium hydroxide may be transferred or transported to a $CO_2$ source, or $CO_2$ absorption application, or an acid gas absorption application, or acid gas source, or any combination thereof.

For example, in some embodiments, the $CO_2$-Lean, Acid-Rich Solid or Solution may comprise sodium acetate. In some embodiments, the regeneration process may comprise reacting sodium acetate solution with sulfur dioxide to produce sodium sulfite and acetic acid. In some embodiments, at least a portion of the sodium sulfite may be separated from the acetic acid. The acetic acid may be further concentrated, or stored, or any combination thereof. The acetic acid may be transferred or transported to an application with demand for carbon dioxide or a $CO_2$ production step. The sodium sulfite may be reacted with calcium oxide, or calcium hydroxide, or milk of lime, or magnesium hydroxide, or milk of magnesia, or any combination thereof to produce an alkaline-earth sulfite solid and sodium hydroxide. The sodium hydroxide may be stored. The sodium hydroxide may be sold or used for an external application. The sodium hydroxide may comprise regenerated $CO_2$ absorption solution, or adsorption material, or any combination thereof and/or may be transferred or transported $CO_2$ source, or $CO_2$ absorption application, or an acid gas absorption application, or acid gas source, or any combination thereof.

In some embodiments, it may be desirable for regeneration to be conducted in a centralized facility, or a facility with more than one source of $CO_2$-Lean, Acid-Rich Solid or Solution, or any combination thereof. For example, in some embodiments, the regeneration system or method may benefit from larger scale, or high capacity utilization, or access to energy, or access to logistics facilities, or continuous operation, or access to a heat source, or access to markets for products, or any combination thereof. For example, thermal decomposition equipment, or sulfur dioxide absorption equipment, or solid-liquid separators, or any combination thereof may benefit from larger scale, or continuous operation, or consistent operation, or high capacity utilization, or any combination thereof.

Some embodiments may comprise a containerized system. For example, in some embodiments, a container comprising $CO_2$-Lean, Acid-Rich Solid or Solution may be transported to the regeneration facility. In some embodiments, $CO_2$-Lean, Acid-Rich Solid or Solution may be transferred from the container to a regeneration system or method. In some embodiments, the regeneration system or method may add $CO_2$-Lean absorption solution, or suspension, or adsorption material, or adsorption suspension, or any combination thereof to the container, which, in some embodiments, may be conducted after removing the $CO_2$-Lean, Acid-Rich Solid or Solution from the container. In some embodiments, the volume of $CO_2$-Lean absorption solution, or suspension, or adsorption material, or adsorption suspension, or any combination thereof added to the container may be lower than the volumetric storage capacity of the container, to, for example, provide sufficient vacant volume to allow for the addition of acid during $CO_2$ production, or the provide sufficient vacant volume to allow for the increase in volume and/or mass when $CO_2$ is absorbed, or any combination thereof.

In some embodiments, the acid may be transported as a liquid or solid. In some embodiments, the acid may be stored or transported separately from the $CO_2$ absorbent or adsorbent. In some embodiments, acid may be stored or transported together with the $CO_2$ absorbent or adsorbent, however may be stored or transported non-contiguously or without substantial direct contact to, for example, prevent an undesired reaction. In some embodiments, the acid may be transported as a free liquid or solid. In some embodiments, the acid may be transported in a swappable and/or a transportable container.

Note: In some embodiments, the absorption or adsorption of $CO_2$ may result in absorption or production of water. For example, a solid or a concentrated solution of sodium hydroxide may absorb water from a gas stream or air. For example, a solid comprising calcium oxide may absorb water from a gas stream or air to form calcium hydroxide. For example, absorption or adsorption of $CO_2$ into calcium hydroxide may result into production or release of water as, for example, a production of the reaction.

Note: In some embodiments, the system or method may employ a solid, or liquid, or aqueous solution, or solution, or organic solution, or nonaqueous solution, or any combination thereof.

Example Description Alkali Hydroxide, or Alkali Bicarbonate, or Alkaline Carbonate Production Systems and Methods

Description

Some embodiments of the present invention may pertain to producing alkali hydroxides, or alkali carbonates, or alkali bicarbonates, or alkali oxides, or any combination thereof.

In some embodiments, alkali hydroxides may be produced using input materials comprising an alkaline earth-weak acid, or an alkaline earth-acid, or an alkali sulfate, or an alkali chloride, or an alkali-weak acid, or alkali-acid, or any combination thereof.

In some embodiments, an alkaline earth input may comprise, including, but not limited to, an alkaline earth-weak acid. Alkaline earth-weak acid may be reacted with an acid to form an alkaline earth-acid and/or weak acid, or weak acid derivative, or weak acid anion derivative, or any combination thereof. In some embodiments, a weak acid may comprise an acid with an acid strength lower than the added 'acid' and/or an acid strength weaker than the acid strength of sulfurous acid or aqueous sulfur dioxide. For example, an alkaline earth-weak acid comprising calcium carbonate may be reacted with an acid comprising acetic acid, which may result in the formation of an alkaline earth-acid comprising calcium acetate and a weak acid comprising carbonic acid or a weak acid derivative comprising carbon dioxide. In some embodiments, at least a portion of carbon dioxide formed may comprise captured carbon dioxide and/or may be stored, or transferred, or utilized, or transported, or converted, or any combination thereof. For example, an alkaline earth-weak acid comprising calcium silicate may be reacted with an acid comprising acetic acid, which may result in the formation of an alkaline earth-acid comprising calcium acetate and a weak acid comprising a silicon oxide acid or a weak acid derivative comprising silicon dioxide. In some embodiments, it may be desirable for the alkaline earth-acid to be soluble and/or dissolve to form an aqueous solution. It may be desirable to separate the alkaline earth-acid from the weak acid, or weak acid derivative. For example, an alkaline earth-acid comprising calcium acetate may be water soluble and/or an aqueous solution of calcium acetate may be substantially separated from a gas comprising carbon dioxide or a solid comprising silicon dioxide. In some embodiments, the added acid may be recycled, or regenerated, or recirculated, or any combination thereof within the process. In some embodiments, the acid may comprise an acid with an acid strength greater than the acid strength of the weak acid or weak acid anion and/or an acid strength weaker than the acid strength of sulfurous acid, or aqueous sulfur dioxide, or any combination thereof. The reaction of an alkaline earth-weak acid input and/or reaction to form an alkaline earth-acid and/or separation and/or other related description may be further described elsewhere in the present specification or elsewhere herein.

In some embodiments, an alkaline earth-acid may comprise an input chemical. In some embodiments, an alkaline earth acid may be produced or formed. For example, in some embodiments, an alkaline earth-acid may be produced or formed from a reaction of a material comprising an alkaline earth-weak acid with an acid. In some embodiments, the acid or acid anion in an alkaline earth-acid may comprise an acid anion which enables the alkaline earth to be soluble or forms a soluble salt with an alkaline earth cation. In some embodiments, the acid or acid anion in an alkaline earth-acid may enable the alkaline earth-acid to undergo a double replacement or double displacement reaction with an alkali sulfate to form an alkaline earth sulfate and an alkali-acid. In some embodiments, an alkaline earth-acid may undergo a double replacement or double displacement reaction with an alkali sulfate to form an alkaline earth sulfate and an alkali-acid and/or wherein the alkaline earth sulfate possesses different properties than the alkali-acid. In some embodiments, an alkaline earth-acid may undergo a double replacement or double displacement reaction with an alkali sulfate to form an alkaline earth sulfate and an alkali-acid and/or wherein the alkaline earth sulfate possesses a lower solubility in water than the alkali-acid. For example, in some embodiments, the alkaline earth sulfate may possess a solubility in terms of grams of salt per 100 mL of water of, including, but not limited to, one or more or any combination of the following percentages lower than the solubility of the alkali-acid: 5 wt %, or 10 wt %, or 20 wt %, or 30 wt %, or 40 wt %, or 50 wt %, or 60 wt %, or 70 wt %, or 80 wt %, or 90 wt %, or 95 wt %, or 99 wt %, or 99.5 wt %. For example, in some embodiments, an alkaline earth-acid may comprise calcium acetate and/or an alkali sulfate may comprise sodium sulfate. In some embodiments, if calcium acetate is mixed with sodium sulfate in the presence of water, a double displacement reaction may occur, which may result in the formation of an aqueous solution comprising sodium acetate and a solid precipitate comprising calcium sulfate. A precipitate comprising calcium sulfate may form because, for example, the solubility of calcium sulfate may be substantially lower than the solubility of sodium acetate. In some embodiments, a solid comprising calcium sulfate may be separated from an aqueous solution comprising sodium acetate solution by a solid-liquid separation.

In some embodiments, alkali sulfate may be employed within the process. In some embodiments, the alkali sulfate may comprise an input. In some embodiments, the alkali sulfate may be supplied as a raw material, or raw chemical, or a treated material, or treated chemical, or purified material, or purified chemical. In some embodiments, the alkali sulfate may be produced from another alkali or alkali source. In some embodiments, the alkali sulfate may be produced from another alkali or alkali source outside of the process. In some embodiments, the alkali sulfate may be produced from another alkali or alkali source within the process.

In some embodiments, alkali sulfate may be from a geological source, or a mined, or any combination thereof. For example, an alkali sulfate comprising sodium sulfate or potassium sulfate may be geologically in a natural mineral form. For example, sodium sulfate may be mined in the form of, including, but not limited to, one or more or any combination of the following: Thenardite, or Mirabilite, or Glauberite, or any combination thereof. As of 2013, the total estimated reserves of natural mineral form sodium sulfate were estimated to be about 3.3 billion tons. For example, potassium sulfate may be mined in the form of, including, but not limited to, one or more or any combination of the following: Kainite, or $KMg(SO_4)\cdot Cl\cdot 3H_2O$, or Schönite, or picromerite, or $K2SO4\cdot MgSO4\cdot 6H_2O$, or Leonite, or $K2SO4\cdot MgSO4\cdot 4H_2O$, or Langbeinite, or K2Mg2(SO4)3 Aphthitalite, or glaserite, or K3Na(SO4)2 Polyhalite, or $K2SO_4\cdot MgSO4\cdot 2CaSO4\cdot 2H_2O$. In some embodiments, alkali sulfate may be further purified, or refined, or separated, or any combination thereof before use or input into the process. In some embodiments, alkali sulfates may be separated from other chemicals in minerals due to including, but not limited to, for example, solubility differences, or substantial changes in solubility due to temperature.

In some embodiments, alkali sulfate may be sourced from a byproduct of a chemical or material production process. For example, sodium sulfate is a byproduct of many chemical production processes. As of 2013, the total world production of byproduct sodium sulfate was estimated to be between 2.0 and 4.0 million tons. For example, sodium sulfate is a byproduct of including, but not limited to, one or more or any combination of the following: lithium production, or lithium refining, or lithium carbonate production, or lithium hydroxide production, or battery recycling, or lead-acid battery recycling, or lithium ion battery recycling, or ascorbic acid production, or rayon production, or excess sulfuric acid neutralization, or excess sodium hydroxide neutralization, or flue gas desulfurization, or pulp & paper manufacturing, or other processes described herein, or other processes in the art. In some embodiments, the alkali sulfate may be added to the process or transferred to the process in a solid form, or aqueous form, or any combination thereof. In some embodiments, a process producing sodium sulfate byproduct may employ or require an input comprising sodium hydroxide, or sodium carbonate, or sodium carbonate, or sodium sulfite, or any combination thereof. In some embodiments, a process producing sodium sulfate byproduct may produce or provide sodium sulfate to one or more or any combination of embodiments and said one or more or any combination of embodiments may produce or provide sodium hydroxide, or sodium carbonate, or sodium bicarbonate, or sodium sulfite, or any combination thereof to the process producing sodium sulfate byproduct. Some embodiments may provide or enable recycling or regenerating or circular economy in the production, or consumption, or any combination thereof of sodium sulfate, or sodium hydroxide, or sodium carbonate, or sodium bicarbonate, or sodium sulfite, or any combination thereof, which may reduce costs, or improve supply chain reliability, or stabilize costs, or reduce risks, or reduce $CO_2$ emissions, or help the environment, or any combination thereof.

In some embodiments, alkali sulfates may be produced from other alkali sources. For example, in some embodiments, alkali sulfates may be produced from alkali chlorides and/or sulfuric acid. For example, potassium sulfate and hydrogen chloride may be produced by reacting potassium chloride with sulfuric acid. For example, sodium sulfate and hydrogen chloride may be produced by reacting sodium chloride with sulfuric acid. For example, sodium sulfate and hydrogen chloride may be produced by reacting sodium chloride with sulfuric acid, using, for example, the Mannheim process. For example, potassium sulfate and nitric acid may be produced by reacting potassium nitrate with sulfuric acid. For example, sodium sulfate and nitric acid may be produced by reacting sodium nitrate with sulfuric acid.

In some embodiments, an acid byproduct may be produced during the production of an alkali sulfate. For example, in some embodiments, hydrogen chloride or hydrochloric acid may be produced as a byproduct of producing sodium sulfate or potassium sulfate using the Mannheim process. In some embodiments, the commercial market for hydrochloric acid may be limited and may be smaller than the potential production of hydrogen chloric or hydrochloric acid. Hydrochloric acid or hydrogen chloride may be difficult to dispose or release because it is highly toxic and reactive. Additionally, releasing hydrogen chloride or hydrochloric acid into the environment may negate some greenhouse gas or carbon dioxide emissions reduction or carbon dioxide removal benefits because hydrogen chloride or hydrochloric acid, if released into the environment, may react with water, bicarbonates, and carbonates, resulting in the production and release of carbon dioxide and the acidification of water bodies and the ocean. As a result, in some embodiments, it may be desirable to produce alkali sulfate from an alkali chloride while substantially avoiding the production of hydrochloric acid or hydrogen chloride as an output.

For example, in some embodiments, alkali sulfates may be produced from alkali chlorides and/or alkaline earth sulfates. For example, in some embodiments, alkali hydroxides may be produced from alkali chloride salt and/or alkaline earth-weak acid salt, wherein sulfate is recirculated, or recycled, or regenerated internally, or any combination thereof and/or alkali sulfate, or alkaline earth sulfate, or any combination thereof may comprise an intermediate. For example, in some embodiments, in some embodiments, sodium hydroxide, or calcium chloride, or weak acid derivative, or any combination thereof may be produced from sodium chloride and calcium-weak acid by a process employing sulfate, or sodium sulfate, or calcium sulfate, or ammonia, or carbon dioxide, or water, or any combination thereof intermediates. For example, in some embodiments, sodium sulfate and calcium chloride may be produced from calcium sulfate and sodium chloride using, for example, intermediates comprising ammonia, or carbon dioxide, or water, or any combination thereof. For example, in some embodiments, calcium sulfate may be reacted with ammonium carbonate, which may result in the formation of ammonium sulfate and calcium carbonate. Calcium carbonate may be separated from ammonium sulfate by, for example, differences in solubility. For example, calcium carbonate may comprise a solid and ammonium sulfate may comprise an aqueous solution and/or a solid comprising calcium carbonate may be separated from an aqueous solution comprising ammonium sulfate by a solid-liquid separation. The aqueous solution comprising ammonium sulfate may be reacted with sodium chloride, which may result in the formation of ammonium chloride and sodium sulfate. In some embodiments, a portion of sodium sulfate may be separated from ammonium chloride by cooling precipitation due to, for example, the substantial reduction in sodium sulfate solubility with decreasing temperature below about 32.3 degrees Celsius. In some embodiments, ammonium chloride and sodium sulfate may be separated by an evaporator and/or crystallizer, and/or due to differences in solubility between ammonium chloride and sodium sulfate. In some embodiments, sodium sulfate may be transferred to further process steps, such as process steps which convert sodium sulfate to sodium hydroxide or sodium carbonate. In some embodiments, sodium sulfate may be transferred, stored, or sold, or utilized, or any combination thereof. In some embodiments, the ammonium chloride, which may comprise a solid or aqueous solution, may be thermally decomposed into ammonia and hydrogen chloride gas. In some embodiments, ammonium chloride may be contacted or thermally decomposed or reacted, or any combination thereof in the presence of a material or chemical comprising calcium-weak acid or alkaline earth-weak acid salt. In some embodiments, the ammonium chloride, or ammonia gas, or hydrogen chloride gas, or any combination thereof may be contacted with or reacted with calcium carbonate, which may result in the formation of ammonia gas, or calcium chloride, or water vapor, or carbon dioxide gas, or any combination thereof. In some embodiments, said calcium carbonate may comprising the calcium carbonate produced from the reaction of ammonium carbonate with calcium sulfate. In some embodiments, ammonia gas, or water vapor, or carbon dioxide gas, or any combination thereof may be separated from calcium chloride, which may comprise a solid phase calcium chloride or an aqueous phase calcium chloride. In some embodiments, calcium chloride may be transferred, stored, or sold, or utilized, or any combination thereof. In some embodiments, ammonia gas, or water vapor, or carbon dioxide gas, or any combination thereof may be cooled and/or reacted to form a solid or aqueous solution comprising ammonium carbonate. In some embodiments, ammonia gas, or water vapor, or carbon dioxide gas, or any combination thereof may be contacted with or reacted in the water recovered or removed during the evaporation or crystallization of sodium sulfate and ammonium chloride. In some embodiments, the ammonium carbonate or other ammonia-carbon dioxide derivative may be recycled or recirculated internally or within the process. For example, in some embodiments, the ammonium carbonate or other ammonia-carbon dioxide derivative may be employed in the reaction with calcium sulfate to, for example, form calcium carbonate and ammonium sulfate. In some embodiments, ammonia and carbon dioxide may be separated. In some embodiments, such as the embodiment shown in FIG. 29, ammonia and carbon dioxide may be separated in the presence of water such that separated or captured carbon dioxide may be produced and/or the process may comprise capturing or separating carbon dioxide. In some embodiments, such as the embodiment shown in FIG. 30, ammonia and carbon dioxide may be separated such that ammonia and carbon dioxide can be reacted to produce urea.

In some embodiments, the production of alkali hydroxide and alkaline earth chloride from an alkali chloride, or an alkaline earth-weak acid, or any combination thereof in a process which recirculates sulfate and/or may prevent production of hydrochloric acid or hydrogen chloride as a byproduct may be desirable. In some embodiments, production of sodium hydroxide and calcium chloride from sodium chloride, or calcium-weak acid anion, or any combination thereof in a process which recirculates sulfate and/or may prevent production of hydrochloric acid or hydrogen chloride as a byproduct may be desirable. For example, producing calcium chloride be desirable due to the calcium chloride byproduct being a valuable product and/or due to the fact calcium chloride, if in excess quantities, can be discarded into the ocean with minimal environmental impact and negligible impact on ocean water composition or pH, unlike hydrogen chloride or hydrochloric acid. For example, in some embodiments, a process which recirculates or recycles sulfate may be desirable because, for example, in some geographies, sulfate may be relatively less abundant than chloride, which may be important if some embodiments are employed to remove or sequester hundreds of millions or billions of tons of $CO_2$ annually from the atmosphere, or oceans, or emissions sources, or any combination thereof, or increase the pH of the ocean, or counteract ocean acidification, or any combination thereof. For example, in some embodiments, a process which recirculates or recycles carbon dioxide may be desirable because, for example, in some geographies, the availability and reliability of $CO_2$ injection or $CO_2$ sequestration may be limited, it may be important if some embodiments are employed to remove or sequester hundreds of millions or billions of tons of $CO_2$ annually from the atmosphere, or oceans, or emissions sources, or any combination thereof, or increase the pH of the ocean, or counteract ocean acidification, or any combination thereof.

In some embodiments, production of alkali sulfate and alkaline earth chloride from an alkali chloride and alkaline earth sulfate may be desirable. In some embodiments, production of sodium sulfate and calcium chloride from sodium chloride and calcium sulfate may be desirable.

For example, in some embodiments, producing sodium sulfate with sulfate from calcium sulfate may be desirable because it may enable sourcing of sulfate from inexpensive calcium sulfate, or gypsum, or phosphogypsum, or any combination thereof, which may be less expensive and/or more abundant than, for example, sulfuric acid. For example, gypsum and phosphogypsum are significant byproducts of the phosphate and phosphoric acid production industry and are generally produced in significant excess to their consumption in the market. In 2008, it was estimated that 100 to 280 Million tons of phosphogypsum is produced annually globally for phosphate and phosphoric acid production. Excess phosphogypsum is generally stored in stacks. Greater than 1 billion tons of phosphogypsum accumulated in stacks are present in Florida, for example.

In some embodiments, alkali sulfate may be employed at a solid phase, or aqueous phase, or any combination thereof. For example, in some embodiments, the alkali sulfate may supplied as or sourced as an aqueous solution. For example, in some embodiments, the alkali sulfate may supplied as or sourced as a solid. In some embodiments, it may be desirable to dissolve solid alkali sulfate in water to form an aqueous alkali sulfate solution, wherein the aqueous alkali sulfate solution may be employed in the reaction between alkali sulfate and alkali earth-acid. In some embodiments, it may be desirable to add a solid, or solid liquid slurry, or any combination thereof comprising alkali sulfate to an alkali earth acid solution. In some embodiments, it may be desirable to add a concentrated aqueous solution comprising alkali sulfate to an aqueous solution comprising an alkali earth acid. For example, an aqueous solution comprising sodium sulfate may be mixed with a solution comprising an alkaline earth-acid. For example, an aqueous solution comprising sodium sulfate, or a solid comprising sodium sulfate, or any combination thereof may be mixed with a solution comprising an calcium acetate, which may result in the formation of an aqueous solution comprising sodium acetate and solid precipitate comprising calcium sulfate. In some embodiments, it may be desirable to for the aqueous solution comprising sodium sulfate to be at a temperature greater than 10° C., or greater than 20° C., or greater than 30° C. because, for example, sodium sulfate solubility may substantially increase with increasing temperature between zero and about 32.3° C. In some embodiments, it may be desirable to maximize sodium sulfate concentration to, for example, reduce potential required water removal, or water separation, or water evaporation in, for example, later steps. In some embodiments, it may be desirable for alkali sulfate concentration, or alkaline earth acid concentration, or alkali acid concentration, or any combination thereof to be a high concentration to, for example, reduce potential required water removal, or water separation, or water evaporation in, for example, later process steps. In some embodiments, it may be desirable for alkali sulfate concentration, or alkaline earth acid concentration, or alkali acid concentration, or any combination thereof to be a relatively low concentration or relative dilute concentration to enable separation of alkali sulfite and acid by means of electrodialysis in later process steps.

In some embodiments, an alkali sulfate may be reacted with an alkaline earth acid, which may result in the formation of an alkali acid and an alkaline earth sulfate. In some embodiments, it may be desirable for the formed alkali acid to comprise an aqueous solution, or dissolved salt, or any combination thereof and/or it may be desirable for the formed alkaline earth sulfate to comprise a solid, or a solid precipitate, or any combination thereof. For example, sodium sulfate may be mixed with or reacted with a calcium acetate, which may result in the formation of sodium acetate and calcium sulfate. In some embodiments, it may be desirable for the sodium sulfate to comprise an aqueous solution, or the calcium acetate to comprise an aqueous solution, or the formed sodium acetate to comprise an aqueous solution, or the formed calcium sulfate to comprise a solid, or any combination thereof. It may be desirable for the reaction of sodium sulfate with calcium acetate to be conducted at a temperature greater than, for example, 10° C., or 20° C., or 30° C., or 35° C., or any combination thereof because, for example, sodium sulfate exhibits greater solubility in water with increasing temperature between up to about 32.3° C. and/or calcium sulfate solubility in water, which is generally significantly lower than sodium sulfate solubility, decreases with increasing solution temperature. Solid precipitate comprising calcium sulfate may be separated from the aqueous solution comprising sodium acetate by, for example, a solid-liquid separation.

In some embodiments, a portion of calcium sulfate may dissolve or may be present at an aqueous state in the solution comprising alkali acid. In some embodiments, a portion of calcium sulfate may dissolve or may be present at an aqueous state in the solution comprising sodium acetate. In some embodiments, it may be desirable for the reaction of calcium acid with an alkali sulfate to form calcium sulfate and an alkali acid may be conducted at an elevated solution temperature, which may include, but is not limited to, greater than or equal to one or more or any combination of the following: 30° C., or 40° C., or 50° C., or 60° C., or 70° C., or 80° C., or 90° C., or 100° C., or 110° C., or 120° C., or 130° C., or 140° C., or 150° C., or 160° C., or 170° C. In some embodiments, it may be desirable to conduct reaction of calcium acid with an alkali sulfate to form calcium sulfate and an alkali acid at an elevated solution temperature because the solubility of calcium sulfate may significantly decrease with increasing temperature. For example, conducting said reaction at an elevated solution temperature may enable a lower dissolved concentration of calcium sulfate, which may prevent or reduce calcium sulfate scaling in later process steps and/or may reduce the concentration or presence of calcium sulfate in produced alkali sulfite or alkali hydroxide. In some embodiments, it may be desirable for the elevated solution temperature to be at a temperature greater than the temperature which a solution comprising alkali sulfite and acid may be distilled, or evaporated, or crystallized, or any combination thereof. In some embodiments, it may be desirable for the elevated solution temperature to be at a temperature greater than the temperature which a solution comprising alkali sulfite and acid may be distilled, or evaporated, or crystallized, or any combination thereof because it may prevent calcium sulfate scale formation from occurring in the heat exchangers and/or other equipment during, for example, the pre-heating or countercurrent heat exchange of a solution comprising alkali sulfite and acid.

In some embodiments, it may be desirable for the reactor employed for the reaction of calcium acid with an alkali sulfate to form calcium sulfate and an alkali acid to comprise a pressurized reactor, which may comprise a reactor with an operating pressure greater than atmospheric pressure, or greater than the pressure of the ambient air adjacent to the reactor, or greater than the pressure of the ambient air at the same elevation of the reactor, or any combination thereof. For example, if said reaction is conducted at an elevated solution temperature, the vapor pressure of the water, or other solvent, or acid, or any combination thereof may necessitate the use of a pressurized reactor.

In some embodiments, a countercurrent heat exchanger may be employed to pre-heat reagents entering the reaction of calcium acid with an alkali sulfate and/or cooling the aqueous solution comprising alkali acid. In some embodiments, calcium sulfate solid or precipitate may be separated or removed by a solid-liquid separation before the aqueous solution comprising alkali acid enters the countercurrent heat exchanger. In some embodiments, it may be desirable for the aqueous alkali acid to be at a lower temperature for the absorption or reaction with sulfur dioxide and/or prevent or minimize the evaporation or vaporization of acid during or after reaction with sulfur dioxide, which may be applicable, for example, if the formed acid is volatile or possesses a vapor pressure. For example, an alkali acid solution comprising sodium acetate may be reacted with sulfur dioxide to form sodium sulfite or sodium bisulfite, which may result in the formation of acetic acid, which may be volatile or may possess a vapor pressure.

In some embodiments, an aqueous solution comprising an alkali-acid may be contacted with or reacted with sulfur dioxide, which may result in the formation of an alkali sulfite and an acid or an aqueous solution comprising an alkali sulfite and an acid. In some embodiments, the alkali sulfite and acid may form at an aqueous phase within a reactor or may comprise an aqueous solution comprising alkali sulfite and acid. For example, an aqueous solution comprising sodium acetate may be reacted with sulfur dioxide, which may result in the formation of an aqueous solution comprising sodium sulfite and acetic acid. It may be desirable for the acid to possess a weaker acid strength than sulfurous acid or aqueous sulfur dioxide. In some embodiments, sulfur dioxide may comprise a dilute gas, or a gas, or a liquid, or an aqueous solution, or a solution, or a solid, or a supercritical fluid, or any combination thereof. For example, an aqueous solution comprising sodium acetate may be contacted with a gas stream comprising dilute concentration of sulfur dioxide. For example, in some embodiments, a dilute concentration of sulfur dioxide gas may comprise, including, but not limited to, one or more or any combination of the following: a sulfur dioxide partial pressure of lower than 1 atm, or 0.9 atm, or 0.8 atm, or 0.7 atm, or 0.6 atm, or 0.5 atm, or 0.4 atm, or 0.3 atm, or 0.2 atm, or 0.1 atm, or 0.05 atm, or any combination thereof and/or a volume percent concentration of sulfur dioxide lower than 100%, or 90%, or 80%, or 70%, or 60%, or 50%, or 40%, or 30%, or 20%, or 10%, or 5%, or any combination thereof. In some embodiments, a gas stream comprising sulfur dioxide may comprise sulfur dioxide from the decomposition of an alkaline earth sulfite. In some embodiments, an alkali acid may be contacted with or reacted with sulfur dioxide in a gas-liquid contactor or reactor, which may include, but is not limited to, an absorption column, or bubble column, or packed column, or membrane contactor, or any combination thereof. In some embodiments, it may be desirable for at least a portion of the alkali sulfite and/or the acid to comprise an aqueous solution, or an aqueous liquid phase, or to be pumpable, or any combination thereof while in the contactor or reactor. In some embodiments, an alkali acid may be reacted with high concentration or high purity or high pressure sulfur dioxide gas, or a liquid comprising sulfur dioxide, or liquid sulfur dioxide, or an aqueous solution comprising sulfurous acid, or an aqueous solution comprising sulfur dioxide, or a solid comprising sulfur dioxide, or a supercritical fluid comprising sulfur dioxide, or any combination thereof. In some embodiments, an alkali sulfate may be reacted with sulfur dioxide in a mixer, or static mixer, or continuous stirred reactor, or a liquid-liquid contactor, or a liquid-liquid mixer, or a liquid-solid mixer, or a gas-liquid contactor, or sparger, or any combination thereof. In some embodiments, a portion of alkali sulfite precipitate may form in the reaction of alkali acid with sulfur dioxide or sulfurous acid. In some embodiments, alkali sulfite may remain a liquid or at an aqueous phase throughout the duration of the reaction of alkali acid with sulfur dioxide. In some embodiments, alkali sulfite may remain a liquid or at an aqueous phase throughout the duration of the reaction of alkali acid with sulfur dioxide, which may be desirable due to, for example, the pumpability of liquids, avoidance of solids entrapment, or preventing or avoiding solids handling in an absorption column, or any combination thereof.

In some embodiments, the reaction of an alkali acid with sulfur dioxide may form an alkali sulfite and an acid, wherein said formed acid may possess a vapor pressure. For example, the reaction of sodium acetate with sulfur dioxide may form sodium sulfite and acetic acid, wherein acetic acid may possess a vapor pressure. In some embodiments, it may be desirable to minimize or prevent losses of acid due to release of acid vapor, or carryover or slip of acid vapor, or any combination thereof.

For example, in some embodiments, if a gas stream comprising sulfur dioxide comprises other gases or comprises dilute sulfur dioxide, acid vapor may be present in the remaining gases during or after the reaction of sulfur dioxide with alkali acid and the formation of acid and alkali sulfite. For example, in some embodiments, as a dilute sulfur dioxide gas is contacted with an alkali acid, sulfur dioxide may react or absorb to form alkali sulfite and/or the acid vapor or acid vapor pressure may accumulate or be released into the remaining gases. In some embodiments, in some embodiments, it may be desirable to design a sulfur dioxide absorption column or absorption process to contact solution comprising alkali acid with the least, or near lowest, or lowest concentration or vapor pressure of acid with the gas lean in sulfur dioxide and rich in acid vapor. For example, in some embodiments, aqueous solution comprising alkali acid entering an absorption process, which may not have substantially reacted with sulfur dioxide, may comprise little free acid or acid unreacted with alkali or may comprise solution with the least, or near lowest, or lowest concentration or vapor pressure. For example, in some embodiments, a sulfur dioxide absorption column may be configured such that gas comprising a high concentration of sulfur dioxide and low concentration of acid vapor is contacted with an aqueous solution comprising a high concentration of alkali sulfite, a low concentration of alkali acid, and a high concentration of aqueous acid or free acid; and/or gas comprising a low concentration of sulfur dioxide and high concentration of acid vapor is contacted with an aqueous solution comprising a low concentration of alkali sulfite, a high concentration of alkali acid, and a low concentration of aqueous acid or free acid. For example, in some embodiments, a sulfur dioxide absorption may be configured such that first, a gas rich in sulfur dioxide and lean in acid vapor is contacted with a solution comprising alkali acid to form a solution comprising alkali sulfite and acid and a gas lean in sulfur dioxide and rich in acid vapor, then, second, the gas lean in sulfur dioxide and rich in acid vapor is contacted with entering solution comprising alkali acid lean in aqueous acid or free acid, absorbing at least a portion of the acid vapor and forming a solution comprising alkali acid relatively rich in aqueous acid or free acid and a gas lean in sulfur dioxide and lean in acid vapor. For example, in some embodiments, an aqueous solution comprising alkali acid may be first contacted with a gas rich in acid vapor and lean in sulfur dioxide, which may result in the absorption of acid vapor and the formation of an aqueous alkali acid relatively rich in dissolved acid or free acid; then, second, the aqueous alkali acid relatively rich in absorbed acid or free acid may be contacted with a gas rich in sulfur dioxide and lean in acid vapor to form a solution comprising aqueous alkali sulfite and acid. For example, some embodiments may utilize the inherently low concentration of acid, or low acid vapor pressure, or any combination thereof of some solutions comprising alkali acid to absorb acid vapor. In some embodiments, it may be desirable to contact gas comprising acid vapor and/or absorb acid vapor into a solution comprising alkali acid, for example, substantially before reacting the alkali acid with sulfur dioxide because, for example, the reaction of alkali acid with sulfur dioxide may produce acid or free acid and/or increase the solution's acid vapor pressure. For example, in some embodiments, an aqueous solution comprising sodium acetate may be first contacted with a gas comprising remaining gases and/or acetic acid vapor, which may result in the formation of an aqueous solution comprising sodium acetate with dissolved or absorbed acetic acid vapor and/or a gas comprising remaining gases comprising a lower concentration of acetic acid vapor. For example, in some embodiments, the aqueous solution comprising sodium acetate with dissolved or absorbed acetic acid vapor may be then, second, contacted with a gas comprising sulfur dioxide, which may result in the formation of an aqueous solution comprising sodium sulfite and acetic acetic acid. For example, in some embodiments, the aqueous solution comprising sodium may enter the process at the first step, then may be transferred into the second step, then may exit the process at or after the second step. For example, in some embodiments, the gas may enter the process at the second step, then may be transferred into the first step, then may exit the process at or after the first step.

For example, in some embodiments, a sulfur dioxide absorption process with acid vapor recovery or removal may comprise an absorption column, wherein a higher elevation portion of the column, or the 'top portion', may comprise absorbing acid vapor into the alkali acid salt solution to form alkali acid salt solution with dissolved acid vapor, and then the lower elevation portion of the column, or 'bottom portion', may comprise absorbing or reacting sulfur dioxide into the alkali acid salt solution with dissolved acid vapor transferred from the higher elevation portion of the column. For example, in some embodiments, a gas comprising sulfur dioxide may enter the absorption process in the bottom portion of the absorption column and/or the remaining gases after sulfur dioxide absorption may exit the top portion of the absorption column.

For example, in some embodiments, a sulfur dioxide absorption process with acid vapor recovery may comprise at least two absorption columns, comprising a first absorption column and a second absorption column. The first absorption column may be configured to absorb acid vapor slip or carryover. The second absorption column may be configured to absorb sulfur dioxide. An aqueous solution comprising an alkali acid may enter the absorption process in the first absorption column, then may be transferred into the second absorption column, and then may exit the second absorption column as a solution comprising alkali sulfite and acid. A gas comprising sulfur dioxide may enter the absorption process in the second absorption column, then may be transferred into the first absorption column, and then may exit the first absorption column as a gas lean in sulfur dioxide. In the second absorption column, a gas comprising sulfur dioxide may be reacted with an aqueous solution comprising an alkali acid and absorbed acid vapor, wherein a solution comprising alkali acid and absorbed acid vapor may enter the second absorption column and then exit as a solution comprising as an alkali sulfite and acid; and/or wherein a gas comprising sulfur dioxide may enter the second absorption column and then exit as a gas comprising remaining gases and acid vapor. In some embodiments, gas may enter the second absorption column near the bottom of the absorption column and/or liquid or solution may enter the second absorption column near the top of the absorption column. In the first absorption column, a gas comprising remaining gases and acid vapor may be contacted with an aqueous solution comprising an alkali acid, wherein a solution comprising alkali acid may enter the first absorption column and exit as a solution comprising an alkali acid and absorbed acid vapor; and/or wherein a gas comprising remaining gases and acid vapor may enter the first absorption column and exit as a gas comprising remaining gases with a lower concentration of acid vapor. In some embodiments, gas may enter the first absorption column near the bottom of the absorption column and/or liquid or solution may enter the first absorption column near the top of the absorption column. In some embodiments, remaining gases may comprise unabsorbed gases, or gases remaining after absorption, or gases exiting an absorption process, or gases exiting an adsorption process, or any combination thereof.

For example, in some embodiments, alkali acid may be reacted with high pressure, or high purity, or liquid, or aqueous, or solid, or any combination thereof sulfur dioxide. For example, in some embodiments, acid vapor release or production may be prevented by employing, for example, high pressure, or high purity, or liquid, or aqueous, or solid, or any combination thereof sulfur dioxide in the reaction of alkali acid with sulfur dioxide. For example, in some embodiments, by employing high pressure, or high purity, or liquid, or aqueous, or solid, or any combination thereof sulfur dioxide in the reaction of alkali acid, a lower proportion of acid vapor may evaporate or form. In some embodiments, for example, an aqueous solution comprising sodium acetate may be reacted with liquid sulfur dioxide, which may result in the formation of a solution comprising aqueous sodium sulfite and acetic acid and/or minimal remaining gases, if any, into which a portion acetic acid may evaporate.

For example, in some embodiments, acid vapor may be removed or further removed from a gas comprising residual or remaining acid vapor, or acid vapor slip, or acid vapor carryover, or any combination thereof by, for example, contacting or reacting said gas with an alkali hydroxide, or alkali carbonate, alkali-weak acid or an alkaline earth oxide, or alkaline earth hydroxide, or alkaline earth carbonate, or alkaline earth-weak acid, or ammonium hydroxide, or ammonium carbonate, or a bicarbonate, or an ammonium-weak acid, or any combination thereof to form, for example, an alkali acid, or alkaline earth-acid, or ammonium-acid, or any combination thereof. In some embodiments, alkali acid, or alkaline earth-acid, or ammonium-acid, or any combination thereof may be, for example, added to a process, or a process described herein employing alkali acid, or alkaline earth-acid, or ammonium-acid, or any combination thereof.

For example, in some embodiments, water produced or sourced without or with a low concentration of dissolved acid, or a low vapor pressure of acid, or a vapor pressure of acid lower than the vapor pressure of acid in a gas, or any combination thereof may be employed to absorb at least a portion of acid vapor from a gas. For example, in some embodiments, water added to the process as makeup water, or to makeup for water removed from the process in aqueous solutions exiting the process, or water added in the nature of process operations, or any combination thereof may be contacted with gas comprising acid vapor to remove or absorb at least a portion of acid vapor.

For example, in some embodiments, a portion of acid vapor may be recovered or absorbed by contacting remaining gases comprising acid vapor with a solvent with which the acid vapor is soluble. In some embodiments, it may be desirable for the solvent to enable or allow for the separation or regeneration of absorbed acid and/or solvent and/or may enable or allow for the separation of the acid from the solvent after absorption of the acid vapor into the solvent. In some embodiments, the solvent may comprise a liquid with a significantly lower vapor pressure, or significantly lower vapor pressure of the acid, or higher boiling point, or any combination thereof than the acid, or remaining gases comprising acid vapor, or any combination thereof. For example, in some embodiments, remaining gases comprising acid vapor comprising acetic acid may be contacted with a solvent comprising, including, but not limited to, one or more or any combination thereof: a glycol, or glycol ether, or glycol polymer, or glycol ether polymer, or an ester, or any combination thereof. For example, in some embodiments, it may be desirable for the absorbed acid to be regenerated or desorbed from the solvent by heating, or stripping, or steam stripping, or distillation, or fractional distillation. In some embodiments, it may be desirable to absorb acid vapor into water. In some embodiments, it may be desirable to absorb acid vapor into a solvent from which the acid may be separated by extractive distillation, or azeotropic distillation, or melt separation, or pressure swing, or electrical method, or other separation method described herein, or a separation method in the art. In some embodiments, it may be desirable to absorb acid vapor into a solvent from which the acid may be separated by a separation method described herein, or a separation method in the art, or any combination thereof. In some embodiments, it may be desirable to absorb and concentrate the acid in the solvent, which may result in a partially separated acid, or a concentrated acid solution.

For example, in some embodiments, acid vapor may be adsorbed to a solid or adsorbent with which the acid vapor has affinity. For example, in some embodiments, acid vapor may be adsorbed to a solid or adsorbent with which the acid vapor has affinity and from which the adsorbed acid may be separated. For example, in some embodiments, acid may be regenerated or separated from an adsorbent by heat, or stripping, or steam stripping, or electrical method, or pressure swing, or any combination thereof.

For example, in some embodiments, acid vapor may be separated or recovered by cryogenic separation, or cooling, or condensing, or absorbing in a cooled solution, or liquefaction, or deposition, or any combination thereof.

In some embodiments, residual acid vapor may be contacted with, or absorbed by, or absorbed by, or any combination thereof a chemical or material comprising, including, but not limited to, one or more or any combination of the following: an alkaline-earth-weak acid, or an alkali-weak acid, or calcium hydroxide, or calcium carbonate, or magnesium hydroxide, or magnesium carbonate, or sodium hydroxide, or sodium carbonate, or sodium bicarbonate.

In some embodiments, a solution comprising alkali sulfite and an acid may be separated. For example, at least a portion of alkali sulfite may be separated from the acid. For example, in some embodiments, an aqueous alkali sulfite may be separated from an aqueous acid by utilizing the difference in solubility between the acid and the alkali sulfite. For example, an alkali sulfite comprising sodium sulfite may be less soluble in water than an acid comprising acetic acid. For example, sodium sulfite may be partially soluble or partially miscible in water, while acetic acid may be fully miscible. In some embodiments, at least a portion of sodium sulfite may be precipitated from a solution comprising acetic acid and sodium sulfite. In some embodiments, the solution comprising alkali sulfite and an acid may undergo evaporation and/or crystallization to, for example, separate water and/or crystallize or separate the alkali sulfite and/or separate the acid. For example, a solution comprising sodium sulfite and acetic acid may undergo evaporation and/or crystallization, wherein a portion of sodium sulfite may crystallize from solution, while a portion of acetic acid may remain at an aqueous or liquid phase, or a portion of acetic the acetic acid may be at a gaseous phase, or a portion of acetic the acetic acid may be at a gaseous phase with water vapor, or any combination thereof. The sodium sulfite solid may be separated from the remaining aqueous solution or liquid by a solid-liquid separation. After separating sodium sulfite, acetic acid may comprise an aqueous solution, or concentrated aqueous solution, or liquid acetic acid, or solid acetic acid, or a vapor, or water-acetic acid condensate, or a vapor comprising water and acetic acid, or a distillate or condensate comprising aqueous acetic acid, or acetic acid vapor, or any combination thereof. It may be important to note that acetic acid may have a melting point at about 16° C., which may be substantially lower than the melting point of sodium sulfite and/or in some embodiments, liquid acetic acid may separated from sodium sulfite by a solid-liquid separation or gaseous acetic acid may be separated from sodium sulfite by a solid-gas or solid-gas-liquid separation.

In some embodiment, evaporation or crystallization may be conducted in a continuous, or semi-continuous, or semi-batch, or batch, or single-stage, or multi-stage, or any combination thereof configuration.

In some embodiments, some acids, such as some carboxylic acids, may have a boiling point near the boiling point of water and/or may form azeotropes with water. In some embodiments, 'water' may comprise an aqueous acid solution, or aqueous carboxylic acid solution, or any combination thereof. In some embodiments, the 'water' or liquid formed from the condensation of vapor from distillation, or evaporation, or crystallization, or any combination thereof may comprise an aqueous carboxylic acid solution. For example, formic acid may form an azeotrope with water, or propanoic acid may form an azeotrope with water, or butyric acid may form an azeotrope with water, or iso-butyric acid may form an azeotrope with water, or any combination thereof. For example, acetic acid may be zeotropic with water, however acetic acid may have a boiling point close to the boiling point of water, which may mean vapor or distillate from a solution comprising water and acetic acid may comprise substantial proportions of both water vapor and acetic acid vapor.

In some embodiments, an alkali sulfite may be separated from an acid, or water, or any combination thereof. In some embodiments, the alkali sulfite may be separated by evaporation, or crystallization, or any combination thereof. For example, an aqueous solution comprising sodium sulfite and acetic acid may be separated by evaporation and/or crystallization, which may result in the formation of a vapor phase or condensate liquid comprising acetic acid and water or aqueous acetic acid and/or a solid comprising sodium sulfite. Sodium sulfite may be separated by solid-liquid separation.

In some embodiments, residual aqueous calcium sulfate may be present in the aqueous solution comprising alkali sulfite and acid. For example, aqueous calcium sulfate may be present in the aqueous solution comprising sodium sulfite and acetic acid. Calcium sulfate may be soluble in water at a low concentration, such as, for example, 2.1 grams per kg of water at 20° C. The solubility of calcium sulfate may substantially decrease with increasing temperature, such as, for example, decreasing by 5-10× between 20° C. and 100° C. In some embodiments, a portion of calcium sulfate may precipitate or scale before or during the separation of alkali sulfite and acid. In some embodiments, precipitated calcium sulfate may be removed or separated, using, for example, a solid-liquid separation method. In some embodiments, heating or pre-heating the solution comprising alkali sulfite and acid may be employed, which may precipitate at least a portion of calcium sulfate, which may be separated. In some embodiments, sodium sulfite, or sodium hydroxide, or any combination thereof may comprise a portion of calcium sulfate impurity, with may be further separated if desired.

In some embodiments, higher purity water or acid may be desired, or water or acid of purity greater than can be achieved by evaporation or boiling or fractional distillation may be desired, or any combination thereof. For example, if higher purity water or acid is desired, techniques or methods for separating water and acid may be employed. If higher purity water or acetic acid is desired, techniques or methods for separating water and carboxylic acid may be employed. For example, techniques or methods for separating liquids or solutions with similar boiling points, azeotropes, or any combination thereof may comprise, including, but not limited to, one or more or any combination thereof: extractive distillation, or azeotropic distillation, or liquid-liquid extraction, or fractional crystallization, or fractional melt crystallization, or salting out, or methods for separating acetic acid in the art, or methods for separating carboxylic acids in the art, or methods for separating carboxylic acids from water in the art, or any combination thereof. For example, acetic acid may be separated from water by extractive liquid-liquid extraction, or distillation, or azeotropic distillation, or any combination thereof by employing an entrainer or extractant comprising, for example, ethyl acetate or Methyl tert-butyl ether (MTBE). For example, in some embodiments, water may be separated from ethyl acetate, or MTBE, or both by mixing with or dissolving an alkali sulfite, or alkali sulfate, or alkali carbonate, or sodium sulfite, or sodium sulfate, or sodium carbonate, or potassium sulfite, or potassium sulfate, or potassium carbonate, or any combination thereof, which may salt out at least a portion of the ethyl acetate, or MTBE. For example, a portion of some carboxylic acids may be 'salted-out' from solution by the dissolution of or addition of an alkali sulfate, or alkali sulfite, or alkali salt, or alkaline-earth salt, or ammonium salt, or salt, or any combination thereof into an aqueous solution comprising carboxylic acid. For example, in some embodiments, sodium sulfate may be dissolved into a solution comprising an aqueous carboxylic acid, which may result in a solution comprising aqueous carboxylic acid and sodium sulfate and/or the formation of a second liquid phase comprising 'salted-out' carboxylic acid. In some embodiments, a liquid-liquid separation may be employed to separate the liquid phase comprising 'salted-out' carboxylic acid from the aqueous phase comprising sodium sulfate.

In some embodiments, a solution comprising alkali sulfite and acid may be at least partially separated. In some embodiments, at least a portion of the concentrating or separation of alkali sulfite and/or acid may be conducted using, for example, a membrane-based process, an electrochemical process, or any combination thereof. In some embodiments, a portion of an acid may be separated from an alkali sulfite by electrodialysis. For example, a solution comprising sodium sulfite and acetic acid may be separated into a separate solution comprising sodium sulfite and a separate solution comprising acetic acid using electrodialysis. For example, in some embodiments, a feed solution comprising an alkali sulfite and an acid may be separated into a concentrate solution comprising a greater concentration of alkali sulfite than the feed solution and a permeate or diluate solution comprising the acid. For example, in some embodiments, a feed solution comprising an sodium sulfite and acetic acid may be separated into a concentrate solution comprising a greater concentration of sodium sulfite than the feed solution and a permeate or diluate solution comprising acetic acid. In some embodiments, the concentrate solution may comprise a portion of acid. In some embodiments, the permeate or diluate solution may comprise a portion of alkali sulfite.

In some embodiments, an aqueous solution comprising alkali sulfite and acid may be at least partially separated or concentrated using reverse osmosis, or nanofiltration, or forward osmosis, or any combination thereof. For example, in some embodiments, an aqueous solution comprising sodium sulfite and acetic acid may be at least partially separated or concentrated using reverse osmosis, or nanofiltration, or forward osmosis, or any combination thereof. For example, in some embodiments, a feed solution comprising an aqueous solution comprising sodium sulfite and acetic acid may be transformed into a concentrate solution comprising sodium sulfite at a higher concentration than in the feed solution and acetic acid, and/or a permeate solution comprising acetic acid. In some embodiments, some acids may permeate a semi-permeable membrane or may have a lower rejection rate while the alkali sulfite may be rejected by the semi-permeable membrane or may have a higher rejection rate, because, for example, some acids may possess a smaller hydration radius than the dissolved ionic salt comprising alkali sulfite. In some embodiments, the concentrate comprising sodium sulfite and acetic acid may be distilled, or evaporated, or any combination thereof and/or sodium sulfite may be precipitated or crystallized. Precipitated or crystallized sodium sulfite may be separated by, for example, a solid-liquid separation. Concentrating the sodium sulfite using a membrane-based process may reduce the quantity of water or acetic acid removal required using more energy intensive methods, such as methods employing gas-liquid phase transitions. In some embodiments, the concentrate comprising sodium sulfite and acetic acid may be mixed with feed solution before or while feed solution is concentrated or separated using the membrane based process, and/or the combined solution of concentrate comprising sodium sulfite and acetic acid and feed solution comprising sodium sulfite and acetic acid may comprise the feed solution entering the membrane based separation. In some embodiments, the permeate comprising acetic acid may be transferred to the reaction with alkaline earth-weak acid. In some embodiments, the permeate comprising aqueous acetic acid may be mixed with distillate comprising aqueous acetic acid before, or while being transferred to, or during, or any combination thereof the reaction with alkaline earth-weak acid.

In some embodiments, an aqueous solution comprising alkali sulfite and acid may be at least partially separated or concentrated using electrodialysis, electrodialysis reversal, or any combination thereof. For example, in some embodiments, an aqueous solution comprising sodium sulfite and acetic acid may be at least partially separated or concentrated using electrodialysis, electrodialysis reversal, or any combination thereof. For example, in some embodiments, a feed solution comprising aqueous sodium sulfite and acetic acid may be transferred into an electrodialysis or electrodialysis reversal process, wherein the feed solution may be separated into a concentrate solution comprising sodium sulfite and a diluate solution comprising acetic acid. In some embodiments, the acid, which may comprise acetic acid, may comprise mostly uncharged aqueous species, while the alkali sulfite, which may comprise sodium sulfite, may comprise mostly charged ionic aqueous species. For example, in an ED or EDR process, the charged species may be transferred into the concentrate solution, while uncharged species may remain in the diluate solution. In some embodiments, it may be desirable for the feed solution to comprise an alkali sulfite concentration which may be low, or low relative to the alkali sulfite salt's solubility limit, or desirable concentration of electrodialysis, or any combination thereof to, for example, reduce or optimize energy consumption of the electrodialysis system, or to enable proper function of the electrodialysis system, or any combination thereof. In some embodiments, it may be desirable for the concentration of alkali sulfite in the feed solution to be lower than, for example, 100 g per kg of water, or 150 g per kg of water, or 200 g per kg of water, or 250 g per kg of water, or any combination thereof. For example, a concentration desirable for electrodialysis, or a low concentration, or any combination thereof may comprise lower than or equal to a concentration of, including, but not limited to, one or more or any combination of the following: 5 g per kg of water, or 10 g per kg of water, or 25 g per kg of water, or 50 g per kg of water, or 75 g per kg of water, or 100 g per kg of water, or 150 g per kg of water, or 200 g per kg of water, or 250 g per kg of water, or any combination thereof.

In some embodiments, the concentrate solution comprising aqueous alkali sulfite may be reacted with an alkaline earth hydroxide, which may result in the formation of an aqueous solution comprising alkali hydroxide and solid comprising alkaline earth sulfite. For example, in some embodiments, a concentrate solution comprising aqueous sodium sulfite may be reacted with calcium hydroxide, which may result in the formation of an aqueous solution comprising sodium hydroxide and solid comprising calcium sulfite. In some embodiments, it may be desirable to further concentrate the aqueous solution comprising alkali hydroxide. For example, the aqueous solution comprising alkali hydroxide may be concentrated using, including, but not limited to, one or more or any combination thereof: MVC distillation, or MSF distillation, or MED distillation, or other an evaporator, or a crystallizer, or another separation method described herein, or another concentrating method described herein, or a separation method described in the art, or any combination thereof. In some embodiments, it may be desirable to crystallize the alkali hydroxide or produce alkali hydroxide solid. In some embodiments, it may be desirable to produce an alkali hydroxide solution, or a concentrated alkali hydroxide solution, or any combination thereof. In some embodiments, it may be desirable to further react the alkali hydroxide solution, with, for example, carbon dioxide, to produce alkali carbonate or alkali bicarbonate. In some embodiments, some dissolved alkaline earth sulfite may be present in the alkali hydroxide or aqueous solution comprising alkali hydroxide. In some embodiments, it may be desirable to separate or remove at least a portion of said dissolved alkaline earth sulfite. For example, in some embodiments, a portion of dissolved alkaline earth sulfite may precipitate during further concentrating of the alkali hydroxide and/or may be separated using a solid-liquid separation. For example, if the alkaline earth sulfite comprises magnesium sulfite, the solution comprising aqueous alkali hydroxide may comprise some aqueous magnesium sulfite because magnesium sulfite may exhibit some solubility in water.

In some embodiments, the diluate solution comprising acid may be transferred to or employed in the reaction of the acid with alkaline earth-weak acid. For example, a diluate comprising aqueous acetic acid may be transferred to and/or reacted with alkaline earth-weak acid.

In some embodiments, an alkali sulfite may be reacted with an alkaline earth oxide or alkaline earth hydroxide, which may result in the formation of an alkali hydroxide. In some embodiments, an alkali sulfite and an alkaline earth oxide or alkaline earth hydroxide may be reacted at a solid phase, or at an aqueous phase, or in the presence of water, or any combination thereof. For example, in some embodiments, an alkali sulfite may comprise sodium sulfite and an alkaline earth oxide or alkaline earth hydroxide may comprise calcium oxide or calcium hydroxide. In some embodiments, sodium sulfite may be dissolved in water, to form, for example, an aqueous solution comprising sodium sulfite. In some embodiments, it may be desirable for the concentration of sodium sulfite to be less than, for example, 3M, or 2.5M, or 2M, or 1.5M, or 1M, or 0.75M, or any combination thereof, to, for example, facilitate the reaction of sodium sulfite and calcium hydroxide. In some embodiments, it may be desirable to add or mix or introduce sodium sulfite as a dilute solution to a reaction with calcium hydroxide. In some embodiments, it may be desirable to add or mix or introduce sodium sulfite as a solid or concentrated solution to a reaction with calcium hydroxide. In some embodiments, calcium oxide may be added or mixed or introduced as a solid or powder to the reaction with sodium sulfite or aqueous sodium sulfite. For example, in some embodiments, calcium oxide may reacted with a solution comprising sodium sulfite, wherein, for example, calcium hydroxide may form as an intermediary or intermediate chemical species in the reaction. In some embodiments, calcium oxide or calcium hydroxide solid or powder may be transferred into a reaction or reactor or mixer using a screw feeder. In some embodiments, calcium hydroxide may be added or mixed or introduced as a solid or powder to the reaction with sodium sulfite or aqueous sodium sulfite. In some embodiments, calcium oxide may be reacted with water to form calcium hydroxide and/or calcium hydroxide may be added or mixed or introduced as a solid or powder to the reaction with sodium sulfite or aqueous sodium sulfite. In some embodiments, calcium hydroxide may comprise a solid-liquid suspension and/or milk of lime, and/or calcium hydroxide may be added or mixed or introduced to a reaction with sodium sulfite as a solid-liquid suspension and/or milk of lime.

In some embodiments, the reaction of calcium hydroxide and sodium sulfite may comprise an equilibrium reaction. For example, in some embodiments, it may be desirable to control the temperatures, or reagent concentrations, or ratio of reagents, or physical state of reagents, or residence time, or reactor design, or reactor configuration, or any combination thereof to, for example, facilitate the reaction of calcium hydroxide and sodium sulfite. For example, in some embodiments, it may be desirable for calcium hydroxide to be present in stoichiometric excess to the sodium sulfite in the reagents, to, for example, facilitate the equilibrium toward the formation of sodium hydroxide. For example, in some embodiments, the calcium hydroxide may be at a ratio with sodium sulfite in the reactants which may be greater than 1 mole calcium hydroxide to 1 mole sodium sulfite. For example, in some embodiments, it may be desirable for the total reaction residence time of reactants or the reaction to be greater than, for example, one or more or any combination of the following: 1 second, or 10 seconds, or 30 seconds, or 1 minute, or 5 minutes, or 10 minutes, or 15 minutes, or 20 minutes, or 25 minutes, or 30 minutes, or 45 minutes, or 1 hour. Some embodiments may employ, including, but not limited to, one or more or any combination of the following: Cascade Reactors, or Cascading Batch Mixing Reactors, or Back-Mix Reactors, or a cascade of well-stirred, jacketed, batch-mix reactors, or any combination thereof. In some embodiments, calcium oxide or calcium hydroxide may be reacted with sodium sulfite to form, for example, at least a portion of calcium sulfite and sodium hydroxide. In some embodiments, calcium oxide or calcium hydroxide may be reacted with sodium sulfite to form, for example, at least a portion of calcium sulfite and sodium hydroxide employing, or using, or within, for example, Cascade Reactors, or Cascading Batch Mixing Reactors, or Back-Mix Reactors, or a cascade of well-stirred, jacketed, batch-mix reactors, or any combination thereof. In some embodiments, the reaction of sodium sulfite and calcium hydroxide may be conducted in a batch configuration, or a semi-batch configuration, or a continuous configuration, or any combination thereof. In some embodiments, it may be desirable to minimize exposure or presence of oxygen, or diatomic oxygen, or dissolved oxygen, or free oxygen, to, for example, minimize or prevent the oxidation of sulfite to sulfate. For example, storage vessels, or transport methods, or reactors, or separators, or any combination thereof may employ an at least partially inert atmosphere or headspace, or an atmosphere or headspace comprising nitrogen gas, or an atmosphere or headspace comprising a lower concentration of diatomic oxygen than standard atmospheric air, or operation without or with a minimized headspace, or any combination thereof.

In some embodiments, a reaction of calcium hydroxide and sodium sulfite may form at least a portion of calcium sulfite and/or sodium hydroxide. In some embodiments, the aqueous solution may comprise sodium hydroxide and/or the solid phase may comprise calcium sulfite. In some embodiments, an aqueous solution may further comprise residual sodium sulfite and/or aqueous calcium hydroxide. In some embodiments, the solid phase may further comprise residual calcium hydroxide. In some embodiments, it may be desirable to separate at least a portion of the solid phase from at least a portion of the aqueous phase using one or more or a combination of solid-liquid separation systems and/or methods.

In some embodiments, an aqueous solution comprising sodium hydroxide may be further purified, or concentrated, or any combination thereof. For example, in some embodiments, an aqueous solution comprising sodium hydroxide may be further concentrated. For example, in some embodiments, at least a portion of water may be removed or separated form an aqueous solution comprising sodium hydroxide by one or more or any combination of separation processes, such as, including, but not limited to, one or more or any combination of the following: mechanical vapor compression distillation, or mechanical vapor recompression distillation, or multieffect distillation, or multistage flash distillation, or distillation, or cryodesalination, or freeze desalination, or solventing out, or electrodialysis, or reverse osmosis, or forward osmosis, or osmotically assisted reverse osmosis, or membrane distillation. In some embodiments, a portion of water removal or sodium hydroxide solution concentrating may be conducted by forward osmosis, or osmotically assisted reverse osmosis, or vapor gas membrane, or membrane distillation, or vapor transfer, or any combination thereof, wherein, for example, aqueous sodium sulfite, which may require diluting, may comprise a draw solution, and/or aqueous sodium hydroxide, which may require concentrating, may comprise a feed solution. In some embodiments, for example, at least a portion of water may transfer from an aqueous solution comprising sodium hydroxide to an aqueous solution comprising sodium sulfite, which may reduce the potential required input energy consumption for concentrating sodium hydroxide. For example, in some embodiments, an aqueous solution comprising sodium hydroxide may further comprise residual calcium hydroxide, or sodium sulfite, or sodium sulfate, or other chemicals than sodium hydroxide, or any combination thereof, and/or in some embodiments, at least a portion of calcium hydroxide, or sodium sulfite, or sodium sulfate, or chemicals other than sodium hydroxide, or any combination thereof may be separated or removed. In some embodiments, if an aqueous solution comprising sodium hydroxide undergoes concentrating, at least a portion of residual calcium hydroxide, if any, may precipitate, or at least a portion of residual sodium sulfite, if any, may precipitate, or at least a portion of residual sodium sulfate, if any, may precipitate, or any combination thereof. In some embodiments, other separation systems and methods described herein or other separation systems and methods described in the art may be employed.

In some embodiments, an aqueous solution comprising sodium hydroxide may be concentrated into a highly concentrated sodium hydroxide solution, such as a solution with a concentration of sodium hydroxide greater than, for example, 20 wt %, or 30 wt %, or 40 wt %, or 50 wt %. In some embodiments, an aqueous solution comprising sodium hydroxide may be transformed or concentrated into a solid or powder comprising sodium hydroxide.

In some embodiments, concentrating and/or purifying sodium hydroxide or an aqueous solution comprising sodium hydroxide may be unnecessary or undesired. For example, in some embodiments, sodium hydroxide or an aqueous solution comprising sodium hydroxide may be employed in ocean or sea or body of water $CO_2$ removal, where, for example, dilute concentrations of sodium hydroxide may be beneficial, for example, due to improved diffusion or dissolution, and/or residual calcium hydroxide may be beneficial due to its propensity or additional capability of removing $CO_2$. In some embodiments, the potential presence of impurities, such as calcium hydroxide, or sodium sulfite, or sodium sulfate, may be inconsequential or beneficial to $CO_2$ removal, for example, in the ocean $CO_2$ removal and/or atmospheric $CO_2$ removal.

In some embodiments, an aqueous solution comprising sodium hydroxide may be converted into sodium carbonate or sodium bicarbonate. For example, an aqueous solution comprising sodium hydroxide may be reacted with $CO_2$, or a gas comprising $CO_2$, or a salt comprising a carbonate or carbamate, or bicarbonate, or any combination thereof and/or form sodium carbonate or sodium bicarbonate.

In some embodiments, at least a portion of water or moisture may be removed from a solid comprising calcium sulfite and/or calcium hydroxide. In some embodiments, a solid comprising calcium sulfite and/or calcium hydroxide may undergo at least a portion of drying. In some embodiments, drying may be conducted using, including, but not limited to, one or more or any combination of the following: heat, or an inert stripping gas, or a desiccant, or a drying surface, or compression, or filter press. In some embodiments, heat recovered from one or more internal steps may be employed to facilitate drying. For example, heat from the reaction of calcium oxide with water may be employed to facilitate drying. In some embodiments, it may be desirable for any drying of calcium sulfite or sulfite to be conducted in a manner which minimizes or prevents exposure or presence of diatomic oxygen or free oxygen.

In some embodiments, a solid comprising calcium sulfite may comprise or further comprise calcium hydroxide. For example, in some embodiments, it may be desirable to separate at least a portion of calcium hydroxide from at least a portion of calcium sulfite. For example, in some embodiments, at least a portion of calcium hydroxide may be separated from calcium sulfite by means of different properties between calcium sulfite and calcium hydroxide, such as, for example, including, but not limited to, one or more or any combination of the following: decomposition temperatures, or change in physical state, or change in volume, or change in physical structure, or change in morphology, or density, or particle size, or solubility properties, or surface tension, or stability of liquid-solid suspensions, or other properties.

For example, in some embodiments, calcium sulfite may comprise a hydrate or possess a hydrate. For example, calcium sulfite may comprise a hydrate, such as, for example, hemihydrate and the tetrahydrate, respectively $CaSO3\cdot\frac{1}{2}(H2O)$ and $CaSO3\cdot 4(H_2O)$. In some embodiments, a solid comprising calcium sulfite and/or calcium hydroxide may be heated to a thermal decomposition temperature of a calcium sulfite hydrate, which may result in, for example, drying or dehydration of at least a portion of the solid comprising calcium sulfite, and/or a change in particulate morphology, or density, or coagulation, or particle size, or other property, or any combination thereof, which may facilitate separation of at least a portion of calcium sulfite from at least a portion of calcium hydroxide, if desired.

For example, in some embodiments, a solid comprising calcium sulfite and/or calcium hydroxide may be heated to a thermal decomposition temperature of calcium hydroxide, which may be, for example, less than the decomposition temperature of calcium sulfite. For example, in some embodiments, calcium hydroxide may begin decomposing at temperatures as low as 370° C. and/or may decompose with a partial pressure of water vapor greater than 1 Bar starting at a temperature greater than or equal to about 512° C. For example, in some embodiments, calcium sulfite may begin decomposing at temperature greater than the initial decomposition temperatures of calcium hydroxide. For example, in some embodiments, a solid comprising calcium sulfite and/or calcium hydroxide may be heated to a temperature wherein the morphology or structure of the calcium hydroxide or calcium oxide changes to, for example, facilitate and/or enable the separation of at least a portion of calcium hydroxide or calcium oxide from calcium sulfite. For example, in some embodiments, a solid comprising calcium sulfite and/or calcium hydroxide may be heated to a temperature wherein calcium hydroxide may at least partially decompose, which may result in a change in particle size, or separation of particles, or change in density, or any combination thereof which may facilitate the separation of at least a portion of calcium oxide or calcium hydroxide from calcium sulfite. For example, in some embodiments, calcium sulfite may have a density of about 2.71 g/mL and calcium oxide may have a density of 3.34 g/mL, which may be a sufficient density difference to enable at least a portion of a separation, if desired. For example, in some embodiments, the evolution of at least a portion of water vapor or the change in morphology during heating, may result, for example, in a change in properties which may facilitate or enable the separation of at least a portion of calcium sulfite from at least a portion of calcium hydroxide, if desired. Example systems and/or methods for separation of at least a portion of calcium hydroxide or calcium sulfite from at least a portion of calcium sulfite or calcium hydroxide may be described elsewhere herein.

In some embodiments, if at least a portion of calcium hydroxide may be separated from calcium sulfite, the at least partially separated calcium hydroxide may be employed as at least a portion of the reactants in the reaction of calcium hydroxide with sodium sulfite, or the at least partially separated calcium hydroxide may be calcined or decomposed to form calcium oxide and/or reacted with water to form calcium hydroxide, or any combination thereof.

For example, in some embodiments, it may be desirable to allow at least a portion of calcium hydroxide to be present in the solid comprising calcium sulfite. For example, in some embodiments, a solid comprising calcium sulfite and calcium hydroxide may be decomposed or calcined into calcium oxide, sulfur dioxide, and water vapor. For example, in some embodiments, if, for example, calcium hydroxide is present in the solid comprising calcium sulfite, it may be desirable to decompose in a manner to minimize energy consumption or temperature of heat, which may comprise to decompose calcium hydroxide into calcium oxide at a lower temperature than, for example, the decomposition temperature of calcium sulfite, then, for example, calcining or decomposing a solid comprising calcium sulfite or a solid comprising calcium sulfite and calcium oxide into, for example, calcium oxide and/or sulfur dioxide. The calcining or decomposition of calcium sulfite and/or calcium hydroxide may be further described elsewhere herein.

In some embodiments, calcium oxide from, for example, the decomposition of a solid comprising calcium sulfite and/or calcium hydroxide comprise calcium oxide reacted with water to form calcium hydroxide and/or may comprise the calcium oxide or calcium hydroxide reactant in the reaction of calcium hydroxide and sodium sulfite. In some embodiments, sulfur dioxide gas produced in, for example, the decomposition of calcium sulfite, may be transferred to or employed in, or may comprise the sulfur dioxide in the reaction of an alkali acid with sulfur dioxide, to form, for example, alkali sulfite and acid.

Example Production of Alkali Hydroxide, or Alkali Carbonate, or Alkali Bicarbonate from Alkali Sulfite Employing Carbon Dioxide Intermediate or Reactant In some embodiments, an alkali sulfite may be converted or transformed into an alkali hydroxide, or alkali carbonate, or alkali bicarbonate by, for example, reaction steps employing a carbon dioxide intermediate or reactant.

For example, in some embodiments, an alkaline-earth weak acid or an alkaline-earth carbonate may be mixed with a solution comprising water and/or carbon dioxide to form, for example, aqueous alkaline-earth carbonate, or aqueous alkaline-earth bicarbonate, or any combination thereof. For example, in some embodiments, said alkaline-earth weak acid may comprise calcium carbonate, or magnesium carbonate, or any combination thereof. For example, in some embodiments, calcium carbonate, or magnesium carbonate, or any combination thereof may be mixed with water and/or carbon dioxide to form a solution comprising aqueous calcium bicarbonate, or magnesium bicarbonate, or any combination thereof. For example, in some embodiments, it may be desirable for the reaction of calcium carbonate, or magnesium carbonate, or water, or carbon dioxide, or any combination thereof to be conducted in the presence of a high $CO_2$ partial pressure and/or at a moderately low temperature. For example, in some embodiments, it may be desirable for the $CO_2$ partial pressure in the reaction of water, or carbon dioxide, or alkaline-earth-weak acid, or calcium carbonate, or magnesium carbonate, or any combination thereof to be greater than or equal to, one or more or any combination of the following: 0.5 Bar, or 1 Bar, or 2 Bar, or 3 Bar, or 4 Bar, or 5 Bar, or 6 Bar, or 7 Bar, or 8 Bar, or 9 Bar, or 10 Bar, or 11 Bar, or 12 Bar, or 13 Bar, or 14 Bar, or 15 Bar, or 20 Bar. For example, in some embodiments, it may be desirable for the temperature of water, or calcium dioxide, or calcium carbonate, or magnesium carbonate, or reaction temperature, or dissolution temperature, or any combination thereof to be less than or equal to, one or more or any combination of the following: 100° C., or 90° C., or 80° C., or 70° C., or 60° C., or 50° C., or 40° C., or 30° C., or 25° C., or 20° C., or 15° C., or 10° C., or 5° C., or 0° C. In some embodiments, it may be desirable for the reaction of calcium carbonate, or magnesium carbonate, or water, or carbon dioxide, or any combination thereof to be conducted at a relatively low temperature because the solubility of calcium carbonate, or calcium bicarbonate, or magnesium carbonate, or magnesium bicarbonate, or any combination thereof may increase with lower temperature. For example, in some embodiments, the solubility of calcium carbonate in water in a $CO_2$ partial pressure of 1 Bar may be 1.3 g/L at 0° C. and 0.59 g/L at 38° C. For example, in some embodiments, the solubility of calcium carbonate in water in a $CO_2$ partial pressure of 10 Bar may be 2.46 g/L at 0° C. and 1.35 g/L at 42° C. For example, in some embodiments, for example, the solubility of magnesium carbonate in water in a given $CO_2$ partial pressure may be greater than the solubility of calcium carbonate in water in the same $CO_2$ partial pressure. For example, in some embodiments, the residence time of the reaction may be greater than or equal to 30 seconds, or 1 minute, or 2 minutes, or 3 minutes, or 5 minutes, or 10 minutes, or 15 minutes, or 20 minutes, or 25 minutes, or 30 minutes, or 45 minutes, or 1 hour, or any combination thereof. For example, in some embodiments, the resulting concentration of dissolved or aqueous calcium carbonate, or dissolved or aqueous calcium bicarbonate, or dissolved or aqueous magnesium carbonate, or dissolved or aqueous magnesium bicarbonate, or any combination thereof may be greater than or equal to, one or more or any combination of the following: 0.01 g/L, or 0.1 g/L, or 0.3 g/L, or 0.5 g/L, or 0.75 g/L, or 1 g/L, or 1.25 g/L, or 1.5 g/L, or 1.75 g/L, or 2.0 g/L, or 2.25 g/L, or 2.50 g/L, or 2.75 g/L, or 3.0 g/L, or 3.5 g/L, or 4 g/L, or 4.5 g/L, or 5 g/L, or 6 g/L, or 7 g/L, or 8 g/L, or 9 g/L, or 10 g/L, or 11 g/L, or 12 g/L, or 13 g/L, or 14 g/L, or 15 g/L, or 16 g/L, or 17 g/L, or 18 g/L, or 19 g/L, or 20 g/L. For example, in some embodiments, calcium carbonate or magnesium carbonate may be mixed with water to form a solid-liquid mixture, then the solid-liquid mixture may be transferred into a pressurized reactor or mixer wherein carbon dioxide may be added or pressurized. For example, in some embodiments, calcium carbonate or magnesium carbonate and water may be added to a reactor, and/or then carbon dioxide may be added to the reactor and/or the reactor may be pressurized with carbon dioxide. For example, in some embodiments, carbon dioxide, water, and calcium carbonate or magnesium carbonate may be simultaneously fed into a reactor, wherein calcium carbonate or magnesium carbonate may be fed into the reactor in a manner which minimizes or reduces or prevents the potential escape of a portion of carbon dioxide from the reactor through, for example, an opening or port employed for the addition or transfer of calcium carbonate or magnesium carbonate into the reactor. For example, in some embodiments, carbon dioxide, water, and calcium carbonate or magnesium carbonate may be simultaneously fed into a reactor. For example, in some embodiments, carbon dioxide may be dissolved in water to form aqueous carbon dioxide or carbonic acid and/or said aqueous carbon dioxide or carbonic acid may be mixed with or reacted with calcium carbonate or magnesium carbonate to form, for example, aqueous calcium carbonate, or aqueous calcium bicarbonate, or aqueous magnesium carbonate, or aqueous magnesium bicarbonate, or any combination thereof. For example, some embodiments may employ one or more batch, or semi-batch, or continuous, CSTR, or any combination thereof reactors or mixing vessels or separators.

In some embodiments, carbon dioxide employed, for example, in the reaction of water, carbon dioxide, and/or calcium carbonate or magnesium carbonate may comprise carbon dioxide produced or generated from the reaction of alkaline-earth carbonate with acid, such as, for example, the reaction of calcium carbonate with acetic acid to form calcium acetate and carbon dioxide.

In some embodiments, it may be desirable for calcium carbonate or magnesium carbonate, water, carbon dioxide, and sodium sulfite to be reacted together or simultaneously to form, for example, sodium bicarbonate and calcium sulfite or magnesium sulfite. For example, calcium carbonate or magnesium carbonate, water, and/or carbon dioxide may be added to an aqueous solution comprising sodium sulfite, which may result in the formation of sodium bicarbonate and calcium sulfite or magnesium sulfite.

In some embodiments, it may be desirable for at least a portion of a reaction of calcium carbonate or magnesium carbonate, water, carbon dioxide, and sodium sulfite to be conducted in multiple steps or multiple reaction steps.

For example, in some embodiments, a solution comprising aqueous calcium carbonate, or aqueous calcium bicarbonate, or aqueous magnesium carbonate, or aqueous magnesium bicarbonate, or any combination thereof may be mixed with or reacted with a solid comprising sodium sulfite, or a solution comprising aqueous sodium sulfite, or any combination thereof to form, for example, a solution comprising aqueous sodium bicarbonate and a solid comprising calcium sulfite, or magnesium sulfite, or any combination thereof. In some embodiments, it may be desirable for the mixing or reaction of aqueous calcium carbonate, or aqueous calcium bicarbonate, or aqueous magnesium carbonate, or aqueous magnesium bicarbonate, or any combination thereof and sodium sulfite or aqueous sodium sulfite to be conducted in high $CO_2$ partial pressure conditions, or in the presence of a $CO_2$ partial pressure greater than atmospheric pressure, or a total vessel or reactor or mixer pressure of greater than atmospheric pressure.

In some embodiments, the reaction between aqueous calcium carbonate, or aqueous calcium bicarbonate, or aqueous magnesium carbonate, or aqueous magnesium bicarbonate, or any combination thereof and sodium sulfite may utilize the significant solubility difference between calcium bicarbonate or magnesium bicarbonate in a $CO_2$ atmosphere, or sodium bicarbonate, and calcium sulfite to, for example, enable a double displacement reaction with precipitation of calcium sulfite, or magnesium sulfite, or any combination thereof. For example, in some embodiments, the solubility of calcium carbonate in water in a high $CO_2$ partial pressure atmosphere may be, for example, 1-3 g/L. For example, in some embodiments, the solubility of calcium sulfite in water may be 0.043 g/L, which is significantly lower than the potential solubility of calcium carbonate or calcium bicarbonate. In some embodiments, calcium sulfite or magnesium sulfite precipitation may be facilitated by depressurization or lowering the partial pressure of carbon dioxide, which may increase the pH of the solution which may decrease or further decrease the solubility of calcium sulfite or magnesium sulfite. In some embodiments, the solubility of calcium sulfite may increase with lower pH and may decrease with higher pH. In some embodiments, the solubility of calcium sulfite or magnesium sulfite may increase with increasing concentration or partial pressure of dissolved carbon dioxide or carbonic acid. In some embodiments, the solubility of calcium sulfite or magnesium sulfite may increase with decreasing concentration or partial pressure of dissolved carbon dioxide or carbonic acid. In some embodiments, the solubility of calcium sulfite or magnesium sulfite may decrease with increasing concentration or partial pressure of dissolved carbon dioxide or carbonic acid. In some embodiments, the solubility of calcium sulfite or magnesium sulfite may decrease with decreasing concentration or partial pressure of dissolved carbon dioxide or carbonic acid.

In some embodiments, at least a portion of calcium sulfite or magnesium sulfite may precipitate when calcium bicarbonate or magnesium bicarbonate may be mixed, or during mixing, with sodium sulfite. In some embodiments, at least a portion calcium sulfite or magnesium sulfite may precipitate after mixing with sodium sulfite and/or after depressurization or reduction in the partial pressure of carbon dioxide, due to, for example, the increase in pH which may result from the depressurization of carbon dioxide or the reduction in $CO_2$ partial pressure, and/or after concentrating or cooling at least a portion of magnesium sulfite. In some embodiments, the formed products may comprise calcium sulfite, or magnesium sulfite, or any combination thereof and/or sodium bicarbonate or sodium carbonate. In some embodiments, the formed reaction products may comprise an aqueous solution. In some embodiments, the formed reaction products may comprise an aqueous solution and a solid, or a solid-liquid mixture, wherein the aqueous solution may comprise aqueous sodium bicarbonate or sodium carbonate or aqueous magnesium sulfite and/or wherein the solid may comprise calcium sulfite or magnesium sulfite. In some embodiments, at least a portion of any carbon dioxide gas released during depressurization or pressure reduction may be transferred, or transferred internally, or recirculated, or re-compressed, or recycled, or any combination thereof. For example, in some embodiments, at least a portion of carbon dioxide or carbon dioxide released during depressurization may be employed as a portion of the carbon dioxide in the reaction of carbon dioxide, water, and/or alkaline-earth weak acid, such as calcium carbonate or magnesium carbonate. In some embodiments, power or energy may be recovered from for example, at least a portion of any depressurization of the aqueous solution and/or at least a portion of any depressurization of carbon dioxide.

In some embodiments, a solid-liquid separation may be conducted. For example, in some embodiments, a solid-liquid mixture comprising sodium bicarbonate and calcium sulfite or magnesium sulfite may be separated into at least a portion of a solid comprising calcium sulfite or magnesium sulfite and at least a portion of a solution comprising aqueous sodium bicarbonate or magnesium sulfite. For example, said solid-liquid separation employ, for example, including, but not limited to, one or more or any combination of the following: a filter, or a filter press, or a decanter, or a settler, or a coalescer, or a centrifuge, or a rotary filter, or a flocculant, or a solid-liquid separation process known in the art, or any combination thereof. Solid-liquid separations, such as solid-liquid separations of calcium sulfite or magnesium sulfite and aqueous solutions, may be further described or described in more detail elsewhere herein.

In some embodiments, magnesium sulfite may be slightly soluble in water. For example, in some embodiments, at least a portion of aqueous magnesium sulfite may be present in the solution comprising aqueous sodium bicarbonate formed form the reaction of magnesium bicarbonate with sodium sulfite. In some embodiments, for example, said aqueous magnesium sulfite may be described as residual magnesium sulfite, or residual dissolved magnesium sulfite, or residual aqueous magnesium sulfite. In some embodiments, it may be desirable to separate or recover at least a portion of aqueous magnesium sulfite from a solution comprising sodium bicarbonate. In some embodiments, it may be desirable to separate at least a portion of magnesium sulfite from at least a portion of sodium bicarbonate. For example, in some embodiments, magnesium sulfite may be recovered during a concentrating process, to, for example, concentrate at least a portion of sodium bicarbonate, or at least a portion of magnesium sulfite, or any combination thereof. For example, in some embodiments, electrodialysis or reverse osmosis may employed to concentrate magnesium sulfite, or sodium bicarbonate, or any combination thereof at a warmer temperature, then the concentrate may be cooled, which may result in the formation of at least a portion of precipitated magnesium sulfite. For example, magnesium sulfite may have temperature dependent solubility. For example, the solubility of magnesium sulfite may increase with increasing temperature. For example, the solubility of magnesium sulfite may decrease with decreasing temperature. For example, in some embodiments, by concentrating a warm solution comprising magnesium sulfite, then cooling the solution, at least a portion of a solid comprising magnesium sulfite may precipitate. In some embodiments, for example, the solubility of magnesium sulfite may be significantly less than the solubility of sodium bicarbonate, which may enable or facilitate a separation process. In some embodiments, for example, the solubility of magnesium sulfite may be significantly less than the solubility of sodium bicarbonate, which may enable the precipitation of at least a portion of magnesium sulfite and at least a portion of sodium bicarbonate remaining at an aqueous phase.

In some embodiments, sodium bicarbonate may be concentrated using electrodialysis. In some embodiments, sodium bicarbonate may be separated from, for example, at least a portion of residual aqueous magnesium sulfite, using, for example, selective electrodialysis. Some embodiments may comprise simultaneously concentrating sodium bicarbonate and/or separating sodium bicarbonate from magnesium sulfite, or any combination thereof, using selective electrodialysis. For example, monovalent selective electrodialysis may be selective for sodium ($Na^+$) and/or bicarbonate ($HCO_3^-$) relative to magnesium ($Mg^{2+}$) and sulfite ($SO_3^{2-}$) because, for example, sodium and/or bicarbonate may be monovalent ions, while magnesium and sulfite may be divalent ions. For example, monovalent selective electrodialysis may be selective for sodium ($Na^+$) and/or bicarbonate ($HCO_3^-$), which may enable the separation of aqueous sodium bicarbonate from aqueous magnesium sulfite. For example, monovalent selective electrodialysis may be selective for sodium ($Na^+$) and/or bicarbonate ($HCO_3^-$), which may result in a concentrate comprising sodium bicarbonate and a diluate comprising magnesium sulfite. In some embodiments, for example, at least a portion of magnesium sulfite may be further concentrated in or may be separated from a diluate comprising magnesium sulfite. For example, in some embodiments, at least a portion of magnesium sulfite may be separated from the diluate as a solid. For example, in some embodiments, magnesium sulfite may be separated by concentration and/or temperature change precipitation or precipitation. For example, in some embodiment, magnesium sulfite may be separated from water or precipitated or any combination thereof by, for example, one or more or any combination of the following steps:

(1) Concentrating a warm solution comprising magnesium sulfite using, for example, electrodialysis or reverse osmosis, to form a concentrate or retentate comprising a magnesium sulfite at a greater concentration.
(2) Cooling the formed concentrate or retentate to precipitate or crystallize at least a portion of a solid comprising magnesium sulfite
(3) Separating at least a portion of said solid comprising magnesium sulfite from at least a portion of the remaining aqueous solution
(4) Mixing said separated remaining aqueous solution with new or additional aqueous magnesium sulfite and/or warming the said mixed solution and/or transferring said warmed solution to (1).

In some embodiments, a concentrate or retentate comprising aqueous sodium bicarbonate may be further concentrated, or purified, or decomposed and/or, in some embodiments, for example at least a portion of sodium bicarbonate or sodium carbonate may be separated as a solid, or precipitated, or decomposed, or any combination thereof.

In some embodiments, for example, a solid comprising magnesium sulfite may be calcined or decomposed to form, for example, a solid comprising magnesium oxide and a gas comprising sulfur dioxide. Said sulfur dioxide formed may comprise the sulfur dioxide in the reaction of alkali carboxylate, such as sodium acetate, with sulfur dioxide to form, for example, alkali sulfite and/or carboxylic acid, such as sodium sulfite or potassium sulfite and acetic acid. In some embodiments, said magnesium oxide formed may be reacted with water to form at least a portion of magnesium hydroxide. In some embodiments, magnesium oxide or magnesium hydroxide may be reacted with carbon dioxide to form, for example, magnesium carbonate. Said formed magnesium carbonate may comprise the magnesium carbonate in the reaction of carbon dioxide, water, and/or magnesium carbonate to form, for example, aqueous magnesium carbonate or aqueous magnesium bicarbonate. In some embodiments, said carbon dioxide may comprise carbon dioxide from one or more or any combination of internal sources or steps. In some embodiments, said carbon dioxide may comprise carbon dioxide from an emissions source, or flue gas carbon dioxide, or $CO_2$ in air, or air, or ocean, or a body of water, or any combination thereof.

In some embodiments, employing magnesium may be desirable. In some embodiments, for example, the reaction of magnesium carbonate with carbon dioxide and water to form magnesium bicarbonate may have faster reaction kinetics and/or greater total solubility of magnesium bicarbonate compared to, for example, the reaction of calcium carbonate with carbon dioxide and water to form calcium bicarbonate. In some embodiments, for example, decomposition of magnesium sulfite into magnesium oxide and sulfur dioxide may occur at a lower temperature, or require less energy (such as a lower enthalpy of reaction or enthalpy of decomposition), or form a lower concentration of sulfite during the decomposition, or produce a higher partial pressure sulfur dioxide gas stream, or possess faster decomposition kinetics, or produce more reactive magnesium oxide, or produce a lower concentration of sulfate during the decomposition reaction, or any combination thereof, compared to, for example, the decomposition of magnesium sulfite into magnesium oxide and sulfur dioxide.

In some embodiments, a solution comprising sodium bicarbonate or sodium carbonate, which may have been separated from a solid comprising calcium sulfite, may be at a relatively dilute concentration. For example, in some embodiments, the concentration of sodium bicarbonate or sodium carbonate in said relatively dilute concentration solution may be less than, or greater than, or equal to, including but not limited to, one or more or any combination of the following: 1 g/L, or 2 g/L, or 3 g/L, or 4 g/L, or 5 g/L, or 6 g/L, or 7 g/L, or 8 g/L, or 9 g/L, or 10 g/L, or 15 g/L, or 20 g/L, or 30 g/L, or 40 g/L, or 50 g/L, or 60 g/L, or 70 g/L, or 80 g/L, or 90 g/L, or 100 g/L. In some embodiments, it may be desirable to concentrate the solution comprising sodium bicarbonate or sodium carbonate. For example, in some embodiments, it may be desirable to concentrate sodium carbonate or sodium bicarbonate in said relatively dilute concentration solution using, for example, including, but not limited to, one or more or any combination of the following: electrodialysis, or electrodialysis reverse, or reverse osmosis, or high-pressure reverse osmosis, or any combination thereof. For example, in some embodiments, the separated or removed water from concentrating may be transferred or employed internally. For example, in some embodiments, separated or removed water may comprise at least a portion of water employed in the reaction or dissolution of water, carbon dioxide, and/or calcium carbonate. For example, in some embodiments, it may be desirable to concentrate at least a portion of sodium carbonate or sodium bicarbonate from a relatively dilute concentration to the desired concentrate concentration using, for example, electrodialysis and/or electrodialysis reversal. For example, in some embodiments, it may be desirable to concentrate at least a portion of sodium carbonate or sodium bicarbonate from a relatively dilute concentration to the desired concentrate or retentate concentration using, for example, reverse osmosis and/or high pressure reverse osmosis. For example, in some embodiments, it may be desirable to concentrate at least a portion of sodium carbonate or sodium bicarbonate from a relatively dilute concentration to the desired concentrate or retentate concentration in, for example, stages, wherein, for example, one or more stages comprise electrodialysis, or one or more stages comprise reverse osmosis, or one or more stages comprise high pressure reverse osmosis, or any combination thereof. For example, in some embodiments, concentrating in stages may be desirable, due to, for example, including, but not limited to, one or more or any combination of the following: reduce energy consumption, or may enable improved removal of at least a portion of contaminants or impurities or residual non-sodium bicarbonate or non-sodium carbonate salts, or enable temperature changes which may facilitate separation or enable solubility of sodium bicarbonate or sodium carbonate at higher concentrations, or any combination thereof. For example, in some embodiments, sodium bicarbonate in a solution comprising sodium bicarbonate may be concentrated from ~5 g/L to ~30 g/L using electrodialysis, then from ~30 g/L to, for example, ~50 g/L or ~60 g/L or ~70 g/L using reverse osmosis, then from ~50 g/L, or ~60 g/L, or ~70 g/L to, for example, ~80 g/L, or ~100 g/L, or ~120 g/L using high pressure reverse osmosis. For example, in some embodiments, the solution may be heated or the temperature of the solution may be increased, for example, before concentrating sodium bicarbonate above about 60 g/L, or about 70 g/L, or about 80 g/L, or any combination thereof, for example, to ensure solubility of sodium bicarbonate in the solution during concentrating.

For example, in some embodiments, if the relatively dilute solution comprising sodium bicarbonate may be concentrated from ~5 g/L sodium bicarbonate concentration to ~100 g/L sodium bicarbonate concentration, then:

(1) For example, in some embodiments, the water separated using electrodialysis from ~5 g/L to ~30 g/L may be about 166.67 $m^3$ water per metric ton of sodium bicarbonate, which may consume, for example, about 0.5 kWh of electricity per $m^3$ of water separated or about 0.083 MWh per ton of sodium bicarbonate. In some embodiments, depending on the temperature of the solution, it may be desirable to increase the temperature of the solution before the next concentrating step or stage to, for example, ensure sodium bicarbonate remains dissolved or at an aqueous phase during concentrating. For example, sodium bicarbonate may have a solubility in water of about 69 g/L at 0° C., or 81.5 g/L at 10° C., or 96 g/L at 20° C., or 111 g/L at 30° C., or 127 g/L at 40° C., or 145 g/L at 50° C.

(2) For example, in some embodiments, the water separated using reverse osmosis from ~30 g/L to ~70 g/L may be about 19 $m^3$ water per metric ton of sodium bicarbonate, which may consume, for example, about 3.5 kWh of electricity per $m^3$ of water separated or about 0.067 MWh per ton of sodium bicarbonate. In some embodiments, depending on the temperature of the solution, it may be desirable to increase the temperature of the solution before the next concentrating step or stage to, for example, ensure sodium bicarbonate remains dissolved or at an aqueous phase during concentrating. For example, sodium bicarbonate may have a solubility in water of about 69 g/L at 0° C., or 81.5 g/L at 10° C., or 96 g/L at 20° C., or 111 g/L at 30° C., or 127 g/L at 40° C., or 145 g/L at 50° C.

(3) For example, in some embodiments, the water separated using high pressure reverse osmosis from ~70 g/L to ~100 g/L may be about 4.29 $m^3$ water per metric ton of sodium bicarbonate, which may consume, for example, about 7 kWh of electricity per $m^3$ of water separated or about 0.03 MWh per ton of sodium bicarbonate.

(4) For example, in some embodiments, the total electricity consumed to concentrate sodium bicarbonate in a solution comprising sodium bicarbonate from a concentration of ~5 g/L to a concentration of ~100 g/L may be about 0.18 MWh per ton of sodium bicarbonate.

In some embodiments, sodium bicarbonate or sodium carbonate in a solution comprising sodium bicarbonate or sodium carbonate may be at least partially concentrated using forward osmosis. For example, in some embodiments, forward osmosis may be conducted with a draw solution comprising seawater. For example, in some embodiments, forward osmosis may be conducted with a draw solution comprising desalination concentrate or retentate or brine. In some embodiments, forward osmosis may be conducted with a draw solution comprising waste brine. For example, in some embodiments, forward osmosis may be conducted with a draw solution comprising a regenerable or switchable or removable salt or polymer or other solute or any combination thereof. For example, in some embodiments, forward osmosis may be conducted with a draw solution comprising a solution available or produced by one or more embodiments and/or may a solution which may benefit from or may require dilution. For example, in some embodiments, the draw solution may comprise sodium sulfite or a solution comprising sodium sulfite and a solution comprising sodium bicarbonate may comprise the feed solution. It may be important to note that sodium bicarbonate may be significantly less soluble in water than sodium sulfite, depending on the solution temperature.

In some embodiments, sodium bicarbonate or sodium carbonate may be separated or recovered by utilizing the change in solubility of sodium bicarbonate or sodium carbonate with temperature. For example, sodium bicarbonate may have a solubility in water of about 69 g/L at 0° C., or 81.5 g/L at 10° C., or 96 g/L at 20° C., or 111 g/L at 30° C., or 127 g/L at 40° C., or 145 g/L at 50° C. For example, sodium carbonate may have a solubility in water of about 70 g/L at 0° C., or 164 g/L at 15° C., or 341 g/L at 27.8° C., or 486.9 g/L at 34.8° C. For example, some embodiments may comprise heating or increasing the temperature or warming of a solution comprising sodium bicarbonate or sodium carbonate, then concentrating the solution comprising warm sodium bicarbonate or sodium carbonate, then cooling the resulting concentrate or retentate comprising sodium bicarbonate or sodium carbonate to form a solid or precipitate comprising sodium bicarbonate or sodium carbonate, then separating the solid comprising sodium bicarbonate or sodium carbonate from the remaining aqueous solution comprising sodium bicarbonate or sodium carbonate. In some embodiments, the process may comprise a loop or cycle. For example, in some embodiments, said remaining aqueous solution comprising sodium bicarbonate or sodium carbonate may be transferred to the step comprising heating or increasing the temperature or warming of a solution comprising sodium bicarbonate or sodium carbonate. For example, in some embodiments, additional or new sodium bicarbonate or sodium carbonate solution may be added to the solution remaining after solid-liquid separation and/or before or after heating or increasing the temperature of the solution (depending on the temperature of the additional or new sodium bicarbonate or sodium carbonate solution), which may enable the recovery or separation of solid sodium bicarbonate or sodium carbonate to be, for example, continuous. For example, in some embodiments, separated or removed water, which may be separated or removed during concentrating, may be transferred or employed or utilized internally. For example, in some embodiments, separated or removed water may comprise at least a portion of water employed in the reaction or dissolution of water, carbon dioxide, and/or calcium carbonate. For example, in some embodiments, one or more or any combination of the following steps may be employed to recover solid sodium bicarbonate from a solution comprising sodium bicarbonate:

(1) Heating or increasing the temperature or warming of a solution comprising sodium bicarbonate or sodium carbonate. For example, in some embodiments, said solution may have a concentration of sodium bicarbonate of, for example, 80 g/L. In some embodiments, the solution in the present step may comprise a solution comprising sodium bicarbonate or sodium carbonate remaining from a solid-liquid separation, such as the remaining aqueous solution in step 4. In some embodiments, additional or new solution comprising sodium bicarbonate or sodium carbonate may be mixed with said solution comprising sodium bicarbonate or sodium carbonate remaining from a solid-liquid separation. In some embodiments, said additional or new solution comprising sodium bicarbonate or sodium carbonate may be at a lower concentration than said solution comprising sodium bicarbonate or sodium carbonate remaining from a solid-liquid separation. In some embodiments, for example, said mixed solution may have a concentration of 70 g/L sodium bicarbonate. In some embodiments, for example, depending on the temperature of the additional or new solution comprising sodium bicarbonate or sodium carbonate, the temperature of said mixed solution may be raised. For example, in some embodiments, the temperature of the solution may be raised from, for example, about 0° C., or 10° C., or 20° C., or 30° C., or any combination thereof to, for example, greater than, or less than, or equal to, one or more or any combination of the following: 20° C., or 30° C., or 40° C., or 50° C., or 60° C., or 70° C.

(2) Concentrating the solution comprising warm sodium bicarbonate or sodium carbonate, using, for example, reverse osmosis, or high pressure reverse osmosis, or electrodialysis, or forward osmosis, or membrane based process, or MVC, or MED, or MSF, or MD, or distillation, or other concentrating system or method, or other water separation system or method, or any combination thereof. For example, in some embodiments, the solution may be concentrated from, for example, a concentration of 70 g/L of sodium bicarbonate to, for example, a concentration of 120 g/L of sodium bicarbonate. In some embodiments, for example, the resulting retentate or concentrate from concentrating may, for example, comprise a concentration of 120 g/L of sodium bicarbonate. For example, in some embodiments, separated or removed water, which may be separated or removed during concentrating, may be transferred or employed or utilized internally.

(3) Cooling the retentate or concentrate solution to precipitate or crystalize or form at least a portion of a solid comprising sodium bicarbonate or sodium carbonate. For example, in some embodiments, a retentate or concentrate solution comprising sodium carbonate following cooling may comprise a solid-liquid mixture, which may comprise a solid comprising sodium bicarbonate or sodium carbonate and/or a remaining aqueous solution comprising sodium bicarbonate or sodium carbonate. In some embodiments, a retentate or concentrate may be cooled to a temperature greater than, or less than, or equal to, one or more or any combination of the following: 0° C., or 10° C., or 20° C., or 30° C., or any combination thereof.

(4) Separating a solid comprising sodium bicarbonate or sodium carbonate from a solution comprising remaining sodium bicarbonate or sodium carbonate. For example, in some embodiments, said separation may be conducted using one or more or any combination of systems or methods for separating at least a portion of a solid from at least a portion of a liquid. In some embodiments, the remaining solution, which may comprise a solution comprising remaining sodium bicarbonate or sodium carbonate, may be comprise a concentration comprising 80 g/L of sodium bicarbonate. In some embodiments, the remaining solution, which may comprise a solution comprising remaining sodium bicarbonate or sodium carbonate, may be transferred to step 1.

For example, in some embodiments, a one or two or more stage crystallization unit may be employed to separate or crystallize sodium carbonate, or sodium bicarbonate, or any combination thereof.

In some embodiments, a solution comprising sodium bicarbonate or sodium carbonate may be concentrated using forward osmosis, or electrodialysis, or reverse osmosis, or high pressure reverse osmosis, or membrane based process, or any combination thereof, then the retentate or concentrate formed may be treated with distillation, or MVC, or MED, or MSF, or MD, or desorption column, or any combination thereof, to form, for example, at least a portion of water and/or at least a portion of solid sodium bicarbonate, or solid sodium carbonate, or gaseous carbon dioxide, or a solution comprising nearly saturated or saturated or supersaturated sodium bicarbonate, or a solution comprising nearly saturated or saturated or supersaturated sodium carbonate, or any combination thereof.

In some embodiments, for example, at least a portion of concentrating may be conducted at a higher temperature, to, for example, enable a higher concentration of sodium bicarbonate or sodium carbonate due to the increase in solubility of sodium bicarbonate or sodium carbonate with increasing temperature.

In some embodiments, sodium bicarbonate or sodium carbonate may comprise a product or output. In some embodiments, sodium bicarbonate may be converted into a solid or solution comprising sodium carbonate and/or a gas comprising carbon dioxide, and/or said sodium carbonate may comprise a product or output. In some embodiments, if a gas comprising $CO_2$ is generated or produced, such as from the decomposition of sodium bicarbonate to sodium carbonate, it may be desirable for said generated or produced $CO_2$ to be recycled, or reused, or employed internally, or employed in one or more embodiments described herein, or any combination thereof. In some embodiments, if a gas comprising $CO_2$ is generated or produced, such as from the decomposition of sodium bicarbonate to sodium carbonate, it may be desirable for said generated or produced $CO_2$ to be employed in an external application or comprise a product.

In some embodiments, it may be desirable to decompose or calcine a solid comprising sodium bicarbonate into a solid comprising sodium carbonate and/or a gas comprising carbon dioxide. In some embodiments, for example, in some embodiments, it may be desirable to dissolved said solid comprising sodium carbonate to form a solution comprising aqueous sodium carbonate and/or reacting said solution comprising aqueous sodium carbonate with a solid, or a solid-liquid mixture, or a suspension, or any combination thereof comprising calcium hydroxide to form, for example, at least a portion of a solution comprising aqueous sodium hydroxide and at least a portion of a solid comprising calcium carbonate. In some embodiments, if a gas comprising $CO_2$ is generated or produced, such as from the decomposition of sodium bicarbonate to sodium carbonate, it may be desirable for said generated or produced $CO_2$ to be recycled, or reused, or employed internally, or employed in one or more embodiments described herein, or any combination thereof. In some embodiments, if a gas comprising $CO_2$ is generated or produced, such as from the decomposition of sodium bicarbonate to sodium carbonate, it may be desirable for said generated or produced $CO_2$ to be employed in an external application or comprise a product.

In some embodiments, it may be desirable to decompose or desorb $CO_2$ from at least a portion of a solution comprising sodium bicarbonate to form at least a portion of a solution comprising sodium carbonate and/or captured carbon dioxide. For example, in some embodiments, a solution comprising aqueous sodium bicarbonate may be decomposed or desorbed or thermally decomposed into a solution comprising aqueous sodium carbonate and a gas comprising carbon dioxide. In some embodiments, it may be desirable for said carbon dioxide to be recycled, or reused, or employed internally or employed within the process or one or more embodiments described herein. In some embodiments, it may be desirable for said solution comprising aqueous sodium bicarbonate to comprise a concentrated solution, to, for example, reduce or minimize energy consumption associated with thermal desorption. For example, in some embodiments, said solution comprising aqueous sodium bicarbonate may comprise a concentrate or retentate comprising sodium bicarbonate produced from the concentrating of an aqueous solution comprising sodium bicarbonate from the separation of a solid comprising calcium sulfite from an aqueous solution comprising sodium bicarbonate. For example, in some embodiments, said solution comprising aqueous sodium bicarbonate may comprise a concentrate or retentate comprising sodium bicarbonate produced from the concentrating of the dilute aqueous solution comprising sodium bicarbonate using, for example, forward osmosis, or electrodialysis, or reverse osmosis. For example, in some embodiments, said solution comprising aqueous sodium bicarbonate may comprise a concentrate or retentate from a concentrating or separation or water removal process comprising, including, but not limited to, electrodialysis, or electrodialysis reversal, or reverse osmosis, or high pressure reverse osmosis, or forward osmosis, or separation or concentrating processes described herein, or separation or concentrating processes described in the art, or any combination thereof.

In some embodiments, a solution comprising sodium bicarbonate may be transformed into a solution comprising sodium carbonate using, for example, a desorption column or a desorption process. In some embodiments, the decomposition of sodium bicarbonate or the desorption of carbon dioxide from sodium bicarbonate may be conducted using relatively low temperature heat. For example, in some embodiments, the decomposition of sodium bicarbonate or the desorption of carbon dioxide may be conducted at a temperature less than or equal to, for example, one or more or any combination of the following: 200° C., or 190° C., or 180° C., or 170° C., or 160° C., or 150° C., or 140° C., or 130° C., or 120° C., or 110° C., or 100° C., or 90° C., or 80° C., or 70° C. For example, in some embodiments, heat provided for the decomposition of sodium bicarbonate or desorption of carbon dioxide may comprise, for example, including, but not limited to, one or more or any combination of the following: waste heat, or heat pump heat, or heat recovered from elsewhere in the process, or combustion heat, or other heat sources described herein, or other heat sources in the art. In some embodiments, it may be desirable to conduct sodium bicarbonate decomposition or thermal desorption at a higher pressure, or pressure greater than atmospheric pressure, to enable, for example, higher partial pressure of $CO_2$ relative to partial pressure of water, or to minimize energy consumption related to water boiling. In some embodiments, heat recovery may be employed. In some embodiments, a counter-current heat exchange may be conducted between the solution comprising sodium bicarbonate entering desorber and solution comprising sodium carbonate exiting the desorber, to, for example, recover at least a portion of sensible heat.

In some embodiments, a solid comprising calcium sulfite may be separated from a solution comprising sodium bicarbonate. In some embodiments, a solid comprising calcium sulfite, which may comprise at least a portion of the solid comprising calcium sulfite separated from a solution comprising sodium bicarbonate, may be decomposed, or thermally decomposed, or calcined, or any combination thereof to form, for example, a solid comprising calcium oxide and a gas comprising sulfur dioxide. In some embodiments, it may be desirable to dehydrate at least a portion of calcium sulfite, or employ heat to dehydrate at least a portion of calcium sulfite, before thermal decomposition of at least a portion of calcium sulfite to at least a portion of calcium oxide and sulfur dioxide. For example, in some embodiments, dehydrating calcium sulfite before thermally decomposing calcium sulfite into calcium oxide may enable the use of lower cost or lower temperature heat relative to the heat required for the thermal decomposition of calcium sulfite into calcium oxide and/or may enable a short residence time in the kiln or calciner, which may improve the reactivity or other properties of the formed solid comprising calcium oxide. The decomposition or calcination of calcium sulfite may be described in further detail elsewhere herein.

In some embodiments, the gas comprising sulfur dioxide produced from the decomposition of calcium sulfite may be employed internally or in one or more or any combination of embodiments described herein. For example, gas comprising sulfur dioxide from the decomposition of a solid comprising calcium sulfite may be transferred to a reaction with an aqueous solution comprising an alkali acid, such as aqueous sodium acetate. For example, gas comprising sulfur dioxide from the decomposition of a solid comprising calcium sulfite may comprise at least a portion of the sulfur dioxide in a reaction of sodium acetate and sulfur dioxide, to form, for example, sodium sulfite and/or acetic acid.

In some embodiments, a solid comprising calcium oxide, which may be formed from the decomposition or calcining of calcium sulfite, may be reacted with carbon dioxide to form, for example, a solid comprising calcium carbonate. In some embodiments, a solid comprising calcium oxide, which may be formed from the decomposition or calcining of calcium sulfite, may be reacted with water to form a solid comprising calcium hydroxide, which may comprise a solid, or solid-liquid mixture, or a suspension, or milk-of-lime, or an aqueous solution, or any combination thereof. In some embodiments, for example, at least a portion of calcium hydroxide may be reacted with at least a portion of carbon dioxide to form, for example, at least a portion of calcium carbonate. In some embodiments, carbon dioxide may comprise carbon dioxide from an internal source, such as one or more or any combination of process steps, or from one or more or any combination embodiments described herein. In some embodiments, carbon dioxide may comprise carbon dioxide from an emissions source, or a point source, or dilute source, or flue gas, or from air, or from a body of water, or in a body of water, or any combination thereof. In some embodiments, the reaction of at least a portion of calcium oxide or calcium hydroxide with at least a portion of carbon dioxide may comprise a carbon dioxide conversion, or removal step. In some embodiments, a solid comprising calcium carbonate may be utilized internally. For example, a solid comprising calcium carbonate from, for example, the reaction of calcium oxide and/or calcium hydroxide with carbon dioxide, may comprise at least a portion of the calcium carbonate in the reaction of water, carbon dioxide, and/or calcium carbonate. In some embodiments, calcium carbonate may comprise a valuable product, such as precipitated calcium carbonate or a sequestration product.

In some embodiments, it may be desirable for sodium bicarbonate or sodium carbonate to be converted or transformed into sodium hydroxide. For example, in some embodiments, a solid or solution or any combination thereof comprising sodium carbonate may be reacted with a solid, or solid-liquid mixture, or solution, or any combination thereof comprising calcium hydroxide to form, for example, a solid comprising calcium carbonate and a solution comprising sodium hydroxide.

In some embodiments, a solid comprising sodium carbonate may be dissolved in water to form a solution comprising aqueous sodium carbonate. In some embodiments, it may be desirable to, for example, employ forward osmosis or osmotically assisted reverse osmosis to concentrate at least a portion of an solution comprising aqueous sodium hydroxide, while, for example, diluting at least a portion of a solution comprising sodium carbonate. In some embodiments, for example, sodium carbonate or a solution comprising sodium carbonate may comprise, for example, a draw solution and/or sodium hydroxide or a solution comprising sodium hydroxide, may comprise, for example, a feed solution. In some embodiments, for example, sodium carbonate or a solution comprising sodium carbonate may comprise a draw solution and/or sodium hydroxide or a solution comprising sodium hydroxide, may comprise a feed solution, for example, wherein water moves from a solution comprising sodium hydroxide to a solution comprising sodium carbonate by, for example, permeating a semi-permeable membrane. [In some embodiments, it may be desirable for sodium carbonate to be dissolved into a warm solution or to comprise a warm solution or to comprise a solution with a temperature greater than 10° C., or 20° C., or 30° C., or any combination thereof, to, for example, enable a higher sodium carbonate concentration, or higher osmotic pressure, or any combination thereof due to, for example, the solubility curve of sodium carbonate.

In some embodiments, calcium oxide or calcium hydroxide, which may comprise the calcium oxide or calcium hydroxide produced from the decomposition of calcium sulfite, may comprise the calcium oxide or calcium hydroxide employed in the reaction of calcium hydroxide and sodium carbonate to form calcium carbonate and sodium hydroxide. In some embodiments, calcium oxide may be added to a solution comprising sodium carbonate, and/or may react to form, for example, sodium hydroxide and calcium sulfite. In some embodiments, calcium oxide may be reacted with water to form calcium hydroxide, which may comprise, for example, including, but not limited to, one or more or any combination of the following: solid calcium hydroxide, or powdered calcium hydroxide, or a solid-liquid mixture or suspension of calcium hydroxide in water, or milk-of-lime. In some embodiments, calcium hydroxide may be added to a solution comprising sodium carbonate, and/or may react to form, for example, sodium hydroxide and calcium sulfite.

In some embodiments, an alkali carbonate may be reacted with an alkaline-earth hydroxide to form an alkali hydroxide and an alkaline-earth carbonate. In some embodiments, sodium carbonate may be reacted with calcium hydroxide to form sodium hydroxide and calcium carbonate. In some embodiments, it may be desirable for the reaction to be conducted with sodium carbonate reagent comprising a solution comprising a sodium carbonate concentration of less than or equal to one or more or any combination of the following: 0.5M, or 1M, or 1.5M, or 2M, or 2.5M, or 3M, or 3.5M, or 4M, or 4.5M, or 5M. In some embodiments it may be desirable to conduct a reaction of sodium carbonate and calcium hydroxide at a temperature less than or equal to, one or more or any combination of the following: 0° C., or 10° C., or 20° C., or 30° C., or 40° C., or 50° C., 60° C., or 70° C., or 80° C., or 90° C., or 100° C., or 110° C., or 120° C., or 130° C. In some embodiments, it may be desirable for the total reaction residence time to be greater than, for example, one or more or any combination of the following: 1 second, or 10 seconds, or 30 seconds, or 1 minute, or 5 minutes, or 10 minutes, or 15 minutes, or 20 minutes, or 25 minutes, or 30 minutes, or 45 minutes, or 1 hour.

In some embodiments, a reaction of sodium carbonate and calcium hydroxide to produce at least a portion of sodium hydroxide and at least a portion of calcium carbonate may be conducted in a manner similar, or employing similar equipment or processes, to systems and methods of reacting sodium sulfite with calcium hydroxide, which may include, but are not limited to, systems and methods described herein.

In some embodiments, the reaction of a calcium oxide or calcium hydroxide and sodium carbonate to produce at least a portion of sodium hydroxide and at least a portion of calcium carbonate conducted in a similar manner to, for example, the causticization of sodium carbonate in the art.

In some embodiments, a solid-liquid mixture comprising a solid comprising calcium carbonate and a liquid comprising aqueous sodium hydroxide may be formed in a reaction of calcium hydroxide or calcium oxide and sodium carbonate. In some embodiments, at least a portion of the solid comprising calcium carbonate may be separated from at least a portion of the solution comprising sodium hydroxide. In some embodiments, said separation may employ one or more solid-liquid separation systems and/or methods described herein, or described in the art, or any combination thereof. In some embodiments, systems and methods for separating calcium carbonate and sodium hydroxide may be similar to or overlapping with systems and methods for separating calcium sulfite and sodium hydroxide, which may be described in more detail elsewhere herein. For example, In some embodiments, systems and methods for separating calcium carbonate and sodium hydroxide may be similar to or overlapping with systems and methods for separating calcium sulfite and sodium hydroxide, which may be described in more detail elsewhere herein, although, in some embodiments, it may be desirable to substitute the term or word or anion ‘sulfite’ with ‘carbonate’.

In some embodiments, it may be desirable to concentrate and/or purify sodium hydroxide. In some embodiments, concentrating or purifying sodium hydroxide or solutions comprising sodium hydroxide may be described in detail elsewhere herein. For example, in some embodiments, concentrating or purifying sodium hydroxide or solutions comprising sodium hydroxide may be described in detail elsewhere herein, although, in some embodiments, it may be desirable to substitute the term or word or anion ‘sulfite’ with ‘carbonate’.

In some embodiments, some applications or embodiments may not require or desire concentrating or purifying of a solution comprising sodium hydroxide. For example, in some embodiments, applications involving, for example, $CO_2$ removal, or $CO_2$ capture, or addition of sodium hydroxide to a body of water to remove or sequester $CO_2$, or any combination thereof may not require or desire concentrating or purifying of a solution comprising sodium hydroxide.

In some embodiments, the solid separated from the reaction of sodium carbonate and calcium hydroxide, which may comprise calcium carbonate, may be employed internally or utilized internally. For example, in some embodiments, at least a portion of the solid comprising calcium carbonate produced, such as in the reaction of calcium hydroxide and sodium carbonate, may comprise at least a portion of the calcium carbonate employed in the reaction of water, carbon dioxide, and/or calcium carbonate to produce, for example, aqueous calcium carbonate or aqueous calcium bicarbonate.

For example, in some embodiments, calcium carbonate, or the produced calcium carbonate, or a solid comprising calcium carbonate may comprise a product, or may comprise a $CO_2$ conversion or $CO_2$ sequestration product, or may comprise precipitated calcium carbonate, or may be sold, or may be employed in another use, or any combination thereof.

Example Description of an Example Potential Configuration or Optimization or Application of Some Embodiments

Example Summary of Some Embodiments

Some embodiments may be configured or optimized for different applications, or business models, or economies. For example, some embodiments of Example 55 may be optimized for maximizing profitability in the absence of $CO_2$ emissions abatement subsidies. For example, some embodiments of Example 55 may be optimized for providing a $CO_2$ conversion option to $CO_2$ emissions sources or point-source emissions without access to $CO_2$ pipeline infrastructure or $CO_2$ sequestration site. For example, some embodiments of Example 55 may be optimized for providing a $CO_2$ conversion alternative to $CO_2$ sequestration or $CO_2$ subsurface injection. For example, some embodiments of Example 55 may be optimized for maximizing $CO_2$ emissions reduction, or $CO_2$ removal, or $CO_2$ removal from the atmosphere or oceans. For example, some embodiments of Example 55 may be optimized for maximizing economic value and emissions impact in economies with $CO_2$ abatement subsidies, such as 45Q in the United States, or carbon taxes in Canada, or the emissions trading system in the European Union.

Example Embodiment of Example 55 Optimized for Maximum $CO_2$ Impact and 45Q Overview: Based on process chemistry, the present embodiment configuration may convert and/or sequester 2 moles of $CO_2$ for every 2 moles of sodium bicarbonate produced.

Inputs: 2 moles $CO_2$, 1 mole Sodium Sulfate, 2 moles Calcium Carbonate

Outputs: 2 moles Sodium Bicarbonate, 1 mole Calcium Carbonate, 1 mole Calcium Sulfate, 1 mole Captured $CO_2$ to Sequestration or Utilization.

Note: Example 62 may be configured similarly and/or may require less energy consumption and/or lower temperature heat.

Description

In some embodiments, steps ‘1-4,’ ‘5-6’, and ‘7-8’ may comprise three separate processes. In some embodiments, steps ‘1-4’ and ‘7-8’ may comprise an integrated process and steps '5-6' may comprise a separate process or may be conducted in a separate location. For example:

Steps '1-4' may comprise a process for producing sodium sulfite and calcium sulfate from sodium sulfate, calcium carbonate, and sulfur dioxide. In the United States, steps '1-4' may qualify as a point-source emissions source for the purpose of 45Q. Captured $CO_2$ produced by Steps '1-4', or more specifically step 1, which may be high pressure, or high purity, or low marginal cost, or any combination thereof, may be sequestered or permanently stored (e.g. subsurface sequestration or carbon dioxide storage) or utilized (e.g. enhanced oil recovery or other utilization application). If qualifying for permanent storage, the project comprising Steps '1-4' may receive \$85 per ton $CO_2$. If qualifying for utilization, the project comprising Steps '1-4' may receive \$60 per ton $CO_2$.

Note: In some embodiments, the sodium sulfite produced by steps '1-4' may be transferred to a project comprising steps '5-6,' by, for example, rail, or freight, or ship, or barge, or truck, or any combination thereof. In some embodiments, the sulfur dioxide employed in steps '1-4' may be transferred from a project comprising step '8' or steps '8-9', wherein said transfer of sulfur dioxide may be conducted by means of, for example, a pipe.

Steps '5-6' may comprise a process for converting carbon dioxide into sodium bicarbonate. Steps '5-6' may comprise a process for converting carbon dioxide, sodium sulfite, and calcium carbonate and into sodium bicarbonate and calcium sulfite. Steps '5-6' may be co-located with a $CO_2$ source or $CO_2$ point source. For example, steps '5-6' may be co-located with, including, but not limited to, one or more or any combination of the following: a blue hydrogen project, or an ammonia plant, or an ethanol plant, or a cement plant, or a steel plant, or a direct air capture $CO_2$ capture facility, or a direct ocean $CO_2$ capture facility, or an oxy-combustion facility, or a $CO_2$ capture facility, or a $CO_2$ pipeline, or any combination thereof. In some embodiments, a project comprising Steps '5-6' may enable a $CO_2$ emissions source or $CO_2$ capture source to stop releasing $CO_2$ into the atmosphere, including if a site does not have access to $CO_2$ pipeline infrastructure or $CO_2$ sequestration infrastructure. $CO_2$ Depending on the end-use of the sodium bicarbonate produced, the project comprising Steps '5-6' may qualify to receive an additional \$60 per ton $CO_2$ converted into sodium bicarbonate for $CO_2$ utilization or to receive an additional \$85 per ton $CO_2$ converted into sodium bicarbonate for permanent $CO_2$ storage under 45Q in the USA. Additionally, the project may sell sodium bicarbonate as a valuable product.

Note: In some embodiments, sodium sulfite may be transferred from a project comprising steps '1-4' to a project comprising steps '5-6'. In some embodiments, calcium sulfite from steps '5-6' may be transferred to a project comprising steps '7-8', by, for example, rail, or freight, or ship, or barge, or truck, or any combination thereof.

Steps '7-8' may comprise a process for permanent removal of $CO_2$ from the air, or may comprise a process for $CO_2$ direct air capture, or a process for converting $CO_2$ into calcium carbonate, or a process for producing ultra-low carbon emissions calcium oxide, or any combination thereof. In some embodiments, Steps '7-8' may receive calcium sulfite from steps '5-6', although a project comprising Steps '7-8' may be in a separate location from steps '5-6'. In some embodiments, Steps '7-8' may transfer $SO_2$ produced by step '7' to step '3'. In some embodiments, Step '8' may comprise directly or indirectly reacting $CO_2$ from the air with calcium oxide produced from the calcination of calcium sulfite. In some embodiments, a project comprising Steps '7-8' may qualify to receive an additional \$180 per ton $CO_2$ converted into calcium carbonate by qualifying for direct air capture permanent removal under 45Q in the USA if the calcium carbonate is buried or stored or utilized in a manner which permanently sequesters the $CO_2$, or may qualify to receive an additional \$130 per ton $CO_2$ converted into calcium carbonate by qualifying for direct air capture utilization under 45Q in the USA if the calcium carbonate is utilized or sold.

Example Embodiment of Example 55 Optimized for Net Negative Emissions in a Real Market Economy (Maximize Economic Value without Subsidies)

Overview: Based on process chemistry, the present embodiment configuration may convert and/or sequester 1 mole of $CO_2$ for every 2 moles of sodium bicarbonate produced.

Inputs: 1 mole $CO_2$, 1 mole Sodium Sulfate, 1 mole Calcium Carbonate

Outputs: 2 moles Sodium Bicarbonate, 1 mole Calcium Sulfate

Description

In some embodiments, Steps '1-8' may comprise an integrated process. In some embodiments, Steps '1-8' may comprise an integrated project and/or may be co-located on a project site.

In some embodiments, at least a portion of the $CO_2$ generated by Step '1' may comprise at least a portion of the $CO_2$ in step '5'. For example, $CO_2$ from step '1' may be transferred by pipe to step '5'.

Note: In some embodiments, step '1' may qualify as an emissions source in 45Q and step '5' may comprise a $CO_2$ conversion or utilization system or method, which may enable a project comprising step '1' and/or step '5' to receive \$60 per ton $CO_2$ or \$85 per ton $CO_2$ depending on the end use of the sodium bicarbonate.

In some embodiments, the $SO_2$ produced by step '7' may comprise at least a portion of the $SO_2$ in step '3'.

In some embodiments, the $CO_2$ in step '8' may comprise $CO_2$ from a point source, or flue gas, or an external $CO_2$ source. In some embodiments, the $CO_2$ in step '8' may comprise $CO_2$ from the air or in the air, which may be reacted with calcium oxide or calcium hydroxide to produce calcium carbonate.

Depending on the $CO_2$ source in step '8' and the end use of the sodium bicarbonate, step '8' may enable the project to receive an additional \$60, or \$85, or \$130, or \$180 per ton $CO_2$.

In some embodiments, the calcium carbonate produced in step '8' may comprise at least a portion of the calcium carbonate employed in step '5'.

Alternatively, calcium carbonate from step '8' may comprise an output comprising precipitated or higher purity calcium carbonate. In some embodiments, said precipitated or higher purity calcium carbonate may comprise a valuable product. In some embodiments, if, for example, the calcium carbonate from step '8' may comprise an output, an additional calcium carbonate input may be required, however the overall net $CO_2$ balance of the process chemistry may remain the same.

Example Embodiment of Example 55 Optimized for Net Neutral Emissions in a Real Market Economy, Zero Emissions Calcium Oxide or Cement Production and Sodium Bicarbonate Production (Maximize Economic Value without Subsidies)

Overview: Based on process chemistry, the present embodiment configuration may comprise a potentially zero emissions ($CO_2$ neutral) method of producing calcium hydroxide, and may not require a $CO_2$ byproduct requiring sequestration.

Inputs: 1 mole Sodium Sulfate, 2 moles Calcium Carbonate

Outputs: 1 mole Calcium Oxide, 2 moles Sodium Bicarbonate, 1 mole Calcium Sulfate Description In some embodiments, Steps '1-7' may comprise an integrated process. In some embodiments, Steps '1-7' may comprise an integrated project and/or may be co-located on a project site.

In some embodiments, at least a portion of the $CO_2$ generated by Step '1' may comprise at least a portion of the $CO_2$ in step '5'. For example, $CO_2$ from step '1' may be transferred by pipe to step '5'.

Note: In some embodiments, step '1' may qualify as an emissions source in 45Q and step '5' may comprise a $CO_2$ conversion or utilization system or method, which may enable a project comprising step '1' and/or step '5' to receive $60 per ton $CO_2$ or $85 per ton $CO_2$ depending on the end use of the sodium bicarbonate.

In some embodiments, the $SO_2$ produced by step '7' may comprise at least a portion of the $SO_2$ in step '3'.

In some embodiments, the calcium oxide produced in step '7' may comprise a valuable product. In some embodiments, the calcium oxide produced in step '7' may comprise a cement or other valuable material.

Example Mass & Energy Flows of an Example Embodiment for Producing Sodium Hydroxide, or Calcium Sulfate, or Captured Carbon Dioxide, or any Combination Thereof Example Inputs and Outputs Table of an Example Embodiment Example Inputs and Outputs Summary Table

| Inputs | Outputs |
|---|---|
| $CaCO_3$(s) | NaOH(s or aq) |
| $Na_2SO_4$(s or aq) | $CaSO_4$(s) |
| Water (optional) | $CO_2$ (captured, g or l or sc) |
| Electricity (e.g. pumping and transferring, MVC distillation or crystallization) | |
| Heat (e.g. natural gas, or hydrogen, or electricity) | |

Example Chemistry of an Example Embodiment (1) $CaCO_3$(s or aq)+2 $CH_3COOH$(aq)→$Ca(CH_3COO)_2$(aq)+$CO_2$(g)
(2) $Ca(CH_3COO)_2$(aq)+$Na_2SO_4$(s or aq)+2 $NaCH_3COO$(aq)→$CaSO_4$(s)
(3) 2 $NaCH_3COO$(aq)+$SO_2$(g or aq)+$H_2O$(l or aq)→$Na_2SO_3$(aq)+2 $CH_3COOH$(aq)
(4) $Na_2SO_3$(aq)+2 $CH_3COOH$(aq)→2 $CH_3COOH$(aq)+$Na_2SO_3$(s)
(5) $Na_2SO_3$(s)+Water→$Na_2SO_3$(aq)
(6) CaO(s)+$H_2O$(l or g or aq)+Water→$Ca(OH)_2$(s or aq or suspension)
(7) $Na_2SO_3$(aq)+$Ca(OH)_2$(s or aq or suspension)→2NaOH(aq)→$CaSO_3$(s)
(8) $CaSO_3$(s)→CaO(s)+$SO_2$(g)
(1) $CaCO_3$(s or aq)+2 $CH_3COOH$(aq)→$Ca(CH_3COO)_2$(aq)+$H_2O$(aq)+$CO_2$(g)
(2) $Ca(CH_3COO)_2$(aq)→$Na_2SO_4$(s or aq)+2 $NaCH_3COO$(aq)+$CaSO_4$(s)
(3) 2 $NaCH_3COO$(aq)+$SO_2$(g or aq)+$H_2O$(l or aq)→$Na_2SO_3$(aq)+2 $CH_3COOH$(aq)
(4) $Na_2SO_3$(aq)+2 $CH_3COOH$(aq)→2 $CH_3COOH$(aq)+$Na_2SO_3$(s)
(5) $Na_2SO_3$(s)+Water→$Na_2SO_3$(aq)
(6a) CaO(s)+$H_2O$(l or g or aq)→$Ca(OH)_2$(s) (Note: Produces heat, may be employed to dehydrate calcium sulfite before calcining) (equipment: lime slaker)
(6b) $Ca(OH)_2$(s)+Water→$Ca(OH)_2$(s or aq or suspension)
(7) $Na_2SO_3$(aq)+$Ca(OH)_2$(s or aq or suspension)→2NaOH(aq)+$CaSO_3$(s)
(8) $CaSO_3$(s)→CaO(s)+$SO_2$(g)
(9) $Na_2SO_3$(aq-dilute)→$Na_2SO_3$(aq-concentrated)+Water Example Summary Enthalpy of Reactions (Molar Basis) of an Example Embodiment (1) Spontaneous reaction at room temperature, goes to completion, exothermic due to dissolution of calcium
(2) Spontaneous reaction at room temperature, goes to completion
(3) −45.04 kJ/mol, reaction occurs in an absorber
(4) Separation, which may comprise high efficiency distillation and/or crystallization
(5) −13.24 kJ/mol, dissolution is spontaneous in water (6) −65.23 kJ/mol if $Ca(OH)_2$ at solid state, or −81.96 kJ/mol if $Ca(OH)_2$ at aqueous state. The reaction is spontaneous and may be conducted in a manner known as 'lime-slacking'

(7) −2.535 kJ/mol, reaction is an equilibrium reaction, concentration and temperature should be controlled to achieve near 100% conversion to sodium hydroxide from sodium sulfite.

(8)+226.3 kJ/mol, it may be desirable for the reaction to be conducted at or above 780° C.

Example Summary of Equipment for Each Step of an Example Embodiment (1) Solid-liquid mixer. It may be desirable for the solid-liquid mixer to be configured with an at least partially closed headspace to enable the high purity and/or pressurization of carbon dioxide generated by the reaction (enabling high purity, high pressure, 'captured' $CO_2$).

(2) Solid-liquid mixer→Liquid-Liquid Mixer→Solid-Liquid Separator.

In some embodiments, solid comprising sodium sulfate may be first mixed with the solution comprising aqueous calcium acetate to form a solution comprising aqueous sodium acetate and a solid comprising calcium sulfate, then, second, the solid-liquid mixture of comprising aqueous sodium acetate and solid calcium sulfate may be separated into a separate solid comprising calcium sulfate and a separate solution comprising aqueous sodium acetate. Solid-liquid separation may comprise, for example, including, but not limited to, one or more or any combination of the following: filter, or decanter, or coalescer, or centrifuge, or rotary filter, or filter press.

In some embodiments, solid comprising sodium sulfate may be first dissolved in a solution comprising water or aqueous acetic acid to form a solution comprising aqueous sodium sulfate in a solid-liquid mixer, then, second, the solution comprising aqueous sodium sulfate may be mixed with the solution comprising aqueous calcium acetate to form a solution comprising aqueous sodium acetate and a solid comprising calcium sulfate, then, third, the solid-liquid mixture of comprising aqueous sodium acetate and solid calcium sulfate may be separated into a separate solid comprising calcium sulfate and a separate solution comprising aqueous sodium acetate. Solid-liquid separation may comprise, for example, including, but not limited to, one or more or any combination of the following: filter, or decanter, or coalescer, or centrifuge, or rotary filter, or filter press.

(3) Absorption column. For example, may comprise, including, but not limited to, one or more or any combination of the following: a gas-liquid contactor, or a bubble column, or a membrane column, or a packed column, or plate column, or tray column, or column, or mixer, or sparger. In some embodiments, it may be desirable to minimize the concentration of diatomic oxygen in the sulfur dioxide or gas comprising sulfur dioxide to, for example, minimize the potential oxidation of sodium sulfite to sodium sulfate.

(4) Distillation Process and/or Crystallization Process. For example, may comprise, including, but not limited to, one or more or any combination of the following: mechanical vapor compression distillation, or mechanical vapor recompression distillation, or mechanical vapor compression crystallizer, or mechanical vapor recompression crystallizer, or crystallizer, or freeze desalination, or reverse osmosis, or high pressure reverse osmosis, or multi-stage flash distillation, or multi-effect distillation, or forward osmosis.

(5) Solid-liquid mixer (6) Lime slacker. For example, may comprise a solid-liquid mixer designed for creating a solid-liquid mixture emulsion of calcium hydroxide and water from calcium oxide and water. For example, the equipment may be configured to enable heat recovery from the reaction of calcium oxide and water, which may be employed, for example, within the process, for example, in drying or other application. In some embodiments, the equipment may be configured to further dilute the concentration of calcium hydroxide in the solid-liquid suspension or slurry or 'milk-of-lime', which may involve, for example, adding additional water. Note: In some embodiments, steps '(6)' and'(7)' may be combined, wherein, for example, calcium oxide solid or calcium hydroxide solid may be added to a solution comprising sodium sulfite to form at least a portion of calcium sulfite and at least a portion of sodium hydroxide.

(7) Solid-Liquid Mixer and Solid-Liquid Separator. In some embodiments, the solid-liquid mixer may be similar to solid-liquid mixers or other equipment employed in a causticization process or a causticizer. In some embodiments, the equipment may be temperature controlled and the rate of mixing, or the flow rates of reactants and products, or the temperature of the reaction, or the concentration of reagents, or the residence time, or any combination thereof may be carefully monitored and/or controlled. Some embodiments may further comprise a solid-liquid separator, which may be configured to separate a least a portion of solid comprising calcium sulfite from at least a portion of aqueous solution comprising sodium hydroxide. Some embodiments may further comprise a concentrator to further concentrate solution comprising sodium hydroxide, which may include, but is not limited to, one or more or any combination of the following: mechanical vapor compression distillation, or mechanical vapor recompression distillation, or mechanical vapor compression crystallizer, or mechanical vapor recompression crystallizer, or crystallizer, or freeze desalination, or reverse osmosis, or high pressure reverse osmosis, or multi-stage flash distillation, or multi-effect distillation, or forward osmosis. For example, in some embodiments, at least a portion of the sodium hydroxide solution may be concentrated by forward osmosis, wherein the aqueous solution comprising sodium sulfite from, for example, step '5,' may be employed as the draw solution, and the aqueous solution comprising sodium hydroxide from, for example, step '7,' may be employed as the feed solution. In some embodiments, it may be desirable for the equipment to minimize exposure to atmospheric air or diatomic oxygen or dissolved oxygen to, for example, prevent or minimize the potential oxidation of sulfite to sulfate.

(8) Calciner or furnace or kiln or equipment for thermal decomposition of calcium sulfite to calcium oxide and sulfur dioxide. Some embodiments may comprise a pre-drying process or pre-heating process to, for example, dry calcium sulfite, or dehydrate calcium sulfite hydrate, or recovery heat, or any combination thereof before or during calcination or decomposition. In some embodiments, it may be desirable for the decomposition of calcium sulfite to be powered by, for example, including but not limited to, one or more or any combination of the following: heat from the combustion of fuel, or electrical heating, or direct heating, or indirect heating, or stored heat, or light, or radiative heating, or nuclear heating, or any combination thereof. In some embodiments, it may be desirable to minimize or reduce the concentration or presence of diatomic oxygen to, for example, prevent or minimize the substantial potential oxidation of sulfite to sulfate, or minimize or reduce the concentration of sulfate in the product comprising calcium oxide.

Example Mass Flow Per 1 Metric Ton of Sodium Hydroxide of an Example Embodiment

Example Inputs and Outputs Mass Flow Summary without Solvent Water per 1 Metric Ton of Sodium Hydroxide Produced

| Inputs | | Outputs | |
|---|---|---|---|
| Chemical Name | Mass (kg) | Chemical Name | Mass (kg) |
| $CaCO_3$ | 1,251.18 | NaOH | 1,000 |
| $Na_2SO_4$ | 1,775.63 | $CaSO_4$ | 1,701.88 |
| $H_2O$ | 225.21 | $CO_2$ (Captured) | 550.17 |

Example Inputs and Outputs Mass Flow Summary with Solvent Water (with Concentrating to ~50 wt % NaOH Solution) per 1 Metric Ton of Sodium Hydroxide Produced

| Inputs | | Outputs | |
|---|---|---|---|
| Chemical Name | Mass (kg) | Chemical Name | Mass (kg) |
| $CaCO_3$ | 1,251.18 | NaOH | 1,000 |
| $Na_2SO_4$ | 1,775.63 | $CaSO_4$ | 1,701.88 |
| $H_2O$ | 225.21 | $CO_2$ (Captured) | 550.17 |
| Water | 1,052.63 | Water (Solvent in Aqueous NaOH) | 1,052.63 |

Example Inputs and Outputs Mass Flow Summary with Solvent Water (dilute solution assuming 1M Reactants in Step 7) per 1 Metric Ton of Sodium Hydroxide Produced

| Inputs | | Outputs | |
|---|---|---|---|
| Chemical Name | Mass (kg) | Chemical Name | Mass (kg) |
| $CaCO_3$ | 1,251.18 | NaOH | 1,000 |
| $Na_2SO_4$ | 1,775.63 | $CaSO_4$ | 1,701.88 |
| $H_2O$ | 225.21 | $CO_2$ (Captured) | 550.17 |
| Water | 12,393.38 | Water (Solvent in Aqueous NaOH) | 12,393.38 |

Example Step 1 Mass Flow with Solvent Water Per 1 Metric Ton of Sodium Hydroxide of an Example Embodiment Example Step 1 Reactants Mass with Solvent Water per 1 Metric Ton of NaOH

| Reactant | Mass (kg) | Example Source |
|---|---|---|
| $CaCO_3$ | 1,251.18 | Process Input |
| $CH_3COOH$ | 1,501.41 | Step 4 |
| Water (Solvent) | 6,307.01 | Step 4 |

Example Step 1 Products Mass with Solvent Water per 1 Metric Ton of NaOH

| Product | Mass (kg) | Next Process Step |
|---|---|---|
| $Ca(CH_3COO)_2$ | 1,977.25 | Step 2 |
| $CO_2$ | 550.17 | Process Output |
| $H_2O$ | 225.21 | Step 2 or Step 3 |
| Water (Solvent) | 6,307.01 | Step 2 |

Example Step 1 Mass Flow with Solvent Water Assumptions and Notes of an Example Embodiment Example step 1 mass flow may assume 100% purity. In practice, the reactants and/or products may have impurities and/or be of a purity less than 100%.

Example step 1 mass flow may assume alkaline earth-weak acid reactant comprises calcium carbonate. In some embodiments, the alkaline earth-weak acid reactant may comprise other alkaline earth-weak acids, such as, including, but not limited to, one or more or any combination of the following: magnesium salts, or calcium-magnesium salts, or dolomite, or silicates, or aluminates, or ferrites, or silica, or other weak acid mineral, or other weak acid intermediate, or other weak acid anion with a weaker acid strength than acetic acid, or other weak acid anion with a weaker acid strength than a carboxylic acid, or high magnesium limestone, or high impurity limestone. In some embodiments, if an alkaline earth-weak acid input comprises a weak acid anion other than carbonate, in some embodiments, less mass of $CO_2$ product may be produced.

Example step 1 mass flow assumes $CO_2$ product comprises high pressure and/or high purity carbon dioxide, which may comprise captured $CO_2$.

Example step 1 mass flow may determine the acetic acid concentration based on the solubility of the product calcium acetate. Example step 1 mass flow may assume it mau be desired for the product calcium acetate to be at an aqueous state.

In some embodiments, it may be desirable to remove at least a portion of water from the product solution comprising calcium acetate in step 1 or the product solution comprising sodium acetate in step 2. For example, it may be desirable to remove at least a portion of water from the product solution comprising calcium acetate in step 1 or the product solution comprising sodium acetate in step 2 due to the acetic acid being at a reacted or anion state or reacted, which may enable the distillation of or vaporization of a portion of water without or with substantially lower amount of co-vaporization or vaporization of acetic acid. For example, it may be desirable to remove at least a portion of water from the product solution comprising calcium acetate in step 1 or the product solution comprising sodium acetate in step 2 due to, for example, the condensation or accumulation or addition or absorption of water potentially present in the gas stream comprising $SO_2$(g) during step 3 and/or the potential need to remove said excess water to maintain the concentration of recycled or recirculated acetic acid in the process.

The mass flow in step 1 may assume the solvent water comprises an aqueous acetic acid solution recovered during step 4 by, for example, a form of distillation. In some embodiments, acetic acid may have a similar boiling point to water and may distill, or boil, or evaporate with water as a vapor or liquid solution or mixture. In some embodiments, step 4 may involve separating water and/or acetic acid by systems and methods in addition to, or instead of, distillation.

Example Step 2 Mass Flow with Solvent Water of an Example Embodiment

Example Step 2 Reactants Mass with Solvent Water per 1 Metric Ton of NaOH

| Reactant | Mass (kg) | Example Source |
|---|---|---|
| $Ca(CH_3COO)_2$ | 1,977.25 | Step 1 |
| $Na_2SO_4$ | 1,775.63 | Process Input |
| Water (Solvent) | 6,307.01 | Step 1 |

Example Step 2 Products Mass with Solvent Water per 1 Metric Ton of NaOH

| Product | Mass (kg) | Next Process Step |
|---|---|---|
| $NACH_3COO$ | 2,051.01 | Step 3 |
| $CaSO_4$ | 1,701.88 | Process Output |
| Water (Solvent) | 6,307.01 | Step 3 |

Example Step 2 Mass Flow with Solvent Water Assumptions and Notes of an Example Embodiment Example step 2 mass flow may assume 100% purity. In practice, the reactants and/or products may have impurities and/or be of a purity less than 100%.

Example step 2 mass flow may assume the alkali sulfate reactant comprises sodium sulfate. In practice, alkali sulfate reactant or input may comprise, for example, other alkali sulfates, such as potassium sulfate or lithium sulfate, and/or other alkali-like sulfates, such as ammonium sulfate.

Example step 2 mass flow may assume $CaSO_4$ is insoluble in water. In practice, $CaSO_4$ may exhibit some solubility in water (for example: 0.26 g/100 mL) and/or a portion of $CaSO_4$ may remain dissolved in the aqueous solution in steps 3 and/or 4. In some embodiments, for example, at least a portion of remaining or residual dissolved $CaSO_4$ may be recovered or separated or removed before or during step 4.

Example step 2 mass flow may assume sodium sulfate may be added as a reactant as a solid to the reactant comprising an aqueous solution of calcium acetate. For example, in some embodiments, sodium sulfate may be added as a solid to the solution comprising calcium acetate and/or the reactants may be mixed until the reaction reaches a desired point, or residence time, or completion, or any combination thereof. In some embodiments, it may be desirable for the sodium sulfate to be dissolved or comprise an aqueous solution comprising sodium sulfate, for example, before or during the reaction with calcium acetate or a solution comprising aqueous calcium acetate. For example, in some embodiments, sodium sulfate may be dissolved in an aqueous solution comprising acetic acid from, for example, step 4. For example, in some embodiments, sodium sulfate may be dissolved water from separating or distilling a portion of water from aqueous calcium acetate product from step 1, or from aqueous sodium acetate product from step 2, or any combination thereof, which may be conducted, for example, before, or during, or simultaneous, or any combination thereof to the reaction of sodium sulfate with calcium acetate.

Example Step 3 Mass Flow with Solvent Water of an Example Embodiment

Example Step 3 Reactants Mass with Solvent Water per 1 Metric Ton of NaOH

| Reactant | Mass (kg) | Example Source |
|---|---|---|
| $NACH_3COO$ | 2,051.01 | Step 2 |
| $SO_2$ | 800.89 | Step 8 |
| $H_2O$ | 225.21 | Step 1 or Step 2 |
| Water (Solvent) | 6,307.01 | Step 2 |

Example Step 3 Products Mass with Solvent Water per 1 Metric Ton of NaOH

| Product | Mass (kg) | Next Process Step |
|---|---|---|
| $Na_2SO_3$ | 1,575.66 | Step 4 |
| $CH_3COOH$ | 1,501.41 | Step 4 |
| Water (Solvent) | 6,307.01 | Step 4 |

Example Step 3 Mass Flow with Solvent Water Assumptions and Notes of an Example Embodiment Example step 3 mass flow may assume 100% purity. In practice, the reactants and/or products may have impurities and/or be of a purity less than 100%.

In some embodiments, some $Na_2SO_3$ may oxidize into $Na_2SO_4$, for example, if diatomic oxygen or dissolved oxygen is present. It may be desirable to minimize the potential presence of diatomic oxygen or dissolved oxygen to, for example, prevent or minimize the formation of sulfate from sulfite or sulfur dioxide.

In some embodiments, some $SO_2$ may comprise makeup $SO_2$, which may comprise a process input, or may be formed from process inputs comprising sulfur or hydrogen sulfide and/or diatomic oxygen, or any combination thereof.

Example step 3 mass flow may assume sodium sulfite product may remain dissolved in solution or remain at an aqueous state. In some embodiments, it may be desirable for sodium sulfite to remain at an aqueous state, to, for example, minimize or prevent solids handling or precipitation in an absorption column. In some embodiments, it may be desirable for at least a portion of the sodium sulfite to precipitate or form a solid state, which may be separated by solid-liquid separation, because, for example, precipitating a portion of sodium sulfite in step 3 may reduce the potential energy consumption and/or separation capacity required in step 3.

Example step 3 mass flow may assume acetic acid losses due to evaporation may be avoided. In some embodiments, acetic acid losses may be substantially avoided due to column design. For example, an absorption column may be designed with solutions comprising the lowest or near lowest free acetic acid concentration entering near the top, such as, for example, a solution comprising sodium acetate and/or lean in sulfur dioxide or sodium sulfite, which may prevent or minimize acetic acid losses due to acetic acid evaporation or 'acetic acid slip.' However, in some embodiments, in practice, some acetic acid losses or acetic acid slip may occur. In some embodiments, a portion of acetic acid vapor or acetic slip, if any, may be recovered by a basic salt or basic salt solution, such as a solid, or solution, or any combination thereof which may comprise, for example, including, but not limited to, one or more or any combination of the following: sodium hydroxide, or calcium oxide, or calcium hydroxide, or sodium sulfide, or calcium sulfide, or sodium carbonate, or sodium bicarbonate, or calcium carbonate, or calcium silicate, or alkaline earth-weak acid, or alkali-weak acid, or ammonium salt, or aqueous ammonia, or an amine, or a weak base, or a strong base.

Example step 3 mass flow may assume sodium sulfite may remain at its chemical state. In some embodiment, some diatomic oxygen or dissolved oxygen, if present, may react with a portion of sodium sulfite and/or form a portion of sodium sulfate. In some embodiments, it may be desirable to minimize or reduce the potential presence of diatomic oxygen or dissolved oxygen in step 3.

Example step 3 mass flow may assume water vapor may not be absorbed from the gas or fluid comprising sulfur dioxide. In some embodiments, for example, water vapor may be present in the gas comprising sulfur dioxide and/or a portion of the water present in the gas comprising sulfur dioxide may be absorbed during step 3. In some embodiments, for example, excess water or additional water absorbed during step 3 may be recovered or removed from the system or process by separating or removing or distilling or evaporating or any combination thereof a portion of water from a solution comprising sodium acetate, or a solution comprising calcium acetate, or any combination thereof before, or during, or after, or any combination thereof step 1 or step 2.

Example Step 4 Mass Flow with Solvent Water of an Example Embodiment

Example Step 4 Reactants Mass with Solvent Water per 1 Metric Ton of NaOH

| Reactant | Mass (kg) | Example Source |
|---|---|---|
| $Na_2SO_3$ | 1,575.66 | Step 3 |
| $CH_3COOH$ | 1,501.41 | Step 3 |
| Water (Solvent) | 6,307.01 | Step 3 |

Example Step 4 Products Mass with Solvent Water per 1 Metric Ton of NaOH

| Product | Mass (kg) | Next Process Step |
|---|---|---|
| $Na_2SO_3$ | 1,575.66 | Step 5 |
| $CH_3COOH$ | 1,501.41 | Step 1 |
| Water (Solvent) | 6,307.01 | Step 1 |

Example Step 4 Mass Flow with Solvent Water Assumptions and Notes of an Example Embodiment Example step 4 mass flow may assume 100% purity. In practice, the reactants and/or products may have impurities and/or be of a purity less than 100%.

Example step 4 mass flow may show fully separating acetic acid or aqueous acetic acid from sodium sulfite. Some embodiments may operate with nearly complete or complete separation of acetic acid or aqueous acetic acid from sodium sulfite. Some embodiments may operate with only partial separation of acetic acid or aqueous acetic acid from sodium sulfite, or without fully separating acetic acid or aqueous acetic acid from sodium sulfite, or without step 4, or any combination thereof.

In some embodiments, step 4 may further comprise removing or separating or precipitating residual dissolved calcium sulfate or magnesium sulfate.

Example step 4 mass flow may assume acetic acid and water separate together from sodium sulfite. In some embodiments, acetic acid has a similar boiling point or vapor pressure as water, and may form an azeotrope or azeotrope-like mixture with water, which may enable the separation from sodium sulfite as an aqueous acetic acid solution. In some embodiments, other weak acids may be employed instead of or in addition to acetic acid, and/or, in some embodiments, some of said other weak acids may have a different boiling point than water, and/or may enable the distillation or separation of water at least partially separately from the weak acid and/or crystallization of sodium sulfite. For example, in some embodiments, citric acid may have a boiling point different from water and/or may enable the distillation or separation of water at least partially separately from the weak acid and/or crystallization of sodium sulfite.

In some embodiments, residual sodium acetate may be present.

Example step 4 mass flow may assume no water was added or removed in preceding steps. In some embodiments, for example, in practice, water may be added or removed, in some cases incidentally, during preceding steps. For example, in some embodiments, some water may be absorbed from a gas or fluid or other stream comprising sulfur dioxide in step 3, which may comprise an example of water added in a preceding step.

Example Step 5 Mass Flow with Solvent Water of an Example Embodiment

| Example Step 5 Reactants Mass with Solvent Water per 1 Metric Ton of NaOH | | |
|---|---|---|
| Reactant | Mass (kg) | Example Source |
| $Na_2SO_3$ | 1,575.66 | Step 4 |
| Water (Solvent) | 6,142.91 | Process Input, and/or from NaOH concentrating during or after Step 7 |

| Example Step 5 Products Mass with Solvent Water per 1 Metric Ton of NaOH | | |
|---|---|---|
| Product | Mass (kg) | Next Process Step |
| $Na_2SO_3$ | 1,575.66 | Step 7 |
| Water (Solvent) | 6,142.91 | Step 7 |

Example Step 5 Mass Flow with Solvent Water Assumptions and Notes of an Example Embodiment Example step 5 mass flow may assume a 100% purity. In practice, the reactants and/or products may have impurities and/or be of a purity less than 100%.

Example step 5 mass flow may assume sodium sulfite may be dissolved in water before step 7. In some embodiments, for example, step 5 may be skipped. In some embodiments, for example, sodium sulfite may be mixed or reacted with calcium hydroxide or calcium oxide as a solid, or in the presence of water, or in the presence of water with calcium hydroxide or calcium oxide, or any combination thereof in, for example, step 7.

In some embodiments, dissolved oxygen or diatomic oxygen may be present and/or may oxidize a portion of sodium sulfite to sodium sulfate. It may be desirable to minimize concentration or presence of dissolved oxygen or diatomic oxygen to, for example, prevent or minimize or reduce the potential oxidation of sodium sulfite to sodium sulfate.

Example step 5 mass flow may assume ~2M concentration of sodium sulfite, and/or ~1M concentration of sodium sulfite when mixed with calcium hydroxide suspension in step 7, and/or to form an aqueous solution of ~2M sodium hydroxide in step 7. In some embodiments, in practice, the desired concentration of sodium sulfite may vary. For example, the desired concentration of sodium sulfite may be less than or greater than or equal to one or more or any combination of the following: 0.05 M, or 0.1 M, or 0.2 M, or 0.3 M, or 0.4 M, or 0.5 M, or 0.6 M, or 0.7 M, or 0.8 M, or 0.9 M, or 1.0 M, or 1.1 M, or 1.2 M, or 1.3 M, or 1.4 M, or 1.5 M, or 1.6 M, or 1.7 M, or 1.8 M, or 1.9 M, or 2.0 M, or 2.25 M, or 2.5 M, or 2.75 M, or 3 M, or 3.5 M, or 4 M, or 4.5 M, or 5 M.

In some embodiments, sodium sulfite or an aqueous solution comprising may be employed as a draw solution in forward osmosis or osmotically assisted reverse osmosis to, for example, concentrate sodium hydroxide while diluting sodium sulfite. For example, in some embodiments, water may be added to sodium sulfite by employing sodium sulfite as a draw solution.

Example Step 6 Mass Flow without Solvent Water of an Example Embodiment

| Example Step 6 Reactants Mass with Solvent Water per 1 Metric Ton of NaOH | | |
|---|---|---|
| Reactant | Mass (kg) | Example Source |
| CaO | 701.02 | Step 8 |
| $H_2O$ | 225.21 | Process Input |
| Water (Solvent) | 6,250.47 | Process Input, and/or from NaOH concentrating during or after Step 7 |

| Example Step 6 Products Mass with Solvent Water per 1 Metric Ton of NaOH | | |
|---|---|---|
| Product | Mass (kg) | Next Process Step |
| $Ca(OH)_2$ | 926.23 | Step 7 |
| Water (Solvent) | 6,250.47 | Step 7 |

Example Step 6 Mass Flow with Solvent Water Assumptions and Notes of an Example Embodiment Example step 6 mass flow may assume 100% purity. In practice, the reactants and/or products may have impurities and/or be of a purity less than 100%.

Example step 6 mass flow may assume calcium oxide may be reacted with water to form calcium hydroxide and/or calcium hydroxide, such as a solid, or as a suspended calcium hydroxide solution or milk of lime, or any combination thereof, may comprise an input to step 7. In some embodiments, calcium oxide may be directly reacted with aqueous sodium sulfite. In some embodiments, calcium oxide and sodium sulfite may be mixed or reacted in the presence of water. In some embodiments, for example, step 6 may be skipped.

In some embodiments, calcium oxide may comprise or further comprise calcium sulfate, or calcium sulfite, or calcium sulfide.

Example Step 7 Mass Flow with Solvent Water of an Example Embodiment

| Example Step 7 Reactants Mass with Solvent Water per 1 Metric Ton of NaOH | | |
|---|---|---|
| Reactant | Mass (kg) | Example Source |
| $Na_2SO_3$ | 1,575.66 | Step 4 or Step 5 |
| Water (Solvent) | 6,142.91 | Step 5 |

-continued

| Example Step 7 Reactants Mass with Solvent Water per 1 Metric Ton of NaOH | | |
|---|---|---|
| Reactant | Mass (kg) | Example Source |
| $Ca(OH)_2$ | 926.23 | Step 6 or Step 8 |
| Water (Solvent) | 6,250.47 | Step 6 |

| Example Step 7 Products Mass with Solvent Water per 1 Metric Ton of NaOH | | |
|---|---|---|
| Product | Mass (kg) | Next Process Step |
| $CaSO_3$ | 1,502.23 | Step 8 |
| NaOH | 1,000 | Process Output |
| Water (Solvent) | 12,393.38 | Process Output, and/or Step 5 and/or Step 6 |

Example Step 7 Mass Flow with Solvent Water Assumptions and Notes of an Example Embodiment Example step 7 mass flow may assume 100% purity. In practice, the reactants and/or products may have impurities and/or be of a purity less than 100%.

Example step 7 mass flow may assume the reactants are present at stoichiometric ratios in the reactor. In some embodiments, in practice, the reaction between $Ca(OH)_2$ and $Na_2SO_3$ may comprise an equilibrium reaction and/or it may be desirable for one reactant to be in stoichiometric excess to facilitate the reaction. For example, in some embodiments, calcium hydroxide may be present in the reactants in stoichiometric excess of sodium sulfite. For example, in some embodiments, sodium sulfite may be present in the reactants in stoichiometric excess of calcium hydroxide. For example, in some embodiments, calcium hydroxide may be present in the solid product comprising calcium sulfite separated and/or transferred to step 8. For example, in some embodiments, sodium sulfite or sodium sulfate may be present in the sodium hydroxide product. For example, in some embodiments, calcium sulfate may be present in the sodium hydroxide product.

In some embodiments, a solid comprising calcium oxide or calcium hydroxide may be reacted with aqueous sodium sulfite. In some embodiments, a solid comprising sodium sulfite may be reacted with an aqueous suspension or aqueous solution or any combination thereof comprising calcium oxide or calcium hydroxide.

Depending on end use of sodium hydroxide, may undergo further concentrating or purification. For example, in some embodiments, at least a portion of potential residual calcium hydroxide, or calcium sulfate, or sodium sulfite, or sodium sulfate, or any combination thereof may be removed or separated. For example, in some embodiments, an aqueous solution comprising sodium hydroxide may be further concentrated to form concentrated sodium hydroxide, or sodium hydroxide of a desired concentration, or solid sodium hydroxide, or any combination thereof. In some embodiments, concentrating sodium hydroxide may enable or facilitate the separation or precipitation of at least a portion of other salts or impurities, which may be less soluble, such as calcium hydroxide, or calcium sulfate, or sodium sulfite, or sodium sulfate. For example, in some embodiments, an ion exchange, or ion extraction, or any combination thereof may be employed.

For example, in some embodiments, if the sodium hydroxide product may be employed for ocean carbon dioxide removal, it may be desirable to minimize purification or concentrating of sodium hydroxide solution. For example, in some embodiments, if the sodium hydroxide product may be employed for ocean carbon dioxide removal, solids comprising calcium sulfite and/or calcium hydroxide may be filtered or otherwise separated from an aqueous solution comprising sodium hydroxide and/or the aqueous solution comprising sodium hydroxide may be added to the ocean, or sea, or other body of water.

For example, in some embodiments, it may be desirable to purify and/or concentrate sodium hydroxide to desired concentration or specifications if, for example, the sodium hydroxide comprises a product.

For example, in some embodiments, sodium hydroxide may be concentrated using one or more or a combination of water separation methods, such as, including, but not limited to, one or more or any combination of the following: mechanical vapor compression distillation, or mechanical vapor recompression distillation, or multi-effect distillation, or multistage flash distillation, or distillation, or cryodesalination, or crystallization, or crystallizer, or membrane distillation, or any combination thereof. For example, in some embodiments, energy consumption associated with at least a portion of the concentrating of the sodium hydroxide may be conducted by employing forward osmosis or osmotically assisted reverse osmosis, which may comprise, for example, employing sodium sulfite or a solution comprising sodium sulfite in or from step 5 as the draw solution being diluted and sodium hydroxide or a solution comprising sodium hydroxide as the feed solution being concentrated. Employing a membrane based process, such as forward osmosis, or osmotically assisted reverse osmosis, or reverse osmosis, or high pressure reverse osmosis, or disc reverse osmosis, or membrane distillation, or any combination thereof, may benefit from the use of a strong base compatible semi-permeable membrane.

In some embodiments, at least a portion of calcium hydroxide may be separated from at least a portion of calcium sulfite product. For example, in some embodiments, at least a portion of calcium hydroxide may be separated utilizing calcium hydroxide's greater solubility in water than calcium sulfite. For example, in some embodiments, at least a portion of calcium hydroxide may be separated utilizing the potentially greater propensity for calcium hydroxide to form suspensions in water than calcium sulfite. For example, in some embodiments, at least a portion of calcium hydroxide may be separated by forming a solid-liquid suspension of calcium hydroxide, or calcium sulfite, or any combination thereof. For example, in some embodiments, at least a portion of calcium hydroxide may be separated by using the difference in density between calcium hydroxide and calcium sulfite. For example, in some embodiments, at least a portion of calcium hydroxide may be separated by using a centrifuge, or decanter, or high density liquid, or any combination thereof. In some embodiments, recovered or recycled calcium hydroxide may be recycled in step 7, or calcined in a calcium hydroxide calciner to calcium oxide and/or calcium oxide transferred to step 6, or any combination thereof.

Example Step 8 Mass Flow of an Example Embodiment

| Example Step 7 Reactants Mass per 1 Metric Ton of NaOH | | |
|---|---|---|
| Reactant | Mass (kg) | Example Source |
| $CaSO_3$ | 1,502.24 | Step 7 |

| Example Step 7 Products Mass per 1 Metric Ton of NaOH | | |
|---|---|---|
| Product | Mass (kg) | Next Process Step |
| CaO | 701.02 | Step 6 or Step 7 |
| $SO_2$ | 800.89 | Step 3 |

Example Step 8 Mass Flow Assumptions and Notes of an Example Embodiment

Example step 8 mass flow may assume 100% purity. In practice, the reactants and/or products may have impurities and/or be of a purity less than 100%.

In some embodiments, the product comprising calcium sulfite may comprise a portion of calcium hydroxide. In some embodiments, a pre-calciner or initial calciner may calcine or decompose the calcium hydroxide to, for example, calcium oxide and water vapor. For example, in some embodiments, a pre-calciner or initial calciner may calcine or decompose the calcium hydroxide to, for example, calcium oxide and water vapor, followed by calcining or decomposing the calcium sulfite to calcium oxide and sulfur dioxide at a higher temperature. For example, in some embodiments, calcining or decomposing calcium hydroxide to calcium oxide may require, for example, a lower temperature and/or less energy than, for example, the decomposition of calcium sulfite to calcium oxide and sulfur dioxide.

In some embodiments, a portion of calcium sulfate may form during the decomposition or calcination of calcium sulfite.

In some embodiments, it may be desirable to conduct the calcination or decomposition in a low diatomic oxygen environment. For example, it may be desirable to employ a low diatomic oxygen concentration, or a diatomic oxygen concentration lower than the concentration of oxygen in air, to, for example, reduce or minimize the potential oxidation of calcium sulfite or sulfite to sulfate or sulfur trioxide.

In some embodiments, it may be desirable to conduct the decomposition or calcination of calcium sulfite at a temperature equal to or greater than 780° C.

Example Total Heat Input Per Metric Ton of Sodium Hydroxide of an Example Embodiment

| Example Total Heat Input per Metric Ton of Sodium Hydroxide | |
|---|---|
| Total Heat Input per 1 Metric Ton of NaOH (MMBtu) | 2.69 MMBtu |
| Total Heat Input per 1 Metric Ton of NaOH (MWh) | 0.79 MWh |

Note: The 'Example Heat Input per Metric Ton of Sodium Hydroxide' may assume calcination employs heat and water separations in the system or process may be conducted with electricity. It may be important to note that heat may be employed as an input in water separations if desired.

Example Electricity Input Per Metric Ton of Sodium Hydroxide of an Example Embodiment

| Example Total Electricity Input per Metric Ton of Sodium Hydroxide | |
|---|---|
| Total Electricity Input without Concentrating NaOH Product (MWh) | 0.16 MWh |
| Total Electricity Input without Concentrating NaOH Product, with Seawater RO Desalination Electricity Consumption to Produce Makeup Water (MWh) | 0.20 MWh |
| Total Electricity Input with Concentrating NaOH Product to 50 wt % NaOH | 0.40 MWh |

Note: The 'Example Electricity Input per Metric Ton of Sodium Hydroxide' may assume water separations in the system or process may be conducted with mechanical vapor compression (MVC) distillation, which may be powered by electricity. It may be important to note that other water separation technologies may be employed instead of or in addition to MVC and/or may be powered by electricity, or heat, or other energy form or energy source.

Example Cost of Inputs Per Metric Ton of Sodium Hydroxide Produced of an Example Embodiment

| Example Cost of Inputs per Metric Ton of Sodium Hydroxide Produced (assuming without Concentrating to 50 wt % NaOH) | | |
|---|---|---|
| Input Description | Input | Cost ($) |
| $CaCO_3$ (Metric Tonnes) | 1.25 | $25.02 |
| $Na_2SO_4$ (Metric Tonnes) | 1.78 | $71.03 |
| $H_2O$ (Metric Tonnes) | 0.23 | $0.11 |
| Water (assuming without Concentrating to 50 wt % NaOH) (Metric Tonnes) | 12.39 | $6.20 |
| Heat (assuming natural gas) (MMBtu) | 2.69 | $6.19 |
| Electricity (MWh) | 0.20 | $9.77 |
| Total | | $118.31 |

| Example Cost of Inputs per Metric Ton of Sodium Hydroxide Produced (assuming with Concentrating to 50 wt % NaOH) | | |
|---|---|---|
| Input Description | Input | Cost ($) |
| $CaCO_3$ (Metric Tonnes) | 1.25 | $25.02 |
| $Na_2SO_4$ (Metric Tonnes) | 1.78 | $71.03 |
| $H_2O$ (Metric Tonnes) | 0.23 | $0.11 |
| Water (assuming with Concentrating to 50 wt % NaOH) (Metric Tonnes) | 1.05 | $0.53 |
| Heat (assuming natural gas) (MMBtu) | 2.69 | $6.19 |
| Electricity (MWh) | 0.40 | $19.78 |
| Total | | $122.66 |

Example Value of Outputs and Example Marginal Net Profit Per Metric Ton of Sodium Hydroxide Produced of an Example Embodiment

| Example Value of Outputs and Example Marginal Net Profit per Metric Ton of Sodium Hydroxide Produced (NaOH Sold as a Product) | | |
|---|---|---|
| Output Description | Output | Value |
| NaOH (Metric Tonnes) | 1 | $600 |
| $CaSO_4$ (Metric Tonnes) | 1.70 | $15.32 |
| $CO_2$ (High Purity, Captured) (45Q Value) (Metric Tonnes) | 0.55 | $33.01 |
| Total | | $648.33 |
| Marginal Net Profit ($) | | $525.67 |
| Unit Profit Margin (%) | | 81% |

| Example Value of Outputs and Example Marginal Net Profit per Metric Ton of Sodium Hydroxide Produced (NaOH Added to the Ocean for $CO_2$ Removal) | | |
|---|---|---|
| Output Description | Output | Value |
| NaOH (Added to the Ocean for $CO_2$ Removal (Metric Tonnes) | 1 | |
| $CaSO_4$ (Metric Tonnes) | 1.70 | $15.32 |
| $CO_2$ (High Purity, Captured) (45Q Value) (Metric Tonnes) | 0.55 | $33.01 |
| Net Permanent $CO_2$ Removal from the Ocean or Atmosphere (Metric Tonnes) | 1.002 | $981.70 |
| Total | | $1,030 |
| Marginal Net Profit ($) | | $911.71 |
| Unit Profit Margin (%) | | 89% |

Example Net Permanent $CO_2$ Removal if Fuel is Natural Gas (without $CO_2$ Capture) and ERCOT Grid Electricity (NaOH May be Added to the Ocean for $CO_2$ Removal) of an Example Embodiment

| Example Net Permanent $CO_2$ Removal if Fuel is Natural Gas (without $CO_2$ Capture) and ERCOT Grid Electricity (NaOH may be added to the ocean for $CO_2$ Removal) | |
|---|---|
| Energy $CO_2$ Emissions (Metric Tons) per Metric Ton NaOH (Nat. Gas Heat) | 0.03882337 Metric Tons $CO_2$ |
| Energy $CO_2$ Emissions (Metric Tons) per Metric Ton NaOH (Electricity) | 0.059775352 Metric Tons $CO_2$ |
| $CO_2$ Removal (Metric Tons) per Metric Ton NaOH by formation of $NaHCO_3$ when added to the Ocean | −1.100332525 Metric Tons $CO_2$ |
| Net $CO_2$ Removal per Metric Ton Sodium Hydroxide Added to the Ocean (Metric Tons $CO_2$) | −1.001733803 Metric Tons $CO_2$ |

| Example Net Permanent $CO_2$ Removal if Fuel is 100% Renewable $CO_2$ Emissions-Free (NaOH may be added to the ocean for $CO_2$ Removal) | |
|---|---|
| Energy $CO_2$ Emissions (Metric Tons) per Metric Ton NaOH (Nat. Gas Heat) | 0 Metric Tons $CO_2$ |
| Energy $CO_2$ Emissions (Metric Tons) per Metric Ton NaOH (Electricity) | 0 Metric Tons $CO_2$ |
| $CO_2$ Removal (Metric Tons) per Metric Ton NaOH by formation of $NaHCO_3$ when added to the Ocean | −1.100332525 Metric Tons $CO_2$ |
| Net $CO_2$ Removal per Metric Ton Sodium Hydroxide Added to the Ocean (Metric Tons $CO_2$) | −1.100332525 Metric Tons $CO_2$ |

Example $CO_2$ Emissions Reduction Compared to Conventional Chloralkali Process if Fuel is Natural Gas (without $CO_2$ Capture) and ERCOT Grid Electricity (NaOH may be sold as a product) of an Example Embodiment

| Example $CO_2$ Emissions Reduction Compared to Conventional Chloralkali Process (if Fuel is Natural Gas (without $CO_2$ Capture) and ERCOT Grid Electricity (NaOH may be sold as a product)) | |
|---|---|
| Example Embodiment Process $CO_2$ Emissions per Metric Ton NaOH (Without Carbon Removal) | 0.099 Metric Tons $CO_2$ |
| Conventional Chlor-Alkali Process CO2 Emissions per Metric Ton NaOH (Without Carbon Removal) | 0.65 Metric Tons $CO_2$ |
| Example Embodiment Emissions Reduction Compared to Chlor-Alkali Process | 85% Reduction in $CO_2$ Emissions |

Example Additional Description and Notes

Note: It may be important to note that in some embodiments which may produce alkali sulfate from alkali chloride, such as the embodiments shown in FIGS. 26A-26D, the reaction of ammonium chloride with a calcium carbonate may comprise reacting ammonium chloride with an alkaline earth weak acid. For example, in some embodiments, calcium carbonate may be provided as an example alkaline earth weak acid. Other alkaline earth weak acid salts or materials may be employed instead of or in addition to calcium carbonate. For example, in some embodiments, said reaction of ammonium chloride may comprise reacting ammonium chloride with an alkaline weak acid, or alkaline earth silicate, or alkaline earth ferrite, or waste cement, or waste concrete, or alkaline mineral, or mine tailings, or fly ash, or alkaline waste products, or alkaline ore, or any combination thereof. In some embodiments, a weak acid derivative other than or in addition to $CO_2$ may be produced (which may result in less $CO_2$ production and/or lower $CO_2$ emissions), such as, for example, including, but not limited to, one or more silicon dioxide, or silicon oxides, or iron oxides, or aluminum oxides, or manganese oxides. In some embodiments, ammonium chloride may comprise a solid, or a gas, or a vapor, or an aqueous solution, or a solution, or a liquid, or any combination thereof. In some embodiments, ammonium chloride may be well suited for reaction with difficult to react alkaline materials or alkaline earth materials, such as waste concrete, or alkaline mineral ores, or sintered alkaline earth materials, because, when under certain conditions, such as when heated, ammonium chloride may form HCl or hydrochloric acid, which may be strongly reactive with a wide range of alkaline materials, which may be advantageous as it may reduce $CO_2$ production and/or $CO_2$ emissions in the process if a wider range of alkaline materials, such as alkaline materials with less or no carbon dioxide deriviative anion, can be employed. In some embodiments, calcium carbonate produced in, for example, the reaction of ammonium carbonate and calcium sulfate, may employed as or may comprise at least a portion of the calcium carbonate or Ca(WA) in the reaction of $CaCO_3$ with acid or carboxylic acid or acetic acid, or in the reaction of Ca(WA) with acid or carboxylic acid or acetic acid. In some embodiments, the ammonium carbonate may comprise ammonium bicarbonate, or a solution comprising ammonium bicarbonate, or a solution comprising a molar ratio of $CO_2$ to ammonia or ammonium greater than 0.5 to 1, or any combination thereof. In some embodiments, calcium carbonate produced in, for example, the reaction of ammonium carbonate and calcium sulfate, may employed as or may comprise at least a portion of the calcium carbonate or Ca(WA) in the reaction of $CaCO_3$ with acid or carboxylic acid or acetic acid, or in the reaction of Ca(WA) with acid or carboxylic acid or acetic acid. In some embodiments, calcium carbonate produced in, for example, the reaction of ammonium carbonate and calcium sulfate, may employed as or may comprise at least a portion of the calcium carbonate or Ca(WA) in the reaction of $CaCO_3$ with acid or carboxylic acid or acetic acid, or in the reaction of Ca(WA) with acid or carboxylic acid or acetic acid, which may enable carbon dioxide to be captured in the process, or may enable carbon dioxide to comprise an intermediate, and/or may enable a reduction of or avoidance of or elimination of the need for a $CO_2$ output or pure $CO_2$ output or $CO_2$ byproduct in, for example, one or more or any combination of embodiments.

Note: Some embodiments may pertain to producing metal oxides or metal hydroxides which may possess overlapping or similar chemistry or similar properties to calcium, or magnesium, or other alkaline-earths. For example, iron, manganese, and/or zinc may possess similar properties to calcium or magnesium in certain aqueous solutions or in compounds with certain anions. For example, iron acetate and manganese acetate are soluble in water, while iron sulfite and manganese sulfite are practically insoluble. For example, the reaction of aqueous iron acetate or aqueous manganese acetate with sulfur dioxide or sodium sulfite may result in the formation of an iron sulfite precipitate or manganese sulfite precipitate. For example, when thermally decomposed, iron sulfite, or manganese sulfite, or zinc sulfite may form a metal oxide and sulfur dioxide gas.

Note: $SO_2(g)$ reacted with or absorbed in aqueous calcium acetate, or aqueous sodium acetate, or aqueous ammonium acetate, or aqueous potassium acetate, or aqueous magnesium acetate, or aqueous alkali acetate, or aqueous alkaline-earth acetate, or any combination thereof may comprise $SO_2(g)$ with a volume percent concentration greater than or equal to one or more or any combination of the following: 0.001%, or 0.01%, or 0.05%, or 0.1%, or 0.2%, or 0.3%, or 0.4%, or 0.5%, or 0.6%, or 0.7%, or 0.8%, or 0.9%, or 1.0%, or 1.5%, or 2%, or 2.5%, or 3%, or 3.5%, or 4%, or 4.5%, or 5%, or 5.5%, or 6%, or 6.5%, or 7%, or 7.5%, or 8%, or 8.5%, or 9%, or 9.5%, or 10%, or 11%, or 12%, or 13%, or 14%, or 15%, or 16%, or 17%, or 18%, or 19%, or 20%, or 25%, or 30%, or 35%, or 40%, or 45%, or 50%, or 55%, or 60%, or 65%, or 70%, or 75%, or 80%, or 85%, or 90%, or 95%, or 96%, or 97%, or 98%, or 99%, or 99.5%, or 99.9%. It is important to note acetate or acetic acid may be provided as an example acid, or acid derivative, or acid anion, or an anion which is a derivative of an acid, wherein said acid may possess an acid strength greater than carbonic acid or an acid of aqueous carbon dioxide or an acid of dissolved carbon dioxide, and/or an acid strength weaker than sulfurous acid or an acid of aqueous sulfur dioxide or an acid of dissolved sulfur dioxide.

Note: $SO_2(g)$ reacted with or absorbed in aqueous calcium acetate, or aqueous sodium acetate, or aqueous ammonium acetate, or aqueous potassium acetate, or aqueous magnesium acetate, or aqueous alkali acetate, or aqueous alkaline-earth acetate, or any combination thereof may comprise a gas mixture comprising at least a portion of $SO_2(g)$. $SO_2(g)$ may comprise, for example, flue gases or combustion gases comprising at least a portion of $SO_2(g)$. Said gas mixture may comprise, for example, flue gases or combustion gases comprising at least a portion of $SO_2(g)$. $SO_2(g)$ may comprise, for example, flue gases or combustion gases employed to decompose a sulfite salt and form a gas mixture comprising at least a portion of $SO_2(g)$. $SO_2(g)$ may comprise, for example, flue gases or combustion gases employed to decompose a sulfite salt and form a gas mixture comprising at least a portion of $SO_2(g)$. $SO_2(g)$ may comprise, for example, flue gases or combustion gases employed to decompose a sulfite salt and form a gas mixture comprising $SO_2(g)$ and $CO_2(g)$. In some embodiments, if $CO_2(g)$ is present in a gas comprising $SO_2(g)$, the $CO_2(g)$ may not react with the acetate salt or the $SO_2(g)$ may react with the acetate salt, or any combination thereof, due to, for example, the acid strength of $SO_2(aq)$ being greater than acetic acid, or the acid strength of acetic acid being greater than $CO_2$ (aq), or the acid strength of $SO_2(aq)$ being greater than $CO_2(aq)$, or any combination thereof. $SO_2(g)$ may comprise a recirculating carrier gas comprising $SO_2(g)$. $SO_2(g)$ may comprise a recirculating carrier gas comprising a relatively inert gas, such as nitrogen, or air, or argon, or fluorocarbon, or noble gas, or any combination thereof and at least a portion of $SO_2(g)$. $SO_2(g)$ may comprise a carrier gas or stripping gas which may comprise a relatively inert gas, such as nitrogen, or air, or argon, or fluorocarbon, or noble gas, or any combination thereof and at least a portion of $SO_2(g)$.

It is important to note acetate or acetic acid may be provided as an example acid, or acid derivative, or acid anion, or an anion which is a derivative of an acid, wherein said acid may possess an acid strength greater than carbonic acid or an acid of aqueous carbon dioxide or an acid of dissolved carbon dioxide, and/or an acid strength weaker than sulfurous acid or an acid of aqueous sulfur dioxide or an acid of dissolved sulfur dioxide.

Note: In some embodiments, $SO_2$(g) from calcining $CaSO_3$ may be further concentrated, or pressurized, or purified.

Note: $SO_2$(g) from calcining $CaSO_3$ may be absorbed into water or an aqueous solution to form sulfurous acid or aqueous sulfur dioxide.

Note: Weak acid or weak acid anion may comprise an acid or acid anion with an acid strength lower than the acid strength of formic acid, or acetic acid, or propionic acid, or butyric acid, or citric acid, or lactic acid, or valeric acid, or caproic acid, or enanthic acid, or caprylic acid, or pelargonic acid, or capric acid, or carboxylic acid, or sulfurous acid.

Note: Weak acid or weak acid anion may comprise an acid or acid anion with a higher pKa than acetic acid, or carboxylic acid, or sulfurous acid.

Note: Acetic acid may be provided as an example acid with an acid strength greater than 'Weak Acid', and an acid strength lower than sulfurous acid or aqueous sulfur dioxide. In some embodiments, where acetic acid or acetate is described, other acids with an acid strength greater than 'Weak Acid', and an acid strength lower than sulfurous acid or aqueous sulfur dioxide may be employed.

Note: It may be important to note that in some embodiments which may produce alkali sulfate from alkali chloride, such as the embodiments shown in FIGS. 26A-26D, the reaction of ammonium chloride with a calcium carbonate may comprise reacting ammonium chloride with an alkaline earth weak acid. For example, in some embodiments, calcium carbonate may be provided as an example alkaline earth weak acid. Other alkaline earth weak acid salts or materials may be employed instead of or in addition to calcium carbonate. For example, in some embodiments, said reaction of ammonium chloride may comprise reacting ammonium chloride with an alkaline weak acid, or alkaline earth silicate, or alkaline earth ferrite, or waste cement, or waste concrete, or alkaline mineral, or mine tailings, or fly ash, or alkaline waste products, or alkaline ore, or any combination thereof. In some embodiments, a weak acid derivative other than or in addition to $CO_2$ may be produced (which may result in less $CO_2$ production and/or lower $CO_2$ emissions), such as, for example, including, but not limited to, one or more silicon dioxide, or silicon oxides, or iron oxides, or aluminum oxides, or manganese oxides. In some embodiments, ammonium chloride may comprise a solid, or a gas, or a vapor, or an aqueous solution, or a solution, or a liquid, or any combination thereof. In some embodiments, ammonium chloride may be well suited for reaction with difficult to react alkaline materials or alkaline earth materials, such as waste concrete, or alkaline mineral ores, or sintered alkaline earth materials, because, when under certain conditions, such as when heated, ammonium chloride may form HCl or hydrochloric acid, which may be strongly reactive with a wide range of alkaline materials, which may be advantageous as it may reduce $CO_2$ production and/or $CO_2$ emissions in the process if a wider range of alkaline materials, such as alkaline materials with less or no carbon dioxide deriviative anion, can be employed. In some embodiments, calcium carbonate produced in, for example, the reaction of ammonium carbonate and calcium sulfate, may employed as or may comprise at least a portion of the calcium carbonate or Ca(WA) in the reaction of $CaCO_3$ with acid or carboxylic acid or acetic acid, or in the reaction of Ca(WA) with acid or carboxylic acid or acetic acid.

Note: Acetic acid, which may comprise an 'acid,' may comprise including, but are not limited to, one or more or any combination of the following: carboxylic acid, or formic acid, or acetic acid, or Glycolic acid, or Glyoxylic acid, or carboxylic acid, or citric acid, or Propionic acid, or Acrylic acid, or Propiolic acid, or Lactic acid, or 3-Hydroxypropionic acid, or Glyceric acid, or Pyruvic acid, or 3-oxopropanoic acid, or 2,3-dioxopropanoic acid, or Malonic acid, or Tartronic acid, or 2,2-dihydroxypropanedioic acid, or Mesoxalic acid, or Glycidic acid, or butyric acid, or isobutyric acid, or crotonic acid, or isocrotonic acid, or vinylacetic acid, or tetrolic acid, or 2-hydroxybutyric acid, or β-hydroxybutyric acid, or γ-hydroxybutyric acid, or α-ketobutyric acid, or acetoacetic acid, or succinic semialdehyde, or succinic acid, or methylmalonic acid, or fumaric acid, or gallic acid, or maleic acid, or gluconic acid, or itaconic acid. or acetylenedicarboxylic acid, or malic acid, or tartaric acid, or oxaloacetic acid, or dioxosuccinic acid, or pentanoic acid, or valeric acid, or isovaleric acid, or 2-methylbutiric acid, or pivalic acid, or β-hydroxyvaleric acid, or γ-hydroxyvaleric acid, or β-hydroxy β-methylbutyric acid, or glutaric acid, or α-ketoglutaric acid, or acetonedicarboxylic acid, or 2-furoic acid, or tetrahydro-2-furoic acid, or Ascorbic Acid, or caproic acid, or adipic acid, or aconitic acid, or isocitric acid, or isocitric acid, or sorbic acid, or enanthic acid, or pimelic acid, or benzoic acid, or salicylic acid, or caprylic acid, or phthalic acid, or isophthalic acid, or terephthalic acid, or pelargonic acid, or trimesic acid, or cinnamic acid, or capric acid, or sebacic acid, or hendecanoic acid, or lauric acid, or mellitic acid, or tridecylic acid, or myristic acid, or pentadecylic acid, or palmitic acid, or margaric acid, or stearic acid, or oleic acid, or linoleic acid.

Note: Acetic acid may be provided as an example acid with an pKa lower than 'Weak Acid', and an pKa greater than sulfurous acid or aqueous sulfur dioxide.

Note: Calcium may be provided as an example alkaline earth. Other alkaline earths, which may include beryllium (Be), or magnesium (Mg), or calcium (Ca), or strontium (Sr), or barium (Ba), or radium (Ra), or any combination thereof, may be employed instead or in addition to calcium.

Note: Ammonia or ammonium (for example: $NH_3$ or $NH_4$+) may be provided as an example cation, or example water soluble salt forming cation, or an example alkali-like cation, or an example alkali-like chemical, or any combination thereof. In some embodiments, other water soluble salt forming cations or water soluble salt forming cation derivatives may include, but are not limited to, amines, or imines, or azines, or ionic liquids, or aqueous $CO_2$ capture absorbents, or aqueous $SO_2$ capture absorbents, or liquid $CO_2$ capture absorbents, or liquid $SO_2$ capture absorbents, or any combination thereof. Sodium (Na) may be provided as an example alkali. Other alkalis or alkali-like chemicals may be employed in addition to, or instead of, for example, sodium. For example, other alkalis or alkali-like chemicals may include, but are not limited to, lithium (Li), or potassium (K), or ammonium ($NH_4$), or ammonia ($NH_3$), or ammonium derivative, or nitrogenous base, or rubidium (Rb), or caesium (Cs). For example, potassium hydroxide may be produced from potassium sulfate, instead of or in addition to, for example, sodium hydroxide and sodium sulfate. For example, potassium acetate, or potassium sulfite may be employed instead of or in addition to, for example, sodium acetate, or sodium sulfite. In some embodiments, it may be desirable to combine multiple different alkalis or alkali-like chemicals. For example, it some embodiments, it may be desirable to combine ammonia and potassium, or ammonia and sodium, or any combination thereof.

Note: Some embodiments may employ Oxalic Acid or Oxalate.

Note: Some embodiments may comprise systems and methods for producing cement, or clinker, or any combination thereof.

- For example, in some embodiments, an alkaline-earth sulfite, such as calcium sulfite or magnesium sulfite, may be mixed or grinded with other components of cement raw mix, such as clay, shale, sand, iron ore, bauxite, fly ash, or slag, then the resulting mixture may be heated in a cement kiln to a calcining temperature, then a fusing temperature to produce cement clinker.
- For example, in some embodiments, an alkaline-earth sulfite, such as calcium sulfite or magnesium sulfite, may be calcined or thermally decomposed to produce an alkaline-earth oxide, such as calcium oxide or magnesium oxide, then the alkaline-earth oxide may be mixed with other components of cement raw mix, such as clay, shale, sand, iron ore, bauxite, fly ash, or slag, then the mixture may be heated or sintered to produce cement clinker.

Note: In some embodiments, dewatering processes or separation processes may recover or separate residual salts or impurities. In some embodiments, dewatering processes or separation processes may separate or remove impurities or separate or remove non-alkali or non-alkaline-earth salts or chemicals. For example, the separation of sodium sulfite from acetic acid may separate or remove a portion of impurities, if present, which may comprise chemicals other than sodium sulfite or acetic acid. For example, the separation or recovery or removal of magnesium sulfite may result in the separation of impurities which may comprise chemicals other than magnesium sulfite. For example, in some embodiments, residual magnesium sulfite may be present in the sodium hydroxide, and/or, in some embodiments, at least a portion of the residual magnesium sulfite may be removed or separated or precipitated during, for example, the concentrating of sodium hydroxide, or crystallization of sodium hydroxide, or any combination thereof, if applicable.

Note: Solids, or liquids, or solutions, or suspensions, or solid-liquid mixtures, or any combination thereof may be transported by, for example, including, but not limited to, one or more or any combination of the following: vehicle, or truck, or train, or watercraft, or aircraft, or pipeline, or conveyor belt, or barge, or riser pipe, or air, or dispersion, or buoyancy, or passive means, or active means, or rail, or human transport, or animal transport, or transport, or spacecraft, or projectile, or rocket, or car.

Note: In some embodiments, sodium hydroxide solution may be concentrated to specifications for sale or use or transport, which may include, but are not limited to, one or more or any combination of the following: concentrating to greater than 33 weight percent sodium hydroxide, or concentrating to greater than or equal to 50 weight percent sodium hydroxide, or concentrating to greater than or equal to 70 weight percent sodium hydroxide, or crystallizing sodium hydroxide, or removing impurities.

Note: In some embodiments, it may be desirable for the acid to be stronger than carbonic acid and weaker than sulfurous acid. In some embodiments, it may be desirable for the acid to result in the formation of a water soluble alkaline-earth salt. In some embodiments, it may be desirable for the reaction of the acid with an alkaline-earth carbonate to produce a water soluble alkaline-earth salt. In some embodiments, it may be desirable for the reaction of the acid with an alkaline-earth carbonate to produce carbon dioxide gas. In some embodiments, the acid may comprise a carboxylic acid, such as formic acid, or acetic acid, or propanoic acid. In some embodiments, it may be desirable for the acid to be non-volatile, or to possess a vapor pressure lower than or equal to water at room temperature, or any combination thereof.

Note: In some embodiments, $CO_2(g)$ reacted with alkaline earth oxide, or alkaline earth hydroxide, or alkali hydroxide, or any combination thereof may comprise air. For example, in some embodiments, air sourced directly from outside may comprise a concentration of $CO_2$ of about 400-700 PPM. For example, air may comprise a dilute concentration of $CO_2(g)$. For example, air may comprise a $CO_2$ concentration lower than 10 vol %, or a $CO_2$ concentration lower than 1 vol %, or a $CO_2$ partial pressure lower than 0.1 Bar, or a $CO_2$ partial pressure lower than 0.01 Bar, or a $CO_2$ partial pressure lower than 0.001 Bar, or any combination thereof.

Note: In some embodiments, water may be removed, or a salt solution may be concentrated, or water may be evaporated, or a solvent may be evaporated, or a salt may be crystalized or precipitated or solidified, or a salt may be separated, or an acid may be separated, or an acid may be evaporated, or an acid may be removed, or water may be removed, or water may be separated, or any combination thereof, which may employ equipment, which may include, but are not limited to, one or more or any combination of the following: Evaporator, or Multistage Flash (MSF), or Multi-Effect Distillation (MED), or Mechanical Vapor Compression (MVC), or Electrodialysis (ED/EDR), or bipolar membrane electrodialysis, or membrane capacitive deionization (MCDI), or electrodeionization (EDI), or Forward Osmosis (FO), or Membrane Distillation (MD), or Distillation, or Reverse Osmosis, or Osmotically Assisted Reverse Osmosis, or Falling Film Evaporator, or Crystallizer, or Steam Evaporator, or Electric Evaporator, or Renewable Energy Powered Evaporator, or Non-Renewable Energy Powered Evaporator, or Heat Pump Heat Source Evaporator, or Waste Heat Evaporator, or Solar Evaporator, or Evaporation Ponds, or solventing-out precipitation, or solvent addition precipitation, or organic solvent addition precipitation, or static crystallization, or falling film crystallization, or suspension crystallization, or freeze concentrating, or Fractional Melt Crystallization, or Melt Crystallization, or dynamic melt crystallization, azeotropic rectification, or azeotropic distillation, or extractive distillation, or soluble solvent addition precipitation, or methane hydrate desalination, or gas hydrate water removal, or gas hydrate desalination, or freeze desalination, or cryodesalination, or electrodialysis reversal, or hydrogen production, or microbial desalination, or methane hydrate crystallization, or hydrate formation and decomposition desalination, or hydrate formation and liberation desalination.

Note: Sodium hydroxide may be provided as an example alkali hydroxide. Other alkali hydroxides may be produced instead of or in addition to sodium hydroxide, which may include, but are not limited to, one or more or any combination of the following: lithium hydroxide, or potassium hydroxide, or rubidium hydroxide, or caesium hydroxide.

Note: In some embodiments, sodium hydroxide produced may be further purified to, for example, improve the grade of sodium hydroxide and/or broaden the suitable applications.

Note: In some embodiments, it may be desirable to separate at least a portion of sodium sulfite from at least a portion of acetic acid or other acid. In some embodiments, it may be desirable to employ electrodialysis or electrodialysis reversal for said separation. In some embodiments, it may be desirable to employ reverse osmosis or nanofiltration for said separation. In some embodiments, reverse osmosis or nanofiltration may be employed, wherein the hydration radius of the sodium sulfite may be sufficiently large to be at least partially rejected by a membrane, while the molecular weight or hydration radius of the acid may be sufficiently small to permeate a membrane at least partially. In some embodiments, it may be desirable for the molecular weight or hydration radius of the acid to be smaller than the molecular weight or hydration radius of sodium sulfite, which may potentially include, but are not limited to, one or more or any combination of the following: formic acid, or acetic acid.

Note: In some embodiments, an alkaline earth sulfite, such as calcium sulfite or magnesium sulfite or calcium-magnesium sulfite, may be thermally decomposed or thermally converted into calcium oxide or magnesium oxide, or calcium-magnesium oxide, or clinker, or any combination thereof in, for example, a calciner, or kiln, or any combination thereof. In some embodiments, thermal decomposition or thermal conversion may be conducted using the combustion of a fuel and/or employing the resulting hot combustion gases. In some embodiments, sulfur dioxide, which may be produced from the decomposition of sulfite, may be separated by, for example, including, absorption in water, or reaction with a salt, or reaction with an acetate salt, or reaction with a salt comprising an anion which is a derivative of an acid with an acid strength or pKa weaker than the acid strength or pKa of sulfur dioxide or aqueous sulfur dioxide or sulfurous acid or any combination thereof, or cryogenic separation, or condensation, or any combination thereof. In some embodiments, thermal decomposition or thermal conversion may be conducted using conductive heat transfer. In some embodiments, sulfur dioxide may be recovered as a liquid or solid by cooling or cryogenic separation or liquefaction. In some embodiments, sulfur dioxide may be recovered as a liquid or solid by cooling or cryogenic separation or liquefaction, with heat recovery or heat exchange to minimize energy consumption. In some embodiments, thermal decomposition or thermal conversion may be conducted by heating the walls of a kiln. In some embodiments, thermal decomposition or thermal conversion may be conducted using convective heat transfer. In some embodiments, thermal decomposition or thermal conversion may be conducted using radiant heat transfer. In some embodiments, thermal decomposition or thermal conversion may be conducted in a sulfur dioxide atmosphere or an atmosphere comprising sulfur dioxide, wherein the decomposition of sulfite salt may result in the formation of sulfur dioxide and/or wherein sulfur dioxide removed may comprise high concentration or purity sulfur dioxide. In some embodiments, thermal decomposition or thermal conversion may be conducted using indirect heating. In some embodiments, the process may be configured to supply heat from more than one or a combination of heat sources. For example, in some embodiments, the process may be configured to enable an operator to switch and/or mix heat or fuel or energy sources as desired, due to, for example, including, but not limited to, one or more or any combination of the following: process economics, availability of energy sources, or cost of energy sources, or operational state of equipment, or maintenance schedule, or time of day, or availability of personnel, or throughput of system, or state of operations. Heat or fuel or energy sources may include, but are not limited to, heat or fuel or energy sources described herein, or known in the art, or any combination thereof.

Note: In some embodiments, thermal decomposition or thermal conversion may be conducted using a recirculating carrier gas. In some embodiments, a recirculating carrier gas may comprise a gas other than sulfur dioxide. For example, it may be desirable for the recirculating carrier gas to comprise air. For example, it may be desirable for the recirculating carrier gas to comprise a relative inert gas, such as nitrogen, or argon, or a noble gas. In some embodiments, a recirculating carrier gas comprising at least a portion of a gas other than sulfur dioxide may be desirable due to, for example, lower thermal decomposition temperature requirements, or the ability of the process to recover dilute concentrations of sulfur dioxide due to the relatively high solubility of sulfur dioxide in water in the later recovery of sulfur dioxide, or the ability of the process to recover dilute concentrations of sulfur dioxide due to reaction with a salt or aqueous salt solution which may react with sulfur dioxide, or any combination thereof. In some embodiments, a recirculated carrier gas may be heated using a wide range of heat sources, which may include, but are not limited to, one or more or any combination of the following: electricity, or renewable sourced electricity, or nuclear heat, or solar heat, or nuclear sourced electricity, or hydropower, or heat pump heat, or thermal storage, or geothermal heat, or steam, or lava, or phase change material, or combustible fuel, or combustion, or natural gas, or oil, or coal, or petcoke, or renewable natural gas, or combustion of alcohol, or combustion of a hydrocarbon, or combustion of methanol, or combustion of ammonia, or combustion of hydroxide, or combustion of a nitrogenous chemical, or combustion of sulfur, or combustion of hydrogen sulfide, or sulfide combustion, or sulfide oxidation, or self-reactive combustion, or resistive heating, or radiative heating, or waste heat, or steam, or heat transfer fluid, or reaction of calcium oxide with water, or reaction of magnesium oxide with water, or energy source described herein, or energy source described in the art. In some embodiments, the process may be configured to heat the recirculating carrier gas using thermal storage. For example, a recirculating carrier gas may be heated by passing through or heating exchanging with a thermal storage material, which may include, but is not limited to, one or more or any combination of the following: rocks, or sand, or solid material, or gravel, or porous material, or cement, or concrete, or bricks, or earth, or stone, or metal, or ceramic material, or composite, or phase change material, or molten metal, or molten salt, or salt, or alloy, or multi-component material, or multiphase material, or any combination thereof.

Note: In some embodiments, the alkali sulfate may be produced by, for example, first reacting alkali chloride with sulfuric acid to produce alkali sulfate and/or hydrochloric acid. In some embodiments, the hydrochloric acid may be separated from the alkali sulfate. For example, potassium chloride, such as potassium chloride from potash, may be reacted with sulfuric acid to produce potassium sulfate and/or hydrochloric acid. The hydrochloric acid may be separated from the potassium sulfate. The potassium sulfate may be an input in one or more systems and/or methods for producing alkali hydroxide or alkali carbonate described herein.

Note: In some embodiments, concentrated sodium hydroxide solution may be contacted with or reacted with carbon dioxide or a gas comprising carbon dioxide, which may result in the formation of $Na_2CO_3(s)$ precipitate. In some embodiments, the $Na_2CO_3$(s) precipitate may be separated from the remaining solution using, for example, a solid-liquid separation. In some embodiments, the $Na_2CO_3$ (s) precipitate may be separated using a decanter. In some embodiments, the $Na_2CO_3$(s) precipitate may be removed while NaOH may be added to make up for sodium removed due to the removal of $Na_2CO_3$(s). In some embodiments, the $Na_2CO_3$(s) precipitate may be separated from the remaining solution and NaOH may be added to the remaining solution.

Note: In some embodiments, calcium hydroxide suspension, such as milk of lime, may comprise the $Ca(OH)_2$(s or aq).

Note: In some embodiments, magnesium hydroxide suspension, such as milk of magnesia, may comprise the $Mg(OH)_2$(s or aq).

Note: In some embodiments, calcium hydroxide suspension may be contacted with carbon dioxide or a gas comprising carbon dioxide, which may result in the formation of calcium carbonate or calcium carbonate solid. In some embodiments, calcium carbonate may precipitate from the suspension and/or may settle and/or may be separated from remaining calcium hydroxide suspension, if any.

Note: In some embodiments, magnesium hydroxide suspension may be contacted with carbon dioxide or a gas comprising carbon dioxide, which may result in the formation of magnesium carbonate or magnesium carbonate solid. In some embodiments, magnesium carbonate may precipitate from the suspension and/or may settle and/or may be separated from remaining magnesium hydroxide suspension, if any.

Note: In some embodiments, it may be desirable for the alkaline earth-acid salt resulting from the reaction of alkaline earth-weak acid material with an acid to have a solubility in water greater than or equal to one or more or any combination of the following: 1 g/100 mL, or 3 g/100 mL, or 5 g/100 mL, or 7 g/100 mL, or 10 g/100 mL, or 15 g/100 mL, or 20 g/100 mL, or 25 g/100 mL, or 30 g/100 mL.

Note: In some embodiments, the reaction of an alkaline-earth carbonate with an acid, which may result in the formation of carbon dioxide gas, may be conducted in a batch configuration. For example, a batch configuration may enable production of greater partial pressure of carbon dioxide, which may enable easier $CO_2$ transport or lower energy consumption $CO_2$ compression, or liquefaction, or formation of supercritical $CO_2$, or any combination thereof, if desired.

For example:

Calcium carbonate may be added to a reactor vessel

If desired, at least a portion of air or other gas may be removed from the reactor vessel by, for example, using a vacuum pump.

A solution comprising acetic acid may be added to the reactor vessel, which may result in the formation of dissolved calcium acetate solution and carbon dioxide gas. The reactor vessel may pressurize with carbon dioxide to a high partial pressure or high total pressure. A high partial pressure of carbon dioxide may comprise a partial pressure of greater than or equal to one or more or any combination of the following: 0.5 Bar, or 1.0 Bar, or 1.5 Bar, or 2.0 Bar, or 2.5 Bar, or 3.0 Bar, or 4 Bar, or 5 Bar, or 6 Bar, or 7 Bar, or 8 Bar, or 9 Bar, or 10 Bar.

The carbon dioxide may be removed from the reactor vessel, and may undergo compression, or undergo liquefaction, or undergo conversion to a solid, or undergo conversion to a supercritical fluid, or transported, or used in one or more or any combination of applications, or injected underground, or converted into a chemical or fuel, or sequestered, or any combination thereof.

Dissolved calcium acetate solution may be converted into calcium oxide, or calcium hydroxide, or calcium carbonate, or acetic acid, or any combination thereof.

Note: In some embodiments, the reaction of an alkali carbonate or alkali bicarbonate with an acid, which may result in the formation of carbon dioxide gas, may be conducted in a batch configuration. For example, a batch configuration may enable production of greater partial pressure of carbon dioxide, which may enable easier $CO_2$ transport or lower energy consumption $CO_2$ compression, or liquefaction, or formation of supercritical $CO_2$, or any combination thereof, if desired.

For example:

Sodium carbonate may be added to a reactor vessel

If desired, at least a portion of air or other gas may be removed from the reactor vessel by, for example, using a vacuum pump.

A solution comprising acetic acid may be added to the reactor vessel, which may result in the formation of dissolved sodium acetate solution and carbon dioxide gas. The reactor vessel may pressurize with carbon dioxide to a high partial pressure or high total pressure. A high partial pressure of carbon dioxide may comprise a partial pressure of greater than or equal to one or more or any combination of the following: 0.5 Bar, or 1.0 Bar, or 1.5 Bar, or 2.0 Bar, or 2.5 Bar, or 3.0 Bar, or 4 Bar, or 5 Bar, or 6 Bar, or 7 Bar, or 8 Bar, or 9 Bar, or 10 Bar.

The carbon dioxide may be removed from the reactor vessel, and may undergo compression, or undergo liquefaction, or undergo conversion to a solid, or undergo conversion to a supercritical fluid, or transported, or used in one or more or any combination of applications, or injected underground, or converted into a chemical or fuel, or sequestered, or any combination thereof.

Dissolved sodium acetate solution may be converted into sodium hydroxide, or sodium carbonate, or acetic acid, or any combination thereof.

Note: In some embodiments, the reaction of an alkaline-earth carbonate with an acid to produce carbon dioxide or captured carbon dioxide may be conducted in a different location than the location of regenerating the alkaline earth-acid salt into the alkaline earth carbonate and the acid. For example, the alkaline-earth carbonate may be reacted with an acid to produce carbon dioxide or captured carbon dioxide in an application requiring carbon dioxide, such as, for example, including, but not limited to, one or more or any combination of the following: a greenhouse, or a farm, or an algae farm, or a cyanobacteria farm, or a photosynthesis cultivation facility, or a $CO_2$ enhanced oil recovery application, or a bottling facility, or a carbonation application, or a wastewater treatment facility, or a fire retarding system, or a medical application, or a medical facility, or a laboratory facility. The remaining alkaline earth-acid salt solution may be transported to a facility, which may be in a different location, to convert or regenerate the alkaline earth-acid salt into the alkaline earth carbonate and the acid. The regenerated alkaline earth carbonate and the acid may be transported to the application requiring carbon dioxide. Some embodiments may comprise an alternative to transporting liquid $CO_2$, or compressed $CO_2$, or supercritical $CO_2$, or combusting fossil fuels, or any combination thereof as a $CO_2$ source for applications requiring a supply of $CO_2$.

Note: In some embodiments, it may be desirable to prevent or minimize the formation of calcium sulfate from calcium sulfite, or sodium sulfate from sodium sulfite, or the oxidation of calcium sulfite to calcium sulfate, or oxidation of sodium sulfite to sodium sulfate, or any combination thereof.

For example, calcium sulfite or sodium sulfite may react with dissolved oxygen to form calcium sulfate or sodium sulfate. In the presence of water, it may be desirable to minimize the concentration of oxygen or the presence of oxygen to prevent or minimize the oxidation of calcium sulfite or sodium sulfite to calcium sulfate or sodium sulfite. In some embodiments, a portion of oxygen may be removed by oxygen removal methods, which may include, but is not limited to, one or more or any combination of the following: catalytic oxidation, or catalytic oxygen removal, or oxygen scavenger, or inert gas, or contact with low oxygen concentration gas, or nitrogen purging, or any combination thereof. In some embodiments, oxygen removal or dissolved oxygen removal may be conducted before contact with calcium sulfite or sodium sulfite.

For example, calcium sulfite may react with gaseous oxygen. In some embodiments, it may be desirable to minimize the concentration, or presence, or contact time, or any combination thereof of calcium sulfite with gaseous oxygen or diatomic oxygen. For example, it may be desirable to decompose calcium sulfite in the presence of an oxygen depleted gas, or an inert gas, or a non-oxygen gas, or any combination thereof. For example, it may be desirable to decompose calcium sulfite in the presence of a gas with a diatomic oxygen concentration lower than 21 volume percent. For example, in some embodiments, it may be desirable to pre-heat calcium sulfite in the presence of an oxygen depleted gas, or an inert gas, or a non-oxygen gas, or any combination thereof.

Note: In some embodiments, it may be desirable to decompose alkaline earth sulfite under conditions to facilitate formation of alkaline earth oxide and sulfur dioxide. Under some conditions, calcium sulfite may decompose or chemically convert into calcium sulfate, or calcium sulfide, or any combination thereof. It may be desirable to carefully control the temperature to facilitate the formation of calcium oxide and sulfur dioxide from calcium sulfite. For example, in some embodiments, it may be desirable to decompose calcium sulfite at a temperature lower than 600 degrees Celsius, or lower than 680 degrees Celsius, or any combination thereof. For example, in some embodiments, it may be desirable to decompose calcium sulfite at a temperature lower than 680 degrees Celsius in the presence of carbon dioxide gas. For example, in some embodiments, it may be desirable to decompose calcium sulfite at a temperature lower than 680 degrees Celsius in the presence of an inert gas. For example, in some embodiments, it may be desirable to decompose calcium sulfite at a temperature greater than 780 degrees Celsius. For example, in some embodiments, it may be desirable to decompose calcium sulfite at a temperature greater than 780 degrees Celsius in the presence of carbon dioxide gas. For example, in some embodiments, it may be desirable to decompose calcium sulfite at a temperature greater than 780 degrees Celsius in the presence of an inert gas. For example, in some embodiments, it may be desirable to decompose calcium sulfite in a low pressure environment, or an environment with a pressure lower than atmospheric pressure, or a vacuum, or any combination thereof. For example, in some embodiments, it may be desirable to decompose calcium sulfite in a high pressure environment, or an environment with a pressure greater than atmospheric pressure, or any combination thereof. For example, in some embodiments, it may be desirable to decompose calcium sulfite in an environment with a pressure about the same as atmospheric pressure, or atmospheric pressure +/−30%, or any combination thereof.

If a portion of calcium sulfate, or calcium sulfide, or any combination thereof are produced, it may be desirable to employ systems and/or methods for recovering or separating calcium sulfate or calcium sulfide. For example, a material comprising calcium oxide, or calcium sulfate, or calcium sulfide, or any combination thereof may be separated by contacting with acetic acid, which may result in calcium oxide reacting with the acetic acid to produce dissolved calcium acetate, the calcium sulfide reacting with the acetic acid to produce dissolved calcium acetate and/or hydrogen sulfide (which may be dissolved or gaseous), and the calcium sulfate remaining mostly at a solid phase unreacted. The calcium sulfate may be separated by a solid-liquid separation, while the calcium acetate may be converted into calcium sulfite, or calcium oxide, or calcium hydroxide, or acetic acid, or any combination thereof using, for example, one or more or any combination of systems or methods described herein.

In some embodiments, calcium sulfite or magnesium sulfite may be decomposed in the presence of a gas, such as a combustion gas, or a carrier gas, or kiln gas, or any combination thereof. In some embodiments, the combustion gas, or a carrier gas, or kiln gas, or any combination thereof may comprise carbon dioxide. For example, the combustion gas, or a carrier gas, or kiln gas, or any combination thereof may comprise greater than or equal to 1%, or 2%, or 3%, or 4%, or 5%, or 10%, or 15%, or 20%, or 25%, or 30%, or 35%, or 40%, or 45%, or 50%, or 55%, or 60%, or 65%, or 70%, or 75%, or 80%, or 85%, or 90%, or 95%, or 99%, or any combination thereof by volume carbon dioxide. In some embodiments, it may be desirable for carbon dioxide to be present because, under some conditions in some embodiments, the presence of carbon dioxide may prevent, or inhibit the formation of calcium sulfate, or calcium sulfide, or elemental sulfur, or any combination thereof during the decomposition of calcium sulfite. In some embodiments, calcium sulfite may react with carbon dioxide to form calcium carbonate and sulfur dioxide, or calcium sulfite may decompose into calcium oxide and sulfur dioxide, or calcium carbonate may decompose into calcium oxide and carbon dioxide, or any combination thereof. In some embodiments, it may be desirable to heat calcium sulfite in the presence of a gas comprising a high partial pressure of carbon dioxide, which may result in an equilibrium wherein calcium sulfite may decompose into sulfur dioxide at a lower temperature than the decomposition temperature of calcium carbonate, which may result in the formation of calcium carbonate and sulfur dioxide before or simultaneous to the decomposition of calcium carbonate into calcium oxide. A high partial pressure of carbon dioxide may comprise a partial pressure of carbon dioxide gas greater than or equal to, including, but not limited to, one or more or any combination of the following: 0.01 Bar, or 0.05 Bar, or 0.1 Bar, or 0.2 Bar, or 0.3 Bar, or 0.4 Bar, or 0.5 Bar, or 0.6 Bar, or 0.7 Bar, or 0.8 Bar, or 0.9 Bar, or 1.0 Bar, or 1.5 Bar, or 2 Bar, or 2.5 Bar, or 3.0 Bar, or 3.5 Bar, or 4.0 Bar, or 4.5 Bar, or 5.0 Bar. In some embodiments, calcium sulfite may be heated in the presence of a high partial pressure of carbon dioxide in a first reactor, or a first portion of a reactor, or any combination thereof, forming calcium carbonate and sulfur dioxide gas, then the formed calcium carbonate may be decomposed into calcium oxide and carbon dioxide in a second reactor, or a second portion of a reactor, or any combination thereof at a higher temperature, or at a lower $CO_2$ partial pressure, or any combination thereof.

In some embodiments, alkaline earth losses may occur, due to, for example, including but not limited to, losses due to the formation of alkaline-earth sulfate. In some embodiments, makeup alkaline earth may be added to replenish alkaline earth in the process. For example, alkaline earth may be added as, for example, including, but not limited to, one or more or any combination of the following: alkaline-earth weak acid, or calcium oxide, or calcium hydroxide, or calcium carbonate, or calcium sulfite, or calcium sulfite, or calcium-carboxylic acid anion, or magnesium oxide, or magnesium hydroxide, or magnesium carbonate, or magnesium sulfite, or magnesium sulfite, or magnesium-carboxylic acid anion, or any combination thereof.

Note: For example, calcium oxide or calcium hydroxide may be recovered or recycled or utilized from a material comprising calcium oxide or calcium hydroxide and a high concentration of calcium sulfate or a high concentration of calcium sulfate contamination by, for example, employing said material as an input to the reaction of alkaline earth-weak acid material with an acid. For example, a material comprising calcium oxide or calcium hydroxide and a high concentration of calcium sulfate or a high concentration of calcium sulfate contamination may be reacted with acetic acid. Calcium oxide, or calcium hydroxide, or calcium carbonate, or calcium sulfide, or any combination thereof may react with the acetic acid, forming of an aqueous solution comprising calcium acetate. The calcium sulfate may not react with the acetic acid, which may result in the calcium sulfate mostly remaining at a solid phase. The remaining calcium sulfate solid may be separated from the calcium acetate solution by a solid-liquid separation. The calcium acetate may be employed in one or more or any combination of processes described herein, including, but not limited, producing one or more or any combination of the following: calcium oxide, or calcium hydroxide, or calcium carbonate, or calcium sulfide, or sodium hydroxide, or sodium carbonate, or sodium bicarbonate, or sodium sulfide. The presently described embodiment may be applicable to other alkaline-earths instead of, or in addition to, calcium, which may include, but are not limited to, one or more or any combination of the following: magnesium, or magnesium sulfate, or magnesium oxide, or magnesium hydroxide, or magnesium carbonate, or magnesium sulfide.

Note: In some embodiments, alkali sulfite may be formed. In some embodiments, an alkali bisulfite, or an alkali metabisulfite, or any combination thereof may form in addition to, or instead of, an alkali sulfite. In some embodiments, an alkali bisulfite, or an alkali metabisulfite, or any combination thereof may form in addition to, or instead of, an alkali sulfite, for example, wherein an alkali sulfite is described.

Note: In some embodiments, organic solutions, or organic solvents, or non-water solvents, or non-aqueous solutions, or any combination thereof may be employed instead of, or in addition to, or in a mixture with, or any combination thereof, water or aqueous solutions.

Note: Some embodiments may employ Cascade Reactors, or Cascading Batch Mixing Reactors, or Back-Mix Reactors, or a cascade of well-stirred, jacketed, batch-mix reactors, or any combination thereof. In some embodiments, calcium oxide or calcium hydroxide may be reacted with sodium sulfite to form, for example, at least a portion of calcium sulfite and sodium hydroxide. In some embodiments, calcium oxide or calcium hydroxide may be reacted with sodium sulfite to form, for example, at least a portion of calcium sulfite and sodium hydroxide employing, or using, or within, for example, Cascade Reactors, or Cascading Batch Mixing Reactors, or Back-Mix Reactors, or a cascade of well-stirred, jacketed, batch-mix reactors, or any combination thereof.

Note: In some embodiments, the reaction of sodium sulfite with calcium hydroxide may be conducted at a range of temperatures. In some embodiments, the reaction of sodium sulfite with calcium hydroxide may be conducted in a reactor between 30-70 degrees Celsius. In some embodiments, the reaction of sodium sulfite with calcium hydroxide may be conducted in a reactor between 5-30 degrees Celsius. In some embodiments, the reaction of sodium sulfite with calcium hydroxide may be conducted in a reactor between 2-20 degrees Celsius. In some embodiments, the reaction of sodium sulfite with calcium hydroxide may be conducted in a reactor between 0-100 degrees Celsius.

Note: In some embodiments, calcium oxide or calcium hydroxide may be reacted with sodium sulfite to form, for example, at least a portion of calcium sulfite and sodium hydroxide. In some embodiments, to, for example, facilitate the conversion of sodium sulfite to sodium hydroxide, it may be desirable to react calcium hydroxide with sodium sulfite at a molar ratio wherein calcium hydroxide is at a stoichiometric excess to sodium sulfite. For example, in a stoichiometrically balanced reaction of calcium hydroxide and sodium sulfite with 100% completion, 1 mole of calcium hydroxide may react with 1 mole of sodium sulfite to produce 1 mole of calcium sulfite and 2 moles of sodium hydroxide. For example, to facilitate higher conversion rates of sodium sulfite to sodium hydroxide, it may be desirable to employ a stoichiometric excess of calcium hydroxide in the reaction of calcium hydroxide with sodium sulfite. For example, in some embodiments, it may be desirable to employ a molar ratio of calcium hydroxide to sodium sulfite greater than or equal to 1 in the reaction. For example, it may be desirable to employ a ratio of greater than or equal to one or more or any combination of the following: 0.9 mole of calcium hydroxide:1 mole of sodium sulfite, or 1.0 mole of calcium hydroxide:1 mole of sodium sulfite, or 1.1 mole of calcium hydroxide:1 mole of sodium sulfite, or 1.2 mole of calcium hydroxide:1 mole of sodium sulfite, or 1.3 mole of calcium hydroxide:1 mole of sodium sulfite, or 1.4 mole of calcium hydroxide:1 mole of sodium sulfite, or 1.5 mole of calcium hydroxide:1 mole of sodium sulfite, or 1.6 mole of calcium hydroxide:1 mole of sodium sulfite, or 1.7 mole of calcium hydroxide:1 mole of sodium sulfite, or 1.8 mole of calcium hydroxide:1 mole of sodium sulfite, or 1.9 mole of calcium hydroxide:1 mole of sodium sulfite, or 2 mole of calcium hydroxide:1 mole of sodium sulfite.

Note: In some embodiments, a portion of calcium hydroxide may be present in the calcium sulfite reaction product, or a portion of aqueous calcium hydroxide may be present in the sodium hydroxide reaction product, or a portion of sodium sulfite may be present in the sodium hydroxide reaction product, or a portion of sodium sulfite may be present in the calcium sulfite reaction product, or a portion of sodium hydroxide may be present in the calcium sulfite reaction product.

Note: In some embodiments, a portion of calcium hydroxide may be present in the calcium sulfite reaction product. In some embodiments, it may be desirable for calcium hydroxide in a solid or solid-liquid mixture comprising calcium sulfite to remain in the solid comprising calcium sulfite entering a calciner or thermal decomposition step. In some embodiments, it may be desirable for at least a portion of calcium hydroxide in a solid or solid-liquid mixture comprising calcium sulfite to be separated and/removed before or while the solid comprising calcium sulfite enters a calciner or thermal decomposition step. In some embodiments, a solid comprising calcium sulfite, which may further comprise calcium hydroxide, may be separated from an aqueous solution comprising sodium hydroxide using, for example, a solid-liquid separation system or method, such as, for example, including, but not limited to, one or more or any combination of the following: filter, or rotating filter, or decanter, or centrifuge, or coalescer, or method for destabilizing suspensions, or flocculation, or aggregation, or vibration, Flotation process, or Density gradient centrifugation, or agitation, or centrifugation, or changing temperature, or changing surface tension, or other methods described herein, or solid-liquid separation methods known in the art. In some embodiments, if at least a portion of calcium hydroxide is separated from at least a portion of calcium sulfite, it may be desirable for the separated calcium hydroxide to be transferred or employed as a reactant or a portion of the calcium hydroxide reactant in, for example, the reaction of calcium hydroxide with sodium sulfite. In some embodiments, if at least a portion of calcium hydroxide is separated from at least a portion of calcium sulfite, it may be desirable for the separated calcium hydroxide to be thermally decomposed or calcined into calcium oxide and/or the calcium oxide (and/or calcium hydroxide which may be formed by reacting the formed calcium oxide with water) may be employed as a reactant or a portion of the calcium hydroxide reactant in, for example, the reaction of calcium hydroxide with sodium sulfite. In some embodiments, it may be desirable for a solid comprising calcium sulfite and calcium hydroxide to be calcined or decomposed to form calcium oxide. In some embodiments, it may be desirable to separate at least a portion of calcium hydroxide from at least a portion of calcium sulfite. Example systems and methods for separating calcium sulfite from calcium hydroxide may be described herein.

In some embodiments, a portion of calcium hydroxide may be separated from a portion of calcium sulfite. In some embodiments, a suspension may be formed from a solid comprising calcium hydroxide and calcium sulfite and/or calcium hydroxide and calcium sulfite may exist as a suspension. For example, in some embodiments, calcium hydroxide and/or calcium sulfite in suspension may interact differently to temperature, or agitation, or centrifugation, or vibration, or ultrasound, or light, or temperature differences, or heating, or cooling, or mixing, or other physical interaction or stimuli, or any combination thereof. In some embodiments, a portion of calcium hydroxide and/or calcium sulfite may be separated by triggering or facilitating the coagulation or settling at least a portion of calcium hydroxide relative to calcium sulfite, or calcium sulfite relative to calcium hydroxide by using one or more physical interactions or stimuli.

In some embodiments, a portion of calcium hydroxide may be separated from a portion of calcium sulfite. In some embodiments, a suspension may be formed from a solid comprising calcium hydroxide and calcium sulfite and/or calcium hydroxide and calcium sulfite may exist as a suspension. For example, in some embodiments, a suspension destabilizer or flocculant or clarifying agent or coagulant or other additive chemical, may be added to a suspension comprising calcium hydroxide and calcium sulfite. In some embodiments, either calcium hydroxide or calcium sulfite may coagulate or settle, for example, at different times or at different additive chemical concentrations. In some embodiments, settled or de-suspended solids comprising calcium sulfite may be separated or removed, followed by, for example, the separation of settled or de-suspended solids comprising calcium hydroxide. In some embodiments, after at least a portion of calcium hydroxide and/or calcium sulfite may be separated or removed from solution, a portion of the additive chemical may be recovered. For example, in some embodiments, a portion of the additive chemical may be recovered by reverse osmosis, or nanofiltration, or ultra-filtration, or any combination thereof. For example, in some embodiments, a portion of the additive chemical may be recovered by reverse osmosis, or nanofiltration, or ultra-filtration, or other semi-permeable membrane based process, or other membrane based process, or any combination thereof. In some embodiments, it may be desirable to employ an additive chemical with a molecular weight or hydration radius greater than the molecular weight or hydration radius of calcium hydroxide. For example, in some embodiments, a portion of the additive chemical may be recovered by reverse osmosis, or nanofiltration, or ultra-filtration, or other semi-permeable membrane based process, or other membrane based process, or any combination thereof, for example, wherein the membrane based process may form a concentrate or retentate comprising additive chemical and a permeate comprising water or an aqueous calcium hydroxide solution. In some embodiments, said permeate may be mixed with a solid comprising calcium hydroxide and calcium sulfite to form a suspension and/or said concentrate or retentate may be added to said suspension to selectively destabilize the suspension to separate, for example, at least a portion of calcium hydroxide from at least a portion of calcium sulfite.

In some embodiments, at least a portion of calcium sulfite may be separated from at least a portion of calcium hydroxide by filtration. For example, in some embodiments, the particle size of calcium hydroxide may be different from the particle size of calcium sulfite. In some embodiments, a suspension comprising calcium hydroxide and calcium sulfite may be separated by filtration, wherein a filter may be sufficiently large to allow one solid chemical through at a greater rate or percentage than the other solid chemical.

Other example systems and methods for separating calcium sulfite from calcium hydroxide may be described, for example, elsewhere herein.

Note: In some embodiments, a portion of aqueous calcium hydroxide may be present in the sodium hydroxide reaction product. In some embodiments, it may be desirable for residual dissolved calcium hydroxide, if any, to remain in the product comprising sodium hydroxide. In some embodiments, it may be desirable for at least a portion of residual dissolved calcium hydroxide, if any, to be separated or removed from in the product comprising sodium hydroxide. In some embodiments, at least a portion of residual dissolved calcium hydroxide, if any, may precipitate or crystallize or separate from a solution comprising sodium hydroxide if, for example, the solution comprising sodium hydroxide undergoes at least a portion of concentrating or water removal. For example, in some embodiments, at least a portion of any dissolved calcium hydroxide in a solution comprising sodium hydroxide may precipitate during water removal due to, for example, the significantly lower solubility of calcium hydroxide in water than sodium hydroxide and/or the decrease in solubility of calcium hydroxide with an increase in temperature. For example, in some embodiments, at least a portion of any dissolved calcium hydroxide in a solution comprising sodium hydroxide may be removed or separated by adding or absorbing carbon dioxide or sulfur dioxide, which may result in the precipitation of calcium carbonate or calcium sulfite due to, for example, the lower solubility of calcium carbonate and/or calcium sulfite in water than calcium hydroxide and/or propensity for calcium hydroxide to form calcium carbonate or calcium sulfite in the presence of carbon dioxide or sulfur dioxide relative to sodium hydroxide in the presence of sodium hydroxide. If carbon dioxide or sulfur dioxide are added, it may be desirable for the amount of added to be at a stoichiometric ratio to the concentration of calcium hydroxide, to, for example, minimize or prevent any substantial potential undesired contamination or formation, or additional contamination or formation, of sodium carbonate or sodium sulfite or sodium sulfate in the product comprising sodium hydroxide.

Note: In some embodiments, a portion of sodium sulfite may be present in the sodium hydroxide reaction product. In some embodiments, it may be desirable for residual dissolved sodium sulfite, if any, to remain in the product comprising sodium hydroxide. In some embodiments, it may be desirable for at least a portion of residual dissolved sodium sulfite, if any, to be separated or removed from in the product comprising sodium hydroxide. In some embodiments, at least a portion of residual dissolved sodium sulfite, if any, may precipitate or crystallize or separate from a solution comprising sodium hydroxide if, for example, the solution comprising sodium hydroxide undergoes at least a portion of concentrating or water removal. For example, in some embodiments, at least a portion of any dissolved sodium sulfite in a solution comprising sodium hydroxide may precipitate during water removal due to, for example, the significantly lower solubility of sodium sulfite in water than sodium hydroxide. For example, in some embodiments, at least a portion of any dissolved sodium sulfite in a solution comprising sodium hydroxide may be separated or removed by adding oxygen or diatomic oxygen or otherwise oxidizing the residual dissolved sodium sulfite to form sodium sulfate. For example, in some embodiments, at least a portion of sodium sulfate, if any, may precipitate if, for example, the solution is cooled or at a cool temperature, due to, for example, the significant decrease in solubility of sodium sulfate with decreasing temperature, especially in decreasing temperature between 35 degrees Celsius to 0 degrees Celsius, and/or the significantly lower solubility of sodium sulfate in water than sodium hydroxide.

Note: In some embodiments, a portion of sodium sulfite may be present in the calcium sulfite reaction product. For example, in some embodiments, it may be desirable to separate at least a portion of residual sodium sulfite, if any, in calcium sulfite reaction product. For example, in some embodiments, at least a portion of residual sodium sulfite, if any, may be removed or separated from calcium sulfite reaction product by washing the calcium sulfite reaction product, due to, for example, the significantly greater solubility in water of sodium sulfite relative to calcium sulfite. In some embodiments, it may be desirable for any washing solution to have a low concentration or minimized concentration of dissolved oxygen to, for example, prevent the oxidation of sulfite to sulfate. In some embodiments, it may be desirable for any drying of calcium sulfite to be conducted with minimal or minimized or reduced presence to diatomic oxygen or dissolved oxygen, to, for example, prevent the oxidation of sulfite to sulfate.

Note: In some embodiments, a portion of sodium hydroxide may be present in the calcium sulfite reaction product. For example, in some embodiments, it may be desirable to separate at least a portion of residual sodium hydroxide, if any, in calcium sulfite reaction product. For example, in some embodiments, at least a portion of residual sodium hydroxide, if any, may be removed or separated from calcium sulfite reaction product by washing the calcium sulfite reaction product, due to, for example, the significantly greater solubility in water of sodium hydroxide relative to calcium sulfite. In some embodiments, it may be desirable for any washing solution to have a low concentration or minimized concentration of dissolved oxygen to, for example, prevent the oxidation of sulfite to sulfate. In some embodiments, it may be desirable for any drying of calcium sulfite to be conducted with minimal or minimized or reduced presence to diatomic oxygen or dissolved oxygen, to, for example, prevent the oxidation of sulfite to sulfate.

Note: In some embodiments, calcium hydroxide employed in the reaction with sodium sulfite may comprise a solid, or a solid-liquid suspension, or an aqueous solution, or any combination thereof. In some embodiments, sodium sulfite employed in the reaction with calcium hydroxide may comprise an aqueous solution. In some embodiments, sodium sulfite employed in the reaction with calcium hydroxide may comprise an aqueous solution, or a solid, or a solid-liquid suspension, or any combination thereof.

Note: In some embodiments, calcium oxide or calcium hydroxide may be reacted with sodium sulfite to form, for example, at least a portion of calcium sulfite and sodium hydroxide. In some embodiments, in the reaction of calcium hydroxide with sodium sulfite, the concentration of sodium sulfite may have a significant influence on the reaction rate and/or conversion rate or efficiency. For example, the activity coefficient of sodium sulfite, or sulfite, may have a relationship with the concentration of sodium sulfite or sulfite in an aqueous solution. For example, in some embodiments, the reaction rate or reaction efficiency may increase with increasing concentration of sodium sulfite to a concentration or concentration range and/or the reaction rate or reaction efficiency may decrease with increasing concentration of sodium sulfite above a concentration or concentration range. For example, in some embodiments, the reaction rate may decrease with increasing concentration of sodium sulfite. For example, in some embodiments, the equilibrium constant may decrease with increasing concentration from a concentration of 0.5 moles sodium sulfite per 50 moles of water to a concentration of 1 mole sodium sulfite per 50 moles of water. In some embodiments, the reaction of sodium sulfite with calcium hydroxide may comprise an equilibrium reaction. In some embodiments, it may be desirable to employ stoichiometric excess of calcium hydroxide relative to sodium sulfite in the reaction of calcium hydroxide with sodium sulfite to, for example, facilitate the reaction, or to increase or facilitate conversion or conversion efficiency of sodium sulfite to sodium hydroxide, or any combination thereof. In some embodiments, it may be desirable to employ a sodium sulfite concentration less than or equal to 1 mole of sodium sulfite per kilogram of water. In some embodiments, it may be desirable to employ a sodium sulfite concentration in the reaction of calcium hydroxide with sodium sulfite of less than or equal to, one or more or any combination of the following: 0.25M, or 0.5M, or 0.75M, or 1M, or 1.5M, or 2M, or 2.5M, or 3M.

Note: In some embodiments, calcium oxide or calcium hydroxide may be reacted with sodium sulfite to form, for example, at least a portion of calcium sulfite and sodium hydroxide. In some embodiments, hydroxide ion activity may increase with increasing concentration and/or sulfite ion activity may decrease with increasing concentration.

Note: In some bench-scale experiments, the following conditions may be beneficial for the reaction of sodium sulfite and calcium hydroxide:

Feed Ratio (Sodium Sulfite:Calcium Hydroxide): 0.59 (i.e. stoichiometrically more Calcium Hydroxide relative to Sodium Sulfite)

Reaction Temperature: 14° C.

Reaction Time: 31 minutes

Conversion Efficiency of Sodium Sulfite to Sodium Hydroxide: 95%

Note: In some embodiments, the reaction time for the reaction of sodium sulfite with calcium hydroxide may vary. In some embodiments, the reaction time may occur in stages. In some embodiments, the reaction time or reaction time to completion or residence time may be greater than, or equal to, or less than, or any combination thereof one or more or any combination of the following: 1 minute, or 5 minutes, or 10 minutes, or 15 minutes, or 20 minutes, or 25 minutes, or 30 minutes, or 35 minutes, or 40 minutes, or 45 minutes, or 50 minutes, or 55 minutes, or 60 minutes, or 1.1 hours, or 1.2 hours, or 1.3 hours, or 1.4 hours, or 1.5 hours, or 1.6 hours, or 1.7 hours, or 1.8 hours, or 1.9 hours, or 2 hours, or 2.5 hours, or 3 hours, or 4 hours, or 5 hours, or 6 hours, or 7 hours, or 8 hours, or 9 hours, or 10 hours.

Note: In some embodiments, calcium oxide or calcium hydroxide may be reacted with sodium sulfite to form, for example, at least a portion of calcium sulfite and sodium hydroxide. In some experiments, in the reaction of calcium hydroxide with sodium sulfite, the conversion efficiency of sodium sulfite to sodium hydroxide increased with a sodium sulfite:calcium hydroxide feed ratio from 0.05 to 0.588. In some experiments, the highest regeneration efficiency was achieved at a sodium sulfite:calcium hydroxide 0.588 feed ratio. In some experiments, conversion efficiency of sodium sulfite to sodium hydroxide decreased with a sodium sulfite calcium hydroxide feed ratio above 0.588. A possible explanation is the activity coefficient of calcium hydroxide may remain relatively unchanged with concentration in the suspension because of calcium hydroxide's low solubility, however the activity coefficient of the sodium sulfite or sulfite may decrease with increasing concentration above a certain concentration or concentration range.

Note: In some embodiments, calcium oxide or calcium hydroxide may be reacted with sodium sulfite to form, for example, at least a portion of calcium sulfite and sodium hydroxide. In some embodiments, lower reaction temperatures may be desired. A possible explanation may be that the activity coefficient of sulfite may decrease with increasing temperature, thus lower temperatures may have a higher activity coefficient, which may be more favorable. In some embodiments, hydroxide activity coefficient may remain constant with temperature. Thus, for example, the equilibrium ratio (and/or thus the reaction efficiency) may decrease with increasing temperature. A possible explanation may be the The Gibbs Free Energy of the reaction of sodium sulfite and calcium hydroxide may be exothermic. The reaction of sodium sulfite and calcium hydroxide may have an enthalpy of reaction or heat of reaction of −2.535 kJ/mol. For example, at higher temperatures or if temperatures are increased, the reaction may become less favorable because, for example, the enthalpy change of reaction may become more positive. In some embodiments, it may be desirable for the reactor or reaction to be temperature controlled and/or cooled to, for example, maintain an optimal reaction temperature.

Note: In some embodiments, calcium oxide or calcium hydroxide may be reacted with sodium sulfite to form, for example, at least a portion of calcium sulfite and sodium hydroxide. In some experiments, the reaction efficiency of sodium sulfite to sodium hydroxide in the reaction of sodium sulfite with calcium hydroxide increased with reaction time from 5 minutes to 31.45 minutes. During an experiment, after 31.45 minutes, the reaction efficiency did not appreciably further increase.

Note: In some embodiments, calcium oxide or calcium hydroxide may be reacted with sodium sulfite to form, for example, at least a portion of calcium sulfite and sodium hydroxide. In some experiments, the reaction efficiency of sodium sulfite to sodium hydroxide in the reaction of sodium sulfite with calcium hydroxide may have been appreciably impacted by the presence of significant calcium sulfite in the lime or calcium hydroxide feed. For example, in some experiments, significant presence of calcium sulfite in the calcium hydroxide feed may have reduced reaction efficiency by 33.66%. In some embodiments, it may be desirable to separate reaction products or solid reaction products comprising calcium hydroxide and/or calcium sulfite. In some embodiments, it may be desirable to separate solid reaction products comprising calcium sulfite. In some embodiments, it may be desirable to separation solid reaction products or solids present from a solution comprising sodium hydroxide. In some embodiments, it may be desirable to separate a solid comprising calcium sulfite and/or calcium hydroxide from a solution comprising sodium hydroxide. In some embodiments, it may be desirable to separate calcium hydroxide from calcium sulfite. In some embodiments, it may be desirable to convert calcium sulfite and/or calcium hydroxide into calcium oxide.

For example, in some embodiments, at least a portion of calcium sulfite may be separated or further separated from calcium hydroxide. In some embodiments, at least a portion of the separated calcium hydroxide may be transferred and/or mixed with calcium hydroxide (lime) feed, or may comprise a portion of calcium hydroxide feed, or any combination thereof for, for example, the reaction of sodium sulfite with calcium hydroxide. In some embodiments, at least a portion of separate calcium sulfite may be thermally decomposed or calcined into at least a portion of calcium oxide and sulfur dioxide.

For example, in some embodiments, at least a portion of calcium sulfite may be separated or further separated from calcium hydroxide. For example, in some embodiments, at least a portion of calcium sulfite may be separated or further separated from calcium hydroxide using one or more or any combination of systems and/or methods. For example, in some embodiments, calcium hydroxide may have a greater affinity to forming a suspension than calcium sulfite. In some embodiments, a portion of calcium hydroxide may be separated from a portion of calcium sulfite by forming a suspension comprising calcium hydroxide while, for example, forming a settled solid comprising calcium sulfite. In some embodiments, a portion of calcium hydroxide may be separated from a portion of calcium sulfite by forming a suspension comprising calcium hydroxide, and/or adding or removing flocculants, or emulsifiers, or dispersants, or any combination thereof. In some embodiments, a portion of calcium hydroxide may be separated from a portion of calcium sulfite by adding or removing, including, but not limited to, one or more or any combination of the following: flocculants, or emulsifiers, or dispersants, or any combination thereof. In some embodiments, a portion of calcium hydroxide may be separated from a portion of calcium sulfite by centrifuging a slurry or material comprising calcium sulfite and calcium hydroxide and/or separating settled solid, which may comprise a greater concentration of, for example, calcium sulfite. For example, in some embodiments, calcium hydroxide may have a different density than calcium sulfite. For example, calcium sulfite may have a greater density than calcium hydroxide. In some embodiments, calcium sulfite may be separated from calcium hydroxide by systems or methods for separating utilizing density differences. For example, in some embodiments, at least a portion of calcium sulfite may be separated from at least a portion of calcium hydroxide by including, but not limited to, one or more or any combination of the following: centrifuging, or decanting, or gravitational separation, or coalescing, or gravitational separation facilitated by a high density liquid, or density based separation facilitated by a high density liquid, or density based separation facilitated by a high density liquid with a density greater than the density of calcium hydroxide and less than the density of calcium sulfite, or any combination thereof. For example, calcium hydroxide may possess a greater solubility in water than calcium sulfite. In some embodiments, the difference in solubility between calcium hydroxide and/or calcium hydroxide may be utilized, to, for example, separate at least a portion of calcium sulfite from calcium hydroxide. In some embodiments, the difference in solubility between calcium hydroxide and/or calcium hydroxide may be utilized to separate at least a portion of calcium sulfite from at least a portion of calcium hydroxide. For example, in some embodiments, a material comprising calcium hydroxide and calcium sulfite may be mixed with or washed with water, which may result in the dissolution of at least a portion of calcium hydroxide, while at least a portion of the calcium sulfite remains a solid. In some embodiments, the solid comprising calcium sulfite may be transferred to, for example, a thermal decomposition process. In some embodiments, calcium hydroxide may be separated from an aqueous solution comprising calcium hydroxide by, for example, utilizing the solubility properties of calcium hydroxide. For example, calcium hydroxide solubility may significantly decrease with increasing temperature. In some embodiments, water employed in washing a mixture comprising calcium hydroxide and/or calcium sulfite to dissolve at least a portion of calcium hydroxide may comprise cold water to promote, for example, dissolution of calcium hydroxide, and/or enable a higher solubility of calcium hydroxide. In some embodiments, cold water may comprise water at a temperature lower than the temperature of warm water or a warm solution and/or may comprise water at a temperature less than or equal to 50° C., or 40° C., or 30° C., or 20° C., or 15° C., or 10° C., or 5° C., or 1° C. In some embodiments, a cold solution comprising calcium hydroxide may be treated to produce separated calcium hydroxide solid using, for example, including, but not limited to, one or more or any combination of the following: heating precipitation, or heating precipitation by increasing solution temperature to trigger the precipitation of at least a portion of calcium hydroxide, or filtration, or reverse osmosis, or electrodialysis, or concentrating while solution is at a lower temperature, or concentrating remaining aqueous solution after precipitation, or concentrating remaining aqueous solution after heating precipitation at a lower temperature using reverse osmosis, or concentrating remaining aqueous solution after heating precipitation at a lower temperature using electrodialysis, or concentrating remaining aqueous solution after heating precipitation at a lower temperature then employing the permeate or diluate as cold water for dissolving calcium hydroxide and/or then employing the concentrate for further precipitation or separation of calcium hydroxide and/or mixing the concentrate with other solution comprising calcium hydroxide undergoing calcium hydroxide separation or precipitation, or any combination thereof. In some embodiments, at least a portion of the separation of calcium hydroxide from calcium sulfite may comprise cake washing or filter cake washing.

For example, in some embodiments, a solid comprising calcium sulfite and/or calcium hydroxide may be decomposed or thermally decomposed or calcined. In some embodiments, said decomposing may comprise dehydration or liberation of water. In some embodiments, said decomposing may comprise forming sulfur dioxide. In some embodiments, said decomposing may comprise forming calcium oxide or alkaline earth oxide. In some embodiments, a solid comprising calcium sulfite and calcium hydroxide may undergo decomposing. In some embodiments, a multi-stage calciner may be employed. In some embodiments, a multi-stage calciner may be employed, wherein an earlier stage is heated to a lower temperature to, for example, enable the decomposition of calcium hydroxide to calcium oxide, which may occur at a lower temperature than the decomposition of calcium sulfite to calcium oxide. In some embodiments, a multi-stage calciner may be employed, wherein an earlier stage is heated to a lower temperature to, for example, enable the decomposition of calcium hydroxide to calcium oxide, which may occur at a temperature, for example, above about 580 degrees Celsius, and/or wherein a later stage is heated to a higher temperature for the decomposition of calcium sulfite to at least a portion of calcium oxide and/or sulfur dioxide, which may occur at, for example, a temperature above about 780 degrees Celsius. It may be desirable for the gases comprising sulfur dioxide produced by or exiting from the later stage to be separate from the earlier stage, to, for example, prevent or minimize the potential reaction of sulfur dioxide with calcium hydroxide or calcium oxide in the earlier stage. It may be desirable to configure the system or method such that the gases comprising sulfur dioxide produced by or exiting from the later stage may be at least partially isolated from the earlier stage, to, for example, prevent or minimize the potential reaction of sulfur dioxide with calcium hydroxide or calcium oxide in, for example, the earlier stage. In some embodiments, heat from the kiln or calcining gases may be recovered.

Note: In some embodiments, aqueous or dissolved calcium hydroxide may be present in the product solution comprising sodium hydroxide. In some embodiments, it may be desirable to separate at least a portion of said calcium hydroxide from at least a portion of said sodium hydroxide. In some embodiments, at least a portion of calcium hydroxide may be separated by, for example, including but not limited to, one or more or any combination of the following: heating precipitation, or precipitation by heating the solution which may reduce the solubility of dissolved calcium hydroxide, or filtration, or centrifugation, or concentrating, or vapor distillation, or during the process of concentrating sodium hydroxide solution, or by addition of a reactant which may induce the precipitation of calcium due to the formation of a lower solubility chemical, or by reacting or contacting with sulfur dioxide to precipitate a portion of calcium sulfite, or by reacting or contacting with carbon dioxide to precipitate a portion of calcium carbonate, or by reacting or contacting with sodium carbonate, or by reacting or contacting with citric acid, or any combination thereof. In some embodiments, it may be desirable to allow residual dissolved calcium hydroxide to remain in the aqueous solution comprising sodium hydroxide. For example, in some embodiments, a solution comprising sodium hydroxide may be employed in $CO_2$ removal, such as, for example, in some embodiments, adding a solution comprising sodium hydroxide to the ocean or a body of water, and/or a solution comprising sodium hydroxide further comprising a portion of dissolved calcium hydroxide may be beneficial.

Note: In some embodiments, at least a portion of magnesium hydroxide may reacted with sodium sulfite to form, for example, at least a portion of sodium hydroxide and magnesium sulfite. In some embodiments, if magnesium hydroxide is employed, the resulting magnesium sulfite may be more soluble than the magnesium hydroxide. In some embodiments, the resulting product from the reaction of sodium sulfite(aq) and magnesium hydroxide(s or aq) may comprise an aqueous solution comprising magnesium sulfite and sodium hydroxide. The magnesium sulfite may be separated from the sodium hydroxide in a crystallization or concentrating, or precipitation, or any combination thereof step due to the significantly lower solubility of magnesium sulfite in water than sodium hydroxide's solubility in water. In some embodiments, magnesium may be desirable, for example, because the decomposition of magnesium sulfite to magnesium oxide and sulfur dioxide may be conducted at a lower temperature and/or require less energy than the decomposition of calcium sulfite to calcium oxide and sulfur dioxide. In some embodiments, magnesium may be desirable, for example, because the decomposition of magnesium hydroxide to magnesium oxide and water may be conducted at a lower temperature and/or require less energy than the decomposition of calcium hydroxide to calcium oxide and water.

Note: In some embodiments, for example, at least a portion of the concentrating of the sodium hydroxide may be conducted with, for example, forward osmosis, or osmotically assisted reverse osmosis, or membrane distillation, or vapor pressure difference, or any combination thereof. For example, in some embodiments, sodium sulfite may need to be diluted from a solid phase to an aqueous solution of an optimized concentration for the reaction of calcium hydroxide with sodium sulfite, which may enable the sodium sulfite to be employed as a draw solution to, for example, concentrate sodium hydroxide while diluting the sodium sulfite. For example, in some embodiments, sodium sulfite may comprise a draw solution and/or sodium hydroxide may comprise feed solution, and/or at least a portion of water may transfer or permeate from the solution comprising sodium hydroxide to the solution comprise sodium sulfite. In some embodiments, employing forward osmosis, or osmotically assisted reverse osmosis, or membrane distillation, or vapor pressure difference, or any combination thereof may be desirable to, for example, reduce energy consumption associated with concentrating sodium hydroxide, if, for example, concentrating sodium hydroxide may be desired.

Note: In some embodiments, it may be desirable to minimize or prevent the presence of diatomic oxygen, or dissolved oxygen, or free oxygen, or any combination thereof. In some embodiments, it may be desirable to minimize or prevent the presence of diatomic oxygen, or dissolved oxygen, or free oxygen, or any combination thereof, to, for example, prevent or minimize any undesired oxidation of sulfite to sulfate. For example, in some embodiments, it may be desirable to minimize or prevent the presence of diatomic oxygen, or dissolved oxygen, or free oxygen, or any combination thereof in the formation of sodium sulfite, or in the reaction of sodium sulfite and calcium hydroxide. For example, in some embodiments, including, but not limited to, one or more or any combination of the following may be desirable: reaction vessels or storage vessels or other equipment to employ inert gas atmospheres or headspace, such as nitrogen gas atmospheres or headspace, or to minimize the volume of atmospheres, or to employ systems or methods to remove dissolved oxygen from water, or to minimize or prevent leaks, or to minimize or prevent exposure to ambient air, or employ solid and/or liquid handling equipment with minimal headspace and/or headspace comprising inert gas, or any combination thereof.

Note: In some embodiments, during the reaction of calcium hydroxide and sodium sulfite, a reaction product comprising calcium sulfite may have a smaller crystal or particle diameter.

Note: In some embodiments, it may be desirable to prevent or minimize the presence of diatomic oxygen or dissolved oxygen. For example, in some embodiments, increasing the concentration of sulfate, which may occur if sodium sulfite is oxidized to sodium sulfate, may reduce the reaction rate or inhibit the reaction of calcium hydroxide and sodium sulfite.

Note: In some embodiments, calcium sulfite crystals produced from the reaction of calcium hydroxide and sodium sulfite may be porous and/or may retain water. In some embodiments, calcium sulfite crystals may be relatively fragile and/or may break under pressure. In some embodiments, calcium sulfite crystal may be thixotropic and may tend to become fluid with vibration or stress. In some embodiments, it may be desirable to add a removable flocculant to facilitate coagulation and/or settling of residual calcium hydroxide and/or product calcium sulfite. In some embodiments, calcium sulfite and/or residual calcium hydroxide may be removed by filtration.

Note: In some embodiments, powdered or solid calcium oxide or calcium hydroxide may be added directly to a solution comprising sodium sulfite. For example, in some embodiments, powdered or solid calcium oxide or calcium hydroxide may be transferred into a mixer or reactor vessel comprising sodium sulfite or aqueous sodium sulfite using, for example, a screw feeder. For example, in some embodiments, powdered or solid calcium oxide or calcium hydroxide may be transferred into the first stage reactor, for example, using a screw feeder, wherein the powdered or solid calcium oxide or calcium hydroxide may be reacted with an aqueous solution comprising sodium sulfite.

Note: In some embodiments, oxidation suppressants, such as sodium thiosulfate, may be employed to reduce, or minimize, or prevent oxidation, for example, of sulfite or sulfur dioxide.

Note: In some embodiments, the reaction rate of a reaction between sodium carbonate and calcium hydroxide may be accelerated or promoted by a diluter solution because the reaction is more exothermic at dilute concentrations: For example, in some embodiments, at 25 degrees Celsius, in a dilute solution, the reaction of sodium carbonate and calcium hydroxide may be slightly exothermic, with an enthalpy of reaction of about −5.4 kJ/mol, assuming that calcium hydroxide is crystalline. In concentrated solution, the reaction of sodium carbonate and calcium hydroxide may be slightly endothermic, with a 20 wt % solution having an enthalpy of reaction of +3.05 kJ/mol.

Note: In some embodiments, the reaction of calcium hydroxide and sodium carbonate may be conducted at any temperature. In some embodiments, it may be desirable for the reaction of calcium hydroxide and sodium carbonate to be conducted in a temperature range of 80-100 degrees Celsius to, for example, increase the rate of reaction, or decrease the viscosity of the solution (which may increase the rate of settling of calcium carbonate product), or to prevent the formation of insoluble double salts that may remove some sodium carbonate from the solution, or any combination thereof.

Note: In some embodiments, at above 40 degrees Celsius, anhydrous sodium sulfite may comprise the solid phase of sodium sulfite. In some embodiments, sodium sulfite solid dehydrates at a temperature of about 33 degrees Celsius. In some embodiments, the solubility of sodium sulfite may steeply increase with increasing temperature from about 13.3 g/100 g $H_2O$ at 0 degrees Celsius to 38 g/100 g $H_2O$ at 33 degrees Celsius. In some embodiments, the solubility of sodium sulfite may decrease with increasing temperature from about 38 g/100 g $H_2O$ at 33 degrees Celsius to about 31.7 g/100 g $H_2O$ at 60 degrees Celsius to about 26.3 g/100 g $H_2O$ at 100 degrees Celsius.

Note: In some embodiments, it may be desirable to separate at least a portion of sodium sulfate, if any, from sodium sulfite. In some embodiments, some sodium sulfite may oxidize to sodium sulfate. In some embodiments, it may be desirable to separate at least a portion of sodium sulfate, if any, from the sodium sulfite before transferring the sodium sulfite to the reaction with calcium hydroxide.

Note: In some embodiments, a sulfur dioxide capture system may be employed to recover residual sulfur dioxide, for example, residual sulfur dioxide gas. In some embodiments, a solution comprising sodium acetate or calcium acetate or magnesium acetate may be employed in a sulfur dioxide scrubbing system or method.

Note: In some embodiments, crystallization of a salt from, for example, an aqueous solution may be conducted using, for example, including but not limited to, one or more or any combination of the following: cooling, or evaporation, addition of a second solvent to reduce the solubility of the solute (technique known as antisolvent or drown-out), or solvent layering, or sublimation, or changing the cation or anion.

Note: In some embodiments, sulfur dioxide may be substituted with nitrogen dioxide.

Note: In some embodiments, sulfite may be substituted with nitrite.

Note: In some embodiments, sulfite may be substituted with nitrate.

Note: In some embodiments, one or more embodiments may employ nitrogen oxides, or nitrogen dioxide, or nitrite, or nitrate, or any combination thereof instead of, or in addition to, for example, sulfur oxides, or sulfur dioxide, or sulfite, or any combination thereof. For example, Note: Sources of alkali sulfate may include, but are not limited to, one or more or any combination of the following: mineral, or mining, or byproduct of a chemical production process, or lithium production, or lithium refining, or potassium production, or potassium refining ascorbic acid production, or fertilizer production, or rayon production, or neutralization of excess caustic soda, or neutralization of excess sodium carbonate, or neutralization of excess sodium bicarbonate, or potash production, or reaction of alkali chloride with sulfuric acid, or oxidation of alkali sulfite, or flue gas desulfurization, or desulfurization process, or battery reclamation, or cellulose processing, or processes involving resorcinol, or production of silica pigments, of production of sodium dichromate, or chromate production, or chrome production, or production of chromium chemicals, or production of boric acid, or production of boron, or production of borates, or lithium carbonate production, or pigment manufacturing, or battery recycling, or aluminum production, or ore purification, or ore refining, or recycling, or lithium recycling, or concrete recycling, or acid neutralization, or carboxylic acid production, or citric acid production, or a process for producing alkali sulfate from alkaline earth sulfate and/or alkali chloride, or a process for producing alkali sulfate from alkaline earth sulfate and/or alkali chloride described herein, or ammonium sulfate waste, or ammonia removal, or ammonia recovery, or fertilizer runoff, or runoff, or ocean, or body of water, or brine, or saline aquifer, or produced water, or sulfur recovery, or other sources of alkali sulfate.

Note: Applications of alkali hydroxide production process, or alkali carbonate production process, or alkali bicarbonate production process may include, but are not limited to, one or more or any combination of the following: lithium production, or lithium extraction, or regeneration of sodium hydroxide from sodium sulfate for recycle within a process, or regeneration of sodium carbonate from sodium sulfate for recycle within a process, or paper production, or aluminum refining, or aluminum extraction, or aluminum production, or metal refining, or metal production, or soap manufacturing, or rayon manufacturing, explosives manufacturing, dyestuffs manufacturing, petroleum products production, or ammonia production, or urea production, or fertilizer production, or pH regulation, or wastewater treatment, or carbon dioxide removal, or removing carbon dioxide from the atmosphere, or sequestering carbon dioxide or dissolved carbon dioxide in the ocean, or increasing alkalinity of the ocean, or increasing seawater pH, or counteracting ocean acidification, or preventing local coral bleaching, or accelerating or facilitating shellfish production or yields, or food making, or crude oil treatment, or degreasing metals, or drilling mud additive, or pH regulation, or organic synthesis, or polymer production, or polymer catalysis, or acid gas removal, or acid gas scrubbing, or increase alkalinity in bentonite mud systems, or bleach production, or mining, or ore processing, or lithium extraction, or alkali metal extraction, or lithium brine processing, or evaporation pond processing, or pH enhancement, or capture of carbon dioxide, or production of sodium carbonate, or production of lithium hydroxide, or production of lithium carbonate, or production of magnesium, or production of boron, or ascorbic acid production, or potash production, or potassium hydroxide production, or fertilizer production, or potassium fertilizer production, or drain cleaner, or food production, or toothpaste, or cosmetic products, or antifreeze production, or petrochemical production, or salt production, or additive production, or acid neutralization, or contaminant neutralization, or pulp and paper production, or steel production, or aluminum production, or metal refining, or lithium production, or chemical synthesis, or organic material dissolution, or cellulose dissolution, or rayon production, or textile production, or fiber production.

Note: Some embodiments may comprise recycling sodium carbonate within a lithium production process. For example, some lithium production processes produce lithium sulfate. For example, the production of lithium from the mineral Spodumene may involve sulfuric acid leaching, which may result in the production of lithium sulfate. In some embodiments, lithium sulfate may be reacted with sodium carbonate to produce lithium carbonate and sodium sulfate. In some embodiments, the sodium sulfate may be converted into sodium hydroxide and/or sodium carbonate using, for example, systems and methods described herein.

Note: Some embodiments may involve recycling sodium hydroxide within a lithium production process. For example, some lithium production processes produce lithium sulfate. For example, the production of lithium from the mineral Spodumene may involve sulfuric acid leaching, which may result in the production of lithium sulfate. In some embodiments, lithium sulfate may be reacted with sodium hydroxide to produce lithium hydroxide and sodium sulfate. In some embodiments, at least a portion of sodium sulfate may be separated by cooling precipitation of sodium sulfate in a solution comprising lithium hydroxide. In some embodiments, the sodium sulfate may be converted into sodium hydroxide and/or sodium carbonate using, for example, systems and methods described herein.

Note: Some embodiments may comprise processes for producing lithium hydroxide or lithium carbonate from lithium sulfate. Lithium may comprise an example alkali or alkali metal. For example, in some embodiments a solution comprising lithium sulfate may be mixed with a solution comprising calcium acetate, which may result in the formation of a solution comprising lithium acetate and a solid comprising calcium sulfate. In some embodiments, the aqueous solution comprising lithium acetate may be separated from the solid comprising calcium sulfate. In some embodiments, the lithium acetate may be reacted with sulfur dioxide to produce lithium sulfite and acetic acid. In some embodiments, the lithium sulfite may be separated from the acetic acid. For example, lithium sulfite may be separated from the acetic acid using, including, but not limited to, one or more or any combination of the following: separation systems and methods described herein, or separation systems and methods described in the art, or precipitation, or solubility, or evaporation, or cooling precipitation, or melting, or crystallization, or reverse electrodialysis, or electrodialysis, or reverse osmosis, or nanofiltration, or a membrane based process, or any combination thereof. In some embodiments, acetic acid may be recycled or recirculated or transferred to a reaction between a material comprising an alkaline earth weak acid, such as calcium carbonate or calcium silicate, and acetic acid to produce an alkaline earth acetate, such as calcium acetate. In some embodiments, the lithium sulfite may be reacted with calcium oxide, or calcium hydroxide, or magnesium oxide, or magnesium hydroxide, or other alkaline earth hydroxide, or other alkaline earth oxide, or any combination thereof to form an alkaline earth sulfite and/or lithium hydroxide. In some embodiments, the alkaline earth sulfite may be thermally decomposed into an alkaline earth oxide and sulfur dioxide, and/or the alkaline earth oxide may be reacted with water to form an alkaline earth hydroxide. In some embodiments, the lithium hydroxide may be sold, or undergo further processing, or crystalized, or concentrated, or any combination thereof. In some embodiments, the lithium hydroxide may be reacted with carbon dioxide to form lithium carbonate. In some embodiments, the lithium hydroxide may undergo further reactions, or processing, or purification, or conversion, or any combination thereof. It is important to note that acetic acid may be provided as an example acid, and/or other acids instead of, or in addition to, acetic acid, may be employed. For example, acetic acid may be provided as an example acid with an acid strength greater than, for example, carbonic acid, or silicon acids, or silicate acids, or aqueous hydrogen sulfide, or metal oxide anions, or metal oxide derivatives with acid like behavior, or other 'weak acids' described herein, or any combination thereof and/or an acid strength weaker than sulfurous acid or aqueous sulfur dioxide.

Note: Some embodiments may pertain to a process for producing high purity alkaline earth oxide, or alkaline earth hydroxide, or precipitated alkaline earth carbonate, or any combination thereof from an input material comprising relatively low purity alkaline earth or alkaline earth-weak acid. Low purity alkaline earth or alkaline earth-weak acid may comprise a weight percent concentration of alkaline earth-weak acid of less than or equal to one or more or any combination of the following: 99 wt %, or 95 wt %, or 90 wt %, or 80 wt %, or 70 wt %, or 60 wt %, or 50 wt %, or 40 wt %, or 30 wt %, or 20 wt %, or 10 wt %, or 5 wt %, or 2.5 wt %, or 1 wt %. Low purity alkaline earth or alkaline earth-weak acid may comprise a weight percent concentration of calcium carbonate, or magnesium carbonate, or any combination thereof of less than or equal to one or more or any combination of the following: 99 wt %, or 95 wt %, or 90 wt %, or 80 wt %, or 70 wt %, or 60 wt %, or 50 wt %, or 40 wt %, or 30 wt %, or 20 wt %, or 10 wt %, or 5 wt %, or 2.5 wt %, or 1 wt %.

Note: In some embodiments, it may be desirable to employ carboxylic acids which have one or more or any combination of the following properties.: boiling point greater than 170 degrees Celsius, or do not have a boiling point, or do not have a vapor phase, or any combination thereof. For example, carboxylic acids citric acid and/or ascorbic acid may meet one or more or any combination of the aforementioned properties. In some embodiments, one or more or any combination of said properties may be desirable because, in some embodiments, it may be desirable for the acid or carboxylic acid to remain at a non-vapor phase during evaporation of water and/or, in some embodiments, it may be desirable to avoid acid or carboxylic acid vapor phase from forming or being released into the remaining gases during or after the absorption of sulfur dioxide.

Note: $CO_2$ may be provided as an example acid gas and/or carbonate may be provided as an example anion. Other acid gases may be absorbed or desorbed or displaced instead of, or in addition to, $CO_2$, which may include, but are not limited to, one or more or any combination of the following: hydrogen sulfide, or sulfur dioxide, or sulfur gases, or mercaptans.

Note: In some embodiments, sodium sulfate may be made by reacting sodium chloride with sulfuric acid to produce sodium sulfate and hydrogen chloride or hydrochloric acid. In some embodiments, potassium sulfate may be made by reacting potassium chloride with sulfuric acid to produce potassium sulfate and hydrogen chloride or hydrochloric acid.

Note: Some embodiments may produce sodium sulfate and calcium chloride from phosphogypsum and sodium chloride. In some embodiments, sodium sulfate and calcium chloride may be dissolved or discarded in the ocean, which may enable the disposal of phosphogypsum by converting practically insoluble or low solubility calcium sulfate into highly soluble and potentially relatively ocean environmentally benign sodium sulfate and calcium chloride.

Note: Some embodiments may involve desorbing carbon dioxide by reacting a salt comprising a carbonate, or bicarbonate, or carbon dioxide derivative, or any combination thereof.

Note: Some embodiments may involve desorbing carbon dioxide by reacting a salt comprising a carbonate, or bicarbonate, or carbon dioxide derivative, or any combination thereof with an acid to produce a salt comprising the acid or the anion of the acid and/or carbon dioxide gas. In some embodiments, the salt comprising the acid or the anion of the acid may be converted into a hydroxide salt and acid by, for example, including, but not limited to, one or more or any combination of the following: a process described herein, or reaction with sulfur dioxide or sulfurous acid and regeneration of sulfur dioxide or sulfurous acid, or bipolar membrane electrodialysis, or chloralkali process, or electrochemical process, or any combination thereof. In some embodiments, the hydroxide salt produced may be reacted with carbon dioxide, which may, include, but is not limited to, a gas comprising carbon dioxide, or a carbon dioxide source, or any combination thereof, to, for example, produce a salt comprising a carbonate, or bicarbonate, or carbon dioxide derivative, or any combination thereof.

Note: Some embodiments may comprise recovering or producing high purity alkaline earth oxide, or alkaline earth hydroxide, or alkaline earth salt, or any combination thereof from a raw material comprising a relatively low purity of alkaline earth or alkaline earth salt. For example, some embodiments may comprise recovering or producing high purity calcium oxide, or calcium hydroxide, or magnesium oxide, or magnesium hydroxide, or magnesium salt, or calcium salt, or any combination thereof from raw material comprising a relatively low purity of alkaline earth or alkaline earth salt.

Note: Some embodiments for acid gas separation, such as $CO_2$ capture, may be integrated with the Merox process for extraction and/or removal of mercaptans. For example, sodium hydroxide may be reacted with RSH, such as a mercaptan or such as $CH_3SH$, to form NaSR. For example:

$$2\ RSH+2\ NaOH \rightarrow 2\ NaSR+2\ H_2O$$

In the above reaction, RSH may be, for example, a mercaptan and R may signify, for example, an organic group such as a methyl, ethyl, propyl or other group.

For example, a gas comprising an acid gas or $CO_2$ reacted with a caustic solution, such as sodium hydroxide, may result in the formation of a sodium-acid gas anion salt. In some embodiments, the remaining gas after absorption, if applicable, may comprise mercaptans, which may be further reacted with sodium hydroxide to produce NaSR. In some embodiments, a gas comprising an acid gas or $CO_2$ reacted with a caustic solution, such as sodium hydroxide, and may form a portion of NaSR.

In some embodiments, NaSR may be regenerated by a reaction with an acid which is stronger than the acidity of the mercaptan acid, or stronger than an acid of hydrogen sulfide, or stronger than carbonic acid, or any combination thereof, and/or may form RSH or mercaptan and/or a sodium-acid anion salt.

In some embodiments, NaSR may be regenerated by heating and/or oxidizing the solution comprising NaSR, which may result in the formation of organic disulfides (RSSR) which may comprise liquids that may be water-insoluble. Organic disulfides (RSSR) may be separated and decanted from the aqueous solution.

$$4\ NaSR+O_2+2\ H_2O \rightarrow 2\ RSSR+4\ NaOH$$

Note: Some embodiments may comprise a process for producing sodium sulfate and calcium chloride from gypsum or phosphogypsum, or calcium sulfate, or any combination thereof and sodium chloride.

Note: Some embodiments may comprise a process for producing sodium hydroxide and calcium chloride from gypsum, or phosphogypsum, or calcium sulfate, or any combination thereof and sodium chloride.

Note: 'WA' may comprise a weak acid, which may include, but not limited to, one or more or any combination of the following: silicic acid, or orthosilicic acid, or silicon acid derivatives, or silicon minerals, or silicon acids, or aluminates, or ferrates, or a derivative thereof or a combination thereof.

Note: Calcium or magnesium-weak acid input may comprise, for example, including, but not limited to, one or more or a combination of the following: carbonates, or bicarbonates, or silicates, or silicate derivatives, or minerals, or concrete, or cement, or waste concrete, or waste cement, or steel slag, or fly ash, or ash, or limestone, or rock.

Note: A portion $SO_2$ may desorb during some concentrating processes

Note: $CO_2$ may desorb during some concentration processes

Note: In some embodiments, higher partial pressure $CO_2$, or higher concentration $CO_2$, or pure $CO_2(g)$, or high partial pressure $CO_2(g)$, or $CO_2(1)$, or $CO_2(g)$, may be employed to facilitate formation of bicarbonate salts. For example, in some embodiments, including, but not limited to, one or more or a combination of the following may be employed:

- At least a portion of $CO_2$ input may be sourced from a reaction of calcium carbonate with sulfurous acid
- At least a portion of $CO_2$ input may be sources from $CO_2$ sources produced within the process, or other $CO_2$ sources, or a combination thereof.
- At least a portion of $CO_2$ input may be sourced from $CO_2$ captured from a combustion source, or a combustion source employed to produce heat, or emissions source, or air, or geological $CO_2$ source, or natural $CO_2$ source, or a combination thereof.

Note: $CO_2$ sources may include, but are not limited to, one or more or any combination of the following: Air, or combustion, or emissions gases, or refinery gases, or Power Plant (Natural gas, coal, oil, petcoke, biofuel, municipal waste), Cement production, chemical production, Waste Water Treatment, Landfill gas, Air, Metal production/refining (such as Iron, Steel, Aluminum, etc.), Glass production, Oil refineries, LNG liquification, HVAC, Transportation vehicles (ships, boats, cars, buses, trains, trucks, airplanes), Natural Gas, Biogas, Alcohol fermentation, Volcanic Activity, Decomposing leaves/biomass, Septic tank, Respiration, Manufacturing facilities, Fertilizer production, or Geothermal processes where $CO_2(g)$ is produced.

Note: Some embodiments may be designed to operate as a low temperature process, where the solutions and/or solid reagents in thermal desorption or decomposition may undergo or operate thermal desorption or decomposition at less than, for example, 150° C., or less than 200° C., or less than 250° C., or less than 300° C., or less than 350° C.

Note: In some embodiments, at least a portion of heat may be supplied by a heat pump, or a refrigeration cycle, or a combination thereof. A heat pump may comprise, including, but not limited to, a mechanical, or absorption, or a combination thereof process. A heat pump may be powered by, including, but not limited to, electricity, or heat, or photons, or chemical reaction, or radiation, or mechanical work, or pneumatic process, or hydraulic process, or expansion, or compression, or evaporation, or absorption, or vapor pressure differences, or osmotic pressure differences, or temperature differences, or pressure differences, or a combination thereof.

Note: In some embodiments, heat greater than or equal to 150° C. may be supplied by heat pumps known in the art. Heat pumps may reduce the total energy consumption required to supply heat.

Note: In some embodiments, at least a portion of CO2 may be supplied by a gas stream comprising CO2 and at least one other gas. For example, said gas stream may comprise, including, but not limited to, one or more or a combination of the following: air, flue gas, waste gases, sour gas, or fermentation gases, purge gases, or a combination thereof.

Note: In some embodiments, sulfides and/or hydrogen sulfide may comprise a weak acid or weak acid anion.

Note: Sources of low cost sodium sulfate may possess a higher purity or require less treatment than, for example, common sources of sodium chloride, such as sodium chloride brines. The use of relatively high purity sodium sulfate input may result in lower pre-treatment or purification costs, for example, compared to some sodium chloride input sources.

Note: Dehydrating sodium bicarbonate or sodium carbonate can be energy intensive and may be unnecessary in embodiments where the end application of sodium bicarbonate or sodium carbonate can employ wet or hydrates sodium bicarbonate or sodium carbonate. For example, in embodiments producing sodium bicarbonate or sodium carbonate for applications which are or may be conducted at an aqueous or wet state, it may be desirable to allow the sodium bicarbonate to remain at a hydrated state. In some embodiments, applications which are or may be conducted at an aqueous or wet state may include, but are not limited to, one or more or a combination of the following: water treatment, or water processing, or waste water treatment, or pH balancing, or alkalinization, or sulfur dioxide scrubbing, or nitrogen oxide scrubbing, or acid scrubbing, or addition to ocean water or other water body to increase alkalinity or enable effective CO2 sequestration.

Note: Separations for recovering water, or concentrating, or crystalizing, or precipitating, or separating, or a combination thereof may include, but are not limited to, one or more or a combination of the following: mechanical vapor compression (MVC), or mechanical vapor recompression, or multi-effect distillation (MED), or multi-stage flash distillation (MSF), or vapor compression (VC) distillation, or vacuum vapor compression (VVC), or membrane distillation, or evaporation, or distillation, or forward osmosis, or reverse osmosis, or nanofiltration, or hot nanofiltration, or hot reverse osmosis, or hot concentrating followed by cooling precipitation, or hot concentrating followed by cooling precipitation and solid-liquid separation, or heating precipitation, centrifuge, settling, or filter, or rotary filter, or calcining, or desorption, or absorption, or coalescing, or decanting, or aggregation, or coagulation, or frothing, or density based methods, or surface tension based methods, or foaming separation, emulsification, or de-emulsification, or flocculation, solventing out, or salting out, or cooling precipitation, or heating, or cryodesalination, or freeze desalination, or zero liquid discharge processes, or crystallization processes, or electrodialysis reversal (EDR), or electrodialysis process.

Note: Some embodiments may employ an inert gas, such as nitrogen or argon, or a gas other than diatomic oxygen, such as CO2, or a combination thereof in the headspace to prevent or reduce or minimize, for example, potential oxidation of or reaction of oxygen with sulfite, metabisulfite, bisulfite, sulfur dioxide, sulfurous acid, or a combination thereof.

Note: Potassium or other alkali or alkali salts may be employed instead of or in addition to sodium. Alternatively, or additionally, ammonia, or ammonium, or amine, or a combination thereof may be employed instead of or in addition to sodium. Alternatively, or additionally, zinc may be employed instead of or in addition to sodium or any combination thereof.

Note: Magnesium or other alkaline earth or alkaline earth salts may be employed instead of or in addition to calcium. Alternatively, or additionally, zinc or other metal cation may be employed instead of or in addition to sodium. Zinc can form sulfites, for example.

Note: Concrete waste is produced in excess of 600 million tons annually in the USA alone, which is more than twice the amount of generated municipal solid waste.

Note: In some embodiments, at least a portion of sulfur dioxide may be lost in one or more or a combination of steps. Alternatively, or additionally, sulfur dioxide may be exit the process as a, for example, a residual, in one or more outputs. Sulfur dioxide or 'make-up sulfur dioxide' may be added to the process. In some embodiments, sulfur dioxide may be stored on site and added as desired or needed to the process. In some embodiments, elemental sulfur, or hydrogen sulfide, or a salt comprising sulfur, or sulfide salt, or sulfite salt, or sulfate salt, or a combination thereof may be a source of sulfur dioxide or sulfurous acid or sulfite, which may be formed by, for example, including, but not limited to, one or more or a combination thereof: combustion, or acid-base reaction, or reaction with an acid, or carbothermic reduction, or thermal or decomposition, or electrolysis, or electrodialysis, or electrochemical reaction.

Note: At least a portion of residual calcium sulfate may be removed. For example, a portion of residual dissolved calcium sulfate may precipitate and may be removed by, for example, including, but not limited to, solid-liquid separation, or removal of calcium sulfate scaling, or a combination thereof.

Note: One or more or a combination of steps in one or more embodiments may require heating and/or cooling. Alternatively, or additionally, heat or heating or cooling or a combination thereof may be recovered from one or more or a combination of reaction steps. In some embodiments, heat or heating or cooling or a combination thereof may be recovered and said recovered heat or heating or cooling or a combination thereof may be transferred or employed in one or more other steps, or in the same step, or in other applications.

Note: Losses may occur during the process. Makeup streams of one or more or a combination of reagents may be added.

Note: Contaminants may exist or accumulate in the process. If desired, one or more contaminants may be at least partially removed periodically, or continuously, or as desired, or a combination thereof.

Note: List of example Silicate Minerals which may be employed may include, but are not limited to, silicate minerals or minerals described in the following reference:

Daval, D. Carbon dioxide sequestration through silicate degradation and carbon mineralisation: promises and uncertainties. npj Mater Degrad 2, 11(2018).

Note: Some embodiments may employ waste concrete, or steel slag, or fly ash, or olivine, or any combination thereof as an input.

Note: If non-calcium of non-magnesium metals dissolve or react with $SO_2$ or carboxylic acid, said metals or metal salts may be separated before or after separation of alkaline earth or alkaline. If said non-calcium of non-magnesium metal salts are still dissolved, said non-calcium of non-magnesium salts may be separated by precipitation, or systems and/or methods for zero liquid discharge, or a combination thereof.

Note: In some embodiments, steam may be employed as a stripping or carrier gas. Steam can be condensed after decomposition of one or more reagents. If steam is employed, it must be contacted at a temperature greater than the decomposition temperature of calcium hydroxide. Contact calcium oxide with steam to form calcium hydroxide may enable the reaction of calcium oxide and water to generate higher temperature and/or higher quality heat, which may be employed within one or more reaction steps or may be employed in a different application.

Note: In some embodiments, a kiln with cryogenic separation of SO2 or CO2 from the flue gas or off gases may be employed. For example, in some embodiments, the separated SO2 or CO2 may be employed in one or more or any combination of reaction steps.

Note: Sodium hydroxide solution may be crystallized from solution and sold.

Note: Sodium hydroxide solution may be sold.

Note: Sodium hydroxide solution may be added to the ocean to increase ocean alkalinity and permanently remove CO2 from the atmosphere (two moles of CO2 for each mole of original calcium oxide).

Note Sodium hydroxide solution may be reacted with flue gas and other CO2 emissions, and then sold or employed as sodium carbonate or bicarbonate.

Note: Sodium hydroxide solution may be reacted with CO2 in the air, producing Sodium carbonate. Sodium carbonate may be sold as a valuable product, or added to the ocean to increase ocean alkalinity and permanently remove more CO2 from the atmosphere/ocean, or a combination thereof.

Note: Some embodiments may thermally decompose alkaline earth sulfite in an electric kiln Note: Some embodiments may thermally decompose alkaline earth sulfite in a natural gas, or coal, or waste incinerator, or biofuel, or biomass, or electricity, or oil, or petcoke, or fossil fuel, or charcoal, or solar thermal, or thermal, or any combination thereof powered kiln.

Note: Thermally decompose calcium sulfite using a hydrogen fuels system. Also, green hydrogen can be produced from solar energy and stored, eliminating the challenge of solar intermittency. Alternatively or additionally, hydrogen may be blue hydrogen, or hydrogen from natural gas, where the carbon or CO2 is removed from the natural gas to produce hydrogen before hydrogen is burned. Alternatively, a process may employ a combination of blue hydrogen (during the night) and solar electricity (during the day). Alternatively, some embodiments may employ one or more or any combination of hydrogen types, or hydrogen derivatives, or any combination thereof, for example, as a fuel.

Note: Some embodiments may recover heat form hydrating calcium oxide to calcium hydroxide to provide heat or steam or both for applications requiring heat.

Note: In some embodiments, remaining flue gas after most or all SO2 is removed or recovered or reacted or separated may comprise at least a portion CO2.

Note: Flue gas CO2 may be concentrated with pressure swing absorption or pressure swing adsorption or gas membrane or both, then the flue gas with higher concentrations of CO2 may be employed as a feedstock in some embodiments.

Note: Convert calcium silicate from the Pidgeon process May employ calcium, or magnesium, or alkaline earth, or a combination thereof. Calcium or magnesium or alkaline earth may be substituted.

Note: The weight percent concentration of SO2 in some embodiments or process steps may be greater than or equal to one or more or a combination of the following: 0.001%, or 0.1%, or 1%, or 2%, or 3%, or 4%, or 5%, or 6%, or 7%, or 8%, or 9%, or 10%, or 11%, or 12%, or 13%, or 14%, or 15%, or 16%, or 17%, or 18%, or 19%, or 20%, or 21%, or 22%, or 23%, or 24%, or 25%, or 26%, or 27%, or 28%, or 29%, or 30%, or 31%, or 32%, or 33%, or 34%, or 35%, or 36%, or 37%, or 38%, or 39%, or 40%, or 41%, or 42%, or 43%, or 44%, or 45%, or 46%, or 47%, or 48%, or 49%, or 50%, or 51%, or 52%, or 53%, or 54%, or 55%, or 56%, or 57%, or 58%, or 59%, or 60%, or 61%, or 62%, or 63%, or 64%, or 65%, or 66%, or 67%, or 68%, or 69%, or 70%, or 71%, or 72%, or 73%, or 74%, or 75%, or 76%, or 77%, or 78%, or 79%, or 80%, or 81%, or 82%, or 83%, or 84%, or 85%, or 86%, or 87%, or 88%, or 89%, or 90%, or 90.5%, or 91%, or 91.5%, or 92%, or 92.5%, or 93%, or 93.5%, or 94%, or 94.5%, or 95%, or 95.5%, or 96%, or 96.5%, or 97%, or 97.5%, or 98%, or 98.5%, or 99%, or 99.5%, or 99.9%, or less than or equal to 100%.

Note: The volume % concentration of 02 in some embodiments or process steps may be less than or equal to one or more or a combination of the following: 0.001%, or 0.1%, or 1%, or 2%, or 3%, or 4%, or 5%, or 6%, or 7%, or 8%, or 9%, or 10%, or 11%, or 12%, or 13%, or 14%, or 15%, or 16%, or 17%, or 18%, or 19%, or 20%, or 21%, or 22%, or 23%, or 24%, or 25%, or 26%, or 27%, or 28%, or 29%, or 30%, or 31%, or 32%, or 33%, or 34%, or 35%, or 36%, or 37%, or 38%, or 39%, or 40%, or 41%, or 42%, or 43%, or 44%, or 45%, or 46%, or 47%, or 48%, or 49%, or 50%, or 51%, or 52%, or 53%, or 54%, or 55%, or 56%, or 57%, or 58%, or 59%, or 60%, or 61%, or 62%, or 63%, or 64%, or 65%, or 66%, or 67%, or 68%, or 69%, or 70%, or 71%, or 72%, or 73%, or 74%, or 75%, or 76%, or 77%, or 78%, or 79%, or 80%, or 81%, or 82%, or 83%, or 84%, or 85%, or 86%, or 87%, or 88%, or 89%, or 90%, or 90.5%, or 91%, or 91.5%, or 92%, or 92.5%, or 93%, or 93.5%, or 94%, or 94.5%, or 95%, or 95.5%, or 96%, or 96.5%, or 97%, or 97.5%, or 98%, or 98.5%, or 99%, or 99.5%, or 99.9%, or less than or equal to 100%.

Note: 'WA' may comprise a weak acid, which may include, but not limited to, one or more or any combination of the following: silicic acid, or orthosilicic acid, or silicon acid derivatives, or silicon minerals, or silicon acids, or aluminates, or ferrates, or a combination thereof.

Note: Some embodiments may involve reacting calcium silicate or a material comprising silicon directly with sulfur dioxide, or liquid sulfur dioxide, or sulfur dioxide in an non-aqueous solution, or any combination thereof.

Note: In some embodiments, contaminants or impurities may dissolve. Contaminants or impurities may include, but are not limited to, one or more or a combination of the following: iron, or aluminum, or alkali metals, or transition metals, or other non-bisulfite soluble salts, or non-alkaline earth bisulfite salts, or a combination thereof. In some embodiments, dissolved contaminants may be present after solid-liquid separation, and/or after calcium sulfite precipitation. In some embodiments, at least a portion of contaminants may be separated periodically or continuously. Contaminants may be separated by, including, but not limited to, one or more or any combination of the following: precipitation, or membrane based process, or cooling, or heating, or crystallization, or cryodesalination, or electrodialysis, or electrodialysis reverse, or selective electrodialysis, or a separation process described herein, or a separation process in the art.

Note: 'Calcium' may also refer to magnesium and/or other alkaline earth metals.

Note: In some embodiments, sulfur dioxide may be sourced from the roasting of sulfide ores, which generally may produce sulfur dioxide. In some embodiments, sulfur dioxide may be sourced from the combustion of sulfur, or hydrogen sulfide, or fuels, or any combination thereof.

Note: In some embodiments, it may be desirable for the partial pressure of CO2(g) reactant to be greater than or equal to one or more or any combination of the following: 0.01 Bar, or 0.05 bar, or 0.1 Bar, or 0.2 Bar, or 0.3 Bar, or 0.4 Bar, or 0.5 Bar, or 0.6 Bar, or 0.7 Bar, or 0.8 Bar, or 0.9 Bar, or 1.0 Bar. For example, it may be desirable for the concentration of CO2(g) reactant to be greater than or equal to one or more or any combination of the following: 1%, or 5%, or 10%, or 20%, or 30%, or 40%, or 50%, or 60%, or 70%, or 80%, or 90%, or 95%. In some embodiments, it may be desirable for the partial pressure of CO2(g) reactant to facilitate or enable the formation of bicarbonate to be greater than or equal to one or more or any combination of the following: 0.01 Bar, or 0.05 bar, or 0.1 Bar, or 0.2 Bar, or 0.3 Bar, or 0.4 Bar, or 0.5 Bar, or 0.6 Bar, or 0.7 Bar, or 0.8 Bar, or 0.9 Bar, or 1.0 Bar. For example, it may be desirable for the concentration of CO2(g) reactant to facilitate or enable the formation of bicarbonate to be greater than or equal to one or more or any combination of the following: 1%, or 5%, or 10%, or 20%, or 30%, or 40%, or 50%, or 60%, or 70%, or 80%, or 90%, or 95%.

Note: In some embodiments, magnesium sulfite may form an aqueous solution comprising aqueous magnesium sulfite. In some embodiments, magnesium sulfite may be separated from at least a portion of calcium sulfite, or calcium carbonate, or magnesium carbonate, or other practically insoluble materials. Calcium sulfite is practically insoluble in water, with a solubility of 0.043 grams per liter at 18° C. Magnesium sulfite is soluble in water, with a solubility of 5.2 grams per liter at 25° C. The reaction of a material comprising calcium and magnesium with aqueous sulfur dioxide may result in the formation of at least a portion of a solid phase comprising calcium and at least a portion of an aqueous phase comprising magnesium sulfite.

Note: Recovering magnesium sulfite from an aqueous solution comprising magnesium sulfite may be conducted using one or more or a combination of methods from separating a dissolved salt from an aqueous solution. Some properties of aqueous magnesium sulfite may enable simple, or low energy, or high throughput, or a combination thereof separation of solid magnesium sulfite from a solution comprising aqueous magnesium sulfite. For example, the solubility of magnesium sulfite increases with temperature—according to Solubilities of magnesium sulfite hydrates by Sohnel, et al, the solubility of magnesium sulfite or magnesium sulfite hexahydrate is 11.04 grams per liter at 43.0° C., or 14.19 grams per liter at 51.4° C., or 19.30 grams per liter at 61.4° C., or 28.87 grams per liter at 71.5° C., or 40.17 grams per liter at 79.0° C., or 53.73 grams per liter at 84.1° C., or 71.21 grams per liter at 88.0° C., or 95.19 grams per liter at 94.0° C. In some embodiments, some liquid phase or aqueous phase reactions or reactions in the presence of a liquid or aqueous phase may be conducted at an elevated temperature, such as, for example, greater than room temperature, or greater than ambient air temperature, or greater than 25° C., or greater than 35° C., or greater than 45° C., or greater than 55° C., or greater than 65° C., or greater than 75° C., or greater than 85° C., or greater than 95° C., or greater than 100° C., or less than the boiling point of the solution at the pressure of the reactor, or greater than 105° C. In some embodiments, by conducting at an elevated temperature, the concentration of magnesium sulfite in the aqueous magnesium sulfite may be greater, or the rate of reaction may be greater, or a combination thereof.

Note: It may be desirable to concentrate the aqueous magnesium sulfite before or during the precipitation of aqueous magnesium sulfite. It may be desirable for at least a portion of said solution to be concentrated. It may be desirable for at least a portion of said solution to be concentrated using distillation. It may be desirable for at least a portion of said solution to be concentrated using a membrane based process at an elevated temperature. It may be desirable for at least a portion of said solution to be concentrated using forward osmosis at an elevated temperature. It may be desirable for at least a portion of said solution to be concentrated using a reverse osmosis at an elevated temperature. It may be desirable for at least a portion of said solution to be heated before or during concentrating. It may be desirable for at least a portion of said solution to be heated before or during concentrating, to, for example, enable greater solubility of aqueous magnesium sulfite. It may be desirable for said aqueous magnesium sulfite to be treated to prevent scaling during concentrating, or to remove at least a portion of non-magnesium sulfite impurities, or a combination thereof. It may be desirable for at least a portion of said solution to be concentrated using a membrane-based process. For example, said aqueous magnesium sulfite solution may comprise a feed solution to a reverse osmosis process, wherein the reverse osmosis process separates said aqueous magnesium sulfite solution into a permeate comprising water and a concentrate comprising a greater concentration of aqueous magnesium sulfite. Said permeate comprising water may be transferred to a countercurrent heat exchanger for heat recovery and/or to a sulfur dioxide absorption process and/or to another step within the process requiring water or water solvent. It may be desirable for the reverse osmosis process to concentrate magnesium sulfite and/or other salts to a concentration lower than their solubility limits at the temperature of the solution to prevent or minimize membrane scaling. It may be desirable for the solution to be at an elevation temperature during the reverse osmosis process due to the greater solubility limit of magnesium sulfite with higher temperature and/or to prevent scaling or precipitation during reverse osmosis concentrating. Said concentrate comprising aqueous magnesium sulfite may be cooled to precipitate at least a portion of magnesium sulfite solid, due to, for example, the lesser solubility of magnesium sulfite in water with decreasing temperature, and/or said magnesium sulfite solid may be separated using a solid-liquid separation process. The remaining solution after separating magnesium sulfite solid using a solid-liquid separation process may comprise residual dissolved magnesium sulfite and/or dissolved non-magnesium sulfite salts or chemicals, and/or may undergo further treatment. For example, said remaining solution after separating magnesium sulfite solid using a solid-liquid separate process may be heated and/or transferred or mixed with additional new aqueous magnesium sulfite solution and/or may comprise at portion the feed solution to the reverse osmosis process. For example, said remaining solution after separating magnesium sulfite solid using a solid-liquid separate process may undergo further reverse osmosis steps. For example, said remaining solution after separating magnesium sulfite solid using a solid-liquid separate process may be heated and/or transferred to another membrane-based process. For example, said remaining solution after separating magnesium sulfite solid using a solid-liquid separate process may be distilled and/or crystalized, which may further separate water from dissolved chemicals and/or separate magnesium sulfite from other salts or chemicals. For example, said remaining solution after separating magnesium sulfite solid using a solid-liquid separate process may be mixed with solution transferred to a sulfur dioxide absorption process. For example, said remaining solution after separating magnesium sulfite solid using a solid-liquid separate process may be further treated with, including, but not limited to, one or more or a combination of the following: ion exchange, or resins, or filters, or chemical treatments, or chemical reactions, or membrane based process, or electrodialysis, or selective electrodialysis, or distillation, or multi-effect distillation, or mechanical vapor recompression distillation, or mechanical vapor compression distillation, or multistage flash distillation, or membrane distillation, or cooling, or heating, or freezing, or crydesalination, or solventing-out, or solvent induced precipitation, or salting-out, or other treatment. One or more solutions comprising water may be transferred to a sulfur dioxide absorption step, or mixed with a solution transferred to a sulfur dioxide absorption step, or a combination thereof.

Note: In some embodiments, the material comprising magnesium and calcium or alkaline earth may further comprise impurities. In some embodiments, the material comprising magnesium carbonate and calcium carbonate may further comprise impurities. For example, the material comprising magnesium carbonate and calcium carbonate may further comprise magnesium sulfate, or calcium sulfate, or sodium salts, or potassium salts, or iron salts, or manganese salts, or silicon chemicals, or silicon salts, or aluminum salts, or zinc salts, or other salts. Additionally, the aqueous solution comprising magnesium sulfite may be exposed to diatomic oxygen or inadvertently exposed to diatomic oxygen, which may result in a portion of the magnesium sulfite converting to magnesium sulfate. In some embodiments, impurities in the solution comprising aqueous magnesium sulfite may comprise dissolved salts or other chemicals other than magnesium sulfite. In some embodiments, although certain chemicals may be classified as 'impurities', some 'impurities' may comprise valuable products. For example, impurities comprising calcium sulfate and/or magnesium sulfate may be separated and may comprise valuable products. In some embodiments, at least a portion of impurities may be separated from an aqueous solution before, or during, or after concentrating and/or separating non-impurities or process reactants or products. For example, in some embodiments, iron sulfite, or manganese sulfite may be practically insoluble in water. Calcium sulfite solid may comprise other chemicals than calcium sulfite, which may include, but are not limited to, non-calcium sulfite salts described herein.

Note: Calcium sulfite or magnesium sulfite produced from a reaction in an aqueous solution or in water may comprise wet calcium sulfite or magnesium sulfite. Wet calcium sulfite may be physically wetted, as in wet calcium sulfite may contain water on the surface of the solid or embedded within the solid. Wet calcium sulfite may comprise hydrated calcium sulfite, which contains a chemically reacted hydrate or wherein water is reacted or part of the calcium sulfite solid. Dry calcium sulfite may comprise calcium sulfite solid which has minimal or no water on its surface or is not physically wetted. Dry calcium sulfite may comprise calcium sulfite solid which is anhydrous. In some embodiments, dry calcium sulfite may comprise calcium sulfite solid may comprise calcium sulfite solid which is partially hydrated, which means it may comprise hydrates of calcium sulfite, although is less hydrated than the potential full hydrate capacity of the calcium sulfite. Transforming wet calcium sulfite to dry calcium sulfite may require energy. Transforming wet calcium sulfite to dry calcium sulfite may comprise ‘drying’. Some embodiments may involve employing wet calcium sulfite as an input to a calcining process to produce calcium oxide. Employing wet calcium sulfite as an input to a calcining process to produce calcium oxide may require more energy than employing dry calcium sulfite. Additionally, the amount and/or quality of energy required to calcine wet calcium sulfite may greater than if the wet calcium sulfite is dried into dry calcium sulfite before calcining. One or more or a combination of systems and methods may be employed to dry or dehydrate calcium sulfite. For example, calcium sulfite may be dried by heating the wet calcium sulfite to liberate water as a liquid or a vapor or both and separating said liberated water. If heating is employed, it may be desirable for the temperature of the heat employed to be less than the temperature of calcining calcium sulfite, or for the energy consumed to provide said heat to be less expensive or less carbon emission intensive than the energy consumed to calcine calcium sulfite, or a combination thereof. For example, said heat may be provided by, including, but not limited to, solar thermal, or heat pump, or waste heat, or steam, or low pressure steam, or stored heat, or process heat, or geothermal heat, or nuclear heat, or co-gen heat, or any combination thereof. For example, calcium sulfite may be dried by a carrier gas or stripping gas. For example, calcium sulfite may be dried by a recirculating carrier gas. For example, said recirculating carrier gas may comprise a gas or gas mixture with a diatomic oxygen concentration lower than 1 percent, or 2 percent, or 3 percent, or 4 percent, or 5 percent, or 6 percent, or 7 percent, or 8 percent, or 9 percent, or 10 percent, or 11 percent, or 12 percent, or 13 percent, or 14 percent, or 15 percent, or 16 percent, or 17 percent, or 18 percent, or 19 percent, or 20 percent, or 21 percent, or 22 percent, or any combination thereof by volume. For example, calcium sulfite may be dried by a recirculating carrier gas, wherein at least a portion of water vapor in the recirculating carrier gas is removed by a regenerable liquid desiccant. For example, calcium sulfite may be dried by a recirculating carrier gas, wherein at least a portion of water vapor in the recirculating carrier gas is removed by a regenerable liquid desiccant, which may include, but is not limited to, a glycol liquid desiccant, or glycol dehydration system, or a salt brine, or lithium bromide, or calcium chloride, or a liquid-liquid phase transition liquid desiccant, or a liquid desiccant regenerated by heat, or a liquid desiccant regenerated by vaporization of water, or a liquid desiccant regenerated by freezing desalination, or a liquid desiccant regenerated by a liquid-liquid phase transition into a water-rich phase and a water-lean phase, or a combination thereof. For example, calcium sulfite may be dried by a recirculating carrier gas, wherein at least a portion of water vapor in the recirculating carrier gas is removed by a regenerable solid desiccant, which may include, but is not limited to, an adsorbent, or gypsum, or silicate, or silica gel, or calcium oxide-calcium hydroxide, or a combination thereof. For example, calcium sulfite may be dried by a liquid desiccant, or a solid desiccant, or a combination thereof. For example, calcium sulfite may be dried by a recirculating carrier gas, wherein at least a portion of water vapor in the recirculating carrier gas is removed by a non-regenerated desiccant, which may comprise a solid or a liquid. For example, a non-regenerated desiccant may comprise a material which reacts with water to form a product, which may be removed from the process as a valuable product, or is disposed. For example, an example non-regenerated solid desiccant may comprise calcium oxide reacted with water or water vapor to form calcium hydroxide. For example, in some embodiments, calcium oxide produced by the process may be reacted with water vapor in said carrier gas, removing at least a portion of said water vapor while forming calcium hydroxide. Said calcium hydroxide may comprise a valuable product, or may be further reacted with water, or may be converted into other derivatives of calcium hydroxide. In some embodiments, at least a portion of heat generated from forming calcium hydroxide, from, for example, calcium oxide, may be employed to power at least a portion of the energy required to dry the wet calcium sulfite solid.

Note: Magnesium sulfite solid produced in one or more steps of the process may comprise wet magnesium sulfite. Wet magnesium sulfite may be physically wetted, as in wet magnesium sulfite may contain water on the surface of the solid or embedded within the solid. Wet magnesium sulfite may comprise hydrated magnesium sulfite solid, which contains a chemically reacted hydrate or wherein water is reacted or part of the magnesium sulfite solid. Dry magnesium sulfite may comprise magnesium sulfite solid which has minimal or no water on its surface or is not physically wetted. Dry magnesium sulfite may comprise magnesium sulfite solid which is anhydrous. In some embodiments, dry magnesium sulfite may comprise magnesium sulfite solid and/or may comprise magnesium sulfite solid which is partially hydrated, which means it may comprise hydrates of magnesium sulfite, although is less hydrated than the potential full hydrate capacity of the magnesium sulfite. Transforming wet magnesium sulfite into dry magnesium sulfite may require energy. Transforming wet magnesium sulfite to dry magnesium sulfite may comprise ‘drying’. Some embodiments may involve employing wet magnesium sulfite as an input to a calcining process to produce magnesium oxide. Employing wet magnesium sulfite as an input to a calcining process to produce magnesium oxide may require more energy than employing dry magnesium sulfite. Additionally, the amount and/or quality of energy required to calcine wet magnesium sulfite may greater than if the wet magnesium sulfite is dried into dry magnesium sulfite before calcining. One or more or a combination of systems and methods may be employed to dry or dehydrate magnesium sulfite. For example, magnesium sulfite may be dried by heating the wet magnesium sulfite to liberate water as a liquid or a vapor or both and separating said liberated water. If heating is employed, it may be desirable for the temperature of the heat employed to be less than the temperature of calcining magnesium sulfite, or for the energy consumed to provide said heat to be less expensive or less carbon emission intensive than the energy consumed to calcine magnesium sulfite, or a combination thereof. For example, said heat may be provided by, including, but not limited to, solar thermal, or heat pump, or waste heat, or steam, or low pressure steam, or stored heat, or process heat, or geothermal heat, or nuclear heat, or co-gen heat, or any combination thereof. For example, magnesium sulfite may be dried by a carrier gas or stripping gas. For example, magnesium sulfite may be dried by a recirculating carrier gas. For example, said recirculating carrier gas may comprise a gas or gas mixture with a diatomic oxygen concentration less than 2 percent by volume. For example, magnesium sulfite may be dried by a recirculating carrier gas, wherein at least a portion of water vapor in the recirculating carrier gas is removed by a regenerable liquid desiccant. For example, magnesium sulfite may be dried by a recirculating carrier gas, wherein at least a portion of water vapor in the recirculating carrier gas is removed by a regenerable liquid desiccant, which may include, but is not limited to, a glycol liquid desiccant, or glycol dehydration system, or a salt brine, or lithium bromide, or calcium chloride, or a liquid-liquid phase transition liquid desiccant, or a liquid desiccant regenerated by heat, or a liquid desiccant regenerated by vaporization of water, or a liquid desiccant regenerated by freezing desalination, or a liquid desiccant regenerated by a liquid-liquid phase transition into a water-rich phase and a water-lean phase, or a combination thereof. For example, magnesium sulfite may be dried by a recirculating carrier gas, wherein at least a portion of water vapor in the recirculating carrier gas is removed by a regenerable solid desiccant, which may include, but is not limited to, an adsorbent, or gypsum, or silicate, or silica gel, or calcium oxide-calcium hydroxide, or an acid, or a combination thereof. For example, magnesium sulfite may be dried by a liquid desiccant, or a solid desiccant, or a combination thereof. For example, magnesium sulfite may be dried by a recirculating carrier gas, wherein at least a portion of water vapor in the recirculating carrier gas is removed by a non-regenerated solid desiccant. For example, a non-regenerated solid desiccant may comprise a material which reacts with water to form a product, which may be removed from the process as a valuable product, or may be disposed, or both. For example, an example non-regenerated solid desiccant may comprise calcium oxide reacted with water or water vapor to form calcium hydroxide. For example, in some embodiments, calcium oxide produced by the process may be reacted with water vapor in said carrier gas, removing at least a portion of said water vapor while forming calcium hydroxide. Said calcium hydroxide may comprise a valuable product, or may be further reacted with water, or may be converted into other derivatives of calcium hydroxide. In some embodiments, at least a portion of heat generated from forming calcium hydroxide, from, for example, calcium oxide, may be employed to power at least a portion of the energy required to dry the wet magnesium sulfite solid.

Note: In some embodiments, excess water may be removed. Similarly, water may be added to the system if desired. Water removal may be conducted by for example, including, but not limited to, one or more or a combination of the following: forward osmosis, decanter, separatory funnel, coalescer, centrifuge, filter, switchable solvent, cyclone, semi-permeable membrane, or electrodialysis, or electrodialysis reversal, nanofiltration, organic solvent nanofiltration, reverse osmosis, ultrafiltration, microfiltration, hot nanofiltration, hot ultrafiltration, distillation, membrane distillation, flash distillation, multi-effect distillation, mechanical vapor compression distillation, or hybrid systems.

Note: In some embodiments, sodium Bicarbonate may be decomposed to form Sodium Carbonate, Sodium hydroxide, Sodium Sesquicarbonate, or a combination thereof, or other sodium-carbon dioxide or sodium bicarbonate derivative chemicals.

Note: Separation devices, or systems, or methods, or any combination thereof may include, but are not limited to, one or more or a combination of the following: decanter, separatory funnel, coalescer, centrifuge, filter, switchable solvent, cyclone, semi-permeable membrane, nanofiltration, organic solvent nanofiltration, reverse osmosis, ultrafiltration, microfiltration, hot nanofiltration, hot ultrafiltration, distillation, membrane distillation, flash distillation, multi-effect distillation, mechanical vapor compression distillation, or hybrid systems, or electrodialysis, or electrodialysis reversal, or osmotically assisted reverse osmosis, or forward osmosis Note: The temperature of recovered heat or ambient heat source may be increased using a heat pump or a refrigeration cycle, if, for example, higher temperature heat is required for one or more process steps or one or more applications. For example, if recovered heat is in the form of steam, said steam may be compressed to a greater pressure, which may enable said steam to condense at a higher temperature and/or supply higher temperature heat.

Note: Heat sources may include, but are not limited to, one or more or a combination of the following: flare gas heat, or combustion, or biofuel, or fossil fuel, or slaking lime, or natural gas combustion, nuclear heat, Waste Heat, Ambient Temperature Changes, or ambient heat, Diurnal Temperature Variation, Thermocline liquid body, thermocline solid body, thermocline gaseous body, Thermocline of a water body, halocline, heat pump, solar thermal, solar thermal pond, light, electricity, steam, combustion, compression, pressure increase, geothermal, radiative heat, condensation, exothermic dissolution, exothermic precipitation, exothermic formation of more liquid phases, exothermic formation of less liquid phases, exothermic phase change, or other heat sources described herein, or other heat sources known in the art.

Note: Systems and methods described herein may be batch, semi-batch, or continuous, or a combination thereof.

Note: Other metals or metal ions or cations which may be present or may be employed, may include, but are not limited to, one or more or a combination of the following: iron, lead, copper, cobalt, nickel, manganese, chromium, silver, scandium, vanadium, titanium, aluminum, magnesium, calcium, sodium, potassium, Yttrium, Zirconium, Niobium, Molybdenum Technetium, Ruthenium, Rhodium, Palladium, Silver, Cadmium, Hafnium, Tantalum, Tungsten, Rhenium, Osmium, Iridium, Platinum, Gold, Mercury, Rutherfordium, Dubnium, Seaborgium, Bohrium, Hassium, Meitnerium, Ununnilium, Unununium, or Ununbium.

Note: Reactions or systems and methods, steps, or a combination thereof herein may comprise a batch, semi-batch, semi-continuous, continuous stirred reactor (CSTR), continuous, or a combination thereof.

Note: Depending on the operating conditions, phases of inputs, concentrations, or a combination thereof, heating or cooling or separating or any combination thereof may be required in one or more or a combination of the steps or parts of one or more or a combination of embodiments.

Note: Some embodiments may employ equipment comprising materials compatible with one or more or a combination of the following: SO2, CO2, or H2O, or sulfur, or sulfur derivatives or one or more of the fuels (if any) employed in heating and/or their combustion products. It may be desirable for said materials to be compatible at temperature ranges of operation.

Note: In some embodiments, it may be desirable for some reagents to be transferred, or stored, or reacting in a nearly diatomic oxygen-free or low oxygen environment.

Note: The present invention may be employed to regenerate CaO from CaCO3 or similar carbonate or bicarbonate molecules in a CO2 capture process. For example, the present invention may be employed in a device to capture CO2 from the air.

Note: The $SO_2$ may be substituted with nitric acid (HNO3). Ca(NO3)2(which may be a resulting byproduct) can be thermally decomposed in a similar manner to CaSO3 to form CaO and NOx or O2 or NO2 or NO or a combination thereof. NOx, NO2, or NO may be converted back into nitric acid through reaction with water in, for example, the NOx+O2 and NOx+H2O reaction steps of the Ostwald process, regenerating the nitric acid in the present embodiment. Advantageously, Ca(NO3)2 may not oxidize in the presence of O2, which may enable the process to operate in an environment with the presence of substantial O2, if desired.

Note: In some embodiments, a carrier gas may comprise a reactive gas or a gas which may be reacted beneficially if desired. For example, steam may be employed as a carrier gas. Advantageously, steam may condense following calcination and the heat generated may be recoverable and the heat generated may exceed initial heat input to generate steam due to, for example, an exothermic reaction of H2O with CaO to produce calcium hydroxide and/or higher temperature steam or raise the temperature of water.

Note: Excess water may be removed from system. Similarly, water may be added to the system if desired.

Note: Reagents or products or other chemicals in one or more embodiments may be passed or cycled or recycled or recirculated through a step more than once. Said 'passed or cycled or recycled or recirculated' may be conducted before, for example, proceeding to a next step. Said passed or cycled or recycled or recirculated' may be conducted in, for example, including, but not limited to, one or more or any combination of the following: equilibrium reaction, absorption solutions, or solutions undergoing precipitation, or distillation solutions, or solution undergoing treatment, or concentrating with a membrane based process, or any combination thereof.

Note: One or more or a combination of the embodiments described herein may be employed as a net carbon dioxide emission negative method for permanently or semi-permanently sequestering carbon dioxide. For example, alkaline oxide or alkaline hydroxide may reacted with $CO_2$ from a wide range of sources. For example, the sodium bicarbonate, or sodium sesquicarbonate, or sodium carbonate or sodium hydroxide or a combination thereof produced by one or more embodiments may be dissolved in the ocean. Adding net carbon dioxide emission negative sodium bicarbonate, or sodium sesquicarbonate, or sodium carbonate or a combination thereof to the ocean may have multiple benefits, which may include, but are not limited to, one or more or a combination of the following: permanent or semi-permanent sequestration of carbon dioxide in the ocean; increasing the pH of ocean water; increasing the concentration of carbonate ions in the ocean; buffering ocean acidification, restoring coral reefs; restoring marine life; local rejuvenation of marine life; local rejuvenation of coral; rejuvenation of coral.

Note: Cooling and/or heating may be conducted at additional or different temperatures and/or at additional or different locations than described herein.

Note: Some embodiments may be constructed by retrofitting pre-existing processes.

Note: One or more or a combination of embodiments of the present invention may require solid handling or solid transfer or solid storage. Solid transfer may include, but is not limited to, conveyor belts, screw conveyors, bucket elevators, belt conveyors, pneumatic conveyors, or a combination thereof. Solid storage or transport or a combination thereof may include, but is not limited to, bin, or silo, hopper cars, bulk sacks, or other solids shipping containers, or a combination thereof.

Note: Temperatures in one or more parts of one or more embodiments may include, but are not limited to, greater than, equal to, or less than one or more or a combination of the following in degrees Celsius: −50, −40, −30, −20, −10, 0, 5, 10, 15, 20, 25, 3035, 40, 45, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000, 1010, 1020, 1030, 1040, 1050, 1060, 1070, 1080, 1090, 1100, 1150, 1200, 1250, 1300, 1350, 1400, 1450, 1500, 1600, 1700, 1800, 1900, 2000, 2250, 2500, 2750, 3000

Note: Sodium may be provided as an example alkali. Other alkali metal salts or cations may be employed instead of or in addition to sodium. For example, potassium or lithium or rubidium or cesium or a combination thereof may be employed. For example, alkali-like cations or salts, such as ammonia or ammonium, may be employed.

Note: Ammonia may be provided as an example weak base or alkali-like cation derivative. Other weak bases or weak base gases may be employed instead of or in addition to ammonia. For example, said other weak bases may include, but are not limited to, one or more or a combination of the following: amines, ammonia derivatives, imines, azines, CO2 capture absorbent cations, CO2 capture absorbents, or a combination thereof, or other weak bases, or other weak gases.

Note: CO2 sources may include, but are not limited to, one or more or a combination of the following: Power Plant (Natural gas, coal, oil, petcoke, biofuel, municipal waste), Cement production, chemical production, Waste Water Treatment, Landfill gas, Air, Metal production/refining (such as Iron, Steel, Aluminum, etc.), Glass production, Oil refineries, LNG liquification, HVAC, Transportation vehicles (ships, boats, cars, buses, trains, trucks, airplanes), Natural Gas, Biogas, Alcohol fermentation, Volcanic Activity, Decomposing leaves/biomass, Septic tank, Respiration, Manufacturing facilities, Fertilizer production, or Geothermal processes where CO2(g) releases from a well or wells.

Note: In some embodiments or process steps, input CO2 vol % concentration may be greater than or equal to one or more or a combination of the following volume percent concentrations: 0%, or 0.001%, or 0.1%, or 0.5%, or 1%, or 1.5%, or 2%, or 2.5%, or 3%, or 3.5%, or 4%, or 4.5%, 5%, or 5.5%, or 6%, or 6.5%, or 7%, or 7.5%, or 8%, or 8.5%, or 9%, or 9.5%, or 10%, or 10.5%, or 11%, or 11.5%, or 12%, or 12.5%, or 13%, or 13.5%, or 14%, or 14.5%, or 15%, or 20%, or 30%, or 40%, or 50%, or 60%, or 70%, or 80%, or 90%, or 100%.

Note: In some embodiments, a gas stream comprising CO2 may be concentrated to a greater concentration of CO2 or a greater partial pressure of CO2 before being absorbed or reacted in one or more or a combination of embodiments of the present invention. Said concentrating may be conducted using including, but not limited to, one or more or a combination of the following: gas membrane, or absorption/desorption CO2 capture, or adsorption/desorption CO2 capture, or recirculated CO2, or desorption CO2, or CO2 from one or more or a combination of higher concentration CO2 sources, or condensation of non-CO2 gas, or cooling, or heating, or deposition, or deposition/sublimination, or cryogenic separation, or compression, or pressurization, electrochemical process, or ion exchange, or electrodialysis, or fuel cell, or a combination thereof.

Note: A gas stream comprising SO2 may be concentrated to a greater concentration of SO2 or a greater partial pressure of SO2 before being absorbed or reacted in one or more or a combination of embodiments of the present invention. Said concentrating may be conducted using including, but not limited to, one or more or a combination of the following: gas membrane, or membrane based process, or absorption/desorption SO2 capture, or adsorption/desorption SO2 capture, or recirculated SO2, or desorption SO2, or SO2 from one or more or a combination of higher concentration SO2 sources, or condensation of non-SO2 gas, or cooling, or heating, or deposition, or deposition/sublimination, or cryogenic separation, or compression, or pressurization, electrochemical process, or ion exchange, or electrodialysis, or fuel cell, or a combination thereof.

Note: Absorption of a gas into a solution containing ammonia and/or absorption of ammonia into a solution may result in the formation of a residual or remaining gas stream comprising residual ammonia. Said residual or remaining gas stream may comprise, for example, remaining unabsorbed gases or inert gases. One or more or a combination of embodiments herein may employ an ammonia recovery or ammonia abatement cycle or system. Alternately or additionally, ammonia may be removed to ultra-low concentrations (e.g. single or double digit PPM concentrations) using hydrochloric acid or sulfuric acid, and/or ammonia or hydrochloric acid may be recovered from the resulting ammonium chloride or ammonium sulfite, which may employ, for example, one or more or a combination of embodiments herein.

Note: Ammonia losses may occur within one or more or a combination of embodiments described herein. Makeup ammonia may be provided, for example, as needed or as desired.

Note: SO2 losses may occur within one or more or a combination of embodiments described herein. Makeup SO2 may be provided, for example, as needed or as desired.

Note: Losses may occur within one or more or a combination of embodiments described herein. Makeup reagents may be provided, for example, as needed or as desired.

Note: In some embodiments, ammonia may form at elevated temperatures. In some embodiments, if oxygen is present, some ammonia may undergo combustion. Ammonia combustion products, even at residual or low concentrations, may be present in one or more gases or liquids or solids or a combination thereof in one or more or a combination of embodiments. Said ammonia combustion products may comprise, including, but not limited to, nitrogen oxides, or nitrogen, or nitric acid, or a derivative thereof, or a combination thereof. Systems and methods for detecting, treating, removing, economically using, recovering, or a combination thereof said ammonia combustion products may be employed.

Note: In some embodiments, ammonia, or methanol, or formic acid, or e-fuels, or $CO_2$-derived fuel, or hydrogen derivative, or any combination thereof may comprise a fuel or may be employed to power one or more steps in one or more embodiments, if desired.

Note: Filling, or reacting, or emptying, or a combination thereof may be conducted simultaneously if desired.

Note: Example alkalis may include, but are not limited to, one or more or any combination of the following: lithium (Li), or sodium (Na), or potassium (K), or rubidium (Rb), or cesium (Cs)

Note: Example alkaline earths may include, but are not limited to, one or more or any combination of the following: beryllium (Be), or magnesium (Mg), or calcium (Ca), or strontium (Sr), or barium (Ba), or radium (Ra).

Note: Calcium may comprise an example alkaline earth. Other alkaline earths may be employed in addition to or instead of calcium where calcium is described herein. For example, in some embodiments, calcium may comprise mixtures of calcium and magnesium, or calcium may instead comprise magnesium.

Note: Sodium may comprise an example alkali. Other alkalis may be employed in addition to or instead of sodium where sodium is described herein. For example, in some embodiments, Sodium may comprise mixtures of sodium and potassium, or sodium and lithium, or potassium, or lithium, or any combination thereof.

Note: An alkaline earth cation-weak acid anion salt may include, but is not limited to, alkaline earth cation salts with one or more or any combination of the following anions: carbonate, or bicarbonate, or sulfite, or sulfide, or silicate, or ferrate, or aluminate, or ferrite, or a silicate, or silicon derivative, or a carboxylic acid salt, or a ferrate salt, or an aluminate salt, or a zincate salt, or an iron derivative salt, or a manganese derivative salt, or a zinc derivative salt, or an aluminum derivative salt, or transition metal oxide anion, or metal oxide anion, or an anion of an acid weaker than sulfurous acid.

Note: Heat produced from the reaction of calcium oxide with water to form calcium hydroxide may be utilized. For example, said heat may be employed within separation steps, or distillation steps, or drying steps, or calcining steps, or decomposition steps, or gas liberating steps, or any combination thereof within the invention. For example, said heat may be utilized in an external application.

Note: Heat produced from the combustion or conversion of hydrogen sulfide, or the production of sulfuric acid, or production of sulfur dioxide, or production or sulfurous acid, or exothermic reactions comprising sulfur chemicals, or any combination thereof may be utilized. For example, said heat may be employed within separation steps, or distillation steps, or drying steps, or calcining steps, or decomposition steps, or gas liberating steps, or any combination thereof within the invention. For example, said heat may be utilized in an external application.

Note: In some embodiments, sodium sulfate may be produced by the reaction of sodium chloride with sulfuric acid or sulfur dioxide or oxygen or any combination thereof, which may produce hydrochloric acid and sodium sulfate.

$$2\ NaCl+H_2SO4\rightarrow 2\ HCl+Na_2SO4$$

$$4\ NaCl+2\ SO2+O2+2\ H2O\rightarrow 4\ HCl+2\ Na2SO4$$

Note: In some embodiments, sodium sulfate may be produced by mining of sodium sulfate deposits or extraction of sodium sulfate from natural resources.

Note: In some embodiments, sodium hydroxide, or sodium carbonate, or sodium sesquicarbonate, or sodium bicarbonate, or any combination thereof may be added to an ocean or sea to, for example, including, but not limited to, one or more or any combination of the following: increase the pH, or increase the local pH, or provide a high quality mechanism to permanently absorb carbon dioxide from the air, or to increase the local pH to improve health of marine ecosystems and corals, or improve biomass production, or improve productivity of a fishery, or facilitate tourism, or grow a local economy, or to improve the health of the ocean, or the prevent or combat algae blooms or cyanobacteria blooms, or any combination thereof.

Note: Sodium sulfate may be a byproduct in the production of, including, but not limited to, lithium carbonate, or chelating agents, or resorcinol, or ascorbic acid, or silica pigments, or nitric acid, or phenol, or any combination thereof.

Note: The present invention may comprise a process for recycling sodium hydroxide or sodium or sodium carbonate in the production of, for example, lithium, or lithium carbonate, or lithium hydroxide, or any combination thereof.

Note: In some embodiments, sodium sulfate may comprise, for example, Mirabilite or Thenardite Note: Some embodiments may be co-located with a process where sodium sulfate is produced as a product, or byproduct, or waste product.

Note: Sodium sulfate is known to be a very significant waste product of the lithium production industry. In some lithium production applications, sodium hydroxide is reacted with lithium sulfate produced from a roasting process to recover lithium, which may result in the production of a sodium sulfate product. Some embodiments of the present invention may enable recycling of sodium sulfate into sodium hydroxide or sodium carbonate.

Note: In some embodiments, sodium hydroxide may facilitate hydrogen production.

Note: MgCa(CO3)2(s) may comprise a solid comprising a mixture of calcium and magnesium salts. MgCa(CO3)2(s) may comprise, for example, including, but not limited to, limestone or dolomite. Alternatively, or additionally, MgCa (CO3)2(s) may comprise a portion of magnesium silicate or magnesium aluminate or magnesium ferrate. Alternatively, or additionally, MgCa(CO3)2(s) may comprise a portion of calcium silicate or calcium aluminate or calcium ferrate.

Note: In some embodiments, a solvent other than or in addition to water may be employed. For example, an organic solvent or inorganic solvent may be present in solution. For example, a glycol, or an alcohol, or a sugar alcohol may be present. For example, an organic solvent or a solvent other than water. For example, ammonia or urea may be present in solution.

Note: Concentration of aqueous magnesium sulfite in a solution comprising aqueous magnesium sulfite may be greater than or equal to one or more or a combination of the following: 0.025 g/L, or 0.05 g/L, or 0.1 g/L, or 0.2 g/L, or 0.3 g/L, 0.4 g/L, or 0.5 g/L, or 0.6 g/L, or 0.7 g/L, or 0.8 g/L, or 0.9 g/L, or 1.0 g/L, or 1.1 g/L, or 1.2 g/L, or 1.3 g/L, or 1.4 g/L, or 1.5 g/L, or 1.6 g/L, or 1.7 g/L, or 1.8 g/L, or 1.9 g/L, or 2 g/L Note: For example, in some embodiments, 'g/L' may comprise grams of solute per liter of solution. For example, 1 g/L of magnesium sulfate may comprise a solution with 1 gram of dissolved magnesium sulfite per liter of total solution.

Note: In some embodiments, temperature of at least a portion of concentrating with reverse osmosis, or forward osmosis, or electrodialysis, or electrodialysis reversal, or selective electrodialysis, or osmotically assisted reverse osmosis, or any combination thereof may be greater than or equal to one or more or a combination of the following: 0° C., or 5° C., or 10° C., or 15° C., or 20° C., or 25° C., or 30° C., or 35° C., or 40° C., or 45° C., or 50° C., or 55° C., or 60° C., or 65° C., or 70° C., or 75° C., or 80° C., or 85° C., or 90° C., or 95° C., or 100° C., or 105° C., or 110° C., or 115° C.

Note: In some embodiments, temperature of calcining at least a portion of calcium sulfite, or magnesium sulfite, or any combination thereof may be greater than or equal to one or more or a combination of the following: 400° C., or 450 C° C., or 500° C., or 550° C., or 600° C., or 650° C., or 700° C., or 750° C., or 775° C., or 800° C., or 825° C., or 850° C., or 875° C., or 900° C.

Note: In some embodiments, temperature of drying or dehydrating or decomposing hydroxide or any combination thereof may be less than or equal to one or more or a combination of the following: 800° C., or 750° C., or 700° C., or 650° C., or 600° C., or 550° C., or 500° C., or 450° C., or 400° C., or 350° C., or 300° C., or 250° C., or 200° C., or 150° C., or 100° C.

Note: In some embodiments, the partial pressure of captured carbon dioxide produced by one or more or a combination of embodiments may be greater than or equal to one or more or a combination of the following: 0.05 atm, or 0.1 atm, or 0.2 atm, or 0.3 atm, or 0.4 atm, or 0.5 atm, or 0.6 atm, or 0.7 atm, or 0.8 atm, or 0.9 atm, or 1 atm, or 1.1 atm, or 1.2 atm, or 1.3 atm, or 1.4 atm, or 1.5 atm, or 1.6 atm, or 1.7 atm, or 1.8 atm, or 1.9 atm, or 2.0 atm, or 2.25 atm, or 2.5 atm, or 2.75 atm, or 3 atm, or 4 atm, or 5 atm, or 6 atm, or 7 atm, or 8 atm, or 9 atm, or 10 atm, or 12.5 atm, or 15 atm, or 17.5 atm, or 20 atm, or 25 atm, or 30 atm, or 35 atm, or 40 atm, or 45 atm, or 50 atm Note: The concentration of carbon dioxide or sulfur dioxide formed by one or more or any combination of embodiments or process steps may comprise a volume percent concentration of carbon dioxide which may include, greater than, or equal to, one or more or a combination of the following: 0.5%, or 1%, or 1.5%, or 2%, or 2.5%, or 3%, or 3.5%, or 4%, or 4.5%, or 5%, or 5.5%, or 6%, or 6.5%, or 7%, or 7.5%, or 8%, or 8.5%, or 9%, or 9.5%, or 10%, or 10.5%, or 11%, or 11.5%, or 12%, or 12.5%, or 13%, or 13.5%, or 14%, or 14.5%, or 15%, or 15.5%, or 16%, or 16.5%, or 17%, or 17.5%, or 18%, or 18.5%, or 19%, or 19.5%, or 20%, or 20.5%, or 21%, or 21.5%, or 22%, or 22.5%, or 23%, or 23.5%, or 24%, or 24.5%, or 25%, or 25.5%, or 26%, or 26.5%, or 27%, or 27.5%, or 28%, or 28.5%, or 29%, or 29.5%, or 30%, or 30.5%, or 31%, or 31.5%, or 32%, or 32.5%, or 33%, or 33.5%, or 34%, or 34.5%, or 35%, or 35.5%, or 36%, or 36.5%, or 37%, or 37.5%, or 38%, or 38.5%, or 39%, or 39.5%, or 40%, or 40.5%, or 41%, or 41.5%, or 42%, or 42.5%, or 43%, or 43.5%, or 44%, or 44.5%, or 45%, or 45.5%, or 46%, or 46.5%, or 47%, or 47.5%, or 48%, or 48.5%, or 49%, or 49.5%, or 50%, or 50.5%, or 51%, or 51.5%, or 52%, or 52.5%, or 53%, or 53.5%, or 54%, or 54.5%, or 55%, or 55.5%, or 56%, or 56.5%, or 57%, or 57.5%, or 58%, or 58.5%, or 59%, or 59.5%, or 60%, or 60.5%, or 61%, or 61.5%, or 62%, or 62.5%, or 63%, or 63.5%, or 64%, or 64.5%, or 65%, or 65.5%, or 66%, or 66.5%, or 67%, or 67.5%, or 68%, or 68.5%, or 69%, or 69.5%, or 70%, or 70.5%, or 71%, or 71.5%, or 72%, or 72.5%, or 73%, or 73.5%, or 74%, or 74.5%, or 75%, or 75.5%, or 76%, or 76.5%, or 77%, or 77.5%, or 78%, or 78.5%, or 79%, or 79.5%, or 80%, or 80.5%, or 81%, or 81.5%, or 82%, or 82.5%, or 83%, or 83.5%, or 84%, or 84.5%, or 85%, or 85.5%, or 86%, or 86.5%, or 87%, or 87.5%, or 88%, or 88.5%, or 89%, or 89.5%, or 90%, or 90.5%, or 91%, or 91.5%, or 92%, or 92.5%, or 93%, or 93.5%, or 94%, or 94.5%, or 95%, or 95.5%, or 96%, or 96.5%, or 97%, or 97.5%, or 98%, or 98.5%, or 99%, or 99.5%, or 100%

Note: 'A portion': In some embodiments, a portion may comprise at least a part of a stream or material, or all of a stream or material. A portion may include, but is not limited to, less than, or greater than, or equal to, one or more or a combination of the following: 0%, or 0.5%, or 1%, or 1.5%, or 2%, or 2.5%, or 3%, or 3.5%, or 4%, or 4.5%, or 5%, or 5.5%, or 6%, or 6.5%, or 7%, or 7.5%, or 8%, or 8.5%, or 9%, or 9.5%, or 10%, or 10.5%, or 11%, or 11.5%, or 12%, or 12.5%, or 13%, or 13.5%, or 14%, or 14.5%, or 15%, or 15.5%, or 16%, or 16.5%, or 17%, or 17.5%, or 18%, or 18.5%, or 19%, or 19.5%, or 20%, or 20.5%, or 21%, or 21.5%, or 22%, or 22.5%, or 23%, or 23.5%, or 24%, or 24.5%, or 25%, or 25.5%, or 26%, or 26.5%, or 27%, or 27.5%, or 28%, or 28.5%, or 29%, or 29.5%, or 30%, or 30.5%, or 31%, or 31.5%, or 32%, or 32.5%, or 33%, or 33.5%, or 34%, or 34.5%, or 35%, or 35.5%, or 36%, or 36.5%, or 37%, or 37.5%, or 38%, or 38.5%, or 39%, or 39.5%, or 40%, or 40.5%, or 41%, or 41.5%, or 42%, or 42.5%, or 43%, or 43.5%, or 44%, or 44.5%, or 45%, or 45.5%, or 46%, or 46.5%, or 47%, or 47.5%, or 48%, or 48.5%, or 49%, or 49.5%, or 50%, or 50.5%, or 51%, or 51.5%, or 52%, or 52.5%, or 53%, or 53.5%, or 54%, or 54.5%, or 55%, or 55.5%, or 56%, or 56.5%, or 57%, or 57.5%, or 58%, or 58.5%, or 59%, or 59.5%, or 60%, or 60.5%, or 61%, or 61.5%, or 62%, or 62.5%, or 63%, or 63.5%, or 64%, or 64.5%, or 65%, or 65.5%, or 66%, or 66.5%, or 67%, or 67.5%, or 68%, or 68.5%, or 69%, or 69.5%, or 70%, or 70.5%, or 71%, or 71.5%, or 72%, or 72.5%, or 73%, or 73.5%, or 74%, or 74.5%, or 75%, or 75.5%, or 76%, or 76.5%, or 77%, or 77.5%, or 78%, or 78.5%, or 79%, or 79.5%, or 80%, or 80.5%, or 81%, or 81.5%, or 82%, or 82.5%, or 83%, or 83.5%, or 84%, or 84.5%, or 85%, or 85.5%, or 86%, or 86.5%, or 87%, or 87.5%, or 88%, or 88.5%, or 89%, or 89.5%, or 90%, or 90.5%, or 91%, or 91.5%, or 92%, or 92.5%, or 93%, or 93.5%, or 94%, or 94.5%, or 95%, or 95.5%, or 96%, or 96.5%, or 97%, or 97.5%, or 98%, or 98.5%, or 99%, or 99.5%, or 100%

Note: Calcining may involve thermally decomposing calcium sulfite and/or magnesium sulfite into calcium oxide and/or magnesium oxide. Calcining may involve thermally decomposing calcium carbonate and/or magnesium carbonate into calcium oxide and/or magnesium oxide. Calcining may involve thermally decomposing an alkaline earth hydroxide into an alkaline earth oxide.

Note: In some embodiments, calcium sulfite and magnesium sulfite may be calcined separately. For example, in some embodiments, calcium sulfite may be calcined in a separate kiln than magnesium sulfite. For example, in some embodiments, calcium sulfite may be calcined in the same kiln as magnesium sulfite, although in different locations within the same kiln. For example, in some embodiments, calcium sulfite may be calcined in the same kiln as magnesium sulfite, although at different times.

Note: In some embodiments, calcium sulfite and magnesium sulfite may be calcined in the same kiln. For example, a material may comprise both calcium sulfite and magnesium sulfite, and said material comprising both calcium sulfite and magnesium sulfite may be calcined. For example, a separate calcium sulfite and magnesium sulfite may be mixed and may be calcined in the same kiln as a mixture.

Note: Some embodiments may involve using an input material comprising a salt of calcium and/or magnesium or other alkaline earth and a weak acid, wherein said weak acid comprises a weak acid anion other than a carbon dioxide derivative, or other than a carbonate. For example, said weak acid anion other than a carbon dioxide derivative may comprise, including, but not limited to, one or more or a combination of the following: a sulfide, or silicon derivative, or silicate, or aluminate, or ferrate, or ferrite, or iron, or zinc, or aluminum, or manganese, or copper, or a combination thereof.

Note: In some embodiments, a material comprising calcium and/or magnesium may comprise calcium silicate or magnesium silicate or both. In some embodiments, a material comprising calcium and/or magnesium may comprise, for example, including, but not limited to, cement, or concrete, or waste concrete, or steel slag, or iron slag, or slag, or a combination thereof.

Note: In some embodiments, the calcium oxide produced by some embodiments may be employed as an input to the Solvay to make, for example, sodium bicarbonate, or sodium carbonate, or sodium hydroxide and/or reduced CO2 emissions. For example, said calcium oxide may be employed in the Solvay process to remove chloride from ammonium chloride. For example, said calcium oxide may be employed in the Solvay process to reacted with sodium carbonate and/or form sodium hydroxide.

Note: Some embodiments may employ high temperature steam in the calcination process. In some embodiments, it may be desirable for the temperature of the steam to be greater than the decomposition temperature or decomposition temperature range of calcium hydroxide. At least a portion of the steam may be condensed after forming a mixture with sulfur dioxide. If steam is employed, it must be contacted at a temperature greater than the decomposition temperature of calcium hydroxide.

Note: In some embodiments, a gas comprising sulfur dioxide may be compressed prior to or during absorption of sulfur dioxide in one or more or a combination of process steps described herein.

Note: One or more or a combination of reagents, or process steps, or a combination thereof may be heated, or cooled, or a combination thereof.

Note: Calcium silicate may comprise a material comprising silicate. A material comprising an impure limestone comprising at a portion a silicate material. For example, a material comprising silicate may comprise clay, or silicon dioxide, or alumino-silicate, or ferrite, or a combination thereof.

Note: Calcining of calcium sulfite or magnesium sulfite may be conducted in the presence of clay, or silicon dioxide, or shale, or sand, or iron ore, or bauxite, or fly ash, and or slag or other materials employed to, for example, produce or facilitate the production of cement, or cement clinker, or a combination thereof.

Note: In some embodiments, it may be desirable to operate the calcination of calcium sulfite and/or cement manufacturing inputs in the presence of diatomic oxygen. For example, in some embodiments, diatomic oxygen present in a flue gas stream, or in hot gases entering or within a kiln, or a combination thereof may react or oxidize sulfur dioxide, or calcium sulfite, or derivatives thereof to form materials or chemicals which may be facilitate the manufacturing of cement or clinker or may enable advantageous properties in the cement or clinker. For example, in some embodiments, diatomic oxygen present in a flue gas stream, or in hot gases entering or within a kiln, or a combination thereof may react or oxidize sulfur dioxide, or calcium sulfite, or derivatives thereof to form calcium sulfate and/or derivatives thereof, which may be an advantageous ingredient or component of some cement or clinker compositions. For example, in some embodiments, diatomic oxygen present in a flue gas stream, or in hot gases entering or within a kiln, or a combination thereof may react or oxidize sulfur dioxide, or calcium sulfite, or derivatives thereof to form compounds or materials comprising sulfur with superior strength, or chemical resistance, or longevity, or pressure, or compressive strength, or water resistance, or temperature resilience, or other resilience, or cost, or adhesive properties, or chemical compatibility, or a combination thereof. For example, in some embodiments, diatomic oxygen present in a flue gas stream, or in hot gases entering or within a kiln, or a combination thereof may react with or oxidize sulfur dioxide, or calcium sulfite, or derivatives thereof to form compounds or materials with superior strength, or chemical resistance, or longevity, or pressure, or compressive strength, or water resistance, or temperature resilience, or other resilience, or cost, or adhesive properties, or chemical compatibility, or a combination thereof. For example, in some embodiments, diatomic oxygen present in a flue gas stream, or in hot gases entering or within a kiln, or a combination thereof may react with or oxidize sulfur dioxide, or calcium sulfite, or derivatives thereof to produce heat, which may reduce energy requirements or increase the energy efficiency of calcining.

Note: In some embodiments, the use of calcium sulfite as an input material for the production of cement may enable cement with superior properties, which may include, but are not limited to, superior strength, or chemical resistance, or longevity, or pressure, or compressive strength, or water resistance, or temperature resilience, or other resilience, or cost, or adhesive properties, or chemical compatibility, or a combination thereof.

Note: In some embodiments, calcium silicate may comprise cement manufacturing inputs. In some embodiments, cement manufacturing inputs may comprise calcium silicate or calcium carbonate. In some embodiments, cement manufacturing inputs may comprise calcium sulfite, or calcium oxide, or a combination thereof.

Note: In some embodiments, weak acids and weak acid anions may include, but are not limited to, one or more or a combination of the following: silicates, or carbonates, or aluminates, or aluminoferrites, or aluminum oxides, or zinc oxides, or iron oxides, or $Al_2O_6$, or $Al_2Fe_2O_{10}$.

Note: In some embodiments, at least a portion of the gases produced during or from the calcination of calcium sulfite may comprise water or water vapor. For example, if hydrogen, or natural gas, or ammonia, or a hydrocarbon, or other combustion, or steam, or a combination thereof is/are employed to provide heat for calcination, water vapor may be generated and/or may be recovered and/or may be reacted with an alkaline earth oxide.

Note: In some embodiments, nitrogen gas may be added to air before combustion with said air to reduce the concentration of oxygen before said air may be employed in the combustion of fuel for calcining calcium sulfite. For example, a nitrogen concentrating process may be employed. For example, an oxygen concentrating or oxygen removal process may be employed.

Note: In some embodiments, at least a portion of oxygen may be removed from air before combustion with said air to reduce the concentration of oxygen before said air may be employed in the combustion of fuel for calcining calcium sulfite. For example, a nitrogen concentrating process may be employed. For example, an oxygen concentrating or oxygen removal process may be employed.

Note: In some embodiments, a portion of gases after combustion and after sulfur dioxide removal may be added to air to reduce the concentration of diatomic oxygen before said air may be employed in the combustion of fuel for calcining calcium sulfite.

Note: In some embodiments, sulfur dioxide or carbon dioxide or both may be added to air to reduce the concentration of diatomic oxygen before said air may be employed in the combustion of fuel for calcining calcium sulfite.

Note: It may be desirable to calcine the calcium sulfite under conditions where the temperature is sufficiently low to prevent produced CaO crystallites from fusing. It may be desirable to calcine calcium sulfite under conditions and temperatures where the specific surface of the calcium oxide remains intact. It may be desirable to produce CaO with non-fused crystals, or where the specific surface of the calcium oxide remains intact, or a combination thereof for applications, which may include, but are not limited to, the steel industry.

Note: It may be desirable to calcine the calcium sulfite under conditions where the temperature is sufficiently high to facilitate the production of fused CaO crystallites. It may be desirable to calcine calcium sulfite under conditions and temperatures which reduce the specific surface of the calcium oxide. It may be desirable to produce CaO with fused crystals, or where the specific surface of the calcium oxide is reduced, or a combination thereof for applications, which may include, but are not limited to, the production of aerated concrete, or sand lime bricks, or a combination thereof.

Note: Heat sources may include, but are not limited to, one or more or a combination of the following: combustion of a fuel, hydrogen, ammonia, natural gas, heavy fuel oil, pulverized coal, liquefied gas, off-gas from steel-making process, wood dust, waste oil, biomass, biofuel, electricity, heat pump, solar thermal, chemical reaction, sulfur, sulfurous fuel, sulfuric acid production, salt production, waste heat, waste gases, nuclear heat, geothermal, quicklime, hydration reaction, oxidation.

Note: One or more of the present embodiments may produce strongly carbon dioxide negative or negative emissions calcium oxide Note: In some embodiments, produced calcium oxide may be reacted with carbon dioxide originating from the air or separated from the air. For example, calcium oxide may be reacted with sodium carbonate or potassium carbonate or sodium carbonate or potassium carbonate solution to produce sodium hydroxide or potassium hydroxide solution and calcium carbonate, which may be a permanent sequestration byproduct. Said sodium hydroxide or potassium hydroxide solution may then be contacted with air or $CO_2$ originating from air to produce a solution comprising sodium carbonate, or potassium carbonate, or a combination thereof.

Note: A portion of the calcium oxide produced may be converted to calcium carbonate by reaction, with, for example, carbon dioxide in the air, or carbon dioxide originating from the air, or an air capture process, or regenerating an alkali-carbonate to an alkali-oxide in an absorption loop, or regenerating an alkali-carbonate to an alkali-oxide in an absorption or separation process, or a combination thereof.

Note: A portion of the cement produced may be employed in the production of non-hydraulic cement, or cement employing at least a portion of $CO_2$ input, or a combination thereof to increase the net $CO_2$ removal or emissions reduction.

Note: In some embodiments, magnesium and calcium may be present in the same input material. For example, slags, or waste concrete, or minerals may comprise at least a portion of magnesium. For example, dolomite may comprise a portion of magnesium. In some embodiments, at least a portion of magnesium sulfite and/or magnesium oxide and/or magnesium hydroxide may be produced separately from calcium sulfite and/or calcium oxide and/or calcium hydroxide. For example, the separation of calcium and magnesium may be conducted by including, but not limited to, the significant difference in solubility in water between magnesium sulfite and calcium sulfite and/or the significant temperature dependent solubility of magnesium sulfite.

Note: The concentration of magnesium oxide, or calcium oxide, or sodium hydroxide, or sodium carbonate, or sodium bicarbonate in an output comprising magnesium oxide, or calcium oxide, or sodium hydroxide, or sodium carbonate, or sodium bicarbonate may be greater than or equal to one or more of the following weight percent concentrations: 0.0001%, or 0.5%, or 1%, or 1.5%, or 2%, or 2.5%, or 3%, or 3.5%, or 4%, or 4.5%, or 5%, or 5.5%, or 6%, or 6.5%, or 7%, or 7.5%, or 8%, or 8.5%, or 9%, or 9.5%, or 10%, or 10.5%, or 11%, or 11.5%, or 12%, or 12.5%, or 13%, or 13.5%, or 14%, or 14.5%, or 15%, or 15.5%, or 16%, or 16.5%, or 17%, or 17.5%, or 18%, or 18.5%, or 19%, or 19.5%, or 20%, or 20.5%, or 21%, or 21.5%, or 22%, or 22.5%, or 23%, or 23.5%, or 24%, or 24.5%, or 25%, or 25.5%, or 26%, or 26.5%, or 27%, or 27.5%, or 28%, or 28.5%, or 29%, or 29.5%, or 30%, or 30.5%, or 31%, or 31.5%, or 32%, or 32.5%, or 33%, or 33.5%, or 34%, or 34.5%, or 35%, or 35.5%, or 36%, or 36.5%, or 37%, or 37.5%, or 38%, or 38.5%, or 39%, or 39.5%, or 40%, or 40.5%, or 41%, or 41.5%, or 42%, or 42.5%, or 43%, or 43.5%, or 44%, or 44.5%, or 45%, or 45.5%, or 46%, or 46.5%, or 47%, or 47.5%, or 48%, or 48.5%, or 49%, or 49.5%, or 50%, or 50.5%, or 51%, or 51.5%, or 52%, or 52.5%, or 53%, or 53.5%, or 54%, or 54.5%, or 55%, or 55.5%, or 56%, or 56.5%, or 57%, or 57.5%, or 58%, or 58.5%, or 59%, or 59.5%, or 60%, or 60.5%, or 61%, or 61.5%, or 62%, or 62.5%, or 63%, or 63.5%, or 64%, or 64.5%, or 65%, or 65.5%, or 66%, or 66.5%, or 67%, or 67.5%, or 68%, or 68.5%, or 69%, or 69.5%, or 70%, or 70.5%, or 71%, or 71.5%, or 72%, or 72.5%, or 73%, or 73.5%, or 74%, or 74.5%, or 75%, or 75.5%, or 76%, or 76.5%, or 77%, or 77.5%, or 78%, or 78.5%, or 79%, or 79.5%, or 80%, or 80.5%, or 81%, or 81.5%, or 82%, or 82.5%, or 83%, or 83.5%, or 84%, or 84.5%, or 85%, or 85.5%, or 86%, or 86.5%, or 87%, or 87.5%, or 88%, or 88.5%, or 89%, or 89.5%, or 90%, or 90.5%, or 91%, or 91.5%, or 92%, or 92.5%, or 93%, or 93.5%, or 94%, or 94.5%, or 95%, or 95.5%, or 96%, or 96.5%, or 97%, or 97.5%, or 98%, or 98.5%, or 99%, or 99.5%, or 99.999%

Note: The concentration of oxygen gas or diatomic oxygen in a head space or a reactor may be lower than or equal to one or more of the following volume percent concentrations: 0.0001%, or 0.5%, or 1%, or 1.5%, or 2%, or 2.5%, or 3%, or 3.5%, or 4%, or 4.5%, or 5%, or 5.5%, or 6%, or 6.5%, or 7%, or 7.5%, or 8%, or 8.5%, or 9%, or 9.5%, or 10%, or 10.5%, or 11%, or 11.5%, or 12%, or 12.5%, or 13%, or 13.5%, or 14%, or 14.5%, or 15%, or 15.5%, or 16%, or 16.5%, or 17%, or 17.5%, or 18%, or 18.5%, or 19%, or 19.5%, or 20%, or 20.5%, or 21%, or 21.5%, or 22%, or 22.5%, or 23%, or 23.5%, or 24%, or 24.5%, or 25%, or 25.5%, or 26%, or 26.5%, or 27%, or 27.5%, or 28%, or 28.5%, or 29%, or 29.5%, or 30%, or 30.5%, or 31%, or 31.5%, or 32%, or 32.5%, or 33%, or 33.5%, or 34%, or 34.5%, or 35%, or 35.5%, or 36%, or 36.5%, or 37%, or 37.5%, or 38%, or 38.5%, or 39%, or 39.5%, or 40%, or 40.5%, or 41%, or 41.5%, or 42%, or 42.5%, or 43%, or 43.5%, or 44%, or 44.5%, or 45%, or 45.5%, or 46%, or 46.5%, or 47%, or 47.5%, or 48%, or 48.5%, or 49%, or 49.5%, or 50%, or 50.5%, or 51%, or 51.5%, or 52%, or 52.5%, or 53%, or 53.5%, or 54%, or 54.5%, or 55%, or 55.5%, or 56%, or 56.5%, or 57%, or 57.5%, or 58%, or 58.5%, or 59%, or 59.5%, or 60%, or 60.5%, or 61%, or 61.5%, or 62%, or 62.5%, or 63%, or 63.5%, or 64%, or 64.5%, or 65%, or 65.5%, or 66%, or 66.5%, or 67%, or 67.5%, or 68%, or 68.5%, or 69%, or 69.5%, or 70%, or 70.5%, or 71%, or 71.5%, or 72%, or 72.5%, or 73%, or 73.5%, or 74%, or 74.5%, or 75%, or 75.5%, or 76%, or 76.5%, or 77%, or 77.5%, or 78%, or 78.5%, or 79%, or 79.5%, or 80%, or 80.5%, or 81%, or 81.5%, or 82%, or 82.5%, or 83%, or 83.5%, or 84%, or 84.5%, or 85%, or 85.5%, or 86%, or 86.5%, or 87%, or 87.5%, or 88%, or 88.5%, or 89%, or 89.5%, or 90%, or 90.5%, or 91%, or 91.5%, or 92%, or 92.5%, or 93%, or 93.5%, or 94%, or 94.5%, or 95%, or 95.5%, or 96%, or 96.5%, or 97%, or 97.5%, or 98%, or 98.5%, or 99%, or 99.5%, or 99.999%

Note: Calcining kilns may include, but are not limited to, one or more or a combination of the following: Shaft kilns, or Counter-current shaft kilns, or Regenerative kilns, or Annular kilns, or Rotary kilns.

Note: In some embodiments, at least a portion of heat may be supplied by a heat pump, or a refrigeration cycle, or a combination thereof. A heat pump may comprise, including, but not limited to, a mechanical, or thermal, or absorption, or a combination thereof process. A heat pump may be powered by, including, but not limited to, electricity, or heat, or photons, or chemical reaction, or radiation, or mechanical work, or pneumatic process, or hydraulic process, or expansion, or compression, or evaporation, or absorption, or vapor pressure differences, or osmotic pressure differences, or temperature differences, or pressure differences, or a combination thereof.

Note: Other acid gases may be employed instead of or in addition to sulfur dioxide, which may include, but are not limited to, nitrogen oxides, or nitrogen dioxide, or nitrogen monoxide, or dinitrogen tetroxide, or nitric acid, or carbon dioxide, or carbonic acid, or hydrogen sulfuric, or sulfonic acid, or hydrosulfuric acid, or organo-sulfurous compounds, or hydrochloric acid, or hydrobromic acid, or hydroiodic acid, or hydrogen cyanide, or sulfuric acid, or perchloric acid, or nitrous acid, or hydrofluoric acid, or nitrogen derivative acids, or halogen derivative acids, or derivatives thereof, or a combination thereof.

Note: Organic acids, or carboxylic acids, or organic acid anions, or a combination thereof may include, but are not limited to, one or more or a combination of the following: citric acid, or aconitates, or citrates, or isocitrates, or alloisocitrate, or oxalic acid, or acetic acid, or carboxylic acids, or lactic acid, or aconitic acid, or formic acid, or uric acid, or malic acid, or tartaric acid, methanoic acid, or hydroxymethanoic acid, or ethanoic acid, or 2-hydroxyethanoic acid, or oxoethanoic acid, or ethanedioic acid, or propanoic acid, or propenoic acid, or propynoic acid, or 2-hydroxypropanoic acid, or 3-hydroxypropanoic acid, or 2,3-dihydroxypropanoic acid, or 2-oxopropanoic acid, or 3-oxopropanoic acid, or 2,3-dioxopropanoic acid, or propanedioic acid, or 2-hydroxypropanedioic acid, or 2,2-dihydroxypropanedioic acid, or oxopropanedioic acid, or oxirane-2-carboxylic acid, or butanoic acid, or 2-methylpropanoic acid, or (E)-but-2-enoic acid, or (Z)-but-2-enoic acid, or 2-methylpropenoic acid, or but-3-enoic acid, or but-2-ynoic acid, or 2-hydroxybutanoic acid, or 3-hydroxybutanoic acid, or 4-hydroxybutanoic acid, or 2-oxobutanoic acid, or 3-oxobutanoic acid, or 4-oxobutanoic acid, or butanedioic acid, or 2-methylpropanedioic acid, or (E)-butenedioic acid, or (Z)-butenedioic acid, or butynedioic acid, or hydroxybutanedioic acid, or 2,3-dihydroxybutanedioic acid, or oxobutanedioic acid, or dioxobutanedioic acid, or pentanoic acid, or 3-methylbutanoic acid, or 2-methylbutanoic acid, or 2,2-dimethylpropanoic acid, or 3-hydroxypentanoic acid, or 4-hydroxypentanoic acid, or 3-hydroxy-3-methylbutanoic acid, or pentanedioic acid, or 2-oxopentanedioic acid, or 3-oxopentanedioic acid, or furan-2-carboxylic acid, or tetrahydrofuran-2-carboxylic acid, or hexanoic acid, or hexanedioic acid, or 2,3-dimethylbutanoic acid, or 3,3-dimethylbutanoic acid, or 2-hydroxypropane-1,2,3-tricarboxylic acid, or prop-1-ene-1,2,3-tricarboxylic acid, or 1-hydroxypropane-1,2,3-tricarboxylic acid, or (2E,4E)-hexa-2,4-dienoic acid, or heptanoic acid, or heptanedioic acid, or cyclohexanecarboxylic acid, or benzenecarboxylic acid, or 2-hydroxybenzoic acid, or 4-carboxybenzoic acid, or 2,2-dimethylpentanoic acid, or 2,3-dimethylpentanoic acid, or 2,4-dimethylpentanoic acid, or 3,3-dimethylpentanoic acid, or 2-ethylpentanoic acid, or 3-ethylpentanoic acid, or 2-methylhexanoic acid, or 3-methylhexanoic acid, or 2,2,3-trimethylbutanoic acid, or 2-ethyl-2-methylbutanoic acid, or 2-ethyl-3-, or methylbutanoic acid, or octanoic acid, or benzene-1,2-dicarboxylic acid, or 2-methylheptanoic acid, or 3-methylheptanoic acid, or 4-methylheptanoic acid, or 5-methylheptanoic acid, or 6-methylheptanoic acid, or 2,2-dimethylhexanoic acid, or 2,3-dimethylhexanoic acid, or 2,4-dimethylhexanoic acid, or 2,5-dimethylhexanoic acid, or 3,3-dimethylhexanoic acid, or 3,4-dimethylhexanoic acid, or 3,5-dimethylhexanoic acid, or 4,4-dimethylhexanoic acid, or 4,5-dimethylhexanoic acid, or 5,5-dimethylhexanoic acid, or 2-ethanehexanoic acid, or 3-ethanehexanoic acid, or 4-ethanehexanoic acid, or 5-ethanehexanoic acid, or 2-octenoic acid, or 3-octenoic acid, or 4-octenoic acid, or 5-octenoic acid, or 6-octenoic acid, or 7-octenoic acid, or nonanoic acid, or benzene-1,3,5-tricarboxylic acid, or (E)-3-phenylprop-2-enoic acid, or decanoic acid, or decanedioic acid, or undecanoic acid, or dodecanoic acid, or benzene-1,2,3,4,5,6-hexacarboxylic acid, or tridecanoic acid, or tetradecanoic acid, or pentadecanoic acid, or hexadecanoic acid, or heptadecanoic acid, or octadecanoic acid, or (9Z)-octadec-9-enoic acid, or (9Z,12Z)-octadeca-9,12-dienoic acid, or (9Z,12Z,15Z)-octadeca-9,12,15-trienoic acid, or (6Z,9Z,12Z)-octadeca-6,9,12-trienoic acid, or (6Z,9Z,12Z,15Z)-octadeca-6,9,12,15-tetraenoic acid, or nonadecanoic acid, or eicosanoic acid, or (5Z,8Z,11Z)-eicosa-5,8,11-trienoic acid, or (5Z,8Z,11Z,14Z)-eicosa-5,8,11,14-tetraenoic acid, or (5Z,8Z,11Z,14Z,17Z)-eicosa-5,8,11,14-pentaenoic acid, orheneicosanoic acid, or docosanoic acid, or (4Z,7Z,10Z,13Z,16Z,19Z)-docosa-4,7,10,13,16,19-hexaenoic acid, or tricosanoic acid, or tetracosanoic acid, or pentacosanoic acid, or hexacosanoic acid, or amino acids, or glutamate, or glutamic acid.

Note: Weak acids or organic acids may include, but are not limited to, one or more or a combination of the following: carboxylic acids, or sulfonic acids, or alcohols, or thiols, or enols, or phenols, or carbonic acid Note: Calcium oxide produced may be reacted with water to produce calcium hydroxide or a solution comprising aqueous calcium hydroxide. The aqueous calcium hydroxide may be reacted sodium carbonate, such as an aqueous solution of sodium carbonate, to produce precipitate calcium carbonate and aqueous sodium hydroxide. The precipitated calcium carbonate may be separated from the aqueous sodium hydroxide and may comprise a valuable byproduct. The aqueous sodium hydroxide may be reacted with a gas comprising carbon dioxide to produce aqueous sodium carbonate. For example, aqueous sodium hydroxide may be reacted with flue gas, or raw gas, or air, or gases produced from fuel combusted to power the calciner, or remaining gases after absorption of sulfur dioxide, or other gas comprising at least a portion CO2, or a combination thereof. Some embodiments of the present invention may be employed to produce CO2-emissions neutral or negative precipitated calcium carbonate. Some embodiments of the present invention may involve producing CO2-emissions neutral or negative precipitated calcium carbonate using CO2 from the air or captured from the air using the presently described process. Some embodiments of the present invention may involve producing CO2-emissions neutral or negative precipitated calcium carbonate using CO2 from emissions sources, or air, or both using the presently described process.

Note: The weight percent concentration of one or more or a combination of reagents may include, but is not limited to, less than, or equal to, or greater than one or more or a combination of the following: 0%, or 0.5%, or 1%, or 1.5%, or 2%, or 2.5%, or 3%, or 3.5%, or 4%, or 4.5%, or 5%, or 5.5%, or 6%, or 6.5%, or 7%, or 7.5%, or 8%, or 8.5%, or 9%, or 9.5%, or 10%, or 10.5%, or 11%, or 11.5%, or 12%, or 12.5%, or 13%, or 13.5%, or 14%, or 14.5%, or 15%, or 15.5%, or 16%, or 16.5%, or 17%, or 17.5%, or 18%, or 18.5%, or 19%, or 19.5%, or 20%, or 20.5%, or 21%, or 21.5%, or 22%, or 22.5%, or 23%, or 23.5%, or 24%, or 24.5%, or 25%, or 25.5%, or 26%, or 26.5%, or 27%, or 27.5%, or 28%, or 28.5%, or 29%, or 29.5%, or 30%, or 30.5%, or 31%, or 31.5%, or 32%, or 32.5%, or 33%, or 33.5%, or 34%, or 34.5%, or 35%, or 35.5%, or 36%, or 36.5%, or 37%, or 37.5%, or 38%, or 38.5%, or 39%, or 39.5%, or 40%, or 40.5%, or 41%, or 41.5%, or 42%, or 42.5%, or 43%, or 43.5%, or 44%, or 44.5%, or 45%, or 45.5%, or 46%, or 46.5%, or 47%, or 47.5%, or 48%, or 48.5%, or 49%, or 49.5%, or 50%, or 50.5%, or 51%, or 51.5%, or 52%, or 52.5%, or 53%, or 53.5%, or 54%, or 54.5%, or 55%, or 55.5%, or 56%, or 56.5%, or 57%, or 57.5%, or 58%, or 58.5%, or 59%, or 59.5%, or 60%, or 60.5%, or 61%, or 61.5%, or 62%, or 62.5%, or 63%, or 63.5%, or 64%, or 64.5%, or 65%, or 65.5%, or 66%, or 66.5%, or 67%, or 67.5%, or 68%, or 68.5%, or 69%, or 69.5%, or 70%, or 70.5%, or 71%, or 71.5%, or 72%, or 72.5%, or 73%, or 73.5%, or 74%, or 74.5%, or 75%, or 75.5%, or 76%, or 76.5%, or 77%, or 77.5%, or 78%, or 78.5%, or 79%, or 79.5%, or 80%, or 80.5%, or 81%, or 81.5%, or 82%, or 82.5%, or 83%, or 83.5%, or 84%, or 84.5%, or 85%, or 85.5%, or 86%, or 86.5%, or 87%, or 87.5%, or 88%, or 88.5%, or 89%, or 89.5%, or 90%, or 90.5%, or 91%, or 91.5%, or 92%, or 92.5%, or 93%, or 93.5%, or 94%, or 94.5%, or 95%, or 95.5%, or 96%, or 96.5%, or 97%, or 97.5%, or 98%, or 98.5%, or 99%, or 99.5%, or 100%

Note: Calcium silicate input or magnesium silicate input may comprise a slag. For example, global iron slag production is estimated to be 320 million to 384 million tons annually and steel stag is estimated to be between 190 million to 280 million tons annually. Other slags may include, but are not limited to, slags from magnesium production. Slags are generally produced when calcium oxide or magnesium oxide are added to a metal production process to remove impurities, or facilitate certain conditions or properties, or a combination thereof. Some embodiments may convert said slags into calcium oxide or magnesium oxide or other alkaline earth oxide. Some embodiments may enable a circular economy in the iron-marking, or steel-making, or other metal production industries because calcium oxide and/or magnesium oxide are used as the inputs which result in the production of slag. If iron or steel makers can recycle at least a portion of slag into calcium oxide or magnesium oxide, iron or steel makers may greatly reduce or eliminate their need to purchase calcium oxide or magnesium oxide, significantly reducing operating costs. If at least a portion of iron or steel stag is recycled into calcium oxide or magnesium oxide, iron and/or steel production lifecycle carbon dioxide emissions will be greatly reduced.

Note: Calcium sulfite and/or magnesium sulfite may comprise hydrates. For example, magnesium sulfite may form a hexahydrate, or a trihydrate, or may be anhydrous. For example, calcium sulfite may form a tetrahydrate, or a hemihydrate, or may be anhydrous. It may be desirable to dehydrate at least a portion of the hydrate of calcium sulfite, or magnesium sulfite, or both before or during calcining of a sulfite into an oxide and sulfur dioxide. It may be desirable to dehydrate at least a portion of the hydrate of calcium sulfite, or magnesium sulfite, or both before calcining of a sulfite into an oxide and sulfur dioxide. For example, magnesium sulfite hexahydrate may be heated to above 40° C., where magnesium sulfite hexahydrate may decompose or dehydrate into magnesium sulfite trihydrate. For example, calcium sulfite tetrahydrate may be heated to decompose or dehydrate into calcium sulfite hemihydrate. For example, calcium and/or magnesium hydrates may be decomposed or dehydrated into anhydrous forms. For example, calcium sulfite hydrate and/or magnesium sulfite hydrate may be heated to decompose or dehydrate into anhydrous forms. Dehydrating hydrates may require heat or other energy. It may be desirable to supply said heat or other energy for dehydrating hydrates from lower cost, or lower quality heat sources, such as, including, but not limited to, one or more or a combination of the following: waste heat, or heat from other process steps, or low quality steam, or medium quality steam, or high quality step, or combustion of one or more fuels, or solar thermal, or slacking lime, or hydrating a oxide to a hydroxide, or other heat source.

Note: At least a portion of the weak acid product, or undissolved materials, or a combination thereof are employed as a concrete aggregate.

Note: At least a portion of the weak acid product, or undissolved materials, or a combination thereof may be disposed of or may comprise a waste product.

Note: A material comprising calcium and/or magnesium may comprise a material comprising an alkaline-earth. Alkaline-earths may include one or more or a combination of the following: beryllium (Be), or magnesium (Mg), or calcium (Ca), or strontium (Sr), or barium (Ba), or radium (Ra)

Note: In some embodiments, a material comprising calcium and/or magnesium or an alkaline earth may further comprise one or more or a combination of the following: iron oxides, or iron, or manganese oxide, or manganese, may include, but are not limited to, one or more or a combination of the following: iron (II), or iron (II,III), or iron (III), or iron (II) oxide, or iron (II,II) oxide, or iron (III) oxide, or iron sulfite, or iron sulfate, or iron sulfide, or iron, or ferrites, or ferrates, or calcium-iron salts, or magnesium iron salts, or iron silicate salts, or iron silicon salts, or iron carbon salts, or manganese salts, or manganese−3, or manganese−2, or manganese−1, or manganese 0, or manganese+1, or manganese+2, or manganese, or manganese+3, or manganese+4, or manganese+5, or manganese+6, or manganese+7, or manganese sulfite, or manganese oxide, or manganese carbonate, or manganese-iron, or calcium-manganese, or calcium-manganese salts, or magnesium-manganese, or magnesium-manganese salts, or manganese silicon, or manganese carbon, or manganese Note: The properties of iron and manganese may be similar. Manganese may be present in some materials which may comprise iron, such as some slags, or concretes, or minerals. In some embodiments, iron and manganese may be used interchangeably.

Note: Solutions comprising salts of metals lead, or copper, or gold, or silver, or zinc, or aluminum, or chromium, or cobalt, or manganese, or rare-earth metals, or iron, or molybdenum, or cadmium, or nickel, or silver, or cobalt, or zinc, or gold, or platinum, or platinum group metals, or a combination thereof may undergo a separations and/or refining process. For example, one or more or a combination of said metals may be separated or produced from solution or from a separated state or both by means of, for example, including, but not limited to, one or more or a combination of the following: electrolytic refining, or electrowinning, or electroextraction, or electrodeposition. For example, a solution comprising aqueous iron bisulfite, or manganese bisulfite, or iron sulfate, or manganese bisulfate, or iron chloride, or magnesium chloride may undergo electroextraction to produce manganese, iron, or a combination thereof. In some embodiments, one or more or a combination of the aforementioned metals may be separated by reaction with hydrogen sulfide or sulfur to produce a sulfide or an insoluble sulfide, then said sulfide may be converted into a form for use as in input to an electroextraction process.

Note: Separation of at least a portion of iron sulfite solid from at least a portion of calcium sulfite solid, or separation of iron from calcium or magnesium, or a combination thereof may be conducted by, including, but not limited to, one or more or a combination of the following: density based separation, or floatation and sinking separation using a dense liquid, or separation using a dense liquid, or separation using a liquid with a lower density than iron sulfite and a greater density than calcium sulfite, or magnetic separation, or magnetic separation of iron from calcium, or oxidation of iron, or reaction of solution comprising dissolved iron with hydrogen sulfide to produce iron sulfide solid precipitate, or reaction of solution comprising calcium with sulfuric acid to form calcium sulfate precipitate, or frothing, or floatation, or solid separation, or centrifuge, or grinding, or pulverization, or reaction of iron sulfite and calcium sulfite solids with sulfuric acid to form dissolved or aqueous iron sulfate and calcium sulfate solid, or reaction of a mixture of calcium oxide and iron oxide with water to form calcium hydroxide dissolved or aqueous and iron oxide solid, or precipitation of iron sulfite before calcium sulfite, or precipitation of calcium sulfite before iron sulfite, or electrodialysis, or electrodialysis reversal, or ion exchange, or iron exchange resin, or iron reaction, or double-salt reaction, or precipitation reaction, or temperature driven precipitation, or concentration driven precipitation Note: In some embodiments, 'oxide' or 'hydroxide' or a combination thereof may be considered weak acids or 'weak acid anions' or a combination thereof.

Note: Separations may include, but are not limited to, one or more or a combination of the following: Separation by density, or Separation by magnetism, or Separation by frothing or surface tension, or Separation by residual solubility differences, or Separation by oxidation, or Separation by ion exchange, or Separation by reaction with an alkali hydroxide solution, or Separation by reaction with hydrogen sulfide, or Separation by reaction with aqueous sulfuric acid, or Separation by density using a high density liquid with a density less than at least one salt and a density greater than one salt, or Separation by density using a high density liquid with a density less than iron sulfite and a density greater than calcium sulfite, or Separation by density using a centrifuge, or Separation by a magnetic field using a mixing and an externally applied magnetic field, or Separation by reaction with and/or dissolution in water, or Grinding or pulverization, or Separation by froth flotation, or Other solid-solid separation method, or Other method for separating iron from calcium, or Other separation method Note: In some embodiments, remaining solution after separating magnesium sulfite solid using a solid-liquid separate process may be further treated with, including, but not limited to, one or more or a combination of the following: ion exchange, or resins, or filters, or chemical treatments, or chemical reactions, or membrane based process, or distillation, or cooling, or heating, or freezing, or cryodesalination, or solventing-out, or solvent induced precipitation, or salting-out, or other treatment. One or more solutions comprising water may be transferred to a sulfur dioxide absorption step, or mixed with a solution transferred to a sulfur dioxide absorption step, or a combination thereof.

Additional Notes

1. Process for producing sodium hydroxide wherein the process comprises:

reacting calcium bearing material with aqueous acetic acid to produce aqueous calcium acetate 1. A process for producing sodium hydroxide wherein the process comprises:

reacting a calcium-silicate salt with aqueous acetic acid to produce aqueous calcium acetate and silicon dioxide solid;

separating said silicon dioxide solid from water;

reacting aqueous calcium acetate with sodium sulfate to produce aqueous sodium acetate and calcium sulfate solid precipitate;

separating said calcium sulfate solid from aqueous sodium acetate;

reacting aqueous sodium acetate with sulfur dioxide to produce aqueous sodium sulfite and acetic acid;

separating sodium sulfite from aqueous acetic acid;

reacting sodium sulfite with calcium hydroxide to produce sodium hydroxide.

1. A process for producing an sodium hydroxide wherein the process comprises:

reacting a calcium carbonate anion salt with aqueous acetic acid to produce aqueous calcium acetate and carbon dioxide;

reacting aqueous calcium acetate with sodium sulfate to produce aqueous sodium acetate and calcium sulfate solid precipitate;

separating said calcium sulfate solid from aqueous sodium acetate;

reacting aqueous sodium acetate with sulfur dioxide to produce aqueous sodium sulfite and acetic acid;

separating sodium sulfite from aqueous acetic acid;

reacting sodium sulfite with calcium hydroxide to produce sodium hydroxide.

Note: In some embodiments, Acetic acid may be nearly miscible or completely miscible in water, while sodium sulfite may be partially miscible. In some embodiments, if water and acetic acid may be removed using distillation or evaporation, sodium sulfite may eventually precipitate or crystallize from solution.

Some embodiments may comprise condensing water vapors into an acetic acid solution following sodium sulfite separation/precipitation/crystallization Calcining calcium sulfite to produce calcium oxide Drying calcium sulfite before calcining by employing calcium oxide as a desiccant (calcium oxide reacts with water or water vapor to produce calcium hydroxide)

1. A process for producing calcium oxide or calcium hydroxide or cement wherein the process comprises:

reacting a calcium carbonate with a solution comprising aqueous acetic acid and aqueous sodium sulfite to produce aqueous sodium acetate, calcium sulfite solid, and carbon dioxide gas;

separating said calcium sulfite solid from aqueous sodium acetate;

decomposing calcium sulfite solid to produce calcium oxide and sulfur dioxide;

reacting aqueous sodium acetate with sulfur dioxide to produce aqueous sodium sulfite and acetic acid.

1. A process for producing calcium oxide or calcium hydroxide or cement wherein the process comprises:

reacting a calcium carbonate with aqueous acetic acid to produce aqueous calcium acetate and carbon dioxide;

reacting aqueous calcium acetate with sodium sulfite to produce aqueous sodium acetate and calcium sulfite solid precipitate;

separating said calcium sulfite solid from aqueous sodium acetate;

reacting aqueous sodium acetate with sulfur dioxide to produce aqueous sodium sulfite and acetic acid;

separating aqueous sodium sulfite from aqueous acetic acid by reverse osmosis or nanofiltration;

Wherein aqueous acetic acid permeates the membrane and sodium sulfite is rejected by the membrane;

decomposing calcium sulfite solid to produce calcium oxide and sulfur dioxide.

1. A process for producing calcium oxide or calcium hydroxide or cement wherein the process comprises:

reacting a calcium carbonate with aqueous acetic acid to produce aqueous calcium acetate and carbon dioxide;

reacting aqueous calcium acetate with sodium sulfite to produce aqueous sodium acetate and calcium sulfite solid precipitate;

separating said calcium sulfite solid from aqueous sodium acetate;

reacting aqueous sodium acetate with sulfur dioxide to produce aqueous sodium sulfite and acetic acid;

separating aqueous sodium sulfite from aqueous acetic acid by reverse osmosis or nanofiltration;

decomposing calcium sulfite solid to produce calcium oxide and sulfur dioxide.

1. A process for producing calcium oxide or calcium hydroxide or cement wherein the process comprises:

reacting a calcium carbonate with aqueous acetic acid to produce aqueous calcium acetate and carbon dioxide;

reacting aqueous calcium acetate with sodium sulfite to produce aqueous sodium acetate and calcium sulfite solid precipitate;

separating said calcium sulfite solid from aqueous sodium acetate;

reacting aqueous sodium acetate with sulfur dioxide to produce aqueous sodium sulfite and acetic acid;

separating sodium sulfite from aqueous acetic acid;

decomposing calcium sulfite solid to produce calcium oxide and sulfur dioxide.

1. A process for producing an calcium oxide and acetic acid from calcium acetate wherein the process comprises:

reacting aqueous calcium acetate with sulfur dioxide to produce aqueous acetic acid and calcium sulfite solid precipitate;

separating said calcium-sulfite solid from water;

calcining said calcium-sulfite solid to produce calcium-oxide, cement, or a combination thereof.

1. A process for producing an calcium oxide wherein the process comprises: reacting an calcium-silicate anion salt with aqueous acetic acid to produce aqueous calcium acetate and silicon dioxide solid;

separating said silicon dioxide solid from water;

reacting aqueous calcium acetate with sulfur dioxide to produce aqueous acetic acid and calcium sulfite solid precipitate;

separating said calcium-sulfite solid from water;

calcining said calcium-sulfite solid to produce calcium-oxide, cement, or a combination thereof.

1. A process for producing an calcium oxide wherein the process comprises: reacting an calcium carbonate with aqueous acetic acid to produce aqueous calcium acetate and carbon dioxide gas;

reacting aqueous calcium acetate with sulfur dioxide to produce aqueous acetic acid and calcium sulfite solid;

separating said calcium-sulfite solid from water;

calcining said calcium-sulfite solid to produce calcium-oxide, cement, or a combination thereof;

Wherein said carbon dioxide gas comprises captured carbon dioxide

Wherein calcium oxide produced is employed to absorb water vapor from a carrier gas employed to remove water from calcium sulfite hydrate or dehydrate calcium sulfite Wherein calcium oxide produced is employed to dry calcium sulfite hydrate Wherein calcium oxide produced is employed to dry calcium sulfite Wherein the heat from the reaction of calcium oxide with water is employed to dry calcium sulfite Absorbing $SO_2$ gas into a solution comprising aqueous calcium acetate to form a calcium sulfite precipitate and aqueous acetic acid Wherein off-gases produced during the decomposition of calcium sulfite are contacted with a solution comprising aqueous calcium acetate to form a calcium sulfite precipitate and aqueous acetic acid Wherein said off-gases comprise nitrogen, oxygen, carbon dioxide, water vapor, and sulfur dioxide Wherein said off-gases comprise nitrogen, oxygen, carbon dioxide, and sulfur dioxide Wherein said off-gases comprise nitrogen, oxygen, and sulfur dioxide Wherein said off-gases comprising nitrogen and sulfur dioxide It may be desirable to employ a high concentration of acetic acid, although a sufficiently low concentration such that calcium acetate is capable of dissolving in the solution.

In some embodiments, sulfur dioxide gas may be added or contacted with the aqueous calcium acetate-rich solution and/or the aqueous calcium acetate may react with sulfur dioxide (or aqueous sulfur dioxide or sulfurous acid) to form calcium sulfite solid precipitate and aqueous acetic acid.

reacting calcium oxide with water to produce calcium hydroxide or milk of lime, wherein the heat generated may be employed to facilitate the drying of calcium sulfite before calcining reacting calcium hydroxide or calcium oxide with carbon dioxide to produce calcium carbonate Wherein said calcium carbonate comprises precipitated calcium carbonate or high purity calcium carbonate Wherein said carbon dioxide comprises a gas comprising carbon dioxide, which may include, but is not limited to, air, or emissions gas, or Formic acid instead of or in addition to acetic acid Wherein said carbon dioxide comprises a gas comprising carbon dioxide, which may include, but is not limited to, carbon dioxide from the reaction of calcium carbonate with acetic acid reacting in the presence of clay or other material to produce cement reacting comprises contacting a gas stream comprising sulfur dioxide with a solution comprising calcium acetate gas stream comprises sulfur dioxide from calcining calcium sulfite gas stream comprises sulfur dioxide from calcining calcium sulfite, and the concentration of SO2 is less than_vol % gas stream comprises sulfur dioxide from calcining calcium sulfite, SO2 is separated and comprises a high concentration SO2 gas with a concentration of SO2 greater than_vol % gas stream comprises sulfur dioxide from calcining calcium sulfite, SO2 is separated and comprises a high concentration SO2 gas with a partial pressure of SO2 greater than_atm sulfur dioxide is separated by cryogenic or cooling condensing from kiln gases or from gases produced or generated during the decomposition of calcium sulfite reacting comprises contacting or mixing liquid sulfur dioxide with a solution comprising calcium acetate reacting comprises contacting or mixing solid sulfur dioxide with a solution comprising calcium acetate continuous, Batch, Semi-batch (describe implementation for each process step)

silicate, or carbonate, or sulfide carboxylic acid or organic acid, such as acetic, or benzoic, or formic, or propanoic, or citric, or lactic, or malic

EXAMPLE EMBODIMENTS

Additional Example Description Example Embodiments Sodium Hydroxide Production with Carboxylic Acid and Sulfur Dioxide Intermediates 1. A process comprising:

reacting a material comprising calcium carbonate with a solution comprising aqueous carboxylic acid to form a gas comprising carbon dioxide and a solution comprising aqueous calcium carboxylate;

reacting the solution comprising aqueous calcium carboxylate with sodium sulfate to form a solution comprising aqueous sodium carboxylate and a solid comprising calcium sulfate;

reacting the solution comprising aqueous sodium carboxylate with sulfur dioxide to form sodium sulfite and carboxylic acid;

separating said sodium sulfite from said aqueous carboxylic acid; and reacting said sodium sulfite with calcium hydroxide to form an aqueous solution comprising sodium hydroxide and a solid comprising calcium sulfite; and decomposing said calcium sulfite to form calcium oxide and sulfur dioxide.

2. The process of example embodiment 1 further comprising reacting calcium oxide with water to form calcium hydroxide.

3. The process of example embodiment 1 wherein said carboxylic acid is selected from formic acid, or acetic acid, or propanoic acid.

4. The process of example embodiment 1 further comprising capturing at least a portion of the carbon dioxide.

5. The process of example embodiment 4 wherein the captured carbon dioxide comprises a concentration greater than 70 percent or a partial pressure greater than 0.7 Bar.

6. The process of example embodiment 1 wherein said carboxylic acid is selected from formic acid, or acetic acid, or propanoic acid, and said carboxylate is selected from formate, or acetate, or propanoate.

7. The process of example embodiment 1 wherein said sodium sulfite and carboxylic acid from said reacting the solution comprising aqueous sodium carboxylate with sulfur dioxide comprise a solution comprising aqueous sodium sulfite and aqueous carboxylic acid at a liquid state.

8. The process of example embodiment 1 wherein said reacting the solution comprising aqueous sodium carboxylate with sulfur dioxide is conducted in an at least two stage absorption column;

Wherein a gas comprising sulfur dioxide enters a first stage comprising reacting a solution comprising aqueous sodium carboxylate from the second stage with a gas comprising sulfur dioxide to form a solution comprising aqueous sodium sulfite and aqueous carboxylic acid; and Wherein remaining gases from the first stage comprise carboxylic acid vapors or carboxylic acid vapor 'slip'; and Wherein said remaining gases from the first stage enter a second stage comprising absorbing at least a portion of said carboxylic acid vapors or carboxylic acid vapor 'slip' from said remaining gases in a solution comprising aqueous sodium carboxylate lean in carboxylic acid; and Wherein the solution moves from the second stage to the first stage; and Wherein the gas moves from the first stage to the second stage.

9. The process of example embodiment 1 wherein said sodium sulfite and carboxylic acid produced from said reacting the solution comprising aqueous sodium carboxylate with sulfur dioxide comprises a solid-liquid mixture comprising sodium sulfite solid and an aqueous solution comprising aqueous sodium sulfite and aqueous carboxylic acid at a liquid state.

10. The process of example embodiment 1 wherein said separating sodium sulfite from carboxylic acid comprises distillation of aqueous carboxylic acid and crystallization of sodium sulfite.

11. The process of example embodiment 10 wherein the wherein the process for distillation and crystallization comprises one or more or any combination of the following: mechanical vapor compression distillation, or mechanical vapor recompression distillation, or mechanical vapor compression crystallizer, or multi-effect distillation, or membrane distillation, or multistage flash distillation.

12. The process of example embodiment 10 wherein the vapor phase and condensate during distillation comprise carboxylic acid and water due to the similar boiling point of the carboxylic acid and water.

13. The process of example embodiment 1 wherein said separating sodium sulfite from carboxylic acid comprises separating sodium sulfite from aqueous carboxylic acid by concentrating with reverse osmosis, or high pressure reverse osmosis, or electrodialysis, or electrodialysis reversal, or forward osmosis, or osmotically assisted reverse osmosis and then precipitating sodium sulfite by cooling precipitation.

14. The process of example embodiment 13 further comprising precipitating sodium sulfite by cooling precipitation.

15. The process of example embodiment 1 wherein said calcium carbonate comprises an alkaline earth-weak acid, or magnesium carbonate, or alkaline earth carbonate, or a calcium silicate, or a calcium aluminate, or calcium ferrite, or a calcium sulfide, or a magnesium silicate, or a magnesium aluminate, or magnesium ferrite, or a magnesium sulfide.

16. The process of example embodiment 1 wherein sulfur dioxide comprises a gas comprising sulfur dioxide from the decomposition of calcium sulfite.

17. The process of example embodiment 1 wherein calcium hydroxide is provided in stoichiometric excess relative to sodium sulfite in the reaction of calcium hydroxide and sodium sulfite.

18. The process of example embodiment 1 wherein the calcium sulfite further comprises residual calcium hydroxide 19. The process of example embodiment 1 further comprising concentrating sodium hydroxide.

20. The process of example embodiment 19 wherein at least a portion of said concentrating of sodium hydroxide comprises forward osmosis or osmotically assisted reverse osmosis; and Wherein the draw solution comprises sodium sulfite after separation from at least a portion of the carboxylic acid; and Wherein the feed solution comprises sodium hydroxide after separation of at least a portion of calcium sulfite.

21. The process of example embodiment 1 wherein said sodium hydroxide is added to a body of water, such as a sea or ocean, to react with or sequester carbon dioxide, increase ocean pH, and reduce ocean acidity.

21. process of example embodiment 1 wherein sodium hydroxide is reacted with carbon dioxide to form sodium carbonate or sodium bicarbonate.

22. A process comprising:

reacting a material comprising magnesium carbonate with a solution comprising aqueous carboxylic acid to form a gas comprising carbon dioxide and a solution comprising aqueous magnesium carboxylate;

reacting the solution comprising aqueous magnesium carboxylate with sodium sulfate to form a solution comprising aqueous sodium carboxylate and a solid comprising magnesium sulfate;

reacting the solution comprising aqueous sodium carboxylate with sulfur dioxide to form sodium sulfite and carboxylic acid;

separating said sodium sulfite from said aqueous carboxylic acid; and reacting said sodium sulfite with calcium hydroxide to form an aqueous solution comprising sodium hydroxide and a solid comprising calcium sulfite; and decomposing said calcium sulfite to form calcium oxide and sulfur dioxide.

23. A process comprising:

reacting a material comprising alkaline earth weak acid with a solution comprising aqueous acid to form a solid or gas or liquid or solution comprising weak acid derivative and a solution comprising aqueous alkaline earth acid anion;

reacting the solution comprising aqueous alkaline earth acid anion with alkali sulfate to form a solution comprising aqueous alkali acid anion and a solid comprising alkaline earth sulfate;

reacting the solution comprising aqueous alkali acid anion with sulfur dioxide to form alkali sulfite and acid;

separating said alkali sulfite from said aqueous acid; and reacting said alkali sulfite with alkaline earth hydroxide to form an aqueous solution comprising alkali hydroxide and a solid comprising alkaline earth sulfite; and decomposing said alkaline earth sulfite to form alkaline earth oxide and sulfur dioxide.

24. The process of example embodiment 23 wherein the alkaline earth comprises one or more or any combination of the following: beryllium (Be), or magnesium (Mg), or calcium (Ca), or strontium (Sr), or barium (Ba), or radium (Ra).

25. The process of example embodiment 23 wherein said weak acid derivative comprises a derivative of an acid with an acid strength lower than or less acidic than formic acid.

26. The process of example embodiment 23 wherein said weak acid comprises an acid with an acid strength lower than or less acidic than formic acid.

27. The process of example embodiment 23 wherein said weak acid derivative comprises carbon dioxide, or hydrogen sulfide, or silicon dioxide, or silicon oxide, or iron oxide, or manganese oxide, or aluminum oxide, or any mixture thereof.

28. The process of example embodiment 23 wherein said acid comprises an acid stronger than the weak acid and weaker than aqueous sulfur dioxide or sulfurous acid.

29. The process of example embodiment 23 wherein said acid comprises a carboxylic acid.

30. The process of example embodiment 23 wherein said alkali comprises one or more or any combination of the following: lithium (Li), or sodium (Na), or potassium (K), or rubidium (Rb), or Cesium (Cs), or Francium (Fr), or ammonia or ammonium ($NH_3$ or $NH_4$).

Additional Example Description Example Embodiments Sodium Hydroxide, or Sodium Bicarbonate, or Sodium Carbonate, or Calcium Carbonate Production with Carboxylic Acid, Sulfur Dioxide, and Carbon Dioxide Intermediates 1. A process comprising:

reacting a material comprising calcium carbonate with a solution comprising aqueous carboxylic acid to form a gas comprising carbon dioxide and a solution comprising aqueous calcium carboxylate;

reacting the solution comprising aqueous calcium carboxylate with sodium sulfate to form a solution comprising aqueous sodium carboxylate and a solid comprising calcium sulfate;

reacting the solution comprising aqueous sodium carboxylate with sulfur dioxide to form sodium sulfite and carboxylic acid;

separating said sodium sulfite from said aqueous carboxylic acid;

reacting calcium carbonate with carbon dioxide and water to form a solution comprising aqueous calcium bicarbonate;

reacting a solution comprising aqueous calcium bicarbonate with sodium sulfite to form a solution comprising aqueous sodium bicarbonate and a solid comprising calcium sulfite;

decomposing said calcium sulfite to form calcium oxide and sulfur dioxide;

decomposing said sodium bicarbonate to form sodium carbonate and carbon dioxide;

reacting said calcium oxide with water to form calcium hydroxide; and reacting said sodium carbonate with said calcium hydroxide to form an aqueous solution comprising sodium hydroxide and a solid comprising calcium carbonate.

2. A process comprising:

reacting a material comprising calcium carbonate with a solution comprising aqueous carboxylic acid to form a gas comprising carbon dioxide and a solution comprising aqueous calcium carboxylate;

reacting the solution comprising aqueous calcium carboxylate with sodium sulfate to form a solution comprising aqueous sodium carboxylate and a solid comprising calcium sulfate;

reacting the solution comprising aqueous sodium carboxylate with sulfur dioxide to form sodium sulfite and carboxylic acid;

separating said sodium sulfite from said aqueous carboxylic acid;

reacting calcium carbonate with carbon dioxide and water to form a solution comprising aqueous calcium bicarbonate;

reacting a solution comprising aqueous calcium bicarbonate with sodium sulfite to form a solution comprising aqueous sodium bicarbonate and a solid comprising calcium sulfite; and decomposing said calcium sulfite to form calcium oxide and sulfur dioxide.

3. The process of example embodiment 2 further comprising decomposing said sodium bicarbonate to form sodium carbonate and carbon dioxide.

4. The process of example embodiment 3 wherein said carbon dioxide comprises a chemical intermediate in the process.

5. The process of example embodiment 1 further comprising reacting calcium oxide with water to form calcium hydroxide.

6. The process of example embodiment 3 further comprising reacting said sodium carbonate with calcium hydroxide to form an aqueous solution comprising sodium hydroxide and a solid comprising calcium carbonate.

7. The process of example embodiment 1 wherein the carbon dioxide reacted in the reaction of calcium carbonate with carbon dioxide and water to form a solution comprising aqueous calcium bicarbonate comprises carbon dioxide from the reaction of calcium carbonate with carboxylic acid.

8. The process of example embodiment 1 wherein calcium oxide is reacted with carbon dioxide to form calcium carbonate.

9. The process of example embodiment 8 wherein the reacted carbon dioxide comprises dilute $CO_2$, or a $CO_2$ from an emissions source, or $CO_2$ from a point source, or $CO_2$ from air, or $CO_2$ in air, or air, or ocean, or body of water.

10. The process of example embodiment 6 wherein said calcium carbonate comprises the calcium carbonate in the reaction of calcium carbonate with carbon dioxide and water to form a solution comprising aqueous calcium bicarbonate.

11. The process of example embodiment 8 wherein said calcium carbonate comprises the calcium carbonate in the reaction of calcium carbonate with carbon dioxide and water to form a solution comprising aqueous calcium bicarbonate.

12. The process of example embodiment 1 further comprising concentrating sodium hydroxide.

13. The process of example embodiment 12 wherein at least a portion of said concentrating of sodium hydroxide comprises forward osmosis or osmotically assisted reverse osmosis; and Wherein the draw solution comprises sodium carbonate; and Wherein the feed solution comprises sodium hydroxide after separation of at least a portion of calcium carbonate.

14. The process of example embodiment 2 further comprising capturing at least a portion of the carbon dioxide.

15. The process of example embodiment 14 wherein the captured carbon dioxide comprises a concentration greater than 70 percent or a partial pressure greater than 0.7 Bar.

16. The process of example embodiment 2 wherein said carboxylic acid is selected from formic acid, or acetic acid, or propanoic acid, and said carboxylate is selected from formate, or acetate, or propanoate.

17. The process of example embodiment 1 wherein said sodium hydroxide is added to a body of water, such as a sea or ocean, to react with or sequester carbon dioxide, increase ocean pH, and reduce ocean acidity.

18. The process of example embodiment 2 wherein said reacting the solution comprising aqueous sodium carboxylate with sulfur dioxide is conducted in an at least two stage absorption column;

Wherein a gas comprising sulfur dioxide enters a first stage comprising reacting a solution comprising aqueous sodium carboxylate from the second stage with a gas comprising sulfur dioxide to form a solution comprising aqueous sodium sulfite and aqueous carboxylic acid; and Wherein remaining gases from the first stage comprise carboxylic acid vapors or carboxylic acid vapor 'slip'; and Wherein said remaining gases from the first stage enter a second stage comprising absorbing at least a portion of said carboxylic acid vapors or carboxylic acid vapor 'slip' from said remaining gases in a solution comprising aqueous sodium carboxylate lean in carboxylic acid; and Wherein the solution moves from the second stage to the first stage; and Wherein the gas moves from the first stage to the second stage.

19. The process of example embodiment 2 wherein said reacting calcium carbonate with carbon dioxide and water is conducted in reactor with an atmosphere comprising $CO_2$.

20. The process of example embodiment 19 wherein the partial pressure of $CO_2$ in said atmosphere comprising $CO_2$ is greater than 1 Bar.

21. The process of example embodiment 2 wherein said reacting a solution comprising aqueous calcium bicarbonate with sodium sulfite is conducted in reactor with an atmosphere comprising $CO_2$.

22. The process of example embodiment 21 wherein the partial pressure of $CO_2$ in said atmosphere comprising $CO_2$ is greater than 0.5 Bar.

23. The process of example embodiment 2 wherein the solution comprising aqueous sodium bicarbonate is depressurized; and Wherein at least a portion of any carbon dioxide released during said depressurization is transferred to the reaction of calcium carbonate with carbon dioxide and water.

24. The process of example embodiment 1 wherein calcium hydroxide is provided in stoichiometric excess relative to sodium carbonate in the reaction of calcium hydroxide and sodium carbonate.

25. The process of example embodiment 1 wherein the calcium carbonate from the reaction of sodium carbonate and calcium hydroxide further comprises residual calcium hydroxide.

26. The process of example embodiment 25 further comprising separating at least a portion of said residual calcium hydroxide.

27. A process comprising:

reacting a material comprising calcium carbonate with a solution comprising aqueous carboxylic acid to form a gas comprising carbon dioxide and a solution comprising aqueous calcium carboxylate;

reacting the solution comprising aqueous calcium carboxylate with sodium sulfate to form a solution comprising aqueous sodium carboxylate and a solid comprising calcium sulfate;

reacting the solution comprising aqueous sodium carboxylate with sulfur dioxide to form sodium sulfite and carboxylic acid;

separating said sodium sulfite from said aqueous carboxylic acid;

reacting magnesium carbonate with carbon dioxide and water to form a solution comprising aqueous magnesium bicarbonate;

reacting a solution comprising aqueous magnesium bicarbonate with sodium sulfite to form a solution comprising aqueous sodium bicarbonate and a solid comprising magnesium sulfite;

decomposing said magnesium sulfite to form magnesium oxide and sulfur dioxide;

reacting said magnesium oxide with carbon dioxide to form magnesium carbonate;

decomposing said sodium bicarbonate to form sodium carbonate and carbon dioxide;

reacting said calcium oxide with water to form calcium hydroxide;

reacting said sodium carbonate with said calcium hydroxide to form an aqueous solution comprising sodium hydroxide and a solid comprising calcium carbonate; and decomposing calcium carbonate into calcium oxide and carbon dioxide.

28. A process comprising:

reacting a material comprising calcium carbonate with a solution comprising aqueous carboxylic acid to form a gas comprising carbon dioxide and a solution comprising aqueous calcium carboxylate;

reacting the solution comprising aqueous calcium carboxylate with sodium sulfate to form a solution comprising aqueous sodium carboxylate and a solid comprising calcium sulfate;

reacting the solution comprising aqueous sodium carboxylate with sulfur dioxide to form sodium sulfite and carboxylic acid;

separating said sodium sulfite from said aqueous carboxylic acid;

reacting magnesium carbonate with carbon dioxide and water to form a solution comprising aqueous magnesium bicarbonate;

reacting a solution comprising aqueous magnesium bicarbonate with sodium sulfite to form a solution comprising aqueous sodium bicarbonate and a solid comprising magnesium sulfite;

decomposing said magnesium sulfite to form magnesium oxide and sulfur dioxide; and reacting said magnesium oxide with carbon dioxide to form magnesium carbonate.

29. The process of example embodiment 28 wherein magnesium oxide is reacted with water to form magnesium hydroxide.

30. The process of example embodiment 28 wherein magnesium oxide is reacted with water to form magnesium hydroxide and magnesium hydroxide is reacted with carbon dioxide.

31. The process of example embodiment 28 wherein the sulfur dioxide in the reaction of aqueous sodium carboxylate with sulfur dioxide comprises the sulfur dioxide from the decomposition of magnesium sulfite.

32. The process of example embodiment 27 wherein calcium carbonate is decomposed into calcium oxide and carbon dioxide in a manner where the carbon dioxide is captured.

33. The process of example embodiment 27 wherein the carbon dioxide in the reaction of magnesium oxide with carbon dioxide comprises carbon dioxide from the decomposition of calcium carbonate.

34. The process of example embodiment 27 wherein the carbon dioxide in the reaction of magnesium oxide with carbon dioxide comprises carbon dioxide from an emissions source, or an internal source, or air.

35. The process of example embodiment 28 wherein at least a portion of any residual dissolved magnesium sulfite is separated from said sodium bicarbonate.

36. The process of example embodiment 35 wherein at least a portion of any residual dissolved magnesium sulfite is separated from said sodium bicarbonate by concentrating and cooling precipitation.

37. The process of example embodiment 35 wherein at least a portion of any residual dissolved magnesium sulfite is separated from said sodium bicarbonate by selective electrodialysis.

38. The process of example embodiment 35 wherein said selective electrodialysis comprises monovalent selective electrodialysis (MSED) or divalent selective electrodialysis (DSED).

39. The process of example embodiments 1, 2, 27, and 28 wherein an alkaline earth instead of or in addition to calcium or magnesium may be employed, and/or wherein an alkali instead of sodium may be employed.

40. The process of example embodiments 1, 2, 27, and 28 wherein the calcium or magnesium may comprise other alkaline earths instead of or in addition to calcium or magnesium, and/or wherein the sodium may comprise another alkali instead of or in addition to sodium.

Additional Example Description Example Embodiments Calcium Oxide or Magnesium Oxide Production with Carboxylic Acid, Sulfur Dioxide, and Alkali Intermediates 1. A process comprising:
   - reacting a material comprising calcium carbonate with a solution comprising aqueous carboxylic acid to form a gas comprising carbon dioxide and a solution comprising aqueous calcium carboxylate;
   - reacting the solution comprising aqueous calcium carboxylate with sodium sulfite to form a solution comprising aqueous sodium carboxylate and a solid comprising calcium sulfite;

reacting the solution comprising aqueous sodium carboxylate with sulfur dioxide to form sodium sulfite and carboxylic acid;

separating at least a portion of said sodium sulfite from said aqueous carboxylic acid.

2. The process of example embodiment 1 further comprising reacting calcium oxide with water to form calcium hydroxide.

3. The process of example embodiment 1 further comprising capturing at least a portion of the carbon dioxide.

4. The process of example embodiment 4 wherein the captured carbon dioxide comprises a concentration greater than 70 percent or a partial pressure greater than 0.7 Bar.

5. The process of example embodiment 1 wherein said carboxylic acid is selected from formic acid, or acetic acid, or propanoic acid, and said carboxylate is selected from formate, or acetate, or propanoate.

6. The process of example embodiment 1 wherein said sodium sulfite and carboxylic acid from said reacting the solution comprising aqueous sodium carboxylate with sulfur dioxide comprise a solution comprising aqueous sodium sulfite and aqueous carboxylic acid at a liquid state.

7. The process of example embodiment 1 wherein said reacting the solution comprising aqueous sodium carboxylate with sulfur dioxide is conducted in an at least two stage absorption column;
   - Wherein a gas comprising sulfur dioxide enters a first stage comprising reacting a solution comprising aqueous sodium carboxylate from the second stage with a gas comprising sulfur dioxide to form a solution comprising aqueous sodium sulfite and aqueous carboxylic acid; and
   - Wherein remaining gases from the first stage comprise carboxylic acid vapors or carboxylic acid vapor 'slip'; and
   - Wherein said remaining gases from the first stage enter a second stage comprising absorbing at least a portion of said carboxylic acid vapors or carboxylic acid vapor 'slip' from said remaining gases in a solution comprising aqueous sodium carboxylate lean in carboxylic acid; and
   - Wherein the solution moves from the second stage to the first stage; and Wherein the gas moves from the first stage to the second stage.

8. The process of example embodiment 1 wherein said sodium sulfite and carboxylic acid produced from said reacting the solution comprising aqueous sodium carboxylate with sulfur dioxide comprises a solid-liquid mixture comprising sodium sulfite solid and an aqueous solution comprising aqueous sodium sulfite and aqueous carboxylic acid at a liquid state.

9. The process of example embodiment 1 wherein said separating sodium sulfite from carboxylic acid comprises distillation of aqueous carboxylic acid and crystallization of sodium sulfite.

10. The process of example embodiment 9 wherein the wherein the process for distillation and crystallization comprises one or more or any combination of the following: mechanical vapor compression distillation, or mechanical vapor recompression distillation, or mechanical vapor compression crystallizer, or multi-effect distillation, or membrane distillation, or multistage flash distillation.

11. The process of example embodiment 9 wherein the vapor phase and condensate during distillation comprise carboxylic acid and water due to the similar boiling point of the carboxylic acid and water.

12. The process of example embodiment 1 wherein said separating sodium sulfite from carboxylic acid comprises separating sodium sulfite from aqueous carboxylic acid by concentrating with reverse osmosis, or high pressure reverse osmosis, or electrodialysis, or electrodialysis reversal, or forward osmosis, or osmotically assisted reverse osmosis and then precipitating sodium sulfite by cooling precipitation.

13. The process of example embodiment 12 further comprising precipitating sodium sulfite by cooling precipitation.

14. The process of example embodiment 1 wherein said calcium carbonate comprises an alkaline earth-weak acid, or magnesium carbonate, or alkaline earth carbonate, or a calcium silicate, or a calcium aluminate, or calcium ferrite, or a calcium sulfide, or a magnesium silicate, or a magnesium aluminate, or magnesium ferrite, or a magnesium sulfide.

15. The process of example embodiment 1 wherein sulfur dioxide comprises a gas comprising sulfur dioxide from the decomposition of calcium sulfite.

16. The process of example embodiment 1 wherein said separating at least a portion of sodium sulfite from carboxylic acid comprises reverse osmosis; and Wherein a solution comprising sodium sulfite and carboxylic acid is transferred into a reverse osmosis system as a feed solution, forming a permeate comprising carboxylic acid and a retentate comprising sodium sulfite and carboxylic acid.

17. The process of example embodiment 16 wherein said permeate comprises the carboxylic acid reacted with calcium carbonate.

18. The process of example embodiment 16 wherein said retentate comprises the sodium sulfite reacted with aqueous calcium carboxylate.

19. The process of example embodiment 1 wherein said separating at least a portion of sodium sulfite from carboxylic acid comprises electrodialysis; and Wherein a solution comprising sodium sulfite and carboxylic acid is transferred into an electrodialysis system as a feed solution, forming a diluate comprising carboxylic acid and a concentrate comprising sodium sulfite and carboxylic acid.

20. The process of example embodiment 19 wherein said diluate comprises the carboxylic acid reacted with calcium carbonate.

21. The process of example embodiment 16 wherein said concentrate comprises the sodium sulfite reacted with aqueous calcium carboxylate.

22. The process of example embodiment 1 wherein at least a portion of the remaining gases after the absorption of sulfur dioxide comprise carboxylic acid vapor.

22. The process of example embodiment 1 wherein at least a portion of any carboxylic acid vapor is recovered by reaction with sodium hydroxide, or sodium bicarbonate, or sodium carbonate, or a calcium carbonate, or calcium oxide, or calcium hydroxide, or magnesium carbonate, or magnesium oxide, or magnesium hydroxide, or an alkaline earth-weak acid, or an alkali weak acid, forming a carboxylate salt.

23. The process of example embodiment 22 wherein the formed carboxylate salt is transferred into one or more steps of the process.

24. The process of example embodiment 1 wherein said calcium oxide is reacted with a solution comprising alkali carbonate to form an alkali hydroxide and calcium carbonate.

25. The process of example embodiment 1 wherein said calcium oxide is reacted with a solution comprising alkali sulfite to form an alkali hydroxide and calcium sulfite.

26. The process of example embodiment 1 wherein said calcium oxide is reacted with carbon dioxide to form calcium carbonate.

27. A process comprising:

reacting a material comprising alkaline earth weak acid with a solution comprising aqueous carboxylic acid to form a gas or solid or liquid comprising a weak acid derivative and a solution comprising aqueous alkaline earth carboxylate;

reacting the solution comprising aqueous alkaline earth carboxylate with an alkali sulfite to form a solution comprising aqueous alkali carboxylate and a solid comprising alkaline earth sulfite;

reacting the solution comprising aqueous alkali carboxylate with sulfur dioxide to form alkali sulfite and carboxylic acid;

separating at least a portion of said alkali sulfite from said aqueous carboxylic acid.

28. The process of example embodiment 27 wherein the alkaline earth comprises one or more or any combination of the following: beryllium (Be), or magnesium (Mg), or calcium (Ca), or strontium (Sr), or barium (Ba), or radium (Ra).

29. The process of example embodiment 27 wherein said alkali comprises one or more or any combination of the following: lithium (Li), or sodium (Na), or potassium (K), or rubidium (Rb), or Cesium (Cs), or Francium (Fr), or ammonia or ammonium ($NH_3$ or $NH_4$).

30. The process of example embodiment 27 wherein said weak acid derivative comprises carbon dioxide, or hydrogen sulfide, or silicon dioxide, or silicon oxide, or iron oxide, or manganese oxide, or aluminum oxide, or any mixture thereof.

The invention claimed is:

1. A process comprising:

reacting a gas comprising sulfur dioxide with aqueous alkali carboxylate to form aqueous alkali sulfite, aqueous carboxylic acid, and a gas comprising carboxylic acid; and then absorbing at least a portion of said gas comprising carboxylic acid in an aqueous alkali carboxylate solution lean in carboxylate to form an aqueous alkali carboxylate;

wherein at least a portion of the formed aqueous alkali carboxylate is employed in the reacting wherein the alkali carboxylate solution lean in carboxylate is less than saturated with carboxylate.

2. The process of claim 1 wherein said formed aqueous alkali sulfite and aqueous carboxylic acid from reacting comprises a solid-liquid mixture and wherein said solid-liquid mixture comprises alkali sulfite solid and aqueous acid.

3. The process of claim 2 wherein said aqueous acid comprises an acid weaker than aqueous sulfur dioxide or sulfurous acid.

4. The process of claim 2 which further comprises separating at least a portion of said alkali sulfite solid from at least a portion of said aqueous acid.

5. The process of claim 4 wherein said separating employs: a filter, or a filter press, or a decanter, or a settler, or a coalescer, or a centrifuge, or a rotary filter.

6. The process of claim 1 wherein said formed aqueous alkali sulfite and aqueous carboxylic acid from reacting comprises a solid-liquid mixture and wherein said solid-liquid mixture comprises alkali sulfite solid and an aqueous solution comprising aqueous alkali sulfite and aqueous acid.

7. The process of claim 6 wherein said aqueous acid comprises an acid weaker than aqueous sulfur dioxide or sulfurous acid.

8. The process of claim 6 which further comprises separating at least a portion of said alkali sulfite solid from at least a portion of said aqueous solution comprising aqueous alkali sulfite and aqueous acid.

9. The process of claim 8 wherein said separating employs: a filter, or a filter press, or a decanter, or a settler, or a coalescer, or a centrifuge, or a rotary filter.

10. The process of claim 1 wherein the alkali carboxylate lean solution comprises a solution comprising a carbonate or bicarbonate salt.

11. The process of claim 1 wherein the gas comprising carboxylic acid further comprises carbon dioxide.

12. The process of claim 1 wherein said alkali carboxylate comprises a cation of one or more of the following: lithium, or sodium, or potassium, or rubidium, or Cesium, or ammonium.

13. The process of claim 1 wherein said carboxylic acid is selected from formic acid, or acetic acid, or propanoic acid, and said carboxylate is selected from formate, or acetate, or propanoate.

14. The process of claim 1 wherein said carboxylic acid comprises an acid weaker than aqueous sulfur dioxide or sulfurous acid.

15. The process of claim 1 wherein said alkali sulfite further comprises an alkali bisulfite or an alkali metabisulfite.

16. The process of claim 1 which further comprises reacting the gas comprising carboxylic acid with an alkali hydroxide, or alkali carbonate, alkali-weak acid or an alkaline earth oxide, or alkaline earth hydroxide, or alkaline earth carbonate, or alkaline earth-weak acid, or ammonium hydroxide, or ammonium carbonate, or a bicarbonate, or an ammonium-weak acid, or any combination thereof to form an alkali acid, or an alkaline earth-acid, or an ammonium-acid.

17. The process of claim 1 wherein the process employs at least one absorption column.

18. The process of claim 1 wherein the process employs at least two absorption columns.

19. The process of claim 1 wherein at least a portion of the gas comprising sulfur dioxide in the reacting step comprises sulfur dioxide captured in an absorption column.

* * * * *